United States Patent
Lazar et al.

(10) Patent No.: US 11,046,776 B2
(45) Date of Patent: Jun. 29, 2021

(54) MULTIVALENT AND MULTIEPITOPIC ANTIBODIES HAVING AGONISTIC ACTIVITY AND METHODS OF USE

(71) Applicant: Genentech, Inc., South San Francisco, CA (US)

(72) Inventors: Greg Lazar, South San Francisco, CA (US); Yanli Yang, South San Francisco, CA (US); Erin H. Christensen, Tiburon, CA (US); Julie Hang, South San Francisco, CA (US); Jeong Kim, San Francisco, CA (US); Seth Harris, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 666 days.

(21) Appl. No.: 15/669,861

(22) Filed: Aug. 4, 2017

(65) Prior Publication Data
US 2018/0057598 A1 Mar. 1, 2018

Related U.S. Application Data

(60) Provisional application No. 62/371,671, filed on Aug. 5, 2016.

(51) Int. Cl.
*A61K 39/395* (2006.01)
*C07K 16/28* (2006.01)
*A61K 45/06* (2006.01)
*A61K 39/00* (2006.01)

(52) U.S. Cl.
CPC .... *C07K 16/2878* (2013.01); *A61K 39/39558* (2013.01); *A61K 45/06* (2013.01); *C07K 16/2818* (2013.01); *A61K 2039/505* (2013.01); *C07K 2299/00* (2013.01); *C07K 2317/21* (2013.01); *C07K 2317/24* (2013.01); *C07K 2317/33* (2013.01); *C07K 2317/34* (2013.01); *C07K 2317/35* (2013.01); *C07K 2317/41* (2013.01); *C07K 2317/51* (2013.01); *C07K 2317/515* (2013.01); *C07K 2317/52* (2013.01); *C07K 2317/526* (2013.01); *C07K 2317/55* (2013.01); *C07K 2317/56* (2013.01); *C07K 2317/71* (2013.01); *C07K 2317/75* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,415,732 A | 11/1983 | Caruthers et al. |
| 4,419,446 A | 12/1983 | Howley et al. |
| 4,424,219 A | 1/1984 | Hashimoto et al. |
| 4,450,254 A | 5/1984 | Isley et al. |
| 4,458,066 A | 7/1984 | Caruthers et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,943,533 A | 7/1990 | Mendelsohn et al. |
| 4,965,199 A | 10/1990 | Capon et al. |
| 5,122,469 A | 6/1992 | Mather et al. |
| 5,212,290 A | 5/1993 | Vogelstein et al. |
| 5,264,365 A | 11/1993 | Georgiou et al. |
| 5,457,105 A | 10/1995 | Barker |
| 5,475,001 A | 12/1995 | Barker |
| 5,500,362 A | 3/1996 | Robinson et al. |

(Continued)

FOREIGN PATENT DOCUMENTS

| | | |
|---|---|---|
| EP | 0 308 936 A2 | 3/1989 |
| EP | 0 328 147 A2 | 8/1989 |

(Continued)

OTHER PUBLICATIONS

Almagro & Fransson, Frontiers in Bioscience 2008; 13:1619-33 (Year: 2008).*

(Continued)

*Primary Examiner* — Meera Natarajan
(74) *Attorney, Agent, or Firm* — Morrison & Foerster LLP

(57) ABSTRACT

Provided herein are tetravalent antigen binding complexes having agonist activity for a cell surface receptor. In some embodiments, the complexes comprise binding specificities for multiple epitopes of the same cell surface receptor. Further provided herein are nucleic acids, vectors, host cells, pharmaceutical compositions, and methods of production related thereto.

96 Claims, 46 Drawing Sheets

Specification includes a Sequence Listing.

(56) References Cited

U.S. PATENT DOCUMENTS

| | | |
|---|---|---|
| 5,508,192 A | 4/1996 | Georgiou et al. |
| 5,571,894 A | 11/1996 | Wels et al. |
| 5,587,458 A | 12/1996 | King et al. |
| 5,591,828 A | 1/1997 | Bosslet et al. |
| 5,616,582 A | 4/1997 | Barker |
| 5,641,870 A | 4/1997 | Barker |
| 5,639,635 A | 6/1997 | Joly et al. |
| 5,648,237 A | 7/1997 | Carter |
| 5,654,307 A | 8/1997 | Bridges et al. |
| 5,679,683 A | 10/1997 | Bridges et al. |
| 5,693,780 A | 12/1997 | Newman et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,116 A | 4/1998 | Hamann et al. |
| 5,747,498 A | 5/1998 | Schnur et al. |
| 5,750,373 A | 5/1998 | Garrard et al. |
| 5,760,041 A | 6/1998 | Wissner et al. |
| 5,767,285 A | 6/1998 | Hamann et al. |
| 5,770,429 A | 6/1998 | Lonberg et al. |
| 5,770,599 A | 6/1998 | Gibson |
| 5,770,701 A | 6/1998 | McGahren et al. |
| 5,770,710 A | 6/1998 | McGahren et al. |
| 5,773,001 A | 6/1998 | Hamann et al. |
| 5,804,396 A | 9/1998 | Plowman |
| 5,807,706 A | 9/1998 | Carter et al. |
| 5,821,333 A | 10/1998 | Carter et al. |
| 5,821,337 A | 10/1998 | Carter et al. |
| 5,866,572 A | 2/1999 | Barker et al. |
| 5,869,046 A | 2/1999 | Presta et al. |
| 5,877,296 A | 3/1999 | Hamann et al. |
| 5,891,996 A | 4/1999 | Mateo De Acosta del Rio et al. |
| 6,002,008 A | 12/1999 | Wissner et al. |
| 6,075,181 A | 6/2000 | Kucherlapati et al. |
| 6,084,095 A | 7/2000 | Bridges et al. |
| 6,140,332 A | 10/2000 | Traxler et al. |
| 6,150,584 A | 11/2000 | Kucherlapati et al. |
| 6,194,551 B1 | 2/2001 | Idusogie et al. |
| 6,235,883 B1 | 5/2001 | Jakobovits et al. |
| 6,248,516 B1 | 6/2001 | Winter et al. |
| 6,265,410 B1 | 7/2001 | Bridges et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,455,534 B2 | 9/2002 | Bridges et al. |
| 6,521,620 B1 | 2/2003 | Bridges et al. |
| 6,596,726 B1 | 7/2003 | Bridges et al. |
| 6,602,863 B1 | 8/2003 | Bridges et al. |
| 6,630,579 B2 | 10/2003 | Chari et al. |
| 6,713,484 B2 | 3/2004 | Bridges et al. |
| 6,737,056 B1 | 5/2004 | Presta |
| 6,884,799 B2 | 4/2005 | Kamal et al. |
| 6,982,321 B2 | 1/2006 | Winter |
| 7,041,870 B2 | 5/2006 | Tomizuka et al. |
| 7,049,311 B1 | 5/2006 | Thurston et al. |
| 7,067,511 B2 | 6/2006 | Thurston et al. |
| 7,087,409 B2 | 8/2006 | Barbas, III et al. |
| 7,189,826 B2 | 3/2007 | Rodman |
| 7,265,105 B2 | 9/2007 | Thurston et al. |
| 7,332,581 B2 | 2/2008 | Presta |
| 7,511,032 B2 | 3/2009 | Liu et al. |
| 7,521,541 B2 | 4/2009 | Egenbrot et al. |
| 7,527,791 B2 | 5/2009 | Adams et al. |
| 7,528,126 B2 | 5/2009 | Howard et al. |
| 7,550,140 B2 | 6/2009 | Bakker et al. |
| 7,557,099 B2 | 7/2009 | Howard et al. |
| 7,642,228 B2 | 1/2010 | Carter et al. |
| 7,695,936 B2 | 4/2010 | Carter et al. |
| 7,696,175 B2 | 4/2010 | Epstein et al. |
| 7,723,485 B2 | 5/2010 | Junutula et al. |
| 7,855,275 B2 | 12/2010 | Eigenbrot et al. |
| 7,959,925 B2 | 6/2011 | Weinberg et al. |
| 7,960,515 B2 | 6/2011 | Min et al. |
| 8,216,805 B2 | 7/2012 | Carter et al. |
| 8,258,268 B2 | 9/2012 | Wu et al. |
| 8,309,300 B2 | 11/2012 | Junutula et al. |
| 9,000,130 B2 | 4/2015 | Bhakata et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2006/0088523 A1 | 4/2006 | Andya et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |
| 2012/0251531 A1 | 10/2012 | Baehner et al. |
| 2013/0089553 A1 | 4/2013 | Carter et al. |
| 2015/0190506 A1 | 7/2015 | Cheung et al. |
| 2015/0307617 A1 | 10/2015 | Du et al. |
| 2015/0307620 A1 | 10/2015 | Vella et al. |
| 2016/0130358 A1 | 5/2016 | Bhakta et al. |
| 2016/0137740 A1 | 5/2016 | Hammond et al. |
| 2016/0152720 A1 | 6/2016 | Kim et al. |
| 2016/0160290 A1 | 6/2016 | Huseni |
| 2016/0161485 A1 | 6/2016 | Chu et al. |
| 2016/0166685 A1 | 6/2016 | Cheung et al. |
| 2016/0355597 A1 | 12/2016 | Rhee et al. |
| 2017/0000885 A1 | 1/2017 | Rhee et al. |
| 2017/0008971 A1 | 1/2017 | Dennis et al. |
| 2017/0015755 A1 | 1/2017 | Walsh et al. |
| 2017/0073386 A1 | 3/2017 | Stewart et al. |
| 2017/0114141 A1 | 4/2017 | Amann et al. |
| 2017/0247467 A1 | 8/2017 | Amann et al. |

FOREIGN PATENT DOCUMENTS

| | | |
|---|---|---|
| EP | 0 659 439 A2 | 6/1995 |
| EP | 0 404 097 B1 | 9/1996 |
| EP | 0 672 141 B1 | 5/2003 |
| EP | 1 691 833 B1 | 3/2010 |
| WO | WO-1987/00195 A1 | 1/1987 |
| WO | WO-1990/03430 A1 | 4/1990 |
| WO | WO-1991/00360 A1 | 1/1991 |
| WO | WO-1992/20373 A1 | 11/1992 |
| WO | WO-1993/01161 A1 | 1/1993 |
| WO | WO-1993/08829 A1 | 5/1993 |
| WO | WO-1993/11161 A1 | 6/1993 |
| WO | WO-1993/16185 A2 | 8/1993 |
| WO | WO-1993/16185 A3 | 8/1993 |
| WO | WO-1993/21232 A1 | 10/1993 |
| WO | WO-1994/04690 A1 | 3/1994 |
| WO | WO-1994/11026 A2 | 5/1994 |
| WO | WO-1994/11026 A3 | 5/1994 |
| WO | WO-1995/12673 A1 | 5/1995 |
| WO | WO-1996/27011 A1 | 9/1996 |
| WO | WO-1996/30347 A1 | 10/1996 |
| WO | WO-1996/33978 A1 | 10/1996 |
| WO | WO-1996/33980 A1 | 10/1996 |
| WO | WO-1996/40210 A1 | 12/1996 |
| WO | WO-1997/38983 A1 | 10/1997 |
| WO | WO-1998/14451 A1 | 4/1998 |
| WO | WO-1998/43960 A1 | 10/1998 |
| WO | WO-1998/50038 A1 | 11/1998 |
| WO | WO-1998/50433 A2 | 11/1998 |
| WO | WO-1998/50433 A3 | 11/1998 |
| WO | WO-1999/06378 A1 | 2/1999 |
| WO | WO-1999/06396 A1 | 2/1999 |
| WO | WO-1999/09016 A1 | 2/1999 |
| WO | WO-1999/24037 A1 | 5/1999 |
| WO | WO-1999/42585 A1 | 8/1999 |
| WO | WO-1999/51642 A1 | 10/1999 |
| WO | WO-2000/12507 A2 | 3/2000 |
| WO | WO-2000/12507 A3 | 3/2000 |
| WO | WO-2000/12507 A8 | 3/2000 |
| WO | WO-2000/29004 A1 | 5/2000 |
| WO | WO-2002/051870 A2 | 7/2002 |
| WO | WO-2002/051870 A3 | 7/2002 |
| WO | WO-2003/035694 A2 | 5/2003 |
| WO | WO-2003/035694 A3 | 5/2003 |
| WO | WO-2003/106498 A2 | 12/2003 |
| WO | WO-2003/106498 A3 | 12/2003 |

(56) References Cited

FOREIGN PATENT DOCUMENTS

| WO | WO-2004/056312 A2 | 7/2004 |
| --- | --- | --- |
| WO | WO-2004/056312 A3 | 7/2004 |
| WO | WO-2004/106381 A1 | 12/2004 |
| WO | WO-2005/023814 A1 | 3/2005 |
| WO | WO-2005/035572 A2 | 4/2005 |
| WO | WO-2005/035572 A3 | 4/2005 |
| WO | WO-2005/061547 A2 | 7/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/121168 A1 | 11/2006 |
| WO | WO-2006/121810 A2 | 11/2006 |
| WO | WO-2006/121810 A3 | 11/2006 |
| WO | WO-2007/005874 A2 | 1/2007 |
| WO | WO-2007/005874 A3 | 1/2007 |
| WO | WO-2007/042261 A2 | 4/2007 |
| WO | WO-2007/042261 A3 | 4/2007 |
| WO | WO-2007/062245 A2 | 5/2007 |
| WO | WO-2007/062245 A3 | 5/2007 |
| WO | WO-2008/049227 A1 | 5/2008 |
| WO | WO-2008/119567 A2 | 10/2008 |
| WO | WO-2008/119567 A3 | 10/2008 |
| WO | WO-2008/119567 A8 | 10/2008 |
| WO | WO-2009/052249 A1 | 4/2009 |
| WO | WO-2009/079335 A1 | 6/2009 |
| WO | WO-2009/089004 A1 | 7/2009 |
| WO | WO-2009/101611 A1 | 8/2009 |
| WO | WO-2009/114335 A2 | 9/2009 |
| WO | WO-2009/114335 A3 | 9/2009 |
| WO | WO-2010/005958 A2 | 1/2010 |
| WO | WO-2010/005958 A3 | 1/2010 |
| WO | WO-2010/027827 A2 | 3/2010 |
| WO | WO-2010/027827 A3 | 3/2010 |
| WO | WO-2010/077634 A1 | 7/2010 |
| WO | WO-2010/096418 A2 | 8/2010 |
| WO | WO-2010/096418 A3 | 8/2010 |
| WO | WO-2010/115629 A2 | 10/2010 |
| WO | WO-2010/115629 A3 | 10/2010 |
| WO | WO-2010/145792 A1 | 12/2010 |
| WO | WO-2011/066342 A2 | 6/2011 |
| WO | WO-2011/066342 A3 | 6/2011 |
| WO | WO-2011/071871 A1 | 6/2011 |
| WO | WO-2012/027328 A2 | 3/2012 |
| WO | WO-2012/027328 A3 | 3/2012 |
| WO | WO-2012/041504 A1 | 4/2012 |
| WO | WO-2012/119787 A1 | 9/2012 |
| WO | WO-2013/008171 A1 | 1/2013 |
| WO | WO-2013/028231 A1 | 2/2013 |
| WO | WO-2013/038191 A2 | 3/2013 |
| WO | WO-2013/038191 A3 | 3/2013 |
| WO | WO-2013/119202 A1 | 8/2013 |
| WO | WO-2014/012479 A1 | 1/2014 |
| WO | WO-2014/043403 A1 | 3/2014 |
| WO | WO-2014/043403 A4 | 3/2014 |
| WO | WO/2014/089113 A1 | 6/2014 |
| WO | WO-2014/135282 A1 | 9/2014 |
| WO | WO-2014/135282 A8 | 9/2014 |
| WO | WO-2014/148895 A1 | 9/2014 |
| WO | WO-2015/017822 A1 | 2/2015 |
| WO | WO-2015/095418 A1 | 6/2015 |
| WO | WO-2015/112900 A1 | 7/2015 |
| WO | WO-2015/112900 A8 | 7/2015 |
| WO | WO-2015/120198 A1 | 8/2015 |
| WO | WO-2015/135558 A1 | 9/2015 |
| WO | WO-2015/153513 A1 | 10/2015 |
| WO | WO-2015/153513 A8 | 10/2015 |
| WO | WO-2015/153857 A1 | 10/2015 |
| WO | WO-2015/153857 A8 | 10/2015 |
| WO | WO-2016/004875 A1 | 1/2016 |
| WO | WO-2016/004876 A1 | 1/2016 |
| WO | WO-2016/034085 A1 | 3/2016 |
| WO | WO-2016/040892 A1 | 3/2016 |
| WO | WO-2016/054555 A2 | 4/2016 |
| WO | WO-2016/054555 A3 | 4/2016 |
| WO | WO-2016/057667 A1 | 4/2016 |
| WO | WO-2016/057841 A1 | 4/2016 |
| WO | WO-2016/061142 A1 | 4/2016 |
| WO | WO-2016/164480 A1 | 10/2016 |
| WO | WO-2016/172485 A2 | 10/2016 |
| WO | WO-2016/172485 A3 | 10/2016 |
| WO | WO-2017/123673 A2 | 7/2017 |
| WO | WO-2017/123673 A3 | 7/2017 |

OTHER PUBLICATIONS

De Genstet al., Dev Comp Immunol 2006; 30:187-98 (Year: 2006).*
Yoshinaga et al., J. Biochem 2008; 143:593-601 (Year: 2008).*
International Search Report for PCT Application No. PCT/US2017/045642, dated Oct. 10, 2017, filed Aug. 4, 2017, 6 pages.
Written Opinion on Search Report for PCT Application No. PCT/US2017/045642, dated Oct. 10, 2017, filed Aug. 4, 2017, 8 pages.
Adams, P. D. et al. "PHENIX: A Comprehensive Python-Based System for Macromolecular Structure Solution," *Acta Crystallographica Section D Biol. Crystallography* D66:213-221, (2010).
Ajani et al. "A Multi-Institutional Phase II Study of BMS-182248-01 (BR96-Doxorubicin Conjugate) Administered Every 21 Days in Patients With Advanced Gastric Adenocarcinoma," *Cancer Jour.* 6(2):78-81, (Mar./Apr. 2000).
Alexander et al. "The Concise Guide to Pharmacology 2013/14: Enzymes," *Br. J. Pharmacol.* 170:1797-1867, (2013).
Almagro et al. "Humanization of Antibodies," *Front. Biosci.* 13:1619-1633, (Jan. 1, 2008).
Antonow et al. "Structure-Activity Relationships of Monomeric C2-Aryl Pyrrolo[2,1-c][1,4]benzodiazepine (PBD) Antitumor Agents," *J. Med. Chem.* 53(7):2927-2941, (Mar. 10, 2010).
Ashkenazi. "Targeting the Extrinsic Apoptotic Pathway in Cancer: Lessons Learned and Future Directions," *J. Clin. Invest* 125(2):487-489, (Feb. 2015).
Atwell et al. "Stable Heterodimers From Remodeling the Domain Interface of a Homodimer Using a Phage Display Library," *J. Mol. Biol.* 270:26-35, (1997).
Baca et al. "Antibody Humanization Using Monovalent Phage Display," *J. Biol. Chem.* 272(16):10678-10684, (Apr. 18, 1997).
Bachmann, B.J. "Derivations and Genotypes of Some Mutant Derivatives of *Escherichia coli* K-12," in *Escherichia coli and Salmonella Typhimurium: Cellular and Molecular Biology*. Washington, DC: American Society for Microbiology, Chapter 72, 2:1190-1219, (1987).
Barnes et al. "Methods for Growth of Cultured Cells in Serum-Free Medium," *Anal. Biochem.*102:255-270, (1980).
Bass et al. "Hormone Phage; An Enrichment Method for Variant Proteins With altered binding Properties," *Proteins* 8:309-314, (1990).
Beaucage et al. "Advances in the Synthesis of Oligonucleotides by the Phosphoramidite Approach," *Tetrahedron* 48(12):2223-2311, (1992).
Bernhard et al. "Cysteine Analogs of Recombinant Barley Ribosome Inactivating Protein From Antibody Conjugates With Enhanced Stability and Potency in Vitro," *Bioconjugate Chem.* 5:126-132, (1994).
Blackman, et al. "The Tetrazine Ligation: Fast Bioconjugation Based on Inverseelectron-Demand Diels-Alder Reactivity," *J. Am. Chem. Soc.* 130:13518-13519, (2008), 8 pages.
Boerner et al. "Production of Antigen-Specific Human Monoclonal Antibodies From in Vitro-Primed Human Splenocytes," *J. Immunol.* 147:86-95, (Jul. 1, 1991).
Brazil, "Immunotherapy: TNFR Superfamily Trimers," *Nature Reviews Drug Discovery* 5(1):20, (2006).
Brennan et al. "Preparation of Bispecific Antibodies by Chemical Recombination of Monoclonal Immunoglobulin $G_1$ Fragments," *Science* 229:81-83, (Jul. 5, 1985).
Brinkley, "A Brief Survey of Methods for Preparing Protein Conjugates With Dyes, Haptens, and Cross-Linking Reagents," *Bioconjugate Chem.* 3(1):2-13, (1992).
Brodeur et al."Mouse-Human Myeloma Partners for the Production of Heterohybridomas," in *Monoclonal Antibody Production Techniques and Applications* pp. 51-63 Marcel Dekker, Inc., New York, (1987).

(56) References Cited

OTHER PUBLICATIONS

Bruggemann, et al. "Comparison of the Effector Functions of Human Immunoglobulins Using a Matched Set of Chimeric Antibodies," *J. Exp. Med.* 166:1351-1361, (Nov. 1, 1987).
Capel et al. "Heterogeneity of Human IgG Fc Receptors," *Immunomethods* 4:25-34 (1994).
Carter et al. "Improved Oligonucleotide Site-Directed Mutagenesis Using M13 Vectors," *Nucleic Acids Res.* 13(12):4431-4443, (1985).
Carter et al. "Humanization of an Anti-p185[HER2] Antibody for Human Cancer Therapy," *Proc. Natl. Acad. Sci. USA* 89:4285-4289, (May 1992).
Chothia. "The Nature of the Accessible and Buried Surfaces in Proteins," *J. Mol. Biol.* 105:1-14, (1975).
Chothia et al. "Canonical Structures for the Hypervariable Regions of Immunoglobulins," *J. Mol. Biol.* 196:901-917, (1987).
Clackson et al. "Making Antibody Fragments Using Phage Display Libraries," *Nature* 352:624-628, (Aug. 15, 1991).
Clynes et al. "Fc Receptors are Required in Passive and Active Immunity to Melanoma," *Proc. Natl. Acad. Sci. USA* 95:652-656, (Jan. 1998).
Compaanet al. "The Crystal Structure of the Costimulatory OX40-OX40L Complex," *Structure*, 14(8):1321-1330, (Aug. 2006).
Cragg et al. "Complement-Mediated Lysis by Anti-CD20 mAb Correlates With Segregation Into Lipid Rafts," *Blood* 101(3):1045-1052, (Feb. 1, 2003, e-pub. Sep. 19, 2002).
Cragg et al. "Antibody Specificity Controls in Vivo Effector Mechanisms of Anti-CD20 Reagents," *Blood* 103:2738-2743, (Apr. 1, 2004, e-pub. Oct. 9, 2003).
Daeron. "Fc Receptor Biology," *Annu. Rev. Immunol.* 15:203-234, (1997).
Dall'Acqua et al. "Antibody Humanization by Framework Shuffling," *Methods* 36(1):43-60, (May 2005).
D'Andrea et al. "Expression Cloning of the Murine Erythropoietin Receptor," *Cell* 57(2):277-285, (Apr. 21, 1989).
Davies et al. "'Camelising' Human Antibody Fragments: NMR Studies on VH Domains," *Febs Lett.* 339:285-290, (1994).
De Haas et al. "Fcγ Receptors of Phagocytes," *J. Lab. Clin. Med.* 126:330-341, (1995).
Dooley et al. "Antibody Repertoire Development in Cartilaginous Fish," *Dev. Comp. Immunol.* 30(1-2):43-56, (2006, e-pub. Jul. 22, 2005).
Dornan et al "Index of Abstracts," *Blood* 51st Ash Annual Meeting Abstracts 114(13):2721-2729, (2009).
Dubowchik et al. "Doxorubicin Immunoconjugates Containing Bivalent, Lysosomally-Cleavable Dipeptide Linages," *Bioorg. & Med. Chem. Letters* 12:1529-1532, (2002).
Eaton et al. "Construction and Characterization of an Active Factor VIII Variant Lacking The Central One-Third of the Molecule," *Biochemistry* 25(26):8343-8347, (Dec. 30, 1986).
Emsley et al. "Features and Development of Coot," *Acta Crystallogr. D Biol. Crystallogr.* D66:486-501, (2010).
Fantl et al. "Signalling by Receptor Tyrosine Kinases," *Annu. Rev. Biochem.* 62:453-481, (1993).
Fellouse et al. "Synthetic Antibodies From a Four-Amino-Acid Code: A Dominant Role for Tyrosine in Antigen Recognition," *Proc. Natl. Acad. Sci. USA* 101(34):12467-12472, (Aug. 24, 2004).
Flatman et al. "Process Analytics for Purification of Monoclonal Antibodies," *J. Chromatogr. B* 848:79-87, (2007, e-pub. Dec. 11, 2006).
Flower "Modelling G-Protein-Coupled Receptors for Drug Design," *Biochim. Biophys. Acta* 1422(3):207-234, (Nov. 16, 1999).
Fukunaga et al. "Expression Cloning of a Receptor for Murine Granulocyte Colony-Stimulating Factor," *Cell* 61(2):341-350, (Apr. 1990).
Fukunaga et al. "Three Different MRNAs Encoding Human Granulocyte Colony-Stimulating Factor Receptor," *Proc. Natl. Acad. Sci. USA* 87:8702-8706, (Nov. 1990).
Gazzano-Santoro et al. "A Non-Radioactive Complement-Dependent Cytotoxicity Assay for Anti-CD20 Monoclonal Antibody," *J. Immunol. Methods* 202:163-171, (1997).

Graham et al. "Characteristics of a Human Cell Line Transformed by DNA From Human Adenovirus Type 5," *J. Gen. Virol.* 36:59-74, (1977).
Griffiths et al. "Human Anti-Self Antibodies With High Specificity From Phage Display Libraries," *EMBO J.* 12(2):725-734, (1993).
Gronwald et al. "Cloning and Expression of a cDNA Coding for the Human Platelet-Derived Growth Factor Receptor: Evidence for More Than One Receptor Class," *Proc. Natl. Acad. Sci. USA* 85:3435-3439, (May 1988).
Gruber et al. "Efficient Tumor Cell Lysis Mediated by a Bispecific Single Chain Antibody Expressed in *Escherichia coli*," *J. Immunol.* 152:5368-5374, (1994).
Guss et al. "Structure of the IgG-Binding Regions of Streptococcal Protein G," *EMBO J.* 5(7):1567-1575, (1986).
Guyer et al. "Immunoglobulin Binding by Mouse Intestinal Epithelial Cell Receptors," *J. Immunol.* 117(2):587-593, (Aug. 1976).
Ham et al. "Media and Growth Requirements," *Meth. Enz.* 58:44-93, (1979).
Hara et al. "Overproduction of Penicillin-Binding 7 Suppresses Thermosensitive Growth Defect At Low Osmolarity Due to an spr Mutation of *Escherichia coli*," *Microbial Drug Resistance* 2(1):63-72, (1996).
Harlow et al. Antibodies: A Laboratory Manual Ch. 14 Cold Spring Harbor Laboratory, Cold Spring Harbor, NY, TOC (1988).
Hartley et al."SG2285, A Novel C2-Aryl-Substituted Pyrrolobenzodiazepine Dimer Pro-Drug That Cross-Links DNA and Exerts Highly Potent Antitumor Activity," *Cancer Res.* 70(17):6849-6858, (Sep. 1, 2010).
Heldin "Dimerization of Cell Surface Receptors in Signal Transduction," *Cell* 80:213-223, (Jan. 27, 1995).
Hellstrom et al. "Strong Antitumor Activities of IgG3 Antibodies to a Human Melanoma-Associated Ganglioside," *Proc. Natl. Acad. Sci. USA* 82:1499-1502, (Mar. 1985).
Hellstrom et al. "Antitumor Effects of L6, an IgG2a Antibody That Reacts With Most Human Carcinomas," *Proc. Natl. Acad. Sci. USA* 83:7059-7063, (Sep. 1986).
Hermanson "Modifications of Nucleic Acids and Oligonucleotides," *Bioconjugate Techniques* Academic Press, San Diego, pp. 40-55, (1996).
Hinman et al. "Preparation and Characterization of Monoclonal Antibody Conjugates of the Calicheamicins: A Novel and Potent Family of Antitumor Antibiotices,"*Cancer Research* 53:3336-3342, (Jul. 15, 1993).
Ho et al. "Site-Directed Mutagenesis by Overlap Extension Using the Polymcrase Chain Reaction," *Gene* 77:51-59, (1989).
Holliger et al. "Specific Killing of Lymphoma Cells by Cytotoxic T-Cells Mediated by a Bispecific Diabody," *Protein Eng.* 9(3):299-305, (Mar. 1996).
Holliger et al. "Diabodies: Small Bivalent and Bispecific Antibody Fragments," *Proc. Natl. Acad. Sci. USA* 90:6444-6448, (Jul. 1993).
Holt et al. "Domain Antibodies: Proteins for Therapy," *Trends Biotechnol.* 21(11):484-490, (Nov. 2003).
Hoogenboom et al. "Overview of Antibody Phage-Display Technology and Its Applications," in *Methods in Molecular Biology* 178:1-37, (2001).
Hoogenboom et al. "By-Passing Immunisation: Human Antibodies From Synthetic Repertoires of Germline $V_H$ Gene Segments Rearranged in Vitro," *J. Mol. Biol.*, 227: 381-388, (1992).
Howard et al. "Synthesis of a Novel C2/C20-Aryl-Substituted Pyrrolo[2,1-c][1,4]Benzodiazepine Dimer Prodrug With Improved Water Solubility and Reduced DNA Reaction Rate," *Bioorganic and Med. Chem. Letters* 19(22):6463-6466, (2009, e-pub. Sep. 9, 2009).
Hudson et al. "Engineered Antibodies," *Nat. Med.* 9(1):129-134, (Jan. 2003).
Hurley et al. "Covalent Binding of Antitumor Antibiotics in the Minor Groove of DNA. Mechanism of Action of CC-1065 and The Pyrrolo(1,4)Benzodiazepines," *Acc. Chem. Res.* 19(8):230-237, (Aug. 1986).
Idusogie et al. "Mapping of the C1q Binding Site on Rituxan, a Chimeric Antibody With a Human IgG1 Fc," *J. Immunol.* 164:4178-4184, (2000).

(56) References Cited

OTHER PUBLICATIONS

Ito et al. "A General Method for Introducing a Series of Mutations Into Cloned DNA Using the Polymerase Chain Reaction," *Gene* 102:67-70, (1991).
Jeffrey et al. "Dipeptide-Based Highly Potent Doxorubicin Antibody Conjugates," *Bioorganic & Med. Chem. Letters* 16:358-362, (2006, e-pub. Nov. 3, 2005).
Johns et al. "Identification of the Epitope for the Epidermal Growth Factor Receptor-Specific Monoclonal Antibody 806 Reveals That It Preferential Recognizes an Untethered Form of the Receptor," *J. Biol. Chem.* 279(29):30375-30384, (2004).
Joly et al. "Overexpression of *Escherichia coli* Oxidoreductases Increases Recombinant Insulin-Like Growth Factor-I Accumulation," *Proc. Natl. Acad. Sci. USA* 95:2773-2777, (Mar. 1998).
Jones et al. "Replacing the Complementarity—Determining Regions in a Human Antibody With Those From a Mouse," *Nature* 321:522-525, (May 29, 1986).
Jones et al. "Human Erythropoietin Receptor: Cloning, Expression, and Biologic Characterization," *Blood* 76(1):31-35, (Jul. 1, 1990).
Jones et al. "Blood-Brain Barrier Transport of Therapeutics via Receptor-Mediation," *Pharm. Res.* 24(9):1759-1771, (Sep. 2007).
Junutula et al. "Site-Specific Conjugation of a Cytotoxic Drug to an Antibody Improves the Therapeutic Index," *Nature Biotech.* 26(8):925-932, (Aug. 2008, e-pub. Jul. 20, 2008).
Kabsch "XDS," *Acta Crystallogr. D Biol. Crystallogr.* D66:125-132, (2010).
Kang et al. "Drozitumab, a Human Antibody to Death Receptor 5, Has Potent Anti-Tumor Activity Against Rhabdomyosarcoma With the Expression of Caspase-8 Predictive of Response," *Clin. Cancer Res.* 17(10):3181-3192, (May 15, 2011), 17 pages.
Kashmiri et al. "SDR Grafting—A New Approach to Antibody Humanization," *Methods* 36:25-34, (2005).
Kimet al. "Localization of the Site of the Murine IgG1 Molecule That Is Involved in Binding to the Murine Intestinal Fc Receptor," *J. Immunol.* 24:2429-2434, (1994).
Kim et al. "Fcγ Receptors Enable Anticancer Action of Proapoptotic and immune-Modulatory Antibodies," *J. Exp. Med.* 210(9):1647-1651, (2013).
King et al. "Monoclonal Antibody Conjugates of Doxorubicin Prepared With Branched Peptide Linkers: Inhibition O fAggregation by Methoxytriethyleneglycol Chains," *J. Med. Chem.* 45:4336-4343, (2002, e-pub. Aug. 14, 2002).
Klimka. "Human Anti-CD30 recombinant Antibodies by Guided Phage Antibody Selection Using Cell Panning," *Br. J. Cancer* 83:252-260, (2000).
Koenig et al. "Deep Sequencing-guided Design of a High Affinity Dual Specificity Antibody to Target Two Angiogenic Factors in Neovascular Age-related Macular Degeneration," *J. Biol. Chem.* 290(36):21773-21786, (Sep. 4, 2015).
Kohler et al. "Continuous Cultures of Fused Cells Secreting Antibody of Predefined Specificity," *Nature* 256:495-497, (Aug. 7, 1975).
Kostelny et al. "Formation of a Bispecific Antibody by the Use of Leucine Zippers," *J. Immunol.* 148(5):1547-1553, (Mar. 1, 1992).
Kozbor. "A Human Hybrid Myeloma for Production of human Monoclonal Antibodies," *J. Immunol.* 133(6):3001-3005, (Dec. 1984).
Kratz et al. "Prodrugs of Anthracyclines in Cancer Chemotherapy," *Current Med. Chem.* 13:477-523, (2006).
Kunkel et al. "Rapid and Efficient Site_Specific Mutagenesis Without Phenotypic Selection," *Proc. Natl. Acad. Sci. USA* 82:488-192, (Jan. 1985).
Lee, C.V. et al. "Bivalent Antibody Phage Display Mimics Natural Immunoglobulin," *J. Immunol. Methods* 284:119-132, (2004).
Lee et al. "High Affinity Human Antibodies From Phage Displayed Synthetic Fab Libraries With a Single Framework Scaffold," *J. Mol. Biol.* 340:1073-1093, (2004).
Leimgruber et al. "Diazotization of Isobutyl- and n-Butylamine," *J. Am. Chem. Soc.* 87(24):5791-5793, (1965).

Leimgruber et al. "The Structure of Anthrarnycin," *J. Am. Chem. Soc.* 87:5793-5795, (1965).
Lemmon et al. "Cell Signaling by Receptor-Tyrosine Kinases," *Cell* 141(7):1117-1134, (Jun. 25, 2010), 35 pages.
Li et al. "Human Antibodies for Immunotherapy Development Generated Via a Human B Cell Hybridoma Technology," *Proc. Natl. Acad. Sci. USA* 103(10):3557-3562, (Mar. 7, 2006).
Li et al. "Receptor Tyrosine Kinase Transmembrane Domains: Function, Dimer Structure and Dimerization Energetics," *Cell Adhesion and Migration* 4(2):249-254, (Apr./May/Jun. 2010).
Lindmark et al. "Binding of Immunoglobulins to Protein A and Immunoglobulin Levels in Mammalian Sera," *J. Immunol. Meth.* 62:1-13, (1983).
Liu et al "Identification of Active Site Residues in the "GyrA" Half of Yeast DNA Topoisomerase II," *J. Biol. Chem.* 273(32):20252-20260, (Aug. 7, 1998).
Lode et al. "Targeted Therapy With a Novel Enediyene Antibiotic Calicheamicin $\theta^I_1$ Effectively Suppress Growth and Dissemination of Liver Metastases in a Syngeneic Model of Murine Neuroblastoma," *Cancer Research* 58:2925-2928, (Jul. 15, 1998).
Lonberg. "Human Antibodies From Transgenic Animals," *Nat. Biotech.* 23(9):1117-1125, (Sep. 2005, e-pub. Sep. 7, 2005).
Lonberg. "Fully Human Antibodies From Transgenic Mouse and Phage Display Platforms," *Curr. Opin. Immunol.* 20:450-459, (2008, e-pub. Jul. 21, 2008).
Lotz et al. "The Nerve Growth Factor/Tumor Necrosis Factor Receptor Family," *J. of Leukocyte Biology* 60(1):1-7, (Jul. 1996).3.
MacAraeg et al. "Use of an Anti-Apoptotic CHO Cell Line for Transient Gene Expression," *Biotechnol Prog.* 29(4):1050-1058, (Jul.-Aug. 2013, e-pub. Jun. 22, 2013).
MacCallum et al. "Antibody-Antigen Interactions: Contact Analysis and Binding Site Topography," *J. Mol. Biol.* 262: 732-745, (1996).
Magocet al. "FLASH: Fast Length Adjustment of Short Reads to Improve Genome Assemblies," *Bioinformatics* 27(21):2957-2963, (2011).
Marks et al. "By-passing immunization. Human Antibodies From V-Gene Libraries Displayed on Phage," *J. Mol. Biol.* 222:581-597, (1991).
Marks et al. "Antibody Engineering," in *Methods in Molecular Biology* 248:161-175 Lo, ed., Human Press, Totowa, NJ, (2003).
Massague "Receptors for the TGF-β Family," *J. Cell* 69(7):1067-1070, (Jun. 26, 1992).
Mather "Establishment and Characterization of Two Distinct Mouse Testicular Epithelial Cell Lines," *Biol. Reprod.* 23:243-252, (1980).
Mather. et al. "Culture of Testicular Cells in Hormone-Supplemented Serum-Free Medium," *Annals N. Y. Acad. Sci.* 383:44-68, (1982).
McCafferty. et al. "Phage Antibodies: Filamentous Phage Displaying Antibody Variable Domains," *Nature* 348:552-554, (Dec. 6, 1990).
McCoy. et al. "Phaser Crystallographic Software," *Journal of Applied Crystallography* 40:658-674, (2007).
Means. et al. "Chemical Modifications of Proteins: History and Applications," *Bioconjugate Chem.* 1(1):2-12, (Jan.-Feb. 1990).
Milstein. "Hybrid Hybridomas and Their Use in Immunohistochemistry," *Nature* 305:537-540, (Oct. 6, 1983).
Miyajima. et al. "Cytokine Receptors and Signal Transduction," *Annu. Rev. Immunol.* 10:295-331, (1992).
Moldenhauer et al. "Therapeutic Potential of Amanitin-Conjugated Anti-Epithelial Cell Adhesion Molecule Monoclonal Antibody Against Pancreatic Carcinoma," *J. Natl. Cancer Inst.* 104(8):622-634, (Apr. 18, 2012, e-pub. Mar. 27, 2012).
Morris "Epitope Mapping Protocols," in *Methods in Molecular Biology* vol. 66 Humana Press, Totowa, NJ, (1996).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Muyldermans et al. "Recognition of Antigens by Single-Domain Antibody Fragments: The Superfluous Luxury of Paired Domains," *Trend Biochem. Sci.* 26(4):230-235, (Apr. 2001).
Nagy et al. "Stability of Cytotoxic Luteinizing Hormone-Releasing Hormone Conjugate (AN-152) Containing Doxorubicin 14-O-

(56) References Cited

OTHER PUBLICATIONS

Hemiglutarate in Mouse and Human Serum in vitro: Implications for the Design of Preclinical Studies," *Proc. Natl. Acad. Sci. USA* 97(2):829-834, (Jan. 18, 2000).

Naismith et al. "Modularity in the TNF-Receptor Family," *Trends in Biochemical Sciences* 23(2):74-79, (Feb. 1998).

Ni. "Research Progress and Future Perspectives in Antibodomics and Antibodomic Drugs," *Xiandai Mianyixue* 26(4):265-268, (Oct. 23, 2006). (Abstract Only).

Nicolaou, et al. "Calicheamicin $\theta^I_1$: A Rationally Designed Molecule with Extremely Potent and Selective DNA Cleaving Properties and Apoptosis Inducing Activity," *Angew Chem. Intl. Ed. Engl.* 33:183-186, (Feb. 1, 1994).

Novick et al. "The Human Interferon Alpha/Beta Receptor: Characterization and Molecular Cloning," *Cell* 77(3):391-400, (May 1994).

Osbourn et al. "From Rodent Reagents to Human Therapeutics Using Antibody Guided Selection," *Methods* 36:61-68, (2005).

Padlan et al. "A Possible Procedure for Reducing the Immunogenicity of Antibody Variable Domains While Preserving Their Ligand-Binding Properties," *Mol. Immunol.* 28(4/5):489-498, (1991).

Patthy. "Homology of a Domain of the Growth Hormone/Prolactin Receptor Family With Type III Modules of Fibronectin," *Cell* 61(1):13-14, (Apr. 6, 1990).

Petkova et al. "Enhanced Half-Life of Genetically Engineered Human IgG1 Antibodies in a Humanized FcRn Mouse Model: Potential Application in Humorally Mediated Autoimmune Disease," *Int. Immunol.* 18(12):1759-1769, (2006).

Pluckthun in *The Pharmacology of Monoclonal Antibodies*, vol. 113, Rosenburg and Moore eds., Springer-Verlag, New York, pp. 269-315, (1994).

Presta et al. "Antibody Engineering," *Curr. Op. Struct. Biol.* 2:593-596, (1992).

Presta et al. "Humanization of an Antibody Directed Against IgE" *J. Immunol.* 151(5):2623-2632, (Sep. 1, 1993).

Proba et al. "Functional Antibody-Single-Chain Fragments From the Cytoplasm O *Escherichia coli*: Influence of Thioredoxin Reductase (TrB)," *Gene* 159:203-207, (1995).

Queen et al. "A Humanized Antibody That Binds to the Interleukin 2 Receptor," *Proc. Natl. Acad. Sci. USA* 86:10029-10033, (Dec. 1989).

Ravetch et al. "Fc Receptors," *Annu. Rev. Immunol.* 9:457-492, (1991).

Reyes et al. "Expression of Human β-Interferon cDNA Under the Control of a Thymidine Kinase Promoter From Herpes Simplex Virus," *Nature* 297:598-601, (1982).

Ridgway et al. "Knobs-Into-Holes Engineering of Antibody $C_H3$ Domains for Heavy Chain Heterdimerization," *Protein Eng.* 9(7):617-21, (1996).

Riechmann et al. "Reshaping Human Antibodies for Therapy," *Nature* 332:323-329, (1988).

Rodrigues et al. "Therapeutic Monoclonal Antibodies in Ophthalmology," *Prog. Retin. Eye Res.* 28(2):117-144, (Mar. 2009, e-pub. Dec. 10, 2008).

Rosok et al. "A Combinatorial Library Strategy for the Rapid Humanization of Anticarcinoma BR96 Fab" *J. Biol. Chem.* 271(37):22611-22618, (Sep. 13, 1996).

Sadowsky et al. "Development of Efficient Chemistry to Generate Site-Specific Disulfide-Linked Protein and Peptide-Payload Conjugates: Application to THIOMAB™ Antibody-Drug Conjugates," *Bioconjug. Chem.* 28(8):2086-2068, (Aug. 16, 2017, e-pub. Jul. 13, 2017).

Saleh et al. "Phase I Trial of the Anti-Lewis Y Drug Immunoconjugate BR96-Doxorubicin in Patients With Lewis Y-Expressing Epithelial Tumors," *J. Clin. Oncology* 18(11):2282-2292, (Jun. 2000).

Scheer et al. "Reorienting the Fab Domains of Trastuzumab Results in Potent HER2 Activators," *PLoS One* 7(12):e51817, (Dec. 20, 2012), 13 pages.

Shalaby et al. "Development of Humanized Bispecific Antibodies Reactive With Cytotoxic Lymphocytes and Tumor Cells Overexpressing The HER2 Protooncogene," *J. Exp. Med.* 175:217-225, (Jan. 1, 1992).

Shields et al. "High resolution Mapping of the Binding Site on Human IgG1 for FcγRI, FcγRII, FcγRIII, and FcRn and Design of IgG1 Variants With Improved Binding to the FcγR," *J. Biol. Chem.* 276(9):6591-6604, (Mar. 2, 2001).

Sidhu et al. "Phage-Displayed Antibody Libraries of Synthetic Heavy Chain Complementarity Determining Regions," *J. Mol. Biol.* 338:299-310, (2004).

Siebenlist et al. "*E. coli* RNA Polymerase Interacts Homologously With Two Different Promoters," *Cell* 20:269-281, (Jun. 1980).

Simmons et al. "Expression of Full-Length Immunoglobulins in *Escherichia coli*: Rapid and Efficient Production of Aglycosylated Antibodies," *J. Immunol. Methods*, 263:133-147, (2002).

Sims et al. "A Humanized CD18 Antibody Can Block Function Without Cell Destruction," *J. Immunol.* 151(4):2296-2308, (Aug. 15, 1993).

Skoda et al. "Murine c-mpl: A Member of the Hematopoietic Growth Factor Receptor Superfamily That Transduces a Proliferative Signal," 12(7):2645-2653, (1993).

Small et al. "STK-1, The Human Homolog of Flk-2/Flt-3, Is Selectively Expressed in CD34+ Human Bone Marrow Cells and is Involved in the Proliferation of Early Progenitor/Stem Cells," *Proc. Natl. Acad. Sci. USA*. 91:459-463, (Jan. 1994).

Smith et al. "The TNF Receptor Superfamily of Cellular and Viral Proteins: Activation, Costimulation, and Death," *Cell* 76(6):959-962, (Mar. 25, 1994).

Stewart et al. "The Role of Fc Gamma Receptors in the Activity of Immunomodulatory Antibodies for Cancer," *Journal for Immuno. Therapy of Cancer* 2:1-10, (2014).

Spiess et al. "Bispecific Antibodies With Natural Architecture Produced by Co-Culture of Bacteria Expressing Two Distinct Half-Antibodies," *Nature Biotech.* 31(8):753-758, (Aug. 2013. E-pub. Jul. 7, 2013).

Spiess et al. "Alternative Molecular Formats and Therapeutic Applications for Bispecific Antibodies," *Mol. Immunol.* 67:95-106, (2015, e-pub. Jan. 27, 2015).

Stragliotto et al. "Multiple Infusion of Anti-Epidermal Growth Factor Receptor (EGFR) Monoclonal Antibody (EMD 55 900) in Patients With Recurrent Malignant Gliomas," *Eur. J. Cancer* 32A(4):636-640, (1996).

Strohl "Optimization of Fc-Mediated Effector Functions of Monoclonal Antibodies," *Current Opinion in Biotechnology*, 20:685-691, (Dec. 2009, e-pub. Nov. 4, 2009).

Suresh et al. "Bispecific Monoclonal Antibodies From Hybrid Hybridomas," *Meth. In Enzymology* 121:210-228, (1986).

Taga et al. "Cytokine Receptors and Signal Transduction" *FASEB Journal* 6:3387-3396, (Dec. 1992).

Thirumurugan et al. "Click Chemistry for Drug Development and Diverse Chemical-Biology Applications," *Chem. Rev.* 113(7):4905-4979, (Mar. 27, 2013).

Thurston et al. "Synthesis of DNA-Interactive Pyrrolo[2,1-c][1,4]Benzodiazepines," *Chem. Rev.* 94(2):433-465, (Mar. 1994).

Tolcher et al. "Randomized Phase II Study of BR96-Doxorubicin Conjugate in Patients With Metastatic Breast Cancer," *J. Clin. Oncology* 17(2):478-484, (Feb. 1999).

Torgov et al. "Generation of an Intensely Potent Anthracycline by a Monoclonal Antibody-β-Galactosidase Conjugate," *Bioconj. Chem.* 16:717-721, (2005, e-pub. Apr. 27, 2005).

Traunecker et al. "Bispecific Single Chain Molecules (Janusins) Target Cytotoxic Lymphocytes on HIV Infected Cells," *EMBO J.* 10(12):3655-3659, (1991).

Tutt et al. "Trispecific F(ab')3 Derivatives That Use Cooperative Signaling Via the TCR/CD3 Complex and CD2 to Activate and Redirect Resting Cytotoxic T Cells," *J. Immunol.* 147(1):60-69, (Jul. 1, 1991).

Ullrich et al. "Human Insulin Receptor and Its Relationship to the Tyrosine Kinase Family of Oncogenes," *Nature* 313(6005):756-761, (Feb. 28-Mar. 6, 1985).

Ullrich et al. "Signal Transduction by Receptors With Tyrosine Kinase Activity," *Cell* 61:203-212, (Apr. 20, 1990).

(56) References Cited

OTHER PUBLICATIONS

The UniProt Consortium, "UniProt: The Universal Protein Knowledgebase," *Nucleic Acids Res.* 45: D158-D169, (2017, e-pub. Nov. 28, 2016).
Urlaub et al. "Isolation of Chinese Hamster Cell Mutants Deficient in Dihydrofolate Reductase Activity," *Proc. Natl. Acad. Sci. U.S.A.* 77:4216-4220, (Jul. 1980).
Uze et al. "Genetic Transfer of a functional Human Interferon Alpha Receptor Into Mouse Cells: Cloning and Expression of Its cDNA," *Cell* 60(2):225-234, (Jan. 26, 1990).
Vallette et al. "Construction of Mutant and Chimeric Genes Using the Polymerase Chain Reaction," *Nucl. Acids Res.* 17(2):723-733, (1989).
Van Dijk et al. "Human Antibodies As Next Generation Therapeutics," *Curr. Opin. Pharmacol.* 5:368-374, (2001).
Vigon et al., "Molecular Cloning and Characterization of MPL, the Human Homolog of the v-mpl Oncogene: Identification of a Member of the Hematopoietic Growth Factor Receptor Superfamily," *Proc. Natl. Acad. Sci. USA* 89:5640-5644, (Jun. 1992).
Vitetta et al, "Redesigning Nature's Poisons to Create Anti-Tumor Reagents," *Science* 238:1098-1104, (1987).
Vollmers et al. "Death by Stress: Natural IgM-Induced Apoptosis," *Methods and Findings in Experimental and Clinical Pharmacology* 27(3):1-7, (2005).
Vollmers et al. "The "Early Birds": Natural IgM Antibodies and Immune Surveillance," *Histology and Histopathology* 20:927-937, (2005).
Voo et al. "Antibodies Targeting human OX40 Expand Effector T Cells and Block Inducible and Natural Regulatory T Cell Function," *J. Immunol.* 191:3641-3650, (2013).
Wang et al. "Structural Biology of Shared Cytokine Receptors," *Ann. Rev. Immunol.* 27:29-60, (2009), 35 pages.
Ward et al. "Binding Activities of a repertoire of Single Immunoglobulin Variable Domains Secreted From *Escherichia coli*," *Nature* 341(6242):544-546, (Oct. 12, 1989).
Wells et al. "Cassette Mutagenesis: An Efficient Method for Generation of Multiple Mutations At Defined Sites," *Gene* 34(2-3):315-323, (1985).
Wilson et al. "An Fcγ Receptor-Dependent Mechanism Drives Antibody-Mediated Target-Receptor Signaling in Cancer Cells," *Cancer Cell* 19:101-113, (Jan. 18, 2011).
Winter et al. "Making Antibodies by Phage Display Technology," *Ann. Rev. Immunol.* 12:433-455, (1994).
Yaniv. "Enhancing Elements for Activation of Eukaryotic Promoters," *Nature* 297:17-18, (1982).
Yu et al. "The Biosynthetic Gene Cluster of the Maytansinoid Antitumor Agent Ansamitocin From *Actinosynnema pretiosum*," *Proc. Nat. Acad. Sci. USA* 99(12):7968-7973, (Jun. 11, 2002).
Zamyatnin. "Protein Volume in Solution," *Prog. Biophys. Mol. Biol.* 24:107-123, (1972).
Zapata et al. "Engineering Linear F(ab')$_2$ Fragments for Efficient Production in *Escherichia coli* and Enhanced Antiproliferative Activity," *Protein Eng.* 8(10):1057-1062, (1995).
Zoller et al. "Oligonucleotide-Directed Mutagenesis Using M13-derived Vectors: An Efficient and General Procedure for the Production of Point Mutations in Any Fragment of DNA," *Nucl. Acids Res.* 10(20):6487-6500, (1982).
Zoller et al. "Oligonucleotide-Directed Mutagenesis of DNA Fragments Cloned Into M13 Vectors," *Methods Enzymol.* 100:468-500, (1983).
U.S. Appl. No. 15/725,208, filed Oct. 4, 2017, for Lazar et al.
International Preliminary Report on Patentability for PCT Application No. PCT/US2017/045642, dated Feb. 14, 2019, filed Aug. 4, 2017, 7 pages.
Digiammarino, E. et al. "Design and Generation of DVD-Ig™ Molecules for Dual-Specific Targeting," *Therapeutic Proteins: Methods and Protocols, Methods in Molecular Biology* 899:145-156, (2012).
Kosloski, M.P. et al. "Pharmacokinetics and Tolerability of a Dual Variable Domain Immunoglobulin ABT-981 Against IL-1α and IL-1β in Healthy Subjects and Patients With Osteoarthritis of the Knee," *Journal of Clinical Pharmacology* 00(0):1-9, (2006).
Lacy, S.E. et al. "Generation and Characterization of ABT-981, A Dual Variable Domain Immunoglobulin (DVD-Ig™) Molecule That Specifically and Potently Neutralizes Both IL-1a and IL-1b," mAbs 7(3):605-619, (May/Jun. 2015).
Miller, K. et al. "Design, Construction, and in Vitro Analyses of Multivalent Antibodies," *Journal of Immunology* 170:4854-4861, (2003).

\* cited by examiner

SEQUENCE LISTING

```
<160> NUMBER OF SEQ ID NOS: 303

<210> SEQ ID NO 1
<211> LENGTH: 249
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

```
<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Ser Tyr Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Asp Met Tyr Pro Asp Asn Gly Asp Ser Ser Tyr Asn Gln Lys Phe Arg
1               5                   10                  15

Glu

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Ala Pro Arg Trp Tyr Phe Ser Val
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Tyr Thr Ser Arg Leu Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Gly His Thr Leu Pro Pro Thr
1               5
```

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Ala Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Glu Ser Tyr Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Asp Met Tyr Pro Asp Asn Ala Asp Ser Ser Tyr Asn Gln Lys Phe Arg
1               5                   10                  15

Glu

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Asp Met Tyr Pro Asp Asn Ala Asp Ala Ser Tyr Asn Gln Lys Phe Arg
1               5                   10                  15

Glu

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Asp Met Tyr Pro Asp Asn Gly Asp Ala Ser Tyr Asn Gln Lys Phe Arg
1               5                   10                  15

Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct -continued

<400> SEQUENCE: 13

Asp Met Tyr Pro Asp Ser Gly Asp Ser Ser Tyr Asn Gln Lys Phe Arg
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Asp Met Tyr Pro Asp Asn Gly Ser Ser Ser Tyr Asn Gln Lys Phe Arg
1               5                   10                  15

Glu

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ala Pro Arg Trp Tyr Phe Ser Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Ala Pro Arg Trp Tyr Ala Ser Val
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ala Pro Arg Trp Ala Phe Ser Val
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Ala Pro Ala Trp Tyr Phe Ser Val
1               5

<210> SEQ ID NO 19
<211> LENGTH: 8
<212> TYPE: PRT

```
<213> ORGANISM: Artificial Sequence
<220> FEATURE:
<223> OTHER INFORMATION: Synthetic Construct

<400> SEQUENCE: 19

Ala Pro Arg Trp Tyr Phe Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ala Pro Arg Ala Tyr Phe Ser Val
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Ala Ala Arg Trp Tyr Phe Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Gly His Thr Leu Pro Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly His Thr Ala Pro Pro Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Gly Ala Thr Leu Pro Pro Thr
1               5

<210> SEQ ID NO 25
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 25

Gln Gln Gly His Ala Leu Pro Pro Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Ala His Thr Leu Pro Pro Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Gln Gln Gly His Thr Leu Ala Pro Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Ala Gly His Thr Leu Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Asn Tyr Leu Ile Glu
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Val Ile Asn Pro Gly Ser Gly Asp Thr Tyr Tyr Ser Glu Lys Phe Lys
1               5                   10                  15

Gly

<210> SEQ ID NO 31
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 31

Val Ile Asn Pro Gly Ser Gly Asp Ala Tyr Tyr Ser Glu Lys Phe Lys
1               5                   10                  15
Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Val Ile Asn Pro Gly Ser Gly Asp Gln Tyr Tyr Ser Glu Lys Phe Lys
1               5                   10                  15
Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Asp Arg Leu Asp Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Ala Arg Leu Asp Tyr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asp Ala Leu Asp Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Arg Ala Asp Tyr
1               5

```
<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

His Ala Ser Gln Asp Ile Ser Ser Tyr Ile Val
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

His Gly Thr Asn Leu Glu Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

His Gly Thr Asn Leu Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

His Gly Thr Asn Leu Glu Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

His Gly Thr Asn Leu Glu Gln
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Val His Tyr Ala Gln Phe Pro Tyr Thr
1               5

<210> SEQ ID NO 43
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ala His Tyr Ala Gln Phe Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Val Ala Tyr Ala Gln Phe Pro Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Val His Ala Ala Gln Phe Pro Tyr Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Val His Tyr Ala Ala Phe Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Val His Tyr Ala Gln Ala Pro Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Val His Tyr Ala Gln Phe Ala Tyr Thr
1               5

<210> SEQ ID NO 49
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 49

Val His Tyr Ala Gln Phe Pro Ala Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Tyr Gly Val Leu
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Met Ile Trp Ser Gly Gly Thr Thr Asp Tyr Asn Ala Ala Phe Ile Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Glu Glu Met Asp Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Arg Ala Ser Gln Asp Ile Ser Asn Phe Leu Asn
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Tyr Thr Ser Arg Leu His Ser
1               5

<210> SEQ ID NO 55
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 55

Gln Gln Gly Asn Thr Leu Pro Trp Thr
1               5

<210> SEQ ID NO 56
<211> LENGTH: 117
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 58
<211> LENGTH: 117
<212> TYPE: PRT
<213> ORGANISM: Artificial Sequence
```

```
<220> FEATURE:
<223> OTHER INFORMATION: Synthetic Construct

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 60
<211> LENGTH: 117
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45
```

Gly Asp Met Tyr Pro Asp Asn Gly Asp Ser Ser Tyr Asn Gln Lys Phe
        50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 64
<211> LENGTH: 117
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Thr Val Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
             85                  90                  95

Thr Phe Gly Gln Gly Thr Lys Val Glu Ile Lys
            100                 105

<210> SEQ ID NO 66
<211> LENGTH: 117
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
         35                  40                  45

Gly Asp Met Tyr Pro Asp Asn Gly Asp Ser Ser Tyr Asn Gln Lys Phe
 50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
             85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 67
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Thr Val Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
             85                  90                  95

```
Thr Phe Gly Gln Gly Thr Lys Val Glu Ile Lys
            100                 105
```

```
<210> SEQ ID NO 68
<211> LENGTH: 117
<212> TYPE: PRT
<213> ORGANISM: Artificial Sequence
<220> FEATURE:
<223> OTHER INFORMATION: Synthetic Construct

<400> SEQUENCE: 68
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115
```

```
<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105
```

```
<210> SEQ ID NO 70
<211> LENGTH: 117
<212> TYPE: PRT
<213> ORGANISM: Artificial Sequence
<220> FEATURE:
<223> OTHER INFORMATION: Synthetic Construct

<400> SEQUENCE: 70
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ala
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 72
<211> LENGTH: 117
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80
```

```
Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 75
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 76
<211> LENGTH: 117
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ala Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asn Gly Asp Ala Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 79
<211> LENGTH: 107
<212> TYPE: PRT
<213> ORGANISM: Artificial Sequence
<220> FEATURE:
<223> OTHER INFORMATION: Synthetic Construct

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 80
<211> LENGTH: 117
<212> TYPE: PRT
<213> ORGANISM: Artificial Sequence
<220> FEATURE:
<223> OTHER INFORMATION: Synthetic Construct

<400> SEQUENCE: 80

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Ser Gly Asp Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 82
<211> LENGTH: 117
<212> TYPE: PRT
<213> ORGANISM: Artificial Sequence
<220> FEATURE:
<223> OTHER INFORMATION: Synthetic Construct

<400> SEQUENCE: 82

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30
```

-continued

Tyr Met Ser Trp Val Arg Gln Ala Pro Gly Gln Gly Leu Glu Trp Ile
            35                  40                  45

Gly Asp Met Tyr Pro Asp Asn Gly Ser Ser Tyr Asn Gln Lys Phe
     50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 83
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105

<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ala
             20                  25                  30

Tyr Met Ser Trp Val Arg Gln Ala Pro Gly Gln Gly Leu Glu Trp Ile
            35                  40                  45

Gly Asp Met Tyr Pro Asp Asn Ala Asp Ala Ser Tyr Asn Gln Lys Phe
     50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu

-continued

```
                100                 105                 110
Val Thr Val Ser Ser
            115

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 86
<211> LENGTH: 117
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Ala
                85                  90                  95

Thr Phe Gly Gln Gly Thr Lys Val Glu Ile Lys
            100                 105
```

<210> SEQ ID NO 88
<211> LENGTH: 117
<212> TYPE: PRT
<213> ORGANISM: Artificial Sequence
<220> FEATURE:
<223> OTHER INFORMATION: Synthetic Construct

<400> SEQUENCE: 88

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115
```

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly His Thr Ala Pro Pro
                    85                  90                  95

Thr Phe Gly Gln Gly Thr Lys Val Glu Ile Lys
            100                 105

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Pro
                85                  90                  95

Thr Phe Gly Gln Gly Thr Lys Val Glu Ile Lys
            100                 105

<210> SEQ ID NO 92
<211> LENGTH: 117
<212> TYPE: PRT
<213> ORGANISM: Artificial Sequence
<220> FEATURE:
```

<223> OTHER INFORMATION: Synthetic Construct

<400> SEQUENCE: 92

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115
```

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Ala Leu Pro Pro
                85                  90                  95

Thr Phe Gly Gln Gly Thr Lys Val Glu Ile Lys
            100                 105
```

<210> SEQ ID NO 94
<211> LENGTH: 117
<212> TYPE: PRT
<213> ORGANISM: Artificial Sequence
<220> FEATURE:
<223> OTHER INFORMATION: Synthetic Construct

<400> SEQUENCE: 94

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
```

```
                  50                  55                  60
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Thr Leu Pro Pro
                 85                  90                  95

Thr Phe Gly Gln Gly Thr Lys Val Glu Ile Lys
            100                 105

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
            115
```

```
<210> SEQ ID NO 97
<211> LENGTH: 107
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Ala Pro
                85                  90                  95

Thr Phe Gly Gln Gly Thr Lys Val Glu Ile Lys
            100                 105

<210> SEQ ID NO 98
<211> LENGTH: 117
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 99
<211> LENGTH: 107
<212> TYPE: PRT
<213> ORGANISM: Artificial Sequence
<220> FEATURE:
<223> OTHER INFORMATION: Synthetic Construct

<400> SEQUENCE: 99

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
```

```
                    20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly His Thr Leu Pro Pro
                85                  90                  95

Thr Phe Gly Gln Gly Thr Lys Val Glu Ile Lys
                100                 105

<210> SEQ ID NO 100
<211> LENGTH: 117
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Ala Trp Gly Gln Gly Thr Leu
                100                 105                 110

Val Thr Val Ser Ser
        115

<210> SEQ ID NO 101
<211> LENGTH: 107
<212> TYPE: PRT
<213> ORGANISM: Artificial Sequence
<220> FEATURE:
<223> OTHER INFORMATION: Synthetic Construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95
```

```
Thr Phe Gly Gln Gly Thr Lys Val Glu Ile Lys
            100                 105
```

<210> SEQ ID NO 102
<211> LENGTH: 117
<212> TYPE: PRT
<213> ORGANISM: Artificial Sequence
<220> FEATURE:
<223> OTHER INFORMATION: Synthetic Construct

<400> SEQUENCE: 102

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Ala Ser Val Trp Gly Gln Gly Thr Leu
            100                 105                 110

Val Thr Val Ser Ser
        115
```

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

```
Glu Val Gln Leu Val Gln Ser Gly Ala Glu Val Lys Lys Pro Gly Ala
```

```
                1               5                   10                  15
            Ser Val Lys Val Ser Cys Lys Ala Ser Gly Tyr Thr Phe Thr Asp Ser
                            20                  25                  30

Tyr Met Ser Trp Val Arg Gln Ala Pro Gly Gln Gly Leu Glu Trp Ile
                            35                  40                  45

Gly Asp Met Tyr Pro Asp Asn Gly Asp Ser Ser Tyr Asn Gln Lys Phe
                            50                  55                  60

Arg Glu Arg Val Thr Ile Thr Arg Asp Thr Ser Thr Ser Thr Ala Tyr
             65                 70                  75                  80

Leu Glu Leu Ser Ser Leu Arg Ser Glu Asp Thr Ala Val Tyr Tyr Cys
                            85                  90                  95

Val Leu Ala Pro Arg Trp Ala Phe Ser Val Trp Gly Gln Gly Thr Leu
                            100                 105                 110

Val Thr Val Ser Ser
                            115
```

<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

```
            Asp Ile Gln Met Thr Gln Ser Pro Ser Ser Leu Ser Ala Ser Val Gly
             1               5                   10                  15

Asp Arg Val Thr Ile Thr Cys Arg Ala Ser Gln Asp Ile Ser Asn Tyr
                            20                  25                  30

Leu Asn Trp Tyr Gln Gln Lys Pro Gly Lys Ala Pro Lys Leu Leu Ile
                            35                  40                  45

Tyr Tyr Thr Ser Arg Leu Arg Ser Gly Val Pro Ser Arg Phe Ser Gly
                            50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Gln Gln Gly His Thr Leu Pro Pro
                            85                  90                  95

Thr Phe Gly Gln Gly Thr Lys Val Glu Ile Lys
                            100                 105
```

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

```
            Glu Val Gln Leu Val Gln Ser Gly Ala Glu Val Lys Lys Pro Gly Ala
             1               5                   10                  15

Ser Val Lys Val Ser Cys Lys Ala Ser Gly Tyr Thr Phe Thr Asp Ser
                            20                  25                  30

Tyr Met Ser Trp Val Arg Gln Ala Pro Gly Gln Gly Leu Glu Trp Ile
                            35                  40                  45

Gly Asp Met Tyr Pro Asp Asn Gly Asp Ser Ser Tyr Asn Gln Lys Phe
                            50                  55                  60

Arg Glu Arg Val Thr Ile Thr Arg Asp Thr Ser Thr Ser Thr Ala Tyr
             65                 70                  75                  80
```

```
Leu Glu Leu Ser Ser Leu Arg Ser Glu Asp Thr Ala Val Tyr Tyr Cys
                85                  90                  95

Val Leu Ala Pro Ala Trp Tyr Phe Ser Val Trp Gly Gln Gly Thr Leu
            100                 105                 110

Val Thr Val Ser Ser
            115

<210> SEQ ID NO 107
<211> LENGTH: 107
<212> TYPE: PRT
<213> ORGANISM: Artificial Sequence
<220> FEATURE:
<223> OTHER INFORMATION: Synthetic Construct

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 108
<211> LENGTH: 117
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ala Val Trp Gly Gln Gly Thr Leu
            100                 105                 110

Val Thr Val Ser Ser
            115

<210> SEQ ID NO 109
<211> LENGTH: 107
<212> TYPE: PRT
<213> ORGANISM: Artificial Sequence
```

```
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Thr Leu Pro Pro
                85                  90                  95

Thr Phe Gly Gln Gly Thr Lys Val Glu Ile Lys
            100                 105

<210> SEQ ID NO 110
<211> LENGTH: 117
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Ala Tyr Phe Ser Val Trp Gly Gln Gly Thr Leu
            100                 105                 110

Val Thr Val Ser Ser
        115

<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Tyr Thr Ser Arg Leu Arg Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly His Thr Leu Pro Pro
                 85                  90                  95
Thr Phe Gly Gln Gly Thr Lys Val Glu Ile Lys
            100                 105
```

<210> SEQ ID NO 112
<211> LENGTH: 117
<212> TYPE: PRT
<213> ORGANISM: Artificial Sequence
<220> FEATURE:
<223> OTHER INFORMATION: Synthetic Construct

<400> SEQUENCE: 112

```
Glu Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Ser
                20                  25                  30
Tyr Met Ser Trp Val Arg Gln Ala Pro Gly Gln Gly Leu Glu Trp Ile
             35                  40                  45
Gly Asp Met Tyr Pro Asp Asn Gly Asp Ser Ser Tyr Asn Gln Lys Phe
 50                  55                  60
Arg Glu Arg Val Thr Ile Thr Arg Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Val Leu Ala Ala Arg Trp Tyr Phe Ser Val Trp Gly Gln Gly Thr Leu
            100                 105                 110
Val Thr Val Ser Ser
            115
```

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Ser Asn Tyr
                20                  25                  30
Leu Asn Trp Tyr Gln Gln Lys Pro Gly Lys Ala Pro Lys Leu Leu Ile
             35                  40                  45
Tyr Tyr Thr Ser Arg Leu Arg Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly His Thr Leu Pro Pro
                 85                  90                  95
Thr Phe Gly Gln Gly Thr Lys Val Glu Ile Lys
            100                 105
```

<210> SEQ ID NO 114

```
<211> LENGTH: 117
<212> TYPE: PRT
<213> ORGANISM: Artificial Sequence
<220> FEATURE:
<223> OTHER INFORMATION: Synthetic Construct

<400> SEQUENCE: 114
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Leu Ala Pro Arg Trp Tyr Phe Ser Val Trp Gly Gln Gly Thr Leu
            100                 105                 110

Val Thr Val Ser Ser
        115

```
<210> SEQ ID NO 115
<211> LENGTH: 107
<212> TYPE: PRT
<213> ORGANISM: Artificial Sequence
<220> FEATURE:
<223> OTHER INFORMATION: Synthetic Construct

<400> SEQUENCE: 115
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

```
<210> SEQ ID NO 116
<211> LENGTH: 117
<212> TYPE: PRT
<213> ORGANISM: Artificial Sequence
<220> FEATURE:
<223> OTHER INFORMATION: Synthetic Construct

<400> SEQUENCE: 116
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

```
Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
 50                      55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Ala Ala Pro Arg Trp Tyr Phe Ser Val Trp Gly Gln Gly Thr Leu
                100                 105                 110

Val Thr Val Ser Ser
            115
```

<210> SEQ ID NO 117
<211> LENGTH: 107
<212> TYPE: PRT
<213> ORGANISM: Artificial Sequence
<220> FEATURE:
<223> OTHER INFORMATION: Synthetic Construct

<400> SEQUENCE: 117

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105
```

<210> SEQ ID NO 118
<211> LENGTH: 114
<212> TYPE: PRT
<213> ORGANISM: Artificial Sequence
<220> FEATURE:
<223> OTHER INFORMATION: Synthetic Construct

<400> SEQUENCE: 118

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Val Ile Asn Pro Gly Ser Gly Asp Thr Tyr Tyr Ser Glu Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
                100                 105                 110
```

Ser Ser

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 120
<211> LENGTH: 114
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 122
<211> LENGTH: 114
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

```
Thr Phe Gly Gln Gly Thr Lys Val Glu Ile Lys
            100                 105
```

<210> SEQ ID NO 124
<211> LENGTH: 114
<212> TYPE: PRT
<213> ORGANISM: Artificial Sequence
<220> FEATURE:
<223> OTHER INFORMATION: Synthetic Construct

<400> SEQUENCE: 124

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105
```

<210> SEQ ID NO 126
<211> LENGTH: 114
<212> TYPE: PRT
<213> ORGANISM: Artificial Sequence
<220> FEATURE:
<223> OTHER INFORMATION: Synthetic Construct

<400> SEQUENCE: 126

```
Glu Val Gln Leu Val Gln Ser Gly Ala Glu Val Lys Lys Pro Gly Ala
```

US 11,046,776 B2

313                                                           314
-continued

```
            1               5                  10                 15
Ser Val Lys Val Ser Cys Lys Ala Ser Gly Tyr Ala Phe Thr Asn Tyr
                    20                  25                  30

Leu Ile Glu Trp Val Arg Gln Ala Pro Gly Gln Gly Leu Glu Trp Ile
                35                  40                  45

Gly Val Ile Asn Pro Gly Ser Gly Asp Thr Tyr Tyr Ser Glu Lys Phe
            50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                    85                  90                  95

Ala Arg Asp Arg Leu Asp Tyr Trp Gly Gln Gly Thr Leu Val Thr Val
                100                 105                 110

Ser Ser

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Asp Ile Gln Met Thr Gln Ser Pro Ser Ser Leu Ser Ala Ser Val Gly
1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
                35                  40                  45

Tyr His Gly Thr Asn Leu Glu Asp Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                    85                  90                  95

Thr Phe Gly Gln Gly Thr Lys Val Glu Ile Lys
                100                 105

<210> SEQ ID NO 128
<211> LENGTH: 114
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Gln Ser Gly Ala Glu Val Lys Lys Pro Gly Ala
1               5                  10                  15

Ser Val Lys Val Ser Cys Lys Ala Ser Gly Tyr Ala Phe Thr Asn Tyr
                    20                  25                  30

Leu Ile Glu Trp Val Arg Gln Ala Pro Gly Gln Gly Leu Glu Trp Ile
                35                  40                  45

Gly Val Ile Asn Pro Gly Ser Gly Asp Thr Tyr Tyr Ser Glu Lys Phe
            50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
```

```
                85                  90                  95
Ala Arg Asp Arg Leu Asp Tyr Trp Gly Gln Gly Thr Leu Val Thr Val
            100                 105                 110

Ser Ser
```

<210> SEQ ID NO 129
<211> LENGTH: 107
<212> TYPE: PRT
<213> ORGANISM: Artificial Sequence
<220> FEATURE:
<223> OTHER INFORMATION: Synthetic Construct

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105
```

<210> SEQ ID NO 130
<211> LENGTH: 114
<212> TYPE: PRT
<213> ORGANISM: Artificial Sequence
<220> FEATURE:
<223> OTHER INFORMATION: Synthetic Construct

<400> SEQUENCE: 130

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct -continued

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 132
<211> LENGTH: 114
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 133
<211> LENGTH: 107
<212> TYPE: PRT
<213> ORGANISM: Artificial Sequence
<220> FEATURE:
<223> OTHER INFORMATION: Synthetic Construct

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Val His Tyr Ala Gln Phe Pro Tyr
                    85                  90                  95

Thr Phe Gly Gln Gly Thr Lys Val Glu Ile Lys
                100                 105

<210> SEQ ID NO 134
<211> LENGTH: 114
<212> TYPE: PRT
<213> ORGANISM: Artificial Sequence
<220> FEATURE:
<223> OTHER INFORMATION: Synthetic Construct

<400> SEQUENCE: 134

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 135
<211> LENGTH: 107
<212> TYPE: PRT
<213> ORGANISM: Artificial Sequence
<220> FEATURE:
<223> OTHER INFORMATION: Synthetic Construct

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 136
<211> LENGTH: 114
<212> TYPE: PRT
<213> ORGANISM: Artificial Sequence
<220> FEATURE:
<223> OTHER INFORMATION: Synthetic Construct
```

<400> SEQUENCE: 136

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 138
<211> LENGTH: 114
<212> TYPE: PRT
<213> ORGANISM: Artificial Sequence
<220> FEATURE:
<223> OTHER INFORMATION: Synthetic Construct

<400> SEQUENCE: 138

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

```
Lys Gly Arg Val Thr Leu Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser
```

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

```
Asp Ile Gln Met Thr Gln Ser Pro Ser Ser Leu Ser Ala Ser Val Gly
  1               5                  10                  15

Asp Arg Val Thr Ile Thr Cys His Ala Ser Gln Asp Ile Ser Ser Tyr
             20                  25                  30

Ile Val Trp Tyr Gln Gln Lys Pro Gly Lys Ser Phe Lys Gly Leu Ile
         35                  40                  45

Tyr His Gly Thr Asn Leu Glu Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
            100                 105
```

<210> SEQ ID NO 140
<211> LENGTH: 114
<212> TYPE: PRT
<213> ORGANISM: Artificial Sequence
<220> FEATURE:
<223> OTHER INFORMATION: Synthetic Construct

<400> SEQUENCE: 140

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Val Ile Asn Pro Gly Ser Gly Asp Thr Tyr Tyr Ser Glu Lys Phe
 50                  55                  60

Lys Gly Arg Val Thr Leu Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser
```

<210> SEQ ID NO 141
<211> LENGTH: 107
<212> TYPE: PRT

<213> ORGANISM: Artificial Sequence
<220> FEATURE:
<223> OTHER INFORMATION: Synthetic Construct

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 142
<211> LENGTH: 114
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Phe Lys Leu Leu Ile
        35                  40                  45

```
Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 144
<211> LENGTH: 114
<212> TYPE: PRT
<213> ORGANISM: Artificial Sequence
<220> FEATURE:
<223> OTHER INFORMATION: Synthetic Construct

<400> SEQUENCE: 144

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 145
<211> LENGTH: 107
<212> TYPE: PRT
<213> ORGANISM: Artificial Sequence
<220> FEATURE:
<223> OTHER INFORMATION: Synthetic Construct

<400> SEQUENCE: 145

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ala Pro Lys Gly Leu Ile
            35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 146
<211> LENGTH: 114

```
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 147
<211> LENGTH: 107
<212> TYPE: PRT
<213> ORGANISM: Artificial Sequence
<220> FEATURE:
<223> OTHER INFORMATION: Synthetic Construct

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala His Tyr Ala Gln Phe Pro Tyr
                85                  90                  95

Thr Phe Gly Gln Gly Thr Lys Val Glu Ile Lys
            100                 105

<210> SEQ ID NO 148
<211> LENGTH: 114
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45
```

Gly Val Ile Asn Pro Gly Ser Gly Asp Thr Tyr Tyr Ser Glu Lys Phe
            50                  55                  60

Lys Gly Arg Val Thr Leu Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 149
<211> LENGTH: 107
<212> TYPE: PRT
<213> ORGANISM: Artificial Sequence
<220> FEATURE:
<223> OTHER INFORMATION: Synthetic Construct

<400> SEQUENCE: 149

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val Ala Tyr Ala Gln Phe Pro Tyr
                85                  90                  95

Thr Phe Gly Gln Gly Thr Lys Val Glu Ile Lys
                100                 105

<210> SEQ ID NO 150
<211> LENGTH: 114
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Ala Ala Gln Phe Pro Tyr
                85                  90                  95

Thr Phe Gly Gln Gly Thr Lys Val Glu Ile Lys
            100                 105

<210> SEQ ID NO 152
<211> LENGTH: 114
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 153
<211> LENGTH: 107
<212> TYPE: PRT
<213> ORGANISM: Artificial Sequence
<220> FEATURE:
<223> OTHER INFORMATION: Synthetic Construct

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

```
Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Ala Phe Pro Tyr
                85                  90                  95

Thr Phe Gly Gln Gly Thr Lys Val Glu Ile Lys
            100                 105
```

<210> SEQ ID NO 154
<211> LENGTH: 114
<212> TYPE: PRT
<213> ORGANISM: Artificial Sequence
<220> FEATURE:
<223> OTHER INFORMATION: Synthetic Construct

<400> SEQUENCE: 154

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 155
<211> LENGTH: 107
<212> TYPE: PRT
<213> ORGANISM: Artificial Sequence
<220> FEATURE:
<223> OTHER INFORMATION: Synthetic Construct

<400> SEQUENCE: 155

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Ala Pro Tyr
                85                  90                  95

Thr Phe Gly Gln Gly Thr Lys Val Glu Ile Lys
            100                 105
```

<210> SEQ ID NO 156
<211> LENGTH: 114
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 157
<211> LENGTH: 107
<212> TYPE: PRT
<213> ORGANISM: Artificial Sequence
<220> FEATURE:
<223> OTHER INFORMATION: Synthetic Construct

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Ala Tyr
                85                  90                  95

Thr Phe Gly Gln Gly Thr Lys Val Glu Ile Lys
            100                 105

<210> SEQ ID NO 158
<211> LENGTH: 114
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr

```
                20                  25                  30
Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Ser Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 159
<211> LENGTH: 107
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Ala
                85                  90                  95

Thr Phe Gly Gln Gly Thr Lys Val Glu Ile Lys
                100                 105

<210> SEQ ID NO 160
<211> LENGTH: 114
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Ser Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Ala Arg Leu Asp Tyr Trp Gly Gln Gly Thr Leu Val Thr Val
```

-continued

Ser Ser

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 162
<211> LENGTH: 114
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ala Leu Asp Tyr Trp Gly Gln Gly Thr Leu Val Thr Val
            100                 105                 110

Ser Ser

<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163

Asp Ile Gln Met Thr Gln Ser Pro Ser Ser Leu Ser Ala Ser Val Gly

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 164
<211> LENGTH: 114
<212> TYPE: PRT
<213> ORGANISM: Artificial Sequence
<220> FEATURE:
<223> OTHER INFORMATION: Synthetic Construct

<400> SEQUENCE: 164

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Ala Asp Tyr Trp Gly Gln Gly Thr Leu Val Thr Val
                100                 105                 110

Ser Ser

<210> SEQ ID NO 165
<211> LENGTH: 107
<212> TYPE: PRT
<213> ORGANISM: Artificial Sequence
<220> FEATURE:
<223> OTHER INFORMATION: Synthetic Construct

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr

Thr Phe Gly Gln Gly Thr Lys Val Glu Ile Lys
             100                 105

<210> SEQ ID NO 166
<211> LENGTH: 113
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Ile Arg Gln Pro Pro Gly Lys Gly Leu Glu Trp Ile
        35                  40                  45

Gly Met Ile Trp Ser Gly Gly Thr Thr Asp Tyr Asn Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 168
<211> LENGTH: 113
<212> TYPE: PRT
<213> ORGANISM: Artificial Sequence
<220> FEATURE:
<223> OTHER INFORMATION: Synthetic Construct

<400> SEQUENCE: 168

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Ile Arg Gln Pro Pro Gly Lys Gly Leu Glu Trp Ile
        35                  40                  45

Gly Met Ile Trp Ser Gly Gly Thr Thr Asp Tyr Asn Ala Ala Phe Ile
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Val
            85                  90                  95

Arg Glu Glu Met Asp Tyr Trp Gly Gln Gly Thr Leu Val Thr Val Ser
            100                 105                 110

Ser
```

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
            85                  90                  95

Thr Phe Gly Gln Gly Thr Lys Val Glu Ile Lys
            100                 105
```

<210> SEQ ID NO 170
<211> LENGTH: 113
<212> TYPE: PRT
<213> ORGANISM: Artificial Sequence
<220> FEATURE:
<223> OTHER INFORMATION: Synthetic Construct

<400> SEQUENCE: 170

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Val Arg Gln Pro Pro Gly Lys Gly Leu Glu Trp Leu
        35                  40                  45

Gly Met Ile Trp Ser Gly Gly Thr Thr Asp Tyr Asn Ala Ala Phe Ile
    50                  55                  60

Ser Arg Leu Thr Ile Ser Lys Asp Thr Ser Lys Asn Gln Val Ser Leu
65                  70                  75                  80
```

```
Lys Leu Ser Ser Val Thr Ala Ala Asp Thr Ala Val Tyr Tyr Cys Val
            85                  90                  95

Arg Glu Glu Met Asp Tyr Trp Gly Gln Gly Thr Leu Val Thr Val Ser
        100                 105                 110

Ser

<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2
<223> OTHER INFORMATION: Xaa = Ser or Ala

<400> SEQUENCE: 172

Xaa Xaa Tyr Met Ser
1               5

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asn or Ser
<220> FEATURE:
<221> NAME/KEY: VARIANT
<222> LOCATION: 7
<223> OTHER INFORMATION: Xaa = Ala or Gly
<220> FEATURE:
<221> NAME/KEY: VARIANT
<222> LOCATION: 8
<223> OTHER INFORMATION: Xaa = Asp or Ser
```

```
<220> FEATURE:
<221> NAME/KEY: VARIANT
<222> LOCATION: 9
<223> OTHER INFORMATION: Xaa = Ala or Ser

<400> SEQUENCE: 173

Asp Met Tyr Pro Asp Xaa Xaa Xaa Xaa Ser Tyr Asn Gln Lys Phe Arg
1               5                   10                  15

Glu

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Tyr or Ala
<220> FEATURE:
<221> NAME/KEY: VARIANT
<222> LOCATION: 6
<223> OTHER INFORMATION: Xaa = Ala or Phe
<220> FEATURE:
<221> NAME/KEY: VARIANT
<222> LOCATION: 7
<223> OTHER INFORMATION: Xaa = Ser or Ala
<220> FEATURE:
<221> NAME/KEY: VARIANT
<222> LOCATION: 8
<223> OTHER INFORMATION: Xaa = Ala or Val

<400> SEQUENCE: 174

Ala Pro Arg Trp Xaa Xaa Xaa Xaa
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or Gln
<220> FEATURE:
<221> NAME/KEY: VARIANT
<222> LOCATION: 3
<223> OTHER INFORMATION: Xaa = Ala or Gly
<220> FEATURE:
<221> NAME/KEY: VARIANT
<222> LOCATION: 4
<223> OTHER INFORMATION: Xaa = Ala or His
<220> FEATURE:
<221> NAME/KEY: VARIANT
<222> LOCATION: 5
<223> OTHER INFORMATION: Xaa = Ala or Thr
<220> FEATURE:
<221> NAME/KEY: VARIANT
<222> LOCATION: 6
<223> OTHER INFORMATION: Xaa = Ala or Leu
<220> FEATURE:
<221> NAME/KEY: VARIANT
<222> LOCATION: 7
<223> OTHER INFORMATION: Xaa = Ala or Pro
<220> FEATURE:
<221> NAME/KEY: VARIANT
<222> LOCATION: 8
<223> OTHER INFORMATION: Xaa = Ala or Pro

<400> SEQUENCE: 175
```

```
Gln Xaa Xaa Xaa Xaa Xaa Xaa Xaa Thr
1               5
```

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Thr, Ala, or Gln

<400> SEQUENCE: 176

```
Val Ile Asn Pro Gly Ser Gly Asp Xaa Tyr Tyr Ser Glu Lys Phe Lys
1               5                   10                  15
Gly
```

<210> SEQ ID NO 177
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Ser, Glu, or Gln

<400> SEQUENCE: 177

```
His Gly Thr Asn Leu Glu Xaa
1               5
```

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Val or Ala
<220> FEATURE:
<221> NAME/KEY: VARIANT
<222> LOCATION: 2
<223> OTHER INFORMATION: Xaa = His or Ala
<220> FEATURE:
<221> NAME/KEY: VARIANT
<222> LOCATION: 9
<223> OTHER INFORMATION: Xaa = Tyr or Ala

<400> SEQUENCE: 178

```
Xaa Xaa Tyr Ala Gln Phe Pro Tyr Xaa
1               5
```

<210> SEQ ID NO 179
<211> LENGTH: 107
<212> TYPE: PRT
<213> ORGANISM: Artificial Sequence
<220> FEATURE:
<223> OTHER INFORMATION: Synthetic Construct

<400> SEQUENCE: 179

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
            20                  25                  30
```

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Phe Leu Thr Ile Ser Asn Leu Glu Gln
65                  70                  75                  80

Glu Asp Val Ala Ala Tyr Phe Cys Gln Gln Gly His Thr Leu Pro Pro
                85                  90                  95

Thr Phe Gly Gly Gly Thr Lys Leu Glu Ile Lys
            100                 105

<210> SEQ ID NO 180
<211> LENGTH: 117
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Ser Trp Val Lys Gln Ser His Gly Lys Thr Leu Glu Trp Ile
        35                  40                  45

Gly Asp Met Tyr Pro Asp Asn Gly Asp Ser Ser Tyr Asn Gln Lys Phe
    50                  55                  60

Arg Glu Lys Val Thr Leu Thr Val Asp Lys Ser Ser Thr Thr Ala Tyr
65                  70                  75                  80

Met Glu Phe Arg Ser Leu Thr Ser Glu Asp Ser Ala Val Tyr Tyr Cys
                85                  90                  95

Val Leu Ala Pro Arg Trp Tyr Phe Ser Val Trp Gly Thr Gly Thr Thr
            100                 105                 110

Val Thr Val Ser Ser
        115

<210> SEQ ID NO 181
<211> LENGTH: 107
<212> TYPE: PRT
<213> ORGANISM: Artificial Sequence
<220> FEATURE:
<223> OTHER INFORMATION: Synthetic Construct

<400> SEQUENCE: 181

Asp Ile Leu Met Thr Gln Ser Pro Ser Ser Met Ser Val Ser Leu Gly
1               5                   10                  15

Asp Thr Val Ser Ile Thr Cys His Ala Ser Gln Asp Ile Ser Ser Tyr
            20                  25                  30

Ile Val Trp Leu Gln Gln Lys Pro Gly Lys Ser Phe Arg Gly Leu Ile
        35                  40                  45

Tyr His Gly Thr Asn Leu Glu Asp Gly Ile Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val His Tyr Ala Gln Phe Pro Tyr
                85                  90                  95

Thr Phe Gly Gly Gly Thr Lys Leu Glu Ile Lys

-continued

<210> SEQ ID NO 182
<211> LENGTH: 114
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Lys Val Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Arg Leu Asp Tyr Trp Gly Gln Gly Thr Thr Leu Thr Val
            100                 105                 110

Ser Ser

<210> SEQ ID NO 183
<211> LENGTH: 117
<212> TYPE: PRT
<213> ORGANISM: Artificial Sequence
<220> FEATURE:
<223> OTHER INFORMATION: Synthetic Construct

<400> SEQUENCE: 183

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 184
<211> LENGTH: 117
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 185
<211> LENGTH: 451
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 186
<211> LENGTH: 219
<212> TYPE: PRT
<213> ORGANISM: Artificial Sequence
<220> FEATURE:
<223> OTHER INFORMATION: Synthetic Construct

<400> SEQUENCE: 186

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 187
<211> LENGTH: 219
<212> TYPE: PRT
<213> ORGANISM: Artificial Sequence
<220> FEATURE:
<223> OTHER INFORMATION: Synthetic Construct

<400> SEQUENCE: 187

Asp Ile Gln Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 188
<211> LENGTH: 450
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Val Glu Ser Gly Gly Gly Leu Val His Pro Gly Gly
1               5                   10                  15

```
Ser Leu Arg Leu Ser Cys Ala Gly Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ser Ala Ile Gly Thr Gly Gly Thr Tyr Tyr Ala Asp Ser Val Met
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                 85                  90                  95

Arg Tyr Asp Asn Val Met Gly Leu Tyr Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
            435                 440                 445

Gly Lys
    450

<210> SEQ ID NO 189
<211> LENGTH: 214
<212> TYPE: PRT
<213> ORGANISM: Artificial Sequence
<220> FEATURE:
<223> OTHER INFORMATION: Synthetic Construct

<400> SEQUENCE: 189

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 190
<211> LENGTH: 118
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115

<210> SEQ ID NO 191
<211> LENGTH: 107
<212> TYPE: PRT
<213> ORGANISM: Artificial Sequence
<220> FEATURE:
<223> OTHER INFORMATION: Synthetic Construct

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 192
<211> LENGTH: 124
<212> TYPE: PRT
<213> ORGANISM: Artificial Sequence
<220> FEATURE:
<223> OTHER INFORMATION: Synthetic Construct

<400> SEQUENCE: 192

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120

```
<210> SEQ ID NO 193
<211> LENGTH: 106
<212> TYPE: PRT
<213> ORGANISM: Artificial Sequence
<220> FEATURE:
<223> OTHER INFORMATION: Synthetic Construct

<400> SEQUENCE: 193

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 194
<211> LENGTH: 122
<212> TYPE: PRT
<213> ORGANISM: Artificial Sequence
<220> FEATURE:
<223> OTHER INFORMATION: Synthetic Construct

<400> SEQUENCE: 194

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120

<210> SEQ ID NO 195
<211> LENGTH: 107
<212> TYPE: PRT
<213> ORGANISM: Artificial Sequence
<220> FEATURE:
<223> OTHER INFORMATION: Synthetic Construct

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Tyr Leu Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 196
<211> LENGTH: 120
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 197
<211> LENGTH: 111
<212> TYPE: PRT
<213> ORGANISM: Artificial Sequence
<220> FEATURE:
<223> OTHER INFORMATION: Synthetic Construct

<400> SEQUENCE: 197

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys

-continued

```
                100                 105                 110

<210> SEQ ID NO 198
<211> LENGTH: 469
<212> TYPE: PRT
<213> ORGANISM: Artificial Sequence
<220> FEATURE:
<223> OTHER INFORMATION: Synthetic Construct

<400> SEQUENCE: 198

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
                20                  25                  30

Pro Gly Gly Ser Met Lys Leu Ser Cys Ala Ala Ser Gly Phe Thr Phe
            35                  40                  45

Ser Asp Ala Trp Met Asp Trp Val Arg Gln Ser Pro Glu Lys Gly Leu
        50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Thr Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

355                 360                 365
Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 199
<211> LENGTH: 233
<212> TYPE: PRT
<213> ORGANISM: Artificial Sequence
<220> FEATURE:
<223> OTHER INFORMATION: Synthetic Construct

<400> SEQUENCE: 199

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

```
<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115

```
<210> SEQ ID NO 201
<211> LENGTH: 108
<212> TYPE: PRT
<213> ORGANISM: Artificial Sequence
<220> FEATURE:
<223> OTHER INFORMATION: Synthetic Construct

<400> SEQUENCE: 201
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

```
<210> SEQ ID NO 202
<211> LENGTH: 121
<212> TYPE: PRT
<213> ORGANISM: Artificial Sequence
<220> FEATURE:
<223> OTHER INFORMATION: Synthetic Construct

<400> SEQUENCE: 202
```

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

```
Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Thr Ala Tyr
 65                 70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
                100                 105                 110

Ala Gly Thr Thr Val Thr Val Ser Pro
                115                 120

<210> SEQ ID NO 203
<211> LENGTH: 108
<212> TYPE: PRT
<213> ORGANISM: Artificial Sequence
<220> FEATURE:
<223> OTHER INFORMATION: Synthetic Construct

<400> SEQUENCE: 203

Asp Ile Val Met Thr Gln Ser His Lys Phe Met Ser Thr Ser Leu Gly
 1               5                   10                  15

Asp Arg Val Ser Ile Thr Cys Lys Ala Ser Gln Asp Val Gly Ala Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
                100                 105

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Met
            35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
 65                 70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
```

Thr Leu Val Thr Val Ser Ser
            115

<210> SEQ ID NO 205
<211> LENGTH: 108
<212> TYPE: PRT
<213> ORGANISM: Artificial Sequence
<220> FEATURE:
<223> OTHER INFORMATION: Synthetic Construct

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic Construct

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 207
<211> LENGTH: 119
<212> TYPE: PRT
<213> ORGANISM: Artificial Sequence
<220> FEATURE:
<223> OTHER INFORMATION: Synthetic Construct

<400> SEQUENCE: 207

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115
```

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115
```

<210> SEQ ID NO 209
<211> LENGTH: 121
<212> TYPE: PRT
<213> ORGANISM: Artificial Sequence
<220> FEATURE:
<223> OTHER INFORMATION: Synthetic Construct

<400> SEQUENCE: 209

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
```

```
                65                  70                  75                  80
Met Glu Leu Ser Ser Leu Arg Ser Glu Asp Thr Ala Val Tyr Tyr Cys
                        85                  90                  95

Ala Arg Met Gly Tyr His Gly Pro His Leu Asp Phe Asp Val Trp Gly
                100                 105                 110

Gln Gly Thr Thr Val Thr Val Ser Ser
        115                 120

<210> SEQ ID NO 210
<211> LENGTH: 108
<212> TYPE: PRT
<213> ORGANISM: Artificial Sequence
<220> FEATURE:
<223> OTHER INFORMATION: Synthetic Construct

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
                100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
                100                 105

<210> SEQ ID NO 212
<211> LENGTH: 121
<212> TYPE: PRT
<213> ORGANISM: Artificial Sequence
<220> FEATURE:
```

<223> OTHER INFORMATION: Synthetic Construct

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 213
<211> LENGTH: 121
<212> TYPE: PRT
<213> ORGANISM: Artificial Sequence
<220> FEATURE:
<223> OTHER INFORMATION: Synthetic Construct

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 214
<211> LENGTH: 138
<212> TYPE: PRT
<213> ORGANISM: Artificial Sequence
<220> FEATURE:
<223> OTHER INFORMATION: Synthetic Construct

<400> SEQUENCE: 214

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe

```
                35                  40                  45
Ser Asp Ala Trp Met Asp Trp Val Arg Gln Ser Pro Glu Lys Gly Leu
 50                  55                  60

Glu Trp Val Ala Glu Ile Arg Ser Lys Ala Asn Asn His Ala Thr Tyr
 65                  70                  75                  80

Tyr Ala Glu Ser Val Asn Gly Arg Phe Thr Ile Ser Arg Asp Asp Ser
                 85                  90                  95

Lys Ser Ser Val Tyr Leu Gln Met Asn Ser Leu Arg Ala Glu Asp Thr
                100                 105                 110

Gly Ile Tyr Tyr Cys Thr Trp Gly Glu Val Phe Tyr Phe Asp Tyr Trp
                115                 120                 125

Gly Gln Gly Thr Thr Leu Thr Val Ser Ser
    130                 135

<210> SEQ ID NO 215
<211> LENGTH: 126
<212> TYPE: PRT
<213> ORGANISM: Artificial Sequence
<220> FEATURE:
<223> OTHER INFORMATION: Synthetic Construct

<400> SEQUENCE: 215

Met Arg Pro Ser Ile Gln Phe Leu Gly Leu Leu Leu Phe Trp Leu His
 1                5                  10                  15

Gly Ala Gln Cys Asp Ile Gln Met Thr Gln Ser Pro Ser Ser Leu Ser
                 20                  25                  30

Ala Ser Leu Gly Gly Lys Val Thr Ile Thr Cys Lys Ser Ser Gln Asp
             35                  40                  45

Ile Asn Lys Tyr Ile Ala Trp Tyr Gln His Lys Pro Gly Lys Gly Pro
 50                  55                  60

Arg Leu Leu Ile His Tyr Thr Ser Thr Leu Gln Pro Gly Ile Pro Ser
 65                  70                  75                  80

Arg Phe Ser Gly Ser Gly Ser Gly Arg Asp Tyr Ser Phe Ser Ile Ser
                 85                  90                  95

Asn Leu Glu Pro Glu Asp Ile Ala Thr Tyr Tyr Cys Leu Gln Tyr Asp
                100                 105                 110

Asn Leu Leu Thr Phe Gly Ala Gly Thr Lys Leu Glu Leu Lys
                115                 120                 125

<210> SEQ ID NO 216
<211> LENGTH: 17
<212> TYPE: PRT
<213> ORGANISM: Artificial Sequence
<220> FEATURE:
<223> OTHER INFORMATION: Synthetic Construct

<400> SEQUENCE: 216

Asp Met Tyr Pro Asp Ala Ala Ala Ser Tyr Asn Gln Lys Phe Arg
 1                5                  10                  15

Glu

<210> SEQ ID NO 217
<211> LENGTH: 8
<212> TYPE: PRT
<213> ORGANISM: Artificial Sequence
<220> FEATURE:
<223> OTHER INFORMATION: Synthetic Construct

<400> SEQUENCE: 217
```

```
Ala Pro Arg Trp Ala Ala Ala Ala
1               5
```

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

```
Gln Ala Ala Ala Ala Ala Ala Thr
1               5
```

<210> SEQ ID NO 219
<211> LENGTH: 19
<212> TYPE: PRT
<213> ORGANISM: Artificial Sequence
<220> FEATURE:
<223> OTHER INFORMATION: Synthetic Construct

<400> SEQUENCE: 219

```
Cys Asp Lys Thr His Thr Cys Pro Pro Cys Pro Ala Pro Glu Leu Leu
1               5                   10                  15

Gly Gly Pro
```

<210> SEQ ID NO 220
<211> LENGTH: 4
<212> TYPE: PRT
<213> ORGANISM: Artificial Sequence
<220> FEATURE:
<223> OTHER INFORMATION: Synthetic Construct

<400> SEQUENCE: 220

```
Gly Gly Gly Ser
1
```

<210> SEQ ID NO 221
<211> LENGTH: 4
<212> TYPE: PRT
<213> ORGANISM: Artificial Sequence
<220> FEATURE:
<223> OTHER INFORMATION: Synthetic Construct

<400> SEQUENCE: 221

```
Ser Gly Gly Gly
1
```

<210> SEQ ID NO 222
<211> LENGTH: 5
<212> TYPE: PRT
<213> ORGANISM: Artificial Sequence
<220> FEATURE:
<223> OTHER INFORMATION: Synthetic Construct

<400> SEQUENCE: 222

```
Gly Gly Gly Gly Ser
1               5
```

<210> SEQ ID NO 223
<211> LENGTH: 5
<212> TYPE: PRT
<213> ORGANISM: Artificial Sequence
<220> FEATURE:
<223> OTHER INFORMATION: Synthetic Construct

<400> SEQUENCE: 223

```
Ser Gly Gly Gly Gly
1               5

<210> SEQ ID NO 224
<211> LENGTH: 6
<212> TYPE: PRT
<213> ORGANISM: Artificial Sequence
<220> FEATURE:
<223> OTHER INFORMATION: Synthetic Construct

<400> SEQUENCE: 224

Gly Gly Gly Gly Gly Ser
1               5

<210> SEQ ID NO 225
<211> LENGTH: 6
<212> TYPE: PRT
<213> ORGANISM: Artificial Sequence
<220> FEATURE:
<223> OTHER INFORMATION: Synthetic Construct

<400> SEQUENCE: 225

Ser Gly Gly Gly Gly Gly
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Construct

<400> SEQUENCE: 226

Gly Gly Gly Gly Gly Gly Ser
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic Construct

<400> SEQUENCE: 227

Ser Gly Gly Gly Gly Gly Gly
1               5

<210> SEQ ID NO 228
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: can be present in repeat of at least 1 and
      up to 2, 3, 4, 5, 6, 7, 8, 9, 10, 15, or 20

<400> SEQUENCE: 228

Gly Gly Gly Gly Ser
1               5

<210> SEQ ID NO 229
<211> LENGTH: 5
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: can be present in repeat of at least 1 and
      up to 2, 3, 4, 5, 6, 7, 8, 9, 10, 15, or 20

<400> SEQUENCE: 229

Ser Gly Gly Gly Gly
1               5

<210> SEQ ID NO 230
<211> LENGTH: 447
<212> TYPE: PRT
<213> ORGANISM: Artificial Sequence
<220> FEATURE:
<223> OTHER INFORMATION: Synthetic Construct

<400> SEQUENCE: 230
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 231
<211> LENGTH: 214
<212> TYPE: PRT
<213> ORGANISM: Artificial Sequence
<220> FEATURE:
<223> OTHER INFORMATION: Synthetic Construct

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 232
<211> LENGTH: 444
<212> TYPE: PRT
<213> ORGANISM: Artificial Sequence
<220> FEATURE:
<223> OTHER INFORMATION: Synthetic Construct

<400> SEQUENCE: 232

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 233
<211> LENGTH: 214
<212> TYPE: PRT
<213> ORGANISM: Artificial Sequence
<220> FEATURE:
<223> OTHER INFORMATION: Synthetic Construct

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 234
<211> LENGTH: 220
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Gln Ser Gly Ala Glu Val Lys Lys Pro Gly Ala

```
                1               5                  10                 15
            Ser Val Lys Val Ser Cys Lys Ala Ser Gly Tyr Thr Phe Thr Asp Ser
                            20                  25                 30

Tyr Met Ser Trp Val Arg Gln Ala Pro Gly Gln Gly Leu Glu Trp Ile
                            35                  40                 45

Gly Asp Met Tyr Pro Asp Asn Gly Asp Ser Ser Tyr Asn Gln Lys Phe
                            50                  55                 60

Arg Glu Arg Val Thr Ile Thr Arg Asp Thr Ser Thr Ser Thr Ala Tyr
             65                 70                  75                 80

Leu Glu Leu Ser Ser Leu Arg Ser Glu Asp Thr Ala Val Tyr Tyr Cys
                            85                  90                 95

Val Leu Ala Pro Arg Trp Tyr Phe Ser Val Trp Gly Gln Gly Thr Leu
                           100                 105                110

Val Thr Val Ser Ser Ala Ser Thr Lys Gly Pro Ser Val Phe Pro Leu
                           115                 120                125

Ala Pro Ser Ser Lys Ser Thr Ser Gly Gly Thr Ala Ala Leu Gly Cys
                           130                 135                140

Leu Val Lys Asp Tyr Phe Pro Glu Pro Val Thr Val Ser Trp Asn Ser
            145                150                 155                160

Gly Ala Leu Thr Ser Gly Val His Thr Phe Pro Ala Val Leu Gln Ser
                           165                 170                175

Ser Gly Leu Tyr Ser Leu Ser Ser Val Val Thr Val Pro Ser Ser Ser
                           180                 185                190

Leu Gly Thr Gln Thr Tyr Ile Cys Asn Val Asn His Lys Pro Ser Asn
                           195                 200                205

Thr Lys Val Asp Lys Lys Val Glu Pro Lys Ser Cys
                           210                 215                220

<210> SEQ ID NO 235
<211> LENGTH: 217
<212> TYPE: PRT
<213> ORGANISM: Artificial Sequence
<220> FEATURE:
<223> OTHER INFORMATION: Synthetic Construct

<400> SEQUENCE: 235

Glu Val Gln Leu Val Gln Ser Gly Ala Glu Val Lys Lys Pro Gly Ala
             1               5                  10                 15

Ser Val Lys Val Ser Cys Lys Ala Ser Gly Tyr Ala Phe Thr Asn Tyr
                            20                  25                 30

Leu Ile Glu Trp Val Arg Gln Ala Pro Gly Gln Gly Leu Glu Trp Ile
                            35                  40                 45

Gly Val Ile Asn Pro Gly Ser Gly Asp Thr Tyr Tyr Ser Glu Lys Phe
                            50                  55                 60

Lys Gly Arg Val Thr Leu Thr Ala Asp Thr Ser Ser Thr Thr Ala Tyr
             65                 70                  75                 80

Leu Glu Leu Ser Ser Leu Arg Ser Glu Asp Thr Ala Val Tyr Tyr Cys
                            85                  90                 95

Ala Arg Asp Arg Leu Asp Tyr Trp Gly Gln Gly Thr Leu Val Thr Val
                           100                 105                110

Ser Ser Ala Ser Thr Lys Gly Pro Ser Val Phe Pro Leu Ala Pro Ser
                           115                 120                125

Ser Lys Ser Thr Ser Gly Gly Thr Ala Ala Leu Gly Cys Leu Val Lys
                           130                 135                140

Asp Tyr Phe Pro Glu Pro Val Thr Val Ser Trp Asn Ser Gly Ala Leu
```

```
                145                 150                 155                 160
        Thr Ser Gly Val His Thr Phe Pro Ala Val Leu Gln Ser Ser Gly Leu
                        165                 170                 175

Tyr Ser Leu Ser Ser Val Val Thr Val Pro Ser Ser Leu Gly Thr
                        180                 185                 190

Gln Thr Tyr Ile Cys Asn Val Asn His Lys Pro Ser Asn Thr Lys Val
                        195                 200                 205

Asp Lys Lys Val Glu Pro Lys Ser Cys
                        210                 215

<210> SEQ ID NO 236
<211> LENGTH: 214
<212> TYPE: PRT
<213> ORGANISM: Artificial Sequence
<220> FEATURE:
<223> OTHER INFORMATION: Synthetic Construct

<400> SEQUENCE: 236

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Ile Ser Asn Tyr
                        20                  25                  30

Leu Asn Trp Tyr Gln Gln Lys Pro Gly Lys Ala Pro Lys Leu Leu Ile
                        35                  40                  45

Tyr Tyr Thr Ser Arg Leu Arg Ser Gly Val Pro Ser Arg Phe Ser Gly
                        50                  55                  60

Ser Gly Ser Gly Thr Asp Phe Thr Leu Thr Ile Ser Ser Leu Gln Pro
        65                      70                  75                  80

Glu Asp Phe Ala Thr Tyr Tyr Cys Gln Gln Gly His Thr Leu Pro Pro
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Cys Val Asp Asn Ala Leu Gln Ser Gly Asn Ser Gln
        145                     150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 237
<211> LENGTH: 214
<212> TYPE: PRT
<213> ORGANISM: Artificial Sequence
<220> FEATURE:
<223> OTHER INFORMATION: Synthetic Construct

<400> SEQUENCE: 237

Asp Ile Gln Met Thr Gln Ser Pro Ser Ser Leu Ser Ala Ser Val Gly
        1               5                   10                  15
```

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 238
<211> LENGTH: 226
<212> TYPE: PRT
<213> ORGANISM: Artificial Sequence
<220> FEATURE:
<223> OTHER INFORMATION: Synthetic Construct

<400> SEQUENCE: 238

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

-continued

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
        180                 185                 190

Gln Thr Tyr Ile Cys Asn Val Asn His Lys Pro Ser Asn Thr Lys Val
    195                 200                 205

Asp Lys Lys Val Glu Pro Lys Ser Cys Asp Lys Thr His Thr Ser Pro
210                 215                 220

Pro Cys
225

<210> SEQ ID NO 239
<211> LENGTH: 229
<212> TYPE: PRT
<213> ORGANISM: Artificial Sequence
<220> FEATURE:
<223> OTHER INFORMATION: Synthetic Construct

<400> SEQUENCE: 239

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Ser Pro Pro Cys
225

<210> SEQ ID NO 240
<211> LENGTH: 571
<212> TYPE: PRT
<213> ORGANISM: Artificial Sequence
<220> FEATURE:
<223> OTHER INFORMATION: Synthetic Construct

<400> SEQUENCE: 240

-continued

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Ser
            20                  25                  30
Tyr Met Ser Trp Val Arg Gln Ala Pro Gly Gln Gly Leu Glu Trp Ile
        35                  40                  45
Gly Asp Met Tyr Pro Asp Asn Gly Asp Ser Ser Tyr Asn Gln Lys Phe
50                  55                  60
Arg Glu Arg Val Thr Ile Thr Arg Asp Thr Ser Thr Ser Thr Ala Tyr
65                  70                  75                  80
Leu Glu Leu Ser Ser Leu Arg Ser Glu Asp Thr Ala Val Tyr Tyr Cys
                85                  90                  95
Val Leu Ala Pro Arg Trp Tyr Phe Ser Val Trp Gly Gln Gly Thr Leu
            100                 105                 110
Val Thr Val Ser Ser Gly Gly Gly Gly Ser Gly Gly Gly Gly Ser Glu
        115                 120                 125
Val Gln Leu Val Gln Ser Gly Ala Glu Val Lys Lys Pro Gly Ala Ser
130                 135                 140
Val Lys Val Ser Cys Lys Ala Ser Gly Tyr Ala Phe Thr Asn Tyr Leu
145                 150                 155                 160
Ile Glu Trp Val Arg Gln Ala Pro Gly Gln Gly Leu Glu Trp Ile Gly
                165                 170                 175
Val Ile Asn Pro Gly Ser Gly Asp Thr Tyr Tyr Ser Glu Lys Phe Lys
            180                 185                 190
Gly Arg Val Thr Leu Thr Ala Asp Thr Ser Thr Ser Thr Ala Tyr Leu
        195                 200                 205
Glu Leu Ser Ser Leu Arg Ser Glu Asp Thr Ala Val Tyr Tyr Cys Ala
210                 215                 220
Arg Asp Arg Leu Asp Tyr Trp Gly Gln Gly Thr Leu Val Thr Val Ser
225                 230                 235                 240
Ser Ala Ser Thr Lys Gly Pro Ser Val Phe Pro Leu Ala Pro Ser Ser
                245                 250                 255
Lys Ser Thr Ser Gly Gly Thr Ala Ala Leu Gly Cys Leu Val Lys Asp
            260                 265                 270
Tyr Phe Pro Glu Pro Val Thr Val Ser Trp Asn Ser Gly Ala Leu Thr
        275                 280                 285
Ser Gly Val His Thr Phe Pro Ala Val Leu Gln Ser Ser Gly Leu Tyr
290                 295                 300
Ser Leu Ser Ser Val Val Thr Val Pro Ser Ser Ser Leu Gly Thr Gln
305                 310                 315                 320
Thr Tyr Ile Cys Asn Val Asn His Lys Pro Ser Asn Thr Lys Val Asp
                325                 330                 335
Lys Lys Val Glu Pro Lys Ser Cys Asp Lys Thr His Thr Cys Pro Pro
            340                 345                 350
Cys Pro Ala Pro Glu Leu Leu Gly Gly Pro Ser Val Phe Leu Phe Pro
        355                 360                 365
Pro Lys Pro Lys Asp Thr Leu Met Ile Ser Arg Thr Pro Glu Val Thr
370                 375                 380
Cys Val Val Val Asp Val Ser His Glu Asp Pro Glu Val Lys Phe Asn
385                 390                 395                 400
Trp Tyr Val Asp Gly Val Glu Val His Asn Ala Lys Thr Lys Pro Arg
                405                 410                 415
```

```
Glu Glu Gln Tyr Asn Ser Thr Tyr Arg Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 241
<211> LENGTH: 331
<212> TYPE: PRT
<213> ORGANISM: Artificial Sequence
<220> FEATURE:
<223> OTHER INFORMATION: Synthetic Construct

<400> SEQUENCE: 241

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys His Ala Ser Gln
    130                 135                 140

Asp Ile Ser Ser Tyr Ile Val Trp Tyr Gln Gln Lys Pro Gly Lys Ser
145                 150                 155                 160

Phe Lys Gly Leu Ile Tyr His Gly Thr Asn Leu Glu Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Val His Tyr
        195                 200                 205
```

```
Ala Gln Phe Pro Tyr Thr Phe Gly Gln Gly Thr Lys Val Glu Ile Lys
210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
                275                 280                 285

Thr Tyr Ser Leu Ser Ser Thr Leu Thr Leu Ser Lys Ala Asp Tyr Glu
290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 242
<211> LENGTH: 571
<212> TYPE: PRT
<213> ORGANISM: Artificial Sequence
<220> FEATURE:
<223> OTHER INFORMATION: Synthetic Construct

<400> SEQUENCE: 242

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser Gly Gly Gly Gly Ser Gly Gly Gly Gly Ser Glu Val Gln Leu
            115                 120                 125

Val Gln Ser Gly Ala Glu Val Lys Lys Pro Gly Ala Ser Val Lys Val
        130                 135                 140

Ser Cys Lys Ala Ser Gly Tyr Thr Phe Thr Asp Ser Tyr Met Ser Trp
145                 150                 155                 160

Val Arg Gln Ala Pro Gly Gln Gly Leu Glu Trp Ile Gly Asp Met Tyr
                165                 170                 175

Pro Asp Asn Gly Asp Ser Ser Tyr Asn Gln Lys Phe Arg Glu Arg Val
                180                 185                 190

Thr Ile Thr Arg Asp Thr Ser Thr Ser Thr Ala Tyr Leu Glu Leu Ser
            195                 200                 205

Ser Leu Arg Ser Glu Asp Thr Ala Val Tyr Tyr Cys Val Leu Ala Pro
        210                 215                 220

Arg Trp Tyr Phe Ser Val Trp Gly Gln Gly Thr Leu Val Thr Val Ser
225                 230                 235                 240
```

```
Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 243
<211> LENGTH: 331
<212> TYPE: PRT
<213> ORGANISM: Artificial Sequence
<220> FEATURE:
<223> OTHER INFORMATION: Synthetic Construct

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30
```

Ile Val Trp Tyr Gln Gln Lys Pro Gly Lys Ser Phe Lys Gly Leu Ile
                35                  40                  45

Tyr His Gly Thr Asn Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Asp Ile Gln Met Thr Gln Ser Pro Ser Ser Leu
                115                 120                 125

Ser Ala Ser Val Gly Asp Arg Val Thr Ile Thr Cys Arg Ala Ser Gln
130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Arg Leu Arg Ser Gly Val Pro
                165                 170                 175

Ser Arg Phe Ser Gly Ser Gly Ser Gly Thr Asp Phe Thr Leu Thr Ile
                180                 185                 190

Ser Ser Leu Gln Pro Glu Asp Phe Ala Thr Tyr Tyr Cys Gln Gln Gly
                195                 200                 205

His Thr Leu Pro Pro Thr Phe Gly Gln Gly Thr Lys Val Glu Ile Lys
                210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
                275                 280                 285

Thr Tyr Ser Leu Ser Ser Thr Leu Thr Leu Ser Lys Ala Asp Tyr Glu
                290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 244
<211> LENGTH: 675
<212> TYPE: PRT
<213> ORGANISM: Artificial Sequence
<220> FEATURE:
<223> OTHER INFORMATION: Synthetic Construct

<400> SEQUENCE: 244

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Lys Ala Pro Gly Gln Gly Leu Glu Trp Ile
                35                  40                  45

Gly Asp Met Tyr Pro Asp Asn Gly Asp Ser Ser Tyr Asn Gln Lys Phe
 50                  55                  60

```
Arg Glu Arg Val Thr Ile Thr Arg Asp Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Glu Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Gly Gly Gly Gly Ser Gly Gly Glu Val Gln Leu Val Gln Ser Gly
225                 230                 235                 240

Ala Glu Val Lys Lys Pro Gly Ala Ser Val Lys Val Ser Cys Lys Ala
                245                 250                 255

Ser Gly Tyr Ala Phe Thr Asn Tyr Leu Ile Glu Trp Val Arg Glu Ala
            260                 265                 270

Pro Gly Gln Gly Leu Glu Trp Ile Gly Val Ile Asn Pro Gly Ser Gly
        275                 280                 285

Asp Thr Tyr Tyr Ser Glu Lys Phe Lys Gly Arg Val Thr Leu Thr Ala
    290                 295                 300

Asp Thr Ser Thr Ser Thr Ala Tyr Leu Glu Leu Ser Ser Leu Arg Ser
305                 310                 315                 320

Glu Asp Thr Ala Val Tyr Tyr Cys Ala Arg Asp Arg Leu Asp Tyr Trp
                325                 330                 335

Gly Gln Gly Thr Leu Val Thr Val Ser Ser Ala Ser Thr Lys Gly Pro
            340                 345                 350

Ser Val Phe Pro Leu Ala Pro Ser Ser Lys Ser Thr Ser Gly Gly Thr
        355                 360                 365

Ala Ala Leu Gly Cys Leu Val Lys Asp Tyr Phe Pro Glu Pro Val Thr
    370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Lys Val Glu Pro Lys Ser
        435                 440                 445

Cys Asp Lys Thr His Thr Cys Pro Pro Cys Pro Ala Pro Glu Leu Leu
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
```

485                 490                 495
His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
            515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
        610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly
        675

<210> SEQ ID NO 245
<211> LENGTH: 214
<212> TYPE: PRT
<213> ORGANISM: Artificial Sequence
<220> FEATURE:
<223> OTHER INFORMATION: Synthetic Construct

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Glu Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Lys Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser 165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 246
<211> LENGTH: 214
<212> TYPE: PRT
<213> ORGANISM: Artificial Sequence
<220> FEATURE:
<223> OTHER INFORMATION: Synthetic Construct

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Lys Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Glu Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 247
<211> LENGTH: 675
<212> TYPE: PRT
<213> ORGANISM: Artificial Sequence
<220> FEATURE:
<223> OTHER INFORMATION: Synthetic Construct

<400> SEQUENCE: 247

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

```
Leu Ile Glu Trp Val Arg Lys Ala Pro Gly Gln Gly Leu Glu Trp Ile
         35                  40                  45

Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
             100                 105                 110

Ser Ser Ala Ser Thr Lys Gly Pro Ser Val Phe Pro Leu Ala Pro Ser
         115                 120                 125

Ser Lys Ser Thr Ser Gly Gly Thr Ala Ala Leu Gly Cys Leu Val Lys
     130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                 165                 170                 175

Tyr Ser Leu Glu Ser Val Val Thr Val Pro Ser Ser Ser Leu Gly Thr
             180                 185                 190

Gln Thr Tyr Ile Cys Asn Val Asn His Lys Pro Ser Asn Thr Lys Val
         195                 200                 205

Asp Lys Lys Val Glu Pro Lys Ser Cys Asp Lys Thr His Thr Gly Gly
     210                 215                 220

Gly Gly Ser Gly Gly Glu Val Gln Leu Val Gln Ser Gly Ala Glu Val
225                 230                 235                 240

Lys Lys Pro Gly Ala Ser Val Lys Val Ser Cys Lys Ala Ser Gly Tyr
                 245                 250                 255

Thr Phe Thr Asp Ser Tyr Met Ser Trp Val Arg Glu Ala Pro Gly Gln
             260                 265                 270

Gly Leu Glu Trp Ile Gly Asp Met Tyr Pro Asn Asn Gly Asp Ser Ser
         275                 280                 285

Tyr Asn Gln Lys Phe Arg Glu Arg Val Thr Ile Thr Arg Asp Thr Ser
     290                 295                 300

Thr Ser Thr Ala Tyr Leu Glu Leu Ser Ser Leu Arg Ser Glu Asp Thr
305                 310                 315                 320

Ala Val Tyr Tyr Cys Val Leu Ala Pro Arg Trp Tyr Phe Ser Val Trp
                 325                 330                 335

Gly Gln Gly Thr Leu Val Thr Val Ser Ser Ala Ser Thr Lys Gly Pro
             340                 345                 350

Ser Val Phe Pro Leu Ala Pro Ser Ser Lys Ser Thr Ser Gly Gly Thr
         355                 360                 365

Ala Ala Leu Gly Cys Leu Val Lys Asp Tyr Phe Pro Glu Pro Val Thr
     370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                 405                 410                 415

Val Pro Ser Ser Ser Leu Gly Thr Gln Thr Tyr Ile Cys Asn Val Asn
             420                 425                 430

His Lys Pro Ser Asn Thr Lys Val Asp Lys Lys Val Glu Pro Lys Ser
         435                 440                 445

Cys Asp Lys Thr His Thr Cys Pro Pro Cys Pro Ala Pro Glu Leu Leu
```

```
                450             455             460
Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
                515                 520                 525

Tyr Arg Val Val Ser Val Leu Thr Val Leu His Gln Asp Trp Leu Asn
                530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
                580                 585                 590

Ser Leu Thr Cys Leu Val Lys Gly Phe Tyr Pro Ser Asp Ile Ala Val
                595                 600                 605

Glu Trp Glu Ser Asn Gly Gln Pro Glu Asn Asn Tyr Lys Thr Thr Pro
                610                 615                 620

Pro Val Leu Asp Ser Asp Gly Ser Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro Gly
    675

<210> SEQ ID NO 248
<211> LENGTH: 214
<212> TYPE: PRT
<213> ORGANISM: Artificial Sequence
<220> FEATURE:
<223> OTHER INFORMATION: Synthetic Construct

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Glu Lys Pro Gly Lys Ser Phe Lys Gly Leu Ile
            35                  40                  45

Tyr His Gly Thr Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Lys Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 249
<211> LENGTH: 214
<212> TYPE: PRT
<213> ORGANISM: Artificial Sequence
<220> FEATURE:
<223> OTHER INFORMATION: Synthetic Construct

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Lys Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Glu Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 250
<211> LENGTH: 567
<212> TYPE: PRT
<213> ORGANISM: Artificial Sequence
<220> FEATURE:
<223> OTHER INFORMATION: Synthetic Construct

<400> SEQUENCE: 250
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Gly Gly Gly Gly Ser Gly Glu Val Gln Leu Val Gln Ser Gly
            115                 120                 125

Ala Glu Val Lys Lys Pro Gly Ala Ser Val Lys Val Ser Cys Lys Ala
            130                 135                 140

Ser Gly Tyr Thr Phe Thr Asp Ser Tyr Met Ser Trp Val Arg Gln Ala
145                 150                 155                 160

Pro Gly Gln Gly Leu Glu Trp Ile Gly Asp Met Tyr Pro Asp Asn Gly
                165                 170                 175

Asp Ser Ser Tyr Asn Gln Lys Phe Arg Glu Arg Val Thr Ile Thr Arg
            180                 185                 190

Asp Thr Ser Thr Ser Thr Ala Tyr Leu Glu Leu Ser Ser Leu Arg Ser
        195                 200                 205

Glu Asp Thr Ala Val Tyr Tyr Cys Val Leu Ala Pro Arg Trp Tyr Phe
    210                 215                 220

Ser Val Trp Gly Gln Gly Thr Leu Val Thr Val Ser Ser Ala Ser Thr
225                 230                 235                 240

Lys Gly Pro Ser Val Phe Pro Leu Ala Pro Ser Ser Lys Ser Thr Ser
                245                 250                 255

Gly Gly Thr Ala Ala Leu Gly Cys Leu Val Lys Asp Tyr Phe Pro Glu
            260                 265                 270

Pro Val Thr Val Ser Trp Asn Ser Gly Ala Leu Thr Ser Gly Val His
        275                 280                 285

Thr Phe Pro Ala Val Leu Gln Ser Ser Gly Leu Tyr Ser Leu Ser Ser
    290                 295                 300

Val Val Thr Val Pro Ser Ser Ser Leu Gly Thr Gln Thr Tyr Ile Cys
305                 310                 315                 320

Asn Val Asn His Lys Pro Ser Asn Thr Lys Val Asp Lys Lys Val Glu
                325                 330                 335

Pro Lys Ser Cys Asp Lys Thr His Thr Cys Pro Pro Cys Pro Ala Pro
            340                 345                 350

Glu Leu Leu Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
```

```
                420             425              430
Trp Leu Asn Gly Lys Glu Tyr Lys Cys Lys Val Ser Asn Lys Ala Leu
            435                 440             445
Pro Ala Pro Ile Glu Lys Thr Ile Ser Lys Ala Lys Gly Gln Pro Arg
        450                 455             460
Glu Pro Gln Val Tyr Thr Leu Pro Pro Ser Arg Glu Glu Met Thr Lys
465                 470             475                 480
Asn Gln Val Ser Leu Thr Cys Leu Val Lys Gly Phe Tyr Pro Ser Asp
                485             490                 495
Ile Ala Val Glu Trp Glu Ser Asn Gly Gln Pro Glu Asn Asn Tyr Lys
            500             505                 510
Thr Thr Pro Pro Val Leu Asp Ser Asp Gly Ser Phe Phe Leu Tyr Ser
        515                 520             525
Lys Leu Thr Val Asp Lys Ser Arg Trp Gln Gln Gly Asn Val Phe Ser
    530                 535             540
Cys Ser Val Met His Glu Ala Leu His Asn His Tyr Thr Gln Lys Ser
545                 550             555                 560
Leu Ser Leu Ser Pro Gly Lys
                565

<210> SEQ ID NO 251
<211> LENGTH: 326
<212> TYPE: PRT
<213> ORGANISM: Artificial Sequence
<220> FEATURE:
<223> OTHER INFORMATION: Synthetic Construct

<400> SEQUENCE: 251

Asp Ile Gln Met Thr Gln Ser Pro Ser Ser Leu Ser Ala Ser Val Gly
1               5                  10                  15
Asp Arg Val Thr Ile Thr Cys His Ala Ser Gln Asp Ile Ser Ser Tyr
            20                  25                  30
Ile Val Trp Tyr Gln Gln Lys Pro Gly Lys Ser Phe Lys Gly Leu Ile
        35                  40                  45
Tyr His Gly Thr Asn Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Val His Tyr Ala Gln Phe Pro Tyr
                85                  90                  95
Thr Phe Gly Gln Gly Thr Lys Val Glu Ile Lys Gly Gly Ser Gly Gly
            100                 105                 110
Asp Ile Gln Met Thr Gln Ser Pro Ser Ser Leu Ser Ala Ser Val Gly
        115                 120                 125
Asp Arg Val Thr Ile Thr Cys Arg Ala Ser Gln Asp Ile Ser Asn Tyr
    130                 135                 140
Leu Asn Trp Tyr Gln Gln Lys Pro Gly Lys Ala Pro Lys Leu Leu Ile
145                 150                 155                 160
Tyr Tyr Thr Ser Arg Leu Arg Ser Gly Val Pro Ser Arg Phe Ser Gly
                165                 170                 175
Ser Gly Ser Gly Thr Asp Phe Thr Leu Thr Ile Ser Ser Leu Gln Pro
            180                 185                 190
Glu Asp Phe Ala Thr Tyr Tyr Cys Gln Gln Gly His Thr Leu Pro Pro
        195                 200                 205
Thr Phe Gly Gln Gly Thr Lys Val Glu Ile Lys Arg Thr Val Ala Ala
```

```
            210                 215                 220
Pro Ser Val Phe Ile Phe Pro Pro Ser Asp Glu Gln Leu Lys Ser Gly
225                 230                 235                 240

Thr Ala Ser Val Val Cys Leu Leu Asn Asn Phe Tyr Pro Arg Glu Ala
                245                 250                 255

Lys Val Gln Trp Lys Val Asp Asn Ala Leu Gln Ser Gly Asn Ser Gln
                260                 265                 270

Glu Ser Val Thr Glu Gln Asp Ser Lys Asp Ser Thr Tyr Ser Leu Ser
            275                 280                 285

Ser Thr Leu Thr Leu Ser Lys Ala Asp Tyr Glu Lys His Lys Val Tyr
        290                 295                 300

Ala Cys Glu Val Thr His Gln Gly Leu Ser Ser Pro Val Thr Lys Ser
305                 310                 315                 320

Phe Asn Arg Gly Glu Cys
                325
```

<210> SEQ ID NO 252
<211> LENGTH: 575
<212> TYPE: PRT
<213> ORGANISM: Artificial Sequence
<220> FEATURE:
<223> OTHER INFORMATION: Synthetic Construct

<400> SEQUENCE: 252

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser Gly Gly Gly Gly Ser Gly Gly Gly Gly Ser Gly Gly Gly Gly
            115                 120                 125

Glu Val Gln Leu Val Gln Ser Gly Ala Glu Val Lys Lys Pro Gly Ala
        130                 135                 140

Ser Val Lys Val Ser Cys Lys Ala Ser Gly Tyr Thr Phe Thr Asp Ser
145                 150                 155                 160

Tyr Met Ser Trp Val Arg Gln Ala Pro Gly Gln Gly Leu Glu Trp Ile
                165                 170                 175

Gly Asp Met Tyr Pro Asp Asn Gly Asp Ser Ser Tyr Asn Gln Lys Phe
                180                 185                 190

Arg Glu Arg Val Thr Ile Thr Arg Asp Thr Ser Thr Ser Thr Ala Tyr
            195                 200                 205

Leu Glu Leu Ser Ser Leu Arg Ser Glu Asp Thr Ala Val Tyr Tyr Cys
        210                 215                 220

Val Leu Ala Pro Arg Trp Tyr Phe Ser Val Trp Gly Gln Gly Thr Leu
225                 230                 235                 240

Val Thr Val Ser Ser Ala Ser Thr Lys Gly Pro Ser Val Phe Pro Leu
```

245                 250                 255
Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val Glu Pro Lys Ser Cys Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 253
<211> LENGTH: 334
<212> TYPE: PRT
<213> ORGANISM: Artificial Sequence
<220> FEATURE:
<223> OTHER INFORMATION: Synthetic Construct

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile

```
            35                  40                  45
Tyr His Gly Thr Asn Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys Gly Gly Ser Gly Gly
            100                 105                 110

Gly Gly Ser Gly Gly Gly Gly Ser Asp Ile Gln Met Thr Gln Ser Pro
            115                 120                 125

Ser Ser Leu Ser Ala Ser Val Gly Asp Arg Val Thr Ile Thr Cys Arg
130                 135                 140

Ala Ser Gln Asp Ile Ser Asn Tyr Leu Asn Trp Tyr Gln Gln Lys Pro
145                 150                 155                 160

Gly Lys Ala Pro Lys Leu Leu Ile Tyr Tyr Thr Ser Arg Leu Arg Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
            195                 200                 205

Gln Gln Gly His Thr Leu Pro Pro Thr Phe Gly Gln Gly Thr Lys Val
210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
            275                 280                 285

Lys Asp Ser Thr Tyr Ser Leu Ser Ser Thr Leu Thr Leu Ser Lys Ala
290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 254
<211> LENGTH: 567
<212> TYPE: PRT
<213> ORGANISM: Artificial Sequence
<220> FEATURE:
<223> OTHER INFORMATION: Synthetic Construct

<400> SEQUENCE: 254

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Thr Ser Thr Ala Tyr
```

```
                65                  70                  75                  80
Leu Glu Leu Ser Ser Leu Arg Ser Glu Asp Thr Ala Val Tyr Tyr Cys
                        85                  90                  95

Ala Arg Asp Arg Leu Asp Tyr Trp Gly Gln Gly Thr Leu Val Thr Val
                100                 105                 110

Ser Ser Ala Ser Thr Lys Gly Pro Glu Val Gln Leu Val Gln Ser Gly
                115                 120                 125

Ala Glu Val Lys Lys Pro Gly Ala Ser Val Lys Val Ser Cys Lys Ala
130                 135                 140

Ser Gly Tyr Thr Phe Thr Asp Ser Tyr Met Ser Trp Val Arg Gln Ala
145                 150                 155                 160

Pro Gly Gln Gly Leu Glu Trp Ile Gly Asp Met Tyr Pro Asp Asn Gly
                165                 170                 175

Asp Ser Ser Tyr Asn Gln Lys Phe Arg Glu Arg Val Thr Ile Thr Arg
                180                 185                 190

Asp Thr Ser Thr Ser Thr Ala Tyr Leu Glu Leu Ser Ser Leu Arg Ser
                195                 200                 205

Glu Asp Thr Ala Val Tyr Tyr Cys Val Leu Ala Pro Arg Trp Tyr Phe
    210                 215                 220

Ser Val Trp Gly Gln Gly Thr Leu Val Thr Val Ser Ser Ala Ser Thr
225                 230                 235                 240

Lys Gly Pro Ser Val Phe Pro Leu Ala Pro Ser Ser Lys Ser Thr Ser
                245                 250                 255

Gly Gly Thr Ala Ala Leu Gly Cys Leu Val Lys Asp Tyr Phe Pro Glu
                260                 265                 270

Pro Val Thr Val Ser Trp Asn Ser Gly Ala Leu Thr Ser Gly Val His
                275                 280                 285

Thr Phe Pro Ala Val Leu Gln Ser Ser Gly Leu Tyr Ser Leu Ser Ser
                290                 295                 300

Val Val Thr Val Pro Ser Ser Ser Leu Gly Thr Gln Thr Tyr Ile Cys
305                 310                 315                 320

Asn Val Asn His Lys Pro Ser Asn Thr Lys Val Asp Lys Lys Val Glu
                325                 330                 335

Pro Lys Ser Cys Asp Lys Thr His Thr Cys Pro Pro Cys Pro Ala Pro
                340                 345                 350

Glu Leu Leu Gly Gly Pro Ser Val Phe Leu Phe Pro Pro Lys Pro Lys
                355                 360                 365

Asp Thr Leu Met Ile Ser Arg Thr Pro Glu Val Thr Cys Val Val Val
                370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
                420                 425                 430

Trp Leu Asn Gly Lys Glu Tyr Lys Cys Lys Val Ser Asn Lys Ala Leu
                435                 440                 445

Pro Ala Pro Ile Glu Lys Thr Ile Ser Lys Ala Lys Gly Gln Pro Arg
                450                 455                 460

Glu Pro Gln Val Tyr Thr Leu Pro Pro Ser Arg Glu Glu Met Thr Lys
465                 470                 475                 480

Asn Gln Val Ser Leu Thr Cys Leu Val Lys Gly Phe Tyr Pro Ser Asp
                485                 490                 495
```

```
Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
            515                 520                 525

Lys Leu Thr Val Asp Lys Ser Arg Trp Gln Gln Gly Asn Val Phe Ser
            530                 535                 540

Cys Ser Val Met His Glu Ala Leu His Asn His Tyr Thr Gln Lys Ser
545                 550                 555                 560

Leu Ser Leu Ser Pro Gly Lys
                565

<210> SEQ ID NO 255
<211> LENGTH: 327
<212> TYPE: PRT
<213> ORGANISM: Artificial Sequence
<220> FEATURE:
<223> OTHER INFORMATION: Synthetic Construct

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Lys Pro Gly Lys Ser Phe Lys Gly Leu Ile
            35                  40                  45

Tyr His Gly Thr Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Arg Thr Val Ala Ala
            100                 105                 110

Pro Asp Ile Gln Met Thr Gln Ser Pro Ser Ser Leu Ser Ala Ser Val
            115                 120                 125

Gly Asp Arg Val Thr Ile Thr Cys Arg Ala Ser Gln Asp Ile Ser Asn
        130                 135                 140

Tyr Leu Asn Trp Tyr Gln Gln Lys Pro Gly Lys Ala Pro Lys Leu Leu
145                 150                 155                 160

Ile Tyr Tyr Thr Ser Arg Leu Arg Ser Gly Val Pro Ser Arg Phe Ser
                165                 170                 175

Gly Ser Gly Ser Gly Thr Asp Phe Thr Leu Thr Ile Ser Ser Leu Gln
            180                 185                 190

Pro Glu Asp Phe Ala Thr Tyr Tyr Cys Gln Gln Gly His Thr Leu Pro
            195                 200                 205

Pro Thr Phe Gly Gln Gly Thr Lys Val Glu Ile Lys Arg Thr Val Ala
        210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
            260                 265                 270

Gln Glu Ser Val Thr Glu Gln Asp Ser Lys Asp Ser Thr Tyr Ser Leu
            275                 280                 285
```

Ser Ser Thr Leu Thr Leu Ser Lys Ala Asp Tyr Glu Lys His Lys Val
    290                 295                 300

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 256
<211> LENGTH: 574
<212> TYPE: PRT
<213> ORGANISM: Artificial Sequence
<220> FEATURE:
<223> OTHER INFORMATION: Synthetic Construct

<400> SEQUENCE: 256

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Ala Ser Thr Lys Gly Pro Ser Val Phe Pro Leu Ala Pro Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Asp Ser Tyr
145                 150                 155                 160

Met Ser Trp Val Arg Gln Ala Pro Gly Gln Gly Leu Glu Trp Ile Gly
                165                 170                 175

Asp Met Tyr Pro Asp Asn Gly Asp Ser Ser Tyr Asn Gln Lys Phe Arg
            180                 185                 190

Glu Arg Val Thr Ile Thr Arg Asp Thr Ser Thr Ser Thr Ala Tyr Leu
        195                 200                 205

Glu Leu Ser Ser Leu Arg Ser Glu Asp Thr Ala Val Tyr Tyr Cys Val
    210                 215                 220

Leu Ala Pro Arg Trp Tyr Phe Ser Val Trp Gly Gln Gly Thr Leu Val
225                 230                 235                 240

Thr Val Ser Ser Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Lys Val Glu Pro Lys Ser Cys Asp Lys Thr His Thr
        340                 345                 350

Cys Pro Pro Cys Pro Ala Pro Glu Leu Leu Gly Gly Pro Ser Val Phe
            355                 360                 365

Leu Phe Pro Pro Lys Pro Lys Asp Thr Leu Met Ile Ser Arg Thr Pro
370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
            405                 410                 415

Lys Pro Arg Glu Glu Gln Tyr Asn Ser Thr Tyr Arg Val Val Ser Val
        420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
        450                 455                 460

Lys Ala Lys Gly Gln Pro Arg Glu Pro Gln Val Tyr Thr Leu Pro Pro
465                 470                 475                 480

Ser Arg Glu Glu Met Thr Lys Asn Gln Val Ser Leu Thr Cys Leu Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Lys
            565                 570

<210> SEQ ID NO 257
<211> LENGTH: 334
<212> TYPE: PRT
<213> ORGANISM: Artificial Sequence
<220> FEATURE:
<223> OTHER INFORMATION: Synthetic Construct

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
            85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Asp Ile Gln Met Thr Gln Ser Pro
            115                 120                 125

Ser Ser Leu Ser Ala Ser Val Gly Asp Arg Val Thr Ile Thr Cys Arg
        130                 135                 140

Ala Ser Gln Asp Ile Ser Asn Tyr Leu Asn Trp Tyr Gln Gln Lys Pro
145                 150                 155                 160

Gly Lys Ala Pro Lys Leu Leu Ile Tyr Tyr Thr Ser Arg Leu Arg Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Gly His Thr Leu Pro Pro Thr Phe Gly Gln Gly Thr Lys Val
        210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
        290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 258
<211> LENGTH: 571
<212> TYPE: PRT
<213> ORGANISM: Artificial Sequence
<220> FEATURE:
<223> OTHER INFORMATION: Synthetic Construct

<400> SEQUENCE: 258

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Gly Gly Gly Gly Ser Gly Gly Gly Gly Ser Glu Val Gln Leu
        115                 120                 125

Val Gln Ser Gly Ala Glu Val Lys Lys Pro Gly Ala Ser Val Lys Val
        130                 135                 140
```

```
Ser Cys Lys Ala Ser Gly Tyr Thr Phe Thr Asp Ser Tyr Ile Ser Trp
145                 150                 155                 160

Val Arg Gln Ala Pro Gly Gln Gly Leu Glu Trp Ile Gly Asp Met Tyr
            165                 170                 175

Pro Asp Asn Gly Asp Ser Ser Tyr Asn Gln Lys Phe Arg Glu Arg Val
        180                 185                 190

Thr Ile Thr Arg Asp Thr Ser Thr Ala Tyr Leu Glu Leu Ser
        195                 200                 205

Ser Leu Arg Ser Glu Asp Thr Ala Val Tyr Tyr Cys Val Leu Ala Pro
        210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
            245                 250                 255

Lys Ser Thr Ser Gly Gly Thr Ala Ala Leu Gly Cys Leu Val Lys Asp
        260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
        290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
            325                 330                 335

Lys Lys Val Glu Pro Lys Ser Cys Asp Lys Thr His Thr Cys Pro Pro
        340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
            405                 410                 415

Glu Glu Gln Tyr Asn Ser Thr Tyr Arg Val Val Ser Val Leu Thr Val
        420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
        450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
        500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
        530                 535                 540

Asn Val Phe Ser Cys Ser Val Met His Glu Ala Leu His Asn His Tyr
545                 550                 555                 560
```

Thr Gln Lys Ser Leu Ser Leu Ser Pro Gly Lys
            565                 570

<210> SEQ ID NO 259
<211> LENGTH: 331
<212> TYPE: PRT
<213> ORGANISM: Artificial Sequence
<220> FEATURE:
<223> OTHER INFORMATION: Synthetic Construct

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Tyr Leu Arg Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Gly
        195                 200                 205

His Thr Leu Pro Pro Thr Phe Gly Gln Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 260
<211> LENGTH: 571

<212> TYPE: PRT
<213> ORGANISM: Artificial Sequence
<220> FEATURE:
<223> OTHER INFORMATION: Synthetic Construct

<400> SEQUENCE: 260

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ile Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

Leu Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Gly Gly Gly Gly Ser Gly Gly Gly Gly Ser Glu Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Ser Tyr Met Ser Trp
145                 150                 155                 160

Val Arg Gln Ala Pro Gly Gln Gly Leu Glu Trp Ile Gly Asp Met Tyr
                165                 170                 175

Pro Asp Asn Gly Asp Ser Ser Tyr Asn Gln Lys Phe Arg Glu Arg Val
            180                 185                 190

Thr Ile Thr Arg Asp Thr Ser Thr Ser Thr Ala Tyr Leu Glu Leu Ser
        195                 200                 205

Ser Leu Arg Ser Glu Asp Thr Ala Val Tyr Tyr Cys Val Leu Ala Pro
210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
370                 375                 380

-continued

```
Cys Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 261
<211> LENGTH: 331
<212> TYPE: PRT
<213> ORGANISM: Artificial Sequence
<220> FEATURE:
<223> OTHER INFORMATION: Synthetic Construct

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Arg Leu Arg Ser Gly Val Pro
                165                 170                 175
```

```
Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Gly
        195                 200                 205

His Thr Leu Pro Pro Thr Phe Gly Gln Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
            275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 262
<211> LENGTH: 571
<212> TYPE: PRT
<213> ORGANISM: Artificial Sequence
<220> FEATURE:
<223> OTHER INFORMATION: Synthetic Construct

<400> SEQUENCE: 262

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ile Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Leu Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser Gly Gly Gly Gly Ser Gly Gly Gly Ser Glu Val Gln Leu
            115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Ser Tyr Ile Ser Trp
145                 150                 155                 160

Val Arg Gln Ala Pro Gly Gln Gly Leu Glu Trp Ile Gly Asp Met Tyr
                165                 170                 175

Pro Asp Asn Gly Asp Ser Ser Tyr Asn Gln Lys Phe Arg Glu Arg Val
                180                 185                 190

Thr Ile Thr Arg Asp Thr Ser Ser Thr Ala Tyr Leu Glu Leu Ser
        195                 200                 205
```

```
Ser Leu Arg Ser Glu Asp Thr Ala Val Tyr Tyr Cys Val Leu Ala Pro
    210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570
```

<210> SEQ ID NO 263
<211> LENGTH: 331
<212> TYPE: PRT
<213> ORGANISM: Artificial Sequence
<220> FEATURE:
<223> OTHER INFORMATION: Synthetic Construct

<400> SEQUENCE: 263

-continued

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Tyr Leu Arg Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Gly
        195                 200                 205

His Thr Leu Pro Pro Thr Phe Gly Gln Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 264
<211> LENGTH: 571
<212> TYPE: PRT
<213> ORGANISM: Artificial Sequence
<220> FEATURE:
<223> OTHER INFORMATION: Synthetic Construct

<400> SEQUENCE: 264

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ile Tyr
            20                  25                  30
```

-continued

Leu Ile Glu Trp Val Arg Gln Ala Pro Gly Gln Gly Leu Glu Trp Ile
           35                  40                  45

Gly Val Ile Asn Pro Gly Ser Gly Asp Thr Tyr Tyr Ser Glu Lys Phe
     50                  55                  60

Leu Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
             100                 105                 110

Ser Ser Gly Gly Gly Gly Ser Gly Gly Gly Gly Ser Glu Val Gln Leu
         115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Ser Tyr Met Ser Trp
145                 150                 155                 160

Val Arg Gln Ala Pro Gly Gln Gly Leu Glu Trp Ile Gly Asp Met Tyr
                 165                 170                 175

Pro Asp Asn Gly Asp Ser Ser Tyr Asn Gln Lys Phe Arg Glu Arg Val
             180                 185                 190

Thr Ile Thr Arg Asp Thr Ser Thr Ser Thr Ala Tyr Leu Glu Leu Ser
         195                 200                 205

Ser Leu Arg Ser Glu Asp Thr Ala Val Tyr Tyr Cys Val Leu Ala Ala
    210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
                 245                 250                 255

Lys Ser Thr Ser Gly Gly Thr Ala Ala Leu Gly Cys Leu Val Lys Asp
             260                 265                 270

Tyr Phe Pro Glu Pro Val Thr Val Ser Trp Asn Ser Gly Ala Leu Thr
         275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                 325                 330                 335

Lys Lys Val Glu Pro Lys Ser Cys Asp Lys Thr His Thr Cys Pro Pro
             340                 345                 350

Cys Pro Ala Pro Glu Leu Leu Gly Gly Pro Ser Val Phe Leu Phe Pro
         355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                 405                 410                 415

Glu Glu Gln Tyr Asn Ser Thr Tyr Arg Val Val Ser Val Leu Thr Val
             420                 425                 430

Leu His Gln Asp Trp Leu Asn Gly Lys Glu Tyr Lys Cys Lys Val Ser
         435                 440                 445

Asn Lys Ala Leu Pro Ala Pro Ile Glu Lys Thr Ile Ser Lys Ala Lys

```
                   450                 455                 460
Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 265
<211> LENGTH: 331
<212> TYPE: PRT
<213> ORGANISM: Artificial Sequence
<220> FEATURE:
<223> OTHER INFORMATION: Synthetic Construct

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Arg Leu Arg Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Gly
        195                 200                 205

His Thr Leu Pro Pro Thr Phe Gly Gln Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
```

```
                    245                 250                 255
Tyr Pro Arg Glu Ala Lys Val Gln Trp Lys Val Asp Asn Ala Leu Gln
                260                 265                 270

Ser Gly Asn Ser Gln Glu Ser Val Thr Glu Gln Asp Ser Lys Asp Ser
            275                 280                 285

Thr Tyr Ser Leu Ser Ser Thr Leu Thr Leu Ser Lys Ala Asp Tyr Glu
        290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 266
<211> LENGTH: 571
<212> TYPE: PRT
<213> ORGANISM: Artificial Sequence
<220> FEATURE:
<223> OTHER INFORMATION: Synthetic Construct

<400> SEQUENCE: 266

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Gly Gly Gly Gly Ser Gly Gly Gly Gly Ser Glu Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Ser Tyr Met Ser Trp
145                 150                 155                 160

Val Arg Gln Ala Pro Gly Gln Gly Leu Glu Trp Ile Gly Asp Met Tyr
                165                 170                 175

Pro Asp Asn Gly Asp Ser Ser Tyr Asn Gln Lys Phe Arg Glu Arg Val
            180                 185                 190

Thr Ile Thr Arg Asp Thr Ser Thr Ser Thr Ala Tyr Leu Glu Leu Ser
        195                 200                 205

Ser Leu Arg Ser Glu Asp Thr Ala Val Tyr Tyr Cys Val Leu Ala Ala
    210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
```

Ser Gly Val His Thr Phe Pro Ala Val Leu Gln Ser Ser Gly Leu Tyr
            275                 280                 285
Ser Leu Ser Ser Val Val Thr Val Pro Ser Ser Ser Leu Gly Thr Gln
290                 295                 300
Thr Tyr Ile Cys Asn Val Asn His Lys Pro Ser Asn Thr Lys Val Asp
305                 310                 315                 320
Lys Lys Val Glu Pro Lys Ser Cys Asp Lys Thr His Thr Cys Pro Pro
            325                 330                 335
Cys Pro Ala Pro Glu Leu Leu Gly Gly Pro Ser Val Phe Leu Phe Pro
        340                 345                 350
Pro Lys Pro Lys Asp Thr Leu Met Ile Ser Arg Thr Pro Glu Val Thr
355                 360                 365
Cys Val Val Val Asp Val Ser His Glu Asp Pro Glu Val Lys Phe Asn
370                 375                 380
Trp Tyr Val Asp Gly Val Glu Val His Asn Ala Lys Thr Lys Pro Arg
385                 390                 395                 400
Glu Glu Gln Tyr Asn Ser Thr Tyr Arg Val Val Ser Val Leu Thr Val
            405                 410                 415
Leu His Gln Asp Trp Leu Asn Gly Lys Glu Tyr Lys Cys Lys Val Ser
        420                 425                 430
Asn Lys Ala Leu Pro Ala Pro Ile Glu Lys Thr Ile Ser Lys Ala Lys
435                 440                 445
Gly Gln Pro Arg Glu Pro Gln Val Tyr Thr Leu Pro Pro Ser Arg Glu
450                 455                 460
Glu Met Thr Lys Asn Gln Val Ser Leu Thr Cys Leu Val Lys Gly Phe
465                 470                 475                 480
Tyr Pro Ser Asp Ile Ala Val Glu Trp Glu Ser Asn Gly Gln Pro Glu
            485                 490                 495
Asn Asn Tyr Lys Thr Thr Pro Pro Val Leu Asp Ser Asp Gly Ser Phe
        500                 505                 510
Phe Leu Tyr Ser Lys Leu Thr Val Asp Lys Ser Arg Trp Gln Gln Gly
515                 520                 525
Asn Val Phe Ser Cys Ser Val Met His Glu Ala Leu His Asn His Tyr
530                 535                 540
Thr Gln Lys Ser Leu Ser Leu Ser Pro Gly Lys
545                 550                 555                 560
            565                 570

<210> SEQ ID NO 267
<211> LENGTH: 331
<212> TYPE: PRT
<213> ORGANISM: Artificial Sequence
<220> FEATURE:
<223> OTHER INFORMATION: Synthetic Construct

<400> SEQUENCE: 267

Asp Ile Gln Met Thr Gln Ser Pro Ser Ser Leu Ser Ala Ser Val Gly
1               5                   10                  15
Asp Arg Val Thr Ile Thr Cys His Ala Ser Gln Asp Ile Ser Ser Tyr
            20                  25                  30
Ile Val Trp Tyr Gln Gln Lys Pro Gly Lys Ser Phe Lys Gly Leu Ile
        35                  40                  45
Tyr His Gly Thr Asn Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Asp Ile Ser Asn Tyr Leu Asn Trp Tyr Gln Gln Lys Pro Gly Lys Ala
145                 150                 155                 160

Pro Lys Leu Leu Ile Tyr Tyr Thr Ser Arg Leu Arg Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Gly
        195                 200                 205

His Thr Leu Pro Pro Thr Phe Gly Gln Gly Thr Lys Val Glu Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 268
<211> LENGTH: 5
<212> TYPE: PRT
<213> ORGANISM: Artificial Sequence
<220> FEATURE:
<223> OTHER INFORMATION: Synthetic Construct

<400> SEQUENCE: 268

Asp Lys Thr His Thr
1               5

<210> SEQ ID NO 269
<211> LENGTH: 12
<212> TYPE: PRT
<213> ORGANISM: Artificial Sequence
<220> FEATURE:
<223> OTHER INFORMATION: Synthetic Construct

<400> SEQUENCE: 269

Asp Lys Thr His Thr Gly Gly Gly Gly Ser Gly Gly
1               5                   10

<210> SEQ ID NO 270
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 270

Gly Gly Gly Gly Ser Gly
1               5

<210> SEQ ID NO 271
<211> LENGTH: 5
<212> TYPE: PRT
<213> ORGANISM: Artificial Sequence
<220> FEATURE:
<223> OTHER INFORMATION: Synthetic Construct

<400> SEQUENCE: 271

Gly Gly Ser Gly Gly
1               5

<210> SEQ ID NO 272
<211> LENGTH: 10
<212> TYPE: PRT
<213> ORGANISM: Artificial Sequence
<220> FEATURE:
<223> OTHER INFORMATION: Synthetic Construct

<400> SEQUENCE: 272

Gly Gly Gly Gly Ser Gly Gly Gly Gly Ser
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Synthetic Construct

<400> SEQUENCE: 273

Gly Gly Gly Gly Ser Gly Gly Gly Ser Gly Gly Gly Gly
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Synthetic Construct

<400> SEQUENCE: 274

Gly Gly Ser Gly Gly Gly Ser Gly Gly Gly Gly Ser
1               5                   10

<210> SEQ ID NO 275
<211> LENGTH: 6
<212> TYPE: PRT
<213> ORGANISM: Artificial Sequence
<220> FEATURE:
<223> OTHER INFORMATION: Synthetic Construct

<400> SEQUENCE: 275

Ala Ser Thr Lys Gly Pro
1               5

<210> SEQ ID NO 276
<211> LENGTH: 6
<212> TYPE: PRT
```

<213> ORGANISM: Artificial Sequence
<220> FEATURE:
<223> OTHER INFORMATION: Synthetic Construct

<400> SEQUENCE: 276

```
Arg Thr Val Ala Ala Pro
1               5
```

<210> SEQ ID NO 277
<211> LENGTH: 13
<212> TYPE: PRT
<213> ORGANISM: Artificial Sequence
<220> FEATURE:
<223> OTHER INFORMATION: Synthetic Construct

<400> SEQUENCE: 277

```
Ala Ser Thr Lys Gly Pro Ser Val Phe Pro Leu Ala Pro
1               5                   10
```

<210> SEQ ID NO 278
<211> LENGTH: 13
<212> TYPE: PRT
<213> ORGANISM: Artificial Sequence
<220> FEATURE:
<223> OTHER INFORMATION: Synthetic Construct

<400> SEQUENCE: 278

```
Arg Thr Val Ala Ala Pro Ser Val Phe Ile Phe Pro Pro
1               5                   10
```

<210> SEQ ID NO 279
<211> LENGTH: 330
<212> TYPE: PRT
<213> ORGANISM: Artificial Sequence
<220> FEATURE:
<223> OTHER INFORMATION: Synthetic Construct

<400> SEQUENCE: 279

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                    180                 185                 190
        His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Glu Glu
        225                 230                 235                 240

Met Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
        305                 310                 315                 320

Gln Lys Ser Leu Ser Leu Ser Pro Gly Lys
                        325                 330

<210> SEQ ID NO 280
<211> LENGTH: 107
<212> TYPE: PRT
<213> ORGANISM: Artificial Sequence
<220> FEATURE:
<223> OTHER INFORMATION: Synthetic Construct

<400> SEQUENCE: 280

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 281
<211> LENGTH: 277
<212> TYPE: PRT
<213> ORGANISM: Homo sapiens

<400> SEQUENCE: 281

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60
```

```
Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 282
<211> LENGTH: 5
<212> TYPE: PRT
<213> ORGANISM: Artificial Sequence
<220> FEATURE:
<223> OTHER INFORMATION: Synthetic Construct

<400> SEQUENCE: 282

Asp Ser Tyr Ile Ser
1               5

<210> SEQ ID NO 283
<211> LENGTH: 8
<212> TYPE: PRT
<213> ORGANISM: Artificial Sequence
<220> FEATURE:
<223> OTHER INFORMATION: Synthetic Construct

<400> SEQUENCE: 283

Ala Ala Arg Trp Tyr Phe Ser Val
1               5

<210> SEQ ID NO 284
<211> LENGTH: 117
<212> TYPE: PRT
<213> ORGANISM: Artificial Sequence
<220> FEATURE:
<223> OTHER INFORMATION: Synthetic Construct

<400> SEQUENCE: 284
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Ile Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 285
<211> LENGTH: 117
<212> TYPE: PRT
<213> ORGANISM: Artificial Sequence
<220> FEATURE:
<223> OTHER INFORMATION: Synthetic Construct

<400> SEQUENCE: 285

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Ala Arg Trp Tyr Phe Ser Val Trp Gly Gln Gly Thr Leu
                100                 105                 110

Val Thr Val Ser Ser
        115

<210> SEQ ID NO 286
<211> LENGTH: 7
<212> TYPE: PRT
<213> ORGANISM: Artificial Sequence
<220> FEATURE:
<223> OTHER INFORMATION: Synthetic Construct

<400> SEQUENCE: 286

Tyr Thr Ser Tyr Leu Arg Ser
1               5

<210> SEQ ID NO 287
<211> LENGTH: 107
<212> TYPE: PRT
<213> ORGANISM: Artificial Sequence
<220> FEATURE:
<223> OTHER INFORMATION: Synthetic Construct

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Tyr Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 288
<211> LENGTH: 5
<212> TYPE: PRT
<213> ORGANISM: Artificial Sequence
<220> FEATURE:
<223> OTHER INFORMATION: Synthetic Construct

<400> SEQUENCE: 288

Ile Tyr Leu Ile Glu
1               5

<210> SEQ ID NO 289
<211> LENGTH: 17
<212> TYPE: PRT
<213> ORGANISM: Artificial Sequence
<220> FEATURE:
<223> OTHER INFORMATION: Synthetic Construct

<400> SEQUENCE: 289

Val Ile Asn Pro Gly Ser Gly Asp Thr Tyr Tyr Ser Glu Lys Phe Leu
1               5                   10                  15

Gly

<210> SEQ ID NO 290
<211> LENGTH: 114
<212> TYPE: PRT
<213> ORGANISM: Artificial Sequence
<220> FEATURE:
<223> OTHER INFORMATION: Synthetic Construct

<400> SEQUENCE: 290

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ile Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

Leu Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

```
Ala Arg Asp Arg Leu Asp Tyr Trp Gly Gln Gly Thr Leu Val Thr Val
            100                 105                 110
Ser Ser

<210> SEQ ID NO 291
<211> LENGTH: 570
<212> TYPE: PRT
<213> ORGANISM: Artificial Sequence
<220> FEATURE:
<223> OTHER INFORMATION: Synthetic Construct

<400> SEQUENCE: 291

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Gly Gly Gly Gly Ser Gly Gly Gly Gly Ser Glu Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Ser Tyr Met Ser Trp
145                 150                 155                 160

Val Arg Gln Ala Pro Gly Gln Gly Leu Glu Trp Ile Gly Asp Met Tyr
                165                 170                 175

Pro Asp Asn Gly Asp Ser Ser Tyr Asn Gln Lys Phe Arg Glu Arg Val
            180                 185                 190

Thr Ile Thr Arg Asp Thr Ser Thr Ser Thr Ala Tyr Leu Glu Leu Ser
        195                 200                 205

Ser Leu Arg Ser Glu Asp Thr Ala Val Tyr Tyr Cys Val Leu Ala Pro
    210                 215                 220

Arg Trp Tyr Phe Ser Val Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
```

```
            340             345             350
Cys Pro Ala Pro Glu Leu Leu Gly Gly Pro Ser Val Phe Leu Phe Pro
            355             360             365

Pro Lys Pro Lys Asp Thr Leu Met Ile Ser Arg Thr Pro Glu Val Thr
370             375             380

Cys Val Val Val Asp Val Ser His Glu Asp Pro Glu Val Lys Phe Asn
385             390             395             400

Trp Tyr Val Asp Gly Val Glu Val His Asn Ala Lys Thr Lys Pro Arg
                405             410             415

Glu Glu Gln Tyr Asn Ser Thr Tyr Arg Val Val Ser Val Leu Thr Val
            420             425             430

Leu His Gln Asp Trp Leu Asn Gly Lys Glu Tyr Lys Cys Lys Val Ser
            435             440             445

Asn Lys Ala Leu Pro Ala Pro Ile Glu Lys Thr Ile Ser Lys Ala Lys
            450             455             460

Gly Gln Pro Arg Glu Pro Gln Val Tyr Thr Leu Pro Pro Ser Arg Glu
465             470             475             480

Glu Met Thr Lys Asn Gln Val Ser Leu Thr Cys Leu Val Lys Gly Phe
            485             490             495

Tyr Pro Ser Asp Ile Ala Val Glu Trp Glu Ser Asn Gly Gln Pro Glu
            500             505             510

Asn Asn Tyr Lys Thr Thr Pro Pro Val Leu Asp Ser Asp Gly Ser Phe
            515             520             525

Phe Leu Tyr Ser Lys Leu Thr Val Asp Lys Ser Arg Trp Gln Gln Gly
            530             535             540

Asn Val Phe Ser Cys Ser Val Met His Glu Ala Leu His Asn His Tyr
545             550             555             560

Thr Gln Lys Ser Leu Ser Leu Ser Pro Gly
            565             570

<210> SEQ ID NO 292
<211> LENGTH: 676
<212> TYPE: PRT
<213> ORGANISM: Artificial Sequence
<220> FEATURE:
<223> OTHER INFORMATION: Synthetic Construct

<400> SEQUENCE: 292

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Lys Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
```

-continued

```
            130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Gly Gly Gly Ser Gly Gly Glu Val Gln Leu Val Gln Ser Gly
225                 230                 235                 240

Ala Glu Val Lys Lys Pro Gly Ala Ser Val Lys Val Ser Cys Lys Ala
                245                 250                 255

Ser Gly Tyr Ala Phe Thr Asn Tyr Leu Ile Glu Trp Val Arg Glu Ala
                260                 265                 270

Pro Gly Gln Gly Leu Glu Trp Ile Gly Val Ile Asn Pro Gly Ser Gly
        275                 280                 285

Asp Thr Tyr Tyr Ser Glu Lys Phe Lys Gly Arg Val Thr Leu Thr Ala
        290                 295                 300

Asp Thr Ser Thr Ser Thr Ala Tyr Leu Glu Leu Ser Ser Leu Arg Ser
305                 310                 315                 320

Glu Asp Thr Ala Val Tyr Tyr Cys Ala Arg Asp Arg Leu Asp Tyr Trp
                325                 330                 335

Gly Gln Gly Thr Leu Val Thr Val Ser Ser Ala Ser Thr Lys Gly Pro
                340                 345                 350

Ser Val Phe Pro Leu Ala Pro Ser Ser Lys Ser Thr Ser Gly Gly Thr
                355                 360                 365

Ala Ala Leu Gly Cys Leu Val Lys Asp Tyr Phe Pro Glu Pro Val Thr
        370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Lys Ser Val Val Thr
                405                 410                 415

Val Pro Ser Ser Ser Leu Gly Thr Gln Thr Tyr Ile Cys Asn Val Asn
                420                 425                 430

His Lys Pro Ser Asn Thr Lys Val Asp Lys Lys Val Glu Pro Lys Ser
                435                 440                 445

Cys Asp Lys Thr His Thr Cys Pro Pro Cys Pro Ala Pro Glu Leu Leu
        450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Pro Ala Pro
545                 550                 555                 560
```

```
Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly Lys
            675

<210> SEQ ID NO 293
<211> LENGTH: 676
<212> TYPE: PRT
<213> ORGANISM: Artificial Sequence
<220> FEATURE:
<223> OTHER INFORMATION: Synthetic Construct

<400> SEQUENCE: 293

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Lys Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Glu Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Gly Gly
    210                 215                 220

Gly Gly Ser Gly Gly Glu Val Gln Leu Val Gln Ser Gly Ala Glu Val
225                 230                 235                 240
```

```
Lys Lys Pro Gly Ala Ser Val Lys Val Ser Cys Lys Ala Ser Gly Tyr
                245                 250                 255
Thr Phe Thr Asp Ser Tyr Met Ser Trp Val Arg Glu Ala Pro Gly Gln
                260                 265                 270
Gly Leu Glu Trp Ile Gly Asp Met Tyr Pro Asp Asn Gly Asp Ser Ser
                275                 280                 285
Tyr Asn Gln Lys Phe Arg Glu Arg Val Thr Ile Thr Arg Asp Thr Ser
                290                 295                 300
Thr Ser Thr Ala Tyr Leu Glu Leu Ser Ser Leu Arg Ser Glu Asp Thr
305                 310                 315                 320
Ala Val Tyr Tyr Cys Val Leu Ala Pro Arg Trp Tyr Phe Ser Val Trp
                325                 330                 335
Gly Gln Gly Thr Leu Val Thr Val Ser Ser Ala Ser Thr Lys Gly Pro
                340                 345                 350
Ser Val Phe Pro Leu Ala Pro Ser Ser Lys Ser Thr Ser Gly Gly Thr
                355                 360                 365
Ala Ala Leu Gly Cys Leu Val Lys Asp Tyr Phe Pro Glu Pro Val Thr
                370                 375                 380
Val Ser Trp Asn Ser Gly Ala Leu Thr Ser Gly Val His Thr Phe Pro
385                 390                 395                 400
Ala Val Leu Gln Ser Ser Gly Leu Tyr Ser Leu Lys Ser Val Val Thr
                405                 410                 415
Val Pro Ser Ser Ser Leu Gly Thr Gln Thr Tyr Ile Cys Asn Val Asn
                420                 425                 430
His Lys Pro Ser Asn Thr Lys Val Asp Lys Lys Val Glu Pro Lys Ser
                435                 440                 445
Cys Asp Lys Thr His Thr Cys Pro Pro Cys Pro Ala Pro Glu Leu Leu
450                 455                 460
Gly Gly Pro Ser Val Phe Leu Phe Pro Pro Lys Pro Lys Asp Thr Leu
465                 470                 475                 480
Met Ile Ser Arg Thr Pro Glu Val Thr Cys Val Val Val Asp Val Ser
                485                 490                 495
His Glu Asp Pro Glu Val Lys Phe Asn Trp Tyr Val Asp Gly Val Glu
                500                 505                 510
Val His Asn Ala Lys Thr Lys Pro Arg Glu Glu Gln Tyr Asn Ser Thr
                515                 520                 525
Tyr Arg Val Val Ser Val Leu Thr Val Leu His Gln Asp Trp Leu Asn
                530                 535                 540
Gly Lys Glu Tyr Lys Cys Lys Val Ser Asn Lys Ala Leu Pro Ala Pro
545                 550                 555                 560
Ile Glu Lys Thr Ile Ser Lys Ala Lys Gly Gln Pro Arg Glu Pro Gln
                565                 570                 575
Val Tyr Thr Leu Pro Pro Ser Arg Glu Glu Met Thr Lys Asn Gln Val
                580                 585                 590
Ser Leu Thr Cys Leu Val Lys Gly Phe Tyr Pro Ser Asp Ile Ala Val
                595                 600                 605
Glu Trp Glu Ser Asn Gly Gln Pro Glu Asn Asn Tyr Lys Thr Thr Pro
                610                 615                 620
Pro Val Leu Asp Ser Asp Gly Ser Phe Phe Leu Tyr Ser Lys Leu Thr
625                 630                 635                 640
Val Asp Lys Ser Arg Trp Gln Gln Gly Asn Val Phe Ser Cys Ser Val
                645                 650                 655
```

```
Met His Glu Ala Leu His Asn His Tyr Thr Gln Lys Ser Leu Ser Leu
            660                 665                 670

Ser Pro Gly Lys
        675

<210> SEQ ID NO 294
<211> LENGTH: 446
<212> TYPE: PRT
<213> ORGANISM: Artificial Sequence
<220> FEATURE:
<223> OTHER INFORMATION: Synthetic Construct

<400> SEQUENCE: 294

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 295
<211> LENGTH: 326
<212> TYPE: PRT
<213> ORGANISM: Homo sapiens

<400> SEQUENCE: 295

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 296
<211> LENGTH: 377
<212> TYPE: PRT
<213> ORGANISM: Homo sapiens

<400> SEQUENCE: 296

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
```

```
305                 310                 315                 320
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 297
<211> LENGTH: 327
<212> TYPE: PRT
<213> ORGANISM: Homo sapiens

<400> SEQUENCE: 297

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65              70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300
```

```
Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 298
<211> LENGTH: 107
<212> TYPE: PRT
<213> ORGANISM: Homo sapiens

<400> SEQUENCE: 298

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 299
<211> LENGTH: 106
<212> TYPE: PRT
<213> ORGANISM: Homo sapiens

<400> SEQUENCE: 299

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 300
<211> LENGTH: 106
<212> TYPE: PRT
<213> ORGANISM: Homo sapiens

<400> SEQUENCE: 300

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
```

-continued

```
                35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 301
<211> LENGTH: 106
<212> TYPE: PRT
<213> ORGANISM: Homo sapiens

<400> SEQUENCE: 301

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
                35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 302
<211> LENGTH: 106
<212> TYPE: PRT
<213> ORGANISM: Homo sapiens

<400> SEQUENCE: 302

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Lys Val Ala Trp Lys Ala Asp Gly Ser Pro
                35                  40                  45

Val Asn Thr Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Ala Glu Cys Ser
            100                 105

<210> SEQ ID NO 303
<211> LENGTH: 106
<212> TYPE: PRT
<213> ORGANISM: Homo sapiens

<400> SEQUENCE: 303
```

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40              45

Val Lys Val Gly Val Glu Thr Thr Lys Pro Ser Lys Gln Ser Asn Asn
    50              55                  60

Lys Tyr Ala Ala Ser Ser Tyr Leu Ser Leu Thr Pro Glu Gln Trp Lys
65              70                  75                  80

Ser His Arg Ser Tyr Ser Cys Arg Val Thr His Glu Gly Ser Thr Val
            85                  90                  95

Glu Lys Thr Val Ala Pro Ala Glu Cys Ser
            100                 105
```

MULTIVALENT AND MULTIEPITOPIC ANTIBODIES HAVING AGONISTIC ACTIVITY AND METHODS OF USE

CROSS REFERENCE TO RELATED APPLICATIONS

This application claims the priority benefit of U.S. Provisional Application Ser. No. 62/371,671, filed Aug. 5, 2016, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392037700SEQLIST.txt, date recorded: Aug. 4, 2017, size: 353 KB).

FIELD OF THE INVENTION

The present invention relates to multivalent and multiepitopic antigen binding complexes having agonistic activity and methods of using the same.

BACKGROUND

Functional antibodies and antigen binding complexes are an important therapeutic option for treatment of a wide variety of diseases. There is a need in the art for better means for identifying functional antibodies and antigen binding complexes, particularly those having agonistic activity, from pools of candidate molecules. There is a further need in the art for antibodies and antigen binding complexes with more potent agonistic activity. The present invention is directed to these and other needs.

The disclosures of all patent and scientific literature cited herein are expressly incorporated in their entirety by reference.

SUMMARY

The invention provides antigen binding complexes (e.g., multivalent and multiepitopic antibodies/antigen binding complexes) having agonistic activity and methods of using the same.

In one aspect, provided herein is a tetravalent antigen binding complex having agonist activity, the complex comprising: a first and a second subunit, wherein each of the first and the second subunits comprises: (i) a first half-antibody comprising a first antibody heavy chain variable domain (VH$_1$) and a first antibody light chain variable domain (VL$_1$), wherein the first half-antibody specifically binds to a first epitope of a cell surface receptor, and (ii) a second half-antibody comprising a second antibody heavy chain variable domain (VH$_2$) and a second antibody light chain variable domain (VL$_2$), wherein the second half-antibody specifically binds to a second epitope of the cell surface receptor; wherein the first and the second subunits are coupled, and wherein the complex has agonist activity for the cell surface receptor bound by the complex. In some embodiments, an antigen binding complex of the present disclosure shows agonist activity in vitro. In some embodiments, each of the first and the second subunits comprises: (i) the first half-antibody, wherein the first half-antibody comprises: (a) a first antibody heavy chain comprising, from N-terminus to C-terminus, the first antibody heavy chain variable domain (VH$_1$), a first antibody heavy chain CH1 domain, a first antibody heavy chain CH2 domain, and a first antibody heavy chain CH3 domain; and (b) a first antibody light chain comprising, from N-terminus to C-terminus, the first antibody light chain variable domain (VL$_1$) and a first antibody light chain constant domain (CL); and (i) the second half-antibody, wherein the second half-antibody comprises: (a) a second antibody heavy chain comprising, from N-terminus to C-terminus, the second antibody heavy chain variable domain (VH$_2$), a second antibody heavy chain CH1 domain, a second antibody heavy chain CH2 domain, and a second antibody heavy chain CH3 domain; and (b) a second antibody light chain comprising, from N-terminus to C-terminus, the second antibody light chain variable domain (VL$_2$) and a second antibody light chain constant domain (CL). In some embodiments, the first and the second subunits are chemically coupled. In some embodiments, the first and the second epitopes of the cell surface receptor are the same. In some embodiments, the first and the second epitopes of the cell surface receptor are different. In some embodiments, each of the first and the second subunits comprises a bispecific antibody, the bispecific antibody comprises two antibody Fc regions with two CH3 domains, each of the two CH3 domains comprises either a protuberance or a cavity, and the protuberance or cavity in the first of the two CH3 domains is positionable in the cavity or protuberance, respectively, in the second of the two CH3 domains. In some embodiments, the two subunits are chemically coupled via a linker. In some embodiments, each of the two subunits comprises two heavy chains and two light chains, and one of the heavy chains of each subunit comprises a cysteine amino acid in the heavy chain selected from T114C, A118C, A140C, L174C, L179C, T187C, T209C, V262C, G371C, Y373C, E382C, S400C, S424C, N434C and Q438C, according to EU numbering. In some embodiments, each of the two subunits comprises two heavy chains and two light chains, and one of the light chains of each subunit comprises a cysteine amino acid in the light chain selected from I106C, R108C, R142C, K149C, and V205C, according to Kabat numbering. In some embodiments, the two subunits are chemically coupled via click chemistry. In some embodiments, the two subunits are coupled via a tetrazine-transcyclooctene (TCO) click reaction. In some embodiments, the linker is between about 10 Å and about 100 Å in length. In some embodiments, the linker is a bis-maleimido polyethylene glycol (PEG) linker. In some embodiments, the PEG linker comprises between one and eleven PEG subunits. In some embodiments, the PEG linker comprises one, two, or three PEG subunits. In some embodiments, each of the subunits comprises an Fc region comprising a modification for attenuating effector function. In some embodiments, each of the subunits comprises an Fc region comprising an amino acid substitution at one or more amino acid residues (EU numbering) selected from (a) 297 in the Fc region of human IgG1, (b) 234 and 235 in the Fc region of human IgG1, (c) 234, 235 and 329 in the Fc region of human IgG1, (d) 234 and 237 in the Fc region of human IgG2, (e) 235, 237 and 318 in the Fc region of human IgG4, (f) 228 and 236 in the Fc region of human IgG4, (g) 268, 309, 330 and 331 in the Fc region of human IgG2, (h) 220, 226, 229 and 238 in the Fc region of human IgG1, (i) 226, 229, 233, 234 and 235 in the Fc region of human IgG1, (j) 234, 235 and 331 in the Fc region of human IgG1, (k) 226 and 230 in the Fc region of human IgG1, and (l) 267 and 328 in the Fc region of human IgG1. In some embodiments, each of the subunits comprises an Fc region comprising one or more amino acid substitutions (EU numbering) selected from (a) N297A in the Fc region of human IgG1, (b) L234A and L235A in the Fc region of human IgG1, (c) L234A, L235A and P329G in the Fc region of human IgG1, (d) V234A and G237A in the Fc region of human IgG2, (e) L235A, G237A and E318A in the Fc region of human IgG4, (f) S228P and L236E in the Fc region of human IgG4, (g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2, (i) C220S, C226S, C229S and P238S in the Fc region of human IgG1, (j) C226S, C229S, E233P, L234V and L235A in the Fc region of human IgG1, (k) L234F, L235E and P331S in the Fc region of human IgG1, (l) C226S and P230S in the Fc region of human IgG1, and (m) S267E and L328F in the Fc region of human IgG1. In some embodiments, each of the subunits comprises an Fc region comprising a modification for attenuating effector function that results in an aglycosylated Fc region. In some embodiments, each of the subunits comprises an Fc region comprising a modification for attenuating effector function that does not result in a modification of the glycosylation pattern of the Fc region. In some embodiments, the cell surface receptor is a member of a receptor family selected from the group consisting of tumor necrosis factor receptor (TNFR) superfamily and G-Protein Coupled Receptor (GPCR) superfamily. In some embodiments, the cell surface receptor is selected from OX40, DR5, GITR, CD27, CD137, and Tie2. In some embodiments, the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments, the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

In another aspect, provided herein is a tetravalent antigen binding complex having agonist activity, wherein said complex comprises: (a) an antibody comprising two antibody heavy chains, each antibody heavy chain comprising a first antibody heavy chain variable domain ($VH_1$), and two antibody light chains, each antibody light chain comprising a first antibody light chain variable domain ($VL_1$), wherein the antibody specifically binds to a first epitope of a cell surface receptor; and (b) two antibody Fab fragments coupled with the antibody, wherein each of the two antibody Fab fragments comprises a second antibody heavy chain variable domain ($VH_2$) and a second antibody light chain variable domain ($VL_2$), wherein each of the two antibody Fab fragments specifically binds a second epitope of the cell surface receptor; wherein the complex has agonist activity for the cell surface receptor bound by the complex. In some embodiments, an antigen binding complex of the present disclosure shows agonist activity in vitro. In some embodiments, each antibody heavy chain comprises, from N-terminus to C-terminus, the first antibody heavy chain variable domain ($VH_1$), a first antibody heavy chain CH1 domain, a first antibody heavy chain CH2 domain, and a first antibody heavy chain CH3 domain; each antibody light chain comprises, from N-terminus to C-terminus, the first antibody light chain variable domain ($VL_1$) and a first antibody light chain constant domain (CL); each of the two antibody Fab fragments comprises a heavy chain Fab fragment comprising, from N-terminus to C-terminus, the second antibody heavy chain variable domain ($VH_2$) and a second antibody heavy chain CH1 domain; and each of the two antibody Fab fragments comprises a light chain Fab fragment comprising, from N-terminus to C-terminus, the second antibody light chain variable domain ($VL_2$) and a second antibody light chain constant domain (CL). In some embodiments, a first of the two antibody Fab fragments is chemically coupled to a first of the two antibody light chains or a first of the two antibody heavy chains, and a second of the two antibody Fab fragments is chemically coupled to a second of the two antibody light chains or a second of the two antibody heavy chains. In some embodiments, each of the two Fab fragments is chemically coupled to the antibody via a linker. In some embodiments, the complex comprises: (i) a first linker joining a first engineered free cysteine of the antibody and an engineered free cysteine of a first of the two Fab fragments, and (ii) a second linker joining a second engineered free cysteine of the antibody and an engineered free cysteine of a second of the two Fab fragments. In some embodiments, the two antibody heavy chains of the antibody each comprise a cysteine amino acid independently selected from T114C, A118C, A140C, L174C, L179C, T187C, T209C, V262C, G371C, Y373C, E382C, S400C, S424C, N434C and Q438C, according to EU numbering. In some embodiments, the two antibody light chains of the antibody each comprise a cysteine amino acid independently selected from I106C, R108C, R142C, K149C, and V205C, according to Kabat numbering. In some embodiments, the two antibody Fab fragments each comprise a C-terminal cysteine amino acid. In some embodiments, the antibody is coupled to both of the two antibody Fab fragments via click chemistry. In some embodiments, the antibody is coupled to both of the two antibody Fab fragments via a tetrazine-transcyclooctene (TCO) click reaction. In some embodiments, the linker is between about 10 Å and about 100 Å in length. In some embodiments, the linker is a bis-maleimido polyethylene glycol (PEG) linker. In some embodiments, the PEG linker comprises between one and eleven PEG subunits. In some embodiments, the PEG linker comprises one, two, or three PEG subunits. In some embodiments, the two antibody Fab fragments are genetically coupled with the antibody; each antibody heavy chain comprises, from N-terminus to C-terminus, the first antibody heavy chain variable domain ($VH_1$), a first antibody heavy chain CH1 domain, the second heavy chain variable domain ($VH_2$), a second heavy chain CH1 domain, an antibody heavy chain CH2 domain, and an antibody heavy chain CH3 domain; and the complex comprises a first antibody light chain comprising, from N-terminus to C-terminus, the first antibody light chain variable domain ($VL_1$) and a first antibody light chain constant domain (CL) and a second antibody light chain comprising, from N-terminus to C-terminus, the second antibody light chain variable domain ($VL_2$) and a second antibody light chain constant domain (CL). In some embodiments, the first antibody light chain comprises a modification for orthogonal pairing with a modification of the first antibody heavy chain variable domain ($VH_1$) and/or the first antibody heavy chain CH1 domain of the antibody heavy chain, and the second antibody light chain comprises a modification for orthogonal pairing with a modification of the second heavy chain variable domain ($VH_2$) and/or the second heavy chain CH1 domain of the antibody heavy chain. In some embodiments, the first and the second epitopes of the cell surface receptor are the same. In some embodiments, the first and the second epitopes of the cell surface receptor are different. In some embodiments, each of the antibody heavy chains of the antibody comprises an Fc region comprising a modification for attenuating effector function. In some embodiments, each of the antibody heavy chains of the antibody comprises an amino acid substitution at one or more amino acid residues (EU numbering) selected from (a) 297 in the Fc region of human IgG1, (b) 234 and 235 in the Fc region of human IgG1, (c) 234, 235 and 329 in the Fc region of human IgG1, (d) 234 and 237 in the Fc region of human IgG2, (e) 235, 237 and 318 in the Fc region of human IgG4, (f) 228 and 236 in the Fc region of human IgG4, (g) 268, 309, 330 and 331 in the Fc region of human IgG2, (h) 220, 226, 229 and 238 in the Fc region of human IgG1, (i) 226, 229, 233, 234 and 235 in the Fc region of human IgG1, (j) 234, 235 and 331 in the Fc region of human IgG1, (k) 226 and 230 in the Fc region of human IgG1, and (l) 267 and 328 in the Fc region of human IgG1. In some embodiments, each of the antibody heavy chains of the antibody comprises an amino acid substitution at one or more amino acid residues (EU numbering) selected from (a) N297A in the Fc region of human IgG1, (b) L234A and L235A in the Fc region of human IgG1, (c) L234A, L235A and P329G in the Fc region of human IgG1, (d) V234A and G237A in the Fc region of human IgG2, (e) L235A, G237A and E318A in the Fc region of human IgG4, (f) S228P and L236E in the Fc region of human IgG4, (g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2, (i) C220S, C226S, C229S and P238S in the Fc region of human IgG1, (j) C226S, C229S, E233P, L234V and L235A in the Fc region of human IgG1, (k) L234F, L235E and P331S in the Fc region of human IgG1, (l) C226S and P230S in the Fc region of human IgG1, and (m) S267E and L328F in the Fc region of human IgG1. In some embodiments, each of the antibody heavy chains of the antibody comprises an Fc region comprising a modification for attenuating effector function that results in an aglycosylated Fc region. In some embodiments, each of the antibody heavy chains of the antibody comprises a modification for attenuating effector function that does not result in a modification of the glycosylation pattern of the Fc region. In some embodiments, the cell surface receptor is a member of a receptor family selected from the group consisting of tumor necrosis factor receptor (TNFR) superfamily and G-Protein Coupled Receptor (GPCR) superfamily. In some embodiments, the cell surface receptor is selected from the group consisting of OX40, DR5, GITR, CD27, CD137, and Tie2. In some embodiments, the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments, the $VH_2$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In some embodiments, the $VH_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments, the $VH_1$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

In another aspect, provided herein are nucleic acids encoding the complex according to any of the above embodiments. In some embodiments, the nucleic acid comprises a first polynucleotide encoding the first antibody heavy chain, a second polynucleotide encoding the first antibody light chain, a third polynucleotide encoding the second antibody heavy chain, and a fourth polynucleotide encoding the second antibody light chain. In some embodiments, the nucleic acid comprises a first polynucleotide encoding the antibody heavy chains, a second polynucleotide encoding the antibody light chains, a third polynucleotide encoding the heavy chain Fab fragments, and a fourth polynucleotide encoding the light chain Fab fragments. In some embodiments, the nucleic acid comprises a first polynucleotide encoding an antibody heavy chain comprising, from N-terminus to C-terminus, the first antibody heavy chain variable domain ($VH_1$), a first antibody heavy chain CH1 domain, the second heavy chain variable domain ($VH_2$), a second heavy chain CH1 domain, an antibody heavy chain CH2 domain, and an antibody heavy chain CH3 domain; a second polynucleotide encoding an antibody light chain comprising, from N-terminus to C-terminus, the first antibody light chain variable domain ($VL_1$) and a first antibody light chain constant domain (CL); and a third polynucleotide encoding an antibody light chain comprising, from N-terminus to C-terminus, the second antibody light chain variable domain ($VL_2$) and a second antibody light chain constant domain (CL). Further provided herein is a vector comprising the nucleic acid according to any of the above embodiments. In some embodiments, the vector is an expression vector. Further provided herein is a host cell comprising the vector according to any of the above embodiments and/or the nucleic acid according to any of the above embodiments. In some embodiments, the host cell is prokaryotic. In some embodiments, the host cell is eukaryotic. Further provided herein is a method of producing a tetravalent antigen binding complex, comprising culturing the host cell according to any of the above embodiments such that the complex is produced. In some embodiments, the method further comprises recovering the complex from the host cell.

In another aspect, provided herein is a pharmaceutical composition comprising the complex according to any one of the above embodiments and a pharmaceutically acceptable carrier.

In another aspect, provided herein is a method of producing a tetravalent antigen binding complex having agonist activity for a cell surface receptor bound by the complex, the method comprising: (a) providing: (i) a first half-antibody comprising a first antibody heavy chain variable domain ($VH_1$) and a first antibody light chain variable domain ($VL_1$), wherein the first half-antibody specifically binds to a first epitope of a cell surface receptor, and wherein the first half-antibody comprises a first engineered free cysteine, and (ii) a second half-antibody comprising a second antibody heavy chain variable domain ($VH_2$) and a second antibody light chain variable domain ($VL_2$), wherein the second half-antibody specifically binds to a second epitope of the cell surface receptor, wherein each of the first and the second half-antibodies comprises an antibody Fc region with a CH3 domain, wherein each of the two CH3 domains comprises either a protuberance or a cavity, wherein the protuberance or cavity in the first of the two CH3 domains is positionable in the cavity or protuberance, respectively, in the second of the two CH3 domains; (b) assembling the first and the second half-antibodies in vitro to form a first subunit; (c) providing: (iii) a third half-antibody comprising the first antibody heavy chain variable domain ($VH_1$) and the first antibody light chain variable domain ($VL_1$), wherein the third half-antibody specifically binds to the first epitope of a cell surface receptor, and wherein the third half-antibody comprises a second engineered free cysteine, and (iv) a fourth half-antibody comprising the second antibody heavy chain variable domain ($VH_2$) and the second antibody light chain variable domain ($VL_2$), wherein the fourth half-antibody specifically binds to the second epitope of the cell surface receptor, wherein each of the third and the fourth half-antibodies comprises an antibody Fc region with a CH3 domain, wherein each of the two CH3 domains comprises either a protuberance or a cavity, wherein the protuberance or cavity in the first of the two CH3 domains is positionable in the cavity or protuberance, respectively, in the second of the two CH3 domains; (d) assembling the third and the fourth half-antibodies in vitro to form a second subunit; and (e) coupling the first and the second subunits via a linker using the first and the second free engineered cysteines, thereby producing the complex. In some embodiments, an antigen binding complex of the present disclosure shows agonist activity in vitro. In some embodiments, the first and the second epitopes of the cell surface receptor are the same. In some embodiments, the first and the second epitopes of the cell surface receptor are different. In some embodiments, the first and the second engineered free cysteines are each a cysteine amino acid in the heavy chain independently selected from T114C, A118C, A140C, L174C, L179C, T187C, T209C, V262C, G371C, Y373C, E382C, S400C, S424C, N434C and Q438C, according to EU numbering. In some embodiments, the first and the second engineered free cysteines are each a cysteine amino acid in the light chain independently selected from I106C, R108C, R142C, K149C, and V205C, according to Kabat numbering. In some embodiments, the linker is a bis-maleimido polyethylene glycol (PEG) linker. In some embodiments, step (e) comprises: (1) reacting the two subunits with the bis-maleimido polyethylene glycol (PEG) linker; and (2) purifying the complex. In some embodiments, purifying the complex comprises subjecting the complex to size exclusion chromatography and/or anion exchange chromatography. In some embodiments, the PEG linker comprises between one and eleven PEG subunits. In some embodiments, the PEG linker comprises one, two, or three PEG subunits. In some embodiments, each of the first and the second subunits comprises an Fc region comprising a modification for attenuating effector function. In some embodiments, each of the first and the second subunits comprises an Fc region comprising an amino acid substitution at one or more amino acid residues (EU numbering) selected from (a) 297 in the Fc region of human IgG1, (b) 234 and 235 in the Fc region of human IgG1, (c) 234, 235 and 329 in the Fc region of human IgG1, (d) 234 and 237 in the Fc region of human IgG2, (e) 235, 237 and 318 in the Fc region of human IgG4, (f) 228 and 236 in the Fc region of human IgG4, (g) 268, 309, 330 and 331 in the Fc region of human IgG2, (h) 220, 226, 229 and 238 in the Fc region of human IgG1, (i) 226, 229, 233, 234 and 235 in the Fc region of human IgG1, (j) 234, 235 and 331 in the Fc region of human IgG1, (k) 226 and 230 in the Fc region of human IgG1, and (l) 267 and 328 in the Fc region of human IgG1. In some embodiments, each of the first and the second subunits comprises an Fc region comprising one or more amino acid substitutions (EU numbering) selected from (a) N297A in the Fc region of human IgG1, (b) L234A and L235A in the Fc region of human IgG1, (c) L234A, L235A and P329G in the Fc region of human IgG1, (d) V234A and G237A in the Fc region of human IgG2, (e) L235A, G237A and E318A in the Fc region of human IgG4, (f) S228P and L236E in the Fc region of human IgG4, (g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2, (i) C220S, C226S, C229S and P238S in the Fc region of human IgG1, (j) C226S, C229S, E233P, L234V and L235A in the Fc region of human IgG1, (k) L234F, L235E and P331S in the Fc region of human IgG1, (l) C226S and P230S in the Fc region of human IgG1, and (m) S267E and L328F in the Fc region of human IgG1. In some embodiments, each of the first and the second subunits comprises an Fc region comprising a modification for attenuating effector function that results in an aglycosylated Fc region. In some embodiments, each of the first and the second subunits comprises an Fc region comprising a modification for attenuating effector function that does not result in a modification of the glycosylation pattern of the Fc region.

In another aspect, provided herein is a method of producing a tetravalent antigen binding complex having agonist activity for a cell surface receptor bound by the complex, the method comprising: (a) providing an antibody comprising two half-antibodies, wherein each half-antibody comprises an antibody heavy chain comprising a first antibody heavy chain variable domain ($VH_1$), and an antibody light chain comprising a first antibody light chain variable domain ($VL_1$), wherein the antibody specifically binds to a first epitope of a cell surface receptor, and wherein each of the two half-antibodies comprises a first engineered free cysteine; (b) providing two antibody Fab fragments, wherein each of the two antibody Fab fragments comprises a second antibody heavy chain variable domain ($VH_2$) and a second antibody light chain variable domain ($VL_2$), wherein each of the two antibody Fab fragments specifically binds a second epitope of the cell surface receptor, and wherein each of the two antibody Fab fragments comprises a second engineered free cysteine; and (c) coupling one of the antibody Fab fragments to each of the two half-antibodies via a linker, thereby producing the complex. In some embodiments, an antigen binding complex of the present disclosure shows agonist activity in vitro. In some embodiments, the first and the second epitopes of the cell surface receptor are the same. In some embodiments, the first and the second epitopes of the cell surface receptor are different. In some embodiments, the first engineered free cysteine is a cysteine amino acid in the heavy chain independently selected from T114C, A118C, A140C, L174C, L179C, T187C, T209C, V262C, G371C, Y373C, E382C, S400C, S424C, N434C and Q438C, according to EU numbering. In some embodiments, the first engineered free cysteine is a cysteine amino acid in the light chain independently selected from I106C, R108C, R142C, K149C, and V205C, according to Kabat numbering. In some embodiments, the second engineered free cysteine is a C-terminal cysteine amino acid. In some embodiments, the linker is a bis-maleimido polyethylene glycol (PEG) linker. In some embodiments, step (c) comprises: (i) reacting each of the two antibody Fab fragments with a bis-maleimido polyethylene glycol (PEG) linker to form two bismal-conjugated antibody Fab fragments; (ii) removing excess bis-maleimido PEG linker; (iii) reacting each of the two bismal-conjugated antibody Fab fragments with the antibody to form the complex; and (iv) purifying the complex. In some embodiments, purifying the complex comprises subjecting the complex to size exclusion chromatography and/or anion exchange chromatography. In some embodiments, the PEG linker comprises between one and eleven PEG subunits. In some embodiments, the PEG linker comprises one, two, or three PEG subunits. In some embodiments, the antibody comprises an Fc region comprising a modification for attenuating effector function. In some embodiments, the antibody comprises an Fc region comprising an amino acid substitution at one or more amino acid residues (EU numbering) selected from (a) 297 in the Fc region of human IgG1, (b) 234 and 235 in the Fc region of human IgG1, (c) 234, 235 and 329 in the Fc region of human IgG1, (d) 234 and 237 in the Fc region of human IgG2, (e) 235, 237 and 318 in the Fc region of human IgG4, (f) 228 and 236 in the Fc region of human IgG4, (g) 268, 309, 330 and 331 in the Fc region of human IgG2, (h) 220, 226, 229 and 238 in the Fc region of human IgG1, (i) 226, 229, 233, 234 and 235 in the Fc region of human IgG1, (j) 234, 235 and 331 in the Fc region of human IgG1, (k) 226 and 230 in the Fc region of human IgG1, and (l) 267 and 328 in the Fc region of human IgG1. In some embodiments, the antibody comprises an Fc region comprising one or more amino acid substitutions (EU numbering) selected from (a) N297A in the Fc region of human IgG1, (b) L234A and L235A in the Fc region of human IgG1, (c) L234A, L235A and P329G in the Fc region of human IgG1, (d) V234A and G237A in the Fc region of human IgG2, (e) L235A, G237A and E318A in the Fc region of human IgG4, (f) S228P and L236E in the Fc region of human IgG4, (g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2, (i) C220S, C226S, C229S and P238S in the Fc region of human IgG1, (j) C226S, C229S, E233P, L234V and L235A in the Fc region of human IgG1, (k) L234F, L235E and P331S in the Fc region of human IgG1, (l) C226S and P230S in the Fc region of human IgG1, and (m) S267E and L328F in the Fc region of human IgG1. In some embodiments, the antibody comprises an Fc region comprising a modification for attenuating effector function that results in an aglycosylated Fc region. In some embodiments, the antibody comprises an Fc region comprising a modification for attenuating effector function that does not result in a modification of the glycosylation pattern of the Fc region.

In another aspect, provided herein is a method of producing a tetravalent antigen binding complex having agonist activity for a cell surface receptor bound by the complex, the method comprising: (a) expressing in a host cell two antibody heavy chains, wherein each antibody heavy chain comprises, from N-terminus to C-terminus, a first antibody heavy chain variable domain ($VH_1$), a first antibody heavy chain CH1 domain ($CH1_1$), a second heavy chain variable domain ($VH_2$), a second heavy chain CH1 domain ($CH1_2$), an antibody heavy chain CH2 domain, and an antibody heavy chain CH3 domain, wherein each $VH_1$ and/or each $CH1_1$ comprises a first modification for orthogonal pairing, wherein each $VH_2$ and/or each $CH1_2$ comprises a second modification for orthogonal pairing, and wherein the first and the second modifications are different; (b) expressing in the host cell two first antibody light chains, wherein each of the two first antibody light chains comprises, from N-terminus to C-terminus, a first antibody light chain variable domain ($VL_1$) and a first antibody light chain constant domain ($CL_1$), and wherein the $VL_1$ and/or the $CL_1$ comprises a modification for orthogonal pairing with the first modification of the antibody heavy chains; and (c) expressing in the host cell two second antibody light chains, wherein each of the two second antibody light chains comprises, from N-terminus to C-terminus, a second antibody light chain variable domain ($VL_2$) and a second antibody light chain constant domain ($CL_2$), and wherein the $VL_2$ and/or the $CL_2$ comprises a modification for orthogonal pairing with the second modification of the antibody heavy chains; wherein the $VH_1$ and $VL_1$ specifically bind to a first epitope of the cell surface receptor; wherein the $VH_2$ and $VL_2$ specifically bind to a second epitope of the cell surface receptor; and wherein upon expression in the host cell, the two antibody heavy chains associate, each of the two heavy chains couples with a first antibody light chain via orthogonal pairing, and each of the two heavy chains couples with a second antibody light chain via orthogonal pairing, thereby producing the complex. In some embodiments, each of the first and the second modifications of the antibody heavy chain are independently selected from VH-Q39K, VH-Q39E, CH1-S183E, CH1-S183K, CH1-A141I, CH1-F170S, CH1-S181M, CH1-S183A, and CH1-V185A (EU numbering). In some embodiments, each of the modifications of the first and the second antibody light chains are independently selected from VL-Q38E, VL-Q38K, CL-V133K, CL-V133E, CL-F116A, CL-L135V, CL-S174A, CL-S176F, and CL-T178V (EU numbering). In some embodiments, the first and the second epitopes of the cell surface receptor are the same. In some embodiments, the first and the second epitopes of the cell surface receptor are different. In some embodiments, each antibody heavy chain comprises an Fc region comprising a modification for attenuating effector function. In some embodiments, each antibody heavy chain comprises an Fc region comprising an amino acid substitution at one or more amino acid residues (EU numbering) selected from (a) 297 in the Fc region of human IgG1, (b) 234 and 235 in the Fc region of human IgG1, (c) 234, 235 and 329 in the Fc region of human IgG1, (d) 234 and 237 in the Fc region of human IgG2, (e) 235, 237 and 318 in the Fc region of human IgG4, (f) 228 and 236 in the Fc region of human IgG4, (g) 268, 309, 330 and 331 in the Fc region of human IgG2, (h) 220, 226, 229 and 238 in the Fc region of human IgG1, (i) 226, 229, 233, 234 and 235 in the Fc region of human IgG1, (j) 234, 235 and 331 in the Fc region of human IgG1, (k) 226 and 230 in the Fc region of human IgG1, and (l) 267 and 328 in the Fc region of human IgG1. In some embodiments, each antibody heavy chain comprises an Fc region comprising one or more amino acid substitutions (EU numbering) selected from (a) N297A in the Fc region of human IgG1, (b) L234A and L235A in the Fc region of human IgG1, (c) L234A, L235A and P329G in the Fc region of human IgG1, (d) V234A and G237A in the Fc region of human IgG2, (e) L235A, G237A and E318A in the Fc region of human IgG4, (f) S228P and L236E in the Fc region of human IgG4, (g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2, (i) C220S, C226S, C229S and P238S in the Fc region of human IgG1, (j) C226S, C229S, E233P, L234V and L235A in the Fc region of human IgG1, (k) L234F, L235E and P331S in the Fc region of human IgG1, (l) C226S and P230S in the Fc region of human IgG1, and (m) S267E and L328F in the Fc region of human IgG1. In some embodiments, each antibody heavy chain comprises an Fc region comprising a modification for attenuating effector function that results in an aglycosylated Fc region. In some embodiments, each antibody heavy chain comprises an Fc region comprising a modification for attenuating effector function that does not result in a modification of the glycosylation pattern of the Fc region.

In some embodiments of any of the above embodiments, the cell surface receptor is a member of a receptor family selected from the group consisting of tumor necrosis factor receptor (TNFR) superfamily and G-Protein Coupled Receptor (GPCR) superfamily. In some embodiments of any of the above embodiments, the cell surface receptor is selected from the group consisting of OX40, DR5, GITR, CD27, CD137, and Tie2. In some embodiments of any of the above embodiments, the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments of any of the above embodiments, the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In some embodiments of any of the above embodiments, the $VH_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments of any of the above embodiments, the $VH_1$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

In some embodiments, an antigen binding complex of the present disclosure shows agonist activity in vitro.

Also provided herein are antigen binding complexes (e.g., tetravalent and biepitopic antigen binding complexes) that bind OX40 and have one or more agonist activities described herein for OX40.

In one aspect, provided herein is a tetravalent antigen binding complex having agonist activity for OX40, the complex comprising four antigen binding domains that bind OX40, wherein each of the four antigen binding domains comprises an antibody heavy chain variable (VH) domain and an antibody light chain variable (VL) domain, wherein the complex comprises one or more antigen binding domains that bind a first epitope of OX40 and one or more antigen binding domains that bind a second epitope of OX40, and the first and second epitopes of OX40 are different. In some embodiments, the antigen binding domains that bind the first epitope do not cross-compete for binding OX40 with the antigen binding domains that bind the second epitope.

In one aspect, provided herein is a tetravalent antigen binding complex having agonist activity for OX40, the complex comprising four antigen binding domains that bind OX40, wherein each of the four antigen binding domains comprises an antibody heavy chain variable (VH) domain and an antibody light chain variable (VL) domain, wherein the complex comprises one or more antigen binding domains that bind a first epitope of OX40 and one or more antigen binding domains that bind a second epitope of OX40, and the antigen binding domains that bind the first epitope do not cross-compete for binding OX40 with the antigen binding domains that bind the second epitope. In some embodiments, the complex comprises two antigen binding domains that bind to the first epitope and two antigen binding domains that bind to the second epitope.

In some embodiments, the first epitope comprises one or more amino acid residues selected from the group consisting of: 114-119, 124, 126, 127, 129, 130, 132, 140, and 142 of SEQ ID NO:281. In some embodiments, the first epitope comprises amino acid residues 114-119, 124, 126, 127, 129, 130, 132, 140, and 142 of SEQ ID NO:281. In some embodiments, the antigen binding domain that binds the first epitope of OX40 comprises: (a) a VH domain comprising an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and (b) a VL domain comprising an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, the VH domain of the antigen binding domain that binds the first epitope of OX40 comprises the amino acid sequence of SEQ ID NO:56, and the VL domain of the antigen binding domain that binds the first epitope of OX40 comprises the amino acid sequence of SEQ ID NO:57. In some embodiments, the second epitope comprises one or more amino acid residues selected from the group consisting of: 68-71, 83-90, 95, and 98 of SEQ ID NO:281. In some embodiments, the second epitope comprises amino acid residues 68-71, 83-90, 95, and 98 of SEQ ID NO:281. In some embodiments, the antigen binding domain that binds the second epitope of OX40 comprises: (a) a VH domain comprising an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; and (b) a VL domain comprising: an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42. In some embodiments, the VH domain of the antigen binding domain that binds the second epitope of OX40 comprises the amino acid sequence of SEQ ID NO:128, and the VL domain of the antigen binding domain that binds the second epitope of OX40 comprises the amino acid sequence of SEQ ID NO:129. In some embodiments, the antigen binding domain that binds the first epitope of OX40 comprises: (a) a VH domain comprising an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and (b) a VL domain comprising an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7; and the antigen binding domain that binds the second epitope of OX40 comprises: (c) a VH domain comprising an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; and (d) a VL domain comprising: an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42. In some embodiments, the VH domain of the antigen binding domain that binds the first epitope of OX40 comprises the amino acid sequence of SEQ ID NO:56, the VL domain of the antigen binding domain that binds the first epitope of OX40 comprises the amino acid sequence of SEQ ID NO:57; the VH domain of the antigen binding domain that binds the second epitope of OX40 comprises the amino acid sequence of SEQ ID NO:128, and the VL domain of the antigen binding domain that binds the second epitope of OX40 comprises the amino acid sequence of SEQ ID NO:129.

In some embodiments, the complex comprises two antibody heavy chain polypeptides and two antibody light chain polypeptides; wherein each of the antibody heavy chain polypeptides comprises: $VH_1$-$L_1$-$VH_2$-$L_2$-$CH_1$-hinge-$CH_2$-$CH_3$ [I]; wherein each of the antibody light chain polypeptides comprises: $VL_1$-$L_3$-$VL_2$-$L_4$-CL [II]; wherein each of the antibody heavy chain polypeptides associates with one antibody light chain polypeptide such that $VH_1$ and $VL_1$ form an antigen binding domain and $VH_2$ and $VL_2$ form an antigen binding domain; $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, $CH_3$ is an antibody third heavy chain constant domain, and $L_1$, $L_2$, $L_3$, and $L_4$ are amino acid linkers. In some embodiments, $VH_1$ and $VL_1$ form an antigen binding domain that binds the first epitope of OX40, and $VH_2$ and $VL_2$ form an antigen binding domain that binds the second epitope of OX40. In some embodiments, $VH_1$ and $VL_1$ form an antigen binding domain that binds the second epitope of OX40, and $VH_2$ and $VL_2$ form an antigen binding domain that binds the first epitope of OX40. In some embodiments, $L_2$ and $L_4$ are 0 amino acids in length. In some embodiments, $L_1$ is between 0 and 20 amino acids in length. In some embodiments, at least 90% of the amino acids of $L_1$ are glycine and/or serine amino acids. In some embodiments, $L_1$ comprises an amino acid sequence selected from the group consisting of GGGGSG (SEQ ID NO:270), GGGGSGGGGS (SEQ ID NO:272), and GGGGSGGGGSGGGG (SEQ ID NO:273). In some embodiments, $L_3$ comprises an amino acid sequence selected from the group consisting of GGSGG (SEQ ID NO:271), GGGGSGGGGS (SEQ ID NO:272), and GGSGGGGSGGGGS (SEQ ID NO:274). In some embodiments, $L_1$ comprises the amino acid sequence GGGGSG (SEQ ID NO:270), and $L_3$ comprises the amino acid sequence GGSGG (SEQ ID NO:271). In some embodiments, $L_1$ and $L_3$ both comprise the amino acid sequence GGGGSGGGGS (SEQ ID NO:272). In some embodiments, $L_1$ comprises the amino acid sequence GGGGSGGGGSGGGG (SEQ ID NO:273), and $L_3$ comprises the amino acid sequence GGSGGGGSGGGGS (SEQ ID NO:274). In some embodiments, $L_1$ comprises an amino acid sequence found within a human antibody constant domain sequence. In some embodiments, $L_1$ comprises the amino acid sequence ASTKGP (SEQ ID NO:275) or ASTKGPSVFPLAP (SEQ ID NO:277). In some embodiments, $L_3$ comprises the amino acid sequence RTVAAP (SEQ ID NO:276) or RTVAAPSVFIFPP (SEQ ID NO:278). In some embodiments, $L_1$ comprises the amino acid sequence ASTKGP (SEQ ID NO:275), and $L_3$ comprises the amino acid sequence RTVAAP (SEQ ID NO:276). In some embodiments, $L_1$ comprises the amino acid sequence ASTKGPSVFPLAP (SEQ ID NO:277), and $L_3$ comprises the amino acid sequence RTVAAPSVFIFPP (SEQ ID NO:278). In some embodiments of any of the above embodiments, $VH_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; $VH_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and $VL_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, $VH_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; $VH_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and $VL_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_1$ comprises the amino acid sequence of SEQ ID NO:128, VL$_1$ comprises the amino acid sequence of SEQ ID NO:129, VH$_2$ comprises the amino acid sequence of SEQ ID NO:56, and VL$_2$ comprises the amino acid sequence of SEQ ID NO:57. In some embodiments, VH$_2$ comprises the amino acid sequence of SEQ ID NO:128 or 290, VL$_2$ comprises the amino acid sequence of SEQ ID NO:129, VH$_1$ comprises the amino acid sequence of SEQ ID NO:56, 284, or 285, and VL$_1$ comprises the amino acid sequence of SEQ ID NO:57 or 287. In any of the complexes described above, a VH$_1$, VH$_2$, VL$_1$, and/or VL$_2$ comprises an HVR-H1, HVR-H2, HVR-H3, HVR-L1, HVR-L2, and/or HVR-L3 that comprise one or more of the sequences listed in Tables 4 and 5. In some embodiments, both of the antibody heavy chain polypeptides comprise the amino acid sequence of SEQ ID NO:240, and both of the antibody light chain polypeptides comprise the amino acid sequence of SEQ ID NO:241; both of the antibody heavy chain polypeptides comprise the amino acid sequence of SEQ ID NO:242, and both of the antibody light chain polypeptides comprise the amino acid sequence of SEQ ID NO:243; both of the antibody heavy chain polypeptides comprise the amino acid sequence of SEQ ID NO:250, and both of the antibody light chain polypeptides comprise the amino acid sequence of SEQ ID NO:251; both of the antibody heavy chain polypeptides comprise the amino acid sequence of SEQ ID NO:252, and both of the antibody light chain polypeptides comprise the amino acid sequence of SEQ ID NO:253; both of the antibody heavy chain polypeptides comprise the amino acid sequence of SEQ ID NO:254, and both of the antibody light chain polypeptides comprise the amino acid sequence of SEQ ID NO:255; both of the antibody heavy chain polypeptides comprise the amino acid sequence of SEQ ID NO:256, and both of the antibody light chain polypeptides comprise the amino acid sequence of SEQ ID NO:257; both of the antibody heavy chain polypeptides comprise the amino acid sequence of SEQ ID NO:258, and both of the antibody light chain polypeptides comprise the amino acid sequence of SEQ ID NO:259; both of the antibody heavy chain polypeptides comprise the amino acid sequence of SEQ ID NO:260, and both of the antibody light chain polypeptides comprise the amino acid sequence of SEQ ID NO:261; both of the antibody heavy chain polypeptides comprise the amino acid sequence of SEQ ID NO:262, and both of the antibody light chain polypeptides comprise the amino acid sequence of SEQ ID NO:263; both of the antibody heavy chain polypeptides comprise the amino acid sequence of SEQ ID NO:264, and both of the antibody light chain polypeptides comprise the amino acid sequence of SEQ ID NO:265; or both of the antibody heavy chain polypeptides comprise the amino acid sequence of SEQ ID NO:266, and both of the antibody light chain polypeptides comprise the amino acid sequence of SEQ ID NO:267. In some embodiments, both of the antibody heavy chain polypeptides comprise the amino acid sequence of SEQ ID NO:240, and both of the antibody light chain polypeptides comprise the amino acid sequence of SEQ ID NO:241; or both of the antibody heavy chain polypeptides comprise the amino acid sequence of SEQ ID NO:242, and both of the antibody light chain polypeptides comprise the amino acid sequence of SEQ ID NO:243. In some embodiments of any of the above embodiments, a C-terminal lysine of a heavy chain polypeptide can be absent or removed. In some embodiments, both of the antibody heavy chain polypeptides comprise the amino acid sequence of SEQ ID NO:242 or 291, and both of the antibody light chain polypeptides comprise the amino acid sequence of SEQ ID NO:243.

In some embodiments, the complex comprises two antibody heavy chain polypeptides and four antibody light chain polypeptides; wherein each of the antibody heavy chain polypeptides comprises: VH$_1$-L$_1$-(CH$_1$)$_x$-L$_2$-VH$_2$-L$_3$-(CH$_1$)$_y$ -hinge-CH$_2$-CH$_3$ [III]; wherein two of the four antibody light chain polypeptides comprise: VL$_1$-(CL)$_x$ [IV]; and wherein two of the four antibody light chain polypeptides comprise: VL$_2$-(CL)$_y$ [V]; wherein each of the antibody heavy chain polypeptides associates with one light chain polypeptide comprising formula [IV] such that VH$_1$ and VL$_1$ form an antigen binding domain and one light chain polypeptide comprising formula [V] such that VH$_2$ and VL$_2$ form an antigen binding domain; and VH$_1$ is a first antibody heavy chain variable domain, VH$_2$ is a second antibody heavy chain variable domain, VL$_1$ is a first antibody light chain variable domain, VL$_2$ is a second antibody light chain variable domain, (CL)$_x$ and (CL)$_y$ are antibody light chain constant domains, (CH$_1$)$_x$ and (CH$_1$)$_y$ are antibody first heavy chain constant domains, hinge is an antibody hinge region, CH$_2$ is an antibody second heavy chain constant domain, CH$_3$ is an antibody third heavy chain constant domain, and L$_1$, L$_2$, and L$_3$ are amino acid linkers. In some embodiments, the complex comprises one or more amino acid substitutions in VH$_1$, VL$_1$, (CH$_1$)$_x$, or (CL)$_x$ that promote VH$_1$ and VL$_1$ forming an antigen binding domain; and/or one or more amino acid substitutions in VH$_2$, VL$_2$, (CH$_1$)$_y$, or (CL)$_y$ that promote VH$_2$ and VL$_2$ forming an antigen binding domain. In some embodiments, the complex comprises one or more of the following pairs of amino acid substitutions: a Q39K substitution in VH$_1$ and a Q38E substitution in VL$_1$, numbering according to Kabat; a Q39K substitution in VH$_2$ and a Q38E substitution in VL$_2$, numbering according to Kabat; a Q39E substitution in VH$_1$ and a Q38K substitution in VL$_1$, numbering according to Kabat; a Q39E substitution in VH$_2$ and a Q38K substitution in VL$_2$, numbering according to Kabat; an S183E substitution in (CH$_1$)$_x$ and a V133K substitution in (CL)$_x$, numbering according to EU index; an S183K substitution in (CH$_1$)$_x$ and a V133E substitution in (CL)$_x$, numbering according to EU index; an S183E substitution in (CH$_1$)$_y$ and a V133K substitution in (CL)$_y$, numbering according to EU index; and an S183K substitution in (CH$_1$)$_y$ and a V133E substitution in (CL)$_y$, numbering according to EU index. In some embodiments, the complex comprises one or more of the following sets of amino acid substitutions: a Q39K substitution in VH$_1$ and a Q38E substitution in VL$_1$, and a Q39E substitution in VH$_2$ and a Q38K substitution in VL$_2$, numbering according to Kabat; a Q39K substitution in VH$_2$ and a Q38E substitution in VL$_2$, and a Q39E substitution in VH$_1$ and a Q38K substitution in VL$_1$, numbering according to Kabat; an S183E substitution in (CH$_1$)$_x$ and a V133K substitution in (CL)$_x$, and an S183K substitution in (CH$_1$)$_y$ and a V133E substitution in (CL)$_y$, numbering according to EU index; or an S183E substitution in (CH$_1$)$_y$ and a V133K substitution in (CL)$_y$, and an S183K substitution in (CH$_1$)$_x$ and a V133E substitution in (CL)$_x$, numbering according to EU index. In some embodiments, the complex comprises: a Q39K substitution in VH$_1$ and a Q38E substitution in VL$_1$, and a Q39E substitution in VH$_2$ and a Q38K substitution in VL$_2$, with numbering according to Kabat; and an S183E substitution in (CH$_1$)$_x$ and a V133K substitution in (CL)$_x$, and an S183K substitution in (CH$_1$)$_y$ and a V133E substitution in (CL)$_y$, numbering according to EU index; or Q39K substitution in VH$_2$ and a Q38E substitution in VL$_2$, and a Q39E substitution in VH$_1$ and a Q38K substitution in VL$_1$, numbering according to Kabat; and or an S183E substitution in (CH$_1$)$_y$, and a V133K substitution in (CL)$_y$, and an S183K substitution in (CH$_1$)$_x$ and a V133E substitution in (CL)$_x$, numbering according to EU index. In some embodiments, VH$_1$ and VL$_1$ form an antigen binding domain that binds the first epitope of OX40, and VH$_2$ and VL$_2$ form an antigen binding domain that binds the second epitope of OX40. In some embodiments, VH$_1$ and VL$_1$ form an antigen binding domain that binds the second epitope of OX40, and VH$_2$ and VL$_2$ form an antigen binding domain that binds the first epitope of OX40. In some embodiments, L$_2$ comprises an amino acid sequence found within a human antibody constant domain sequence. In some embodiments, L$_2$ comprises the amino acid sequence DKTHT (SEQ ID NO:268) or DKTH-TGGGGSGG (SEQ ID NO:269). In some embodiments, L$_1$ and L$_3$ are 0 amino acids in length. In some embodiments of any of the above embodiments, VH$_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_1$ comprises the amino acid sequence of SEQ ID NO:128, VL$_1$ comprises the amino acid sequence of SEQ ID NO:129, VH$_2$ comprises the amino acid sequence of SEQ ID NO:56, and VL$_2$ comprises the amino acid sequence of SEQ ID NO:57. In some embodiments, VH$_2$ comprises the amino acid sequence of SEQ ID NO:128 or 290, VL$_2$ comprises the amino acid sequence of SEQ ID NO:129, VH$_1$ comprises the amino acid sequence of SEQ ID NO:56, 284, or 285, and VL$_1$ comprises the amino acid sequence of SEQ ID NO:57 or 287. In any of the complexes described above, a VH$_1$, VH$_2$, VL$_1$, and/or VL$_2$ comprises an HVR-H1, HVR-H2, HVR-H3, HVR-L1, HVR-L2, and/or HVR-L3 that comprise one or more of the sequences listed in Tables 4 and 5. In some embodiments, both of the antibody heavy chain polypeptides comprise the amino acid sequence of SEQ ID NO:244 or 292, both of the antibody light chain polypeptides comprising formula [IV] comprise the amino acid sequence of SEQ ID NO:245, and both of the antibody light chain polypeptides comprising formula [V] comprise the amino acid sequence of SEQ ID NO:246; or both of the antibody heavy chain polypeptides comprise the amino acid sequence of SEQ ID NO:247 or 293, both of the antibody light chain polypeptides comprising formula [IV] comprise the amino acid sequence of SEQ ID NO:248, and both of the antibody light chain polypeptides comprising formula [V] comprise the amino acid sequence of SEQ ID NO:249. In some embodiments of any of the above embodiments, a C-terminal lysine in the heavy chain polypeptide can be absent or removed.

In some embodiments, the complex comprises a first antibody heavy chain polypeptide that comprises: VH$_1$-L$_1$-CH$_1$-L$_2$-VH$_1$-L$_3$-CH$_1$-hinge-CH$_2$-(CH$_3$)$_x$ [VI]; two first antibody light chain polypeptides that each comprise: VL$_1$-CL [VII]; a second antibody heavy chain polypeptide that comprises: VH$_2$-L$_7$-CH$_1$-L$_8$-VH$_2$-L$_9$-CH$_1$-hinge-CH$_2$-(CH$_3$)$_y$ [VIII]; and two second antibody light chain polypeptides that each comprise: VL$_2$-CL [IX]; wherein the first antibody heavy chain polypeptide associates with two first antibody light chain polypeptides comprising formula [VII] such that each VH$_1$ forms an antigen binding domain with a VL$_1$; wherein the second antibody heavy chain polypeptide associates with two second antibody light chain polypeptides comprising formula [IX] such that each VH$_2$ forms an antigen binding domain with a VL$_2$; and VH$_1$ is a first antibody heavy chain variable domain, VH$_2$ is a second antibody heavy chain variable domain, VL$_1$ is a first antibody light chain variable domain, VL$_2$ is a second antibody light chain variable domain, CL is an antibody light chain constant domain, CH$_1$ is an antibody first heavy chain constant domain, hinge is an antibody hinge region, CH$_2$ is an antibody second heavy chain constant domain, (CH$_3$)$_x$ and (CH$_3$)$_y$ are antibody third heavy chain constant domains, and L$_1$, L$_2$, L$_3$, L$_7$, L$_8$, and L$_9$ are amino acid linkers. In some embodiments, (CH$_3$)$_x$ comprises a protuberance or cavity, (CH$_3$)$_y$ comprises a protuberance or cavity, and the protuberance or cavity of (CH$_3$)$_x$ is positionable in the protuberance or cavity of (CH$_3$)$_y$. In some embodiments, (CH$_3$)$_x$ comprises a T366Y substitution, and (CH$_3$)$_y$ comprises a Y407T substitution, numbering according to EU index; (CH$_3$)$_x$ comprises a T366W substitution, and (CH$_3$)$_y$ comprises a Y407A substitution, numbering according to EU index; (CH$_3$)$_x$ comprises a F405A substitution, and (CH$_3$)$_y$ comprises a T394W substitution, numbering according to EU index; (CH$_3$)$_x$ comprises a Y407T substitution, and (CH$_3$)$_y$ comprises a T366Y substitution, numbering according to EU index; (CH$_3$)$_x$ comprises T366Y and F405A substitutions, and (CH$_3$)$_y$ comprises T394W and Y407T substitutions, numbering according to EU index; (CH$_3$)$_x$ comprises T366W and F405W substitutions, and (CH$_3$)$_y$ comprises T394S and Y407A substitutions, numbering according to EU index; (CH$_3$)$_x$ comprises F405W and Y407A substitutions, and (CH$_3$)$_y$ comprises T366W and T394S substitutions, numbering according to EU index; (CH$_3$)$_x$ comprises a F405W substitution, and (CH$_3$)$_y$ comprises a T394S substitution, numbering according to EU index; (CH$_3$)$_y$ comprises a T366Y substitution, and (CH$_3$)$_x$ comprises a Y407T substitution, numbering according to EU index; (CH$_3$)$_y$ comprises a T366W substitution, and (CH$_3$)$_x$ comprises a Y407A substitution, numbering according to EU index; (CH$_3$)$_y$ comprises a F405A substitution, and (CH$_3$)$_x$ comprises a T394W substitution, numbering according to EU index; (CH$_3$)$_y$ comprises a Y407T substitution, and (CH$_3$)$_x$ comprises a T366Y substitution, numbering according to EU index; (CH$_3$)$_y$ comprises T366Y and F405A substitutions, and (CH$_3$)$_x$ comprises T394W and Y407T substitutions, numbering according to EU index; (CH$_3$)$_y$ comprises T366W and F405W substitutions, and (CH$_3$)$_x$ comprises T394S and Y407A substitutions, numbering according to EU index; (CH$_3$)$_y$ comprises F405W and Y407A substitutions, and (CH$_3$)$_x$ comprises T366W and T394S substitutions, numbering according to EU index; or (CH$_3$)$_y$ comprises a F405W substitution, and (CH$_3$)$_x$ comprises a T394S substitution, numbering according to EU index. In some embodiments, VH$_1$ and VL$_1$ form an antigen binding domain that binds the first epitope of OX40, and VH$_2$ and VL$_2$ form an antigen binding domain that binds the second epitope of OX40. In some embodiments, VH$_1$ and VL$_1$ form an antigen binding domain that binds the second epitope of OX40, and VH$_2$ and VL$_2$ form an antigen binding domain that binds the first epitope of OX40. In some embodiments, L$_2$ and L$_8$ both comprise an amino acid sequence found within a human antibody constant domain sequence. In some embodiments, L$_2$ and L$_8$ both comprise the same amino acid sequence selected from the group consisting of DKTHT (SEQ ID NO:268) and DKTHTGGGGSGG (SEQ ID NO:269). In some embodiments, L$_1$, L$_3$, L$_7$, and L$_9$ are 0 amino acids in length. In some embodiments of any of the above embodiments, VH$_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_1$ comprises the amino acid sequence of SEQ ID NO:128, VL$_1$ comprises the amino acid sequence of SEQ ID NO:129, VH$_2$ comprises the amino acid sequence of SEQ ID NO:56, and VL$_2$ comprises the amino acid sequence of SEQ ID NO:57. In some embodiments, VH$_2$ comprises the amino acid sequence of SEQ ID NO:128 or 290, VL$_2$ comprises the amino acid sequence of SEQ ID NO:129, VH$_1$ comprises the amino acid sequence of SEQ ID NO:56, 284, or 285, and VL$_1$ comprises the amino acid sequence of SEQ ID NO:57 or 287. In any of the complexes described above, a VH$_1$, VH$_2$, VL$_1$, and/or VL$_2$ comprises an HVR-H1, HVR-H2, HVR-H3, HVR-L1, HVR-L2, and/or HVR-L3 that comprise one or more of the sequences listed in Tables 4 and 5.

In some embodiments, the complex comprises an antibody comprising two antibody heavy chains associated with two antibody light chains, and two antibody Fab fragments; wherein each of the antibody heavy chains of the antibody comprises: VH$_1$-CH$_1$-hinge-CH$_2$-CH$_3$ [X]; wherein each of the antibody light chains of the antibody comprises: VL$_1$-CL [VII]; wherein each of the antibody Fab fragments comprises: a heavy chain fragment comprising: VH$_2$-CH$_1$ [XI]; and a light chain comprising: VL$_2$-CL [IX]; wherein each of the antibody heavy chains is associated with one of the antibody light chains such that VH$_1$ and VL$_1$ form an antigen binding domain; wherein each of the antibody Fab fragments comprises one heavy chain fragment comprising formula [XI] associated with one light chain fragment comprising formula [IX] such that VH$_2$ and VL$_2$ form an antigen binding domain; each of the antibody Fab fragments is coupled with one of the antibody heavy chains or one of the antibody light chains of the antibody via linker L$_1$; and VH$_1$ is a first antibody heavy chain variable domain, VH$_2$ is a second antibody heavy chain variable domain, VL$_1$ is a first antibody light chain variable domain, VL$_2$ is a second antibody light chain variable domain, CL is an antibody light chain constant domain, CH$_1$ is an antibody first heavy chain constant domain, hinge is an antibody hinge region, CH$_2$ is an antibody second heavy chain constant domain, and CH$_3$ is an antibody third heavy chain constant domain. In some embodiments, each of the L$_1$ linkers is a bis-maleimido polyethylene glycol (PEG) linker. In some embodiments, the PEG linker comprises between one and eleven PEG subunits. In some embodiments, the PEG linker comprises one, two, or three PEG subunits. In some embodiments, each of the L$_1$ linkers couples a first engineered free cysteine of one of the antibody heavy chains or one of the antibody light chains with a second engineered free cysteine of one of the antibody Fab fragments. In some embodiments, the first engineered free cysteine is a cysteine amino acid in the antibody heavy chain independently selected from the group consisting of T114C, A118C, A140C, L174C, L179C, T187C, T209C, V262C, G371C, Y373C, E382C, S400C, S424C, N434C and Q438C, according to EU numbering. In some embodiments, the first engineered free cysteine is a cysteine amino acid in the antibody light chain independently selected from the group consisting of I106C, R108C, R142C, K149C, and V205C, according to Kabat numbering. In some embodiments, the second engineered free cysteine is a C-terminal cysteine residue. In some embodiments, VH$_1$ and VL$_1$ form an antigen binding domain that binds the first epitope of OX40, and VH$_2$ and VL$_2$ form an antigen binding domain that binds the second epitope of OX40. In some embodiments, VH$_1$ and VL$_1$ form an antigen binding domain that binds the second epitope of OX40, and VH$_2$ and VL$_2$ form an antigen binding domain that binds the first epitope of OX40. In some embodiments of any of the above embodiments, VH$_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and $VL_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, $VH_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; $VH_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and $VL_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, $VH_1$ comprises the amino acid sequence of SEQ ID NO:128, $VL_1$ comprises the amino acid sequence of SEQ ID NO:129, $VH_2$ comprises the amino acid sequence of SEQ ID NO:56, and $VL_2$ comprises the amino acid sequence of SEQ ID NO:57. In some embodiments, $VH_2$ comprises the amino acid sequence of SEQ ID NO:128 or 290, $VL_2$ comprises the amino acid sequence of SEQ ID NO:129, $VH_1$ comprises the amino acid sequence of SEQ ID NO:56, 284, or 285, and $VL_1$ comprises the amino acid sequence of SEQ ID NO:57 or 287. In any of the complexes described above, a $VH_1$, $VH_2$, $VL_1$, and/or $VL_2$ comprises an HVR-H1, HVR-H2, HVR-H3, HVR-L1, HVR-L2, and/or HVR-L3 that comprise one or more of the sequences listed in Tables 4 and 5. In some embodiments, each of the antibody heavy chains of the antibody comprises the amino acid sequence of SEQ ID NO:232, each of the antibody light chains of the antibody comprises the amino acid sequence of SEQ ID NO:237, each of the antibody Fab fragments comprises a heavy chain fragment comprising the amino acid sequence of SEQ ID NO:239, and each of the antibody Fab fragments comprises a light chain fragment comprising the amino acid sequence of SEQ ID NO:231. In some embodiments, each of the antibody heavy chains of the antibody comprises the amino acid sequence of SEQ ID NO:230 or 294, each of the antibody light chains of the antibody comprises the amino acid sequence of SEQ ID NO:236, each of the antibody Fab fragments comprises a heavy chain fragment comprising the amino acid sequence of SEQ ID NO:238, and each of the antibody Fab fragments comprises a light chain fragment comprising the amino acid sequence of SEQ ID NO:233. In some embodiments of any of the above embodiments, a C-terminal lysine of a heavy chain polypeptide can be absent or removed.

In some embodiments, the complex comprises two antibodies, wherein each of the antibodies comprises: a first antibody heavy chain comprising: $VH_1$-$CH_1$-hinge-$CH_2$-$(CH_3)_x$ [X]; a first antibody light chain comprising: $VL_1$-CL [VII]; a second antibody heavy chain comprising: $VH_2$-$CH_1$-hinge-$CH_2$-$(CH_3)_y$ [XII]; and a second antibody light chain that comprises: $VL_2$-CL [IX]; wherein the first antibody heavy chain associates with the first antibody light chain such that $VH_1$ and $VL_1$ form an antigen binding domain; wherein the second antibody heavy chain associates with the second antibody light chain such that $VH_2$ and $VL_2$ form an antigen binding domain; wherein the two antibodies are coupled via linker $L_1$; and $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, and $(CH_3)_x$ and $(CH_3)_y$ are antibody third heavy chain constant domains. In some embodiments, $(CH_3)_x$ comprises a protuberance or cavity, $(CH_3)_y$ comprises a protuberance or cavity, and the protuberance or cavity of $(CH_3)_x$ is positionable in the protuberance or cavity of $(CH_3)_y$. In some embodiments, $(CH_3)_x$ comprises a T366Y substitution, and $(CH_3)_y$ comprises a Y407T substitution, numbering according to EU index; $(CH_3)_x$ comprises a T366W substitution, and $(CH_3)_y$ comprises a Y407A substitution, numbering according to EU index; $(CH_3)_x$ comprises a F405A substitution, and $(CH_3)_y$ comprises a T394W substitution, numbering according to EU index; $(CH_3)_x$ comprises a Y407T substitution, and $(CH_3)_y$ comprises a T366Y substitution, numbering according to EU index; $(CH_3)_x$ comprises T366Y and F405A substitutions, and $(CH_3)_y$ comprises T394W and Y407T substitutions, numbering according to EU index; $(CH_3)_x$ comprises T366W and F405W substitutions, and $(CH_3)_y$ comprises T394S and Y407A substitutions, numbering according to EU index; $(CH_3)_x$ comprises F405W and Y407A substitutions, and $t(CH_3)_y$ comprises T366W and T394S substitutions, numbering according to EU index; $(CH_3)_x$ comprises a F405W substitution, and $(CH_3)_y$ comprises a T394S substitution, numbering according to EU index; $(CH_3)_y$ comprises a T366Y substitution, and $(CH_3)_x$ comprises a Y407T substitution, numbering according to EU index; $(CH_3)_y$ comprises a T366W substitution, and $(CH_3)_x$ comprises a Y407A substitution, numbering according to EU index; $(CH_3)_y$ comprises a F405A substitution, and $(CH_3)_x$ comprises a T394W substitution, numbering according to EU index; $(CH_3)_y$ comprises a Y407T substitution, and $(CH_3)_x$ comprises a T366Y substitution, numbering according to EU index; $(CH_3)_y$ comprises T366Y and F405A substitutions, and $(CH_3)_x$ comprises T394W and Y407T substitutions, numbering according to EU index; $(CH_3)_y$ comprises T366W and F405W substitutions, and $(CH_3)_x$ comprises T394S and Y407A substitutions, numbering according to EU index; $(CH_3)_y$ comprises F405W and Y407A substitutions, and $(CH_3)_x$ comprises T366W and T394S substitutions, numbering according to EU index; or $(CH_3)_y$ comprises a F405W substitution, and $(CH_3)_x$ comprises a T394S substitution, numbering according to EU index. In some embodiments, the $L_1$ linker is a bis-maleimido polyethylene glycol (PEG) linker. In some embodiments, the PEG linker comprises between one and eleven PEG subunits. In some embodiments, the PEG linker comprises one, two, or three PEG subunits. In some embodiments, the $L_1$ linker couples a first engineered free cysteine of a first of the two antibodies with a second engineered free cysteine of a second of the two antibodies. In some embodiments, at least one of the first or the second engineered free cysteine is a cysteine residue in the heavy chain independently selected from the group consisting of T114C, A118C, A140C, L174C, L179C, T187C, T209C, V262C, G371C, Y373C, E382C, S400C, S424C, N434C and Q438C, according to EU numbering. In some embodiments, at least one of the first or the second engineered free cysteine is a cysteine residue in the light chain independently selected from the group consisting of I106C, R108C, R142C, K149C, and V205C, according to Kabat numbering. In some embodiments, VH$_1$ and VL$_1$ form an antigen binding domain that binds the first epitope of OX40, and VH$_2$ and VL$_2$ form an antigen binding domain that binds the second epitope of OX40. In some embodiments, VH$_1$ and VL$_1$ form an antigen binding domain that binds the second epitope of OX40, and VH$_2$ and VL$_2$ form an antigen binding domain that binds the first epitope of OX40. In some embodiments of any of the above embodiments, VH$_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_1$ comprises the amino acid sequence of SEQ ID NO:128, VL$_1$ comprises the amino acid sequence of SEQ ID NO:129, VH$_2$ comprises the amino acid sequence of SEQ ID NO:56, and VL$_2$ comprises the amino acid sequence of SEQ ID NO:57. In some embodiments, VH$_2$ comprises the amino acid sequence of SEQ ID NO:128 or 290, VL$_2$ comprises the amino acid sequence of SEQ ID NO:129, VH$_1$ comprises the amino acid sequence of SEQ ID NO:56, 284, or 285, and VL$_1$ comprises the amino acid sequence of SEQ ID NO:57 or 287. In any of the complexes described above, a VH$_1$, VH$_2$, VL$_1$, and/or VL$_2$ comprises an HVR-H1, HVR-H2, HVR-H3, HVR-L1, HVR-L2, and/or HVR-L3 that comprise one or more of the sequences listed in Tables 4 and 5.

In some embodiments, the complex comprises a first antibody comprising two antibody heavy chains and two antibody light chains, each of the two antibody heavy chains of the first antibody comprises: VH$_1$-CH$_1$-hinge-CH$_2$-CH$_3$ [X]; and each of the two antibody light chains of the first antibody comprises: VL$_1$-CL [VII]; and a second antibody comprising two antibody heavy chains and two antibody light chains, each of the two antibody heavy chains of the second antibody comprises: VH$_2$-CH$_1$-hinge-CH$_2$-CH$_3$ [XII]; and each of the two antibody light chains of the second antibody comprises: VL$_2$-CL [IX]; each of the antibody heavy chains of the first antibody associates with one of the antibody light chains of the first antibody such that VH$_1$ and VL$_1$ form an antigen binding domain; wherein each of the antibody heavy chains of the second antibody associates with one of the antibody light chains of the second antibody such that VH$_2$ and VL$_2$ form an antigen binding domain; the first and the second antibodies are coupled via linker L$_1$; and VH$_1$ is a first antibody heavy chain variable domain, VH$_2$ is a second antibody heavy chain variable domain, VL$_1$ is a first antibody light chain variable domain, VL$_2$ is a second antibody light chain variable domain, CL is an antibody light chain constant domain, CH$_1$ is an antibody first heavy chain constant domain, hinge is an antibody hinge region, CH$_2$ is an antibody second heavy chain constant domain, and CH$_3$ is an antibody third heavy chain constant domain. In some embodiments, the L$_1$ linker is a bis-maleimido polyethylene glycol (PEG) linker. In some embodiments, the PEG linker comprises between one and eleven PEG subunits. In some embodiments, the PEG linker comprises one, two, or three PEG subunits. In some embodiments, the L$_1$ linker couples a first engineered free cysteine of a first of the two antibodies with a second engineered free cysteine of a second of the two antibodies. In some embodiments, at least one of the first or the second engineered free cysteine is a cysteine residue in the heavy chain independently selected from the group consisting of T114C, A118C, A140C, L174C, L179C, T187C, T209C, V262C, G371C, Y373C, E382C, S400C, S424C, N434C and Q438C, according to EU numbering. In some embodiments, at least one of the first or the second engineered free cysteine is a cysteine residue in the light chain independently selected from the group consisting of I106C, R108C, R142C, K149C, and V205C, according to Kabat numbering. In some embodiments, VH$_1$ and VL$_1$ form an antigen binding domain that binds the first epitope of OX40, and VH$_2$ and VL$_2$ form an antigen binding domain that binds the second epitope of OX40. In some embodiments, VH$_1$ and VL$_1$ form an antigen binding domain that binds the second epitope of OX40, and VH$_2$ and VL$_2$ form an antigen binding domain that binds the first epitope of OX40. In some embodiments of any of the above embodiments, VH$_1$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_2$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_2$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, VH$_2$ comprises an HVR-H1 comprising the amino acid sequence of SEQ ID NO:29 or 288, an HVR-H2 comprising the amino acid sequence of SEQ ID NO:30 or 289, and an HVR-H3 comprising the amino acid sequence of SEQ ID NO:33; VL$_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; VH$_1$ comprises an HVR-H1 comprising the amino acid sequence of SEQ ID NO:2 or 282, an HVR-H2 comprising the amino acid sequence of SEQ ID NO:3, and an HVR-H3 comprising the amino acid sequence of SEQ ID NO:4 or 283; and VL$_1$ comprises an HVR-L1 comprising the amino acid sequence of SEQ ID NO:5, an HVR-L2 comprising the amino acid sequence of SEQ ID NO:6 or 286, and an HVR-L3 comprising the amino acid sequence of SEQ ID NO:7. In some embodiments, $VH_1$ comprises the amino acid sequence of SEQ ID NO:128, $VL_1$ comprises the amino acid sequence of SEQ ID NO:129, $VH_2$ comprises the amino acid sequence of SEQ ID NO:56, and $VL_2$ comprises the amino acid sequence of SEQ ID NO:57. In some embodiments, $VH_2$ comprises the amino acid sequence of SEQ ID NO:128 or 290, $VL_2$ comprises the amino acid sequence of SEQ ID NO:129, $VH_1$ comprises the amino acid sequence of SEQ ID NO:56, 284, or 285, and $VL_1$ comprises the amino acid sequence of SEQ ID NO:57 or 287. In any of the complexes described above, a $VH_1$, $VH_2$, $VL_1$, and/or $VL_2$ comprises an HVR-H1, HVR-H2, HVR-H3, HVR-L1, HVR-L2, and/or HVR-L3 that comprise one or more of the sequences listed in Tables 4 and 5.

In some embodiments of any of the above embodiments, $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_1$ comprises the amino acid sequence of SEQ ID NO:128, $VL_1$ comprises the amino acid sequence of SEQ ID NO:129, $VH_2$ comprises the amino acid sequence of SEQ ID NO:56, and $VL_2$ comprises the amino acid sequence of SEQ ID NO:57. In some embodiments, $VH_2$ comprises the amino acid sequence of SEQ ID NO:128, $VL_2$ comprises the amino acid sequence of SEQ ID NO:129, $VH_1$ comprises the amino acid sequence of SEQ ID NO:56, and $VL_1$ comprises the amino acid sequence of SEQ ID NO:57.

In some embodiments of any of the above embodiments, the complex comprises one or more of a CL domain comprising a sequence selected from the group consisting of SEQ ID NOs: 279 and 295-297. In some embodiments of any of the above embodiments, the complex comprises one or more of a $CH_1$-hinge-$CH_2$-$CH_3$ region comprising a sequence selected from the group consisting of SEQ ID NOs:298-303. In some embodiments of any of the above embodiments, one or more of a CL, $CH_1$, hinge, $CH_2$, or $CH_3$ domain in any of the complexes described herein can include one or more amino acid substitutions.

In some embodiments of any of the above embodiments, the complex comprises an antibody Fc region that comprises a modification for attenuating effector function. In some embodiments, the complex comprises an antibody Fc region that comprises an amino acid substitution at one or more amino acid positions (EU numbering) selected from the group consisting of:
  (a) 297 in the Fc region of human IgG1,
  (b) 234 and 235 in the Fc region of human IgG1,
  (c) 234, 235 and 329 in the Fc region of human IgG1,
  (d) 234 and 237 in the Fc region of human IgG2,
  (e) 235, 237 and 318 in the Fc region of human IgG4,
  (f) 228 and 236 in the Fc region of human IgG4,
  (g) 268, 309, 330 and 331 in the Fc region of human IgG2,
  (h) 220, 226, 229 and 238 in the Fc region of human IgG1,
  (i) 226, 229, 233, 234 and 235 in the Fc region of human IgG1,
  (j) 234, 235 and 331 in the Fc region of human IgG1,
  (k) 226 and 230 in the Fc region of human IgG1, and
  (l) 267 and 328 in the Fc region of human IgG1.

In some embodiments, the complex comprises an antibody Fc region that comprises one or more amino acid substitutions (EU numbering) selected from the group consisting of:
  (a) N297A in the Fc region of human IgG1,
  (b) L234A and L235A in the Fc region of human IgG1,
  (c) L234A, L235A and P329G in the Fc region of human IgG1,
  (d) V234A and G237A in the Fc region of human IgG2,
  (e) L235A, G237A and E318A in the Fc region of human IgG4,
  (f) S228P and L236E in the Fc region of human IgG4,
  (g) one or more substitutions in the region spanning amino acid residues 118 to 260 in the Fc region of human IgG2 or in the region spanning amino acids 261 to 447 in the Fc region of human IgG4,
  (h) H268Q, V309L, A330S and A331S in the Fc region of human IgG2,
  (i) C220S, C226S, C229S and P238S in the Fc region of human IgG1,
  (j) C226S, C229S, E233P, L234V and L235A in the Fc region of human IgG1,
  (k) L234F, L235E and P331S in the Fc region of human IgG1,
  (l) C226S and P230S in the Fc region of human IgG1, and
  (m) S267E and L328F in the Fc region of human IgG1.

In some embodiments, the complex comprises an antibody Fc region that comprises a modification for attenuating effector function that results in an aglycosylated Fc region. In some embodiments, the complex comprises an antibody Fc region that comprises a modification for attenuating effector function that does not eliminate glycosylation of the Fc region.

Further provided herein are one or more polynucleotides encoding one or more polypeptides of the complex of any of the above embodiments. Further provided herein are one or more vectors comprising the one or more polynucleotides of any of the above embodiments. Further provided herein are one or more host cells comprising the one or more polynucleotides of any of the above embodiments or the one or more vectors of any of the above embodiments. Further provided herein is a pharmaceutical formulation comprising the complex of any of the above embodiments and a pharmaceutically acceptable carrier.

Further provided herein is a method of treating an individual having cancer comprising administering to the individual an effective amount of the complex of any of the above embodiments. In some embodiments, the method further comprises administering to the individual an additional therapeutic agent. In some embodiments, the additional therapeutic agent comprises a chemotherapeutic agent. In some embodiments, the additional therapeutic agent comprises a PD-1 axis binding antagonist. In some embodiments, the cancer is epithelial ovarian cancer, fallopian tube cancer, primary peritoneal cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer (including platinum sensitive and platinum resistant ovarian cancer), liver cancer, bladder cancer, hepatoma, breast cancer, colon cancer, colorectal cancer, fallopian tube, peritoneal, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; post-transplant lymphoproliferative disorder (PTLD), or abnormal vascular proliferation associated with phakomatoses, edema (such as that associated with brain tumors), and Meigs' syndrome, including metastatic forms of those cancers. In some embodiments, the cancer is Urothelial carcinoma (uBC), melanoma, non-small cell lung cancer (NSCLC), triple-negative breast cancer (TNBC), renal, or bladder cancer.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

3C8) and biepitopic (1A7-3C8 and 3C8-1A7) antibodies using OX40 expressing Jurkat cells with a luciferase reporter.

Figure 16:
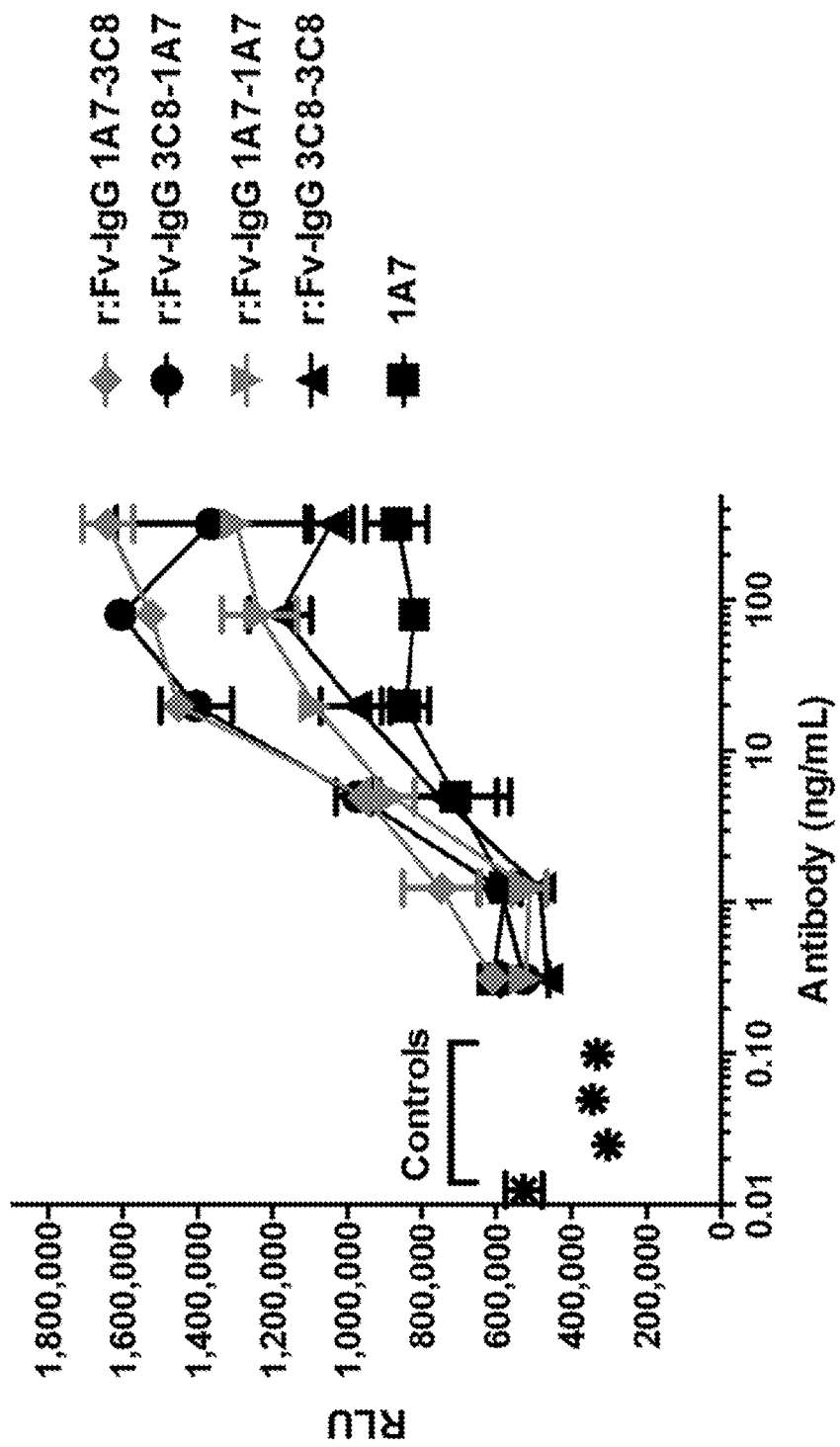

FIG. 16 shows co-stimulation of CD4+ memory T cell proliferation by anti-OX40 native (1A7) or r:Fv-IgG antibodies in the presence of anti-CD3 antibody and FcγRIIa+ L cells. T cell proliferation was monitored by CellTiter-Glo® (Promega). L cells in this assay are FcγRII$^+$ but lack CD80. The four controls are L cells, L cells+anti-CD3, L cells+ T cells, and L cells+ T cells+anti-CD3. All antibodies tested included anti-CD3.

Figure 17:
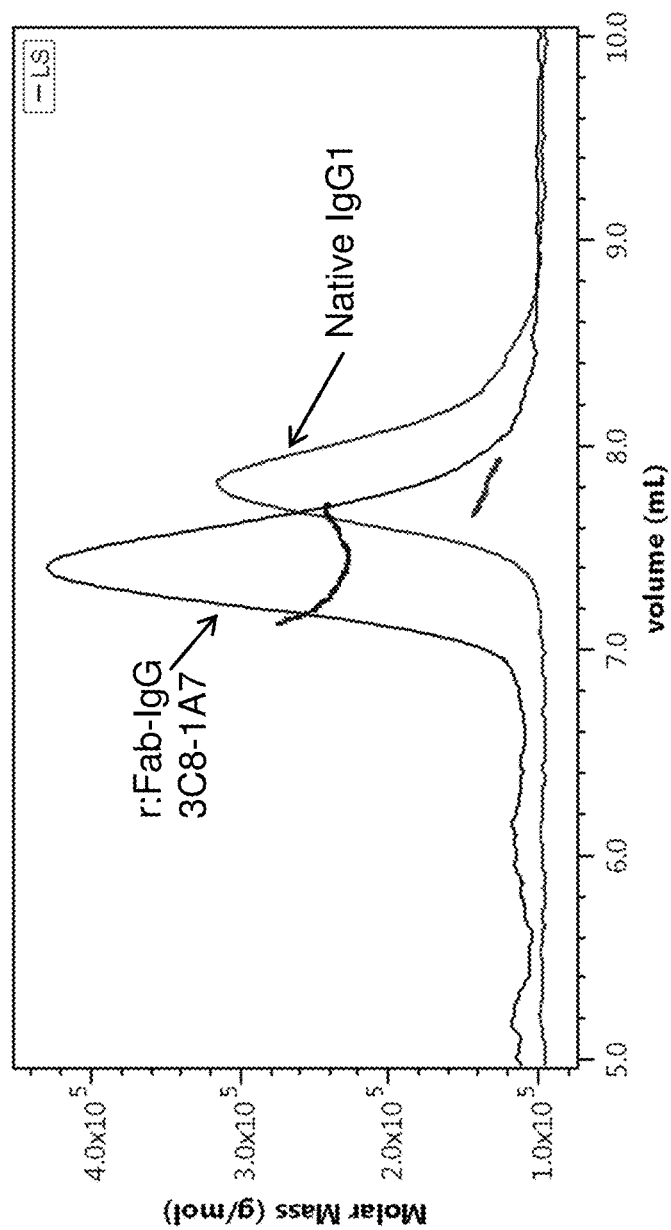

FIG. 17 shows SEC-MALS data on r:Fab-IgG 3C8-1A7 anti-OX40 antibody compared to a native IgG1 antibody, as labeled.

Figure 18:
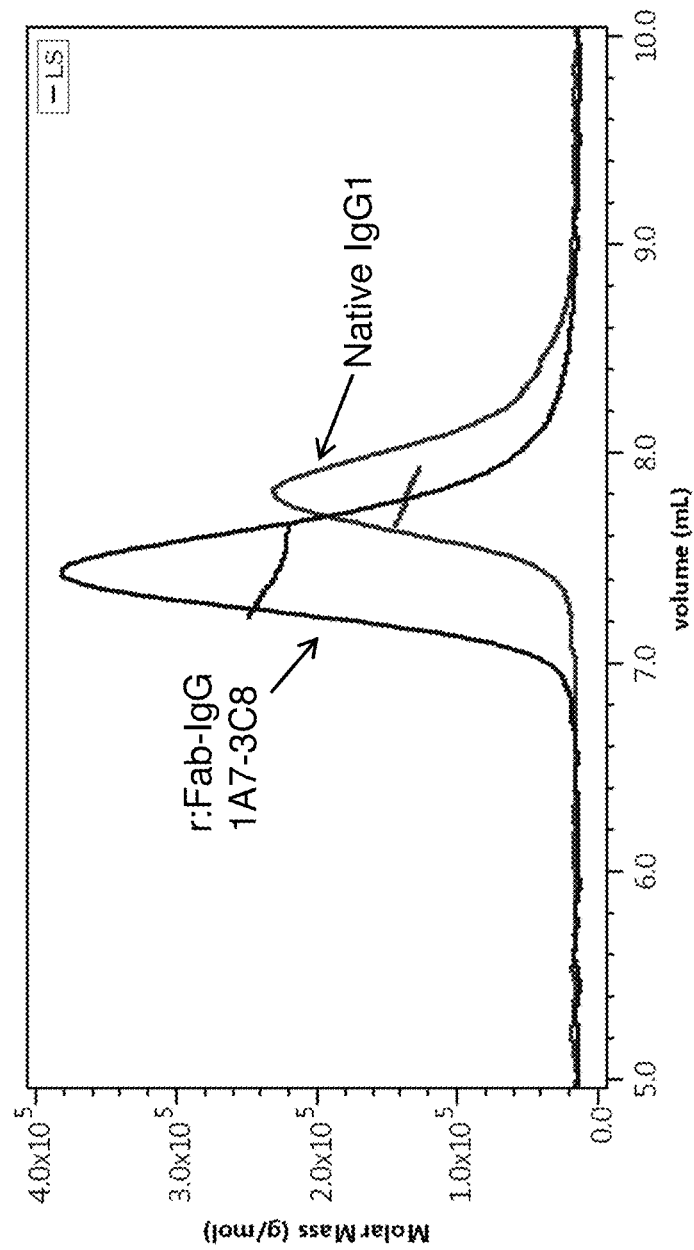

FIG. 18 shows SEC-MALS data on r:Fab-IgG 1A7-3C8 anti-OX40 antibody compared to a native IgG1 antibody, as labeled.

Figure 19:
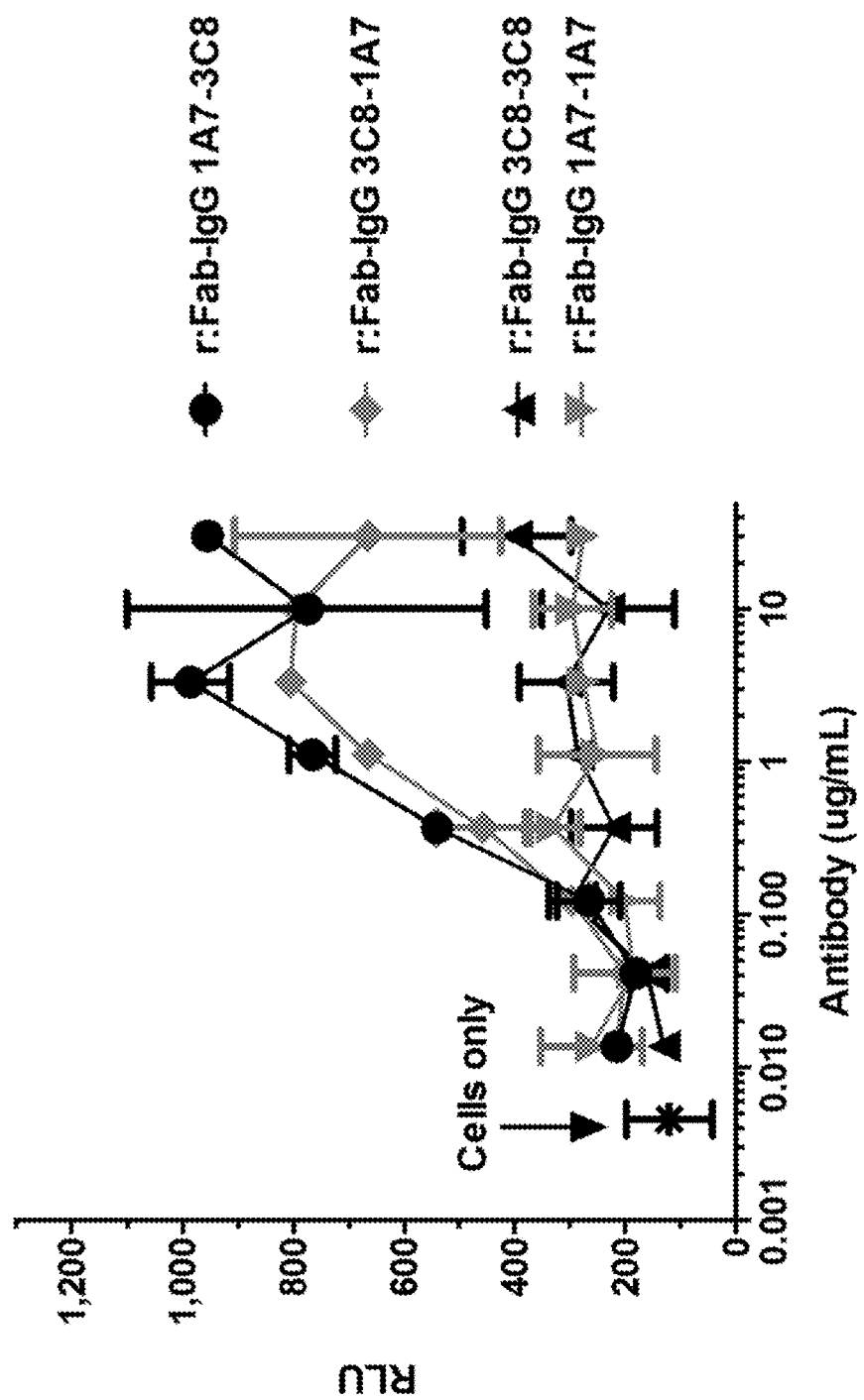

FIG. 19 shows agonist activity of anti-OX40 native recombinant Fab-IgG monoepitopic (1A7-1A7 and 3C8-3C8) and biepitopic (1A7-3C8 and 3C8-1A7) antibodies using OX40 expressing Jurkat cells with a luciferase reporter.

Figure 20:
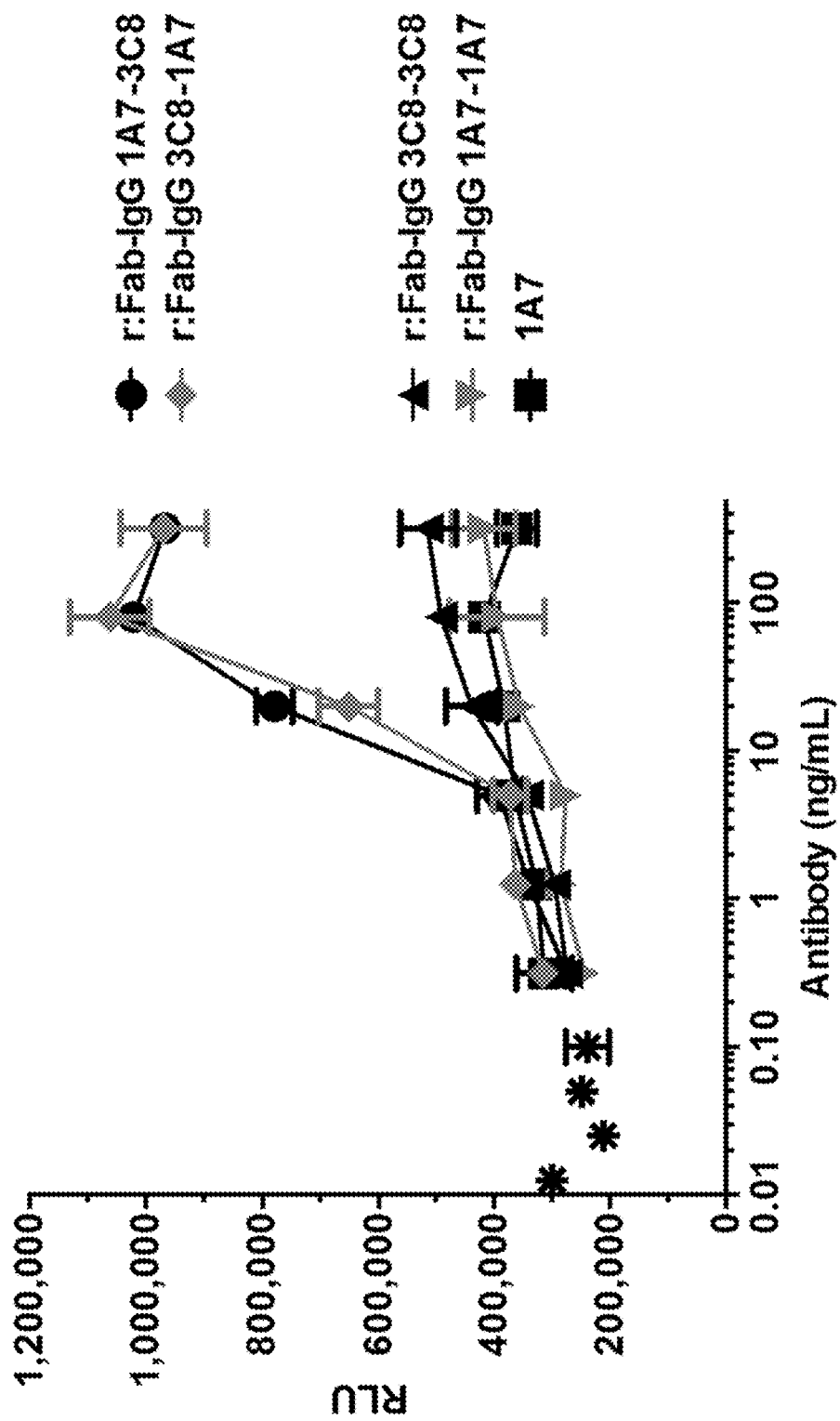

FIG. 20 shows co-stimulation of CD4+ memory T cell proliferation by anti-OX40 native (1A7) or r:Fab-IgG antibodies in the presence of anti-CD3 antibody and FcγRIIa+ L cells. T cell proliferation was monitored by CellTiter-Glo® (Promega). L cells in this assay are FcγRII$^+$ but lack CD80. The four controls are L cells, L cells+anti-CD3, L cells+ T cells, and L cells+ T cells+anti-CD3. All antibodies tested included anti-CD3.

Figure 21:
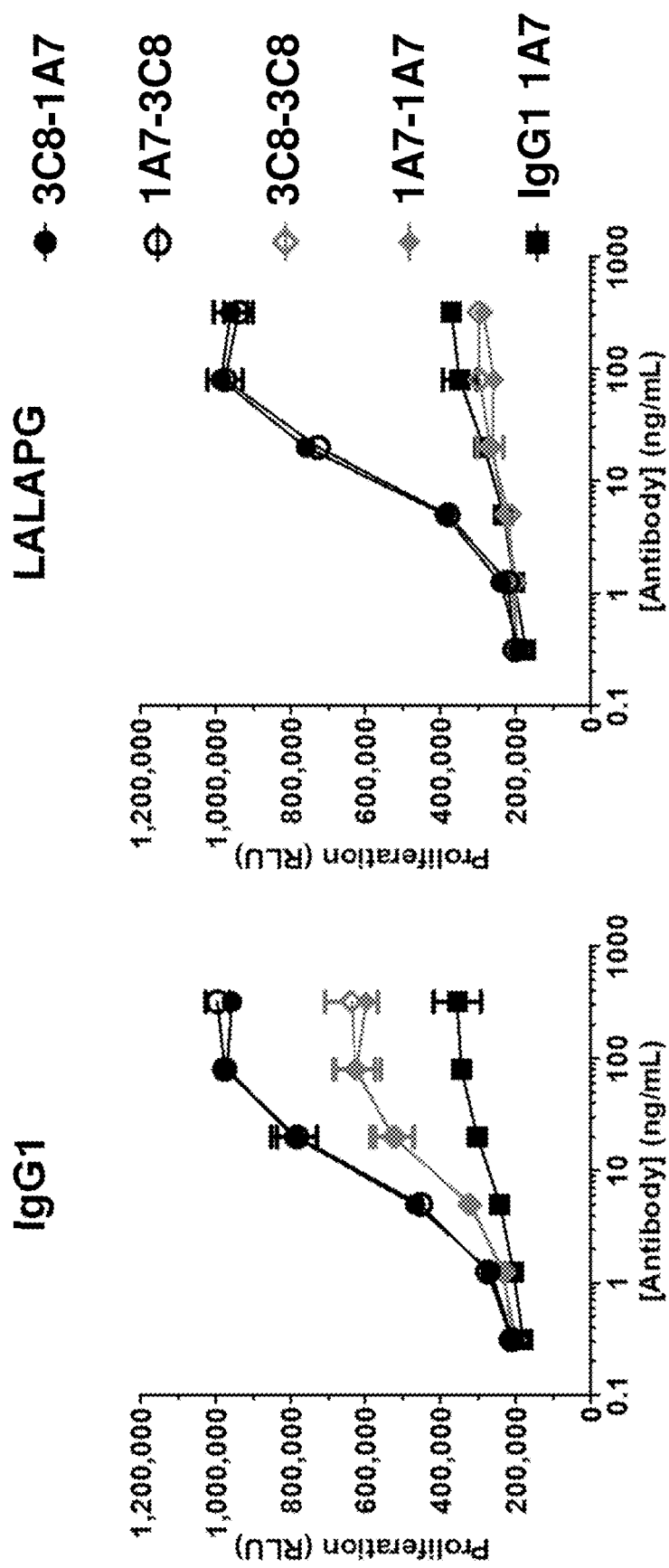

FIG. 21 shows co-stimulation of CD4+ memory T cell proliferation by anti-OX40 antibodies in the presence of anti-CD3 antibody and FcγRIIa+ L cells. The left graph shows results from IgG1 versions, while the right graph shows results from IgG1 LALAPG versions of the r:Fv-IgGs. r:Fv-IgG's included were 3C8-1A7, 1A7-3C8, 3C8-3C8, and 1A7-1A7. IgG1 1A7 refers to the human IgG1 version of the 1A7 antibody on both left and right panels of the figure.

Figure 22:
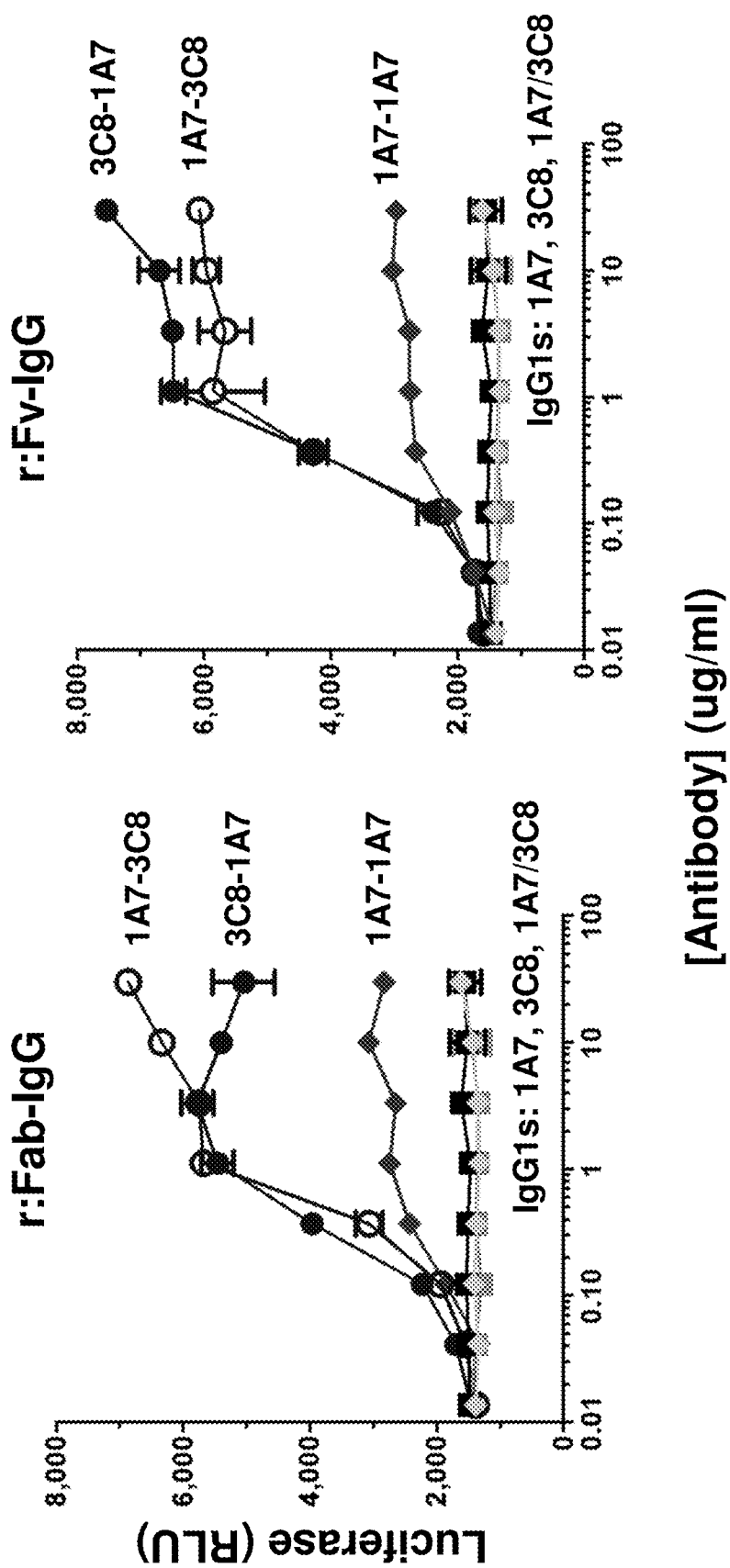

FIG. 22 shows agonist activity of anti-OX40 control and r:Fab-IgG and r:Fv-IgG antibodies in the OX40 expressing Jurkat cells luciferase reporter assay. r:Fab-IgG (left panel) and r:Fv-IgG (right panel) include both biepitopic (1A7-3C8 and 3C8-1A7) formats as well as the monoepitopic 1A7-1A7 format. Bivalent IgG1 controls include 1A7, 3C8, and a bivalent biepitopic antibody 1A7/3C8. All heavy chain constant regions were human IgG1 in these assays.

Figure 23:
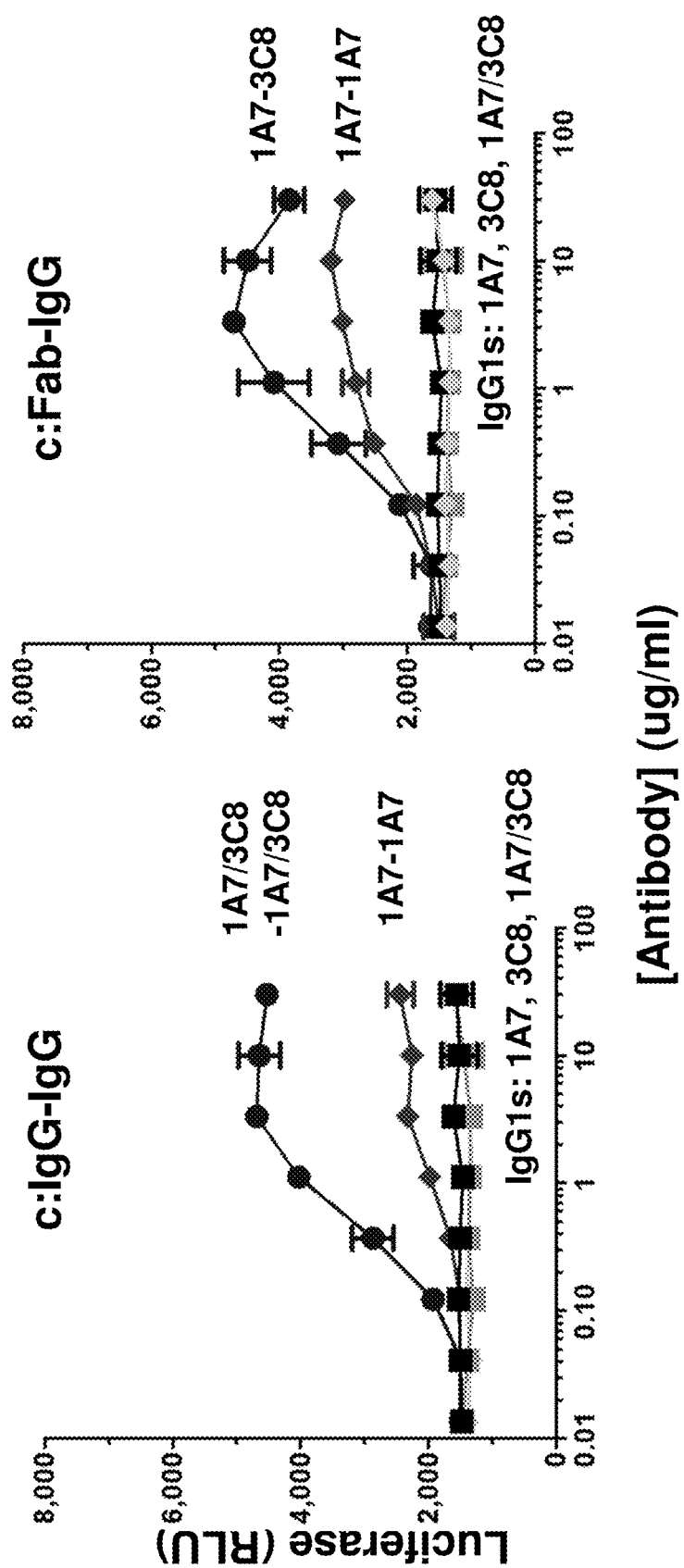

FIG. 23 shows agonist activity of anti-OX40 control and cIgG-IgG and c:Fab-IgG antibodies in the OX40 expressing Jurkat cells luciferase reporter assay. c:IgG-IgG (left panel) and c:Fab-IgG (right panel) include both biepitopic formats (c:IgG-IgG 1A7/3C8-1A7/3C8 and c:Fab-IgG 1A7-3C8) as well as the monoepitopic 1A7-1A7 format. Bivalent IgG1 controls include 1A7, 3C8, and a bivalent biepitopic antibody 1A7/3C8. All heavy chain constant regions were human IgG1 in these assays.

Figure 24:
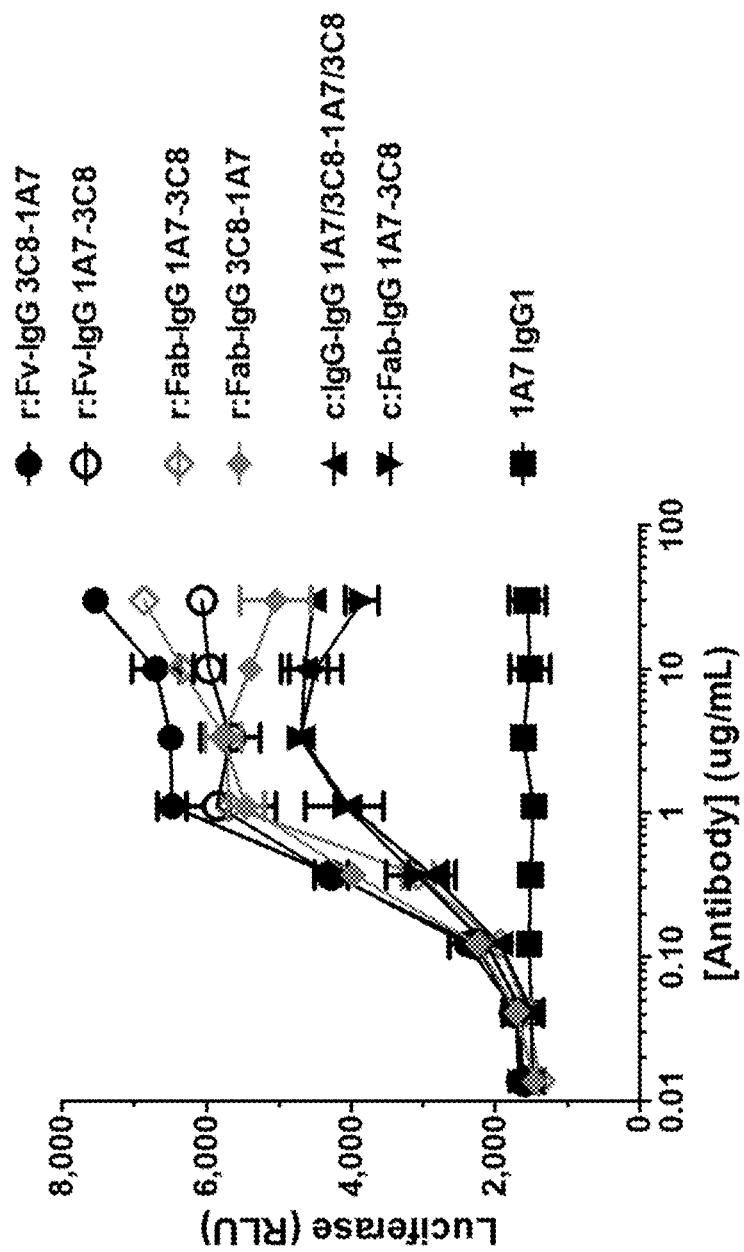

FIG. 24 shows agonist activity of control and tetravalent biepitopic anti-OX40 antibodies in the OX40 expressing Jurkat cells luciferase reporter assay. All heavy chain constant regions were human IgG1 in these assays.

Figure 25:
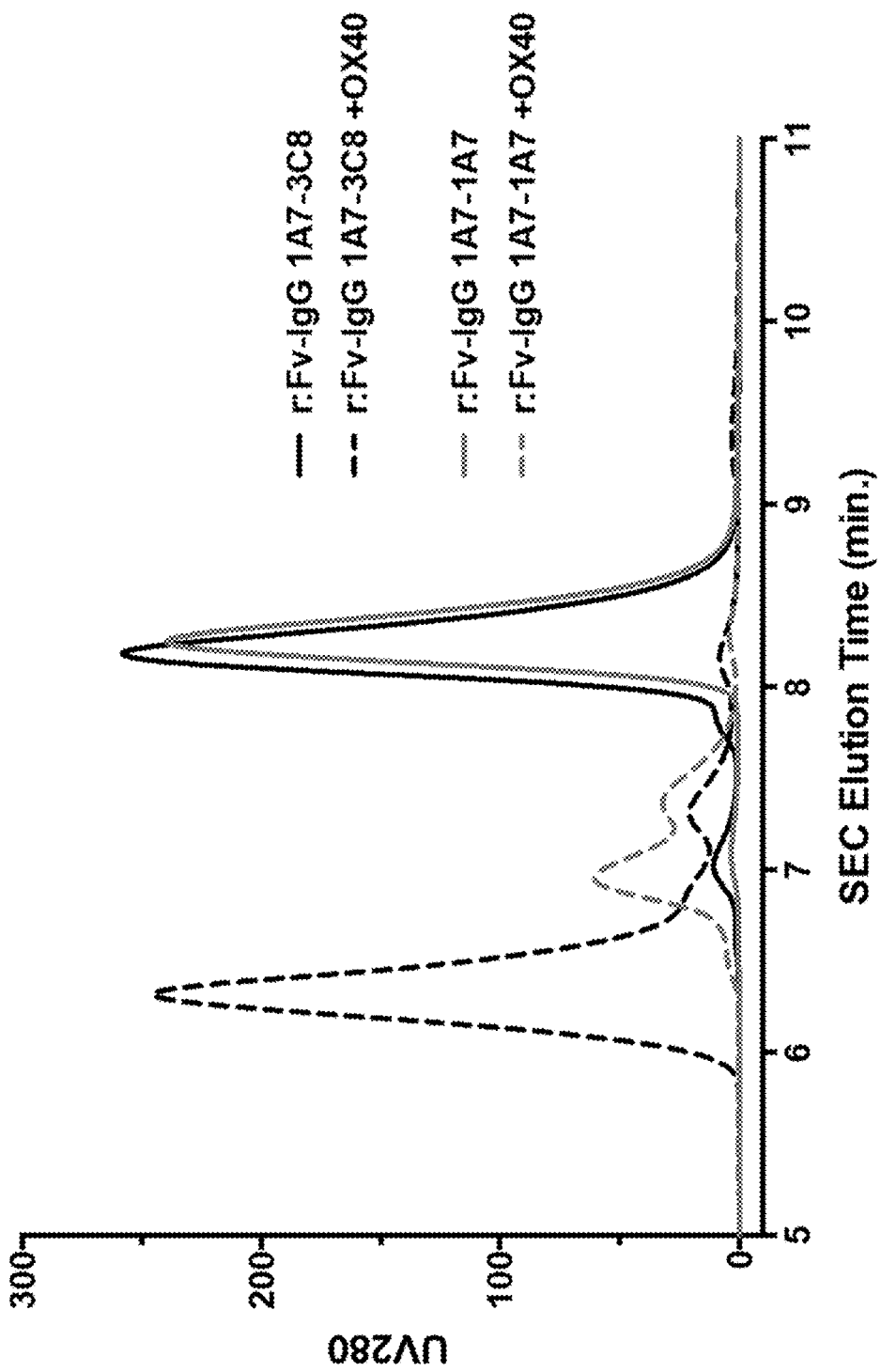

FIG. 25 shows Size Exclusion Chromatography (SEC) chromatograms for biepitopic r:Fv-IgG 1A7-3C8 (black) and monoepitopic r:Fv-IgG 1A7-1A7 (gray) alone (solid lines) and in complex with target OX40 (dashed lines). Earlier elution time is proportional to greater protein size.

Figure 26:
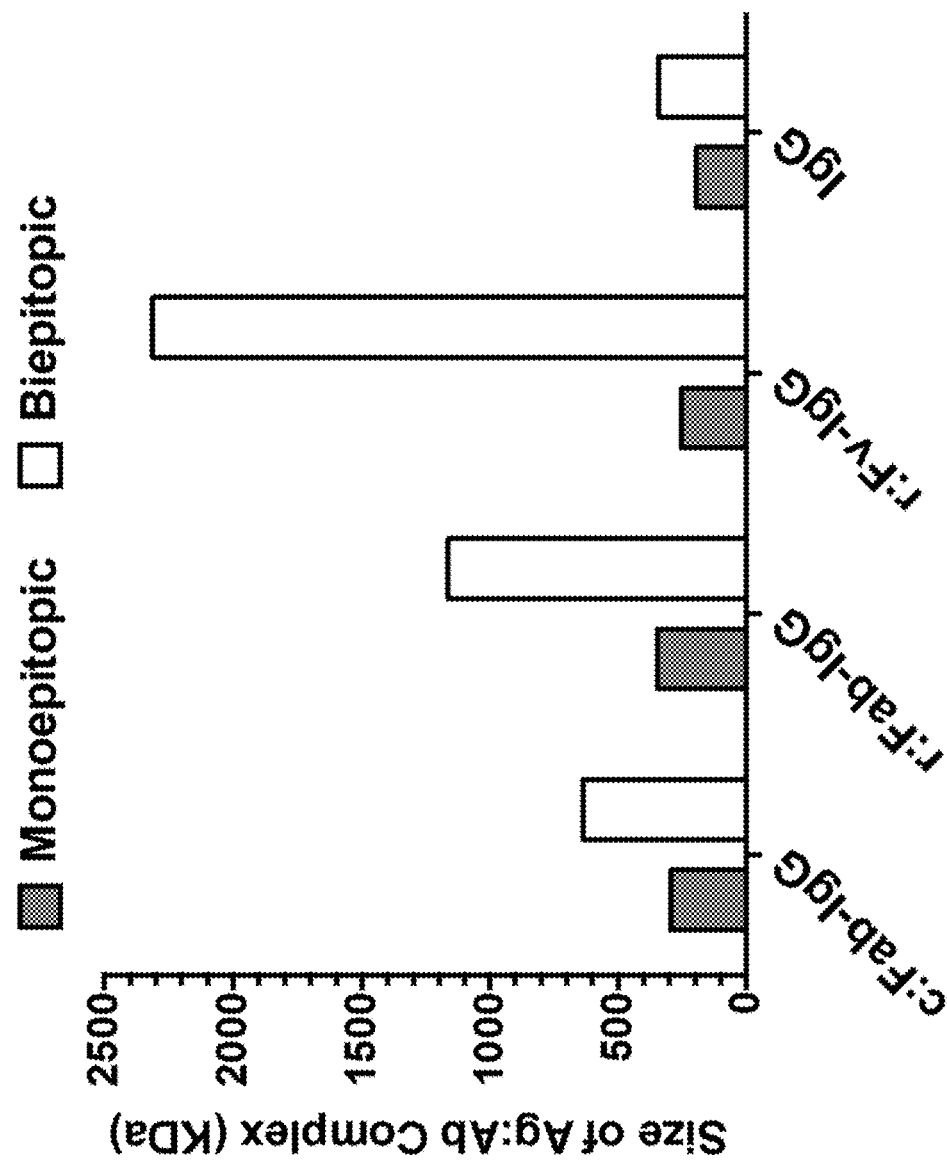

FIG. 26 shows results from Multiple Angle Light Scattering (MALS) data upon SEC column elution. The Y axis reflects size of antibody/OX40 complex in KDa. Monoepitopic formats are shown as gray bars, biepitopic formats are shown as open white bars.

Figure 27:
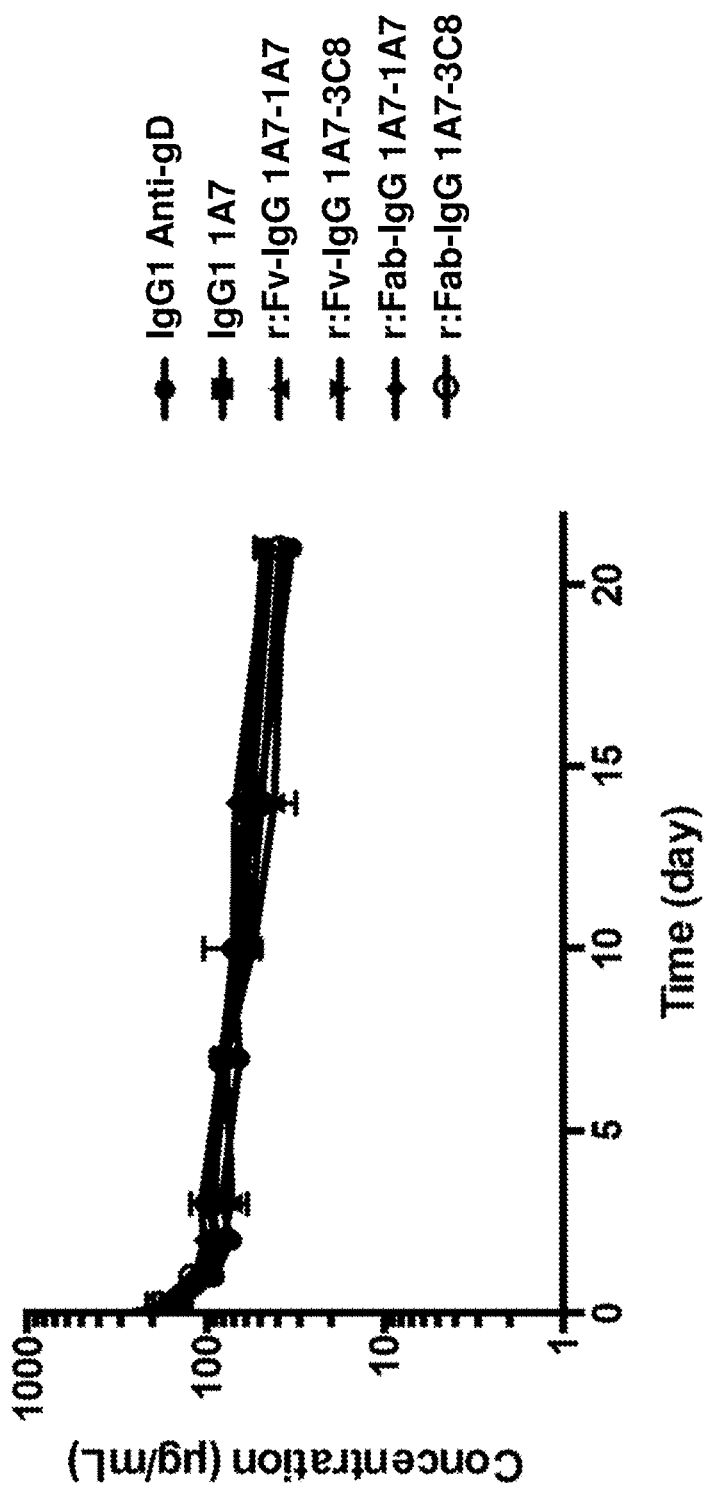

FIG. 27 shows pharmacokinetics (PK) of anti-OX40 r:Fv-IgG and r:Fab-IgG antibody formats in C.B-17 SCID mice. IgG1 1A7 and IgG1 anti-gD were included as controls.

Figure 28:
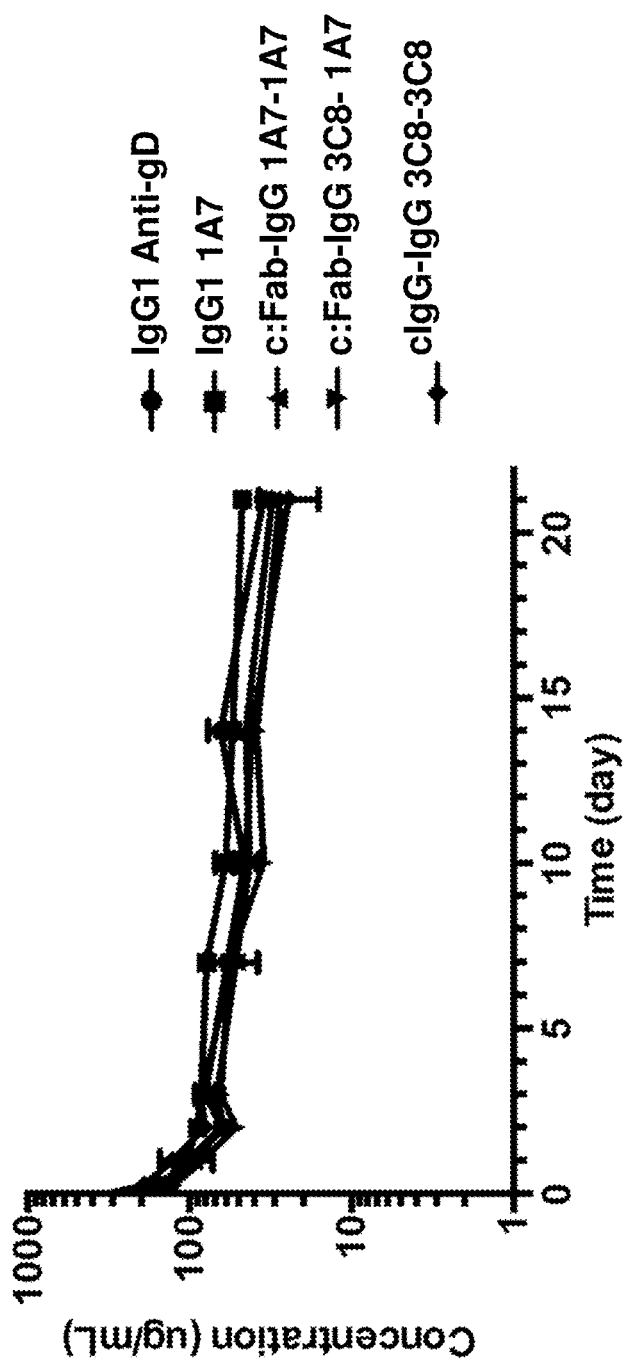

FIG. 28 shows PK of anti-OX40 c:Fab-IgG and c:IgG-IgG antibody formats in C.B-17 SCID mice. IgG1 1A7 and IgG1 anti-gD were included as controls.

Figure 29:
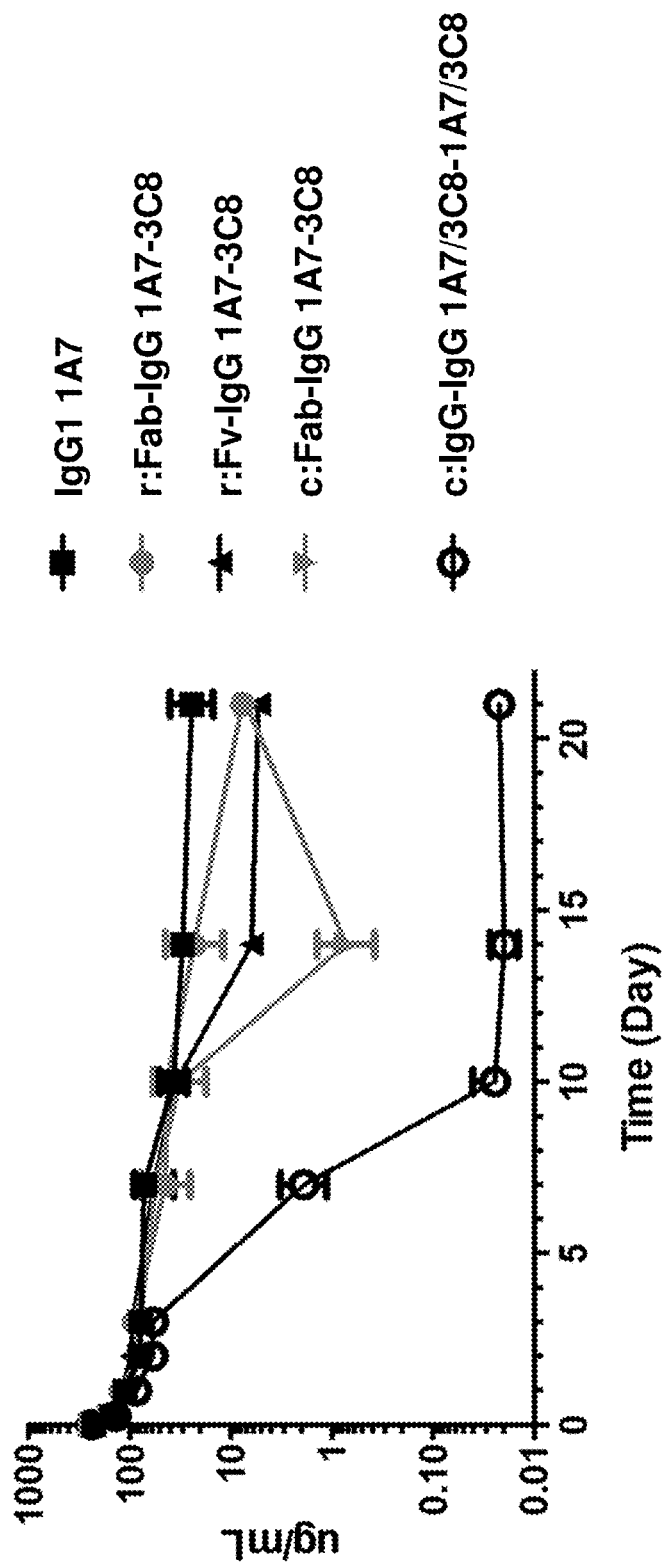

FIG. 29 shows PK of anti-OX40 r:Fv-IgG, r:Fab-IgG, c:Fab-IgG, and c:IgG-IgG antibody formats in C57BL-6 mice. IgG1 1A7 was included as a control.

Figure 30:
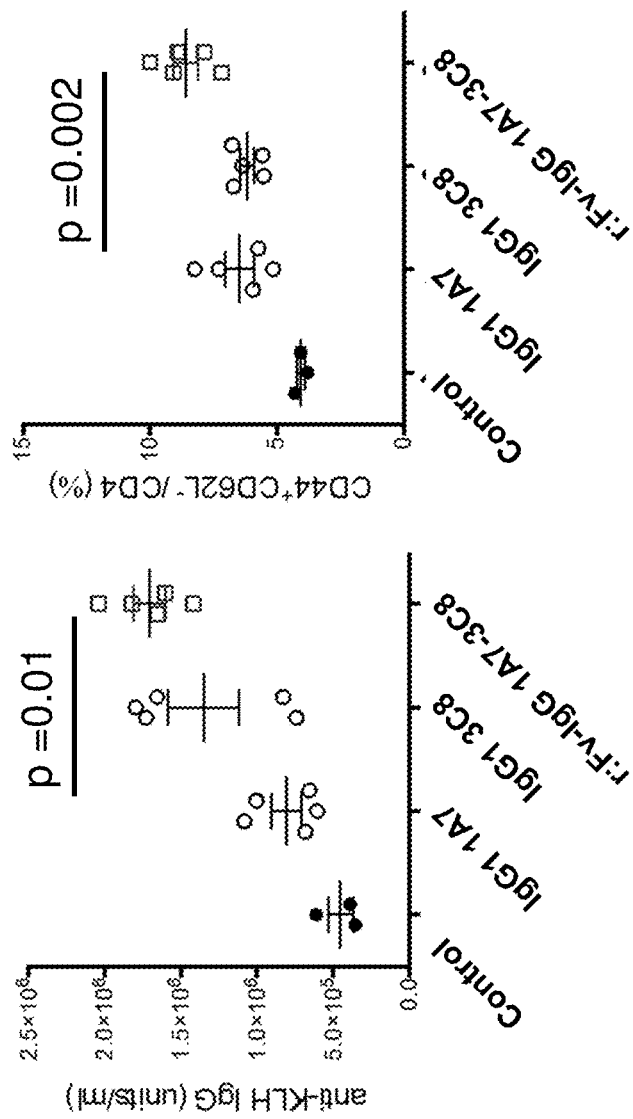

FIG. 30 shows results from the KLH immunization PD experiment in human OX40 knockin (hOX40ki) mice comparing r:Fv-IgG 1A7-3C8 to IgG1 versions of 1A7 and 3C8. The left panel shows level of detected anti-KLH IgG, and the right panel shows percent expansion of CD4 T cells. p values comparing r:Fv-IgG to IgG1 1A7 are shown.

Figure 31:
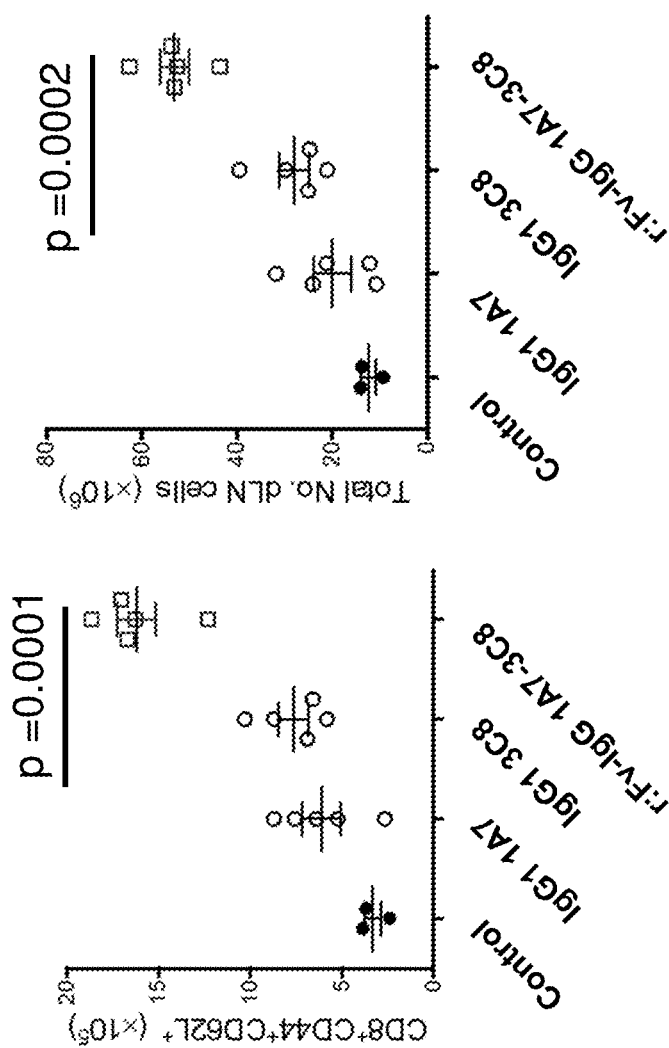

FIG. 31 shows results from the KLH immunization PD experiment in hOX40ki mice comparing r:Fv-IgG 1A7-3C8 to IgG1 versions of 1A7 and 3C8. The left panel shows total number of CD8+ T cells, and the right panel shows total number of cells in the draining lymph node. p values comparing r:Fv-IgG to IgG1 1A7 are shown.

Figure 32:
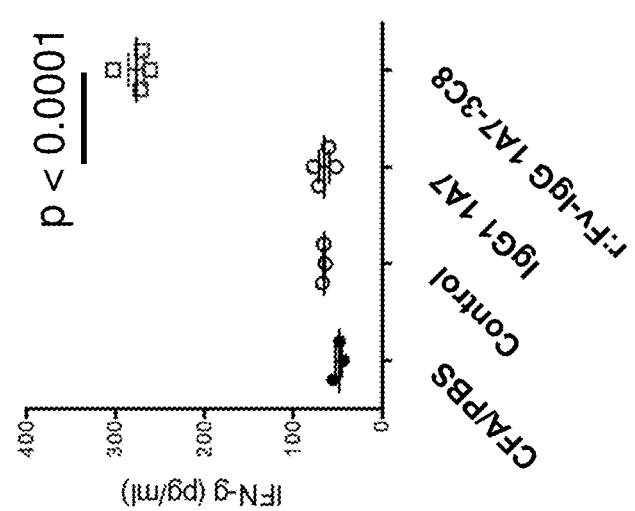

FIG. 32 shows results from the KLH immunization PD experiment in hOX40ki mice comparing r:Fv-IgG 1A7-3C8 to IgG1 versions of 1A7 and 3C8. The graph shows release of interferon gamma (IFN-γ) after ex vivo restimulation of purified CD4+ T cells with KLH. p values comparing r:Fv-IgG to IgG1 1A7 are shown.

Figure 33:
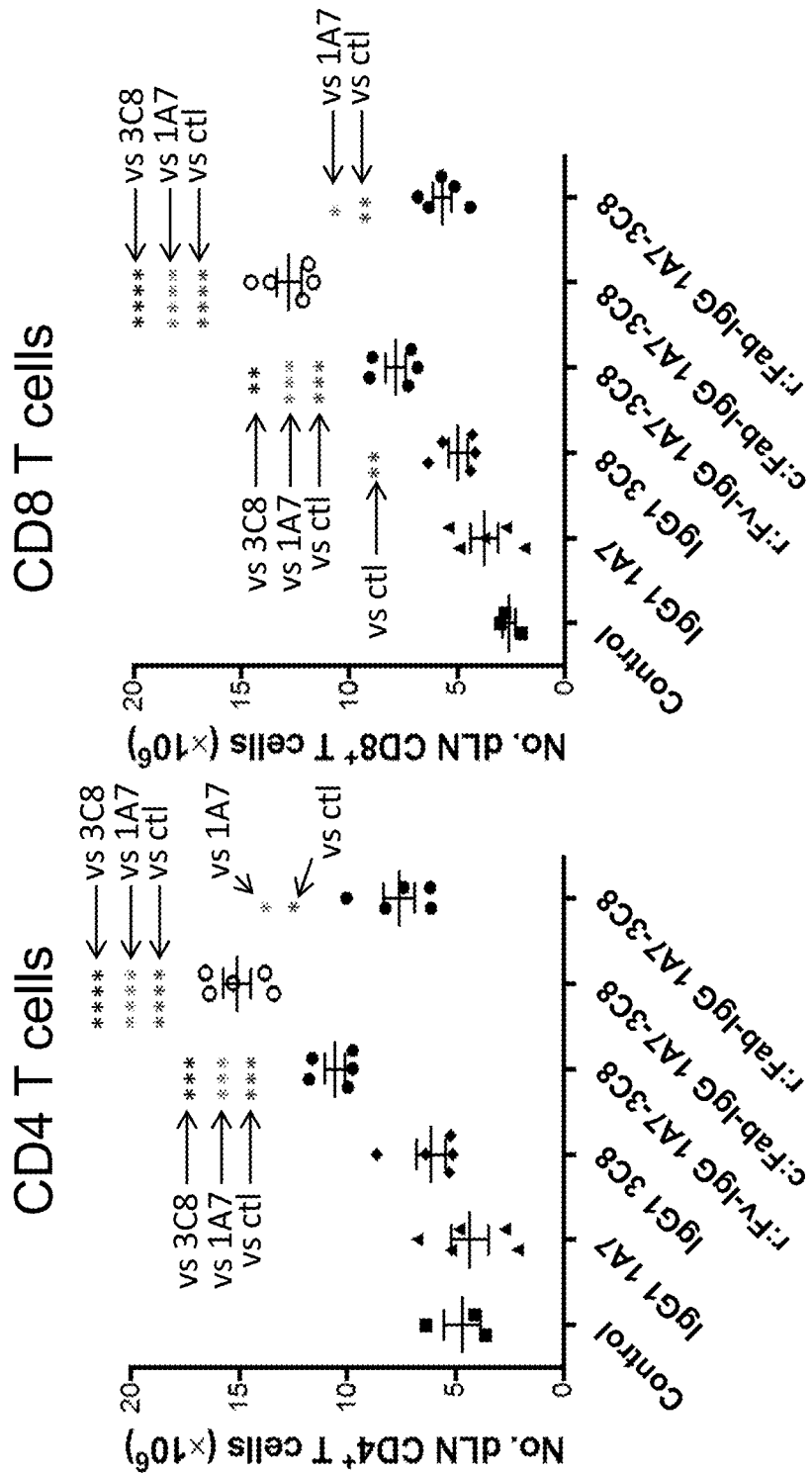

FIG. 33 shows results from the KLH immunization PD experiment in hOX40ki mice comparing anti-OX40 biepitopic r:Fv-IgG, r:Fab-IgG, and c:Fab-IgG antibody formats, along with IgG1 versions of 1A7 and 3C8. The left panel shows total number of CD4 T cells, and the right panel shows total number of CD8 T cells in the draining lymph node. Three p values are shown comparing tetravalent biepitopic formats to IgG1 3C8 ("vs 3C8"), IgG1 1A7 ("vs 1A7"), and control IgG1 anti-gD ("vs ctl"), as indicated. Number of asterisks represents p value as follows: *<0.05, <0.005, *<0.0005, *<0.00005.

Figure 34:
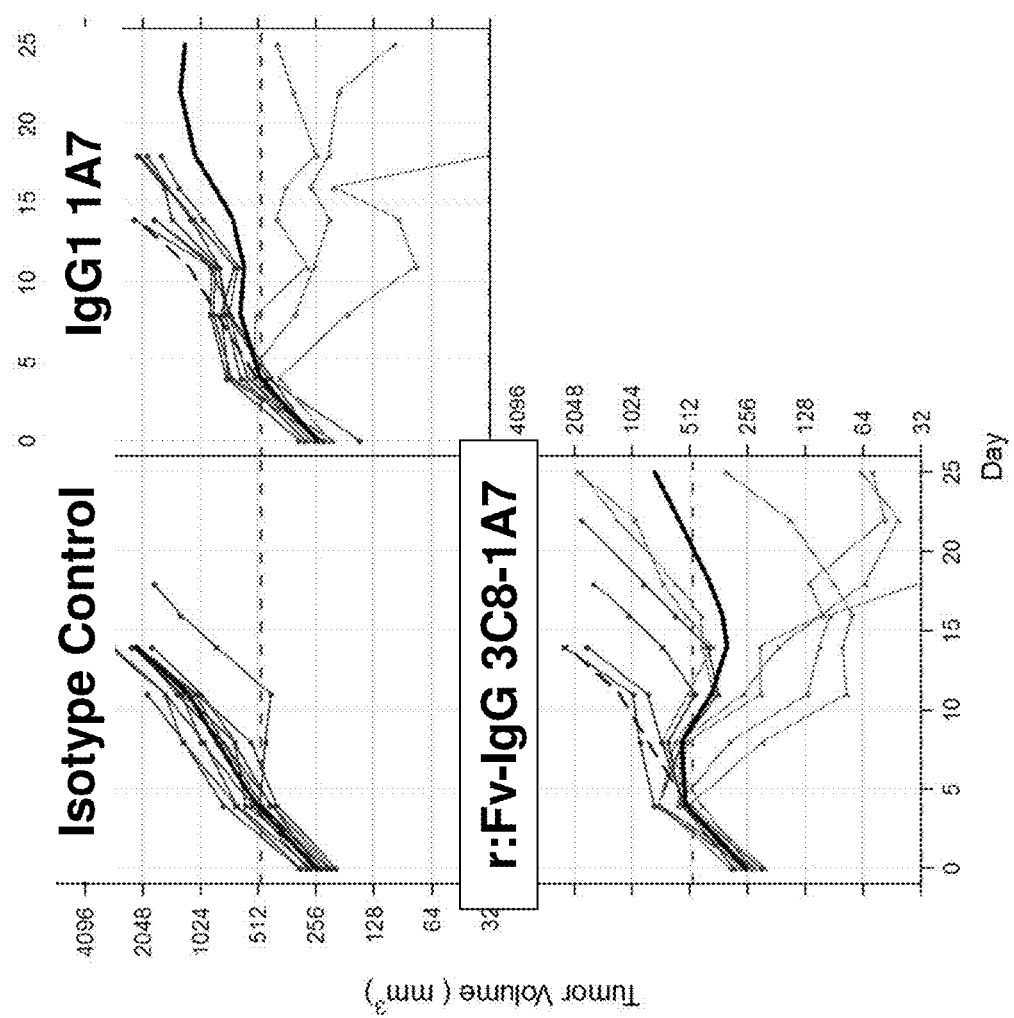

FIG. 34 shows anti-tumor activity of antibodies in a syngeneic E.G7-OVA (EL4 expressing chicken ovalbumin (OVA)) lymphoma tumor model in female hOX40ki C57BL/6 mice. Test articles included tetravalent biepitopic r:Fv-IgG 3C8-1A7, IgG1 1A7, and isotype control IgG1 anti-gD.

Figure 35:
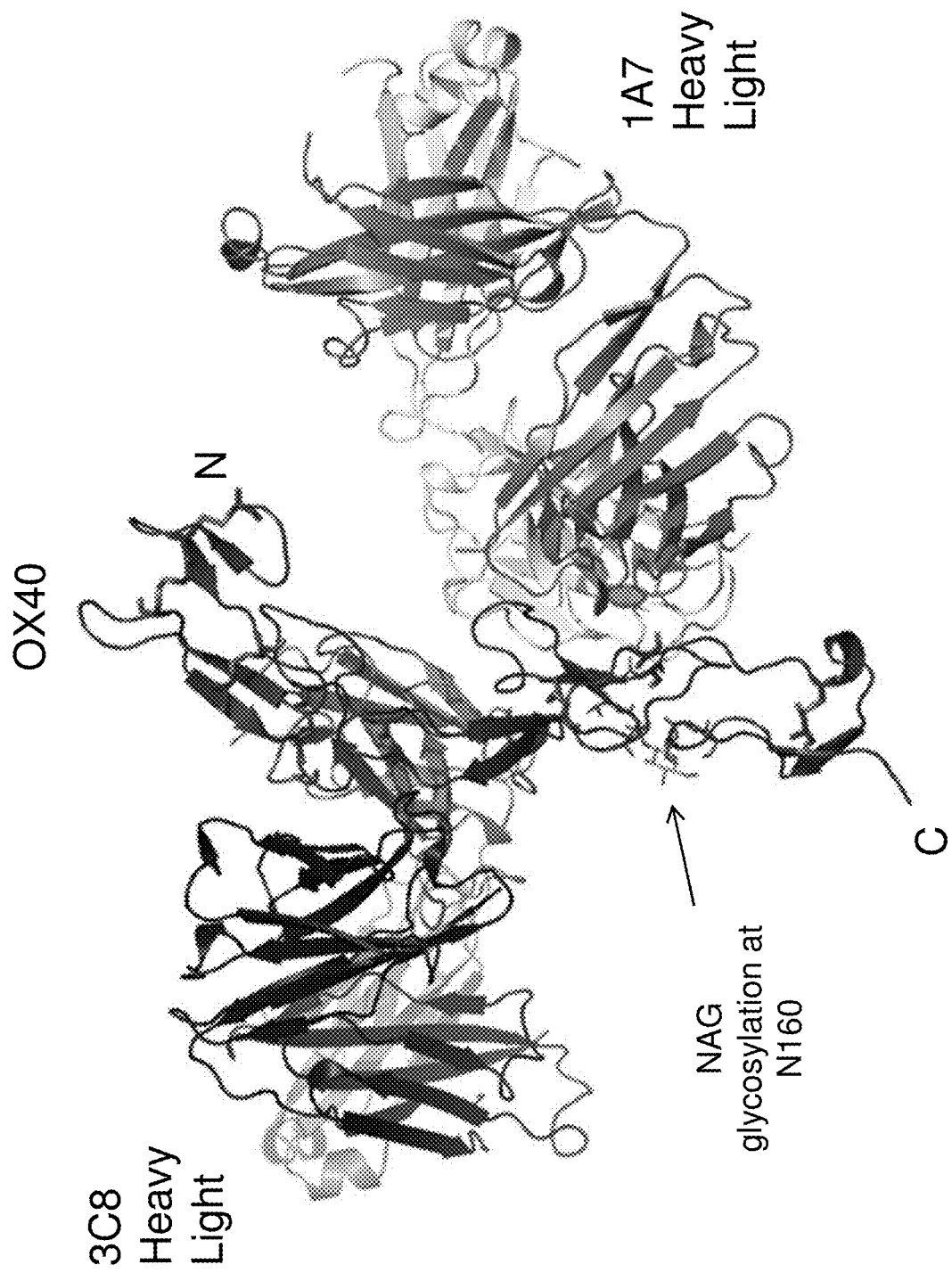

FIG. 35 shows the crystallographic structure of the ternary complex between OX40 and the 1A7 and 3C8 Fabs. An N-linked glycosylation is highlighted at position 160 of the OX40 receptor.

Figure 36:
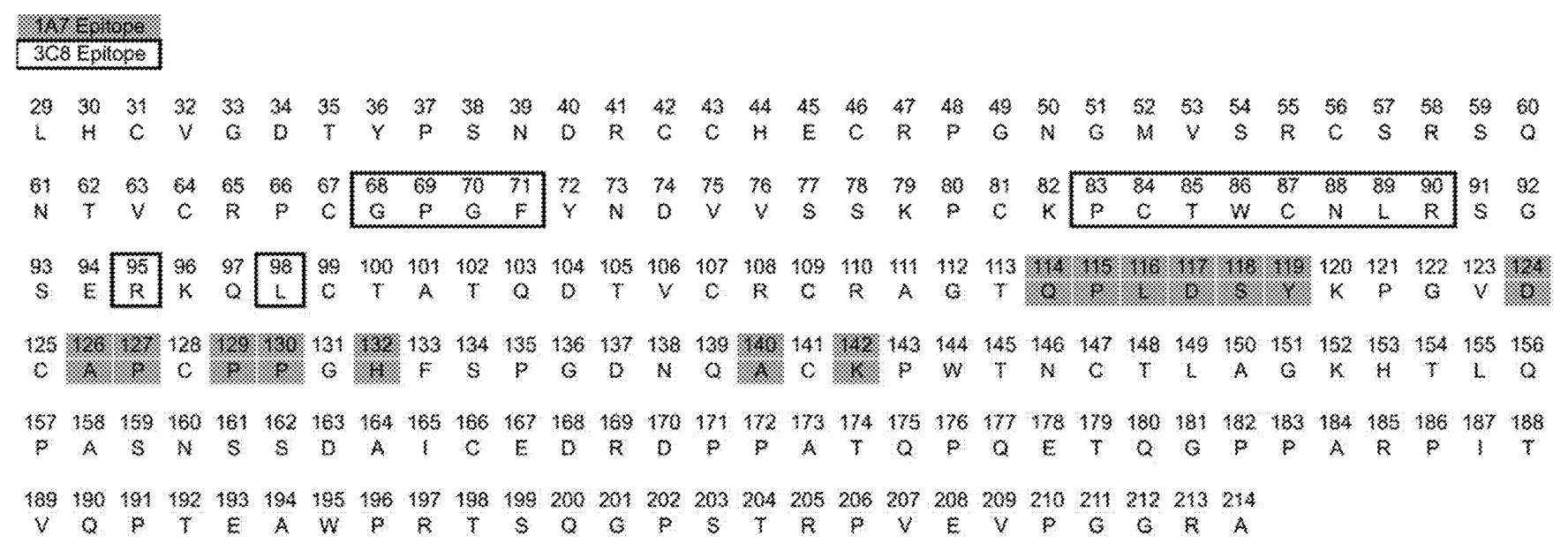

FIG. 36 shows the sequence of human OX40 highlighting the binding epitopes of 1A7 (grey boxes) and 3C8 (black outlined boxes) based on the ternary complex structure. Shown are residues 29-214 of SEQ ID NO:281.

Figure 37:
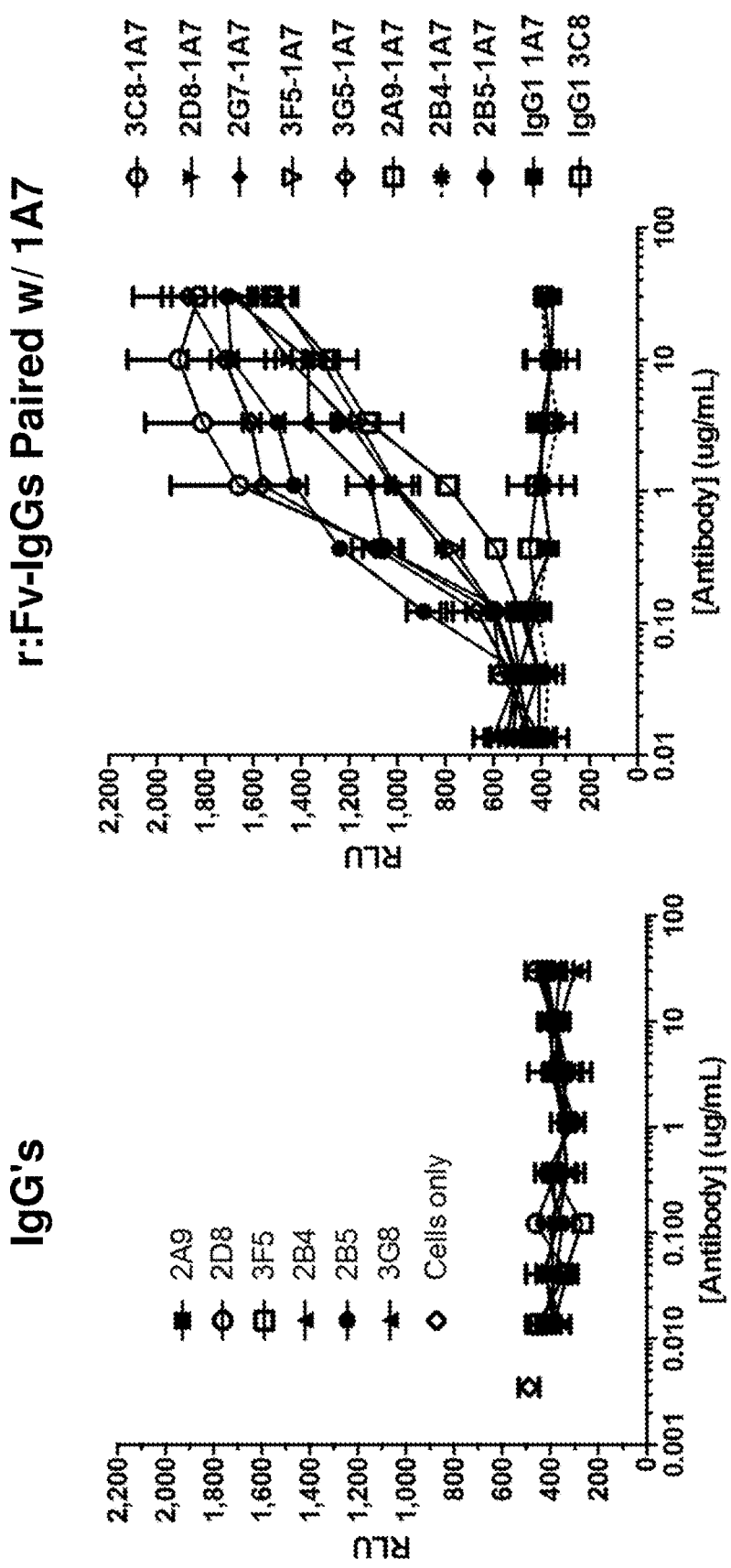

FIG. 37 shows agonist activity of IgG and r:Fv-IgG antibodies tested in the OX40+ Jurkat cell luciferase reporter assay. All heavy chain constant regions were human IgG1 in these assays.

Figure 38:
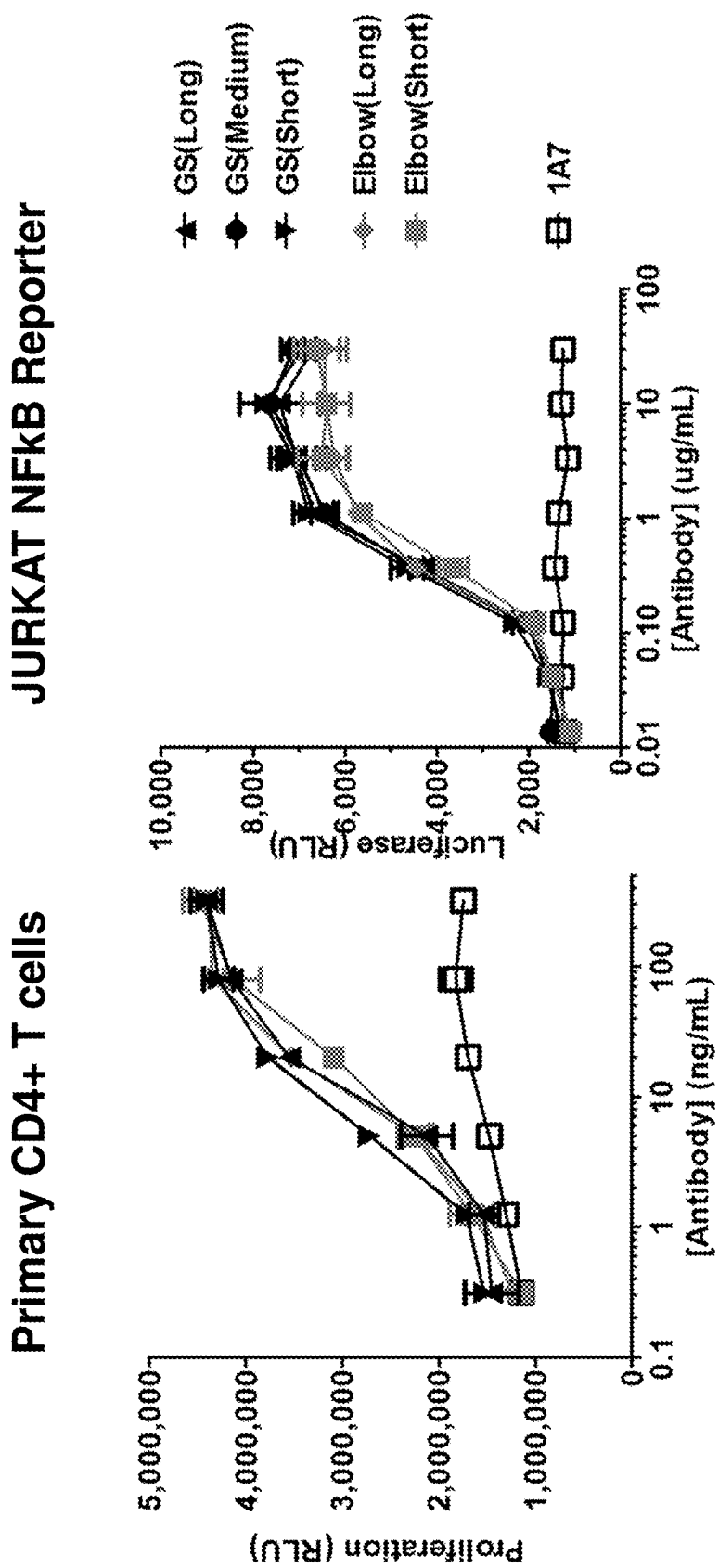

FIG. 38 shows OX40 agonist activity of engineered linker variants of r:Fv-IgGs and 1A7 human IgG1 (1A7) control antibody in both the primary human T cell assay (left panel) and OX40+ Jurkat cell luciferase reporter assay (right panel). The primary cell assay included CD4+ memory T cells, anti-CD3 antibody, and FcγRIIa+ L cells. GS(Long), GS(Medium), GS(Short), Elbow(Long), and Elbow(Short) refers to linker variants of r:Fv-IgG 3C8-1A7 as described in Example 16.

Figure 39:
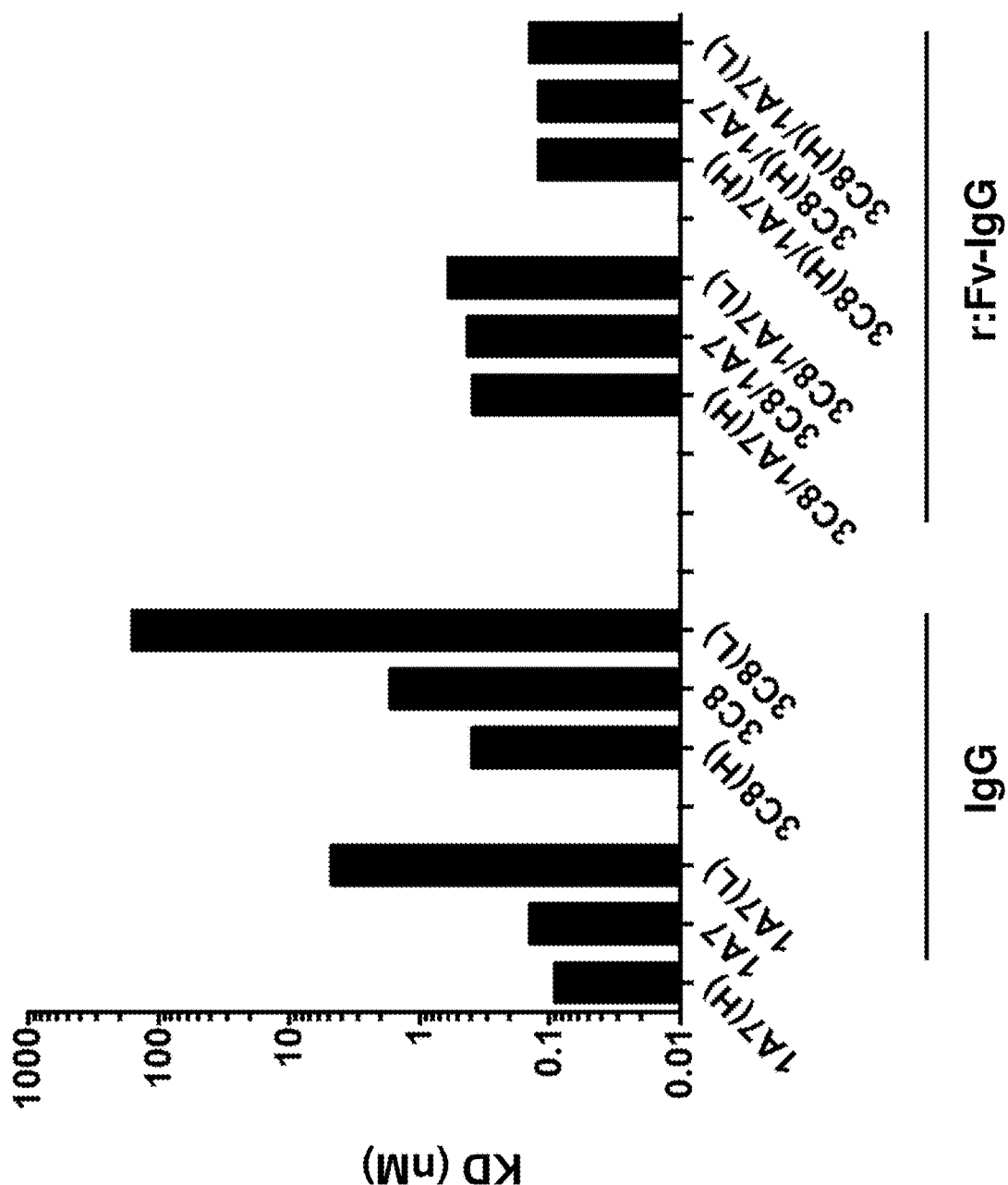

FIG. 39 shows a plot of the affinities of high and low affinity variant versions of IgG1 and r:Fv-IgG formats. H corresponds to High (lower KD, stronger affinity) and L corresponds to Low (higher KD, weaker affinity) variants. Parentheses designate whether the 3C8 Fv and/or 1A7 Fv were increased or reduced in affinity. For example, 3C8(H)/1A7(L) corresponds to an r:Fv-IgG 3C8-1A7 in which the 3C8 Fv has stronger affinity (N31I/K64L variant) and in which the 1A7 Fv has weaker affinity (P96A variant) relative to the r:Fv-IgG 3C8-1A7 parent.

Figure 40:
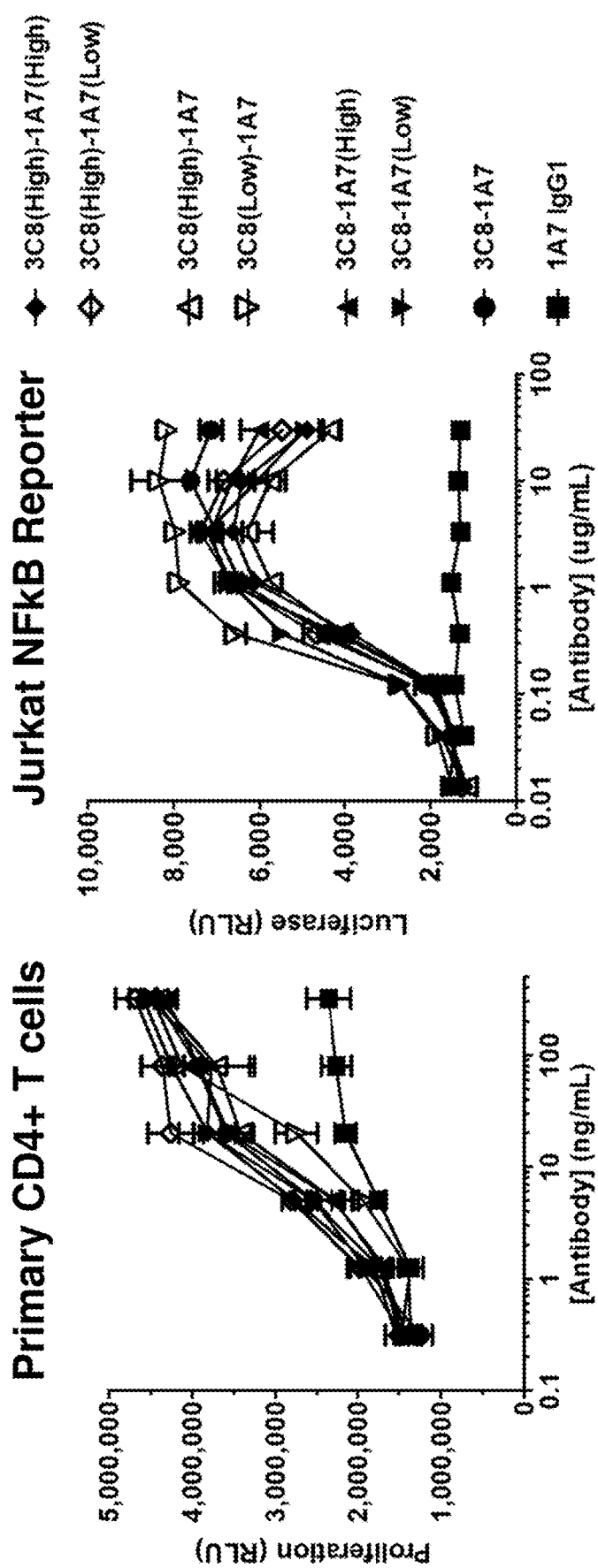

FIG. 40 shows OX40 agonist activity of engineered affinity variants of r:Fv-IgGs and 1A7 human IgG1 (1A7) and 3C8 human IgG1 (3C8) control antibodies in both the primary human T cell assay (left panel) and OX40+ Jurkat cell luciferase reporter assay (right panel). The primary cell assay included CD4+ memory T cells, anti-CD3 antibody, and FcγRIIa+ L cells. High corresponds to stronger affinity (lower KD) and Low corresponds to weaker affinity (higher KD) variants relative to the r:Fv-IgG 3C8-1A7 parent. Parentheses designate whether the 3C8 Fv and/or 1A7 Fv were increased or reduced in affinity. For example, 3C8 (High)-1A7(Low) corresponds to an r:Fv-IgG 3C8-1A7 in which the 3C8 Fv has stronger affinity (N31I/K64L variant) and in which the 1A7 Fv has weaker affinity (P96A variant) relative to the r:Fv-IgG 3C8-1A7 parent.

Figure 41:
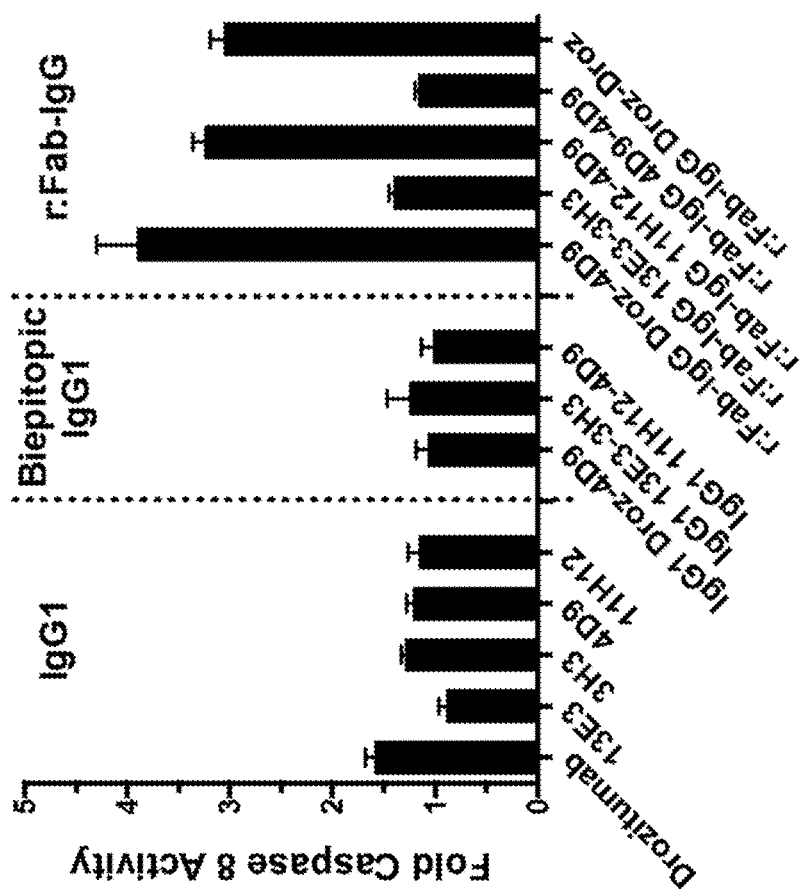

FIG. 41 shows caspase 8 activity for IgG1, biepitopic IgG1, and biepitopic r:Fab-IgG versions of anti-DR5 antibodies against HT-29 cells. Antibodies were tested at 50 nM concentration. Drozitumab is abbreviated to Droz. IgG1 antibodies include Drozitumab, 13E3, 3H3, 4D9, and 11H12. Bivalent biepitopic IgG1 antibodies include IgG1 Droz-4D9, IgG1 13E3-3H3, and IgG1 11H12-4D9. r:Fab-IgGs include tetravalent monoepitopics r:Fab-IgG 4D9-4D9 and r:Fab-IgG Droz-Droz and tetravalent biepitopics r:Fab-IgG Droz-4D9, r:Fab-IgG 13E3-3H3, and r:Fab-IgG 11H12-4D9.

Figure 42:
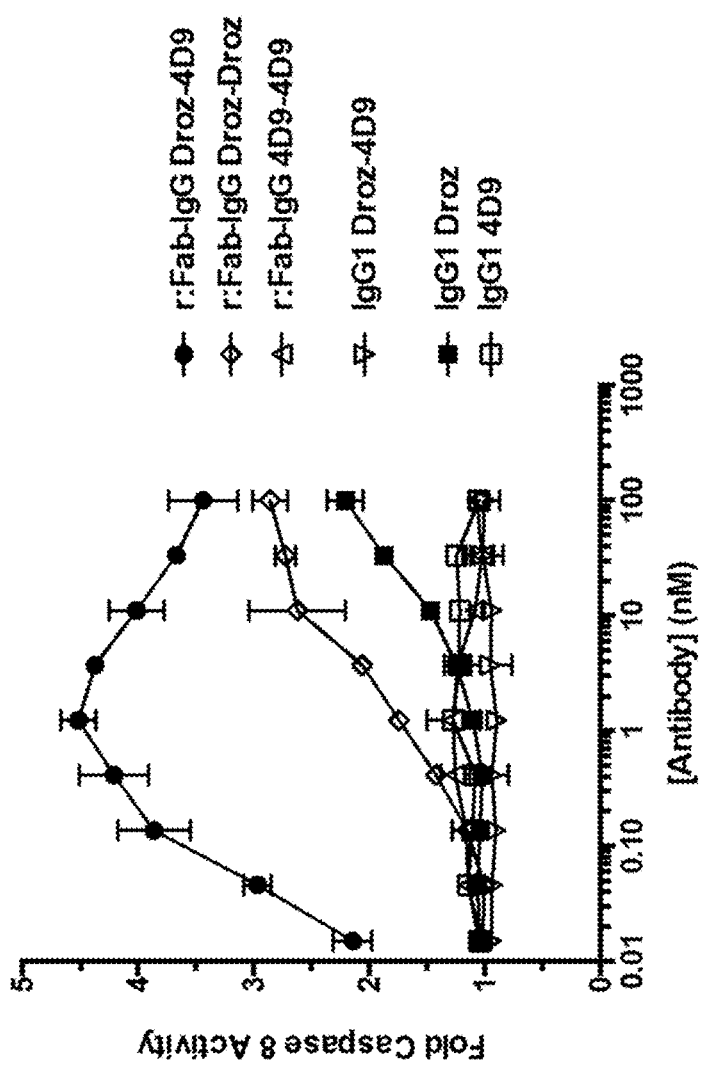

FIG. 42 shows dose-response caspase 8 activity for IgG1, biepitopic IgG1, and biepitopic r:Fab-IgG versions of anti-DR5 antibodies against HT-29 cells. Drozitumab is abbreviated to Droz. IgG1 antibodies include IgG1 Droz and IgG1 4D9. Bivalent biepitopic IgG1 antibodies include IgG1 Droz-4D9. r:Fab-IgGs include tetravalent monoepitopics r:Fab-IgG 4D9-4D9 and r:Fab-IgG Droz-Droz, and tetravalent biepitopic r:Fab-IgG Droz-4D9.

Figure 43:
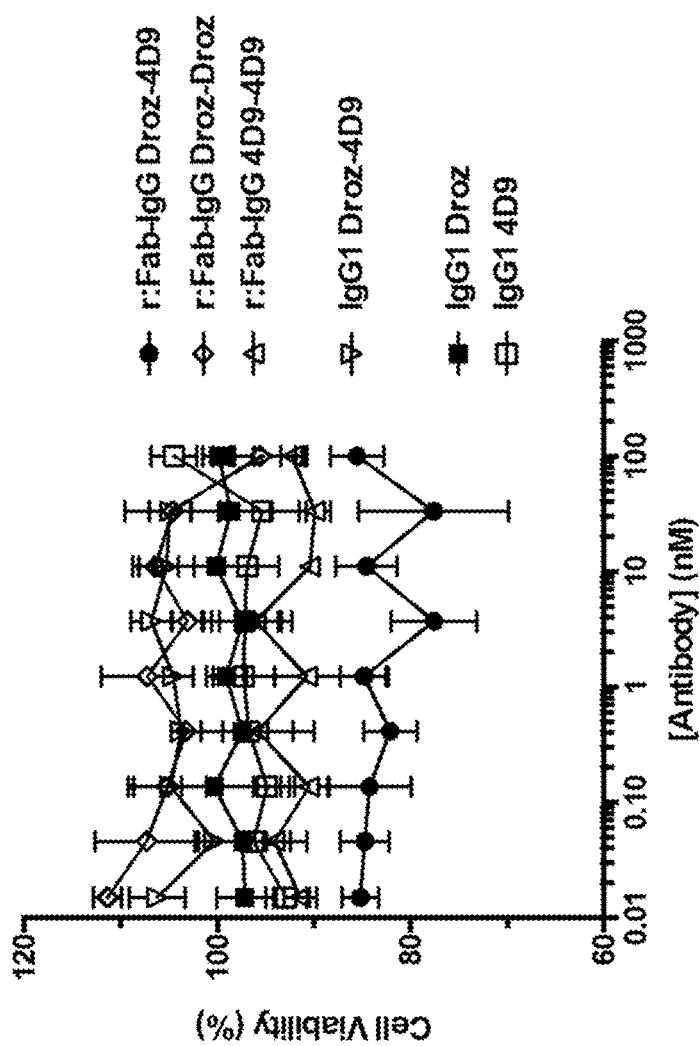

FIG. 43 shows dose-response anti-proliferative activity for IgG1, biepitopic IgG1, and biepitopic r:Fab-IgG versions of anti-DR5 antibodies against HT-29 cells. Drozitumab is abbreviated to Droz. IgG1 antibodies include IgG1 Droz and IgG1 4D9. Bivalent biepitopic IgG1 antibodies include IgG1 Droz-4D9. r:Fab-IgGs include tetravalent monoepitopics r:Fab-IgG 4D9-4D9 and r:Fab-IgG Droz-Droz, and tetravalent biepitopic r:Fab-IgG Droz-4D9.

Figure 44:
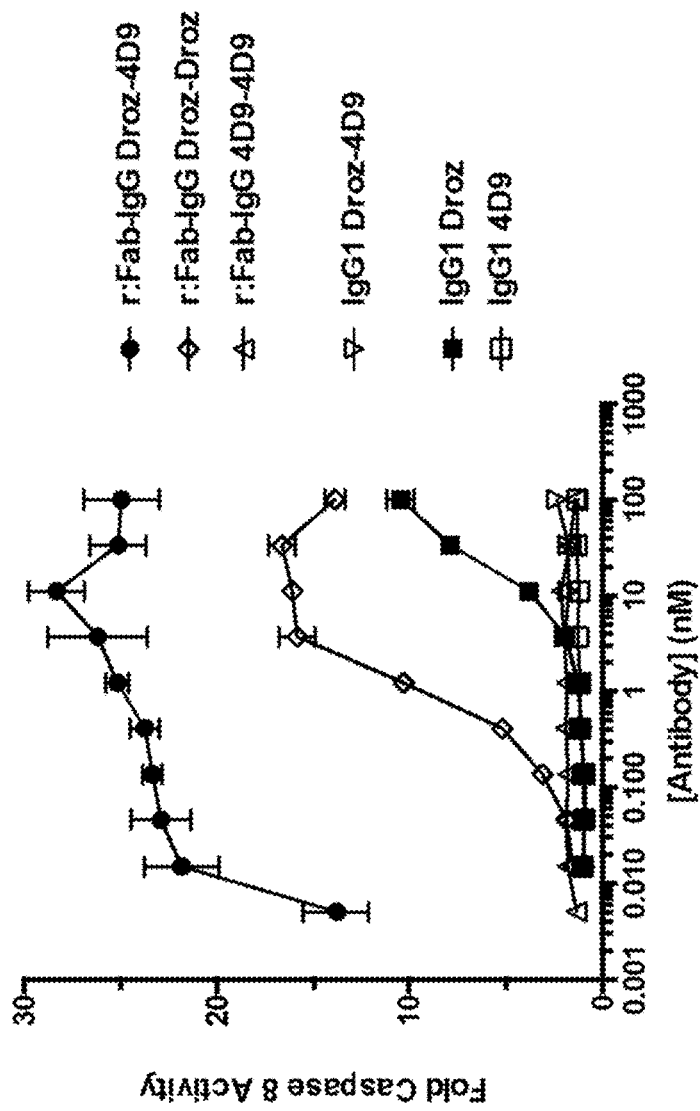

FIG. 44 shows dose-response caspase 8 activity for IgG1, biepitopic IgG1, and biepitopic r:Fab-IgG versions of anti-DR5 antibodies against Colo205 cells. Drozitumab is abbreviated to Droz. IgG1 antibodies include IgG1 Droz and IgG1 4D9. Bivalent biepitopic IgG1 antibodies include IgG1 Droz-4D9. r:Fab-IgGs include tetravalent monoepitopics r:Fab-IgG 4D9-4D9 and r:Fab-IgG Droz-Droz, and tetravalent biepitopic r:Fab-IgG Droz-4D9.

Figure 45:
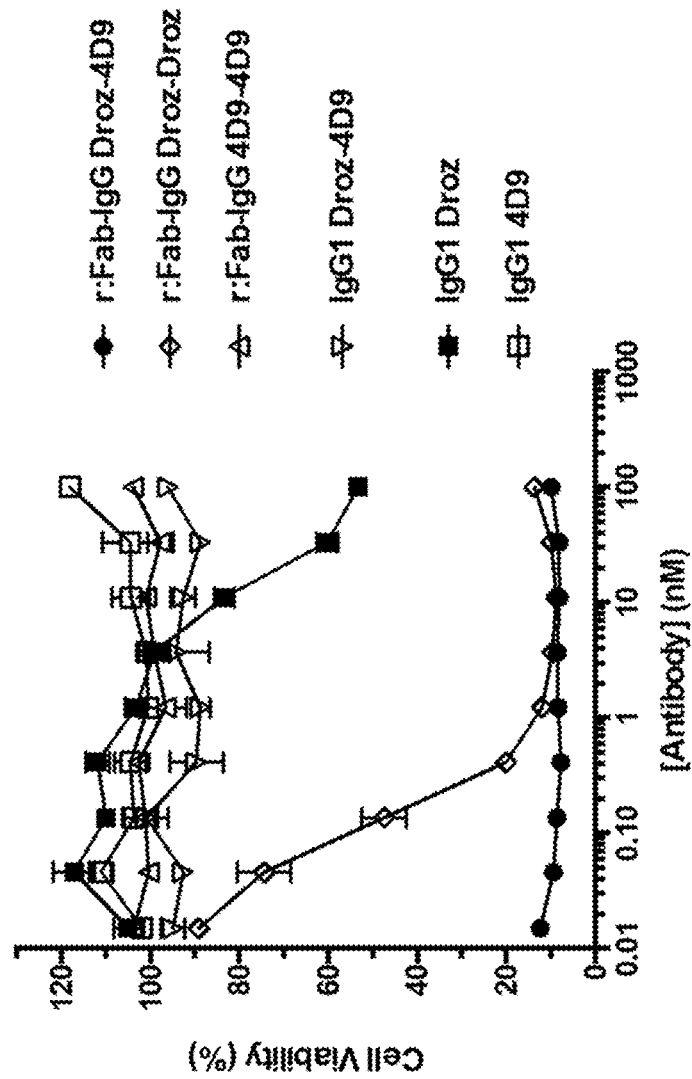

FIG. 45 shows dose-response antiproliferative activity for IgG1, biepitopic IgG1, and biepitopic r:Fab-IgG versions of anti-DR5 antibodies against Colo205 cells. Drozitumab is abbreviated to Droz. IgG1 antibodies include IgG1 Droz and IgG1 4D9. Bivalent biepitopic IgG1 antibodies include IgG1 Droz-4D9. r:Fab-IgGs include tetravalent monoepitopics r:Fab-IgG 4D9-4D9 and r:Fab-IgG Droz-Droz, and tetravalent biepitopic r:Fab-IgG Droz-4D9.

DETAILED DESCRIPTION

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al, Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

"Framework" or "FR" refers to variable domain residues other than hypervariable region (HVR) residues. The FR of a variable domain generally consists of four FR domains: FR1, 1-R2, FR3, and FR4. Accordingly, the HVR and FR sequences generally appear in the following sequence in VH (or VL): FR1-H1(L1)-FR2-H2(L2)-FR3-H3(L3)-FR4.

"Antibody fragments" comprise a portion of an intact antibody, preferably comprising the "antigen binding region" thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pliickthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et ah, Proc. Natl. Acad. Set USA, 90:6444-6448 (1993).

The term "multispecific antibody" is used in the broadest sense and specifically covers an antibody that has poly-epitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 μM, 3 μM to 0.001 μM, 1 μM to 0.001 μM, 0.5 μM to 0.001 μM, or 0.1 μM to 0.001 μM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. Sci. USA 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al, Nature 332: 323-329 (1988); and Presta, Curr. Op. Struct. Biol. 2:593-596 (1992).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding and antibody-dependent cell-mediated cytotoxicity (ADCC); phagocytosis; down regulation of cell surface receptors.

"Antibody-dependent cell-mediated cytotoxicity" or "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et ah, Proc. Natl. Acad. Set (USA) 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (Clq) to a molecule (e.g. polypeptide (e.g., an antibody)) complexed with a cognate antigen. To assess complement activation, a CDC assay, e.g. as described in Gazzano-Santoro et al., J. Immunol. Methods 202: 163 (1996), may be performed.

The terms "Fc receptor" or "FcR" are used to describe a receptor that binds to the Fc region of an antibody. In some embodiments, the FcR is a native sequence human FcR.

Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an activating receptor) and FcγRIIB (an inhibiting receptor), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, {see Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al, J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc sequence of an immunoglobulin generally comprises two constant domains, a CH2 domain and a CH3 domain, and optionally comprises a CH4 domain By "Fc polypeptide" herein is meant one of the polypeptides that make up an Fc region, e.g., a monomeric Fc. An Fc region may be obtained from any suitable immunoglobulin, such as IgG1 lgG2, lgG3, or lgG4 subtypes, IgA, IgE, IgD or IgM. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "modified Fc region" or "Fc variant" comprises an amino acid sequence which differs from that of a native sequence Fc region by virtue of at least one amino acid modification, preferably one or more amino acid substitution(s). Preferably, the modified Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The modified Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

The term "agonist", "agonistic", "agonism" or "agonize" as used herein in general refers to a binding molecule (e.g., an antigen binding polypeptide or antigen binding complex) which binds to a receptor on the surface of a cell and is capable of initiating/mimicking/stimulating a reaction or activity that is similar to or the same as that initiated/mimicked/stimulated by the receptor's natural ligand. In exemplary embodiments, an agonist as described herein is capable of inducing/augmenting/enhancing/stimulating the activation of a signal transduction pathway associated with the receptor.

The term "cell surface receptor," as used herein, refers to any native cell surface receptor from any vertebrate source, including mammals such as primates (e.g. humans) and rodents (e.g., mice and rats), unless otherwise indicated. The term encompasses "full-length," unprocessed cell surface receptor as well as any form of cell surface receptor that results from processing in the cell. The term also encompasses naturally occurring variants of cell surface receptor, e.g., splice variants or allelic variants.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include epithelial ovarian cancer, fallopian tube cancer, primary peritoneal cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer (including platinum sensitive and platinum resistant ovarian cancer), liver cancer, bladder cancer, hepatoma, breast cancer, colon cancer, colorectal cancer, fallopian tube, peritoneal, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "effective amount" of an agent, e.g., a pharmaceutical formulation, refers to an amount effective, at dosages and for periods of time necessary, to achieve the desired therapeutic or prophylactic result.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Antigen Binding Complexes with Agonist Activity

Provided herein are antigen binding complexes, e.g., tetravalent antigen binding complexes, having agonist activity. A variety of configurations for the antigen binding complexes of the present disclosure are described and illustrated herein, with different formats including both mono-epitopic and bi- or multi-epitopic forms (see, e.g., FIGS. 3A & 3B). As demonstrated herein, targeting a cell surface receptor with a tetravalent antigen binding complex having agonist activity for the cell surface receptor results in strong receptor activation. Moreover, it is a surprising discovery of the present disclosure that targeting multiple epitopes of a cell surface receptor with an antigen binding complex (e.g., a tetravalent antigen binding complex) having agonist activity for the cell surface receptor results in a synergistic increase in receptor-mediated signaling (e.g., as compared to targeting only a single epitope with an equivalent number of antigen binding moieties). Importantly, the present disclosure demonstrates that antigen binding regions (e.g., antibody CDRs and/or variable domains) of antibodies that already show agonist activity when in monovalent form demonstrate superior agonist activity when used in the multivalent, biepitopic formats described herein. Exemplary antigen binding complex formats are described infra.

In some embodiments, an antigen binding complex (e.g., a tetravalent antigen binding complex) of the present disclosure comprises two subunits. In some embodiments, each subunit comprises an antibody. In some embodiments, the antibody is a bispecific antibody. For example, in some embodiments, each subunit comprises a first half-antibody comprising a first antibody heavy chain variable domain ($VH_1$) and a first antibody light chain variable domain ($VL_1$), and a second half-antibody comprising a second antibody heavy chain variable domain ($VH_2$) and a second antibody light chain variable domain ($VL_2$). As used herein, a "half-antibody" can refer to a single antibody light chain paired with a single antibody heavy chain.

In some embodiments, the first half-antibody comprises a first antibody heavy chain comprising, coupled from N-terminus to C-terminus, the first antibody heavy chain variable domain ($VH_1$), a first antibody heavy chain CH1 domain, a first antibody heavy chain CH2 domain, and a first antibody heavy chain CH3 domain; and a first antibody light chain comprising, coupled from N-terminus to C-terminus, the first antibody light chain variable domain ($VL_1$) and a first antibody light chain constant domain (CL). In some embodiments, the second half-antibody comprises a second antibody heavy chain comprising, coupled from N-terminus to C-terminus, the second antibody heavy chain variable domain ($VH_2$), a second antibody heavy chain CH1 domain, a second antibody heavy chain CH2 domain, and a second antibody heavy chain CH3 domain; and a second antibody light chain comprising, coupled from N-terminus to C-terminus, the second antibody light chain variable domain ($VL_2$) and a second antibody light chain constant domain (CL).

In some embodiments, a complex comprises a first antibody comprising two antibody heavy chains and two antibody light chains, wherein each of the two antibody heavy chains of the first antibody comprises: $VH_1$-$CH_1$-hinge-$CH_2$-$CH_3$ [X]; and wherein each of the two antibody light chains of the first antibody comprises: $VL_1$-CL [VII]; and a second antibody comprising two antibody heavy chains and two antibody light chains, wherein each of the two antibody heavy chains of the second antibody comprises: $VH_2$-$CH_1$-hinge-$CH_2$-$CH_3$ [XII]; and wherein each of the two antibody light chains of the second antibody comprises: $VL_2$-CL [IX]; wherein each of the antibody heavy chains of the first antibody associates with one of the antibody light chains of the first antibody such that $VH_1$ and $VL_1$ form an antigen binding domain; wherein each of the antibody heavy chains of the second antibody associates with one of the antibody light chains of the second antibody such that $VH_2$ and $VL_2$ form an antigen binding domain; wherein the first and the second antibodies are coupled via linker $L_1$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, and $CH_3$ is an antibody third heavy chain constant domain.

In some embodiments, one or both of the subunits comprises a first half-antibody (e.g., $VH_1$ and $VL_1$) that specifically binds one epitope (e.g., of a cell surface receptor), and a second half-antibody (e.g., $VH_2$ and $VL_2$) that specifically binds a different epitope (e.g., of the same cell surface receptor). In some embodiments, one or both of the subunits comprises a first half-antibody (e.g., $VH_1$ and $VL_1$) that specifically binds one epitope (e.g., of a cell surface receptor), and a second half-antibody (e.g., $VH_2$ and $VL_2$) that specifically binds the same epitope. In some embodiments, the first and second half-antibodies are coupled, e.g., as described herein (including without limitation chemical or genetic coupling, such as coupling with a linker of the present disclosure). As used herein, a "different" epitope can refer to an epitope that is partially or completely non-overlapping with another epitope. An exemplary configuration of the antigen binding complex is described and illustrated herein as a "c:IgG-IgG" format (see, e.g., FIGS. 3A & 3B).

In some embodiments, a complex comprises two antibodies, wherein each of the antibodies comprises: a first antibody heavy chain that comprises: $VH_1$-$CH_1$-hinge-$CH_2$-$(CH_3)_x$ [X]; that is associated with a first antibody light chain that comprises: $VL_1$-CL [VII]; and a second antibody heavy chain that comprises: $VH_2$-$CH_1$-hinge-$CH_2$-$(CH_3)_y$ [XII]; that is associated with a second antibody light chain that comprises: $VL_2$-CL [IX]; wherein each of the first antibody heavy chains associates with one of the first antibody light chains such that $VH_1$ and $VL_1$ form an antigen binding domain; wherein each of the second antibody heavy chains associates with one of the second antibody light chains such that $VH_2$ and $VL_2$ form an antigen binding domain; wherein the two antibodies are coupled via linker $L_1$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, and $(CH_3)_x$ and $(CH_3)_y$ are antibody third heavy chain constant domains.

In some embodiments, $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57. In some embodiments, $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57. In some embodiments, a VH domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:56 or 128. In some embodiments, a VL domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:57 or 129.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

In some embodiments, an antigen binding complex (e.g., a tetravalent antigen binding complex) of the present disclosure comprises an antibody and two or more antibody Fab fragments coupled with the antibody. In some embodiments, the antibody comprises two antibody heavy chains and two antibody light chains. In some embodiments, the complex includes two antibody Fab fragments (see, e.g., FIGS. 3A & 3B). In some embodiments, one or both of the antibody heavy chains comprises a first antibody heavy chain variable domain ($VH_1$). In some embodiments, one or both of the antibody light chains comprises a first antibody light chain variable domain ($VL_1$).

In some embodiments, each antibody heavy chain comprises, coupled from N-terminus to C-terminus, the first antibody heavy chain variable domain ($VH_1$), a first antibody heavy chain CH1 domain, a first antibody heavy chain CH2 domain, and a first antibody heavy chain CH3 domain. In some embodiments, each antibody light chain comprises, coupled from N-terminus to C-terminus, the first antibody light chain variable domain ($VL_1$) and a first antibody light chain constant domain (CL). In some embodiments, each of the two antibody Fab fragments comprises a heavy chain Fab fragment comprising, coupled from N-terminus to C-terminus, the second antibody heavy chain variable domain ($VH_2$) and a second antibody heavy chain CH1 domain. In some embodiments, each of the two antibody Fab fragments comprises a light chain Fab fragment comprising, coupled from N-terminus to C-terminus, the second antibody light chain variable domain ($VL_2$) and a second antibody light chain constant domain (CL).

In some embodiments, the antibody specifically binds to an epitope of a cell surface receptor of the present disclosure. In some embodiments, one or both of the antibody Fab fragments comprises a second antibody heavy chain variable domain ($VH_2$) and a second antibody light chain variable domain ($VL_2$). In some embodiments, one or both of the antibody Fab fragments specifically binds a different epitope of the same cell surface receptor as the antibody. In some embodiments, one or both of the antibody Fab fragments specifically binds the same epitope of the cell surface receptor as the antibody. In some embodiments, the complex has agonist activity for the cell surface receptor bound by the complex.

In some embodiments, the two Fab fragments are chemically coupled to the antibody, e.g., with a linker of the present disclosure. In some embodiments, the two Fab fragments are genetically coupled to the antibody, e.g., with a polypeptide linker of the present disclosure.

In some embodiments, each of the two Fab fragments is coupled to a different heavy or light chain of the antibody. Exemplary configurations of the antigen binding complex are described and illustrated herein as "c:Fab-IgG" formats (see, e.g., FIGS. 3A & 3B). A variety of configurations by which a Fab fragment can be coupled to an antibody heavy or light chain are described herein, including genetic or chemical coupling, and using a variety of linkers of the present disclosure. In some embodiments, more than two Fab fragments are coupled to the antibody.

In some embodiments, the two Fab fragments are genetically coupled to the antibody, e.g., by producing antibody heavy and/or light chains comprising more than one VH or VL domain, respectively.

In some embodiments, a complex comprises an antibody comprising two antibody heavy chains associated with two antibody light chains, and two antibody Fab fragments; wherein each of the antibody heavy chains of the antibody comprises: $VH_1$-$(CH_1)_x$-hinge-$CH_2$-$CH_3$ [X]; wherein each of the antibody light chains of the antibody comprises: $VL_1$-$(CL)_x$ [VII]; wherein each of the antibody Fab fragments comprises: a heavy chain fragment comprising: $VH_2$-$(CH_1)y$ [XI]; and a light chain comprising: $VL_2$-$(CL)_y$ [IX]; wherein each of the antibody heavy chains is associated with one of the antibody light chains such that $VH_1$ and $VL_1$ form an antigen binding domain; wherein each of the antibody Fab fragments comprises one heavy chain fragment comprising formula [XI] associated with one light chain fragment comprising formula [IX] such that $VH_2$ and $VL_2$ form an antigen binding domain; wherein each of the antibody Fab fragments is coupled with one of the antibody heavy chains or one of the antibody light chains of the antibody via linker $L_1$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, $(CL)_x$ and $(CL)_y$ are antibody light chain constant domains, $(CH_1)_x$ and $(CH_1)_y$ are antibody first heavy chain constant domains, hinge is an antibody hinge region, $CH_2$ is an antibody second heavy chain constant domain, and $CH_3$ is an antibody third heavy chain constant domain.

In some embodiments, $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57. In some embodiments, $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57. In some embodiments, a VH domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:56 or 128. In some embodiments, a VL domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:57 or 129. In some embodiments, each of the antibody heavy chains of the antibody comprises an amino acid sequence having at least 90%, at least 91%, at least 92%, at least 93%, at least 94%, at least 95%, at least 96%, at least 97%, at least 98%, at least 99%, or 100% identity to SEQ ID NO:232, each of the antibody light chains of the antibody comprises an amino acid sequence having at least 90%, at least 91%, at least 92%, at least 93%, at least 94%, at least 95%, at least 96%, at least 97%, at least 98%, at least 99%, or 100% identity to SEQ ID NO:237, each of the antibody Fab fragments comprises a heavy chain fragment comprising an amino acid sequence having at least 90%, at least 91%, at least 92%, at least 93%, at least 94%, at least 95%, at least 96%, at least 97%, at least 98%, at least 99%, or 100% identity to SEQ ID NO:239, and each of the antibody Fab fragments comprises a light chain fragment comprising an amino acid sequence having at least 90%, at least 91%, at least 92%, at least 93%, at least 94%, at least 95%, at least 96%, at least 97%, at least 98%, at least 99%, or 100% identity to SEQ ID NO:231. In some embodiments, each of the antibody heavy chains of the antibody comprises an amino acid sequence having at least 90%, at least 91%, at least 92%, at least 93%, at least 94%, at least 95%, at least 96%, at least 97%, at least 98%, at least 99%, or 100% identity to SEQ ID NO:230, each of the antibody light chains of the antibody comprises an amino acid sequence having at least 90%, at least 91%, at least 92%, at least 93%, at least 94%, at least 95%, at least 96%, at least 97%, at least 98%, at least 99%, or 100% identity to SEQ ID NO:236, each of the antibody Fab fragments comprises a heavy chain fragment comprising an amino acid sequence having at least 90%, at least 91%, at least 92%, at least 93%, at least 94%, at least 95%, at least 96%, at least 97%, at least 98%, at least 99%, or 100% identity to SEQ ID NO:238, and each of the antibody Fab fragments comprises a light chain fragment comprising an amino acid sequence having at least 90%, at least 91%, at least 92%, at least 93%, at least 94%, at least 95%, at least 96%, at least 97%, at least 98%, at least 99%, or 100% identity to SEQ ID NO:233. In some embodiments, each of the antibody heavy chains of the antibody comprises the amino acid sequence of SEQ ID NO:230 or 294, each of the antibody light chains of the antibody comprises the amino acid sequence of SEQ ID NO:236, each of the antibody Fab fragments comprises a heavy chain fragment comprising the amino acid sequence of SEQ ID NO:238, and each of the antibody Fab fragments comprises a light chain fragment comprising the amino acid sequence of SEQ ID NO:233

Figure 3A:
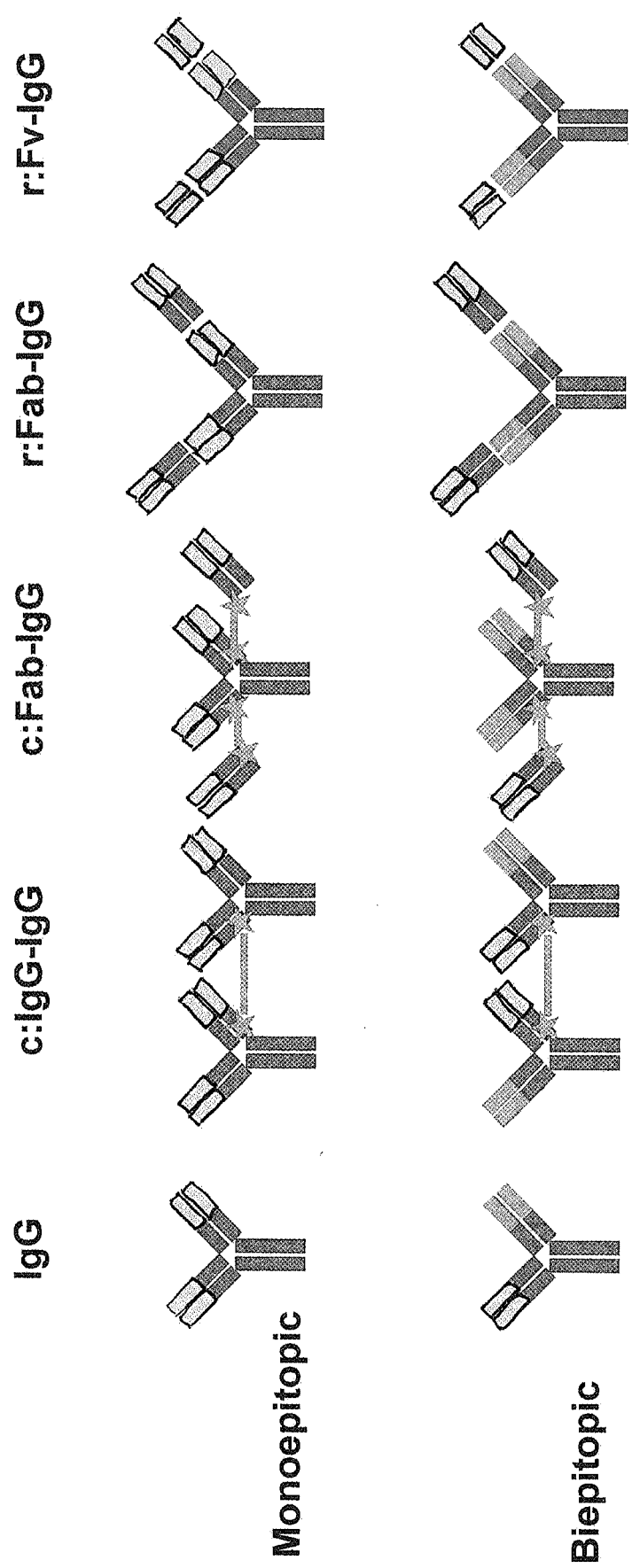
FIGS. 3A & 3B show exemplary antibody formats of the present disclosure. Schematic illustrations are provided for a coupled IgG-IgG (c:IgG-IgG) wherein two full length IgGs are coupled (e.g., chemically coupled), a coupled Fab-IgG (c:Fab-IgG) wherein two Fabs are coupled (e.g., chemically coupled) to a full length IgG, a recombinant Fab-IgG (r:Fab-IgG) wherein an extra set of Fab arms is fused recombinantly to an IgG, and a recombinant Fv-IgG (r:Fv-IgG) wherein an extra set of Fv regions is fused recombinantly to an IgG. For each format are illustrated a monoepitopic version (top row), wherein all four variable regions bind the same epitope on the target antigen, and a biepitopic version (bottom row), wherein two variable regions bind one epitope and the other variable regions bind a different epitope on the target antigen. Lines between antibodies, or between antibodies and Fab fragments, represent linkers, and stars represent attachment points where the linker is chemically coupled (e.g., at an engineered cysteine of the antibody or Fab fragment).
Figure 3B:
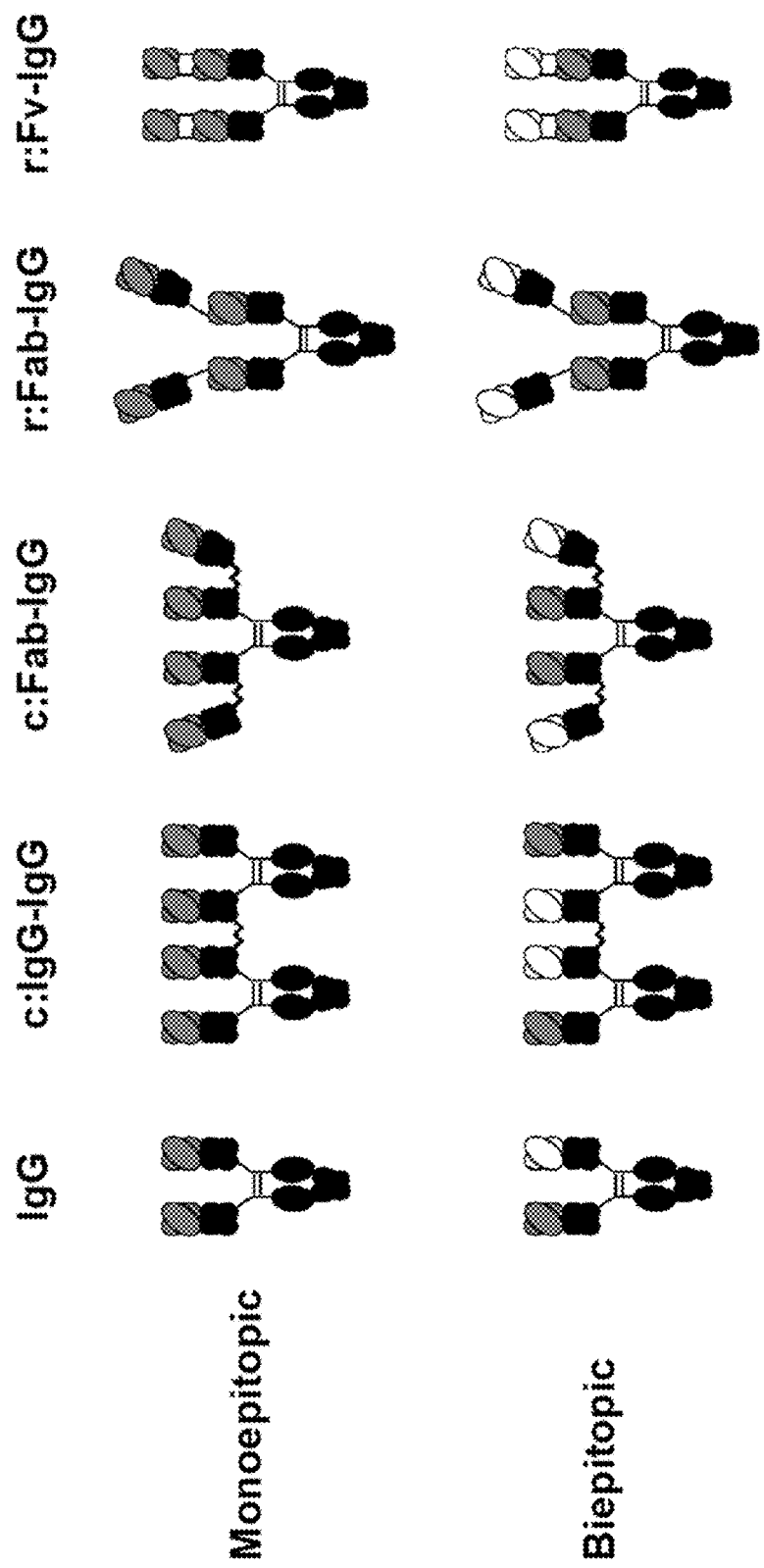

An exemplary configuration of the antigen binding complex is described and illustrated herein as an "r:Fab-IgG" format (see, e.g., FIGS. 3A & 3B). A variety of configurations, including both mono-epitopic and bi- or multi-epitopic forms, are contemplated. For example, in some embodiments, the antibody heavy chain comprises, from N-terminus to C-terminus, a first heavy chain variable domain ($VH_1$), a first heavy chain CH1 domain, a second heavy chain variable domain ($VH_2$), a second heavy chain CH1 domain, a heavy chain CH2 domain, a heavy chain CH3 domain, and, optionally (e.g., for IgM or IgE antibodies), a heavy chain CH4 domain. In some embodiments, the antibody light chain comprises, from N-terminus to C-terminus, a first light chain variable domain ($VL_1$), a first light chain constant domain (e.g., VK or VL), a second light chain variable domain ($VL_2$), and a second light chain constant domain (e.g., VK or VL). In some embodiments, the first heavy chain variable domain ($VH_1$) and the first light chain variable domain ($VL_1$) recognize a first epitope of a cell surface receptor, and the second heavy chain variable domain ($VH_2$) and the second light chain variable domain ($VL_2$) recognize the same epitope of the cell surface receptor. In some embodiments, the first heavy chain variable domain ($VH_1$) and the first light chain variable domain ($VL_1$) recognize a first epitope of a cell surface receptor, and the second heavy chain variable domain ($VH_2$) and the second light chain variable domain ($VL_2$) recognize a different epitope of the same cell surface receptor. In some embodiments, the two Fab fragments are coupled to the antibody by expressing an antibody heavy chain comprising, from N-terminus to C-terminus, a first heavy chain variable domain ($VH_1$), a first heavy chain CH1 domain, a second heavy chain variable domain ($VH_2$), a second heavy chain CH1 domain, a heavy chain CH2 domain, a heavy chain CH3 domain, and, optionally (e.g., for IgM or IgE antibodies), a heavy chain CH4 domain, and co-expressing with (or otherwise assembling with in vitro) the antibody a first light chain comprising, from N-terminus to C-terminus, a first light chain variable domain ($VL_1$) and a first light chain constant domain (CL; e.g., VK or VL) and a second light chain comprising, from N-terminus to C-terminus, a second light chain variable domain ($VL_2$) and a second light chain constant domain (CL; e.g., VK or VL). Thus, the antigen binding complex comprises two modified heavy chains, each having two distinct light chains coupled to it.

Descriptions of techniques suitable for producing an r:Fab-IgG antigen binding complex may be found, e.g., in International Patent Publication No. WO/2010/145792. It is a surprising discovery of the present disclosure that multi-epitopic r:Fab-IgG antigen binding complexes displayed superior agonist activity in both Jurkat T cell and primary T cell systems (see FIGS. 19 and 20).

In some embodiments, the first antibody light chain comprises a modification for orthogonal pairing with a first modification of the antibody heavy chain, and the second antibody light chain comprises a modification for orthogonal pairing with a second modification of the antibody heavy chain. For example, each of the $VH_1$ and $VL_1$, and/or each of the CH1 and CL, may include cognate modifications of an orthogonal variant pair, such that the $VH_1$ and $VH_2$ domains of the antibody each couple with their respective VL domain from the light chain. In some embodiments, the $VL_1$ domain of the first antibody light chain comprises a modification for orthogonal pairing with a modification of the $VH_1$ domain of the antibody heavy chain. In some embodiments, the CL domain of the first antibody light chain comprises a modification for orthogonal pairing with a modification of the first CH1 domain of the antibody heavy chain. In some embodiments, the $VL_2$ domain of the second antibody light chain comprises a modification for orthogonal pairing with a modification of the $VH_2$ domain of the antibody heavy chain. In some embodiments, the CL domain of the second antibody light chain comprises a modification for orthogonal pairing with a modification of the second CH1 domain of the antibody heavy chain. Exemplary orthogonal variant pairs for promoting such pairing are described in PCT/US2016/028850 and may include, without limitation, VH/VL regions with variant pairs VH-Q39K/VL-Q38E or VH Q39E/VL Q38K (Kabat numbering); CH1/CL regions with variant pairs -CH1-S183E/CL-V133K or CH1-S183K/CL-V133E (EU numbering); or variants selected from CH1 A141I, F170S, S181M, S183A, V185A, and CL F116A, L135V, S174A, S176F, and T178V (EU numbering).

In some embodiments, a complex of the present disclosure comprises two antibody heavy chain polypeptides and four antibody light chain polypeptides; wherein each of the antibody heavy chain polypeptides comprises: $VH_1$-$L_1$-$(CH_1)_x$-$L_2$-$VH_2$-$L_3$-$(CH_1)_y$-hinge-$CH_2$-$CH_3$ [III]; wherein two of the four antibody light chain polypeptides comprise: $VL_1$-$(CL)_x$ [IV]; and wherein two of the four antibody light chain polypeptides comprise: $VL_2$-$(CL)_y$ [V]; wherein each of the antibody heavy chain polypeptides associates with one light chain polypeptide comprising formula [IV] such that $VH_1$ and $VL_1$ form an antigen binding domain and one light chain polypeptide comprising formula [V] such that $VH_2$ and $VL_2$ form an antigen binding domain; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, $(CL)_x$ and $(CL)_y$ are antibody light chain constant domains, $(CH_1)_x$ and $(CH_1)_y$ are antibody first heavy chain constant domains, hinge is an antibody hinge region, $CH_2$ is an antibody second heavy chain constant domain, $CH_3$ is an antibody third heavy chain constant domain, and $L_1$, $L_2$, and $L_3$ are amino acid linkers. In some embodiments, the complex comprises one or more amino acid substitutions in $VH_1$, $VL_1$, $(CH_1)_x$, or $(CL)_x$ that promote $VH_1$ and $VL_1$ forming an antigen binding domain; and/or one or more amino acid substitutions in $VH_2$, $VL_2$, $(CH_1)_y$, or $(CL)_y$ that promote $VH_2$ and $VL_2$ forming an antigen binding domain. See, e.g., International Pub. No. WO2016172485 and Example 6. For example, exemplary substitutions include without limitation VH-Q39K/VL-Q38E or VH Q39E/VL Q38K (Kabat numbering), CH1-S183E/CL-V133K or CH1-S183K/CL-V133E (EU numbering); CH1 A141I, F170S, S181M, S183A, V185A; and CL F116A, L135V, S174A, S176F, and T178V (EU numbering). In some embodiments, both of the antibody heavy chain polypeptides comprise an amino acid sequence having at least 90%, at least 91%, at least 92%, at least 93%, at least 94%, at least 95%, at least 96%, at least 97%, at least 98%, at least 99%, or 100% identity to SEQ ID NO:244, both of the antibody light chain polypeptides comprising formula [IV] comprise an amino acid sequence having at least 90%, at least 91%, at least 92%, at least 93%, at least 94%, at least 95%, at least 96%, at least 97%, at least 98%, at least 99%, or 100% identity to SEQ ID NO:245, and both of the antibody light chain polypeptides comprising formula [V] comprise an amino acid sequence having at least 90%, at least 91%, at least 92%, at least 93%, at least 94%, at least 95%, at least 96%, at least 97%, at least 98%, at least 99%, or 100% identity to SEQ ID NO:246. In some embodiments, both of the antibody heavy chain polypeptides comprise the amino acid sequence of SEQ ID NO:244 or 292, both of the antibody light chain polypeptides comprising formula [IV] comprise the amino acid sequence of SEQ ID NO:245, and both of the antibody light chain polypeptides comprising formula [V] comprise the amino acid sequence of SEQ ID NO:246. In some embodiments, both of the antibody heavy chain polypeptides comprise an amino acid sequence having at least 90%, at least 91%, at least 92%, at least 93%, at least 94%, at least 95%, at least 96%, at least 97%, at least 98%, at least 99%, or 100% identity to SEQ ID NO:247, both of the antibody light chain polypeptides comprising formula [IV] comprise an amino acid sequence having at least 90%, at least 91%, at least 92%, at least 93%, at least 94%, at least 95%, at least 96%, at least 97%, at least 98%, at least 99%, or 100% identity to SEQ ID NO:248, and both of the antibody light chain polypeptides comprising formula [V] comprise an amino acid sequence having at least 90%, at least 91%, at least 92%, at least 93%, at least 94%, at least 95%, at least 96%, at least 97%, at least 98%, at least 99%, or 100% identity to SEQ ID NO:249. In some embodiments, both of the antibody heavy chain polypeptides comprise the amino acid sequence of SEQ ID NO:247 or 293, both of the antibody light chain polypeptides comprising formula [IV] comprise the amino acid sequence of SEQ ID NO:249, and both of the antibody light chain polypeptides comprising formula [V] comprise the amino acid sequence of SEQ ID NO:248.

In some embodiments, a complex comprises a first antibody heavy chain polypeptide that comprises: $VH_1-L_1-CH_1-L_2-VH_1-L_3-CH_1$-hinge-$CH_2-(CH_3)_x$ [VI]; two first antibody light chain polypeptides that each comprise: $VL_1$-CL [VII]; a second antibody heavy chain polypeptide that comprises: $VH_2-L_7-CH_1-L_8-VH_2-L_9-CH_1$-hinge-$CH_2-(CH_3)_y$ [VIII]; and two second antibody light chain polypeptides that each comprise: $VL_2$-CL [IX]; wherein the first antibody heavy chain polypeptide associates with two first antibody light chain polypeptides comprising formula [VII] such that each $VH_1$ forms an antigen binding domain with a $VL_1$; wherein the second antibody heavy chain polypeptide associates with two second antibody light chain polypeptides comprising formula [IX] such that each $VH_2$ forms an antigen binding domain with a $VL_2$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, $(CH_3)_x$ and $(CH_3)_y$ are antibody third heavy chain constant domains, and $L_1$, $L_2$, $L_3$, $L_7$, $L_8$, and $L_9$ are amino acid linkers. In some embodiments, $(CH_3)_x$ comprises a protuberance or cavity, wherein $(CH_3)_y$ comprises a protuberance or cavity, and wherein the protuberance or cavity of $(CH_3)_x$ is positionable in the protuberance or cavity of $(CH_3)_y$. See. e.g., Table C.

In some embodiments, $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57. In some embodiments, $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57. In some embodiments, a VH domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:56 or 128. In some embodiments, a VL domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:57 or 129.

Another exemplary configuration of the antigen binding complex is described and illustrated herein as an "r:Fv-IgG" format (see, e.g., FIGS. 3A & 3B). A variety of configurations, including both mono-epitopic and bi- or multi-epitopic forms, are contemplated. For example, in some embodiments, the antibody heavy chain comprises, from N-terminus to C-terminus, a first heavy chain variable domain ($VH_1$), a second heavy chain variable domain ($VH_2$), a heavy chain CH1 domain, a heavy chain CH2 domain, a heavy chain CH3 domain, and, optionally, a heavy chain CH4 domain. In some embodiments, the antibody light chain comprises, from N-terminus to C-terminus, a first light chain variable domain ($VL_1$), a second light chain variable domain ($VL_2$), and a light chain constant domain (e.g., VK or VL). In some embodiments, the first heavy chain variable domain ($VH_1$) and the first light chain variable domain ($VL_1$) recognize a first epitope of a cell surface receptor, and the second heavy chain variable domain ($VH_2$) and the second light chain variable domain ($VL_2$) recognize the same epitope of the cell surface receptor. In some embodiments, the first heavy chain variable domain ($VH_1$) and the first light chain variable domain ($VL_1$) recognize a first epitope of a cell surface receptor, and the second heavy chain variable domain ($VH_2$) and the second light chain variable domain ($VL_2$) recognize a different epitope of the same cell surface receptor.

In some embodiments, an antigen binding complex (e.g., a tetravalent antigen binding complex) of the present disclosure comprises two or more antibody heavy chains and/or two or more antibody light chains. In some embodiments, each heavy chain comprises a heavy chain variable domain (VH) and a set of heavy chain constant domains, e.g., a CH1 domain, a CH2 domain, a CH3 domain, and, optionally (e.g., for IgM or IgE antibodies), a CH4 domain. In some embodiments, each light chain comprises a light chain variable domain (VL) and a constant light (CL) domain (e.g., kappa or lambda). In some embodiments, the heavy chains of each subunit comprise one or more modifications that reduce effector function, e.g., as described herein.

In certain embodiments of any of the above formats, the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments, the $VH_1$ comprises one, two, or three antibody HVR sequences selected from: (i) HVR-H1 comprising the amino acid sequence of SEQ ID NO:2, (ii) HVR-H2 comprising the amino acid sequence of SEQ ID NO:3, and (iii) HVR-H3 comprising the amino acid sequence of SEQ ID NO:4; and/or the $VL_1$ comprises one, two, or three antibody HVR sequences selected from: (iv) HVR-L1 comprising the amino acid sequence of SEQ ID NO:5, (v) HVR-L2 comprising the amino acid sequence of SEQ ID NO:6, and (vi) HVR-L3 comprising an amino acid sequence selected from SEQ ID NO:7. In some embodiments, the $VH_1$ comprises the amino acid sequence of SEQ ID NO:56 and/or the $VL_1$ comprises the amino acid sequence of SEQ ID NO:57. In certain embodiments of any of the above formats, the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In some embodiments, the $VH_2$ comprises one, two, or three antibody HVR sequences selected from: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or the $VL_2$ comprises one, two, or three antibody HVR sequences selected from: (iv) HVR-L1 comprising the amino acid sequence of SEQ ID NO:37, (v) HVR-L2 comprising the amino acid sequence of SEQ ID NO:39, and (vi) HVR-L3 comprising an amino acid sequence selected from SEQ ID NO:42. In some embodiments, the $VH_2$ comprises the amino acid sequence of SEQ ID NO:126 and/or the $VL_2$ comprises the amino acid sequence of SEQ ID NO:129. In certain embodiments of any of the above formats, the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In certain embodiments, the $VH_1$ comprises the amino acid sequence of SEQ ID NO:56, the $VL_1$ comprises the amino acid sequence of SEQ ID NO:57, the $VH_2$ comprises the amino acid sequence of SEQ ID NO:126, and the $VL_2$ comprises the amino acid sequence of SEQ ID NO:129.

In certain embodiments of any of the above formats, the $VH_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or the $VL_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In some embodiments, the $VH_2$ comprises one, two, or three antibody HVR sequences selected from: (i) HVR-H1 comprising the amino acid sequence of SEQ ID NO:2, (ii) HVR-H2 comprising the amino acid sequence of SEQ ID NO:3, and (iii) HVR-H3 comprising the amino acid sequence of SEQ ID NO:4; and/or the $VL_2$ comprises one, two, or three antibody HVR sequences selected from: (iv) HVR-L1 comprising the amino acid sequence of SEQ ID NO:5, (v) HVR-L2 comprising the amino acid sequence of SEQ ID NO:6, and (vi) HVR-L3 comprising an amino acid sequence selected from SEQ ID NO:7. In some embodiments, the $VH_2$ comprises the amino acid sequence of SEQ ID NO:56 and/or the $VL_2$ comprises the amino acid sequence of SEQ ID NO:57. In certain embodiments of any of the above formats, the $VH_1$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or the $VL_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In some embodiments, the $VH_1$ comprises one, two, or three antibody HVR sequences selected from: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or the $VL_1$ comprises one, two, or three antibody HVR sequences selected from: (iv) HVR-L1 comprising the amino acid sequence of SEQ ID NO:37, (v) HVR-L2 comprising the amino acid sequence of SEQ ID NO:39, and (vi) HVR-L3 comprising an amino acid sequence selected from SEQ ID NO:42. In some embodiments, the $VH_1$ comprises the amino acid sequence of SEQ ID NO:126 and/or the $VL_1$ comprises the amino acid sequence of SEQ ID NO:129. In certain embodiments of any of the above formats, the $VH_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; the $VL_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; the $VH_1$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and the $VL_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42. In certain embodiments, the $VH_1$ comprises the amino acid sequence of SEQ ID NO:126, the $VL_1$ comprises the amino acid sequence of SEQ ID NO:129, the $VH_2$ comprises the amino acid sequence of SEQ ID NO:56, and the $VL_2$ comprises the amino acid sequence of SEQ ID NO:57.

In some embodiments, a complex comprises two antibody heavy chain polypeptides and two antibody light chain polypeptides; wherein each of the antibody heavy chain polypeptides comprises: $VH_1$-$L_1$-$VH_2$-$L_2$-$CH_1$-hinge-$CH_2$-$CH_3$ [1]; wherein each of the antibody light chain polypeptides comprises: $VL_1$-$L_3$-$VL_2$-$L_4$-CL [II]; wherein each of the antibody heavy chain polypeptides associates with one antibody light chain polypeptide such that $VH_1$ and $VL_1$ form an antigen binding domain and $VH_2$ and $VL_2$ form an antigen binding domain; wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, $CH_3$ is an antibody third heavy chain constant domain, and $L_1$, $L_2$, $L_3$, and $L_4$ are amino acid linkers.

In some embodiments, $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57. In some embodiments, $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57. In some embodiments, a VH domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:56 or 128. In some embodiments, a VL domain comprises an amino acid sequence having at least 90%, at least 91%, at least 92%, at least 93%, at least 94%, at least 95%, at least 96%, at least 97%, at least 98%, at least 99%, or 100% identity to SEQ ID NOs:57 or 129. In some embodiments, an antibody heavy chain polypeptide according to formula [I] comprises an amino acid sequence having at least 90%, at least 91%, at least 92%, at least 93%, at least 94%, at least 95%, at least 96%, at least 97%, at least 98%, at least 99%, or 100% identity to SEQ ID NOs: 240, 242, 250, 252, 254, 256, 258, 260, 262, 264, or 266. In some embodiments, an antibody heavy chain polypeptide according to formula [I] comprises an amino acid sequence having at least 90%, at least 91%, at least 92%, at least 93%, at least 94%, at least 95%, at least 96%, at least 97%, at least 98%, at least 99%, or 100% identity to SEQ ID NOs: 240 or 242. In some embodiments, an antibody heavy chain polypeptide according to formula [I] comprises the amino acid sequence of SEQ ID NO:242 or 291.

In any of the complexes described above, a $VH_1$, $VH_2$, $VL_1$, and/or $VL_2$ comprises an HVR-H1, HVR-H2, HVR-H3, HVR-L1, HVR-L2, and/or HVR-L3 that comprise one or more of the sequences listed in Tables 4 and 5.

A complex of the present disclosure can have one or more of the agonist activities described below.

In some embodiments, the OX40 agonist complex binds human OX40 with an affinity of less than or equal to about 0.45 nM. In some embodiments, the OX40 agonist complex binds human OX40 with an affinity of less than or equal to about 1 nM. In some embodiments, the OX40 complex binds human OX40 with an affinity of less than or equal to about 0.4 nM. In some embodiments, the OX40 complex binds human OX40 with an affinity of less than or equal to about 0.5 nM. In some embodiments, the binding affinity is determined using radioimmunoassay.

In some embodiments, the OX40 agonist complex binds human OX40 and cynomolgus OX40. In some embodiments, binding is determined using a FACS assay. In some embodiments, binding to human OX40 has an EC50 of about 0.2 ug/ml. In some embodiments, binding to human OX40 has an EC50 of about 0.3 ug/ml or lower. In some embodiments, binding to cynomolgus OX40 has an EC50 of about 1.5 ug/ml. In some embodiments, binding to cynomolgus OX40 has an EC50 of about 1.4 ug/ml.

In some embodiments, the OX40 agonist complex does not bind to rat OX40 or mouse OX40.

In some embodiments, the OX40 agonist complex does not induce apoptosis in OX40-expressing cells (e.g., Treg). In some embodiments, apoptosis is assayed using an antibody concentration of 30 ug/ml, e.g., by determining whether apoptosis has occurred using annexin V and proprodium iodide stained Treg.

In some embodiments, the OX40 agonist complex increases memory T cell proliferation and/or increasing cytokine production by the memory cell. In some embodiments, the cytokine is IFN-γ. In some embodiments, the OX40 agonist complex enhances memory T cell function, for example by increasing memory T cell proliferation and/or increasing cytokine production by the memory cell. In some embodiments, the cytokine is gamma interferon.

In some embodiments, the OX40 agonist complex increases CD4+ effector T cell proliferation and/or increases cytokine production by the CD4+ effector T cell as compared to proliferation and/or cytokine production prior to treatment with the OX40 agonist complex. In some embodiments, the cytokine is IFN-γ.

In some embodiments, the anti-human OX40 agonist complex enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist complex). In some embodiments, the cytokine is gamma interferon. In some embodiments, the anti-human OX40 agonist complex increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with anti-human OX40 agonist complex. In some embodiments, the anti-human OX40 agonist complex increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with anti-human OX40 agonist complex.

In some embodiments, the number of CD4+ effector T cells is elevated relative to prior to administration of the OX40 agonist complex. In some embodiments, CD4+ effector T cell cytokine secretion is elevated relative to prior to administration of the OX40 agonist complex. In some embodiments of any of the methods, the CD8+ effector T cells in the individual have enhanced proliferation, cytokine secretion and/or cytolytic activity relative to prior to the administration of the OX40 agonist complex. In some embodiments, the number of CD8+ effector T cells is elevated relative to prior to administration of the OX40 agonist complex. In some embodiments, CD8+ effector T cell cytokine secretion is elevated relative to prior to administration of the OX40 agonist complex.

In some embodiments, the anti-human OX40 agonist complex increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist complex. In some embodiments, the anti-human OX40 agonist complex increases number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 agonist complex.

In some embodiments, the number of intratumoral (infiltrating) CD8+ effector T cells (e.g., total number of CD8+ effector T cells, or e.g., percentage of CD8+ in CD45+ cells) is elevated relative to prior to administration of the OX40 agonist complex. In some embodiments of any of the methods of the invention, number of intratumoral (infiltrating) CD8+ effector T cells that express gamma interferon (e.g., percentage of CD8+ cells that express gamma interferon in total CD8+ cells) is increased relative to prior to administration of the OX40 agonist complex.

In some embodiments, the memory T cells in the individual have enhanced proliferation and/or cytokine secretion relative to prior to the administration of the OX40 agonist complex. In some embodiments, the number of memory T cells is elevated relative to prior to administration of the OX40 agonist complex. In some embodiments, memory T cell cytokine secretion (level) is elevated relative to prior to administration of the OX40 agonist complex. In some embodiments of any of the methods, the Treg in the individual have decreased inhibition of effector T cell function (e.g., proliferation and/or cytokine secretion) relative to prior to the administration of the OX40 agonist complex. In some embodiments, the number of effector T cells is elevated relative to prior to administration of the OX40 agonist complex. In some embodiments, effector T cell cytokine secretion (level) is elevated relative to prior to administration of the OX40 agonist complex.

In some embodiments, the OX40 agonist complex inhibits Treg suppression of effector T cell function. In some embodiments, effector T cell function is effector T cell proliferation and/or cytokine production. In some embodiments, the effector T cell is a CD4+ effector T cell.

In some embodiments, the OX40 agonist complex inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the OX40 agonist complex reduces the number of intratumoral (infiltrating) Treg (e.g., total number of Treg or e.g., percentage of Fox3p+ cells in CD4+ cells).

In some embodiments, the number of intratumoral (infiltrating) Treg (e.g., total number of Treg or e.g., percentage of Fox3p+ cells in CD4+ cells) is reduced relative to prior to administration of the OX40 agonist complex.

In some embodiments, the number of intratumoral (infiltrating) CD4+ effector T cells (e.g., total number of CD4+ effector T cells, or e.g., percentage of CD4+ cells in CD45+ cells) is elevated relative to prior to administration of the OX40 agonist complex. In some embodiments of any of the methods of the invention, number of intratumoral (infiltrating) CD4+ effector T cells that express gamma interferon (e.g., total gamma interferon expressing CD4+ cells, or e.g., percentage of gamma interferon expressing CD4+ cells in total CD4+ cells) is elevated relative to prior to administration of the OX40 agonist complex.

In some embodiments, the OX40 agonist complex increases OX40 signal transduction in a target cell that expresses OX40. In some embodiments, OX40 signal transduction is detected by monitoring NFkB downstream signaling.

In some embodiments, the OX40 agonist complex is stable after treatment at 40° C. for two weeks.

In some embodiments, the OX40 agonist complex competes for binding to human OX40 with OX40L. In some embodiments, addition of OX40L does not enhance OX40 complex function in an in vitro assay.

According to another embodiment, the OX40 agonist complexes include any one, any combination, or all of the following properties: (1) binds human OX40 with an affinity of less than or equal to about 0.45 nM, in some embodiments, binds human OX40 with an affinity of less than or equal to about 0.4 nM, in some embodiments, binds human OX40 with an affinity of less than or equal to about 0.5 nM, in some embodiments, the binding affinity is determined using radioimmunoassay; (2) binds human OX40 and cynomolgus OX40, in some embodiments, binding is determined using a FACS assay, (3) binds human OX40 with an EC50 of about 0.2 ug/ml, in some embodiments, binds to human OX40 has an EC50 of about 0.3 ug/ml or lower, in some embodiments, binds to cynomolgus OX40 with an EC50 of about 1.5 ug/ml, in some embodiments, binds to cynomolgus OX40 has an EC50 of about 1.4 ug/ml, (4) does not substantially bind to rat OX40 or mouse OX40, (5) enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist complex), (6) enhances memory T cell function, for example by increasing memory T cell proliferation and/or increasing cytokine production by the memory cell, (7) inhibits Treg function, for example, by decreasing Treg suppression of effector T cell function (e.g., effector T cell proliferation and/or effector T cell cytokine secretion). In some embodiments, the effector T cell is a CD4+ effector T cell, (8) increases OX40 signal transduction in a target cell that expresses OX40 (in some embodiments, OX40 signal transduction is detected by monitoring NFkB downstream signaling), and (9) is stable after treatment at 40° C. for two weeks.

Further contemplated herein are bispecific or multispecific antibodies, wherein each arm of a bispecific or multispecific antibody binds to the same cell surface receptor, e.g., OX40. In some embodiments, each arm of a bispecific or multispecific antibody binds to a different epitope of the same cell surface receptor, e.g., OX40. For example, in certain embodiments, a bispecific antibody may comprise two arms, wherein each arm binds a different epitope of OX40. It is to be understood that any of the exemplary antibodies, antigen binding domains, and/or antibody fragments that bind OX40 (e.g., HVRs, VH, and/or VL domains of any of the OX40 agonist antibodies described herein) may be combined in a bispecific or multispecific antibody in any combination.

Any of the other antibody HVR sequences, VH/VL sequences, and/or binding specificities described herein may be used in addition to or in place of one or more of the sequences described above.

Antigen Binding Polypeptides

Antigen binding polypeptides or subunits suitable for forming the complexes described herein comprise at least one antigen binding region for a cell surface receptor. The antigen binding polypeptides described herein may comprise an antibody, an antigen binding region of an antibody (e.g., an antibody fragment) fused to an Fc region, or a non-antibody antigen binding region protein fused to an Fc region. In exemplary embodiments, the antigen binding polypeptide is an antibody which binds to a cell surface receptor and has a modified Fc region.

In some embodiments, an antibody or subunit described herein contains at least two polypeptides. In some embodiments, the two polypeptides are half-antibodies, e.g., a single heavy chain (comprising a heavy chain variable region, a CH1 domain, and an Fc domain) and a single light chain (comprising a light chain variable region and CL domain). In particular, the Fc region for each antibody is a dimer formed between two polypeptides (either a homodimer or a heterodimer as described further below). Similarly, the antigen binding region attached to one of the polypeptides of the Fc region may contain two polypeptides, e.g., when the antigen binding region is an antibody fragment it may contain heavy and light chain variable regions.

Antibodies

In certain embodiments, an antigen binding complex (e.g., a tetravalent antigen binding complex having agonist activity) of the present disclosure, or a subunit thereof, provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antigen binding complex (e.g., a tetravalent antigen binding complex having agonist activity) of the present disclosure, or a subunit thereof, provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acid, Sci, USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies suitable as antigen binding polypeptides or subunits as described herein may be isolated by screening combinatorial libraries for polypeptides with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Antigen Binding Region of an Antibody

In certain embodiments, the antigen binding complexes (e.g., a tetravalent antigen binding complex having agonist activity) of the present disclosure or subunit(s) thereof described herein comprise an antigen binding region that binds to a cell surface receptor and an Fc region. In an exemplary embodiment, the antigen binding polypeptides, antibodies, or subunits described herein comprise an antigen binding region of an antibody that binds to a cell surface receptor fused to an Fc region. In some embodiments, an antigen binding region of the present disclosure refers to an antigen binding domain comprising a heavy chain variable domain (VH) and light chain variable domain (VL). In exemplary embodiments, an antigen binding region of an antibody refers to an antibody fragment, such as, for example, a Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein. Antibody fragments can be made from any of the antibodies described herein, including for example, monoclonal, chimeric, humanized, human, bispecific, multispecific, DAF, etc. antibody formats.

The antigen binding complexes (e.g., a tetravalent antigen binding complex having agonist activity) of the present disclosure or subunit(s) thereof described herein may comprise one or more polypeptides. In certain embodiments, the antigen binding regions comprises one polypeptide, such as, for example a single chain Fv (scFv) wherein the heavy and light chain variable regions of an antibody are attached via a linker. In other embodiments, the antigen binding region comprises two polypeptide, such as, for example a Fab antibody fragment wherein the heavy and light chain variable regions are separate polypeptide chains that naturally associate to form an antigen binding region having 6 CDRs.

In some embodiments, the complex comprises one or more amino acid substitutions in $VH_1$, $VL_1$, $(CH_1)_x$, or $(CL)_x$ that promote $VH_1$ and $VL_1$ forming an antigen binding domain; and/or one or more amino acid substitutions in $VH_2$, $VL_2$, $(CH_1)_y$, or $(CL)_y$ that promote $VH_2$ and $VL_2$ forming an antigen binding domain. See, e.g., International Pub. No. WO2016172485 and Example 6. For example, exemplary substitutions include without limitation VH-Q39K/VL-Q38E or VH Q39E/VL Q38K (Kabat numbering), CH1-S183E/CL-V133K or CH1-S183K/CL-V133E (EU numbering); CH1 A141I, F170S, S181M, S183A, V185A; and CL F116A, L135V, S174A, S176F, and T178V (EU numbering).

In certain embodiments a multispecific antigen-binding protein comprises a CH1 domain of H1 comprising (including consisting of and consisting essentially of) A141I, F170S, S181M, S183A, and V185A mutations (EU numbering) and a CL domain of L1 comprising (including consisting of or consisting essentially of) F116A, L135V, S174A, S176F, and T178V mutations (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H2 of the multispecific antigen-binding protein comprises (such as consists of or consists essentially of) an S183E substitution mutation (EU numbering), and the CL domain of L2 of the multispecific antigen-binding protein comprises (such as consists of or consists essentially of) a V133K substitution mutation (EU numbering In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H2 of the multispecific antigen-binding protein comprises (such as consists of or consists essentially of) an S183E substitution mutation (EU numbering), and the CL domain of L2 of the multispecific antigen-binding protein comprises (such as consists of or consists essentially of) a V133K substitution mutation (EU numbering).

Non-Antibody Antigen Binding Regions

In certain embodiments, the antigen binding polypeptides described herein comprise an antigen binding region that binds to a cell surface receptor and an Fc region. In an exemplary embodiment, the antigen binding polypeptides described herein comprise a non-antibody antigen binding region that binds to a cell surface receptor fused to an Fc region. Examples of non-antibody antigen binding regions include, for example, ligands, ligand fragments, or multimers thereof, that bind to a cell surface receptor. Examples of non-antibody antigen binding regions that bind to OX40 are described below. Examples of non-antibody binding regions that bind to Tie2 are described in WO 2008/049227.

Attachment of an Antigen Binding Region to an Fc Region

The antigen binding regions described herein (both antibody derived antigen binding regions and non-antibody antigen binding regions) may be fused to a variant Fc region as described herein. Any method for covalently attaching two polypeptides may be used to fuse together the antigen binding region with the Fc domain, including for example, expression as a single polypeptide (with or without an intervening polypeptide linker), chemical linkage or linkage via a polymeric group (such as, for example, a single or branched polyethylene glycol (PEG) linker). In certain embodiments, the linker may be a cleavable linker.

In certain embodiments, a linker may be a polypeptide linker. In one embodiment, the polypeptide linker is a hinge sequence from an antibody, or a variant thereof. For example, the hinge sequence may comprise amino acid residues 216-238 (EU numbering) of an antibody, such as, for example, an IgG1, IgG2, IgG3 or IgG4 antibody, or fragments or derivatives thereof. In an exemplary embodiment, a hinge based linker comprises the sequence CDKTH-TCPPCPAPELLGGP (SEQ ID NO:219), or fragments or derivatives thereof. In certain embodiments, the polypeptide linker may be a flexible linker of varying length (e.g., 5, 10, 15, 20, 25, 30, 35, 40, 45, 50 or more amino acids). Suitable linkers are known in the art, see for example, Protein Engineering, 9(3), 299-305, 1996. Exemplary peptide linkers include, for example:

| | |
|---|---|
| Ser | |
| Gly-Ser | |
| Gly-Gly-Ser | |
| Ser-Gly-Gly | |
| Gly-Gly-Gly-Ser | (SEQ ID NO: 220) |
| Ser-Gly-Gly-Gly | (SEQ ID NO: 221) |
| Gly-Gly-Gly-Gly-Ser | (SEQ ID NO: 222) |
| Ser-Gly-Gly-Gly-Gly | (SEQ ID NO: 223) |
| Gly-Gly-Gly-Gly-Gly-Ser | (SEQ ID NO: 224) |
| Ser-Gly-Gly-Gly-Gly-Gly | (SEQ ID NO: 225) |
| Gly-Gly-Gly-Gly-Gly-Gly-Ser | (SEQ ID NO: 226) |
| Ser-Gly-Gly-Gly-Gly-Gly-Gly | (SEQ ID NO: 227) |
| (Gly-Gly-Gly-Gly-Ser)$_n$ | (SEQ ID NO: 228) |
| and | |
| (Ser-Gly-Gly-Gly-Gly)$_n$ | (SEQ ID NO: 229) | wherein n is an integer not less than one. In certain embodiments n may be 1, 2, 3, 4, 5, 6, 7, 8, 9, 10, 15, or 20.

In some embodiments, a linker is between 0 and 20 amino acids in length (inclusive), e.g., 0, 1, 2, 3, 4, 5, 6, 7, 8, 9, 10, 11, 12, 13, 14, 15, 16, 17, 18, 19, or 20 amino acids in length.

In some embodiments, at least 90%, at least 91%, at least 92%, at least 93%, at least 94%, at least 95%, at least 96%, at least 97%, at least 98%, at least 99%, or 100% of the amino acids of a linker are glycine and/or serine amino acids. For example, in some embodiments, a linker of the present disclosure comprises the sequence GGGGSG (SEQ ID NO:270), GGGGSGGGGS (SEQ ID NO:272), GGGGSGGGGSGGGG (SEQ ID NO:273), GGSGG (SEQ ID NO:271), GGGGSGGGGS (SEQ ID NO:272), or GGSGGGGSGGGGS (SEQ ID NO:274).

In some embodiments, a linker comprises an amino acid sequence found within a human antibody constant domain sequence (e.g., a $CH_1$ domain or hinge region sequence). In some embodiments, a linker of the present disclosure comprises the sequence ASTKGP (SEQ ID NO:275), ASTKGPSVFPLAP (SEQ ID NO:277), RTVAAP (SEQ ID NO:276), or RTVAAPSVFIFPP (SEQ ID NO:278). In some embodiments, a linker comprises both an amino acid sequence found within a human antibody constant domain sequence (e.g., a $CH_1$ domain or hinge region sequence) and a sequence having at least 90%, at least 91%, at least 92%, at least 93%, at least 94%, at least 95%, at least 96%, at least 97%, at least 98%, at least 99%, or 100% glycine and/or serine amino acids.

In certain embodiments, a linker may be a chemical linker. Suitable chemical linkers are known in the art and commercially available. Exemplary chemical linkers include, for example, N-hydroxy succinimide (NHS), disuccinimidyl suberate (DSS), bis(sulfosuccinimidyl)suberate ($BS^3$), dithiobis(succinimidyl propionate) (DSP), dithiobis (sulfosuccinimidyl propionate) (DTSSP), ethylene glycolbis (succinimidyl succinate) (EGS), ethylene glycolbis(sulfosuccinimidyl succinate) (sulfo-EGS), disuccinimidyl tartrate (DST), disulfosuccinimidyl tartrate (sulfo-DST), bis[2-(succinimido oxycarbonyloxy)ethyl]sulfone (BSOCOES), and bis[2-(sulfosuccinimido oxycarbonyloxy) ethyl]sulfone (sulfo-BSOCOES).

In certain embodiments, an antigen binding region of an antibody is expressed as a single polypeptide with the Fc domain. As the Fc domain is a dimer, each polypeptide contained in the Fc dimer may be fused to an antigen binding region of an antibody or only of the polypeptides contained in the Fc dimer may be fused to an antigen binding region of an antibody.

In certain embodiments, a non-antibody antigen binding region is expressed as a single polypeptide with the Fc domain. As the Fc domain is a dimer, each polypeptide contained in the Fc dimer may be fused to a non-antibody antigen binding region or only of the polypeptides contained in the Fc dimer may be fused to a non-antibody antigen binding region.

Antigen Binding Regions Comprising OX40 Agonists

In one embodiment, the antigen binding polypeptide or complex described herein comprises an antigen binding region that binds to and agonizes human OX40. In certain embodiments, the antigen binding polypeptide comprises an antigen binding region of an anti-human OX40 agonist antibody. In certain embodiments, the antigen binding polypeptide comprises an antigen binding region that is a non-antibody OX40 agonist. Any of the variable domains of any of the exemplary OX40 agonist antibodies described infra can be used in a complex of the present disclosure.

OX40 Agonist Antibodies

Certain aspects of the present disclosure relate to antigen binding complexes that bind OX40. In some embodiments, the complex is a tetravalent antigen binding complex having agonist activity for OX40 (e.g., human OX40). Exemplary antibody subunits and exemplary features thereof are described infra. Without wishing to be bound to theory, it is thought that agonist antigen binding complexes (e.g., tetravalent agonist antigen binding complexes) may be particularly advantageous for scenarios in which antibody cross-linking by effector cells may be important for agonist activity (e.g., by inducing clustering of, and subsequent signaling by, the target), but effector cells may not be plentiful at the site of action (e.g., in a tumor with low levels of effector cells). In these scenarios, an agonist antigen binding complex such as a tetravalent agonist antigen binding complex may allow for and/or enhance agonist activity in the absence of plentiful effector cells.

In some embodiments, the antigen binding complex comprises an anti-human OX40 agonist antibody or Fab fragment that comprises at least one, two, three, four, five, or all six HVRs for the same antibody as listed in Table A. For example, in certain embodiments, the OX40 antibody or Fab fragment included in the complex contains all six of the HVRs from the same antibody as listed in Table A. In other embodiments, the complex comprises an anti-human OX40 agonist antibody or Fab fragment that comprises a heavy chain variable region ($V_H$) and/or a light chain variable region ($V_L$) as for the same antibody as listed in Table A below. It will be appreciated, however, that the HVR, $V_H$, and/or $V_L$ sequences as listed in Table A with reference to particular antibodies are not limited to these particular antibodies; instead, these sequences can be suitably combined in a variety of configurations not explicitly listed in Table A by one of skill in the art.

In some embodiments, the anti-human OX40 agonist antibody or Fab fragment comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In some embodiments, the anti-human OX40 agonist antibody or Fab fragment comprises at least one, at least two, or all three VH HVR sequences selected from (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4. In one embodiment, the antibody or Fab fragment comprises HVR-H3 comprising the amino acid sequence of SEQ ID NO:4. In another embodiment, the antibody or Fab fragment comprises HVR-H3 comprising the amino acid sequence of SEQ ID NO:4 and HVR-L3 comprising the amino acid sequence of SEQ ID NO:7. In a further embodiment, the antibody or Fab fragment comprises HVR-H3 comprising the amino acid sequence of SEQ ID NO:4, HVR-L3 comprising the amino acid sequence of SEQ ID NO:7, and HVR-H2 comprising the amino acid sequence of SEQ ID NO:3. In a further embodiment, the antibody or Fab fragment comprises (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4.

In some embodiments, the anti-human OX40 agonist antibody or Fab fragment comprises at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the antibody or Fab fragment comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In one embodiment, the anti-human OX40 agonist antibody or Fab fragment comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In some embodiments, the anti-human OX40 agonist antibody or Fab fragment comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:26.

In some embodiments, the anti-human OX40 agonist antibody or Fab fragment comprises HVR-H3 comprising the amino acid sequence of SEQ ID NO:4 and HVR-L3 comprising the amino acid sequence of SEQ ID NO:26. In a further embodiment, the antibody comprises HVR-H3 comprising the amino acid sequence of SEQ ID NO:4, HVR-L3 comprising the amino acid sequence of SEQ ID NO:26, and HVR-H2 comprising the amino acid sequence of SEQ ID NO:3.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:26.

In one embodiment, the anti-human OX40 agonist antibody or Fab fragment comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26.

In some embodiments, the anti-human OX40 agonist antibody or Fab fragment comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:27.

In one embodiment, the anti-human OX40 agonist antibody or Fab fragment comprises HVR-H3 comprising the amino acid sequence of SEQ ID NO:4 and HVR-L3 comprising the amino acid sequence of SEQ ID NO:27. In a further embodiment, the antibody comprises HVR-H3 comprising the amino acid sequence of SEQ ID NO:4, HVR-L3 comprising the amino acid sequence of SEQ ID NO:27, and HVR-H2 comprising the amino acid sequence of SEQ ID NO:3.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:27.

In one embodiment, the anti-human OX40 agonist antibody or Fab fragment comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27.

In some embodiments, the anti-human OX40 agonist antibody or Fab fragment comprises at least one, two, three, four, five, or six HVRs selected from (a) HVR-H1 comprising the amino acid sequence of SEQ ID NO:2, 8 or 9; (b) HVR-H2 comprising the amino acid sequence of SEQ ID NO:3, 10, 11, 12, 13 or 14; (c) HVR-H3 comprising the amino acid sequence of SEQ ID NO:4, 15, or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27, or 28.

In some embodiments, the anti-human OX40 agonist antibody or Fab fragment comprises at least one, at least two, or all three VH HVR sequences selected from (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19. In one embodiment, the antibody or Fab fragment comprises HVR-H3 comprising the amino acid sequence of SEQ ID NO: 4, 15, or 19. In another embodiment, the antibody comprises HVR-H3 comprising the amino acid sequence of SEQ ID NO:4, 15, or 19 and HVR-L3 comprising the amino acid sequence of SEQ ID NO: 7, 22, 23, 24, 25, 26, 27, or 28. In a further embodiment, the antibody or Fab fragment comprises HVR-H3 comprising the amino acid sequence of SEQ ID NO: 4, 15, or 19, HVR-L3 comprising the amino acid sequence of SEQ ID NO: 7, 22, 23, 24, 25, 26, 27, or 28, and HVR-H2 comprising the amino acid sequence of SEQ ID NO: 3, 10, 11, 12, 13 or 14. In a further embodiment, the antibody or Fab fragment comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19.

In some embodiments, the anti-human OX40 agonist antibody or Fab fragment comprises at least one, at least two, or all three VL HVR sequences selected from (a) HVR-L1 comprising the amino acid sequence of SEQ ID NO: 5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28. In one embodiment, the antibody or Fab fragment comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO: 7, 22, 23, 24, 25, 26, 27, or 28.

In some embodiments, the anti-human OX40 agonist antibody or Fab fragment comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; (c) HVR-H3 comprising the amino acid sequence of SEQ ID NO: 4, 15, or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO: 7, 22, 23, 24, 25, 26, 27, or 28.

In some embodiments, the anti-human OX40 agonist antibody or Fab fragment comprises at least one, two, three, four, five, or six HVRs selected from (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:175. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

In some embodiments, the anti-human OX40 agonist antibody or Fab fragment comprises at least one, at least two, or all three VH HVR sequences selected from (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In one embodiment, the antibody or Fab fragment comprises HVR-H3 comprising the amino acid sequence of SEQ ID NO:174. In another embodiment, the antibody or Fab fragment comprises HVR-H3 comprising the amino acid sequence of SEQ ID NO:174 and HVR-L3 comprising the amino acid sequence of SEQ ID NO:175. In a further embodiment, the antibody or Fab fragment comprises HVR-H3 comprising the amino acid sequence of SEQ ID NO:174, HVR-L3 comprising the amino acid sequence of SEQ ID NO:175, and HVR-H2 comprising the amino acid sequence of SEQ ID NO:173. In a further embodiment, the antibody or Fab fragment comprises (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

In one embodiment, the anti-human OX40 agonist antibody or Fab fragment comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:175. In some embodiments, HVR-L3 is not QAAAAAAAT (SEQ ID NO: 218).

In some embodiments, the anti-human OX40 agonist antibody or Fab fragment comprises at least one, at least two, or all three VH HVR sequences selected from (i) HVR-H1 comprising the amino acid sequence of SEQ ID NO:172, (ii) HVR-H2 comprising the amino acid sequence of SEQ ID NO:173, and (iii) HVR-H3 comprising an amino acid sequence selected from SEQ ID NO:174; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:175.

In some embodiments, the anti-human OX40 agonist antibody or Fab fragment comprises (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:175. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

All possible combinations of the above substitutions are encompassed by the consensus sequences of SEQ ID NO:172, 173, 174 and 175.

In some embodiments, the anti-human OX40 agonist antibody or Fab fragment comprises at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42.

In some embodiments, the anti-human OX40 agonist antibody or Fab fragment comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody or Fab fragment comprises HVR-H3 comprising the amino acid sequence of SEQ ID NO:33. In another embodiment, the antibody or Fab fragment comprises HVR-H3 comprising the amino acid sequence of SEQ ID NO:33 and HVR-L3 comprising the amino acid sequence of SEQ ID NO:42. In a further embodiment, the antibody or Fab fragment comprises HVR-H3 comprising the amino acid sequence of SEQ ID NO:33, HVR-L3 comprising the amino acid sequence of SEQ ID NO:42, and HVR-H2 comprising the amino acid sequence of SEQ ID NO:30. In a further embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody or Fab fragment comprises at least one, at least two, or all three VL HVR sequences selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In one embodiment, the antibody or Fab fragment comprises (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In some embodiments, the anti-human OX40 agonist antibody or Fab fragment comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody or Fab fragment comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (c) HVR-L3 comprising the amino acid sequence of SEQ ID NO:42.

In one embodiment, the anti-human OX40 agonist antibody or Fab fragment comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42.

In some embodiments, the anti-human OX40 agonist antibody or Fab fragment comprises at least one, at least two, or all three VL HVR sequences selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In one embodiment, the antibody or Fab fragment comprises (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In some embodiments, the anti-human OX40 agonist antibody or Fab fragment comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody or Fab fragment comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42.

In some embodiments, the anti-human OX40 agonist antibody or Fab fragment comprises at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising the amino acid sequence of SEQ ID NO:42.

In some embodiments, the anti-human OX40 agonist antibody or Fab fragment comprises at least one, at least two, or all three VL HVR sequences selected from (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42. In one embodiment, the antibody or Fab fragment comprises (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:40, and (c) HVR-L3 comprising the amino acid sequence of SEQ ID NO:42.

In one embodiment, the anti-human OX40 agonist antibody or Fab fragment comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising an amino acid sequence selected from SEQ ID NO:42.

In some embodiments, the anti-human OX40 agonist antibody or Fab fragment comprises at least one, two, three, four, five, or six HVRs selected from (a) HVR-H1 comprising the amino acid sequence of SEQ ID NO:29; (b) HVR-H2 comprising the amino acid sequence of SEQ ID NO:30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39, 40 or 41; and (f) HVR-L3 comprising the amino acid sequence of SEQ ID NO:42, 43, or 44.

In some embodiments, the anti-human OX40 agonist antibody or Fab fragment comprises at least one, at least two, or all three VH HVR sequences selected from (a) HVR-H1 comprising the amino acid sequence of SEQ ID NO:29; (b) HVR-H2 comprising the amino acid sequence of SEQ ID NO: 30, 31, or 32; and (c) HVR-H3 comprising the amino acid sequence of SEQ ID NO:33. In another embodiment, the antibody or Fab fragment comprises HVR-H3 comprising the amino acid sequence of SEQ ID NO:33 and HVR-L3 comprising the amino acid sequence of SEQ ID NO: 42, 43, or 44. In a further embodiment, the antibody or Fab fragment comprises HVR-H3 comprising the amino acid sequence of SEQ ID NO:33, HVR-L3 comprising the amino acid sequence of SEQ ID NO: 42, 43, or 44, and HVR-H2 comprising the amino acid sequence of SEQ ID NO: 39, 40 or 41. In a further embodiment, the antibody or Fab fragment comprises (a) HVR-H1 comprising the amino acid sequence of SEQ ID NO:29; (b) HVR-H2 comprising the amino acid sequence of SEQ ID NO:30, 31, or 32; and (c) HVR-H3 comprising the amino acid sequence of SEQ ID NO:33.

In some embodiments, the anti-human OX40 agonist antibody or Fab fragment comprises at least one, at least two, or all three VL HVR sequences selected from (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44. In one embodiment, the antibody or Fab fragment comprises (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO: 30, 31, or 32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO: 39, 40 or 41, and (c) HVR-L3 comprising the amino acid sequence of SEQ ID NO: 42, 43, or 44.

In some embodiments, the anti-human OX40 agonist antibody or Fab fragment comprises (a) HVR-H1 comprising the amino acid sequence of SEQ ID NO:29; (b) HVR-H2 comprising the amino acid sequence of SEQ ID NO: 30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 39, 40 or 41; and (f) HVR-L3 comprising an amino acid sequence selected from SEQ ID NO: 42, 43, or 44.

In some embodiments, the anti-human OX40 agonist antibody or Fab fragment comprises at least one, at least two, or all three VH HVR sequences selected from (a) HVR-H1 comprising the amino acid sequence of SEQ ID NO:29; (b) HVR-H2 comprising the amino acid sequence of SEQ ID NO:175; and (c) HVR-H3 comprising the amino acid sequence of SEQ ID NO:33. In another embodiment, the antibody or Fab fragment comprises HVR-H3 comprising the amino acid sequence of SEQ ID NO:33 and HVR-L3 comprising the amino acid sequence of SEQ ID NO:177. In a further embodiment, the antibody or Fab fragment comprises HVR-H3 comprising the amino acid sequence of SEQ ID NO:33, HVR-L3 comprising the amino acid sequence of SEQ ID NO:178, and HVR-H2 comprising the amino acid sequence of SEQ ID NO:176. In a further embodiment, the antibody or Fab fragment comprises (a) HVR-H1 comprising the amino acid sequence of SEQ ID NO:29; (b) HVR-H2 comprising the amino acid sequence of SEQ ID NO:176; and (c) HVR-H3 comprising the amino acid sequence of SEQ ID NO:33.

In some embodiments, the anti-human OX40 agonist antibody or Fab fragment comprises at least one, at least two, or all three VL HVR sequences selected from (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:177. In one embodiment, the antibody or Fab fragment comprises (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:178.

In some embodiments, the anti-human OX40 agonist antibody or Fab fragment comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:176, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:177, and (c) HVR-L3 comprising the amino acid sequence of SEQ ID NO:178.

In one embodiment, the anti-human OX40 agonist antibody or Fab fragment comprises (a) HVR-H1 comprising the amino acid sequence of SEQ ID NO:29; (b) HVR-H2 comprising the amino acid sequence of SEQ ID NO:176; (c)

HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:177; and (f) HVR-L3 comprising an amino acid sequence selected from SEQ ID NO:178.

In any of the above embodiments, an anti-OX40 agonist antibody or Fab fragment is humanized. In one embodiment, an anti-OX40 antibody or Fab fragment comprises HVRs as in any of the above embodiments and further comprises an acceptor human framework, e.g. a human immunoglobulin framework or a human consensus framework.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO: SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO: 57, 59, 61, 63, 65, 67, 69, 71, 73, 75, 77, 79, 81, 83, 85, 87, 89, 91, 93, 95, 97, 99, 101, 109, 115 or 117. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO: 57, 59, 61, 63, 65, 67, 69, 71, 73, 75, 77, 79, 81, 83, 85, 87, 89, 91, 93, 95, 97, 99, 101, 109, 115 or 117, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:56. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO:56, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO:57. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO: 57. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO: 57, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:180. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:180. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO:180, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO:179. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO: 179. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO: 179, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:94. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:94. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO:94, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO:95. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:95. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO:95, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:26.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:96. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:96. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO:96, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO:97. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO:97. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO:97, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:27.

In another embodiment, the anti-human OX40 agonist antibody or Fab fragment comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 118, 120, 122, 124, 126, 128, 130, 132, 134, 136, 138, 140, 142, 144, 146, or 148. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO: 118, 120, 122, 124, 126, 128, 130, 132, 134, 136, 138, 140, 142, 144, 146, or 148. In certain embodiments, substitutions, insertions, or deletions occur in regions outside the HVRs (i.e., in the FRs). Optionally, the anti-human OX40 agonist antibody or Fab fragment comprises the VH sequence in SEQ ID NO: SEQ ID NO: 118, 120, 122, 124, 126, 128, 130, 132, 134, 136, 138, 140, 142, 144, 146, or 148, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO:30, and (c) HVR-H3 comprising the amino acid sequence of SEQ ID NO:33.

In another embodiment, the anti-human OX40 agonist antibody or Fab fragment comprises a light chain variable domain (VL) having at least 90%, 91%, 92%, 93%, 94%, 95%, 96%, 97%, 98%, 99%, or 100% sequence identity to the amino acid sequence of SEQ ID NO: 119, 121, 123, 125, 127, 129, 131, 133, 135, 137, 139, 141, 143, 145, 147, or 149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody or Fab fragment comprising that sequence retains the ability to bind to OX40. In certain embodiments, a total of 1 to 10 amino acids have been substituted, inserted and/or deleted in SEQ ID NO: 119, 121, 123, 125, 127, 129, 131, 133, 135, 137, 139, 141, 143, 145, 147, or 149. In certain embodiments, the substitutions, insertions, or deletions occur in regions outside the HVRs (i.e., in the FRs). Optionally, the anti-human OX40 agonist antibody or Fab fragment comprises the VL sequence in SEQ ID NO: 119, 121, 123, 125, 127, 129, 131, 133, 135, 137, 139, 141, 143, 145, 147, or 149, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In certain embodiments, the anti-human OX40 agonist antibody or Fab fragment comprises the VH and VL sequences in SEQ ID NO:56 and SEQ ID NO:57, respectively, including post-translational modifications of those sequences. In one embodiment, the anti-human OX40 agonist antibody or Fab fragment comprises the VH and VL sequences in SEQ ID NO:58 and SEQ ID NO:59, respectively, including post-translational modifications of those sequences. In one embodiment, the anti-human OX40 agonist antibody or Fab fragment comprises the VH and VL sequences in SEQ ID NO:60 and SEQ ID NO:61, respectively, including post-translational modifications of those sequences. In one embodiment, the anti-human OX40 agonist antibody or Fab fragment comprises the VH and VL sequences in SEQ ID NO:62 and SEQ ID NO:63, respectively, including post-translational modifications of those sequences. In one embodiment, the anti-human OX40 agonist antibody or Fab fragment comprises the VH and VL sequences in SEQ ID NO:64 and SEQ ID NO:65, respectively, including post-translational modifications of those sequences. In one embodiment, the anti-human OX40 agonist antibody or Fab fragment comprises the VH and VL sequences in SEQ ID NO:66 and SEQ ID NO:67, respectively, including post-translational modifications of those sequences. In one embodiment, the anti-human OX40 agonist antibody or Fab fragment comprises the VH and VL sequences in SEQ ID NO:68 and SEQ ID NO:69, respectively, including post-translational modifications of those sequences. In one embodiment, the anti-human OX40 agonist antibody or Fab fragment comprises the VH and VL sequences in SEQ ID NO:70 and SEQ ID NO:71, respectively, including post-translational modifications of those sequences. In one embodiment, the anti-human OX40 agonist antibody or Fab fragment comprises the VH and VL sequences in SEQ ID NO:72 and SEQ ID NO:73, respectively, including post-translational modifications of those sequences. In one embodiment, the anti-human OX40 agonist antibody or Fab fragment comprises the VH and VL sequences in SEQ ID NO:74 and SEQ ID NO:75, respectively, including post-translational modifications of those sequences. In one embodiment, the anti-human OX40 agonist antibody or Fab fragment comprises the VH and VL sequences in SEQ ID NO:76 and SEQ ID NO:77, respectively, including post-translational modifications of those sequences. In one embodiment, the anti-human OX40 agonist antibody or Fab fragment comprises the VH and VL sequences in SEQ ID NO:78 and SEQ ID NO:79, respectively, including post-translational modifications of those sequences. In one embodiment, the anti-human OX40 agonist antibody or Fab fragment comprises the VH and VL sequences in SEQ ID NO:80 and SEQ ID NO:81, respectively, including post-translational modifications of those sequences. In one embodiment, the anti-human OX40 agonist antibody or Fab fragment comprises the VH and VL sequences in SEQ ID NO:82 and SEQ ID NO:83, respectively, including post-translational modifications of those sequences. In one embodiment, the anti-human OX40 agonist antibody or Fab fragment comprises the VH and VL sequences in SEQ ID NO:84 and SEQ ID NO:85, respectively, including post-translational modifications of those sequences. In one embodiment, the anti-human OX40 agonist antibody or Fab fragment comprises the VH and VL sequences in SEQ ID NO:86 and SEQ ID NO:87, respectively, including post-translational modifications of those sequences. In one embodiment, the anti-human OX40 agonist antibody or Fab fragment comprises the VH and VL sequences in SEQ ID NO:88 and SEQ ID NO:89, respectively, including post-translational modifications of those sequences. In one embodiment, the anti-human OX40 agonist antibody or Fab fragment comprises the VH and VL sequences in SEQ ID NO:90 and SEQ ID NO:91, respectively, including post-translational modifications of those sequences. In one embodiment, the anti-human OX40 agonist antibody or Fab fragment comprises the VH and VL sequences in SEQ ID NO:92 and SEQ ID NO:93, respectively, including post-translational modifications of those sequences. In one embodiment, the anti-human OX40 agonist antibody or Fab fragment comprises the VH and VL sequences in SEQ ID NO:94 and SEQ ID NO:95, respectively, including post-translational modifications of those sequences. In one embodiment, the anti-human OX40 agonist antibody or Fab fragment comprises the VH and VL sequences in SEQ ID NO:96 and SEQ ID NO:97, respectively, including post-translational modifications of those sequences. In one embodiment, the anti-human OX40 agonist antibody or Fab fragment comprises the VH and VL sequences in SEQ ID NO:98 and SEQ ID NO:99, respectively, including post-translational modifications of those sequences. In one embodiment, the anti-human OX40 agonist antibody or Fab fragment comprises the VH and VL sequences in SEQ ID NO:100 and SEQ ID NO:101, respectively, including post-translational modifications of those sequences. In one embodiment, the anti-human OX40 agonist antibody or Fab fragment comprises the VH and VL sequences in SEQ ID NO:108 and SEQ ID NO:109, respectively, including post-translational modifications of those sequences. In one embodiment, the anti-human OX40 agonist antibody or Fab fragment comprises the VH and VL sequences in SEQ ID NO:114 and SEQ ID NO:115, respectively, including post-translational modifications of those sequences. In one embodiment, the anti-human OX40 agonist antibody or Fab fragment comprises the VH and VL sequences in SEQ ID NO:116 and SEQ ID NO:117, respectively, including post-translational modifications of those sequences. In one embodiment, the antibody or Fab fragment comprises the VH and VL sequences in SEQ ID NO:183 and SEQ ID NO:65, respectively, including post-translational modifications of those sequences. In one embodiment, the antibody or Fab fragment comprises the VH and VL sequences in SEQ ID NO:184 and SEQ ID NO:69, respectively, including post-translational modifications of those sequences.

In one embodiment, the anti-human OX40 agonist antibody or Fab fragment comprises the VH and VL sequences in SEQ ID NO:118 and SEQ ID NO:119, respectively, including post-translational modifications of those sequences. In one embodiment, the anti-human OX40 agonist antibody or Fab fragment comprises the VH and VL sequences in SEQ ID NO:120 and SEQ ID NO:121, respectively, including post-translational modifications of those sequences. In one embodiment, the anti-human OX40 agonist antibody or Fab fragment comprises the VH and VL sequences in SEQ ID NO:122 and SEQ ID NO:123, respectively, including post-translational modifications of those sequences. In one embodiment, the anti-human OX40 agonist antibody or Fab fragment comprises the VH and VL sequences in SEQ ID NO:124 and SEQ ID NO:125, respectively, including post-translational modifications of those sequences. In one embodiment, the anti-human OX40 agonist antibody or Fab fragment comprises the VH and VL sequences in SEQ ID NO:126 and SEQ ID NO:127, respectively, including post-translational modifications of those sequences. In one embodiment, the anti-human OX40 agonist antibody or Fab fragment comprises the VH and VL sequences in SEQ ID NO:128 and SEQ ID NO:129, respectively, including post-translational modifications of those sequences. In one embodiment, the anti-human OX40 agonist antibody or Fab fragment comprises the VH and VL sequences in SEQ ID NO:130 and SEQ ID NO:131, respectively, including post-translational modifications of those sequences. In one embodiment, the anti-human OX40 agonist antibody or Fab fragment comprises the VH and VL sequences in SEQ ID NO:132 and SEQ ID NO:133, respectively, including post-translational modifications of those sequences. In one embodiment, the anti-human OX40 agonist antibody or Fab fragment comprises the VH and VL sequences in SEQ ID NO:134 and SEQ ID NO:135, respectively, including post-translational modifications of those sequences. In one embodiment, the anti-human OX40 agonist antibody or Fab fragment comprises the VH and VL sequences in SEQ ID NO:136 and SEQ ID NO:137, respectively, including post-translational modifications of those sequences. In one embodiment, the anti-human OX40 agonist antibody or Fab fragment comprises the VH and VL sequences in SEQ ID NO:138 and SEQ ID NO:139, respectively, including post-translational modifications of those sequences. In one embodiment, the anti-human OX40 agonist antibody or Fab fragment comprises the VH and VL sequences in SEQ ID NO:140 and SEQ ID NO:141, respectively, including post-translational modifications of those sequences. In one embodiment, the anti-human OX40 agonist antibody or Fab fragment comprises the VH and VL sequences in SEQ ID NO:142 and SEQ ID NO:143, respectively, including post-translational modifications of those sequences. In one embodiment, the anti-human OX40 agonist antibody or Fab fragment comprises the VH and VL sequences in SEQ ID NO:144 and SEQ ID NO:145, respectively, including post-translational modifications of those sequences. In one embodiment, the anti-human OX40 agonist antibody or Fab fragment comprises the VH and VL sequences in SEQ ID NO:146 and SEQ ID NO:147, respectively, including post-translational modifications of those sequences.

As described above, certain aspects of the present disclosure relate to complexes. It is to be understood that any of the exemplary antibodies, antigen binding domains, and/or antibody Fab fragments that bind OX40 (e.g., HVRs, VH, and/or VL domains of any of the OX40 agonist antibodies described herein) may be combined in a complex of the present disclosure in any combination or configuration. In some embodiments, a complex may comprise two or more different OX40 agonist antibodies or antigen binding polypeptides that bind to the same epitope of OX40. In some embodiments, a complex may comprise two or more different OX40 agonist antibodies or antigen binding polypeptides that bind to different epitopes of OX40 (e.g., partially non-overlapping or completely non-overlapping epitopes of an OX40 polypeptide, such as human OX40).

In some embodiments, a complex of the present disclosure comprises four antigen binding domains that bind OX40, wherein each of the four antigen binding domains comprises an antibody heavy chain variable (VH) domain and an antibody light chain variable (VL) domain, wherein the complex comprises one or more antigen binding domains that bind a first epitope of OX40 and one or more antigen binding domains that bind a second epitope of OX40, and wherein the first and second epitopes of OX40 are different. In some embodiments, the antigen binding domains that bind the first epitope do not cross-compete for binding OX40 with the antigen binding domains that bind the second epitope.

In some embodiments, a complex of the present disclosure comprises four antigen binding domains that bind OX40, each of the four antigen binding domains comprising an antibody heavy chain variable (VH) domain and an antibody light chain variable (VL) domain. In some embodiments, the complex comprises one or more antigen binding domains that bind a first epitope of OX40 and one or more antigen binding domains that bind a second epitope of OX40, where the antigen binding domains that bind the first epitope do not cross-compete for binding OX40 with the antigen binding domains that bind the second epitope. In some embodiments, competition between two antigen binding domains is performed by testing each antigen binding domain as part of a separate antibody or fragment thereof, rather than testing the two domains as part of a shared complex. Exemplary competition assays are provided infra. In some embodiments, a first antigen binding domains that does not cross-compete for binding with OX40 with a second antigen binding domain blocks binding of the second antigen binding domain to OX40 in a competition assay by 50% or less.

In some embodiments, an antigen binding domain of the present disclosure binds an epitope of OX40 (e.g., human OX40) comprising one or more amino acid residues (e.g., 1, 2, 3, 4, 5, 6, 7, 8, 9, 10, 11, 12, 13, or 14 residues) selected from: residues 114-119, 124, 126, 127, 129, 130, 132, 140, and 142 of SEQ ID NO:281. In some embodiments, an antigen binding domain of the present disclosure binds an epitope of OX40 (e.g., human OX40) comprising one or more amino acid residues (e.g., 1, 2, 3, 4, 5, 6, 7, 8, 9, 10, 11, 12, 13, or 14 residues) selected from: residues 68-71, 83-90, 95, and 98 of SEQ ID NO:281.

Full sequence of human OX40 with signal peptide (signal peptide underlined):

(SEQ ID NO: 281)
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI.

In some embodiments, the OX40 agonist antibody binds human OX40 with an affinity of less than or equal to about 0.45 nM. In some embodiments, the OX40 agonist antibody binds human OX40 with an affinity of less than or equal to about 1 nM. In some embodiments, the OX40 antibody binds human OX40 with an affinity of less than or equal to about 0.4 nM. In some embodiments, the OX40 antibody binds human OX40 with an affinity of less than or equal to about 0.5 nM. In some embodiments, the binding affinity is determined using radioimmunoassay.

In some embodiments, the OX40 agonist antibody binds human OX40 and cynomolgus OX40. In some embodiments, binding is determined using a FACS assay. In some embodiments, binding to human OX40 has an EC50 of about 0.2 ug/ml. In some embodiments, binding to human OX40 has an EC50 of about 0.3 ug/ml or lower. In some embodiments, binding to cynomolgus OX40 has an EC50 of about 1.5 ug/ml. In some embodiments, binding to cynomolgus OX40 has an EC50 of about 1.4 ug/ml.

In some embodiments, the OX40 agonist antibody does not bind to rat OX40 or mouse OX40.

In some embodiments, the OX40 agonist antibody does not induce apoptosis in OX40-expressing cells (e.g., Treg). In some embodiments, apoptosis is assayed using an antibody concentration of 30 ug/ml, e.g., by determining whether apoptosis has occurred using annexin V and pro-prodium iodide stained Treg.

In some embodiments, the OX40 agonist antibody increases memory T cell proliferation and/or increasing cytokine production by the memory cell. In some embodiments, the cytokine is IFN-γ. In some embodiments, the OX40 agonist antibody enhances memory T cell function, for example by increasing memory T cell proliferation and/or increasing cytokine production by the memory cell. In some embodiments, the cytokine is gamma interferon.

In some embodiments, the OX40 agonist antibody increases CD4+ effector T cell proliferation and/or increases cytokine production by the CD4+ effector T cell as compared to proliferation and/or cytokine production prior to treatment with the OX40 agonist antibody. In some embodiments, the cytokine is IFN-γ.

In some embodiments, the anti-human OX40 agonist antibody enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody). In some embodiments, the cytokine is gamma interferon. In some embodiments, the anti-human OX40 agonist antibody increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with anti-human OX40 agonist antibody. In some embodiments, the anti-human OX40 agonist antibody increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with anti-human OX40 agonist antibody.

In some embodiments, the number of CD4+ effector T cells is elevated relative to prior to administration of the OX40 agonist antibody. In some embodiments, CD4+ effector T cell cytokine secretion is elevated relative to prior to administration of the OX40 agonist antibody. In some embodiments of any of the methods, the CD8+ effector T cells in the individual have enhanced proliferation, cytokine secretion and/or cytolytic activity relative to prior to the administration of the OX40 agonist antibody. In some embodiments, the number of CD8+ effector T cells is elevated relative to prior to administration of the OX40 agonist antibody. In some embodiments, CD8+ effector T cell cytokine secretion is elevated relative to prior to administration of the OX40 agonist antibody.

In some embodiments, the anti-human OX40 agonist antibody increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist antibody. In some embodiments, the anti-human OX40 agonist antibody increases number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 agonist antibody.

In some embodiments, the number of intratumoral (infiltrating) CD8+ effector T cells (e.g., total number of CD8+ effector T cells, or e.g., percentage of CD8+ in CD45+ cells) is elevated relative to prior to administration of the OX40 agonist antibody. In some embodiments of any of the methods of the invention, number of intratumoral (infiltrating) CD8+ effector T cells that express gamma interferon (e.g., percentage of CD8+ cells that express gamma interferon in total CD8+ cells) is increased relative to prior to administration of the OX40 agonist antibody.

In some embodiments, the memory T cells in the individual have enhanced proliferation and/or cytokine secretion relative to prior to the administration of the OX40 agonist antibody. In some embodiments, the number of memory T cells is elevated relative to prior to administration of the OX40 agonist antibody. In some embodiments, memory T cell cytokine secretion (level) is elevated relative to prior to administration of the OX40 agonist antibody. In some embodiments of any of the methods, the Treg in the individual have decreased inhibition of effector T cell function (e.g., proliferation and/or cytokine secretion) relative to prior to the administration of the OX40 agonist antibody. In some embodiments, the number of effector T cells is elevated relative to prior to administration of the OX40 agonist antibody. In some embodiments, effector T cell cytokine secretion (level) is elevated relative to prior to administration of the OX40 agonist antibody.

In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell.

In some embodiments, the OX40 agonist antibody inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the OX40 agonist antibody reduces the number of intratumoral (infiltrating) Treg (e.g., total number of Treg or e.g., percentage of Fox3p+ cells in CD4+ cells).

In some embodiments, the number of intratumoral (infiltrating) Treg (e.g., total number of Treg or e.g., percentage of Fox3p+ cells in CD4+ cells) is reduced relative to prior to administration of the OX40 agonist antibody.

In some embodiments, the number of intratumoral (infiltrating) CD4+ effector T cells (e.g., total number of CD4+ effector T cells, or e.g., percentage of CD4+ cells in CD45+ cells) is elevated relative to prior to administration of the OX40 agonist antibody. In some embodiments of any of the methods of the invention, number of intratumoral (infiltrating) CD4+ effector T cells that express gamma interferon (e.g., total gamma interferon expressing CD4+ cells, or e.g., percentage of gamma interferon expressing CD4+ cells in total CD4+ cells) is elevated relative to prior to administration of the OX40 agonist antibody.

In some embodiments, the OX40 agonist antibody increases OX40 signal transduction in a target cell that expresses OX40. In some embodiments, OX40 signal transduction is detected by monitoring NFkB downstream signaling.

In some embodiments, the OX40 agonist antibody is stable after treatment at 40° C. for two weeks.

In some embodiments, the OX40 agonist antibody competes for binding to human OX40 with OX40L. In some embodiments, addition of OX40L does not enhance OX40 antibody function in an in vitro assay.

According to another embodiment, the OX40 agonist antibodies include any one, any combination, or all of the following properties: (1) binds human OX40 with an affinity of less than or equal to about 0.45 nM, in some embodiments, binds human OX40 with an affinity of less than or equal to about 0.4 nM, in some embodiments, binds human OX40 with an affinity of less than or equal to about 0.5 nM, in some embodiments, the binding affinity is determined using radioimmunoassay; (2) binds human OX40 and cynomolgus OX40, in some embodiments, binding is determined using a FACS assay, (3) binds human OX40 with an EC50 of about 0.2 ug/ml, in some embodiments, binds to human OX40 has an EC50 of about 0.3 ug/ml or lower, in some embodiments, binds to cynomolgus OX40 with an EC50 of about 1.5 ug/ml, in some embodiments, binds to cynomolgus OX40 has an EC50 of about 1.4 ug/ml, (4) does not substantially bind to rat OX40 or mouse OX40, (5) enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody), (6) enhances memory T cell function, for example by increasing memory T cell proliferation and/or increasing cytokine production by the memory cell, (7) inhibits Treg function, for example, by decreasing Treg suppression of effector T cell function (e.g., effector T cell proliferation and/or effector T cell cytokine secretion). In some embodiments, the effector T cell is a CD4+ effector T cell, (8) increases OX40 signal transduction in a target cell that expresses OX40 (in some embodiments, OX40 signal transduction is detected by monitoring NFkB downstream signaling), and (9) is stable after treatment at 40° C. for two weeks.

Exemplary anti-OX40 HVR, VH, and VL sequences suitable for use in any of the antibodies and/or Fab fragments described herein in any suitable combination of the present disclosure are provided in Table A.

TABLE A

OX40 Antibody Sequences

| Name | SEQUENCE | SEQ ID NO: |
|---|---|---|
| Human OX40 (lacking the signal peptide) | LHCVGDTYPSNDRCCHECRPGNGMVSRCSRSQNTVCR PCGPGFYNDVVSSKPCKPCTWCNLRSGSERKQLCTAT QDTVCRCRAGTQPLDSYKPGVDCAPCPPGHFSPGDNQ ACKPWTNCTLAGKHTLQPASNSSDAICEDRDPPATQP QETQGPPARPITVQPTEAWPRTSQGPSTRPVEVPGGR AVAAILGLGLVLGLLGPLAILLALYLLRRDQRLPPDA HKPPGGGSFRTPIQEEQADAHSTLAKI | 1 |
| HVR-H1-1A7.gr.1 1A7.gr.2 1A7.gr.3 1A7.gr.4 1A7.gr.5 1A7.gr.5' 1A7.gr.6 1A7.gr.7 1A7.gr.7' 1A7.gr.NADS 1A7.gr.NADA 1A7.gr.NGDA 1A7.gr.SGDS 1A7.gr.NGSS 1A7.Ala.1 1A7.Ala.2 1A7.Ala.3 1A7.Ala.4 1A7.Ala.5 1A7.Ala.6 1A7.Ala.7 1A7.Ala.8 1A7.Ala.9 1A7.Ala.10 1A7.Ala.11 1A7.Ala.12 1A7.Ala.13 | DSYMS | 2 |

TABLE A-continued

OX40 Antibody Sequences

| Name | SEQUENCE | SEQ ID NO: |
|---|---|---|
| 1A7.Ala.14 | | |
| 1A7.Ala.15 | | |
| 1A7.Ala.16 | | |
| HVR-H2- | DMYPDNGDSSYNQKFRE | 3 |
| 1A7.gr.1 | | |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-H3- | APRWYFSV | 4 |
| 1A7.gr.1 | | |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7-Ala.15 | | |
| 1A7.Ala.16 | | |
| HVR-L1- | RASQDISNYLN | 5 |
| 1A7.gr.1 | | |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-L2- | YTSRLRS | 6 |
| 1A7.gr.1 | | |
| 1A7.gr.2 | | |
| 1A7.gr.3 | | |
| 1A7.gr.4 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |

TABLE A-continued

OX40 Antibody Sequences

| Name | SEQUENCE | SEQ ID NO: |
|---|---|---|
| HVR-L3-1A7.gr.1 1A7.gr.2 1A7.gr.3 1A7.gr.4 1A7.gr.5 1A7.gr.5' 1A7.gr.6 1A7.gr.7 1A7.gr.7' 1A7.gr.DA 1A7.gr.ES 1A7.gr.NADS 1A7.gr.NADA 1A7.gr.NGDA 1A7.gr.SGDS 1A7.gr.NGSS 1A7.gr.DANADA 1A7.Ala.8 1A7.Ala.9 1A7.Ala.10 1A7.Ala.11 1A7.Ala.12 1A7.Ala.13 1A7.Ala.14 1A7.Ala.15 1A7.Ala.16 | QQGHTLPPT | 7 |
| HVR-H1-1A7.gr.DA | DAYMS | 8 |
| HVR-H1-1A7.gr.ES 1A7.gr.DANADA | ESYMS | 9 |
| HVR-H2-1A7.gr.NADS | DMYPDNADSSYNQKFRE | 10 |
| HVR-H2-1A7.gr.NADA 1A7.gr.DANADA | DMYPDNADASYNQKFRE | 11 |
| HVR-H2-1A7.gr.NGDA | DMYPDNGDASYNQKFRE | 12 |
| HVR-H2-1A7.gr.SGDS | DMYPDSGDSSYNQKFRE | 13 |
| HVR-H2-1A7.gr.NGSS | DMYPDNGSSSYNQKFRE | 14 |
| HVR-H3-1A7.Ala.8 | APRWYFSA | 15 |
| HVR-H3-1A7.Ala.9 | APRWYASV | 16 |
| HVR-H3-1A7.Ala.10 | APRWAFSV | 17 |

TABLE A-continued

OX40 Antibody Sequences

| Name | SEQUENCE | SEQ ID NO: |
|---|---|---|
| HVR-H3-1A7.Ala.11 | APAWYFSV | 18 |
| HVR-H3-1A7.Ala.12 | APRWYFAV | 19 |
| HVR-H3-1A7.Ala.13 | APRAYFSV | 20 |
| HVR-H3-1A7.Ala.14 | AARWYFSV | 21 |
| HVR-L3-1A7.Ala.1 | QQGHTLPAT | 22 |
| HVR-L3-1A7.Ala.2 | QQGHTAPPT | 23 |
| HVR-L3-1A7.Ala.3 | QQGATLPPT | 24 |
| HVR-L3-1A7.Ala.4 | QQGHALPPT | 25 |
| HVR-L3-1A7.Ala.5 | QQAHTLPPT | 26 |
| HVR-L3-1A7.Ala.6 | QQGHTLAPT | 27 |
| HVR-L3-1A7.Ala.7 | QAGHTLPPT | 28 |
| HVR-H1-3C8.gr.1 3C8.gr.2 3C8.gr.3 3C8.gr.4 3C8.gr.5 3C8.gr.5.SG 3C8.gr.5.EG 3C8.gr.5.QG 3C9.gr.5.DQ 3C8.gr.5.DA 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 3C8.A.7 3C8.A.8 3C8.A.9 3C8.A.10 | NYLIE | 29 |
| HVR-H2-3C8.gr.1 3C8.gr.2 3C8.gr.3 3C8.gr.4 3C8.gr.5 3C8.gr.5.SG | VINPGSGDTYYSEKFKG | 30 |

TABLE A-continued

OX40 Antibody Sequences

| Name | SEQUENCE | SEQ ID NO: |
|---|---|---|
| 3C8.gr.5.EG | | |
| 3C8.gr.5.QG | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.1 | | |
| 3C8.A.2 | | |
| 3C8.A.3 | | |
| 3C8.A.4 | | |
| 3C8.A.5 | | |
| 3C8.A.6 | | |
| 3C8.A.7 | | |
| 3C8.A.8 | | |
| 3C8.A.9 | | |
| 3C8.A.10 | | |
| HVR-H2-3C8.gr.5.DA | VINPGSDAYYSEKFKG | 31 |
| HVR-H2-3C8.gr.5.DQ | VINPGSGDQYYSEKFKG | 32 |
| HVR-H3-3C8.gr.1 3C8.gr.2 3C8.gr.3 3C8.gr.4 3C8.gr.5 3C8.gr.5.SG 3C8.gr.5.EG 3C8.gr.5.QG 3C8.gr.5.DA 3C8.gr.5.DQ 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 3C8.A.7 | DRLDY | 33 |
| HVR-H3-3C8.A.8 | ARLDY | 34 |
| HVR-H3-3C8.A.9 | DALDY | 35 |
| HVR-H3-3C8.A.10 | DRADY | 36 |
| HVR-L1-3C8.gr.1 3C8.gr.2 3C8.gr.3 3C8.gr.4 3C8.gr.5 3C8.gr.5.SG 3C8.gr.5.EG 3C8.gr.5.QG 3C8.gr.5.DA 3C8.gr.5.DQ 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 3C8.A.7 3C8.A.8 3C8.A.9 3C8.A.10 | HASQDISSYIV | 37 |
| HVR-L2-3C8.gr.1 3C8.gr.2 3C8.gr.3 3C8.gr.4 3C8.gr.5 3C8.gr.5.DA 3C8.gr.5.DQ 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 3C8.A.7 3C8.A.8 3C8.A.9 3C8.A.10 | HGTNLED | 38 |
| HVR-L2-3C8.gr5.SG | HGTNLES | 39 |
| HVR-L2-3C8.gr.5.EG | HGTNLEE | 40 |
| HVR-L2-3C8.gr.5.QG | HGTNLEQ | 41 |
| HVR-L3-3C8.gr.1 3C8.gr.2 3C8.gr.3 3C8.gr.4 3C8.gr.5 3C8.gr.5.SG | VHYAQFPYT | 42 |

TABLE A-continued

OX40 Antibody Sequences

| Name | SEQUENCE | SEQ ID NO: |
|---|---|---|
| 3C8.gr.5.EG | | |
| 3C8.gr.5.QG | | |
| 3C8.gr.5.DA | | |
| 3C8.gr.5.DQ | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.8 | | |
| 3C8.A.9 | | |
| 3C8.A.10 | | |
| HVR-L3-3C8.A.1 | AHYAQFPYT | 43 |
| HVR-L3-3C8.A.2 | VAYAQFPYT | 44 |
| HVR-L3-3C8.A.3 | VHAAQFPYT | 45 |
| HVR-L3-3C8.A.4 | VHYAAFPYT | 46 |
| HVR-L3-3C8.A.5 | VHYAQAPYT | 47 |
| HVR-L3-3C8.A.6 | VHYAQFAYT | 48 |
| HVR-L3-3C8.A.7 | VHYAQFPAT | 49 |
| HVR-H1-1D2.gr.1 1D2.gr.2 1D2.gr.3 | DYGVL | 50 |
| HVR-H2-1D2.gr.1 1D2.gr.2 1D2.gr.3 | MIWSGGTTDYNAAFIS | 51 |
| HVR-H3-1D2.gr.1 1D2.gr.2 1D2.gr.3 | EEMDY | 52 |
| HVR-L1-1D2.gr.1 1D2.gr.2 1D2.gr.3 | RASQDISNFLN | 53 |
| HVR-L2-1D2.gr.1 1D2.gr.2 1D2.gr.3 | YTSRLHS | 54 |
| HVR-L3-1D2.gr.1 1D2.gr.2 1D2.gr.3 | QQGNTLPWT | 55 |
| 1A7.gr.1 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 56 |
| 1A7.gr.1 $V_L$ | DIQMTQSPSSLSASVGDRVTITCRASQDISNYLNWYQ QKPGKAPKLLIYYTSRLRSGVPSRFSGSGSGTDFTLT ISSLQPEDFATYYCQQGHTLPPTFGQGTKVEIK | 57 |
| 1A7.gr.2 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 58 |
| 1A7.gr.2 $V_L$ | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIK | 59 |
| 1A7.gr.3 $V_H$ | EVQLVQSGAEVKKPGASVKVSCKASGYTFTDSYMSW VRQAPGQGLEWIGDMYPDNGDSSYNQKFRERVTLTV DTSTSTAYLELSSLRSEDTAVYYCVLAPRWYFSVWGQ GTLVTVSS | 60 |
| 1A7.gr.3 $V_L$ | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIK | 61 |
| 1A7.gr.4 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 62 |
| 1A7.gr.4 $V_L$ | DIQMTQSPSSLSASVGDRVTITCRASQDISNYLNWYQQ KPGKTVKLLIYYTSRLRSGVPSRFSGSGSGTDFTLTIS SLQPEDFATYYCQQGHTLPPTFGQGTKVEIK | 63 |
| 1A7.gr.5 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 64 |
| 1A7.gr.5 $V_L$ | DIQMTQSPSSLSASVGDRVTITCRASQDISNYLNWYQQ KPGKTVKLLIYYTSRLRSGVPSRFSGSGSGTDFTLTIS SLQPEDFATYYCQQGHTLPPTFGQGTKVEIK | 65 |
| 1A7.gr.6 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 66 |
| 1A7.gr.6 $V_L$ | DIQMTQSPSSLSASVGDRVTITCRASQDISNYLNWYQQ KPGKTVKLLIYYTSRLRSGVPSRFSGSGSGKDYTLTIS SLQPEDFATYFCQQGHTLPPTFGQGTKVEIK | 67 |
| 1A7.gr.7 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 68 |
| 1A7.gr.7 $V_L$ | DIQMTQSPSSLSASVGDRVTITCRASQDISNYLNWYQQ KPGKTVKLLIYYTSRLRSGVPSRFSGSGSGKDYTLTIS SLQPEDFATYFCQQGHTLPPTFGQGTKVEIK | 69 |
| 1A7.gr.DA $V_H$ | EVQLVQSGAEVKKPGASVKVSCKASGYTFTDAYMSW VRQAPGQGLEWIGDMYPDNGDSSYNQKFRERVTITRD TSTSTAYLELSSLRSEDTAVYYCVLAPRWYFSVWGQG TLVTVSS | 70 |
| 1A7.gr.DA $V_L$ | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIK | 71 |
| 1A7.gr.ES $V_H$ | EVQLVQSGAEVKKPGASVKVSCKASGYTFTESYMSW VRQAPGQGLEWIGDMYPDNGDSSYNQKFRERVTITRD TSTSTAYLELSSLRSEDTAVYYCVLAPRWYFSVWGQG TLVTVSS | 72 |

TABLE A-continued

OX40 Antibody Sequences

| Name | SEQUENCE | SEQ ID NO: |
|---|---|---|
| 1A7.gr.ES $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 73 |
| 1A7.gr.NADS $V_H$ | EVQLVQSGAEVKKPGASVKVSCKASGYTFTDSYMSWVRQAPGQGLEWIGDMYPDNADSSYNQKFRERVTITRDTSTSTAYLELSSLRSEDTAVYYCVLAPRWYFSVWGQGTLVTVSS | 74 |
| 1A7.gr.NADS $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 75 |
| 1A7.gr.NADA $V_H$ | EVQLVQSGAEVKKPGASVKVSCKASGYTFTDSYMSWVRQAPGQGLEWIGDMYPDNADASYNQKFRERVTITRDTSTSTAYLELSSLRSEDTAVYYCVLAPRWYFSVWGQGTLVTVSS | 76 |
| 1A7.gr.NADA $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 77 |
| 1A7.gr.NGDA $V_H$ | EVQLVQSGAEVKKPGASVKVSCKASGYTFTDSYMSWVRQAPGQGLEWIGDMYPDNGDASYNQKFRERVTITRDTSTSTAYLELSSLRSEDTAVYYCVLAPRWYFSVWGQGTLVTVSS | 78 |
| 1A7.gr.NGDA $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 79 |
| 1A7.gr.SGDS $V_H$ | EVQLVQSGAEVKKPGASVKVSCKASGYTFTDSYMSWVRQAPGQGLEWIGDMYPDSGDSSYNQKFRERVTITRDTSTSTAYLELSSLRSEDTAVYYCVLAPRWYFSVWGQGTLVTVSS | 80 |
| 1A7.gr.SGDS $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 81 |
| 1A7.gr.NGSS $V_H$ | EVQLVQSGAEVKKPGASVKVSCKASGYTFTDSYMSWVRQAPGQGLEWIGDMYPDNGSSSYNQKFRERVTITRDTSTSTAYLELSSLRSEDTAVYYCVLAPRWYFSVWGQGTLVTVSS | 82 |
| 1A7.gr.NGSS $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 83 |
| 1A7.gr.DANADA $V_H$ | EVQLVQSGAEVKKPGASVKVSCKASGYTFTDAYMSWVRQAPGQGLEWIGDMYPDNADASYNQKFRERVTITRDTSTSTAYLELSSLRSEDTAVYYCVLAPRWYFSVWGQGTLVTVSS | 84 |
| 1A7.gr.DANADA $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 85 |
| 1A7.Ala.1 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 86 |
| 1A7.Ala.1 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPATFGQGTKVEIK | 87 |
| 1A7.Ala.2 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 88 |
| 1A7.Ala.2 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTAPPTFGQGTKVEIK | 89 |
| 1A7.Ala.3 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 90 |
| 1A7.Ala.3 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGATLPPTFGQGTKVEIK | 91 |
| 1A7.Ala.4 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 92 |
| 1A7.Ala.4 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHALPPTFGQGTKVEIK | 93 |
| 1A7.Ala.5 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 94 |
| 1A7.Ala.5 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQAHTLPPTFGQGTKVEIK | 95 |
| 1A7.Ala.6 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 96 |
| 1A7.Ala.6 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLAPTFGQGTKVEIK | 97 |
| 1A7.Ala.7 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 98 |
| 1A7.Ala.7 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQAGHTLPPTFGQGTKVEIK | 99 |
| 1A7.Ala.8 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSAWGQGTLVTVSS | 100 |
| 1A7.Ala.8 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 101 |
| 1A7.Ala.9 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYASVWGQGTLVTVSS | 102 |
| 1A7.Ala.9 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 103 |
| 1A7.Ala.10 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWAFSVWGQGTLVTVSS | 104 |

TABLE A-continued

OX40 Antibody Sequences

| Name | SEQUENCE | SEQ ID NO: |
|---|---|---|
| 1A7.Ala.10 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 105 |
| 1A7.Ala.11 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPAWYFSVWGQGTLVTVSS | 106 |
| 1A7.Ala.11 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 107 |
| 1A7.Ala.12 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFAVWGQGTLVTVSS | 108 |
| 1A7.Ala.12 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 109 |
| 1A7.Ala.13 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRAYFSVWGQGTLVTVSS | 110 |
| 1A7.Ala.13 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 111 |
| 1A7.Ala.14 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAARWYFSVWGQGTLVTVSS | 112 |
| 1A7.Ala.14 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 113 |
| 1A7.Ala.15 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCALAPRWYFSVWGQGTLVTVSS | 114 |
| 1A7.Ala.15 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 115 |
| 1A7.Ala.16 $V_H$ | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVAAPRWYFSVWGQGTLVTVSS | 116 |
| 1A7.Ala.16 $V_L$ | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 117 |
| 3C8.gr.1 $V_H$ | EVQLVQSGAEVKKPGASVKVSCKASGYAFTNYLIEWVRQAPGQGLEWIGVINPGSGDTYYSEKFKGRVTITRDTSTSTAYLELSSLRSEDTAVYYCARDRLDYWGQGTLVTVSS | 118 |
| 3C8.gr.1 $V_L$ | DIQMTQSPSSLSASVGDRVTITCHASQDISSYIVWYQQKPGKAPKLLIYHGTNLEDGVPSRFSGSGSGTDFTLTISSLQPEDFATYYCVHYAQFPYTFGQGTKVEIK | 119 |
| 3C8.gr.2 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 120 |
| 3C8.gr.2 $V_L$ | DIQMTQSPSSLSASVGDRVTITCHASQDISSYIVWYQQKPGKAPKLLIYHGTNLEDGVPSRFSGSGSGTDFTLTISSLQPEDFATYYCVHYAQFPYTFGQGTKVEIK | 121 |
| 3C8.gr.3 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 122 |
| 3C8.gr.3 $V_L$ | DIQMTQSPSSLSASVGDRVTITCHASQDISSYIVWYQQKPGKAPKLLIYHGTNLEDGVPSRFSGSGSGTDFTLTISSLQPEDFATYYCVHYAQFPYTFGQGTKVEIK | 123 |
| 3C8.gr.4 $V_H$ | EVQLVQSGAEVKKPGASVKVSCKASGYAFTNYLIEWVRQAPGQGLEWIGVINPGSGDTYYSEKFKGRVTITADTSTSTAYLELSSLRSEDTAVYYCARDRLDYWGQGTLVTVSS | 124 |
| 3C8.gr.4 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 125 |
| 3C8.gr.5 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 126 |
| 3C8.gr.5 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 127 |
| 3C8.gr.5.SG $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 128 |
| 3C8.gr.5.SG $V_L$ | DIQMTQSPSSLSASVGDRVTITCHASQDISSYIVWYQQKPGKSFKGLIYHGTNLESGVPSRFSGSGSGTDFTLTISSLQPEDFATYYCVHYAQFPYTFGQGTKVEIK | 129 |
| 3C8.gr.5.EG $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 130 |
| 3C8.gr.5.EG $V_L$ | DIQMTQSPSSLSASVGDRVTITCHASQDISSYIVWYQQKPGKSFKGLIYHGTNLEEGVPSRFSGSGSGTDFTLTISSLQPEDFATYYCVHYAQFPYTFGQGTKVEIK | 131 |
| 3C8.gr.5.QG $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 132 |
| 3C8.gr.5.QG $V_L$ | DIQMTQSPSSLSASVGDRVTITCHASQDISSYIVWYQQKPGKSFKGLIYHGTNLEQGVPSRFSGSGSGTDFTLTISSLQPEDFATYYCVHYAQFPYTFGQGTKVEIK | 133 |
| 3C8.gr.6 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 134 |
| 3C8.gr.6 $V_L$ | DIQMTQSPSSLSASVGDRVTITCHASQDISSYIVWYQQKPGKSFKGLIYHGTNLEDGVPSRFSGSGSGADYTLTISSLQPEDFATYYCVHYAQFPYTFGQGTKVEIK | 135 |
| 3C8.gr.7 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 136 |

TABLE A-continued

OX40 Antibody Sequences

| Name | SEQUENCE | SEQ ID NO: |
|---|---|---|
| 3C8.gr.7 $V_L$ | DIQMTQSPSSLSASVGDRVTITCHASQDISSYIVWYQQKPGKSFKGLIYHGTNLEDGVPSRFSGSGSGADYTLTISSLQPEDFATYYCVHYAQFPYTFGQGTKVEIK | 137 |
| 3C8.gr.8 $V_H$ | EVQLVQSGAEVKKPGASVKVSCKASGYAFTNYLIEWVRQAPGQGLEWIGVINPGSGDTYYSEKFKGRVTLTRDTSTSTAYLELSSLRSEDTAVYYCARDRLDYWGQGTLVTVSS | 138 |
| 3C8.gr.8 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 139 |
| 3C8.gr.9 $V_H$ | EVQLVQSGAEVKKPGASVKVSCKASGYAFTNYLIEWVRQAPGQGLEWIGVINPGSGDTYYSEKFKGRVTLTRDTSTSTAYLELSSLRSEDTAVYYCARDRLDYWGQGTLVTVSS | 140 |
| 3C8.gr.9 $V_L$ | DIQMTQSPSSLSASVGDRVTITCHASQDISSYIVWYQQKPGKSPKLLIYHGTNLEDGVPSRFSGSGSGTDFTLTISSLQPEDFATYYCVHYAQFPYTFGQGTKVEIK | 141 |
| 3C8.gr.10 $V_H$ | EVQLVQSGAEVKKPGASVKVSCKASGYAFTNYLIEWVRQAPGQGLEWIGVINPGSGDTYYSEKFKGRVTLTRDTSTSTAYLELSSLRSEDTAVYYCARDRLDYWGQGTLVTVSS | 142 |
| 3C8.gr.10 $V_L$ | DIQMTQSPSSLSASVGDRVTITCHASQDISSYIVWYQQKPGKAFKLLIYHGTNLEDGVPSRFSGSGSGTDFTLTISSLQPEDFATYYCVHYAQFPYTFGQGTKVEIK | 143 |
| 3C8.gr.11 $V_H$ | EVQLVQSGAEVKKPGASVKVSCKASGYAFTNYLIEWVRQAPGQGLEWIGVINPGSGDTYYSEKFKGRVTLTRDTSTSTAYLELSSLRSEDTAVYYCARDRLDYWGQGTLVTVSS | 144 |
| 3C8.gr.11 $V_L$ | DIQMTQSPSSLSASVGDRVTITCHASQDISSYIVWYQQKPGKAPKGLIYHGTNLEDGVPSRFSGSGSGTDFTLTISSLQPEDFATYYCVHYAQFPYTFGQGTKVEIK | 145 |
| 3C8.A.1 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 146 |
| 3C8.A.1 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCAHYAQFPYTFGQGTKVEIK | 147 |
| 3C8.A.2 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 148 |
| 3C8.A.2 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVAYAQFPYTFGQGTKVEIK | 149 |
| 3C8.A.3 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 150 |
| 3C8.A.3 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHAAQFPYTFGQGTKVEIK | 151 |
| 3C8.A.4 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 152 |
| 3C8.A.4 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAAFPYTFGQGTKVEIK | 153 |
| 3C8.A.5 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 154 |
| 3C8.A.5 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQAPYTFGQGTKVEIK | 155 |
| 3C8.A.6 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 156 |
| 3C8.A.6 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFAYTFGQGTKVEIK | 157 |
| 3C8.A.7 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRLDYWGQGTLVTVSS | 158 |
| 3C8.A.7 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPATFGQGTKVEIK | 159 |
| 3C8.A.8 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARARLDYWGQGTLVTVSS | 160 |
| 3C8.A.8 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 161 |
| 3C8.A.9 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDALDYWGQGTLVTVSS | 162 |
| 3C8.A.9 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 163 |
| 3C8.A.10 $V_H$ | EVQLVQSGAEVKKPGASVKVSCKASGYAFTNYLIEWVRQAPGQGLEWIGVINPGSGDTYYSEKFKGRVTLTADTSTSTAYLELSSLRSEDTAVYYCARDRADYWGQGTLVTVSS | 164 |
| 3C8.A.10 $V_L$ | DIQMTQSPSSLSASVGDRVTITCHASQDISSYIVWYQQKPGKSFKGLIYHGTNLEDGVPSRFSGSGSGTDFTLTISSLQPEDFATYYCVHYAQFPYTFGQGTKVEIK | 165 |
| 1D2.gr.1 $V_H$ | EVQLVESGPGLVKPSETLSLTCTVSGFSLTDYGVLWIRQPPGKGLEWIGMIWSGGTTDYNAAFISRVTISVDTSKNQFSLKLSSVTAADTAVYYCVREEMDYWGQGTLVTVSS | 166 |
| 1D2.gr.1 $V_L$ | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPWTFGQGTKVEIK | 167 |
| 1D2.gr.2 $V_H$ | EVQLVESGPGLVKPSETLSLTCTVSGFSLTDYGVLWIRQPPGKGLEWIGMIWSGGTTDYNAAFISRVTISKDTSKNQVSLKLSSVTAADTAVYYCVREEMDYWGQGTLVTVSS | 168 |

TABLE A-continued

OX40 Antibody Sequences

| Name | SEQUENCE | SEQ ID NO: |
|---|---|---|
| 1D2.gr.2 $V_L$ | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPWTFGQGTKVEIK | 169 |
| 1D2.gr.3 $V_H$ | EVQLVESGPGLVKPSETLSLTCTVSGFSLTDYGVLWVRQPPGKGLEWLGMIWSGGTTDYNAAFISRLTISKDTSKNQVSLKLSSVTAADTAVYYCVREEMDYWGQGTLVTVSS | 170 |
| 1D2.gr.3 $V_L$ | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPWTFGQGTKVEIK | 171 |
| CON1 (1A7) HVR-H1 | $X_1X_2$YMS, wherein $X_1$ is D or E, and $X_2$ is S or A | 172 |
| CON1 (1A7) HVR-H2 | DMYPD$X_1X_2X_3X_4$SYNQKFRE, wherein $X_1$ is N or S, $X_2$ is A or G, $X_3$ is D or S, and $X_4$ is A or S | 173 |
| CON1 (1A7) HVR-H3 | APRW$X_1X_2X_3X_4$, wherein $X_1$ is Y or A, $X_2$ is A or F, $X_3$ is S or A, and $X_4$ is A or V. | 174 |
| CON1 (1A7) HVR-L3 | Q$X_1X_2X_3X_4X_5X_6X_7$T, wherein $X_1$ is A or Q, $X_2$ is A or G, $X_3$ is A or H, $X_4$ is A or T, $X_5$ is A or L, $X_6$ is A or P, and $X_7$ is A or P. | 175 |
| CON2 (3C8) HVR-H2 | VINPGSGD$X_1$YYSEKFKG, wherein $X_1$ is T, A or Q. | 176 |
| CON2 (3C8) HVR-L2 | HGTNLE$X_1$, wherein $X_1$ is S, E, or Q. | 177 |
| CON2 (3C8) HVR-L3 | $X_1X_2$YAQFPY$X_3$, wherein $X_1$ is V or A, $X_2$ is H or A, and $X_3$ is Y or A. | 178 |
| 1A7 $V_L$ | DIQMTQTTSSLSASLGDRVTISCRASQDISNYLNWYQQKPDGTVKLLIYYTSRLRSGVPSRFSGSGSGKDYFLTISNLEQEDVAAYFCQQGHTLPPTFGGGTKLEIK | 179 |
| 1A7 $V_H$ | EVQLQQSGPELVKPGASVKISCKASGYTFTDSYMSWVKQSHGKTLEWIGDMYPDNGDSSYNQKFREKVTLTVDKSSTTAYMEFRSLTSEDSAVYYCVLAPRWYFSVWGTGTTVTVSS | 180 |
| 3C8 $V_L$ | DILMTQSPSSMSVSLGDTVSITCHASQDISSYIVWLQQKPGKSFRGLIYHGTNLEDGIPSRFSGSGSGADYSLTISSLESEDFADYYCVHAQFPYTFGGGTKLEIK | 181 |
| 3C8 $V_H$ | QVQLQQSGAELVRPGTSVKVSCKASGYAFTNYLIEWVKQRPGQGLEWIGVINPGSGDTYYSEKFKGKVTLTADKSSSTAYMQLSSLTSEDSAVYFCARDRLDYWGQGTTLTVSS | 182 |
| 1A7.gr.5' $V_H$ | EVQLVQSGAEVKKPGASVKVSCKASGYTFTDSYMSWVRQAPGQGLEWIGDMYPDNGDSSYNQKFRERVTLTVDTSTSTAYLELSSLRSEDTAVYYCVLAPRWYFSVWGQGTLVTVSS | 183 |
| 1A7.gr.7' $V_H$ | EVQLVQSGAEVKKPGASVKVSCKASGYTFTDSYMSWVRQAPGQGLEWIGDMYPDNGDSSYNQKFRERVTLTVDTSTSTAYLELSSLRSEDTAVYYCVLAPRWYFSVWGQGTLVTVSS | 184 |
| 1A7 HVR-H1 M34I variant | DSYIS | 282 |
| 1A7 HVR-H3 P96A variant | AARWYFSV | 283 |
| 1A7 VH M34I variant | EVQLVQSGAEVKKPGASVKVSCKASGYTFTDSYISWVRQAPGQGLEWIGDMYPDNGDSSYNQKFRERVTITRDTSTSTAYLELSSLRSEDTAVYYCVLAPRWYFSVWGQGTLVTVSS | 284 |
| 1A7 VH P96A variant | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAARWYFSVWGQGTLVTVSS | 285 |
| 1A7 HVR-L2 R53Y variant | YTSYLRS | 286 |
| 1A7 VL R53Y variant | DIQMTQSPSSLSASVGDRVTITCRASQDISNYLNWYQQKPGKAPKLLIYYTSYLRSGVPSRFSGSGSGTDFTLTISSLQPEDFATYYCQQGHTLPPTFGQGTKVEIK | 287 |
| 3C8 HVR-H1 N31I variant | IYLIE | 288 |
| 3C8 HVR-H2 K64L variant | VINPGSGDTYYSEKFLG | 289 |
| 3C8 VH N31I + K64L variant | EVQLVQSGAEVKKPGASVKVSCKASGYAFTIYLIEWVRQAPGQGLEWIGVINPGSGDTYYSEKFLGRVTLTADTSTSTAYLELSSLRSEDTAVYYCARDRLDYWGQGTLVTVSS | 290 |

In some embodiments, the OX40 agonist antibody is an anti-human OX40 agonist antibody described in U.S. Pat. No. 7,550,140. In some embodiments, the anti-human OX40 agonist antibody comprises a heavy chain comprising the sequence of EVQLVESGGGLVQPGGSLRLSCAASGFTFSNYTMNWVRQAPGKGLEWVSAISGSGGSTYYADSVKGRFTISRDNSKNTLYLQMNSLRAEDTAVYYCAKDRYSQVHYALDYW GQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPKSCDK THTCPPCPAPELLGGPSVFLFPPKPKDTLMISRTPEVTCVVVDVSH EDPEVKFNWYVD GVEVHNAKTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO:185) and/or a light chain comprising the sequence of DIVMTQSPDSLPVTPGEPASISCRSSQSLLHSNGYNYLDWYLQKAGQSPQLLIYLGSN RASGVPDRFSGSGSGTDFTLKISRVEAEDVGVYYCQQYYNHPTTFGQGTKLEIKRTV AAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO:186). In some embodiments, the antibody comprises at least one, two, three, four, five, or six hypervariable region (HVR) sequences of antibody 008 as described in U.S. Pat. No. 7,550,140. In some embodiments, the antibody comprises a heavy chain variable region sequence and/or a light chain variable region sequence of antibody 008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises the sequence of DIQMTQSPD-SLPVTPGEPASISCRSSQSLLHSNGYNYLDWYLQK-AGQSPQLLIYLGSN RASGVPDRFSGSGSGTDFTLKIS-RVEAEDVGVYYCQQYYNHPTTFGQGTKLEIKRTV AAPSVFIFPPSDEQLKSGTASVVCLLNNFY-PREAKVQWKVDNALQSGNSQESVTEQD SKDSTYS-LSSTLTLSKADYEKHKVYACE-VTHQGLSSPVTKSFNRGEC (SEQ ID NO:187). In some embodiments, the antibody comprises at least one, two, three, four, five, or six hypervariable region (HVR) sequences of antibody SC02008 as described in U.S. Pat. No. 7,550,140. In some embodiments, the antibody comprises a heavy chain variable region sequence and/or a light chain variable region sequence of antibody SC02008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises a heavy chain comprising the sequence of EVQLVESGGGLVHPGGSLRLS-CAGSGFTFSSYAMHWVRQAPGKGLEWVSAIGTGGG TYYADSVMGRFTISRDNSKNTLYLQMNSLRAED-TAVYYCARYDNVMGLYWFDYW GQGTLVTVSSAS-TKGPSVFPLAPSSKSTSGGTAALGCLVKDYF-PEPVTVSWNSGALT SGVHTFPAVLQSSGLYS-LSSVVTVPSSSLGTQTYICNVNHKPSNTKVDKRVE-PKSCDK THTCPPCPA-PELLGGPSVFLFPPKPKDTLMISRTPEVTCVVVDVSH EDPEVKFNWYVD GVEVHNAKTKPREEQYN-STYRVVSVLTVLHQDWLNGKEYKCKVSNKALPA-PIEKTI SKAKGQPREPQVYTLPPSREEMTKNQVSLT-CLVKGFYPSDIAVEWESNGQPENNYKT TPPVLDSDGSFFLYSK-LTVDKSRWQQGNVFSCSVMHEALHNHYTQKSLSL-SPGK (SEQ ID NO:188) and/or a light chain comprising the sequence of EIVLTQSPATLSLSPGERATLSCRASQSVS-SYLAWYQQKPGQAPRLLIYDASNRATGI PARFSGSGSGTDFTLTISSLEPEDFAVYYCQQRSNWP-PAFGGGTKVEIKRTVAAPSVFI FPPSDEQLKSG-TASVVCLLNNFYPREAKVQWKVD-NALQSGNSQESVTEQDSKDSTY SLSSTLTLSKADYEKHKVYACE-VTHQGLSSPVTKSFNRGEC (SEQ ID NO:189). In some embodiments, the antibody comprises at least one, two, three, four, five, or six hypervariable region (HVR) sequences of antibody 023 as described in U.S. Pat. No. 7,550,140. In some embodiments, the antibody comprises a heavy chain variable region sequence and/or a light chain variable region sequence of antibody 023 as described in U.S. Pat. No. 7,550,140.

In some embodiments, the OX40 agonist antibody is an anti-human OX40 agonist antibody described in U.S. Pat. No. 7,960,515. In some embodiments, the anti-human OX40 agonist antibody comprises a heavy chain variable region comprising the sequence of EVQLVESGG-GLVQPGGSLRLSCAASGFTFSSYSMNWVRQAPGK-GLEWVSYISSSSST IDYADSVKGRFTISRDNAKNS-LYLQMNSLRDEDTAVYYCARESGWYLFDYWGQGT LVTVSS (SEQ ID NO:190) and/or a light chain variable region comprising the sequence of DIQMTQSPSSL-SASVGDRVTITCRASQGISSWLAWYQQK-PEKAPKSLIYAASSLQSGV PSRFSGSGSGTDFTLTISSLQPEDFATYYCQQYN-SYPPTFGGGTKVEIK (SEQ ID NO:191). In some embodiments, the antibody comprises at least one, two, three, four, five, or six hypervariable region (HVR) sequences of antibody 11D4 as described in U.S. Pat. No. 7,960,515. In some embodiments, the antibody comprises a heavy chain variable region sequence and/or a light chain variable region sequence of antibody 11D4 as described in U.S. Pat. No. 7,960,515.

In some embodiments, the OX40 agonist antibody is an anti-human OX40 agonist antibody described in U.S. Pat. No. 7,960,515. In some embodiments, the anti-human OX40 agonist antibody comprises a heavy chain variable region comprising the sequence of EVQLVESGG-GLVQPGRSLRLSCAASGFTFDDYAMHWVRQAPGK-GLEWVSGISWNS GSIGYADSVKGRFTISRDNAKNS-LYLQMNSLRAEDTALYYCAKDQSTADYYFYYGM DVWGQGTTVTVSS (SEQ ID NO:192) and/or a light chain variable region comprising the sequence of EIV-VTQSPATLSLSPGERATLSCRASQSVSSY-LAWYQQKPGQAPRLLIYDASNRATGI PARFSGSGSGTDFTLTISSLEPED-FAVYYCQQRSNWPTFGQGTKVEIK (SEQ ID NO:193). In some embodiments, the antibody comprises at least one, two, three, four, five, or six hypervariable region (HVR) sequences of antibody 18D8 as described in U.S. Pat. No. 7,960,515. In some embodiments, the antibody comprises a heavy chain variable region sequence and/or a light chain variable region sequence of antibody 18D8 as described in U.S. Pat. No. 7,960,515.

In some embodiments, the OX40 agonist antibody is an anti-human OX40 agonist antibody described in WO 2012/027328. In some embodiments, the anti-human OX40 agonist antibody comprises a heavy chain variable region comprising the sequence of QVQLVQSGSELKKPGASVKVSCK-ASGYTFTDYSMHWVRQAPGQGLKWMGWINTE TGEPTYADDFKGRFVFSLDTSVSTAYLQISSLKAED-TAVYYCANPYYDYVSYYAMD YWGQGTTVTVSS (SEQ ID NO:194) and/or a light chain variable region comprising the sequence of DIQMTQSPSSL-SASVGDRVTITCKASQDVSTA-VAWYQQKPGKAPKLLIYSASYLYTG VPSRFSGSGSGTDFTFTISSLQPEDIATYYCQQHYST-PRTFGQGTKLEIK (SEQ ID NO:195). In some embodiments, the antibody comprises at least one, two, three, four, five, or six hypervariable region (HVR) sequences of antibody hu106-222 as described in WO 2012/027328. In some embodiments, the antibody comprises a heavy chain variable region sequence and/or a light chain variable region sequence of antibody hu106-222 as described in WO 2012/027328.

In some embodiments, the OX40 agonist antibody is an anti-human OX40 agonist antibody described in WO 2012/027328. In some embodiments, the anti-human OX40 agonist antibody comprises a heavy chain variable region comprising the sequence of EVQLVESGGGLVQPGGSLRLSCAASEYEFP-SHDMSWVRQAPGKGLELVAAINSDGG STYYPDT-MERRFTISRDNAKNSLYLQMNSLRAEDTAVYYCAR- HYDDYYAWFAYWG QGTMVTVSS (SEQ ID NO:196) and/or a light chain variable region comprising the sequence of EIVLTQSPATLSLSPGERATLSCRASKSVST-SGYSYMHWYQQKPGQAPRLLIYLASNL ESGVPARFSGSGSGTDFTLTISSLEPEDFAVYYCQHS-RELPLTFGGGTKVEIK (SEQ ID NO:197). In some embodiments, the antibody comprises at least one, two, three, four, five or six hypervariable region (HVR) sequences of antibody Hu119-122 as described in WO 2012/027328. In some embodiments, the antibody comprises a heavy chain variable region sequence and/or a light chain variable region sequence of antibody Hu119-122 as described in WO 2012/027328.

In some embodiments, the OX40 agonist antibody is an anti-human OX40 agonist antibody described in WO 2013/028231. In some embodiments, the anti-human OX40 agonist antibody comprises a heavy chain comprising the sequence of MYLGLNYVFIVFLLNGVQSEVKLEESGG-GLVQPGGSMKLSCAASGFTFSDAWMDW VRQS-PEKGLEWVAEIRSKANNHATYYAESVNGRFTISRDD-SKSSVYLQMNSLRAED TGIYYCTWGEVFYFDYWGQGTTLTVSSAS-TKGPSVFPLAPSSKSTSGGTAALGCLVK DYF-PEPVTVSWNSGALTSGVHTFPAVLQSSGLYS-LSSVVTVPSSSLGTQTYITCNVNH KPSNTKVDKKVEPKSCDKTHTCPPCPA-PELLGGPSVFLFPPKPKDTLMISRTPEVTCV VVDVSHEDPEVKFNWYVDGVEVHNAKTKPRE-EQYNSTYRVVSVLTVLHQDWLNG KEYKCKVSNKA-LPAPIEKTISKAKGQPREPQVYTLPPSRDELT-KNQVSLTCLVKGFYP SDIAVEWESNGQPENNYKTTPPVLDSDGSFFLYSK-LTVDKSRWQQGNVFSCSVMHE ALHNHYTQKSLSL-SPGK (SEQ ID NO:198) and/or a light chain comprising the sequence of MRPSIQFLGLLL-FWLHGAQCDIQMTQSPSSLSASLGGKVTITCK-SSQDINKYIAWYQH KPGKGPRLLIHYTSTLQP-GIPSRFSGSGSGRDYSFSISNLEPEDIATYYCLQYDN LLTFG AGTKLELKRTVAAPSVFIFPPSDEQLKSG-TASVVCLLNNFYPREAKVQWKVDNALQS GNSQESVTEQDSKDSTYSLSSTLTLSKADYEKHKVY-ACEVTHQGLSSPVTKSFNRGE C (SEQ ID NO:199). In some embodiments, the anti-human OX40 agonist antibody comprises a heavy chain variable region comprising the sequence of MYLGLNYVFIVFLLNGVQSEVKLEESGG-GLVQPGGSMKLSCAASGFTFSDAWMDW VRQS-PEKGLEWVAEIRSKANNHATYYAESVNGRFTISRDD-SKSSVYLQMNSLRAED TGIYYCTWGEVFYFDYWGQGTTLTVSS (SEQ ID NO:214) and/or a light chain variable region comprising the sequence of MRPSIQFLGLLL-FWLHGAQCDIQMTQSPSSLSASLGGKVTITCK-SSQDINKYIAWYQH KPGKGPRLLIHYTSTLQP-GIPSRFSGSGSGRDYSFSISNLEPEDIATYYCLQYDNLLTFG AGTKLELK (SEQ ID NO:215). In some embodiments, the antibody comprises at least one, two, three, four, five, or six hypervariable region (HVR) sequences of antibody Mab CH 119-43-1 as described in WO 2013/028231. In some embodiments, the antibody comprises a heavy chain variable region sequence and/or a light chain variable region sequence of antibody Mab CH 119-43-1 as described in WO 2013/028231.

In some embodiments, the OX40 agonist antibody is an anti-human OX40 agonist antibody described in WO 2013/038191. In some embodiments, the anti-human OX40 agonist antibody comprises a heavy chain variable region comprising the sequence of EVQLQQSGPELVKPGASVKMSCKASGYTFT-SYVMHWVKQKPGQGLEWIGYINPYN DGT-KYNEKFKGKATLTSDKSSSTAYMELSSLTSEDSAVYY-CANYYGSSLSMDYWG QGTSVTVSS (SEQ ID NO:200) and/or a light chain variable region comprising the sequence of DIQMTQTTSSLSASLGDRVTISCRASQDIS-NYLNWYQQKPDGTVKLLIYYTSRLHSGV PSRFSGSGSGTDYSLTISNLEQEDI-ATYFCQQGNTLPWTFGGGTKLEIKR (SEQ ID NO:201). In some embodiments, the antibody comprises at least one, two, three, four, five, or six hypervariable region (HVR) sequences of antibody clone 20E5 as described in WO 2013/038191. In some embodiments, the antibody comprises a heavy chain variable region sequence and/or a light chain variable region sequence of antibody clone 20E5 as described in WO 2013/038191.

In some embodiments, the OX40 agonist antibody is an anti-human OX40 agonist antibody described in WO 2013/038191. In some embodiments, the anti-human OX40 agonist antibody comprises a heavy chain variable region comprising the sequence of EVQLQQSGPELVKPGASVKISCK-TSGYTFKDYTMHWVKQSHGKSLEWIGGIYPNNG GSTYNQNFKDKATLTVDKSSSTAYMEFRSLTSED-SAVYYCARMGYHGPHLDFDVW GAGTTVTVSP (SEQ ID NO:202) and/or a light chain variable region comprising the sequence of DIVMTQSHKFMSTSLGDRVSITCK-ASQDVGAAVAWYQQKPGQSPKLLIYWASTRHT GVPDRFTGGGSGTDFTLTISNVQSEDLTDYFCQQY-INYPLTFGGGTKLEIKR (SEQ ID NO:203). In some embodiments, the antibody comprises at least one, two, three, four, five, or six hypervariable region (HVR) sequences of antibody clone 12H3 as described in WO 2013/038191. In some embodiments, the antibody comprises a heavy chain variable region sequence and/or a light chain variable region sequence of antibody clone 12H3 as described in WO 2013/038191.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKP-GASVKVSCKASGYTFTSYVMHWVRQAPGQR-LEWMGYINPY NDGTKYNEKFKGRVTITSDTSAS-TAYMELSSLRSEDTAVYYCANYYGSSLSMDYWG QGTLVTVSS (SEQ ID NO:204) and/or a light chain variable region comprising the sequence of DIQMTQSPSSL-SASVGDRVTITCRASQDIS-NYLNWYQQKPGKAPKLLIYYTSRLHSGV PSRFSGSGSGTDYTLTISSLQPEDFA-TYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKP-GASVKVSCKASGYTFTSYVMHWVRQAPGQR-LEWMGYINPY NDGTKYNEKFKGRVTITSDTSAS-TAYMELSSLRSEDTAVYYCANYYGSSLSMDYWG QGTLVTVSS (SEQ ID NO:204) and/or a light chain variable region comprising the sequence of DIQMTQSPSSLSASVGDRVTITCRASQDISNYLNWYQQKPGKAVKLLIYYTSRLHSGVPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATITSDTSASTAYMELSSLRSEDTAVYYCANYYGSSLSMDYWGQGTLVTVSS (SEQ ID NO:207) and/or a light chain variable region comprising the sequence of DIQMTQSPSSLSASVGDRVTITCRASQDISNYLNWYQQKPGKAPKLLIYYTSRLHSGVPSRFSGSGSGTDYTLTISSLQPEDFATYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATITSDTSASTAYMELSSLRSEDTAVYYCANYYGSSLSMDYWGQGTLVTVSS (SEQ ID NO:207) and/or a light chain variable region comprising the sequence of DIQMTQSPSSLSASVGDRVTITCRASQDISNYLNWYQQKPGKAVKLLIYYTSRLHSGVPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAPKLLIYYTSRLHSGVPSRFSGSGSGTDYTLTISSLQPEDFATYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAVKLLIYYTSRLHSGVPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWMGGIYPNNGGSTYNQNFKDRVTITADKSTSTAYMELSSLRSEDTAVYYCARMGYHGPHLDFDV WGQGTTVTVSS (SEQ ID NO:209) and/or a light chain variable region comprising the sequence of DIQMTQSPSSLSASVGDRVTITCKASQDVGAAVAWYQQKPGKAPKLLIYWASTRHTGVPSRFSGSGSGTDFTLTISSLQPEDFATYYCQQYINYPLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWMGGIYPNNGGSTYNQNFKDRVTITADKSTSTAYMELSSLRSEDTAVYYCARMGYHGPHLDFDV WGQGTTVTVSS (SEQ ID NO:209) and/or a light chain variable region comprising the sequence of DIQMTQSPSSLSASVGDRVTITCKASQDVGAAVAWYQQKPGKAPKLLIYWASTRHTGVPDRFSGGGSGTDFTLTISSLQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRVTLTADKSTSTAYMELSSLRSED-TAVYYCARMGYHGPHLDFDV WGQGTTVTVSS (SEQ ID NO:212) and/or a light chain variable region comprising the sequence of DIQMTQSPSSLSASVGDRVTITCK-ASQDVGAAVAWYQQKPGKAPKLLIYWASTRHT GVPSRFSGSGSGTDFTLTISSLQPEDFATYYCQQYINY-PLTFGGGTKVEIKR (SEQ ID NO:210 In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRVTLTADKSTSTAYMELSSLRSED-TAVYYCARMGYHGPHLDFDV WGQGTTVTVSS (SEQ ID NO:212) and/or a light chain variable region comprising the sequence of DIQMTQSPSSLSASVGDRVTITCK-ASQDVGAAVAWYQQKPGKAPKLLIYWASTRHT GVPDRFSGGGSGTDFTLTISSLQPEDFATYYCQQY-INYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRATLTVDKSTSTAYMELSSLRSED-TAVYYCARMGYHGPHLDFDV WGQGTTVTVSS (SEQ ID NO:213) and/or a light chain variable region comprising the sequence of DIQMTQSPSSLSASVGDRVTITCK-ASQDVGAAVAWYQQKPGKAPKLLIYWASTRHT GVPSRFSGSGSGTDFTLTISSLQPEDFATYYCQQYINY-PLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRATLTVDKSTSTAYMELSSLRSED-TAVYYCARMGYHGPHLDFDV WGQGTTVTVSS (SEQ ID NO:213) and/or a light chain variable region comprising the sequence of DIQMTQSPSSLSASVGDRVTITCK-ASQDVGAAVAWYQQKPGKAPKLLIYWASTRHT GVPDRFSGGGSGTDFTLTISSLQPEDFATYYCQQY-INYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the agonist anti-human OX40 antibody is L106 BD (Pharmingen Product #340420). In some embodiments, the antibody comprises at least one, two, three, four, five or six hypervariable region (HVR) sequences of antibody L106 (BD Pharmingen Product #340420). In some embodiments, the antibody comprises a heavy chain variable region sequence and/or a light chain variable region sequence of antibody L106 (BD Pharmingen Product #340420).

In some embodiments, the agonist anti-human OX40 antibody is ACT35 (Santa Cruz Biotechnology, Catalog #20073). In some embodiments, the antibody comprises at least one, two, three, four, five or six hypervariable region (HVR) sequences of antibody ACT35 (Santa Cruz Biotechnology, Catalog #20073). In some embodiments, the antibody comprises a heavy chain variable region sequence and/or a light chain variable region sequence of antibody ACT35 (Santa Cruz Biotechnology, Catalog #20073).

In some embodiments, the OX40 agonist antibody is MEDI6469. In some embodiments, the antibody comprises at least one, two, three, four, five, or six hypervariable region (HVR) sequences of antibody MEDI6469. In some embodiments, the antibody comprises a heavy chain variable region sequence and/or a light chain variable region sequence of antibody MEDI6469.

In some embodiments, the OX40 agonist antibody is MEDI0562. In some embodiments, the antibody comprises at least one, two, three, four, five, or six hypervariable region (HVR) sequences of antibody MEDI0562. In some embodiments, the antibody comprises a heavy chain variable region sequence and/or a light chain variable region sequence of antibody MEDI0562.

Non-Antibody OX40 Agonists

In certain embodiments, the antigen binding polypeptides described herein comprise antigen binding regions comprising non-antibody OX40 agonists. Non-antibody OX40 agonists are well known in the art.

OX40L (also known as CD134L) serves as a ligand for OX40. As such, agonists that present part or all of OX40L may serve as OX40 agonists. In some embodiments, an OX40 agonist may include one or more extracellular domains of OX40L. Examples of extracellular domains of OX40L may include OX40-binding domains. In some embodiments, an OX40 agonist may be a soluble form of OX40L that includes one or more extracellular domains of OX40L but lacks other, insoluble domains of the protein, e.g., transmembrane domains. In some embodiments, an OX40 agonist is a soluble protein that includes one or more extracellular domains of OX40L able to bind OX40L.

In some embodiments, an OX40 agonist may be any one of the OX40 agonists described in U.S. Pat. No. 7,696,175 or European Patent No. EP0672141 B1. In some embodiments, an OX40 agonist may be any one of the OX40 agonists described in International Publication No. WO2006/121810, such as an OX40 immunoadhesin. In some embodiments, the OX40 agonist is MEDI6383.

Fc Modifications that Reduce Effector Function

In certain embodiments, an antibody, subunit, or antigen binding polypeptide described herein comprises one or more amino acid modifications for attenuating effector function (such as CDC and/or ADCC). In exemplary embodiments, the modification to attenuate effector function is a modification that alters the glycosylation pattern of the Fc region, e.g., a modification that results in an aglycosylated Fc region. In exemplary embodiments, the modification to attenuate effector function is a modification that does not alter the glycosylation pattern of the Fc region. In certain embodiments, the modification to attenuate effector function reduces or eliminates binding to human effector cells, binding to one or more Fc receptors, and/or binding to cells expressing an Fc receptor. In an exemplary embodiment, the Fc variants described herein comprise an N297G or N297A modification in the Fc region of human IgG1. In an exemplary embodiment, the Fc variants described herein comprise the following modifications: L234A, L235A and P329G in the Fc region of human IgG1, that result in attenuated effector function.

In various embodiments, Fc variants having reduced effector function refer to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wild-type Fc region (e.g., an Fc region not having a mutation to reduce effector function, although it may have other mutations). In certain embodiments, Fc variants having reduced effector function refer to Fc variants that eliminate all detectable effector function as compared to a wild-type Fc region. Assays for measuring effector function are known in the art and described below.

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity). The primary cells for mediating ADCC, NK cells, express FcγRIII only, whereas monocytes express FcγRI, FcγRII and FcγRIII. FcR expression on hematopoietic cells is summarized in Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)).

Fc variants with reduced effector function include those having amino acid substitutions at one or more of the following amino acid residues: 238, 265, 269, 270, 297, 327 and 329 (U.S. Pat. No. 6,737,056). Such Fc variants include Fc variants with substitutions at two or more of amino acid positions 265, 269, 270, 297 and 327, including the so-called "DANA" Fc variant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields et al., *J. Biol. Chem.* 9(2): 6591-6604 (2001)).

In certain embodiments, the present disclosure contemplates an antigen binding complex variant that possesses some but not all effector functions, which make it a desirable candidate for applications in which the half life of the complex in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

In certain embodiments, Fc variants described herein can comprise one or more modifications in the Fc region that result in diminished C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000). In exemplary embodiments, the Fc variants described herein comprise a modification at lysine 322 in the Fc region of human IgG1 (EU numbering of residues). In some embodiments, the modification(s) result in diminished C1q binding and/or CDC, e.g., as compared to an Fc region without the modification(s). For example, in certain embodiments, Fc variants described herein comprise a K322A modification in the Fc region of human IgG1 (EU numbering of residues), e.g., as described in U.S. Pat. No. 6,194,551, WO 99/51642, and Idusogie et al. *J. Immunol.* 164: 4178-4184 (2000). Other such exemplary modifications (in the Fc region of human IgG1, and according to EU numbering of residues) include but are not limited to D270K, D270V, P329A, and P331A.

In certain embodiments, the Fc variants described herein comprise modifications to the Fc region that reduce effector function as described in Strohl, Current Opinion in Biotechnology, 20; 685-691 (2009). In exemplary embodiments, the Fc variants described herein comprise modifications at one or more amino acid residues selected from the following (EU numbering of residues):
(a) N297A in the Fc region of human IgG1;
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1,
wherein the modifications reduce effector function of the Fc domain In other exemplary embodiments, the Fc variants described herein comprise modifications that attenuate effector function selected from the following (EU numbering of residues):
(a) N297A in the Fc region of human IgG1;
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

In certain embodiments, the Fc variants described herein do not comprise an N297A modification to attenuate effector function.

In an exemplary embodiment, an agonist antigen binding complex provided herein binds to and agonizes OX40 in the absence of FcR binding. In an exemplary embodiment, the agonist antigen binding complex provided herein binds to and agonizes OX40 while having reduced FcR binding as compared to the equivalent antigen binding complex that does not contain a mutation in the Fc region to attenuate effector function. In various embodiments, the agonist antigen binding complex provided herein binds to and agonizes OX40 while having FcR binding that is reduced by at least 10%, 20%, 30%, 40%, 50%, 60%, 70%, 80%, 90%, 95% or more as compared to the equivalent antigen binding complex that does not contain a mutation in the Fc region to attenuate effector function. In certain embodiments, the agonist antigen binding complex provided herein binds to and agonizes OX40 while having FcR binding that is reduced by at least 50%, 75%, 80%, 85%, 90, 95%, 97%, 98% or more as compared to the equivalent antigen binding complex that does not contain a mutation in the Fc region to attenuate effector function.

III. Production of Antigen Binding Complexes with Agonist Activity

Certain aspects of the present disclosure relate to methods of producing an antigen binding complex (e.g., a tetravalent antigen binding complex) having agonist activity for a cell surface receptor.

In some embodiments, the methods include assembling a first and a second subunit, and coupling the first and the second subunits via a linker. In some embodiments, the first and/or the second subunits are bispecific antibodies. A variety of techniques for assembling a bi- or multi-specific antibody are known in the art and described herein (e.g., see infra). For example, in some embodiments, the methods include providing a first half-antibody and a second half-antibody, then assembling the first and the second half-antibodies in vitro to form a first subunit or bispecific antibody. In some embodiments, the first half-antibody comprises a first antibody heavy chain variable domain ($VH_1$) and a first antibody light chain variable domain ($VL_1$). In some embodiments, the second half-antibody comprises a second antibody heavy chain variable domain ($VH_2$) and a second antibody light chain variable domain ($VL_2$). In some embodiments, the methods further include providing a third half-antibody and a fourth half-antibody, then assembling the third and the fourth half-antibodies in vitro to form a second subunit or bispecific antibody. In some embodiments, the third half-antibody comprises the first antibody heavy chain variable domain ($VH_1$) and the first antibody light chain variable domain ($VL_1$). In some embodiments, the fourth half-antibody comprises the second antibody heavy chain variable domain ($VH_2$) and the second antibody light chain variable domain ($VL_2$). In some embodiments, one or both of the subunits comprises a first half-antibody (e.g., $VH_1$ and $VL_1$) that specifically binds one epitope (e.g., of a cell surface receptor), and a second half-antibody (e.g., $VH_2$ and $VL_2$) that specifically binds a different epitope (e.g., of the same cell surface receptor). In some embodiments, one or both of the subunits comprises a first half-antibody (e.g., $VH_1$ and $VL_1$) that specifically binds one epitope (e.g., of a cell surface receptor), and a second half-antibody (e.g., $VH_2$ and $VL_2$) that specifically binds the same epitope. While this represents an exemplary method for producing an antigen binding complex (e.g., a "c:IgG-IgG" format as illustrated in FIGS. 3A & 3B), the present disclosure contemplates other suitable methods of production using techniques known in the art, including other techniques for generating a bispecific antibody, different linkers, different coupling strategies, and so forth.

In some embodiments, the first and second subunits are chemically coupled via a linker. A variety of chemical coupling techniques are known in the art and described herein (e.g., see infra). For example, in some embodiments, one half-antibody from each subunit includes an engineered free cysteine, and the engineered free cysteines are coupled using techniques known in the art and described herein (e.g., see infra). Thus, this asymmetry allows for a consistent configuration of the complex, as only one pairing is possible. Exemplary free cysteines are described herein and include, without limitation, a cysteine amino acid in the heavy chain selected from T114C, A118C, A140C, L174C, L179C, T187C, T209C, V262C, G371C, Y373C, E382C, S400C, S424C, N434C and Q438C, according to EU numbering; and a cysteine amino acid in the light chain selected from I106C, R108C, R142C, K149C, and V205C, according to Kabat numbering.

In some embodiments, the first and second subunits are chemically coupled via a bis-maleimido polyethylene glycol (PEG) linker of the present disclosure. For example, in some embodiments, coupling the subunits includes reacting the two subunits with a bis-maleimido polyethylene glycol (PEG) linker of the present disclosure and purifying the complex. A variety of purification techniques known in the art may be used. In some embodiments, the purification comprises size exclusion chromatography and/or anion exchange chromatography.

In some embodiments, the methods include providing an antibody and two antibody Fab fragments, then coupling one of the antibody Fab fragments to each of the two half-antibodies via a linker. In some embodiments, the antibody comprises two half-antibodies. In some embodiments, each half-antibody comprises an antibody heavy chain comprising a first antibody heavy chain variable domain ($VH_1$), and an antibody light chain comprising a first antibody light chain variable domain ($VL_1$). In some embodiments, each antibody Fab fragment comprises a second antibody heavy chain variable domain ($VH_2$) and a second antibody light chain variable domain ($VL_2$). In some embodiments, the complex comprises a two half-antibodies, each with a $VH_1$ and a $VL_1$ that specifically binds one epitope (e.g., of a cell surface receptor), and two Fab fragments, each with a $VH_2$ and a $VL_2$ that specifically binds a different epitope (e.g., of the same cell surface receptor). In some embodiments, the complex comprises a two half-antibodies, each with a $VH_1$ and a $VL_1$ that specifically binds one epitope (e.g., of a cell surface receptor), and two Fab fragments, each with a $VH_2$ and a $VL_2$ that specifically binds the same epitope of the cell surface receptor. While this represents an exemplary method for producing an antigen binding complex (e.g., a "c:Fab-IgG" format as illustrated in FIGS. 3A & 3B), the present disclosure contemplates other suitable methods of production using techniques known in the art, including different linkers (e.g., a polypeptide linker), different coupling strategies (e.g., genetic coupling using single chain antibodies or half-antibodies linked to the Fab fragment(s)), and so forth.

In some embodiments, the two Fab fragments are each chemically coupled to the antibody via a linker. A variety of chemical coupling techniques are known in the art and described herein (e.g., see infra). For example, in some embodiments, each half-antibody and Fab fragment includes an engineered free cysteine, each Fab fragment is coupled to one half-antibody via the engineered free cysteines, and the engineered free cysteines are coupled using techniques known in the art and described herein (e.g., see infra). Exemplary free cysteines are described herein and include, without limitation, a cysteine amino acid in the heavy chain selected from T114C, A118C, A140C, L174C, L179C, T187C, T209C, V262C, G371C, Y373C, E382C, S400C, S424C, N434C and Q438C, according to EU numbering; and a cysteine amino acid in the light chain selected from a C-terminal cysteine, I106C, R108C, R142C, K149C, and V205C, according to Kabat numbering. For example, in certain embodiments (e.g., as described in reference to FIGS. 6 & 7), each Fab fragment is chemically coupled to an antibody light chain via a linker, using a C-terminal free engineered cysteine on the Fab fragment and a K149C free engineered cysteine on the antibody light chain.

In some embodiments, the antibody and the two Fab fragments are chemically coupled via a bis-maleimido polyethylene glycol (PEG) linker of the present disclosure. For example, in some embodiments, coupling the subunits includes reacting each of the two antibody Fab fragments with a bis-maleimido polyethylene glycol (PEG) linker to form two bismal-conjugated antibody Fab fragments, removing excess bis-maleimido PEG linker, reacting each of the two bismal-conjugated antibody Fab fragments with the antibody to form the complex, and purifying the complex. A variety of purification techniques known in the art may be used. In some embodiments, the purification comprises size exclusion chromatography and/or anion exchange chromatography.

In some embodiments, the methods include expressing in a host cell two antibody heavy chains. In some embodiments, each antibody heavy chain comprises, from N-terminus to C-terminus, a first antibody heavy chain variable domain ($VH_1$), a first antibody heavy chain CH1 domain ($CH1_1$), a second heavy chain variable domain ($VH_2$), a second heavy chain CH1 domain ($CH1_2$), an antibody heavy chain CH2 domain, and an antibody heavy chain CH3 domain. In some embodiments, each $VH_1$ and/or each $CH1_1$ comprises a first modification for orthogonal pairing, and each $VH_2$ and/or each $CH1_2$ comprises a different, second modification for orthogonal pairing, e.g., as compared to the modification of the $VH_1$ and/or $CH1_1$. In some embodiments, the methods further include expressing in the host cell two first antibody light chains. In some embodiments, each of the two first antibody light chains comprises, from N-terminus to C-terminus, a first antibody light chain variable domain ($VL_1$) and a first antibody light chain constant domain ($CL_1$). In some embodiments, the $VL_1$ and/or the $CL_1$ comprises a modification for orthogonal pairing with the first modification of the antibody heavy chains. In some embodiments, the methods further include expressing in the host cell two second antibody light chains. In some embodiments, each of the two second antibody light chains comprises, from N-terminus to C-terminus, a second antibody light chain variable domain ($VL_2$) and a second antibody light chain constant domain ($CL_2$). In some embodiments, the $VL_2$ and/or the $CL_2$ comprises a modification for orthogonal pairing with the second modification of the antibody heavy chains. Upon expression in the host cell, the two antibody heavy chains associate, each of the two heavy chains couples with a first antibody light chain via orthogonal pairing, and each of the two heavy chains couples with a second antibody light chain via orthogonal pairing. In some embodiments, the antigen binding complex is biepitopic. While this represents an exemplary method for producing an antigen binding complex (e.g., a "r:Fab-IgG" format as illustrated in FIGS. 3A & 3B), the present disclosure contemplates other suitable methods of production using techniques known in the art, including different linkers (e.g., a polypeptide linker), different coupling strategies (e.g., genetic coupling using single chain antibodies or half-antibodies linked to the Fab fragment(s)), and so forth.

Exemplary orthogonal variant pairs are described herein; for further descriptions, see, e.g., PCT/US2016/028850. For example, in some embodiments, the first and/or the second modification of the antibody heavy chain are selected from VH-Q39K, VH-Q39E, CH1-S183E, CH1-S183K, CH1-A141I, CH1-F170S, CH1-S181M, CH1-S183A, and CH1-V185A (EU numbering). In some embodiments, the modifications of the first and/or the second antibody light chains are selected from VL-Q38E, VL-Q38K, CL-V133K, CL-V133E, CL-F116A, CL-L135V, CL-S174A, CL-S176F, and CL-T178V (EU numbering).

Bispecific Antibodies

In certain embodiments, an antigen binding polypeptide, subunit, or antibody provided herein is multispecific, e.g. bispecific. Multispecific antibodies are monoclonal antibodies that have binding specificities for at least two different sites or epitopes. In some embodiments, a bispecific antibody, subunit, or antigen binding polypeptide has binding specificities for at least two different epitopes of the same target, e.g., a cell surface receptor.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

In some embodiments, e.g., as exemplified infra, a bispecific antibody is created by "knob-in-hole" engineering. For example, two half-antibodies can be assembled into a bispecific antibody in vitro, where a first half-antibody comprises an amino acid modification in its CH3 domain that forms a protuberance, and the second half-antibody comprises an amino acid modification in its CH3 domain that forms a cavity. The protuberance is positionable into the cavity, thereby forming the bispecific antibody upon assembly.

In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE B

Properties of amino acid residues

| Amino acid | One-letter abbreviation | Mass[a] (daltons) | Volume[b] ($Å^3$) | Accessible surface area[c] ($Å^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43rd ed. Cleveland, Chemical Rubber Publishing Co., 1961.
[b]Values from A. A. Zamyatnin, Prog. Biophys. Mol. Biol. 24: 107-123, 1972.
[c]Values from C. Chothia, J. Mol. Biol. 105: 1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE C

Exemplary sets of corresponding knob-and hole-forming mutations

| CH3 of first immunoglobulin | CH3 of second immunoglobulin |
|---|---|
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code). Multiple mutations are separated by a colon.

In some embodiments, an immunoglobulin polypeptide comprises a CH3 domain comprising one or more amino acid substitutions listed in Table C above. In some embodiments, a bispecific antibody comprises a first immunoglobulin polypeptide comprising a CH3 domain comprising one or more amino acid substitutions listed in the left column of Table C, and a second immunoglobulin polypeptide comprising a CH3 domain comprising one or more corresponding amino acid substitutions listed in the right column of Table C.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as *E. coli*, or eukaryotic host cells, such as CHO cells. Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat Biotechnol* 31:753-8, 2013. In some embodiments, modified immunoglobulin polypeptides may be expressed separately in CHO cells and assembled in vitro using the methods described above.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol,* 152:5368 (1994).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain ($V_H$) and a variable light chain ($V_L$) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

Additional descriptions of methods for making multispecific antibodies may be found in Spiess, C. et al. (2015) *Mol. Immunol.* 67:95-106 (see, e.g., Table 2). These include, without limitation, the following technologies (with exemplary mutations in the first and second heavy chains included): knobs-into-holes (T366W in first heavy chain; T366S, L368A, and Y407V in second heavy chain), Duo-Body® (F405L in first heavy chain; K409R in second heavy chain), Azymetric™ (T350V, L351Y, F405A, and Y407V in first heavy chain; T350V, T366L, K392L, and T394W in second heavy chain), Amgen charge-pair (K409D and K392D in first heavy chain; D399K and E356K in second heavy chain), Rinat-Pfizer charge-pair (D221E, P228E, and L368E in first heavy chain; D221R, P228R, and K409R in second heavy chain), HA-TF (S364H and F405A in first heavy chain; Y349T and T394F in second heavy chain), SEEDBody (IgA/G chimeras in first and second heavy chains), and differential protein A affinity (H435R in first heavy chain).

Coupling

In some embodiments, two antigen binding polypeptides, antibodies, or subunits are coupled. In some embodiments, an antibody and one or more Fab fragments are coupled. As used herein, coupled and grammatical variants thereof may refer to a state of two or more macromolecules being connected or joined by one or more chemical bonds or forces (e.g., a non-covalent bond, a covalent bond, an ionic bond or charge-charge interaction, a hydrogen bond, an aromatic stacking interaction, or a Van der Waals interaction).

In some embodiments, the macromolecules can be provided as separate entities and chemically coupled together, e.g., via a chemical reaction. As non-limiting examples, the c:IgG-IgG and c:Fab-IgG formats described and illustrated herein (see FIGS. 3A & 3B) may be produced by chemically coupling two antibodies (e.g., bispecific antibodies) or an antibody and two or more Fab fragments, respectively. In some embodiments, chemically coupling two macromolecules may include joining the macromolecules with a linker of the present disclosure.

In some embodiments, the macromolecules can include distinguishable units or modules but genetically or recombinantly produced as a single entity (e.g., a single polypeptide chain). As non-limiting examples, the r:Fab-IgG and r:Fv-IgG formats described and illustrated herein (see FIGS. 3A & 3B) may be produced by coupling Fab fragments or Fvs. In some embodiments, coupling two macromolecules may include genetic coupling, whereby the two macromolecules are engineered (e.g., using recombinant techniques) to be encoded by a single polynucleotide or open-reading frame and expressed as a single polypeptide chain. In some embodiments, genetically coupling two macromolecules may include engineering the macromolecules with a linker of the present disclosure.

In some embodiments, two antigen binding polypeptides or subunits are coupled via a linker. In some embodiments, an antibody and two or more Fab fragments are coupled via a linker. For example, two antibodies (e.g., two bispecific antibodies) or an antibody and two or more Fab fragments may be coupled via a linker.

In some embodiments, a linker of the present disclosure is between about 10 Å and about 100 Å in length. For example, a linker of the present disclosure may have any length within a range of lengths having an upper limit of 15 Å, 20 Å, 25 Å, 30 Å, 35 Å, 40 Å, 45 Å, 50 Å, 55 Å, 60 Å, 65 Å, 70 Å, 75 Å, 80 Å, 85 Å, 90 Å, 95 Å, and 100 Å; and an independently selected lower limit of 10 Å, 15 Å, 20 Å, 25 Å, 30 Å, 35 Å, 40 Å, 45 Å, 50 Å, 55 Å, 60 Å, 65 Å, 70 Å, 75 Å, 80 Å, 85 Å, 90 Å, and 95 Å, wherein the upper limit is greater than the lower limit.

A variety of linkers are known in the art. In some embodiments, a linker can be a chemical linker. Suitable chemical linkers are known in the art and commercially available. Exemplary chemical linkers include, for example, N-hydroxy succinimide (NHS), disuccinimidyl suberate (DSS), bis(sulfosuccinimidyl)suberate ($BS^3$), dithiobis(succinimidyl propionate) (DSP), dithiobis(sulfosuccinimidyl propionate) (DTSSP), ethylene glycolbis(succinimidyl succinate) (EGS), ethylene glycolbis(sulfosuccinimidyl succinate) (sulfo-EGS), disuccinimidyl tartrate (DST), disulfosuccinimidyl tartrate (sulfo-DST), bis[2-(succinimido oxycarbonyloxy)ethyl]sulfone (BSOCOES), and bis[2-(sulfosuccinimido oxycarbonyloxy) ethyl]sulfone (sulfo-BSOCOES).

In certain embodiments, the linker can be a bis-maleimido polyethylene glycol (PEG) linker. The PEG linker may be composed of a number of PEG units or monomers, e.g., to achieve a desired length. It is contemplated that a variety of PEG lengths could be utilized. For example, in some embodiments, the PEG linker comprises between one and eleven PEG subunits. In some embodiments, the PEG linker comprises 1, 2, 3, 4, 5, 6, 7, 8, 9, 10, or 11 PEG subunits. In certain embodiments, the PEG linker comprises one, two, or three PEG subunits.

In some embodiments, a linker can be a polypeptide linker. In one embodiment, the polypeptide linker is a hinge sequence from an antibody, or a variant thereof. For example, the hinge sequence may comprise amino acid residues 216-238 (EU numbering) of an antibody, such as, for example, an IgG1, IgG2, IgG3 or IgG4 antibody, or fragments or derivatives thereof. In an exemplary embodiment, a hinge based linker comprises the sequence CDKTH-TCPPCPAPELLGGP (SEQ ID NO:219) or fragments or derivatives thereof. In certain embodiments, the polypeptide linker may be a flexible linker of varying length (e.g., 5, 10, 15, 20, 25, 30, 35, 40, 45, 50 or more amino acids). Suitable linkers are known in the art, see for example, Protein Engineering, 9(3), 299-305, 1996. Exemplary peptide linkers include, for example:

```
Ser

Gly-Ser

Gly-Gly-Ser

Ser-Gly-Gly (SEQ ID NO: 220)
Gly-Gly-Gly-Ser (SEQ ID NO: 221)
Ser-Gly-Gly-Gly (SEQ ID NO: 222)
Gly-Gly-Gly-Gly-Ser (SEQ ID NO: 223)
Ser-Gly-Gly-Gly-Gly (SEQ ID NO: 224)
Gly-Gly-Gly-Gly-Gly-Ser (SEQ ID NO: 225)
Ser-Gly-Gly-Gly-Gly-Gly (SEQ ID NO: 226)
Gly-Gly-Gly-Gly-Gly-Gly-Ser (SEQ ID NO: 227)
Ser-Gly-Gly-Gly-Gly-Gly-Gly (SEQ ID NO: 228)
(Gly-Gly-Gly-Gly-Ser)_n
and
                                    (SEQ ID NO: 229)
(Ser-Gly-Gly-Gly-Gly)_n
``` wherein n is an integer not less than one. In certain embodiments n may be 1, 2, 3, 4, 5, 6, 7, 8, 9, 10, 15, or 20.

In some embodiments, two antigen binding polypeptides or subunits are coupled via click chemistry. In some embodiments, an antibody and two or more Fab fragments are coupled via click chemistry. For example, two antibodies (e.g., two bispecific antibodies) or an antibody and two or more Fab fragments may be coupled via click chemistry. As known in the art, click chemistry may refer to a variety of chemical reactions, typically biorthogonal in nature and used to join two or more modular chemical units, that are easy to form, widely applicable, high-yielding, stereospecific and/or regiospecific, insensitive to oxygen and water, use readily available reagents, and/or generate inoffensive byproducts removable by non-chromatographic methods. Exemplary classes of click reactions include, without limitation, cycloadditions (e.g., 1,3-dipolar cycloadditions), non-aldol carbonyl chemistry, nucleophilic ring openings, and additions to carbon-carbon multiple bonds. Additional descriptions of click chemistry and exemplary click reactions may be found, e.g., in Thirumurugan, P. et al. (2013) Chem. Rev. 113:4905-4979.

In some embodiments, two antigen binding polypeptides are coupled via a tetrazine-transcyclooctene (TCO) click reaction. For example, one antigen binding polypeptide may be coupled with tetrazine, and the other antigen binding polypeptide may be coupled with TCO; upon the click reaction, the two antigen binding polypeptides are coupled.

Exemplary descriptions of a tetrazine-TCO click reaction may be found, e.g., in Blackman, M. L. et al. (2008) *J. Am. Chem. Soc.* 130:13518-9.

Engineered Cysteines

In some embodiments, two antigen binding polypeptides, antibodies, or subunits are coupled via engineered free cysteines. In some embodiments, an antibody and one or more Fab fragments are coupled via engineered free cysteines. For example, in some embodiments, two antigen binding polypeptides or subunits, or an antibody and one or more Fab fragments, are coupled via THIOMAB™ (Genentech) antibody technology. Exemplary descriptions of THIOMAB™ antibody technology may be found, e.g., in U.S. Pat. Nos. 7,521,541; 7,855,275; 8,309,300; and 9,000,130; as well as US PG Pub No. 20160130358. In some embodiments, THIOMAB™ antibody technology is used to couple antigen binding polypeptides, subunits, antibodies, or Fab fragments via a linker.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or nonspecific, by misfolding or loss of tertiary structure (Zhang et al (2002) Anal. Biochem. 311:1-9).

Antibodies/subunits/Fab fragments with cysteine substitutions (THIOMAB™ antibodies) at sites where the engineered cysteines are available for conjugation but do not perturb immunoglobulin folding and assembly or alter antigen binding and effector functions (Junutula, et al., 2008b Nature Biotech., 26(8):925-932; Dornan et al (2009) Blood 114(13):2721-2729; U.S. Pat. Nos. 7,521,541; 7,723,485; WO2009/052249).

In some embodiments, a cysteine engineered antibody/subunit/Fab fragment refers to an antibody in which one or more residues of an antibody are substituted with cysteine residues. The thiol group(s) of the cysteine engineered antibodies can be conjugated via a linker. In particular embodiments, the substituted residues occur at accessible sites of the antibody. By substituting those residues with cysteine, reactive thiol groups are thereby positioned at accessible sites of the antibody and may be used to conjugate the antibody or Fab fragment to other moieties. For example, a THIOMAB™ antibody may be an antibody with a single mutation of a non-cysteine native residue to a cysteine in the light chain (e.g., G64C, I106C, R108C, K149C or R142C according to Kabat numbering) or in the heavy chain (e.g., HC-D101C, HC-V184C, or HC-T205C according to Kabat numbering, or HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (i.e., HC-A136C according to Kabat numbering is HC-A140C according to EU numbering).

In some embodiments, a free cysteine amino acid refers to a cysteine amino acid residue which has been engineered into a parent antibody, has a thiol functional group (—SH), and is not paired as an intramolecular or intermolecular disulfide bridge.

Exemplary free engineered cysteine amino acids are known in the art and described herein. In some embodiments, a heavy chain comprises a cysteine amino acid in the heavy chain selected from T114C, A118C, A140C, L174C, L179C, T187C, T209C, V262C, G371C, Y373C, E382C, S400C, S424C, N434C and Q438C, according to EU numbering. In some embodiments, a light chain comprises a cysteine amino acid in the light chain selected from I106C, R108C, R142C, K149C, and V205C, according to Kabat numbering. In some embodiments, a Fab fragment comprises a C-terminal cysteine amino acid.

It should be noted that a single site mutation yields a single engineered cysteine residue in a ThioFab, while a single site mutation yields two engineered cysteine residues in a THIOMAB™ antibody, due to the dimeric nature of the IgG antibody. Mutants with engineered cysteine (Cys) residues were evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the range of 0.0 to 1.0. Specifically, the thiol reactivity values of cysteine engineered antibodies of the invention are in the range of 0.1 to 1.0. In certain embodiments, the thiol reactivity values of cysteine engineered antibodies of the disclosure are in the ranges of 0.0 to 0.1, 0.1 to 0.5, 0.1 to 0.6, 0.1 to 0.7, 0.1 to 0.8, 0.1 to 0.9, or 0.1 to 1.0. In certain embodiments, the thiol reactivity values of cysteine engineered antibodies of the disclosure are in the ranges of 0.2 to 1.0, 0.3 to 1.0, 0.4 to 1.0, 0.5 to 1.0, 0.6 to 1.0, 0.7 to 1.0, or 0.8 to 1.0. In certain embodiments, the thiol reactivity values of cysteine engineered antibodies of the disclosure are in the range of 0.6 to 1.0. In certain embodiments, the thiol reactivity values of cysteine engineered antibodies of the disclosure are in the ranges of 0.7 to 1.0. In certain embodiments, the thiol reactivity values of cysteine engineered antibodies of the invention are in the ranges of 0.8 to 10. In certain embodiments, the thiol reactivity values of cysteine engineered antibodies of the disclosure are in the ranges of 0.5 to 0.8. In certain embodiments, the thiol reactivity values of cysteine engineered antibodies of the disclosure are in the ranges of 0.5 to 0.9. In certain embodiments, the thiol reactivity values of cysteine engineered antibodies of the disclosure are in the ranges of 0.5 to 0.7. In certain embodiments, the thiol reactivity values of cysteine engineered antibodies of the present disclosure are in the ranges of 0.5 to 1.0.

The design, selection, and preparation methods of the present disclosure enable cysteine engineered antibodies which are reactive with electrophilic functionality. Reactive cysteine residues on an antibody surface allow coupling via a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies/subunits/Fab fragments of the present disclosure preferably retain the antigen binding capability of their wild type, parent counterparts. Thus, cysteine engineered antibodies are capable of binding, preferably specifically, to antigens, e.g., an epitope of a cell surface receptor.

Cysteine engineered antibodies/subunits/Fab fragments of the present disclosure may be site-specifically and efficiently coupled with a thiol-reactive reagent. One example of a thiol-reactive reagent is N-ethyl maleimide (NEM). In an exemplary embodiment, reaction of a THIOMAB™ antibody with a biotin-linker reagent provides a biotinylated THIOMAB™ antibody by which the presence and reactivity of the engineered cysteine residue may be detected and measured. Reaction of a THIOMAB™ antibody with a multifunctional linker reagent provides a THIOMAB™ antibody with a functionalized linker which may be further reacted with an antibody or Fab fragment. In certain embodiments, the THIOMAB™ antibody is a ThioFab.

The exemplary methods described here may be applied generally to the identification and production of antibodies, and more generally, to other proteins through application of the design and screening steps described herein.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

Vectors, Host Cells and Recombinant Methods

For recombinant production of an antigen binding complex (e.g., a tetravalent antigen binding complex having agonist activity) of the present disclosure, or a subunit thereof, provided herein, the nucleic acid encoding it is isolated and inserted into a replicable vector for further cloning (amplification of the DNA) or for expression. DNA encoding the antigen binding polypeptide is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. In some embodiments, the host cell is an isolated host cell, e.g., a host cell derived from a multicellular organism that is grown as an isolated cell, such as a cell line derived from an invertebrate (e.g., insect) or vertebrate (e.g., mouse, human, Chinese hamster ovary (CHO) cell, etc.) organism that is grown in cell culture. In cases where an antigen binding polypeptide is an antibody, it will be appreciated that constant regions of any isotype can be used for this purpose, including IgG, IgM, IgA, IgD, and IgE constant regions, and that such constant regions can be obtained from any human or animal species.

a. Generating Antigen Binding Polypeptides Using Prokaryotic Host Cells i. Vector Construction Polynucleotide sequences encoding polypeptide components of the antigen binding complexes (e.g., a tetravalent antigen binding complex having agonist activity) of the present disclosure or subunit(s) thereof provided herein can be obtained using standard recombinant techniques. Desired polynucleotide sequences may be isolated and sequenced from, for example, antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In some embodiments, a polynucleotide sequence of the present disclosure includes a mutation, e.g., one that encodes for an amino acid substitution described herein, such as an engineered free cysteine or a modification for attenuating effector function of an Fc region. DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e. mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed of protocols and formats, including those commercially available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. Oligonucleotides are prepared by the phosphoramidite synthesis method (U.S. Pat. Nos. 4,415,732; 4,458,066; Beaucage, S. and Iyer, R. (1992) "Advances in the synthesis of oligonucleotides by the phosphoramidite approach", Tetrahedron 48:2223-2311). This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.™.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding, for example, the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of the expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to operably ligate them to cistrons encoding the genes of the antigen binding polypeptide protein, e.g., the target light and heavy chains (Siebenlist et al., (1980) Cell 20: 269), using linkers or adaptors to supply any required restriction sites.

In one embodiment, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected should be one that is recognized and processed {i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another embodiment, the production of the immunoglobulins can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. See Proba and Pluckthun Gene, 159:203 (1995).

Prokaryotic host cells suitable for expressing antigen binding polypeptides (e.g., antibodies) of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E coli* strains include strain W31 10 (Bachmann, Cellular and Molecular Biology, vol. 2 (Washington, D.C.: American Society for Microbiology, 1987), pp. 1 190-1219; ATCC Deposit No. 27,325) and derivatives thereof, including strain 33D3 having genotype W31 10 AfhuA (AtonA) ptr3 lac Iq lacL8 AompTA(nmpc-fepE) degP41 kanR (U.S. Pat. No. 5,639,635). Other strains and derivatives thereof, such as *E coli* 294 (ATCC 31,446), *E coli* B, *E coli*x 1776 (ATCC 31,537) and *E coli* RV308 (ATCC 31,608) are also suitable. In one embodiment, *E coli* Alpp finds particular use. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Polypeptide Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one embodiment of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment of the invention, antigen binding polypeptides (such as, for example, an antibody) production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To minimize proteolysis of expressed antigen binding polypeptides (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), Proc. Natl. Acad. Sci. USA 95:2773-2777; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention. In a second embodiment, the E. coli strain is deficient for a lipoprotein of the outer membrane (Δlpp).

iii. Antigen Binding Polypeptide Purification

In one embodiment, the antigen binding complex (e.g., a tetravalent antigen binding complex having agonist activity) of the present disclosure or a subunit thereof produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one embodiment, Protein A immobilized on a solid phase is used for immunoaffinity purification of, for example, antigen binding polypeptides of the invention. Protein A is a 41 kD cell wall protein from Staphylococcus aureus which binds with a high affinity to the Fc region of antigen binding polypeptides. Lindmark et al. (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antigen binding polypeptide of interest to Protein A. The solid phase is then washed to remove contaminants non-specifically bound to the solid phase. The antigen binding polypeptide (such as, for example, an antibody) is recovered from the solid phase by elution.

b. Generating Antigen Binding Polypeptides Using Eukaryotic Host Cells

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired antigen binding polypeptide(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-1 and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired Fc-containing polypeptide(s) (e.g., antibody) nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

For production of Fc-containing polypeptide(s) (such as, for example, an antibody) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a Hind 111 E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding an antigen binding polypeptide(s) (such as, for example, an antibody) by higher eukaryotes can be increased by inserting an enhancer sequence into the vector. Many enhancer sequences are now known from mammalian genes (e.g., globin, elastase, albumin, a-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR ($CH_1$)$_x$ Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N. Y. Acad. Sci. 383:44-68 (1982)); MRC 5 cells; FS4 cells; and a human hepatoma line (Hep G2).

Host cells are transformed with the above-described expression or cloning vectors for desired antigen binding polypeptide(s) (such as, for example, an antibody) production and cultured in conventional nutrient media modified as appropriate for inducing promoters, selecting transformants, or amplifying the genes encoding the desired sequences.

viii. Culturing the Host Cells

The host cells used to produce a desired antigen binding complex (e.g., a tetravalent antigen binding complex having agonist activity) of the present disclosure or a subunit thereof may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or U.S. Pat. No. 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Antigen Binding Polypeptides

When using recombinant techniques, the antigen binding complexes (e.g., a tetravalent antigen binding complex having agonist activity) of the present disclosure or subunit(s) thereof can be produced intracellularly, or directly secreted into the medium. If the polypeptide is produced intracellularly, as a first step, the particulate debris, either host cells or lysed fragments, are removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the polypeptide(s) of interest and contaminants may be subjected to low pH hydrophobic interaction chromatography using an elution buffer at a pH between about 2.5-4.5, preferably performed at low salt concentrations (e.g., from about 0-0.25M salt). The production of the antigen binding polypeptides can alternatively or additionally (to any of the foregoing particular methods) comprise dialyzing a solution comprising a mixture of the polypeptides.

x. Antigen Binding Polypeptide Production Using Baculovirus

Recombinant baculovirus may be generated by co-transfecting a plasmid encoding an antigen binding polypeptide and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antigen binding polypeptide sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antigen binding polypeptide may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antigen binding polypeptide can then be purified, for example, by Ni2+-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaI; 10% glycerol pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted His10-tagged antigen binding polypeptide are pooled and dialyzed against loading buffer.

Alternatively, purification of the antigen binding polypeptide can be performed using known chromatography techniques, including for instance, Protein A or protein G column chromatography. In one embodiment, the antigen binding polypeptide of interest may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available.

THIOMAB™ antibodies are full length antibodies that include native cysteine residues that form disulfide bonds within the antibody. Accordingly, these native cysteine residues do not have any reactive thiol groups to conjugate with drug-maleimide (unless treated with a reducing agent). Hence, the newly engineered Cys residue, can remain unpaired, and able to react with, i.e. conjugate to, an electrophilic linker reagent or drug-linker intermediate, such as a drug-maleimide.

Thiol reactivity may also be generalized to certain domains of an antibody, such as the light chain constant domain (CL) and heavy chain constant domains, CH1, CH2 and CH3. Cysteine replacements resulting in thiol reactivity values of about 0.1, 0.2, 0.3, 0.4, 0.5, 0.6, 0.7, 0.8, 0.9, and 0.95 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2.

Target Molecules & Methods of Use

The antigen binding complexes (e.g., a tetravalent antigen binding complex having agonist activity) of the present disclosure or subunit(s) thereof can be used to interact with a target to activate a signal transduction pathway. In certain embodiments, the target can be any target that activates, initiates, modulates and/or regulates a signal transduction pathway. Examples of molecules that may be targeted by an antigen binding polypeptide or an antigen binding complex as described herein include, but are not limited to, cell surface receptors. In certain embodiments, the cell surface receptor may be a receptor that oligomerizes, e.g. dimerizes (homodimerizes or heterodimerizes), by combining with the ligand and thereby transduce a signal into cells.

In certain embodiments, the target can be any target that oligomerizes, e.g., upon interaction with its ligand, to activate a signal transduction pathway. In certain embodiments, the target can be a multimeric receptor. The term "multimeric receptor," as used herein, refers to a receptor that requires the oligomerization of two or more, three or more, four or more, five or more or six or more receptors, e.g., of the same type and/or from the same family, for signaling activity. See, e.g., Heidin (1995) Cell 80:213-223.

In certain embodiments, the target receptor can be "dimeric" and require oligomerization of two receptors for activity. Non-limiting examples of dimeric receptors include neurotrophic receptors, nerve growth factors, growth factors, serine/threonine kinase receptors and receptor tyrosine kinases (RTKs). See, e.g., Li and Hristova (2010) Cell Adhesion and Migration 4(2):249-254.

In certain embodiments, the target receptor can be "trimeric" and require oligomerization of three receptors for activity. Non-limiting examples of trimeric receptors include Tumor necrosis factor receptors (TNFRs). See, e.g., Brazil (2006) Nature Reviews Drug Discovery 5:20.

In certain embodiments, the target can be any target that results in "agonism," as defined above, when interacting with an antigen binding polypeptide or antigen binding complex of the present disclosure, wherein the agonism is enhanced over the monomeric parental antibody.

Cell surface receptors include, for example, receptors that belong to receptor families such as the hematopoietic factor receptor family, cytokine receptor family, tyrosine kinase receptor family, serine/threonine kinase receptor family, TNF receptor family, G protein-coupled receptor (GPCR) family, GPI-anchored receptor family, tyrosine phosphatase receptor family, adhesion factor family, and hormone receptor family Various references that relate to receptors belonging to these receptor families and their characteristics are available and include, for example, Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim Biophys. Acta, 1422: 207-234; and M. Miyasaka ed., Cell Technology, supplementary volume, Handbook series, "Handbook for Adhesion Factors" (1994) (Shujunsha, Tokyo, Japan).

In certain embodiments, cell surface receptors include, for example, hormone receptors and cytokine receptors. An exemplary hormone receptor includes, for example, estrogen receptor. Exemplary cytokine receptors include, for example, hematopoietic factor receptor, lymphokine receptor, growth factor receptor, differentiation control factor receptor and the like. Examples of cytokine receptors are erythropoietin (EPO) receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor. Additional non-limiting examples of cytokine receptors are disclosed in Wang et al. (2009) Ann. Rev. Immunol. 27:29-60.

In certain embodiments, the target can include members of the tumor necrosis factor receptor (TNFR) family Non-limiting examples of TNFRs include TNFR1, TNFR2, lymphotoxin 13 receptor, OX40, CD40, Fas, decoy receptor 3, CD27, CD70, CD226, CD137, ICOS, 2B4, CD30, 4-1BB, death receptor 3 (DR3), death receptor 4 (DR4), death receptor 5 (DR5), death receptor 6 (DR6), decoy receptor 1, decoy receptor 2, receptor activator of NF-kappa B (RANK), osteoprotegerin (OPG), TWEAK receptor, TACI, BAFF receptor (BAFF-R), HVEM (herpes virus entry mediator, nerve growth factor receptor, B cell maturation antigen (BCMA), glucocorticoid-induced TNF receptor (GITR), toxicity and JNK inducer (TAJ), RELT, TNFRSF22, TNFRSF23, ectodysplasin A2 isoform receptor and ectodysplasin 1, anhidrotic receptor. Additional non-limiting examples of TNFRs are disclosed in Naismith and Sprang (1998) Trends in Biochemical Sciences 23(2):74-79.

In certain embodiments, the target can include members of the low density lipoprotein receptor (LDLR) family Non-limiting examples of LDLRs include LDLR, Low-density lipoprotein receptor-related protein (LRP)1, LRP10, LRP1B, LRP2, LRP4, LRP5, LRP5L, LRP6, LRP8, Nidogen (NID)-1, NID2, Sortilin-related receptor, L (SORL1) and Very-low-density-lipoprotein receptor (VLDLR).

In certain embodiments, the target can include members of the receptor tyrosine kinases (RTK) family Non-limiting examples of RTKs include Leukocyte receptor tyrosine kinase (LTK), Receptor tyrosine kinase-like orphan receptors (RORs), Ephrin receptors (Ephs), Trk receptor, insulin receptor (IR) and Tie2. Additional non-limiting examples of RTKs are disclosed in Alexander et al. (2013) The Concise Guide to Pharmacology 2013/14: Enzymes. Br. J. Pharmacol. 170: 1797-1867; Li and Hristova (2010); and Lemmon and Schlessinger (2010) Cell 141(7):1117-1134.

In other embodiments, the cell surface receptor may be a growth hormone receptor, an insulin receptor, a leptin receptor, a Flt-3 ligand receptor, or an insulin-like growth factor (IGF)-I receptor. Exemplary receptors include, for example, hEPOR (Simon, S. et al. (1990) Blood 76, 31-3); mEPOR (D'Andrea, A D. et al. (1989) Cell 57, 277-285); hG-CSFR (Fukunaga, R. et al. (1990) Proc. Natl. Acad. Sci. USA. 87, 8702-8706); mG-CSFR (Fukunaga, R. et al. (1990) Cell 61, 341-350); hTPOR (Vigon, I. et al. (1992) 89, 5640-5644); mTPOR (Skoda, R C. et al. (1993) 12, 2645-2653); hInsR (Ullrich, A. et al. (1985) Nature 313, 756-761); hFlt-3 (Small, D. et al. (1994) Proc. Natl. Acad. Sci. USA. 91, 459-463); hPDGFR (Gronwald, R G K. et al. (1988) Proc. Natl. Acad. Sci. USA. 85, 3435-3439); hIFNa/b R (Uze, G. et al. (1990) Cell 60, 225-234; and Novick, D. et al. (1994) Cell 77, 391-400).

In certain embodiments, the target can include members of the nerve growth factor receptor family and/or the neurotrophin receptor family Non-limiting examples of nerve growth factor receptors and neurotrophin receptors include p75 (also referred to as low affinity nerve growth factor receptor (LNGFR)), TrkA, TrkB and TrkC. Additional non-limiting examples of nerve growth factor receptors and neurotrophin receptors are disclosed in Lotz et al. (1996) J. of Leukocyte Biology 60(1):1-7.

In certain embodiments, the target can include members of the growth factor receptor family. For example, and not by way of limitation, a growth factor receptor can be a receptor that signals through the JAK/STAT, MAP kinase and PI3 kinase pathways. Non-limiting examples of growth factor receptors include fibroblast growth factor receptors (FGFRs), ErbB family of receptors (e.g., epidermal growth factor receptor (EGFR)), vascular endothelial growth factor receptors (VEGFR) and Platelet-derived growth factor receptors (PDGFRs).

In certain embodiments, the target can include receptors that form heterodimers or heterotrimers to induce a cell signal. For example, and not by way of limitation, the target can be a member of the serine/threonine kinase receptor family Non-limiting examples of serine/threonine kinase receptors include activin A receptor type II-like I (ALK1), activin A receptor, type I (ALK2), bone morphogenetic protein receptor, type IA (BMPR1A), activin A receptor, type IB (ALK4), activin A receptor, type IC (ALK7), transforming growth factor, beta receptor 1 (TGFBR1), bone morphogenetic protein receptor, type IB (BMPR1B), transforming growth factor, beta receptor II (TGFBR2), bone morphogenetic protein receptor, type II (BMPR2), anti-Mullerian hormone receptor, type II (MISR2), activin A receptor, type HA (ActR2), activin A receptor, type JIB (ActR2B) and transforming growth factor, beta receptor III (TGFBR3).

In certain embodiments, potential targets exclude the following: 5T4; ADAM-10; ADAM-12; ADAM 17; AFP; AXL; ANGPT2 anthrax antigen; BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNM B; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM 1; IFNA1; IFNA1; IFNB1 bispecific; IgE Fc; IGF1R; IGHE connecting region; IL12B; IL13; IL15; IL17A; ILIA; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolyaccharide LPS; LTA; MET; MM P14; MMp15; MST1R; MSTN; MUC1; MUC4; MUC16; MUC5AC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS Oil; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; TF; TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; and Vimentin.

In an exemplary embodiment, the cell surface receptor is OX40.

In another exemplary embodiment, the cell surface receptor is DR5.

In another exemplary embodiment, the cell surface receptor is GITR.

In another exemplary embodiment, the cell surface receptor is CD27.

In another exemplary embodiment, the cell surface receptor is CD137.

In another exemplary embodiment, the cell surface receptor is Tie2.

In certain embodiments, the antigen binding polypeptides or antigen binding complexes described herein may be used for agonizing a cell surface receptor in a subject comprising administering to the subject the complex or the antigen binding polypeptide described herein.

In certain embodiments, the antigen binding complexes (e.g., a tetravalent antigen binding complex having agonist activity) of the present disclosure or subunit(s) thereof described herein may be used for treating or preventing various diseases or disorders that would benefit from receptor agonism, including, for example, tumors, including pre-cancerous, non-metastatic, metastatic, and cancerous tumors (e.g., early stage cancer), cancers, allergic or inflammatory disorders, autoimmune disease, hormone disorders, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease. In some embodiments, the cancer is Urothelial carcinoma (uBC), melanoma, non-small cell lung cancer (NSCLC), triple-negative breast cancer (TNBC), renal, or bladder cancer.

In certain embodiments, the target can include a cell surface receptor expressed in the eye. Without wishing to be bound to theory, it is thought that the antigen binding complexes described herein may be beneficial in ocular therapies due to, e.g., their enhanced agonism for cell surface receptors and/or their increased size (e.g., as compared to a typical monoclonal antibody), which results in a longer-acting therapeutic. Exemplary ocular targets include, without limitation, an epithelial growth factor (EGF) receptor, a vascular endothelial growth factor (VEGF) receptor, Tie2, and a fibroblast growth factor receptor. Ocular targets are discussed in greater detail in Rodrigues, E. B. et al. (2009) *Prog. Retin. Eye Res.* 28:117-44.

In certain embodiments, the target can include a cell surface receptor expressed on a cancer or other malignant cell used for targeting an antibody-drug conjugate (ADC). Without wishing to be bound to theory, it is thought that the antigen binding complexes described herein may be beneficial for use as ADCs by targeting a receptor and promoting cellular internalization, thereby delivering a therapeutic compound of interest. Generally, ADCs target a cell surface antigen expressed by a cancer cell or target of a cancer therapeutic. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antigen binding complex is capable of binding may be a member of a subset of one of the above-mentioned categories, wherein the other subset(s) of said category comprise other molecules/antigens that have a distinct characteristic (with respect to the antigen of interest). Exemplary targets for ADCs include, without limitation, HER2, MUC16, STEAP1, NAPI2B, LY6E, B7H4, CD79B, and CD22.

An exemplary embodiment of an antibody-drug conjugate (ADC) compound comprises an antigen binding complex (Ab), and a drug moiety (D) wherein the complex is attached by a linker moiety (L) to D; the composition having Formula I:

$$Ab\text{-}(L\text{-}D)_p \qquad I$$

where p is 1, 2, 3, or 4. Drug moieties may be attached to a complex of the present disclosure, e.g., using a cysteine engineered antibody with a free engineered cysteine.

The ADC compounds of the invention include those with utility for anticancer activity. In particular, the compounds include a complex conjugated, i.e. covalently attached by a linker, to a drug moiety, i.e. toxin. When the drug is not conjugated to an antibody, the drug has a cytotoxic or cytostatic effect. The biological activity of the drug moiety is thus modulated by conjugation to an antigen binding complex. The antibody-drug conjugates (ADC) of the invention selectively deliver an effective dose of a cytotoxic agent to tumor tissue whereby greater selectivity, i.e. a lower efficacious dose, may be achieved.

The drug moiety (D) of the antibody-drug conjugates (ADC) includes any compound, moiety or group which has a cytotoxic or cytostatic effect. Drug moieties include: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, a pyrrolobenzodiazepine (PBD), a 1-(Chloromethyl)-2,3-dihydro-1H-benzo[e]indole (CBI) dimer, a CBI-PBD heterodimer, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions.

Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2OR$)(U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701, 5,770,710; 5,773,001; 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al Cancer Research 53:3336-3342 (1993), Lode et al Cancer Research 58:2925-2928 (1998).

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

In some embodiments, the immunoconjugate comprises an antigen binding complex conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, an ADC comprises anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

In some embodiments, the immunoconjugate comprises an antigen binding complex conjugated to one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. In some embodiments, the one or more amatoxin molecules are one or more α-amanitin molecules.

Other drug moieties include protein toxins such as: diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes (WO 93/21232).

In certain embodiments, the antigen binding complex is bispecific, and the targets can include a cell surface receptor expressed on a cancer or other malignant cell and a cell surface receptor expressed by an immune cell, such as a T cell (e.g., a T cell dependent bispecific complex or TDB). Without wishing to be bound to theory, it is thought that the antigen binding complexes described herein may be beneficial for use as TDBs, e.g., due to their improved avidity, which can lead to greater cellular selectivity and/or therapeutic index.

Exemplary T cell-expressed targets include, without limitation, CD3. CD3 (cluster of differentiation 3) T-cell co-receptor is a protein complex and is composed of four distinct chains. In mammals, the complex contains a CD3γ chain, a CD3δ chain, and two CD3E chains. These chains associate with the T-cell receptor (TCR) and the ζ-chain to generate an activation signal in T lymphocytes. The TCR, ζ-chain, and CD3 molecules together form the TCR complex. The term "CD3" as used herein, refers to any native CD3 from any human source. The term encompasses "full-length" and unprocessed protein as well as any form of the protein or one or more of the CD3 chains (polypeptides) that result from processing in the cell (e.g., mature polypeptides). The term also encompasses naturally occurring variants and isoforms of CD3, e.g., splice variants or allelic variants. For example, descriptions of CD3γ chain, CD3δ chain, and CD3ε chains and sequences are provided at www.uniprot.org/uniprot/P04234, www.uniprot.org/uniprot/P07766, and www.uniprot.org/uniprot/P09693.

In some embodiments, the bispecific complex binds to a human CD3 epsilon (CD3ε) polypeptide. In some embodiments, the bispecific complex binds to a human CD3 epsilon polypeptide in native T-cell receptor (TCR) complex in association with other TCR subunits. In some embodiments, the bispecific complex binds to a human CD3 gamma (CD3γ) polypeptide. In some embodiments, the bispecific complex binds a human CD3 gamma polypeptide in native T-cell receptor (TCR) complex in association with other TCR subunits.

Assays are known for identifying anti-CD3 antibodies thereof having biological activity. Biological activity may include, for example, binding to a CD3 polypeptide (e.g., CD3 on the surface of a T cell), or a peptide fragment thereof, either in vivo, in vitro, or ex vivo. In the case of a multispecific (e.g., bispecific) antigen binding complex of the invention (e.g., a TDB antibody having one anti-cancer antigen arm and another arm that recognizes a CD3 polypeptide), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing HER2 on their cell surfaces), and/or target cell killing. Antibodies having such biological activity in vivo and/or in vitro are provided. In certain embodiments, a complex of the present disclosure is tested for such biological activity.

In certain embodiments, the target can include a cell surface receptor expressed on a cell of the blood-brain barrier (BBB). Without wishing to be bound to theory, it is thought that the antigen binding complexes described herein may be beneficial for use in transporting a therapeutic (e.g., a therapeutic compound, or a bispecific antigen binding complex with specificity for target of interest and a component of the BBB) across the BBB, e.g., for treatment of a disorder or disease of the brain due to their potential for receptor-mediated uptake. Exemplary targets expressed by cells of the BBB include, without limitation, the transferrin receptor, the insulin-like growth factor receptor, the insulin receptor, low density lipoprotein receptor-related proteins 1 and 2, and the diphtheria toxin receptor. Further description of BBB targeting of therapeutics may be found, e.g., in Jones, A. R. and Shusta, E. V. (2007) *Pharm. Res.* 24:1759-71.

Uses of OX40 Agonists

In certain embodiments, an antigen binding complex (e.g., a tetravalent antigen binding complex having agonist activity) of the present disclosure that binds to OX40 as described herein may be used for enhancing an immune response, treating cancer, preventing cancer, enhancing efficacy of other cancer therapy, enhancing vaccine efficacy, treating a viral or bacterial disease or disorder, or modulating a T cell response in a subject.

In one aspect, provided is a method for enhancing immune function (e.g., by upregulating cell-mediated immune responses) in an individual having cancer comprising administering to the individual an effective amount of an antigen binding complex (e.g., a tetravalent antigen binding complex having agonist activity) that binds to OX40 as described herein. In one aspect, provided is a method for enhancing T cell function in an individual having cancer comprising administering to the individual an effective amount of an antigen binding complex (e.g., a tetravalent antigen binding complex having agonist activity) that binds to OX40 as described herein.

In some embodiments, "enhancing T cell function" includes inducing, causing or stimulating an effector or memory T cell to have a renewed, sustained or amplified biological function. Examples of enhancing T-cell function include: increased secretion of γ-interferon from CD8+ effector T cells, increased secretion of γ-interferon from CD4+ memory and/or effector T-cells, increased proliferation of CD4+ effector and/or memory T cells, increased proliferation of CD8+ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

In one aspect, provided is a method for enhancing immune function (e.g., by reducing immune dysfunction and/or a dysfunctional immune response or immune cell) in an individual having cancer comprising administering to the individual an effective amount of an antigen binding complex (e.g., a tetravalent antigen binding complex having agonist activity) that binds to OX40 as described herein. In some embodiments, "dysfunction" in the context of immune dysfunction refers to a state of reduced immune responsiveness to antigenic stimulation. In some embodiments, "dysfunctional" also includes refractory or unresponsive to antigen recognition, specifically, impaired capacity to translate antigen recognition into downstream T-cell effector functions, such as proliferation, cytokine production (e.g., gamma interferon) and/or target cell killing.

In one aspect, provided is a method for treating tumor immunity and/or enhancing tumor immunogenicity in an individual having cancer comprising administering to the individual an effective amount of an antigen binding complex (e.g., a tetravalent antigen binding complex having agonist activity) that binds to OX40 as described herein. In some embodiments, "tumor immunity" refers to the process in which tumors evade immune recognition and clearance. Thus, in some embodiments, as a therapeutic concept, tumor immunity is "treated" when such evasion is attenuated, and the tumors are recognized and attacked by the immune system. Examples of tumor recognition include tumor binding, tumor shrinkage and tumor clearance. In some embodiments, "immunogenicity" refers to the ability of a particular substance to provoke an immune response. Tumors are immunogenic and enhancing tumor immunogenicity aids in the clearance of the tumor cells by the immune response.

In some embodiments, an antigen binding complex (e.g., a tetravalent antigen binding complex having agonist activity) that binds to OX40 as described herein enhances CD4+ effector T cell function, for example, by increasing CD4+ effector T cell proliferation and/or increasing gamma interferon production by the CD4+ effector T cell (for example, as compared to proliferation and/or cytokine production prior to treatment with an agonist antigen binding complex that binds to OX40). In some embodiments, the cytokine is gamma interferon. In some embodiments, an antigen binding complex (e.g., a tetravalent antigen binding complex having agonist activity) that binds to OX40 as described herein increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with an agonist antigen binding complex that binds to OX40. In some embodiments, an antigen binding complex (e.g., a tetravalent antigen binding complex having agonist activity) that binds to OX40 as described herein increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with an agonist antigen binding complex that binds to OX40.

In some embodiments, an antigen binding complex (e.g., a tetravalent antigen binding complex having agonist activity) that binds to OX40 as described herein increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist antibody. In some embodiments, an antigen binding complex (e.g., a tetravalent antigen binding complex having agonist activity) that binds to OX40 as described herein increases the number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with an agonist antigen binding complex that binds to OX40.

In some embodiments, an antigen binding complex (e.g., a tetravalent antigen binding complex having agonist activity) that binds to OX40 as described herein enhances memory T cell function, for example by increasing memory T cell proliferation and/or increasing cytokine production by the memory cell. In some embodiments, the cytokine is gamma interferon.

In some embodiments, an antigen binding complex (e.g., a tetravalent antigen binding complex having agonist activity) that binds to OX40 as described herein inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the anti-human OX40 agonist antigen binding complex reduces the number of intratumoral (infiltrating) Treg (e.g., total number of Treg or e.g., percentage of Fox3p+ cells in CD4+ cells).

In one embodiment, the present disclosure provides methods for enhancing an immune response in a mammal, comprising administering to the mammal a therapeutically effective amount of an antigen binding complex (e.g., a tetravalent antigen binding complex having agonist activity) that binds to OX40. In certain embodiments, the methods involve stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or an animal not treated using the claimed methods. In one embodiment, the method enhances a cellular immune response, particularly a cytotoxic T cell response. In another embodiment, the cellular immune response is a T helper cell response. In still another embodiment, the immune response is a cytokine production, particularly IL-2 production.

In another embodiment, the present disclosure provides method of treating cancer in a mammal, comprising administering to the mammal a therapeutically effective amount of an antigen binding complex (e.g., a tetravalent antigen binding complex having agonist activity) that binds to OX40. In certain embodiments, the methods involve causing a desirable or beneficial effect in a mammal diagnosed with a cancer. The desirable or beneficial effect may include inhibition of further growth or spread of cancer cells, death of cancer cells, inhibition of reoccurrence of cancer, reduction of pain associated with the cancer, or improved survival of the animal. Inhibition of reoccurrence of cancer contemplates cancer sites and surrounding tissue which have previously been treated by radiation, chemotherapy, surgery, or other techniques. The effect can be either subjective or objective. For example, if the animal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

In one embodiment, the present disclosure provides methods for preventing cancer in a mammal, comprising administering to the mammal a therapeutically effective amount of an antigen binding complex (e.g., a tetravalent antigen binding complex having agonist activity) that binds to OX40. In certain embodiments, the method involves delaying, inhibiting, or preventing the onset of a cancer in a mammal in which the onset of oncogenesis or tumorigenesis is not evidenced but a predisposition for cancer is identified whether determined by genetic screening or otherwise. The term also encompasses treating a mammal having premalignant conditions to stop the progression of, or cause regression of, the premalignant conditions towards malignancy. Examples of premalignant conditions include hyperplasia, dysplasia, and metaplasia.

In certain embodiments, cancers that are amenable to treatment by the antigen binding complexes (e.g., a tetravalent antigen binding complex having agonist activity) that bind to OX40 as described herein include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: non-small cell lung cancer, glioblastoma, neuroblastoma, melanoma, breast carcinoma (e.g. triple-negative breast cancer), gastric cancer, colorectal cancer (CRC), and hepatocellular carcinoma. Yet, in some embodiments, the cancer is selected from: non-small cell lung cancer, colorectal cancer, glioblastoma and breast carcinoma (e.g. triple-negative breast cancer), including metastatic forms of those cancers. In some embodiments, the cancer is Urothelial carcinoma (uBC), melanoma, non-small cell lung cancer (NSCLC), triple-negative breast cancer (TNBC), renal, or bladder cancer.

In some embodiments, examples of cancer further include, but are not limited to, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone—MALT lymphoma, nodal marginal zone lymphoma, hairy cell leukemia, plasmacytoma and/or plasma cell myeloma, low grade/ follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

In some embodiments of any of the methods, the cancer is a B-cell proliferative disorder. In some embodiments, the B-cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma.

In some embodiments of any of the methods of the invention, the cancer displays human effector cells (e.g., is infiltrated by human effector cells). Methods for detecting human effector cells are well known in the art, including, e.g., by IHC. In some embodiments, the cancer display high levels of human effector cells. In some embodiments, human effector cells are one or more of NK cells, macrophages, monocytes. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

Antigen binding complexes (e.g., a tetravalent antigen binding complex having agonist activity) described herein can be used either alone or in combination with other agents in a therapy. For instance, an antigen binding complex (e.g., a tetravalent antigen binding complex having agonist activity) described herein may be co-administered with at least one additional therapeutic agent.

Such combination therapies noted above encompass combined administration (where two or more therapeutic agents are included in the same or separate formulations), and separate administration, in which case, administration of the antigen binding polypeptide (e.g., antibody) or complex described herein can occur prior to, simultaneously, and/or following, administration of the additional therapeutic agent or agents. In one embodiment, administration of the antigen binding polypeptide (e.g., antibody) or complex described herein and administration of an additional therapeutic agent occur within about one month, or within about one, two or three weeks, or within about one, two, three, four, five, or six days, of each other. Antigen binding polypeptides (e.g., antibodies) or complexes described herein can also be used in combination with radiation therapy.

In some embodiments, an antigen binding polypeptide (e.g., antibody) or complex described herein may be administered in conjunction with a chemotherapy or chemotherapeutic agent. In some embodiments, an antigen binding polypeptide (e.g., antibody) or complex described herein may be administered in conjunction with a radiation therapy or radiotherapeutic agent. In some embodiments, an antigen binding polypeptide (e.g., antibody) or complex described herein may be administered in conjunction with a targeted therapy or targeted therapeutic agent. In some embodiments, an antigen binding polypeptide (e.g., antibody) or complex described herein may be administered in conjunction with an immunotherapy or immunotherapeutic agent, for example a monoclonal antibody.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PM-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PM-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PM 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., At211, I131, I125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In some embodiments, an antigen binding polypeptide (e.g., antibody) or complex described herein may be administered in conjunction with a PARP inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE), amrubicine, carfilzomib, pralatrexate, and/or enzastaurin.

In some embodiments, an antigen binding polypeptide (e.g., antibody) or complex described herein may be administered in conjunction with a PD-1 axis binding antagonist.

A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO), Merck 3475 (MK-3475, pembrolizumab, KEYTRUDA), CT-011 (Pidilizumab), MEDI-0680 (AMP-514), PDR001, REGN2810, BGB-108, and BGB-A317. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A (atezolizumab), MEDI4736 (durvalumab), MDX-1105, and MSB0010718C (avelumab). MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1 106-04, ONO-4538, BMS-936558 or nivolumab. In some embodiments, the anti-PD-1 antibody is nivolumab (CAS Registry Number: 946414-94-4).

In some embodiments, an antigen binding polypeptide (e.g., antibody) or complex described herein may be administered in conjunction with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an antigen binding polypeptide (e.g., antibody) or complex described herein may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In some embodiments, an antigen binding polypeptide (e.g., antibody) or complex described herein may be administered in conjunction with an antagonist directed against CTLA-4 (also known as CD152), e.g., a blocking antibody. In some embodiments, an antigen binding polypeptide (e.g., antibody) or complex described herein may be administered in conjunction with ipilimumab (also known as MDX-010, MDX-101, or Yervoy®). In some embodiments, an antigen binding polypeptide (e.g., antibody) or complex described herein may be administered in conjunction with tremelimumab (also known as ticilimumab or CP-675,206). In some embodiments, an antigen binding polypeptide (e.g., antibody) or complex described herein may be administered in conjunction with an antagonist directed against B7-H3 (also known as CD276), e.g., a blocking antibody. In some embodiments, an antigen binding polypeptide (e.g., antibody) or complex described herein may be administered in conjunction with MGA271. In some embodiments, an antigen binding polypeptide (e.g., antibody) or complex described herein may be administered in conjunction with an antagonist directed against a TGF beta, e.g., metelimumab (also known as CAT-192), fresolimumab (also known as GC1008), or LY2157299.

In some embodiments, an antigen binding polypeptide (e.g., antibody) or complex described herein may be administered in conjunction with a treatment comprising adoptive transfer of a T cell (e.g., a cytotoxic T cell or CTL) expressing a chimeric antigen receptor (CAR). In some embodiments, an antigen binding polypeptide (e.g., antibody) or complex described herein may be administered in conjunction with UCART19. In some embodiments, an antigen binding polypeptide (e.g., antibody) or complex described herein may be administered in conjunction with WT128z. In some embodiments, an antigen binding polypeptide (e.g., antibody) or complex described herein may be administered in conjunction with KTE-C19 (Kite). In some embodiments, an antigen binding polypeptide (e.g., antibody) or complex described herein may be administered in conjunction with CTL019 (Novartis). In some embodiments, an antigen binding polypeptide (e.g., antibody) or complex described herein may be administered in conjunction with a treatment comprising adoptive transfer of a T cell comprising a dominant-negative TGF beta receptor, e.g, a dominant-negative TGF beta type II receptor. In some embodiments, an antigen binding polypeptide (e.g., antibody) or complex described herein may be administered in conjunction with a treatment comprising a HERCREEM protocol (see, e.g., ClinicalTrials.gov Identifier NCT00889954).

In some embodiments, an antigen binding polypeptide (e.g., antibody) or complex described herein may be administered in conjunction with an antagonist directed against CD19. In some embodiments, an antigen binding polypeptide (e.g., antibody) or complex described herein may be administered in conjunction with MOR00208. In some embodiments, an antigen binding polypeptide (e.g., antibody) or complex described herein may be administered in conjunction with an antagonist directed against CD38. In some embodiments, an antigen binding polypeptide (e.g., antibody) or complex described herein may be administered in conjunction with daratumumab.

In some embodiments, an antigen binding polypeptide (e.g., antibody) or complex described herein may be administered in conjunction with an agonist directed against CD137 (also known as TNFRSF9, 4-1BB, or ILA), e.g., an activating antibody. In some embodiments, an antigen binding polypeptide (e.g., antibody) or complex described herein may be administered in conjunction with urelumab (also known as BMS-663513). In some embodiments, an antigen binding polypeptide (e.g., antibody) or complex described herein may be administered in conjunction with an agonist directed against CD40, e.g., an activating antibody. In some embodiments, an antigen binding polypeptide (e.g., antibody) or complex described herein may be administered in conjunction with CP-870893. In some embodiments, an antigen binding polypeptide (e.g., antibody) or complex described herein may be administered in conjunction with an agonist directed against OX40 (also known as CD134), e.g., an activating antibody. In some embodiments, an antigen binding polypeptide (e.g., antibody) or complex described herein may be administered in conjunction with a different anti-OX40 antibody (e.g., AgonOX). In some embodiments, an antigen binding polypeptide (e.g., antibody) or complex described herein may be administered in conjunction with an agonist directed against CD27, e.g., an activating antibody. In some embodiments, an antigen binding polypeptide (e.g., antibody) or complex described herein may be administered in conjunction with CDX-1127. In some embodiments, an antigen binding polypeptide (e.g., antibody) or complex described herein may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, an antigen binding polypeptide (e.g., antibody) or complex described herein may be administered in conjunction with an agonist directed against CD137 (also known as TNFRSF9, 4-1BB, or ILA), e.g., an activating antibody. In some embodiments, an antigen binding polypeptide (e.g., antibody) or complex described herein may be administered in conjunction with urelumab (also known as BMS-663513). In some embodiments, an antigen binding polypeptide (e.g., antibody) or complex described herein may be administered in conjunction with an agonist directed against CD40, e.g., an activating antibody. In some embodiments, an antigen binding polypeptide (e.g., antibody) or complex described herein may be administered in conjunction with CP-870893 or R07009789. In some embodiments, an antigen binding polypeptide (e.g., antibody) or complex described herein may be administered in conjunction with an agonist directed against OX40 (also known as CD134), e.g., an activating antibody). In some embodiments, an antigen binding polypeptide (e.g., antibody) or complex described herein may be administered in conjunction with an agonist directed against CD27, e.g., an activating antibody. In some embodiments, an antigen binding polypeptide (e.g., antibody) or complex described herein may be administered in conjunction with CDX-1127 (also known as varlilumab). In some embodiments, an antigen binding polypeptide (e.g., antibody) or complex described herein may be administered in conjunction with an antagonist directed against indoleamine-2,3-dioxygenase (IDO). In some embodiments, with the IDO antagonist is 1-methyl-D-tryptophan (also known as 1-D-MT). In some embodiments, the IDO antagonist is an IDO antagonist shown in WO2010/005958 (the contents of which are expressly incorporated by record herein). In some embodiments the IDO antagonist is 4-({2-[(Aminosulfonyl)amino]ethyl}amino)-N-(3-bromo-4-fluorophenyl)-N'-hydroxy-1,2,5-oxadiazole-3-carboximidamide (e.g., as described in Example 23 of WO2010/005958). In some embodiments the IDO antagonist is

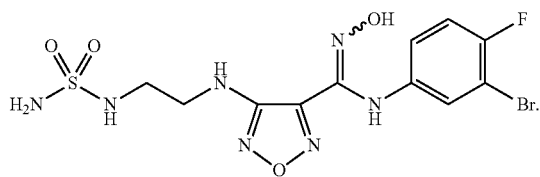 [SMILES: NS(=O)(=O)NCCNc1nonc1C(=NO)Nc1ccc(F)c(Br)c1]

In some embodiments, the IDO antagonist is INCB24360. In some embodiments, the IDO antagonist is Indoximod (the D isomer of 1-methyl-tryptophan). In some embodiments, an antigen binding polypeptide (e.g., antibody) or complex described herein may be administered in conjunction with an antibody-drug conjugate. In some embodiments, the antibody-drug conjugate comprises mertansine or monomethyl auristatin E (MMAE). In some embodiments, an antigen binding polypeptide (e.g., antibody) or complex described herein may be administered in conjunction with an anti-NaPi2b antibody-MMAE conjugate (also known as DNIB0600A, RG7599 or lifastuzumab vedotin). In some embodiments, an antigen binding polypeptide (e.g., antibody) or complex described herein may be administered in conjunction with trastuzumab emtansine (also known as T-DM1, ado-trastuzumab emtansine, or KADCYLA®, Genentech). In some embodiments, an antigen binding polypeptide (e.g., antibody) or complex described herein may be administered in conjunction with an anti-MUC16 antibody-MMAE conjugate, DMUC5754A. In some embodiments, an antigen binding polypeptide (e.g., antibody) or complex described herein may be administered in conjunction with an anti-MUC16 antibody-MMAE conjugate, DMUC4064A. In some embodiments, an antigen binding polypeptide (e.g., antibody) or complex described herein may be administered in conjunction with an antibody-drug conjugate targeting the endothelin B receptor (EDNBR), e.g., an antibody directed against EDNBR conjugated with MMAE. In some embodiments, an antigen binding polypeptide (e.g., antibody) or complex described herein may be administered in conjunction with an antibody-drug conjugate targeting the lymphocyte antigen 6 complex, locus E (Ly6E), e.g., an antibody directed against Ly6E conjugated with MMAE, (also known as DLYE5953A). In some embodiments, an antigen binding polypeptide (e.g., antibody) or complex described herein may be administered in conjunction with polatuzumab vedotin. In some embodiments, an antigen binding polypeptide (e.g., antibody) or complex described herein may be administered in conjunction with an antibody-drug conjugate targeting CD30. In some embodiments, an antigen binding polypeptide (e.g., antibody) or complex described herein may be administered in conjunction with ADCETRIS (also known as brentuximab vedotin). In some embodiments, an antigen binding polypeptide (e.g., antibody) or complex described herein may be administered in conjunction with polatuzumab vedotin.

In some embodiments, an antigen binding polypeptide (e.g., antibody) or complex described herein may be administered in conjunction with an angiogenesis inhibitor. In some embodiments, an antigen binding polypeptide (e.g., antibody) or complex described herein may be administered in conjunction with an antibody directed against a VEGF, e.g., VEGF-A. In some embodiments, an antigen binding polypeptide (e.g., antibody) or complex described herein may be administered in conjunction with bevacizumab (also known as AVASTIN®, Genentech). In some embodiments, an antigen binding polypeptide (e.g., antibody) or complex described herein may be administered in conjunction with an antibody directed against angiopoietin 2 (also known as Ang2). In some embodiments, an antigen binding polypeptide (e.g., antibody) or complex described herein may be administered in conjunction with MEDI3617. In some embodiments, an antigen binding polypeptide (e.g., antibody) or complex described herein may be administered in conjunction with an antibody directed against VEGFR2. In some embodiments, an antigen binding polypeptide (e.g., antibody) or complex described herein may be administered in conjunction with ramucirumab. In some embodiments, an antigen binding polypeptide (e.g., antibody) or complex described herein may be administered in conjunction with a VEGF Receptor fusion protein. In some embodiments, an antigen binding polypeptide (e.g., antibody) or complex described herein may be administered in conjunction with aflibercept. In some embodiments, an antigen binding polypeptide (e.g., antibody) or complex described herein may be administered in conjunction with ziv-aflibercept (also known as VEGF Trap or Zaltrap®). In some embodiments, an antigen binding polypeptide (e.g., antibody) or complex described herein may be administered in conjunction with a bispecific antibody directed against VEGF and Ang2. In some embodiments, an antigen binding polypeptide (e.g., antibody) or complex described herein may be administered in conjunction with RG7221 (also known as vanucizumab). In some embodiments, an antigen binding polypeptide (e.g., antibody) or complex described herein may be administered in conjunction with an angiogenesis inhibitor and in conjunction with a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antigen binding polypeptide (e.g., antibody) or complex described herein may be administered in conjunction with bevacizumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antigen binding polypeptide (e.g., antibody) or complex described herein may be administered in conjunction with bevacizumab and MDX-1106 (nivolumab, OPDIVO). In some embodiments, an antigen binding polypeptide (e.g., antibody) or complex described herein may be administered in conjunction with bevacizumab and Merck 3475 (MK-3475, pembrolizumab, KEYTRUDA). In some embodiments, an antigen binding polypeptide (e.g., antibody) or complex described herein may be administered in conjunction with bevacizumab and CT-011 (Pidilizumab). In some embodiments, an antigen binding polypeptide (e.g., antibody) or complex described herein may be administered in conjunction with bevacizumab and MEDI-0680 (AMP-514). In some embodiments, an antigen binding polypeptide (e.g., antibody) or complex described herein may be administered in conjunction with bevacizumab and PDR001. In some embodiments, an antigen binding polypeptide (e.g., antibody) or complex described herein may be administered in conjunction with bevacizumab and REGN2810. In some embodiments, an antigen binding polypeptide (e.g., antibody) or complex described herein may be administered in conjunction with bevacizumab and BGB-108. In some embodiments, an antigen binding polypeptide (e.g., antibody) or complex described herein may be administered in conjunction with bevacizumab and BGB-A317. In some embodiments, an antigen binding polypeptide (e.g., antibody) or complex described herein may be administered in conjunction with bevacizumab and YW243.55.S70. In some embodiments, an antigen binding polypeptide (e.g., antibody) or complex described herein may be administered in conjunction with bevacizumab and MPDL3280A. In some embodiments, an antigen binding polypeptide (e.g., antibody) or complex described herein may be administered in conjunction with bevacizumab and MEDI4736. In some embodiments, an antigen binding polypeptide (e.g., antibody) or complex described herein may be administered in conjunction with bevacizumab and MDX-1105. In some embodiments, an antigen binding polypeptide (e.g., antibody) or complex described herein may be administered in conjunction with bevacizumab and MSB0010718C (avelumab).

In some embodiments, an antigen binding polypeptide (e.g., antibody) or complex described herein may be administered in conjunction with an antineoplastic agent. In some embodiments, an antigen binding polypeptide (e.g., antibody) or complex described herein may be administered in conjunction with an agent targeting CSF-1R (also known as M-CSFR or CD115). In some embodiments, an antigen binding polypeptide (e.g., antibody) or complex described herein may be administered in conjunction with anti-CSF-1R antibody (also known as IMC-CS4 or LY3022855) In some embodiments, an antigen binding polypeptide (e.g., antibody) or complex described herein may be administered in conjunction with anti-CSF-1R antibody, RG7155 (also known as R05509554 or emactuzumab). In some embodiments, an antigen binding polypeptide (e.g., antibody) or complex described herein may be administered in conjunction with an interferon, for example interferon alpha or interferon gamma. In some embodiments, an antigen binding polypeptide (e.g., antibody) or complex described herein may be administered in conjunction with Roferon-A (also known as recombinant Interferon alpha-2a). In some embodiments, an antigen binding polypeptide (e.g., antibody) or complex described herein may be administered in conjunction with GM-CSF (also known as recombinant human granulocyte macrophage colony stimulating factor, rhu GM-CSF, sargramostim, or Leukine®). In some embodiments, an antigen binding polypeptide (e.g., antibody) or complex described herein may be administered in conjunction with IL-2 (also known as aldesleukin or Proleukin®). In some embodiments, an antigen binding polypeptide (e.g., antibody) or complex described herein may be administered in conjunction with IL-12. In some embodiments, an antigen binding polypeptide (e.g., antibody) or complex described herein may be administered in conjunction with IL27. In some embodiments, an antigen binding polypeptide (e.g., antibody) or complex described herein may be administered in conjunction with IL-15. In some embodiments, an antigen binding polypeptide (e.g., antibody) or complex described herein may be administered in conjunction with ALT-803. In some embodiments, an antigen binding polypeptide (e.g., antibody) or complex described herein may be administered in conjunction with an antibody targeting CD20. In some embodiments, the antibody targeting CD20 is obinutuzumab (also known as GA101 or Gazyva®) or rituximab. In some embodiments, an antigen binding polypeptide (e.g., antibody) or complex described herein may be administered in conjunction with an antibody targeting GITR. In some embodiments, the antibody targeting GITR is TRX518. In some embodiments, the antibody targeting GITR is MK04166 (Merck).

In some embodiments, an antigen binding polypeptide (e.g., antibody) or complex described herein may be administered in conjunction with an inhibitor of Bruton's tyrosine kinase (BTK). In some embodiments, an antigen binding polypeptide (e.g., antibody) or complex described herein may be administered in conjunction with ibrutinib. In some embodiments, an antigen binding polypeptide (e.g., antibody) or complex described herein may be administered in conjunction with an inhibitor of Isocitrate dehydrogenase 1 (IDH1) and/or Isocitrate dehydrogenase 2 (IDH2). In some embodiments, an antigen binding polypeptide (e.g., antibody) or complex described herein may be administered in conjunction with AG-120 (Agios).

In some embodiments, an antigen binding polypeptide (e.g., antibody) or complex described herein may be administered in conjunction with obinutuzumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody).

In some embodiments, an antigen binding polypeptide (e.g., antibody) or complex described herein may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an antigen binding polypeptide (e.g., antibody) or complex described herein may be administered in conjunction with an adjuvant. In some embodiments, an antigen binding polypeptide (e.g., antibody) or complex described herein may be administered in conjunction with a treatment comprising a TLR agonist, e.g., Poly-ICLC (also known as Hiltonol®), LPS, MPL, or CpG ODN. In some embodiments, an antigen binding polypeptide (e.g., antibody) or complex described herein may be administered in conjunction with tumor necrosis factor (TNF) alpha. In some embodiments, an antigen binding polypeptide (e.g., antibody) or complex described herein may be administered in conjunction with IL-1. In some embodiments, an antigen binding polypeptide (e.g., antibody) or complex described herein may be administered in conjunction with HMGB1. In some embodiments, an antigen binding polypeptide (e.g., antibody) or complex described herein may be administered in conjunction with an IL-10 antagonist. In some embodiments, an antigen binding polypeptide (e.g., antibody) or complex described herein may be administered in conjunction with an IL-4 antagonist. In some embodiments, an antigen binding polypeptide (e.g., antibody) or complex described herein may be administered in conjunction with an IL-13 antagonist. In some embodiments, an antigen binding polypeptide (e.g., antibody) or complex described herein may be administered in conjunction with an IL-17 antagonist. In some embodiments, an antigen binding polypeptide (e.g., antibody) or complex described herein may be administered in conjunction with an HVEM antagonist. In some embodiments, an antigen binding polypeptide (e.g., antibody) or complex described herein may be administered in conjunction with an ICOS agonist, e.g., by administration of ICOS-L, or an agonistic antibody directed against ICOS. In some embodiments, an antigen binding polypeptide (e.g., antibody) or complex described herein may be administered in conjunction with a treatment targeting CX3CL1. In some embodiments, an antigen binding polypeptide (e.g., antibody) or complex described herein may be administered in conjunction with a treatment targeting CXCL9. In some embodiments, an antigen binding polypeptide (e.g., antibody) or complex described herein may be administered in conjunction with a treatment targeting CXCL10. In some embodiments, an antigen binding polypeptide (e.g., antibody) or complex described herein may be administered in conjunction with a treatment targeting CCL5. In some embodiments, an antigen binding polypeptide (e.g., antibody) or complex described herein may be administered in conjunction with an LFA-1 or ICAM1 agonist. In some embodiments, an antigen binding polypeptide (e.g., antibody) or complex described herein may be administered in conjunction with a Selectin agonist.

In some embodiments, an antigen binding polypeptide (e.g., antibody) or complex described herein may be administered in conjunction with an inhibitor of B-Raf. In some embodiments, an antigen binding polypeptide (e.g., antibody) or complex described herein may be administered in conjunction with vemurafenib (also known as Zelboraf®). In some embodiments, an antigen binding polypeptide (e.g., antibody) or complex described herein may be administered in conjunction with dabrafenib (also known as Tafinlar®). In some embodiments, an antigen binding polypeptide (e.g., antibody) or complex described herein may be administered in conjunction with encorafenib (LGX818).

In some embodiments, an antigen binding polypeptide (e.g., antibody) or complex described herein may be administered in conjunction with an EGFR inhibitor. In some embodiments, an antigen binding polypeptide (e.g., antibody) or complex described herein may be administered in conjunction with erlotinib (also known as Tarceva®). In some embodiments, an antigen binding polypeptide (e.g., antibody) or complex described herein may be administered in conjunction with an inhibitor of EGFR-T790M. In some embodiments, an antigen binding polypeptide (e.g., antibody) or complex described herein may be administered in conjunction with gefitinib. In some embodiments, an antigen binding polypeptide (e.g., antibody) or complex described herein may be administered in conjunction with afatinib. In some embodiments, an antigen binding polypeptide (e.g., antibody) or complex described herein may be administered in conjunction with cetuximab (also known as Erbitux®). In some embodiments, an antigen binding polypeptide (e.g., antibody) or complex described herein may be administered in conjunction with panitumumab (also known as Vectibix®). In some embodiments, an antigen binding polypeptide (e.g., antibody) or complex described herein may be administered in conjunction with rociletinib. In some embodiments, an antigen binding polypeptide (e.g., antibody) or complex described herein may be administered in conjunction with AZD9291. In some embodiments, an antigen binding polypeptide (e.g., antibody) or complex described herein may be administered in conjunction with an inhibitor of a MEK, such as MEK1 (also known as MAP2K1) and/or MEK2 (also known as MAP2K2). In some embodiments, an antigen binding polypeptide (e.g., antibody) or complex described herein may be administered in conjunction with cobimetinib (also known as GDC-0973 or XL-518). In some embodiments, an antigen binding polypeptide (e.g., antibody) or complex described herein may be administered in conjunction with trametinib (also known as Mekinist®). In some embodiments, an antigen binding polypeptide (e.g., antibody) or complex described herein may be administered in conjunction with binimetinib.

In some embodiments, an antigen binding polypeptide (e.g., antibody) or complex described herein may be administered in conjunction an inhibitor of B-Raf (e.g., vemurafenib or dabrafenib) and an inhibitor of MEK (e.g., MEK1 and/or MEK2 (e.g., cobimetinib or trametinib). In some embodiments, an antigen binding polypeptide (e.g., antibody) or complex described herein may be administered in conjunction with an inhibitor of ERK (e.g., ERK1/2). In some embodiments, an antigen binding polypeptide (e.g., antibody) or complex described herein may be administered in conjunction with GDC-0994). In some embodiments, an antigen binding polypeptide (e.g., antibody) or complex described herein may be administered in conjunction with an inhibitor of B-Raf, an inhibitor of MEK, and an inhibitor of ERK1/2. In some embodiments, an antigen binding polypeptide (e.g., antibody) or complex described herein may be administered in conjunction with an inhibitor of EGFR, an inhibitor of MEK, and an inhibitor of ERK1/2. In some embodiments, an antigen binding polypeptide (e.g., antibody) or complex described herein may be administered in conjunction with one or more MAP kinase pathway inhibitor. In some embodiments, an antigen binding polypeptide (e.g., antibody) or complex described herein may be administered in conjunction with CK127. In some embodiments, an antigen binding polypeptide (e.g., antibody) or complex described herein may be administered in conjunction with an inhibitor of K-Ras.

In some embodiments, an antigen binding polypeptide (e.g., antibody) or complex described herein may be administered in conjunction with an inhibitor of c-Met. In some embodiments, an antigen binding polypeptide (e.g., antibody) or complex described herein may be administered in conjunction with onartuzumab (also known as MetMAb). In some embodiments, an antigen binding polypeptide (e.g., antibody) or complex described herein may be administered in conjunction with an inhibitor of anaplatic lymphoma kinase (ALK). In some embodiments, an antigen binding polypeptide (e.g., antibody) or complex described herein may be administered in conjunction with AF802 (also known as CH5424802 or alectinib). In some embodiments, an antigen binding polypeptide (e.g., antibody) or complex described herein may be administered in conjunction with crizotinib. In some embodiments, an antigen binding polypeptide (e.g., antibody) or complex described herein may be administered in conjunction with ceritinib. In some embodiments, an antigen binding polypeptide (e.g., antibody) or complex described herein may be administered in conjunction with an inhibitor of a phosphatidylinositol 3-kinase (PI3K). In some embodiments, an antigen binding polypeptide (e.g., antibody) or complex described herein may be administered in conjunction with buparlisib (BKM-120). In some embodiments, an antigen binding polypeptide (e.g., antibody) or complex described herein may be administered in conjunction with pictilisib (also known as GDC-0941). In some embodiments, an antigen binding polypeptide (e.g., antibody) or complex described herein may be administered in conjunction with buparlisib (also known as BKM-120). In some embodiments, an antigen binding polypeptide (e.g., antibody) or complex described herein may be administered in conjunction with perifosine (also known as KRX-0401). In some embodiments, an antigen binding polypeptide (e.g., antibody) or complex described herein may be administered in conjunction with a delta-selective inhibitor of a phosphatidylinositol 3-kinase (PI3K). In some embodiments, an antigen binding polypeptide (e.g., antibody) or complex described herein may be administered in conjunction with idelalisib (also known as GS-1101 or CAL-101). In some embodiments, an antigen binding polypeptide (e.g., antibody) or complex described herein may be administered in conjunction with taselisib (also known as GDC-0032). In some embodiments, an antigen binding polypeptide (e.g., antibody) or complex described herein may be administered in conjunction with BYL-719. In some embodiments, an antigen binding polypeptide (e.g., antibody) or complex described herein may be administered in conjunction with an inhibitor of an Akt. In some embodiments, an antigen binding polypeptide (e.g., antibody) or complex described herein may be administered in conjunction with MK2206. In some embodiments, an antigen binding polypeptide (e.g., antibody) or complex described herein may be administered in conjunction with GSK690693. In some embodiments, an antigen binding polypeptide (e.g., antibody) or complex described herein may be administered in conjunction with ipatasertib (also known as GDC-0068). In some embodiments, an antigen binding polypeptide (e.g., antibody) or complex described herein may be administered in conjunction with an inhibitor of mTOR. In some embodiments, an antigen binding polypeptide (e.g., antibody) or complex described herein may be administered in conjunction with sirolimus (also known as rapamycin). In some embodiments, an antigen binding polypeptide (e.g., antibody) or complex described herein may be administered in conjunction with temsirolimus (also known as CCI-779 or Torisel®). In some embodiments, an antigen binding polypeptide (e.g., antibody) or complex described herein may be administered in conjunction with everolimus (also known as RAD001). In some embodiments, an antigen binding polypeptide (e.g., antibody) or complex described herein may be administered in conjunction with ridaforolimus (also known as AP-23573, MK-8669, or deforolimus). In some embodiments, an antigen binding polypeptide (e.g., antibody) or complex described herein may be administered in conjunction with OSI-027. In some embodiments, an antigen binding polypeptide (e.g., antibody) or complex described herein may be administered in conjunction with AZD8055. In some embodiments, an antigen binding polypeptide (e.g., antibody) or complex described herein may be administered in conjunction with INK128. In some embodiments, an antigen binding polypeptide (e.g., antibody) or complex described herein may be administered in conjunction with a dual PI3K/mTOR inhibitor. In some embodiments, an antigen binding polypeptide (e.g., antibody) or complex described herein may be administered in conjunction with XL765. In some embodiments, an antigen binding polypeptide (e.g., antibody) or complex described herein may be administered in conjunction with GDC-0980. In some embodiments, an antigen binding polypeptide (e.g., antibody) or complex described herein may be administered in conjunction with BEZ235 (also known as NVP-BEZ235). In some embodiments, an antigen binding polypeptide (e.g., antibody) or complex described herein may be administered in conjunction with BGT226. In some embodiments, an antigen binding polypeptide (e.g., antibody) or complex described herein may be administered in conjunction with GSK2126458. In some embodiments, an antigen binding polypeptide (e.g., antibody) or complex described herein may be administered in conjunction with PF-04691502. In some embodiments, an antigen binding polypeptide (e.g., antibody) or complex described herein may be administered in conjunction with PF-05212384 (also known as PKI-587).

In some embodiments, an antigen binding polypeptide (e.g., antibody) or complex described herein may be administered in conjunction with an agent that selectively degrades the estrogen receptor. In some embodiments, an antigen binding polypeptide (e.g., antibody) or complex described herein may be administered in conjunction with GDC-0927. In some embodiments, an antigen binding polypeptide (e.g., antibody) or complex described herein may be administered in conjunction with an inhibitor of HER3. In some embodiments, an antigen binding polypeptide (e.g., antibody) or complex described herein may be administered in conjunction with duligotuzumab. In some embodiments, an antigen binding polypeptide (e.g., antibody) or complex described herein may be administered in conjunction with an inhibitor of LSD1. In some embodiments, an antigen binding polypeptide (e.g., antibody) or complex described herein may be administered in conjunction with an inhibitor of MDM2. In some embodiments, an antigen binding polypeptide (e.g., antibody) or complex described herein may be administered in conjunction with an inhibitor of BCL2. In some embodiments, an antigen binding polypeptide (e.g., antibody) or complex described herein may be administered in conjunction with venetoclax. In some embodiments, an antigen binding polypeptide (e.g., antibody) or complex described herein may be administered in conjunction with an inhibitor of CHK1. In some embodiments, an antigen binding polypeptide (e.g., antibody) or complex described herein may be administered in conjunction with GDC-0575. In some embodiments, an antigen binding polypeptide (e.g., antibody) or complex described herein may be administered in conjunction with an inhibitor of activated hedgehog signaling pathway. In some embodiments, an antigen binding polypeptide (e.g., antibody) or complex described herein may be administered in conjunction with ERIVEDGE.

In some embodiments, an antigen binding polypeptide (e.g., antibody) or complex described herein may be administered in conjunction with radiation therapy. In some embodiments, an antigen binding polypeptide (e.g., antibody) or complex described herein may be administered in conjunction with gemcitabine. In some embodiments, an antigen binding polypeptide (e.g., antibody) or complex described herein may be administered in conjunction with nab-paclitaxel (ABRAXANE). In some embodiments, an antigen binding polypeptide (e.g., antibody) or complex described herein may be administered in conjunction with trastuzumab. In some embodiments, an antigen binding polypeptide (e.g., antibody) or complex described herein may be administered in conjunction with TVEC. In some embodiments, an antigen binding polypeptide (e.g., antibody) or complex described herein may be administered in conjunction with IL27. In some embodiments, an antigen binding polypeptide (e.g., antibody) or complex described herein may be administered in conjunction with cyclophosphamide. In some embodiments, an antigen binding polypeptide (e.g., antibody) or complex described herein may be administered in conjunction with an agent that recruits T cells to the tumor. In some embodiments, an antigen binding polypeptide (e.g., antibody) or complex described herein may be administered in conjunction with lirilumab (IPH2102/BMS-986015). In some embodiments, an antigen binding polypeptide (e.g., antibody) or complex described herein may be administered in conjunction with Idelalisib. In some embodiments, an antigen binding polypeptide (e.g., antibody) or complex described herein may be administered in conjunction with an antibody that targets CD3 and CD20. In some embodiments, an antigen binding polypeptide (e.g., antibody) or complex described herein may be administered in conjunction with REGN1979. In some embodiments, an antigen binding polypeptide (e.g., antibody) or complex described herein may be administered in conjunction with an antibody that targets CD3 and CD19. In some embodiments, an antigen binding polypeptide (e.g., antibody) or complex described herein may be administered in conjunction with blinatumomab.

In some embodiments, an antigen binding polypeptide (e.g., antibody) or complex described herein may be administered in conjunction with an oncolytic virus. In some embodiments, an antigen binding polypeptide (e.g., antibody) or complex described herein may be administered in conjunction with carboplatin and nab-paclitaxel. In some embodiments, an antigen binding polypeptide (e.g., antibody) or complex described herein may be administered in conjunction with carboplatin and paclitaxel. In some embodiments, an antigen binding polypeptide (e.g., antibody) or complex described herein may be administered in conjunction with cisplatin and pemetrexed. In some embodiments, an antigen binding polypeptide (e.g., antibody) or complex described herein may be administered in conjunction with cisplatin and gemcitabine. In some embodiments, an antigen binding polypeptide (e.g., antibody) or complex described herein may be administered in conjunction with FOLFOX. In some embodiments, an antigen binding polypeptide (e.g., antibody) or complex described herein may be administered in conjunction with FOLFIRI.

Such combination therapies noted above encompass combined administration (where two or more therapeutic agents are included in the same or separate formulations), and separate administration, in which case, administration of the antigen binding polypeptide (e.g., antibody) or complex described herein can occur prior to, simultaneously, and/or following, administration of the additional therapeutic agent and/or adjuvant. Antibodies or complexes of the invention can also be used in combination with radiation therapy.

An antibody or complex of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or complexes of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or complex need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or complex of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody or complex is suitably administered to the patient at one time or over a series of treatments. Depending on the type and severity of the disease, about 1 µg/kg to 40 mg/kg of antibody or complex can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Use of Tie2 Agonists

In certain embodiments, the present disclosure provides methods for treating or preventing a disease or disorder in a mammal, comprising administering to the mammal a therapeutically effective amount of an antigen binding complex (e.g., a tetravalent antigen binding complex having agonist activity) that binds to Tie 2. In certain embodiments, a Tie2 agonist as described herein may be used to stimulate angiogenesis, and can be used in a variety of clinical situations in which promotion of angiogenesis is desirable. Non-limiting examples of such indications include vascularization of regenerative tissues, ischemic limb disease, cerebral ischemia, conditions of vascular inflammation including arteriosclerosis, avascular necrosis, stimulation of hair growth and erectile dysfunction. In certain embodiments, a Tie2 agonist as described herein may be used for decreasing vascular permeability, e.g. at a site of leaky vessels. Such a method can be used in a variety of clinical situations, non-limiting examples of which include stroke, macular degeneration, macular edema, lymph edema, breakdown of the blood-retinal barrier, breakdown of the blood-brain barrier (e.g., during chemotherapeutic treatment) and normalization of tumor vasculature to facilitate drug delivery and increase radiation sensitivity. In certain embodiments, a Tie2 agonist as described herein may be used to inhibit apoptosis of endothelial cells. Such a method can be used in a variety of clinical situations, non-limiting examples of which include kidney fibrosis, stroke, macular degeneration and diabetic complications (e.g., in the kidney, eye, skin and/or limbs). In other embodiments, a Tie2 agonist as described herein may be used in stimulating wound healing.

Screening Assays

Also provided herein are methods for identifying polypeptides that have agonist activity. In particular, an antigen binding polypeptide may not have agonist activity when expressed as an individual polypeptide (e.g., an individual antibody, antibody fragment, ligand, etc.), however, when the same polypeptide is presented in the context of a tetravalent complex as described herein, the complex may exhibit agonist activity. Therefore, by screening for agonist activity of individual polypeptides, there may be a number of candidates that are discarded as false negatives, e.g., polypeptides that have the ability to act as an agonist when contained in a complex but do not exhibit such activity when presented in isolated form. Therefore, the antigen binding complexes as described herein may be used in an initial screen of candidate polypeptides to identify those having agonist activity.

Accordingly, in certain embodiments, the present disclosure provides novel methods for identifying an antigen binding complex (e.g., a tetravalent antigen binding complex) having agonist activity. The methods include providing a plurality of antigen binding complexes (e.g., a tetravalent antigen binding complex having agonist activity) as described herein, screening the antigen binding complexes against a cell surface receptor, and selecting antigen binding complexes having agonist activity for the cell surface receptor. In certain embodiments, the antigen binding complexes may be provided as libraries of antigen binding complexes whose amino acid sequences differ from each other. Such libraries provide a tremendously useful resource for identifying antigen binding complex which bind to the cell surface receptor and has agonist activity for the cell surface receptor.

In certain embodiments, the antigen binding complexes useful in such a screening assay may be a library wherein each antigen binding complex is tetravalent. In some embodiments, the complex is monospecific or monoepitopic, wherein each antigen binding polypeptide in a given complex binds the same epitope, and each tetravalent complex contains a different antibody that binds to the same target, e.g., essentially a library of complexes of monospecific antibodies raised to a given cell surface target. In some embodiments, the complex is biepitopic, wherein each complex comprises two or more antigen binding polypeptides that bind different epitopes (e.g., of the same target), and each tetravalent complex targets a different combination of epitopes, e.g., essentially a library of complexes of monospecific antibodies raised to a given cell surface target. Such libraries would be useful, for example, for identifying an antibody (or antigen binding complex) that binds to cell surface receptor and agonizes the receptor.

The antigen binding complexes or the antigen binding polypeptides described herein can be characterized for their physical/chemical properties and biological functions by various assays known in the art. For example, as exemplified herein, complex formation may be assayed, e.g., using Size Exclusion Chromatography (SEC) to monitor the formation and/or purity of complexes.

In certain embodiments, antigen binding complexes or antigen binding polypeptides can be characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments, antigen binding complexes or antigen binding polypeptides may be analyzed for biological activity, such as, for example, antigen binding activity. Antigen binding assays are known in the art and can be used herein including, for example, any direct or competitive binding assays using techniques such as Western blots, radioimmunoassays, ELISA (enzyme linked immnosorbent assay), "sandwich" immunoassays, immunoprecipitation assays, fluorescent immunoassays, and protein A immunoassays.

In another aspect, competition assays may be used to identify an antibody that competes with a reference antibody for binding to a target. In certain embodiments, such a competing antibody binds to the same epitope (e.g., a linear or a conformational epitope) that is bound by the reference antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, an immobilized target polypeptide is incubated in a solution comprising a first labeled antibody that binds to a target polypeptide (e.g., OX40) and a second unlabeled antibody that is being tested for its ability to compete with the first antibody for binding to the target polypeptide. The second antibody may be present in a hybridoma supernatant. As a control, immobilized target polypeptide is incubated in a solution comprising the first labeled antibody but not the second unlabeled antibody. After incubation under conditions permissive for binding of the first antibody to the target polypeptide, excess unbound antibody is removed, and the amount of label associated with immobilized target polypeptide is measured. If the amount of label associated with immobilized target polypeptide is substantially reduced in the test sample relative to the control sample, then that indicates that the second antibody is competing with the first antibody for binding to target polypeptide. See Harlow and Lane (1988) *Antibodies: A Laboratory Manual* ch. 14 (Cold Spring Harbor Laboratory, Cold Spring Harbor, N.Y.).

In other embodiments, the antigen binding complexes or antigen binding polypeptides described herein may be analyzed for agonist activity. In some embodiments, the agonist activity is tested in vitro (e.g., in a cell-free or cell-based assay, as opposed to an in vivo assay in an intact mammal). In certain embodiments, agonist activity of the antigen binding complexes or antigen binding polypeptides described herein can be determined by analyzing whether or not a cell that is depending on a ligand for growth will grow in the same way when an antigen binding complex or polypeptide is added during cell culture as compared to when a ligand is added. If the cell grows in the same or in a similar manner, then the antigen binding complex or polypeptide is determined to have agonistic activity. In certain embodiments, agonist activity of the antigen binding complexes or antigen binding polypeptides described herein can be determined by analyzing whether or not a cell line having intrinsic ligand-dependent activities (not limited to growth) shows the same reaction when an antigen binding complex or polypeptide is added during cell culture as compared to when the ligand is added. If the cell line shows the same or a similar reaction as for the ligand, then the antigen binding complex or polypeptide is determined to have agonistic activity.

In certain embodiments, cells capable of transducing the above-mentioned cell growth signals express the receptors responsive to the ligand on the cell surface. These cells transduce cell growth signals when the ligand (or agonist antigen binding complex or polypeptide) binds to the receptor. In certain embodiments, cells useful for screening for agonist activity proliferate or transduce a signal upon binding of a ligand to a cell surface receptor on the cell. In other embodiments, when the cell surface receptor is one that does not transduce a signal into the cell, then chimeric receptors made by fusing the extracellular domain (e.g., ligand binding domain) of a non-transducing receptor to the intracellular domain of a receptor that does transduce a signal into the cell. Receptors suitable for constructing chimeric receptors by fusion with ligand-binding receptors include any receptor that transduces a signal, including, for example, the G-CSF receptor, mpl, neu, GM-CSF receptor, EPO receptor, c-Kit, and FLT-3 receptors. Cells used to express such receptors include, for example, BaF3, NFS60, FDCP-1, FDCP-2, CTLL-2, DA-1, and KT-3.

In certain embodiments, agonistic activity refers to any activity caused by ligand (or antigen binding complex or polypeptide) binding that induces a specific reaction in a cell, such as, for example, inducing a change in a certain physiological activity by transmitting a signal into a cell. Such physiological activities include, for example, growth activities, growth-inducing activities, survival activities, differentiation activities, differentiation-inducing activities, transcriptional activities, membrane transport activities, binding activities, proteolytic activities, phosphorylation/dephosphorylation activities, oxidation-reduction activities, transfer activities, nucleolytic activities, dehydration activities, cell death-inducing activities, and apoptosis-inducing activities.

The agonistic activities described herein can be determined by methods known to those skilled in the art. For example, agonistic activity can be evaluated by methods which use cell growth as an indicator. More specifically, an antigen binding complex or polypeptide whose agonistic activity is to be determined is added to cells that show agonist-dependent growth, and the cells are cultured. Next, a reagent that shows a color reaction at a particular wavelength depending on viable cell count, such as WST-8, is added, and the absorbance is measured. The agonistic activity can be determined using the measured absorbance as an indicator.

In certain embodiments, agonist activity is determined using an indicator that can monitor quantitative and/or qualitative changes in the cell upon exposure to a ligand (or antigen binding complex or polypeptide). For example, it is possible to use cell-free assay indicators, cell-based assay indicators, tissue-based assay indicators, and in vivo assay indicators. Indicators that can be used in cell-free assays include enzymatic reactions, quantitative and/or qualitative changes in proteins, DNAs, or RNAs. Such enzymatic reactions include, for example, amino acid transfers, sugar transfers, dehydrations, dehydrogenations, and substrate cleavages. Alternatively, protein phosphorylations, dephosphorylations, dimerizations, multimerizations, hydrolyses, and dissociations; DNA or RNA amplifications, cleavages, and extensions can be used as the indicator in cell-free assays. For example, protein phosphorylations downstream of a signal transduction pathway may be used as a detection indicator. Alterations in cell phenotype, for example, quantitative and/or qualitative alterations in products, alterations in growth activity, alterations in cell number, morphological alterations, or alterations in cellular properties, can be used as the indicator in cell-based assays. The products include, for example, secretory proteins, surface antigens, intracellular proteins, and mRNAs. The morphological alterations include, for example, alterations in dendrite formation and/or dendrite number, alteration in cell flatness, alteration in cell elongation/axial ratio, alterations in cell size, alterations in intracellular structure, heterogeneity/homogeneity of cell populations, and alterations in cell density. Such morphological alterations can be observed under a microscope. Cellular properties to be used as the indicator include anchor dependency, cytokine-dependent response, hormone dependency, drug resistance, cell motility, cell migration activity, pulsatory activity, and alteration in intracellular substances. Cell motility includes cell infiltration activity and cell migration activity. The alterations in intracellular substances include, for example, alterations in enzyme activity, mRNA levels, levels of intracellular signaling molecules such as $Ca^{2+}$ and cAMP, and intracellular protein levels. When a cell membrane receptor is used, alterations in the cell proliferating activity induced by receptor stimulation can be used as the indicator. The indicators to be used in tissue-based assays include functional alterations adequate for the subject tissue. In in vivo assays, alterations in tissue weight, alterations in the blood system (for example, alterations in blood cell counts, protein contents, or enzyme activities), alterations in electrolyte levels, and alterations in the circulating system (for example, alterations in blood pressure or heart rate).

Any suitable method for measuring such detection indicators may be used in connection with the methods described herein. For example, absorbance, luminescence, color development, fluorescence, radioactivity, fluorescence polarization, surface plasmon resonance signal, time-resolved fluorescence, mass, absorption spectrum, light scattering, and fluorescence resonance energy transfer may be used. These measurement methods are known to those skilled in the art and may be selected appropriately depending on the purpose. For example, absorption spectra can be obtained by using a conventional photometer, plate reader, or such; luminescence can be measured with a luminometer or such; and fluorescence can be measured with a fluorometer or such. Mass can be determined with a mass spectrometer. Radioactivity can be determined with a device such as a gamma counter depending on the type of radiation. Fluorescence polarization can be measured with BEACON (TaKaRa). Surface plasmon resonance signals can be obtained with BIACORE. Time-resolved fluorescence, fluorescence resonance energy transfer, or such can be measured with ARVO or such. Furthermore, a flow cytometer can also be used for measurements. It is possible to use one of the above methods to measure two or more different types of detection indicators. A greater number of detection indicators may also be examined by using two or more measurement methods simultaneously and/or consecutively. For example, fluorescence and fluorescence resonance energy transfer can be measured at the same time with a fluorometer.

OX40 Assays

As described above, certain aspects of the present disclosure relate to agonist activity for a cell surface receptor. As will be recognized by one of skill in the art, the particular assay(s) used to determine agonist activity for a cell surface receptor may depend upon the particular cell surface receptor. Exemplary assays related to determining OX40 activity are provided below. Based on this guidance and common knowledge in the art, one of skill in the art may suitably identify assays for other cell surface receptors described herein.

In one aspect, assays are provided for identifying an agonist antigen binding complex that binds to OX40 having biological activity. Biological activity may include, e.g., binding OX40 (e.g., binding human and/or cynomolgus OX40), increasing OX40-mediated signal transduction (e.g., increasing NFkB-mediated transcription), depleting cells that express human OX40 (e.g., T cells), depleting cells that express human OX40 by ADCC and/or phagocytosis, enhancing T effector cell function (e.g., CD4+ effector T cell), e.g., by increasing effector T cell proliferation and/or increasing cytokine production (e.g., gamma interferon) by effector T cells, enhancing memory T cell function (e.g., CD4+ memory T cell), e.g., by increasing memory T cell proliferation and/or increasing cytokine production by memory T cells (e.g., gamma interferon), or inhibiting regulatory T cell function (e.g., by decreasing Treg suppression of effector T cell function (e.g., CD4+ effector T cell function). In certain embodiments, the agonist antigen binding complex that binds to OX40 has one or more of the listed biological activities in the absence of binding to human effector cells. In certain embodiments, the agonist antigen binding complex that binds to OX40 has one or more of the listed biological activities and does bind to human effector cells. Antibodies having such biological activity in vivo and/or in vitro are also provided.

In certain embodiments, an antibody of the invention is tested for such biological activity.

T cell costimulation may be assayed using methods known in the art and exemplary methods are disclosed herein. For example, T cells (e.g., memory or effector T cells) may be obtained from peripheral white blood cells (e.g., isolated from human whole blood using Ficoll gradient centrifugation). Memory T cells (e.g., CD4+ memory T cells) or effector T cells (e.g. CD4+ Teff cells) may be isolated from PBMC using methods known in the art. For example, the Miltenyi CD4+ memory T cell isolation kit or Miltenyi naïve CD4+ T cell isolation kit may be used. Isolated T cells are cultured in the presence of antigen presenting cells (e.g., irradiated L cells that express CD32 and CD80), and activated by addition of anti-CD3 antibody in the presence or absence of an agonist antigen binding complex that binds to OX40. The effect of an agonist antigen binding complex that binds to OX40 antibody on T cell proliferation may be measured using methods well known in the art. For example, the CellTiter-Glo® kit (Promega) may be used, and results read on a Multilabel Reader (Perkin Elmer). The effect of an agonist antigen binding complex that binds to OX40 on T cell function may also be determined by analysis of cytokines produced by the T cell. In one embodiment, production of interferon gamma by CD4+ T cells is determined, e.g., by measurement of interferon gamma in cell culture supernatant. Methods for measuring interferon gamma are well-known in the art.

Treg cell function may be assayed using methods known in the art and exemplary methods are disclosed herein. In one example, the ability of Treg to suppress effector T cell proliferation is assayed. T cells are isolated from human whole blood using methods known in the art (e.g., isolating memory T cells or naïve T cells). Purified CD4+ naïve T cells are labeled (e.g., with CFSE) and purified Treg cells are labeled with a different reagent. Irradiated antigen presenting cells (e.g., L cells expressing CD32 and CD80) are co-cultured with the labeled purified naïve CD4+ T cells and purified Tregs. The co-cultures are activated using anti-CD3 antibody and tested in the presence or absence of an agonist antigen binding complex that binds to OX40. Following a suitable time (e.g., 6 days of coculture), the level of CD4+ naïve T cell proliferation is tracked by dye dilution in reduced label staining (e.g., reduced CFSE label staining) using FACS analysis.

OX40 signaling may be assayed using methods well known in the art and exemplary methods are disclosed herein. In one embodiment, transgenic cells are generated that express human OX40 and a reporter gene comprising the NFkB promoter fused to a reporter gene (e.g., beta luciferase). Addition of an agonist antigen binding complex that binds to OX40 to the cells results in increased NFkB transcription, which is detected using an assay for the reporter gene.

Phagocytosis may be assayed, e.g., by using monocyte-derived macrophages, or U937 cells (a human histiocytic lymphoma cells line with the morphology and characteristics of mature macrophages). OX40 expressing cells are added to the monocyte-derived macrophages or U937 cells in the presence or absence of an agonist antigen binding complex that binds to OX40. Following culturing of the cells for a suitable period of time, the percentage of phagocytosis is determined by examining percentage of cells that double stain for markers of 1) the macrophage or U937 cell and 2) the OX40 expressing cell, and dividing this by the total number of cells that show markers of the OX40 expressing cell (e.g., GFP). Analysis may be done by flow cytometry. In another embodiment, analysis may be done by fluorescent microscopy analysis.

Cells for use in any of the above in vitro assays include cells or cell lines that naturally express OX40 or that have been engineered to express OX40. Such cells include activated T cells, Treg cells and activated memory T cells that naturally express OX40. Such cells also include cell lines that express OX40 and cell lines that do not normally express OX40 but have been transfected with nucleic acid encoding OX40. Exemplary cell lines provided herein for use in any of the above in vitro assays include transgenic BT474 cells (a human breast cancer cell line) that express human OX40.

IV. Pharmaceutical Compositions

The antigen binding complexes (e.g., a tetravalent antigen binding complex having agonist activity) of the present disclosure or subunit(s) thereof as described herein may be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the complexes or proteins to be administered will be governed by such considerations, and is the minimum amount necessary to prevent, ameliorate, or treat a particular disorder (for example, a cancer, allergic or inflammatory disorder, or autoimmune disorder). In certain embodiments, the complexes and proteins described herein may optionally be formulated with one or more agents currently used to prevent or treat the disorder. The effective amount of such other agents depends on the amount of complexes or proteins present in the formulation, the type of disorder or treatment, and other factors discussed above.

Therapeutic formulations are prepared using standard methods known in the art by mixing the active ingredient having the desired degree of purity with optional physiologically acceptable carriers, excipients or stabilizers (Remington's Pharmaceutical Sciences (20th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

In certain embodiments, the formulation contains a pharmaceutically acceptable salt, preferably sodium chloride, and preferably at about physiological concentrations.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antigen binding complex or the antigen binding polypeptide, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antigen binding complex(es) or antigen binding polypeptide(s) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The complexes described herein may be administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein or complex of this invention. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

V. Articles of Manufacture

Another embodiment of the invention is an article of manufacture containing one or more antigen binding complexes (e.g., a tetravalent antigen binding complex having agonist activity) as described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is an antigen binding complex or polypeptide as described herein. The label or package insert indicates that the composition is used for treating the particular condition. The label or package insert will further comprise instructions for administering the antigen binding complex or polypeptide composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Exemplary complexes, methods, nucleic acids, vectors, host cells, and compositions are set out in the following items:

Item 1: A tetravalent antigen binding complex having agonist activity, the complex comprising:
a first and a second subunit, wherein each of the first and the second subunits comprises:
(i) a first half-antibody comprising a first antibody heavy chain variable domain ($VH_1$) and a first antibody light chain variable domain ($VL_1$), wherein the first half-antibody specifically binds to a first epitope of a cell surface receptor, and
(ii) a second half-antibody comprising a second antibody heavy chain variable domain ($VH_2$) and a second antibody light chain variable domain ($VL_2$), wherein the second half-antibody specifically binds to a second epitope of the cell surface receptor; wherein the first and the second subunits are coupled, and wherein the complex has agonist activity for the cell surface receptor bound by the complex.

Item 2: The complex of item 1, wherein each of the first and the second subunits comprises:

(i) the first half-antibody, wherein the first half-antibody comprises:
  (a) a first antibody heavy chain comprising, from N-terminus to C-terminus, the first antibody heavy chain variable domain (VH$_1$), a first antibody heavy chain CH1 domain, a first antibody heavy chain CH2 domain, and a first antibody heavy chain CH3 domain; and
  (b) a first antibody light chain comprising, from N-terminus to C-terminus, the first antibody light chain variable domain (VL$_1$) and a first antibody light chain constant domain (CL); and
(i) the second half-antibody, wherein the second half-antibody comprises:
  (a) a second antibody heavy chain comprising, from N-terminus to C-terminus, the second antibody heavy chain variable domain (VH$_2$), a second antibody heavy chain CH1 domain, a second antibody heavy chain CH2 domain, and a second antibody heavy chain CH3 domain; and
  (b) a second antibody light chain comprising, from N-terminus to C-terminus, the second antibody light chain variable domain (VL$_2$) and a second antibody light chain constant domain (CL).

Item 3: The complex of item 2, wherein the first and the second subunits are chemically coupled.

Item 4: The complex of any one of items 1-3, wherein the first and the second epitopes of the cell surface receptor are the same.

Item 5: The complex of any one of items 1-3, wherein the first and the second epitopes of the cell surface receptor are different.

Item 6: The complex of item 5, wherein each of the first and the second subunits comprises a bispecific antibody, wherein the bispecific antibody comprises two antibody Fc regions with two CH3 domains, wherein each of the two CH3 domains comprises either a protuberance or a cavity, and wherein the protuberance or cavity in the first of the two CH3 domains is positionable in the cavity or protuberance, respectively, in the second of the two CH3 domains.

Item 7: The complex of any one of items 1-6, wherein the two subunits are chemically coupled via a linker.

Item 8: The complex of item 7, wherein the linker joins a first engineered free cysteine of the first subunit and a second engineered free cysteine of the second subunit.

Item 9: The complex of item 8, wherein each of the two subunits comprises two heavy chains and two light chains, and wherein one of the heavy chains of each subunit comprises a cysteine amino acid in the heavy chain selected from the group consisting of T114C, A118C, A140C, L174C, L179C, T187C, T209C, V262C, G371C, Y373C, E382C, S400C, S424C, N434C and Q438C, according to EU numbering.

Item 10: The complex of item 8, wherein each of the two subunits comprises two heavy chains and two light chains, and wherein one of the light chains of each subunit comprises a cysteine amino acid in the light chain selected from the group consisting of I106C, R108C, R142C, K149C, and V205C, according to Kabat numbering.

Item 11: The complex of item 7, wherein the two subunits are chemically coupled via click chemistry.

Item 12: The complex of item 11, wherein the two subunits are coupled via a tetrazine-transcyclooctene (TCO) click reaction.

Item 13: The complex of item 11 or item 12, wherein the linker is between about 10 Å and about 100 Å in length.

Item 14: The complex of item 7, wherein the linker is a bis-maleimido polyethylene glycol (PEG) linker.

Item 15: The complex of item 13, wherein the PEG linker comprises between one and eleven PEG subunits.

Item 16: The complex of item 15, wherein the PEG linker comprises one, two, or three PEG subunits.

Item 17: The complex of any one of items 2-16, wherein each of the subunits comprises an Fc region comprising a modification for attenuating effector function.

Item 18: The complex of item 17, wherein each of the subunits comprises an Fc region comprising an amino acid substitution at one or more amino acid residues (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

Item 19: The complex of item 17 or item 18, wherein each of the subunits comprises an Fc region comprising one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

Item 20: The complex of any one of items 17-19, wherein each of the subunits comprises an Fc region comprising a modification for attenuating effector function that results in an aglycosylated Fc region.

Item 21: The complex of any one of items 17-19, wherein each of the subunits comprises an Fc region comprising a modification for attenuating effector function that does not result in a modification of the glycosylation pattern of the Fc region.

Item 22: The complex of any one of items 1-21, wherein the cell surface receptor is a member of a receptor family selected from the group consisting of tumor necrosis factor receptor (TNFR) superfamily and G-Protein Coupled Receptor (GPCR) superfamily.

Item 23: The complex of any one of items 1-22, wherein the cell surface receptor is selected from the group consisting of OX40, DR5, GITR, CD27, CD137, and Tie2.

Item 24: The complex of item 23, wherein the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

Item 25: The complex of item 23 or item 24, wherein the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

Item 26: A tetravalent antigen binding complex having agonist activity, wherein said complex comprises:
(a) an antibody comprising two antibody heavy chains, each antibody heavy chain comprising a first antibody heavy chain variable domain ($VH_1$), and two antibody light chains, each antibody light chain comprising a first antibody light chain variable domain ($VL_1$), wherein the antibody specifically binds to a first epitope of a cell surface receptor; and
(b) two antibody Fab fragments coupled with the antibody, wherein each of the two antibody Fab fragments comprises a second antibody heavy chain variable domain ($VH_2$) and a second antibody light chain variable domain ($VL_2$), wherein each of the two antibody Fab fragments specifically binds a second epitope of the cell surface receptor;
wherein the complex has agonist activity for the cell surface receptor bound by the complex.

Item 27: The complex of item 26, wherein each antibody heavy chain comprises, from N-terminus to C-terminus, the first antibody heavy chain variable domain ($VH_1$), a first antibody heavy chain CH1 domain, a first antibody heavy chain CH2 domain, and a first antibody heavy chain CH3 domain; wherein each antibody light chain comprises, from N-terminus to C-terminus, the first antibody light chain variable domain ($VL_1$) and a first antibody light chain constant domain (CL); wherein each of the two antibody Fab fragments comprises a heavy chain Fab fragment comprising, from N-terminus to C-terminus, the second antibody heavy chain variable domain ($VH_2$) and a second antibody heavy chain CH1 domain; and wherein each of the two antibody Fab fragments comprises a light chain Fab fragment comprising, from N-terminus to C-terminus, the second antibody light chain variable domain ($VL_2$) and a second antibody light chain constant domain (CL).

Item 28: The complex of item 27, wherein a first of the two antibody Fab fragments is chemically coupled to a first of the two antibody light chains or a first of the two antibody heavy chains, and wherein a second of the two antibody Fab fragments is chemically coupled to a second of the two antibody light chains or a second of the two antibody heavy chains.

Item 29: The complex of any one of items 26-28, each of the two Fab fragments is chemically coupled to the antibody via a linker.

Item 30: The complex of item 29, comprising:
(i) a first linker joining a first engineered free cysteine of the antibody and an engineered free cysteine of a first of the two Fab fragments, and
(ii) a second linker joining a second engineered free cysteine of the antibody and an engineered free cysteine of a second of the two Fab fragments.

Item 31: The complex of item 30, wherein the two antibody heavy chains of the antibody each comprise a cysteine amino acid independently selected from the group consisting of T114C, A118C, A140C, L174C, L179C, T187C, T209C, V262C, G371C, Y373C, E382C, S400C, S424C, N434C and Q438C, according to EU numbering.

Item 32: The complex of item 30, wherein the two antibody light chains of the antibody each comprise a cysteine amino acid independently selected from the group consisting of I106C, R108C, R142C, K149C, and V205C, according to Kabat numbering.

Item 33: The complex of any one of items 30-32, wherein the two antibody Fab fragments each comprise a C-terminal cysteine amino acid.

Item 34: The complex of item 29, wherein the antibody is coupled to both of the two antibody Fab fragments via click chemistry.

Item 35: The complex of item 34, wherein the antibody is coupled to both of the two antibody Fab fragments via a tetrazine-transcyclooctene (TCO) click reaction.

Item 36: The complex of item 34 or item 35, wherein the linker is between about 10A and about 100 Å in length.

Item 37: The complex of item 29, wherein the linker is a bis-maleimido polyethylene glycol (PEG) linker.

Item 38: The complex of item 37, wherein the PEG linker comprises between one and eleven PEG subunits.

Item 39: The complex of item 38, wherein the PEG linker comprises one, two, or three PEG subunits.

Item 40: The complex of item 26, wherein the two antibody Fab fragments are genetically coupled with the antibody; wherein each antibody heavy chain comprises, from N-terminus to C-terminus, the first antibody heavy chain variable domain ($VH_1$), a first antibody heavy chain CH1 domain, the second heavy chain variable domain ($VH_2$), a second heavy chain CH1 domain, an antibody heavy chain CH2 domain, and an antibody heavy chain CH3 domain; and wherein the complex comprises a first antibody light chain comprising, from N-terminus to C-terminus, the first antibody light chain variable domain ($VL_1$) and a first antibody light chain constant domain (CL) and a second antibody light chain comprising, from N-terminus to C-terminus, the second antibody light chain variable domain ($VL_2$) and a second antibody light chain constant domain (CL).

Item 41: The complex of item 40, wherein the first antibody light chain comprises a modification for orthogonal pairing with a modification of the first antibody heavy chain variable domain ($VH_1$) and/or the first antibody heavy chain CH1 domain of the antibody heavy chain, and wherein the second antibody light chain comprises a modification for orthogonal pairing with a modification of the second heavy chain variable domain ($VH_2$) and/or the second heavy chain CH1 domain of the antibody heavy chain.

Item 42: The complex of any one of items 26-41, wherein the first and the second epitopes of the cell surface receptor are the same.

Item 43: The complex of any one of items 26-41, wherein the first and the second epitopes of the cell surface receptor are different.

Item 44: The complex of any one of items 26-43, wherein each of the antibody heavy chains of the antibody comprises an Fc region comprising a modification for attenuating effector function.

Item 45: The complex of item 44, wherein each of the antibody heavy chains of the antibody comprises an amino acid substitution at one or more amino acid residues (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

Item 46: The complex of item 44 or item 45, wherein each of the antibody heavy chains of the antibody comprises an amino acid substitution at one or more amino acid residues (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

Item 47: The complex of any one of items 44-46, wherein each of the antibody heavy chains of the antibody comprises an Fc region comprising a modification for attenuating effector function that results in an aglycosylated Fc region.

Item 48: The complex of any one of items 44-46, wherein each of the antibody heavy chains of the antibody comprises a modification for attenuating effector function that does not result in a modification of the glycosylation pattern of the Fc region.

Item 49: The complex of any one of items 26-48, wherein the cell surface receptor is a member of a receptor family selected from the group consisting of tumor necrosis factor receptor (TNFR) superfamily and G-Protein Coupled Receptor (GPCR) superfamily.

Item 50: The complex of any one of items 26-49, wherein the cell surface receptor is selected from the group consisting of OX40, DR5, GITR, CD27, CD137, and Tie2.

Item 51: The complex of item 50, wherein the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

Item 52: The complex of item 50 or item 51, wherein the $VH_2$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

Item 53: The complex of item 50, wherein the $VH_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

Item 54: The complex of item 50 or item 53, wherein the $VH_1$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the $VL_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

Item 55: A nucleic acid encoding the complex according to any one of items 1-25.

Item 56: The nucleic acid of item 55, wherein the nucleic acid comprises a first polynucleotide encoding the first antibody heavy chain, a second polynucleotide encoding the first antibody light chain, a third polynucleotide encoding the second antibody heavy chain, and a fourth polynucleotide encoding the second antibody light chain.

Item 57: A nucleic acid encoding the complex according to any one of items 26-54.

Item 58: The nucleic acid of item 57, wherein the nucleic acid comprises a first polynucleotide encoding the antibody heavy chains, a second polynucleotide encoding the antibody light chains, a third polynucleotide encoding the heavy chain Fab fragments, and a fourth polynucleotide encoding the light chain Fab fragments.

Item 59: The nucleic acid of item 57, wherein the nucleic acid comprises a first polynucleotide encoding an antibody heavy chain comprising, from N-terminus to C-terminus, the first antibody heavy chain variable domain ($VH_1$), a first antibody heavy chain CH1 domain, the second heavy chain variable domain ($VH_2$), a second heavy chain CH1 domain, an antibody heavy chain CH2 domain, and an antibody heavy chain CH3 domain; a second polynucleotide encoding an antibody light chain comprising, from N-terminus to C-terminus, the first antibody light chain variable domain ($VL_1$) and a first antibody light chain constant domain (CL); and a third polynucleotide encoding an antibody light chain comprising, from N-terminus to C-terminus, the second antibody light chain variable domain ($VL_2$) and a second antibody light chain constant domain (CL).

Item 60: A vector comprising the nucleic acid of any one of items 55-59.

Item 61: The vector of item 60, wherein the vector is an expression vector.

Item 62: A host cell comprising the vector of item 60 or item 61.

Item 63: The host cell of item 62, wherein the host cell is prokaryotic.

Item 64: The host cell of item 62, wherein the host cell is eukaryotic.

Item 65: A method of producing a tetravalent antigen binding complex, comprising culturing the host cell of item 62 such that the complex is produced.

Item 66: The method of item 65, further comprising recovering the complex from the host cell.

Item 67: A pharmaceutical composition comprising the complex according to any one of items 1-54 and a pharmaceutically acceptable carrier.

Item 68: A method of producing a tetravalent antigen binding complex having agonist activity for a cell surface receptor bound by the complex, the method comprising:
(a) providing:
 (i) a first half-antibody comprising a first antibody heavy chain variable domain (VH$_1$) and a first antibody light chain variable domain (VL$_1$), wherein the first half-antibody specifically binds to a first epitope of a cell surface receptor, and wherein the first half-antibody comprises a first engineered free cysteine, and
 (ii) a second half-antibody comprising a second antibody heavy chain variable domain (VH$_2$) and a second antibody light chain variable domain (VL$_2$), wherein the second half-antibody specifically binds to a second epitope of the cell surface receptor, wherein each of the first and the second half-antibodies comprises an antibody Fc region with a CH3 domain, wherein each of the two CH3 domains comprises either a protuberance or a cavity, wherein the protuberance or cavity in the first of the two CH3 domains is positionable in the cavity or protuberance, respectively, in the second of the two CH3 domains;
(b) assembling the first and the second half-antibodies in vitro to form a first subunit;
(c) providing:
 (iii) a third half-antibody comprising the first antibody heavy chain variable domain (VH$_1$) and the first antibody light chain variable domain (VL$_1$), wherein the third half-antibody specifically binds to the first epitope of a cell surface receptor, and wherein the third half-antibody comprises a second engineered free cysteine, and
 (iv) a fourth half-antibody comprising the second antibody heavy chain variable domain (VH$_2$) and the second antibody light chain variable domain (VL$_2$), wherein the fourth half-antibody specifically binds to the second epitope of the cell surface receptor, wherein each of the third and the fourth half-antibodies comprises an antibody Fc region with a CH3 domain, wherein each of the two CH3 domains comprises either a protuberance or a cavity, wherein the protuberance or cavity in the first of the two CH3 domains is positionable in the cavity or protuberance, respectively, in the second of the two CH3 domains;
(d) assembling the third and the fourth half-antibodies in vitro to form a second subunit; and
(e) coupling the first and the second subunits via a linker using the first and the second free engineered cysteines, thereby producing the complex.

Item 69: The method of item 68, wherein the first and the second epitopes of the cell surface receptor are the same.

Item 70: The method of item 68, wherein the first and the second epitopes of the cell surface receptor are different.

Item 71: The method of any one of items 68-71, wherein the first and the second engineered free cysteines are each a cysteine amino acid in the heavy chain independently selected from the group consisting of T114C, A118C, A140C, L174C, L179C, T187C, T209C, V262C, G371C, Y373C, E382C, S400C, S424C, N434C and Q438C, according to EU numbering.

Item 72: The method of any one of items 68-71, wherein the first and the second engineered free cysteines are each a cysteine amino acid in the light chain independently selected from the group consisting of I106C, R108C, R142C, K149C, and V205C, according to Kabat numbering.

Item 73: The method of any one of items 68-72, wherein the linker is a bis-maleimido polyethylene glycol (PEG) linker.

Item 74: The method of item 73, wherein step (e) comprises:
(1) reacting the two subunits with the bis-maleimido polyethylene glycol (PEG) linker; and
(2) purifying the complex.

Item 75: The method of item 74, wherein purifying the complex comprises subjecting the complex to size exclusion chromatography and/or anion exchange chromatography.

Item 76: The method of any one of items 73-75, wherein the PEG linker comprises between one and eleven PEG subunits.

Item 77: The method of any one of items 73-76, wherein the PEG linker comprises one, two, or three PEG subunits.

Item 78: The method of any one of items 68-77, wherein each of the first and the second subunits comprises an Fc region comprising a modification for attenuating effector function.

Item 79: The method of item 78, wherein each of the first and the second subunits comprises an Fc region comprising an amino acid substitution at one or more amino acid residues (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

Item 80: The method of item 78 or item 79, wherein each of the first and the second subunits comprises an Fc region comprising one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4, (h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

Item 81: The method of any one of items 78-80, wherein each of the first and the second subunits comprises an Fc region comprising a modification for attenuating effector function that results in an aglycosylated Fc region.

Item 82: The method of any one of items 78-80, wherein each of the first and the second subunits comprises an Fc region comprising a modification for attenuating effector function that does not result in a modification of the glycosylation pattern of the Fc region.

Item 83: A method of producing a tetravalent antigen binding complex having agonist activity for a cell surface receptor bound by the complex, the method comprising:
(a) providing an antibody comprising two half-antibodies, wherein each half-antibody comprises an antibody heavy chain comprising a first antibody heavy chain variable domain ($VH_1$), and an antibody light chain comprising a first antibody light chain variable domain ($VL_1$), wherein the antibody specifically binds to a first epitope of a cell surface receptor, and wherein each of the two half-antibodies comprises a first engineered free cysteine;
(b) providing two antibody Fab fragments, wherein each of the two antibody Fab fragments comprises a second antibody heavy chain variable domain ($VH_2$) and a second antibody light chain variable domain ($VL_2$), wherein each of the two antibody Fab fragments specifically binds a second epitope of the cell surface receptor, and wherein each of the two antibody Fab fragments comprises a second engineered free cysteine; and
(c) coupling one of the antibody Fab fragments to each of the two half-antibodies via a linker, thereby producing the complex.

Item 84: The method of item 83, wherein the first and the second epitopes of the cell surface receptor are the same.

Item 85: The method of item 83, wherein the first and the second epitopes of the cell surface receptor are different.

Item 86: The method of any one of items 83-85, wherein the first engineered free cysteine is a cysteine amino acid in the heavy chain independently selected from the group consisting of T114C, A118C, A140C, L174C, L179C, T187C, T209C, V262C, G371C, Y373C, E382C, S400C, S424C, N434C and Q438C, according to EU numbering.

Item 87: The method of any one of items 83-85, wherein the first engineered free cysteine is a cysteine amino acid in the light chain independently selected from the group consisting of I106C, R108C, R142C, K149C, and V205C, according to Kabat numbering.

Item 88: The method of any one of items 83-87, wherein the second engineered free cysteine is a C-terminal cysteine amino acid.

Item 89: The method of any one of items 83-88, wherein the linker is a bis-maleimido polyethylene glycol (PEG) linker.

Item 90: The method of item 89, wherein step (c) comprises:
(i) reacting each of the two antibody Fab fragments with a bis-maleimido polyethylene glycol (PEG) linker to form two bismal-conjugated antibody Fab fragments;
(ii) removing excess bis-maleimido PEG linker;
(iii) reacting each of the two bismal-conjugated antibody Fab fragments with the antibody to form the complex; and
(iv) purifying the complex.

Item 91: The method of item 90, wherein purifying the complex comprises subjecting the complex to size exclusion chromatography and/or anion exchange chromatography.

Item 92: The method of any one of items 89-91, wherein the PEG linker comprises between one and eleven PEG subunits.

Item 93: The method of any one of items 89-92, wherein the PEG linker comprises one, two, or three PEG subunits.

Item 94: The method of any one of items 83-93, wherein the antibody comprises an Fc region comprising a modification for attenuating effector function.

Item 95: The method of item 94, wherein the antibody comprises an Fc region comprising an amino acid substitution at one or more amino acid residues (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

Item 96: The method of item 94 or item 95, wherein the antibody comprises an Fc region comprising one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

Item 97: The method of any one of items 94-96, wherein the antibody comprises an Fc region comprising a modification for attenuating effector function that results in an aglycosylated Fc region.

Item 98: The method of any one of items 94-96, wherein the antibody comprises an Fc region comprising a modification for attenuating effector function that does not result in a modification of the glycosylation pattern of the Fc region.

Item 99: A method of producing a tetravalent antigen binding complex having agonist activity for a cell surface receptor bound by the complex, the method comprising:

(a) expressing in a host cell two antibody heavy chains, wherein each antibody heavy chain comprises, from N-terminus to C-terminus, a first antibody heavy chain variable domain ($VH_1$), a first antibody heavy chain CH1 domain ($CH1_1$), a second heavy chain variable domain ($VH_2$), a second heavy chain CH1 domain ($CH1_2$), an antibody heavy chain CH2 domain, and an antibody heavy chain CH3 domain, wherein each $VH_1$ and/or each $CH1_1$ comprises a first modification for orthogonal pairing, wherein each $VH_2$ and/or each $CH1_2$ comprises a second modification for orthogonal pairing, and wherein the first and the second modifications are different;

(b) expressing in the host cell two first antibody light chains, wherein each of the two first antibody light chains comprises, from N-terminus to C-terminus, a first antibody light chain variable domain ($VL_1$) and a first antibody light chain constant domain ($CL_1$), and wherein the $VL_1$ and/or the $CL_1$ comprises a modification for orthogonal pairing with the first modification of the antibody heavy chains; and (c) expressing in the host cell two second antibody light chains, wherein each of the two second antibody light chains comprises, from N-terminus to C-terminus, a second antibody light chain variable domain ($VL_2$) and a second antibody light chain constant domain ($CL_2$), and wherein the $VL_2$ and/or the $CL_2$ comprises a modification for orthogonal pairing with the second modification of the antibody heavy chains;

wherein the $VH_1$ and $VL_1$ specifically bind to a first epitope of the cell surface receptor;

wherein the $VH_2$ and $VL_2$ specifically bind to a second epitope of the cell surface receptor; and wherein upon expression in the host cell, the two antibody heavy chains associate, each of the two heavy chains couples with a first antibody light chain via orthogonal pairing, and each of the two heavy chains couples with a second antibody light chain via orthogonal pairing, thereby producing the complex.

Item 100: The method of item 99, wherein each of the first and the second modifications of the antibody heavy chain are independently selected from the group consisting of VH-Q39K, VH-Q39E, CH1-S183E, CH1-S183K, CH1-A141I, CH1-F170S, CH1-S181M, CH1-S183A, and CH1-V185A (EU numbering).

Item 101: The method of item 99 or item 100, wherein each of the modifications of the first and the second antibody light chains are independently selected from the group consisting of VL-Q38E, VL-Q38K, CL-V133K, CL-V133E, CL-F116A, CL-L135V, CL-S174A, CL-S176F, and CL-T178V (EU numbering).

Item 102: The method of any one of items 99-101, wherein the first and the second epitopes of the cell surface receptor are the same.

Item 103: The method of any one of items 99-101, wherein the first and the second epitopes of the cell surface receptor are different.

Item 104: The method of any one of items 99-103, wherein each antibody heavy chain comprises an Fc region comprising a modification for attenuating effector function.

Item 105: The method of item 104, wherein each antibody heavy chain comprises an Fc region comprising an amino acid substitution at one or more amino acid residues (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

Item 106: The method of item 104 or item 105, wherein each antibody heavy chain comprises an Fc region comprising one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

Item 107: The method of any one of items 104-106, wherein each antibody heavy chain comprises an Fc region comprising a modification for attenuating effector function that results in an aglycosylated Fc region.

Item 108: The method of any one of items 104-106, wherein each antibody heavy chain comprises an Fc region comprising a modification for attenuating effector function that does not result in a modification of the glycosylation pattern of the Fc region.

Item 109: The method of any one of items 68-108, wherein the cell surface receptor is a member of a receptor family selected from the group consisting of tumor necrosis factor receptor (TNFR) superfamily and G-Protein Coupled Receptor (GPCR) superfamily.

Item 110: The method of any one of items 68-109, wherein the cell surface receptor is selected from the group consisting of OX40, DR5, GITR, CD27, CD137, and Tie2.

Item 111: The method of item 110, wherein the $VH_1$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the $VL_1$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

Item 112: The method of item 110 or item 111, wherein the $VH_2$ comprises: (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the VL$_2$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

Item 113: The method of item 110, wherein the VH$_2$ comprises: (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and wherein the VL$_2$ comprises: (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

Item 114: The method of item 110 or item 113, wherein the VH$_1$ comprises: (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and wherein the VL$_1$ comprises: (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. Exploration of Biepitopic Antibodies to Enhance Agonist Activity

There is growing interest in discovering antibodies that mediate agonist activity against target receptors. Agonist antibodies engage a receptor in a manner that is productive for signaling, in effect acting as a surrogate ligand. For some targets antibody-mediated agonism may be possible via bivalent engagement of the receptor, taking advantage of the homodimeric nature of IgG. However some receptor systems require multivalent cross-linking to elicit activity, whereby receptors are pulled together into a cluster to elicit optimal signaling. For these receptors, antibody cross-linking in vivo is typically enabled by engagement of antibody Fc with Fc receptors (Wilson et al., 2011, Cancer Cell 19:101-13; Kim & Ashkenazi, 2013, J Exp Med 210:1647-51; Stewart et al., 2014 Journal for ImmunoTherapy of Cancer 2:1-10).

The potential of biepitopic engagement of OX40 to enhance antibody-mediated receptor agonism was explored. OX40 is a TNFRSF member co-stimulatory molecule expressed on antigen experienced effector T (Teff) and regulatory T (Treg) cells, including infiltrating cells in mouse and human tumors. Activation of OX40 by agonist antibodies has been shown to promote anti-tumor immunity by enhancing Teff activation and inhibiting Treg mediated suppression (Voo et al., 2013, J. Immunol, 191:3641-50). Agonism by anti-OX40 antibodies has been shown to provide costimulatory activity similar to the natural ligand OX40L, but in a manner that requires cross-linking in vitro or via Fc/FcγR-mediated cross-linking in vivo (Voo et al., 2013, J. Immunol, 191:3641-50).

Materials and Methods

A biepitopic anti-OX40 antibody was generated by constructing a bispecific antibody comprised of two separate variable regions. One variable region comprises an anti-OX40 humanized antibody with VH and VL sequences as set forth in SEQ ID NOs: 56 and 57, respectively. While the variable region comprising these domains is more completely described as 1A7.gr.1, herein this variable region will be abbreviated as 1A7. In other words, 1A7 herein refers to the humanized 1A7.gr.1 variable region as defined by SEQ ID NOs: 56 and 57. One variable region comprises an anti-OX40 humanized antibody with VH and VL sequences as set forth in SEQ ID NOs: 126 and 129, respectively. While the variable region comprising these domains is more completely described as 3C8.gr.5.SG, herein this variable region will be abbreviated as 3C8. In other words, 3C8 herein refers to the humanized 3C8.gr.5.SG variable region as defined by SEQ ID NOs: 126 and 129.

Bispecific antibody was generated using knobs-into-hole variants and in vitro assembly of separate half-antibodies (Spiess et al., 2013, Nat Biotechnol 31(8):753-8). DNA encoding antibody heavy and light chains were constructed in the pRK mammalian expression vector (Eaton et al., 1986, Biochemistry 25:8343-8347) using standard molecular biology techniques. Plasmids encoding heavy chain and light chain of antibodies with mutations for expi293 or CHO cell expression were constructed through gene synthesis (Genewiz) or through mutagenesis using QuikChange Lightning Multi Site-Directed Mutagenesis Kit (Agilent Cat. 210514) and Q5 Site-Directed Mutagenesis Kit (New England BioLab Cat. E0554S). DNA encoding the 1A7 VH region was subcloned into a variant human IgG1 (hIgG1) comprising "knob" mutation T366W (EU numbering), a C-terminal 6His tag, and with or without N297G (EU numbering) mutation. DNA encoding the 3C8 VH region was subcloned into a variant human IgG1 (hIgG1) comprising "hole" mutations T366S/L368A/Y407V (EU numbering), a C-terminal Flag tag, and with or without N297G mutation.

A variety of mutational strategies have been described for reducing the effector function properties of monoclonal antibodies (Strohl, 2009, Curr Opin in Biotech 20:685-691). Two approaches were used to engineer an effector-attenuated version of the antibodies of the present disclosure. First, antibodies were constructed in the context of an aglycosylated Fc region by combining them with the substitution N297G, which removes the conserved N-linked glycosylation site at position 297 of the Fc region. The second approach utilized substitutions L234A, L235A, and P329G (EU numbering) (the L234A/L235A/P329G triple variant is referred to as LALAPG), which has previously been shown to reduce binding to Fc receptors and complement (see e.g., US PG Publication No. 2012/0251531). DNA encoding VL regions for both antibodies were constructed with human Ckappa (hCk) constant chains.

pRK vector DNA encoding 1A7 and 3C8 light and heavy (native and half antibodies) were cotransfected into HEK293 cells for expression, and resulting protein was purified. After expression, the Expi293 cells were settled under gravity. The supernatants were transferred to a 50 mL Falcon tube (Corning, Corning, N.Y.) containing 0.2 mL (50% slurry) of MabSelect Sure resin (GE Healthcare Life Sciences, Pittsburgh, Pa.) using a Freedom EVO 200 liquid handling workstation (Tecan, Morrisville, N.C.). The supernatant/ resin mixtures were incubated overnight on an Innova 2000 platform shaker (New Brunswick Scientific, Enfield, Conn.) at 270 RPM. After settling, the resin was transferred to a 96-well 2 ml filter plate with a 25-µm membrane (Thompson Instruments, Oceanside, Calif.) and washed twice with 1 mL PBS buffer pH 7.4 to remove any unbound protein and medium components by centrifugation at 2,000 rpm for 5 minutes using a Sorvall HT6 Centrifuge (Thermo Scientific, Waltham, Mass.). The plate containing resin was stacked on top of 0.2 µm 96-well filter plate (Orochem, Naperville, Ill., USA) and 96-well elution capture plate (Orochem, Naperville, Ill.). The bound half-antibodies were eluted from the resin with elution buffer (50 mM Phosphoric Acid, pH 2.9) in 2 sequential elution steps (total volume of elution—0.668 mL) by centrifugation at 2,000 rpm for 5 minutes and pH of the eluate was raised by addition of $1/12^{th}$ volume of neutralization buffer (1 M Arginine, 0.685 M Succinate, pH 5.0). Concentration of the half-antibody preps was calculated after measuring the absorbance at 280 nm using a NanoDrop 2000 spectrophotometer (Thermo Scientific, Wilmington, Del.).

Half-antibodies were assembled into biepitopic antibodies. Half-antibodies purified as described above were normalized to the same concentration and mixed in a 1:1 ratio using a Hamilton Star liquid handling workstation (Hamilton Robotics, Reno, Nev.). The pH of the mixture of half-antibodies was raised to 8.0 by adding 1M Arginine pH 9.5 solution. Reduced L-Glutathione in 0.5 M Stock in 1 M Arginine, pH 9.5 (Sigma-Aldrich, St. Louis, Mo.) was added so that final L-Glutathione concentration was 200 times excess over the amount of protein in the solution. This mixture was incubated at 32° C. for 24 hours to allow the half-antibodies to assemble into biepitopic antibodies.

The desired biepitopic antibodies (heterodimer composed of knob and hole half-antibodies) generated during assembly were purified away from other species (unassembled half-antibodies and knob-knob or hole-hole homodimers) by a 2-step process involving His-tag purification in a first step followed by Flag-tag purification in a second step. The first step involved use of 1.2 mL liquid handling tips (Dynamic Devices LLC, Wilmington, Del.) that were custom-packed (Glygen Corp, Columbia, Md.) with 0.1 mL of Ni-NTA Agarose resin (Qiagen, Valencia, Calif.). Using a Lynx LM1200 liquid handling workstation, all His-tagged species (including the unassembled Knob half-antibody, Knob-Knob homodimer and Knob-Hole heterodimer) were captured onto the resin tips by pipetting for 15 cycles. The resin tips were washed with 1 mL PBS pH 7.4 and the His-Tagged species were eluted from the tips in 2 sequential elution steps (total volume of elution=0.6 mL) with elution buffer (50 mM Sodium Phosphate, 500 mM Sodium Chloride, 300 mM Imidazole pH 7.5). The eluted samples were diluted 1:1 with reagent-grade water to prepare them for the next step.

To the solution obtained after first post assembly step purification, 0.4 mL of a 50% anti-FLAG antibody resin slurry was added using a Freedom EVO 200 liquid handling workstation and the resulting mixture was incubated on a Forma Orbital shaker (Thermo Electron Corporation, Madison, Wis.) at 250 RPM for 3 hours at 4° C. The resin was separated from the supernatant by centrifuging at 2,000 RPM for 5 minutes and transferred to a filter plate to be washed with 1 mL PBS pH 7.4 to remove any unbound proteins. The plate was stacked on top of 0.2 µm 96-well filter plate and 96-well elution capture plate. The bound biepitopic antibody (heterodimer) was eluted off the resin in 3 sequential elutions using a total of 1.57 mL elution buffer (50 mM Phosphoric Acid, pH 2.9) by centrifuging at 2,000 rpm for 5 minutes and neutralized with 0.11 mL of 20×PBS, pH 11.0 to adjust the pH of the purified biepitopic antibody solution to 6.0. Concentration of the biepitopic antibody was calculated after measuring the absorbance at 280 nm using a NanoDrop 2000 spectrophotometer.

Quality of the final purified biepitopic antibodies was assessed using analytical SEC HPLC and mass spectrometry. SEC was carried out by injecting 0.03 mL onto a TSKGel SuperSW3000 column (Tosoh Bioscience, King of Prussia, Pa.) attached to a Dionex UltiMate 3000 HPLC System (Thermo Scientific, Waltham, Mass.). The analysis was done with an isocratic gradient (200 mM Potassium Phosphate, 250 mM Potassium Chloride, pH 7.2). UV detection was set at 280 nM. Mass spectrometric data was acquired using an Agilent 6224 TOF LC-MS system (Agilent Technologies, Santa Clara, Calif., USA). Biepitopic antibody samples were reduced with 100 mM dithiothreitol (G-Biosciences, St. Louis, Mo.) at 37° C. for 20 minutes. The polypeptide chains were separated with a PLRP-S reversed phase column (Agilent Technologies, Santa Clara, Calif., USA). Intact masses of the reduced light and heavy chains were obtained by Maximun Entropy Deconvolution using MassHunter software (Qualitative Analysis B.03.01).

Results

Figure 1:
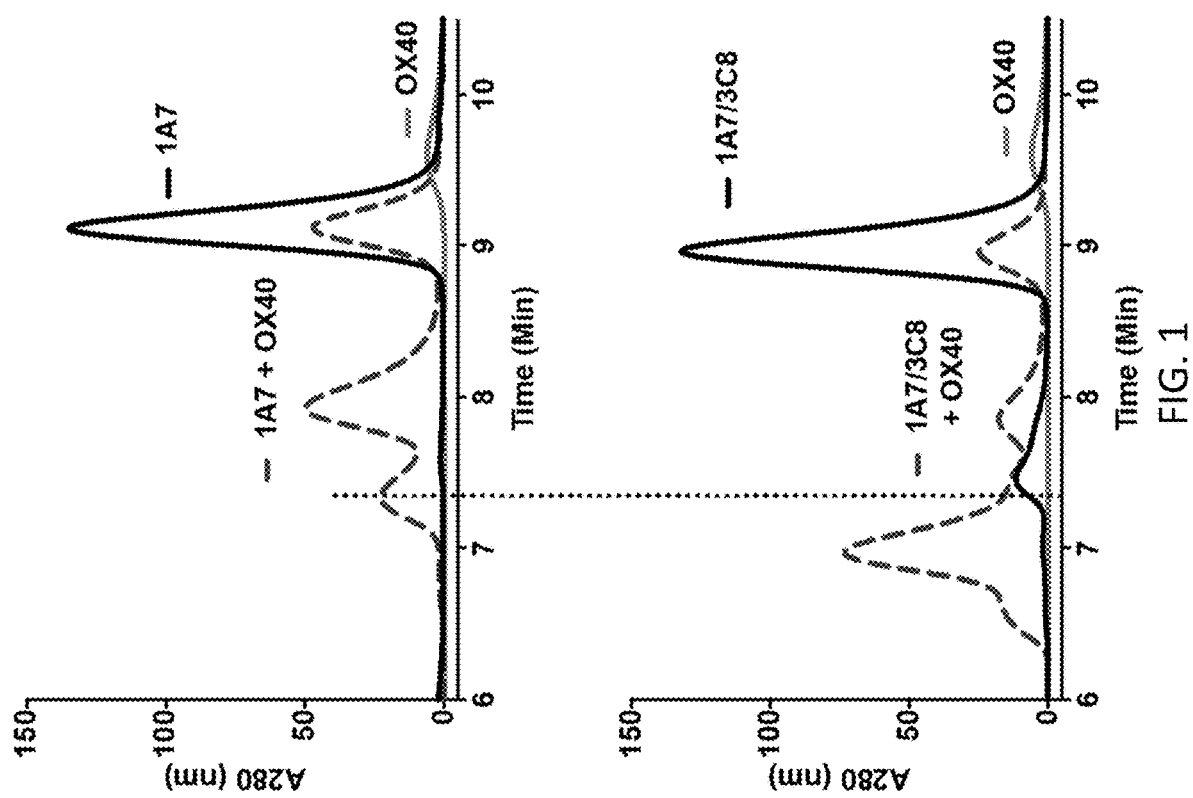
FIG. 1 shows Analytical Size Exclusion Chromatography (aSEC) chromatograms demonstrating that biepitopic 1A7/3C8 anti-OX40 antibody is able to promote higher order complexes in the presence of target antigen relative to monoepitopic antibody.

The ability of biepitopic 1A7/3C8 antibody to form higher-order complexes in the presence of OX40 was investigated using aSEC. 1A7 or 1A7/3C8 biepitopic antibody was mixed with human OX40 (G&P Biosciences FCL2479) at 2:1 ratio, incubated at RT for 2 hours, the mixtures were run on TSKGel SuperSW3000 column. The data are shown in FIG. 1. At the 2:1 antibody:OX40 ratio, monoepitopic 1A7 IgG1 antibody forms three species: free antibody, antibody with one arm bound, and antibody with 2 arms bound. In contrast, 1A7/3C8 forms species larger than 1:2 antibody:OX40 stoichiometry. The results indicate that biepitopic anti-OX40 antibody is able to promote higher order complexes in the presence of target antigen relative to monoepitopic antibody.

Example 2. Design of Multivalent Monoepitopic and Biepitopic Antibody Formats

Figure 2:
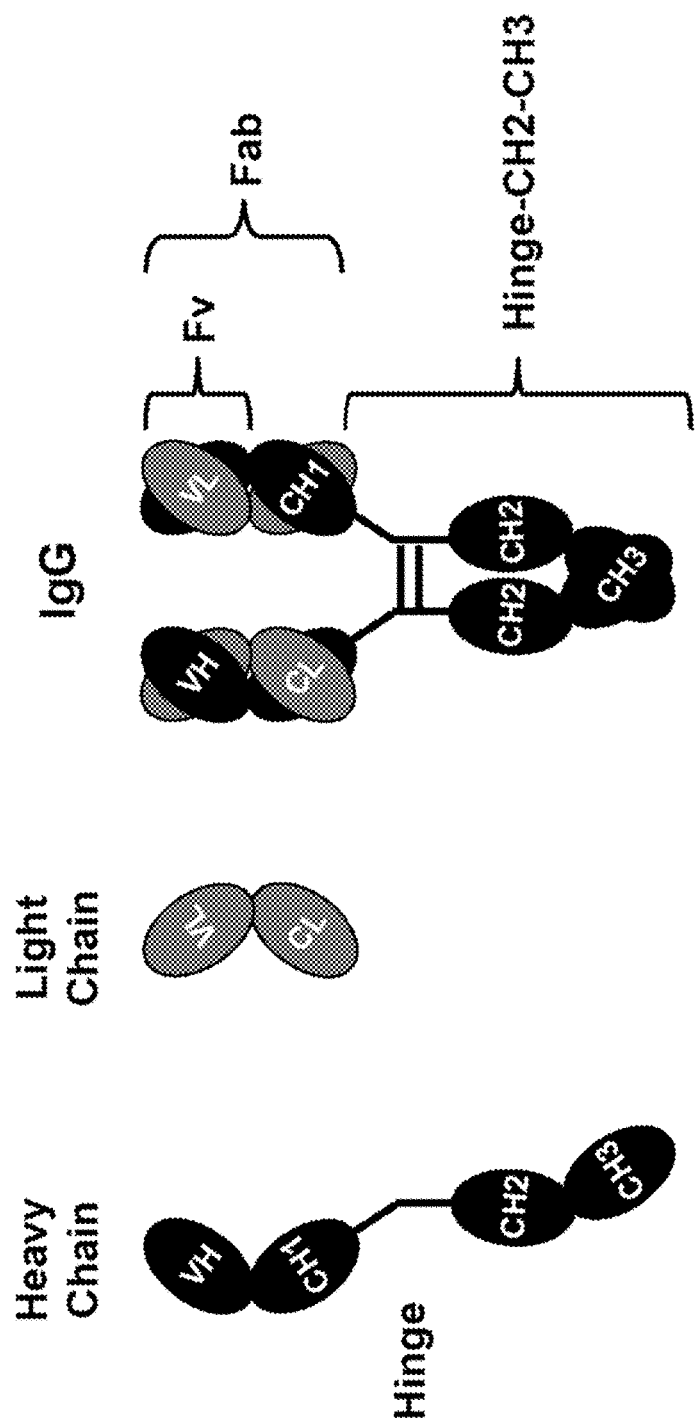
FIG. 2 illustrates the elements of an antibody that may be used to construct the novel antibody formats described herein.

A combination of multivalency and multiepitopic targeting was explored in attempt to engineer antibody formats with enhanced agonist activities. FIG. 2 depicts the structure of an IgG antibody that illustrates the elements used in engineering novel multivalent and multiepitopic antibody formats. IgG comprises a heavy chain and a light chain. Heavy chain comprises variable heavy domain (VH), constant heavy domain 1 (CH1), hinge, constant heavy domain 2 (CH2), and constant heavy domain 3 (CH3). Light chain comprises variable light domain (VL) and constant light domain (CL). CL can be constant kappa (Ck) or constant lambda (Cl). Fv region with specificity for target comprises variable heavy (VH) and variable light (VL) domains. Fab region with specificity for target comprises variable heavy (VH) and variable light (VL) domains, and constant heavy domain 1 (CH1) and constant light (CL). The IgG region excluded by the Fab region is heavy chain Hinge-CH2-CH3. FIGS. 3A & 3B show a series of multivalent and multiepitopic antibody formats that were engineered and characterized. Beyond a bivalent native IgG, four tetravalent (valency=4) formats were engineered: a coupled IgG-IgG (c:IgG-IgG) wherein two full length IgGs are chemically coupled, a coupled Fab-IgG (c:Fab-IgG) wherein two Fabs are chemically coupled to a full length IgG, a recombinant Fab-IgG (r:Fab-IgG) wherein two additional Fab arms are coupled genetically to an IgG, and a recombinant Fv-IgG (r:Fv-IgG) wherein two additional Fv regions are coupled genetically to an IgG. For each of these formats constructs were explored wherein all four variable regions bind the same epitope on the target antigen (referred to herein as monoepitopic), or wherein two variable regions bind one epitope and the other variable regions bind a distinct epitope on the target antigen (referred to herein as biepitopic).

All four variable regions may bind the same epitope on the target antigen, referred to herein as monoepitopic. For example all four variable regions may be the anti-OX40 1A7 variable region, or all four variable regions may be the anti-OX40 3C8 variable region. Alternatively, two variable regions may bind one epitope and the other two variable regions may bind a distinct epitope on the target antigen, referred to herein as biepitopic. For example two of the variable regions may be the 1A7 variable region, and the other two variable regions may be the 3C8 variable region.

Figure 4:
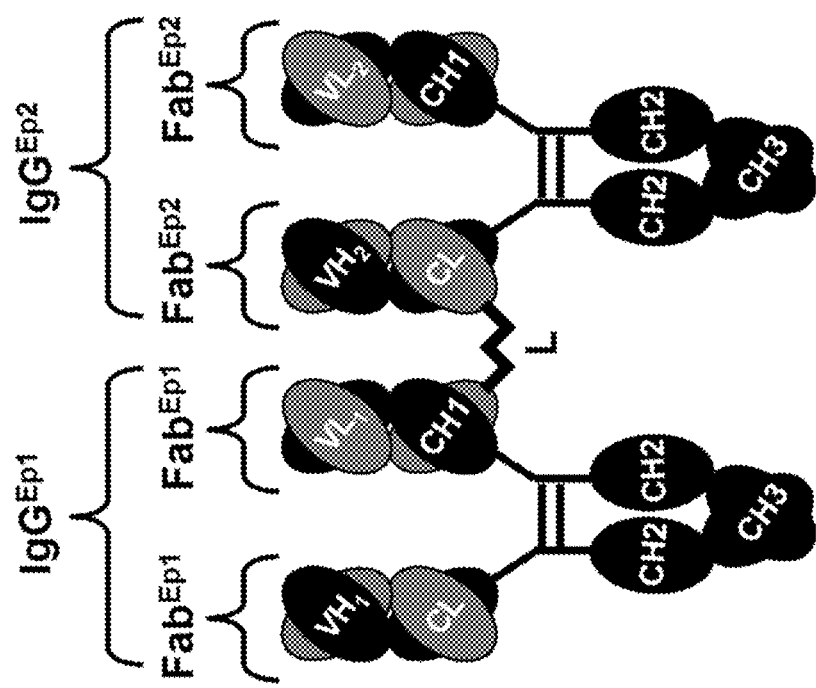
FIG. 4 depicts a first version of a biepitopic c:IgG-IgG format, in accordance with some embodiments.
Figure 5:
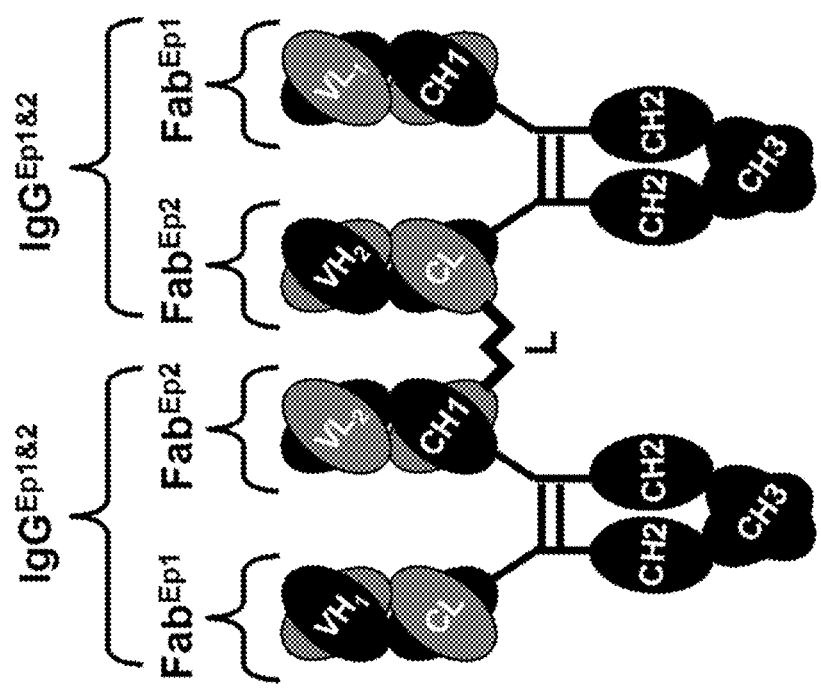
FIG. 5 depicts a second version of a biepitopic c:IgG-IgG format, in accordance with some embodiments.

A coupled IgG-IgG (c:IgG-IgG) format is described herein wherein two full length IgGs are chemically coupled. FIG. 4 illustrates the components of one version of a biepitopic c:IgG-IgG. In this version c:IgG-IgG comprises an $IgG^{Ep1}$ with specificity for epitope 1 chemically coupled to an $IgG^{Ep2}$ with specificity for epitope 2. $IgG^{Ep2}$ is linked to $IgG^{Ep1}$ through a chemical linker L. A variety of linkers may be used to connect $IgG^{Ep1}$ and $IgG^{Ep2}$. The site of attachment of $IgG^{Ep1}$ and $IgG^{Ep2}$ may vary. The c:IgG-IgG format described comprises four separate protein chains: $IgG^{Ep1}$ heavy chain (HC) composed of $VH_1$-Hinge-CH2-CH3, $IgG^{Ep1}$ light chain (LC) composed of $VL_1$-CL, $IgG^{Ep2}$ HC composed of $VH_2$-CH1-Hinge-CH2-CH3, and $IgG^{Ep2}$ LC composed of $VL_2$-CL. FIG. 5 illustrates the components of another version of a biepitopic c:IgG-IgG. In this version c:IgG-IgG comprises a biepitopic $IgG^{Ep1\&2}$ with specificity for both epitopes 1 and 2 chemically coupled to itself. $IgG^{Ep1\&2}$ is coupled through a chemical linker L. A variety of linkers may be used to couple $IgG^{Ep1\&2}$. The site of attachment of $IgG^{Ep1\&2}$ may vary. The c:IgG-IgG format described comprises four separate protein chains: $IgG^{Ep1}$ heavy chain (HC) composed of $VH_1$-Hinge-CH2-CH3, $IgG^{Ep1}$ light chain (LC) composed of $VL_1$-CL, $IgG^{Ep2}$HC composed of $VH_2$-CH1-Hinge-CH2-CH3, and $IgG^{Ep2}$ LC composed of $VL_2$-CL. In the examples described herein, c:IgG-IgG's are constructed and tested that comprise the variable regions of the 1A7 and 3C8 antibodies. In a preferred embodiment, $IgG^{Ep1\&2}$ comprises the 1A7 variable region and the 3C8 variable region, referred to as c:IgG-IgG 1A7/3C8-1A7/3C8.

Figure 6:
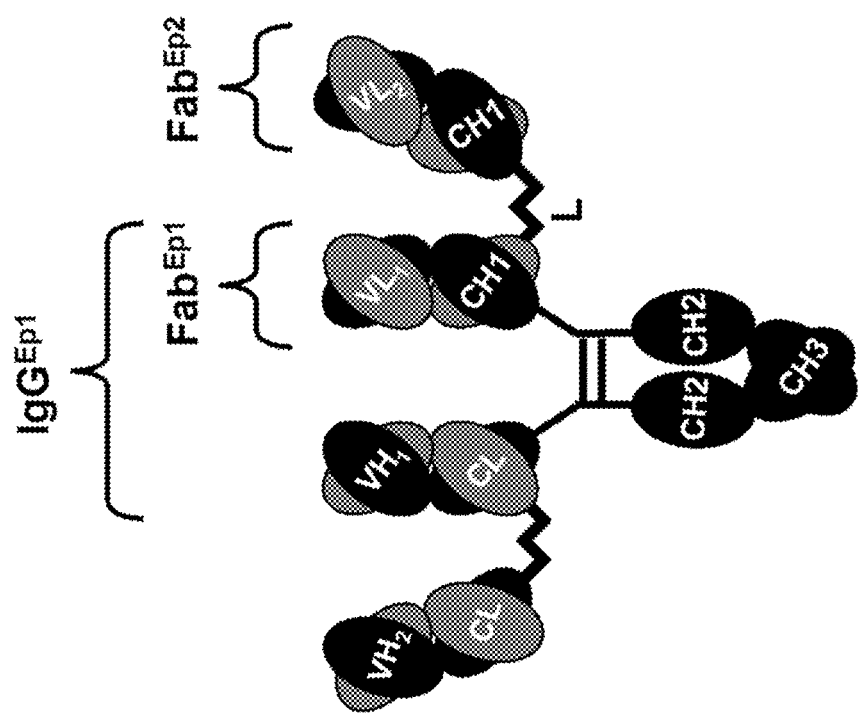
FIG. 6 depicts a biepitopic c:Fab-IgG format, in accordance with some embodiments.

A coupled Fab-IgG (c:Fab-IgG) format is described herein wherein two Fabs are chemically coupled to a full length IgG. FIG. 6 illustrates the components of the c:Fab-IgG format. c:Fab-IgG comprises an $IgG^{Ep1}$ with specificity for epitope 1 chemically coupled to $Fab^{Ep2}$ with specificity for epitope 2. $Fab^{Ep2}$ is linked to $IgG^{Ep1}$ through a chemical linker L. A variety of linkers may be used to connect $IgG^{Ep1}$ and $Fab^{Ep2}$. The site of attachment of $IgG^{Ep1}$ and $Fab^{Ep2}$ may vary. The c:Fab-IgG format comprises four separate protein chains: $IgG^{Ep1}$ heavy chain (HC) composed of $VH_1$-Hinge-CH2-CH3, $IgG^{Ep1}$ light chain (LC) composed of $VL_1$-CL, $Fab^{Ep2}$ HC composed of $VH_2$-CH1, and $Fab^{Ep2}$ LC composed of $VL_2$-CL.

In the examples described herein, c:Fab-IgG's were constructed and tested that comprise the variable regions of the 1A7 and 3C8 antibodies. In some embodiments, $IgG^{Ep1}$ comprises the 1A7 variable region and $Fab^{Ep2}$ comprises the 3C8 variable region, referred to as c:Fab-IgG 3C8-1A7. In some embodiments, $IgG^{Ep1}$ comprises the 3C8 variable region and $Fab^{Ep2}$ comprises the 1A7 variable region, referred to as c:Fab-IgG 1A7-3C8.

Figure 7:
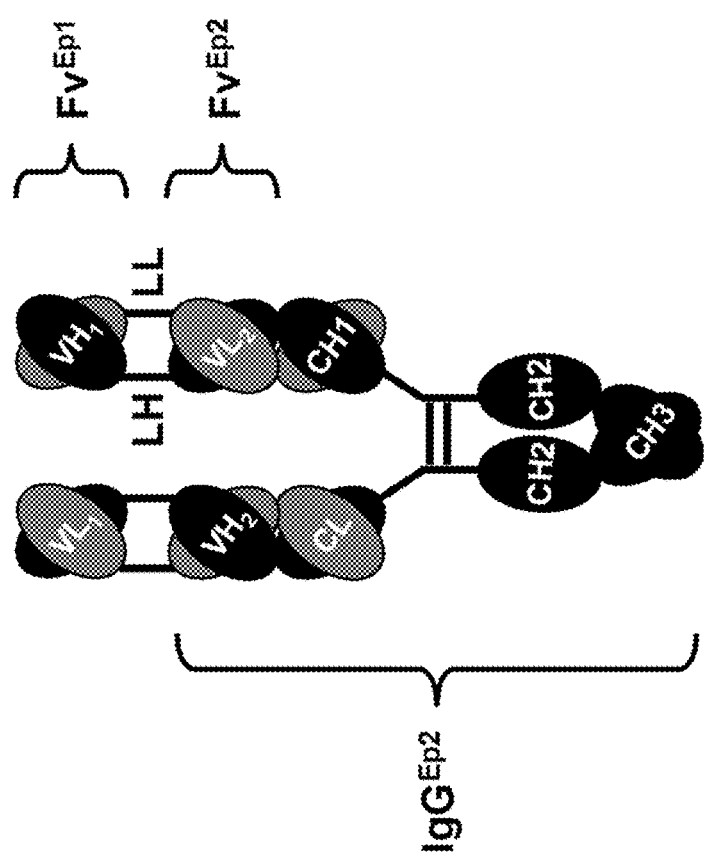
FIG. 7 depicts a biepitopic r:Fv-IgG format, in accordance with some embodiments.

A recombinant Fv-IgG (r:Fv-IgG) is described herein wherein two additional variable regions are genetically linked to an IgG. FIG. 7 illustrates the components of the r:Fv-IgG format. r:Fv-IgG comprises a single heavy chain and a single light chain. r:Fv-IgG comprises an $IgG^{Ep2}$ with specificity for epitope 2 linked N-terminally to $Fv^{Ep1}$ with specificity for epitope 1. $Fv^{Ep1}$ is linked to $IgG^{Ep2}$ through heavy chain linker LH and light chain linker LL. A variety of linkers may be used to connect $Fv^{Ep2}$ to $Fv^{Ep1}$. The heavy chain comprises regions $VH_1$-LH-$VH_2$-CH1-Hinge-CH2-CH3. The light chain comprises regions $VL_1$-LL-$VL_2$-CL. In this format, $Fv^{Ep2}$ with specificity for epitope 2 comprises $VH_2$ and $VL_2$ domains, and $Fv^{Ep1}$ with specificity for epitope 1 comprises $VH_1$ and $VL_1$ domains.

In the examples described herein, r:Fv-IgG's were constructed and tested that comprise the variable regions of the 1A7 and 3C8 antibodies. In some embodiments, $Fv^{Ep1}$ comprises the 3C8 variable region and $Fv^{Ep2}$ comprises the 1A7 variable region, referred to as r:Fv-IgG 3C8-1A7. In some embodiments, $Fv^{Ep1}$ comprises the 1A7 variable region and $Fv^{Ep2}$ comprises the 3C8 variable region, referred to as r:Fv-IgG 1A7-3C8. Sequences of the heavy and light chains of exemplary r:Fv-IgG's are listed in SEQ IDs 240-243. Exemplary linkers LH and LL are provided in SEQ IDs 270-278 and described below in Example 16. Alternate exemplary r:Fv-IgG's with different linkers LH and LL, described below in Example 16, are listed in SEQ IDs 250-257. Alternate exemplary r:Fv-IgG's comprising Fv's with differing OX40 affinities, as described below in Example 17, are listed in SEQ IDs 258-267.

Figure 8:
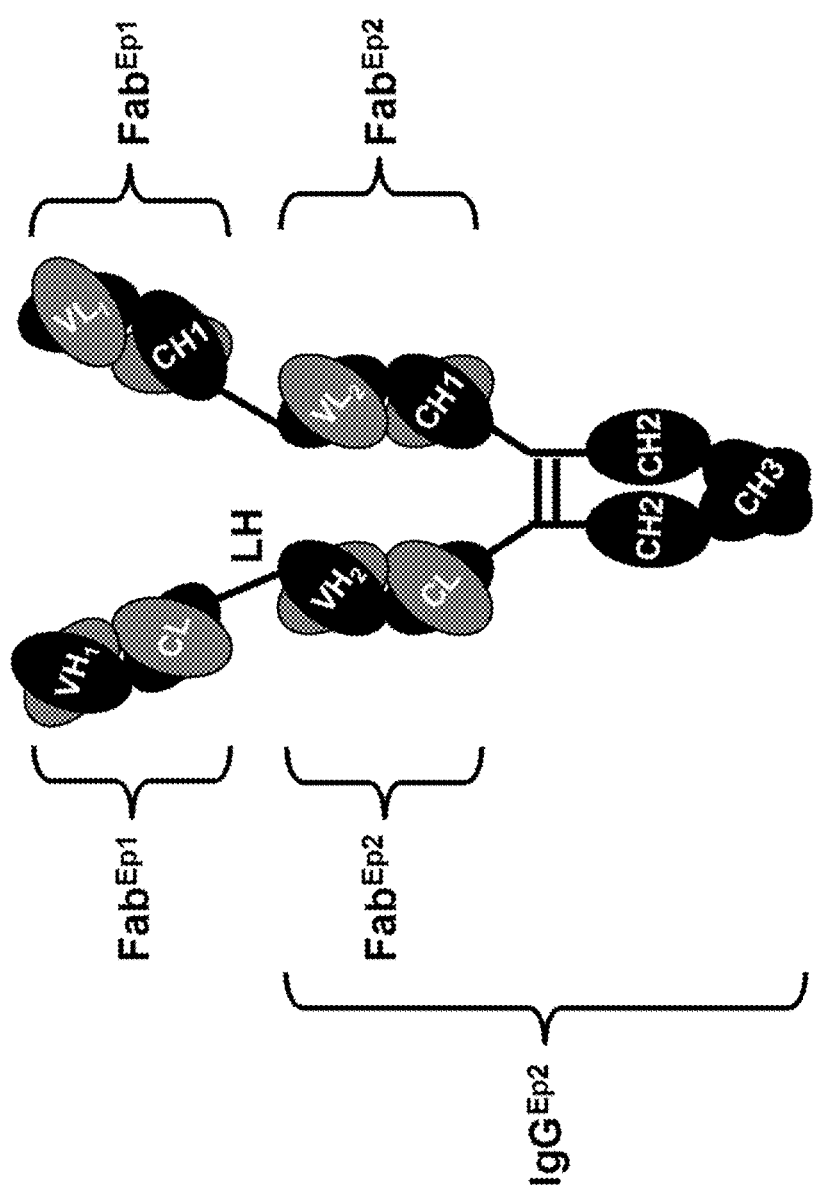
FIG. 8 depicts a first version of a biepitopic r:Fab-IgG format, in accordance with some embodiments.

A recombinant Fab-IgG (r:Fab-IgG) is described herein wherein two additional Fab arms are linked genetically to an IgG. FIG. 8 illustrates the components of one version of the r:Fab-IgG format comprising one homodimeric HC and two LC's. This r:Fab-IgG version (referred to herein as r:Fab-IgG V1) comprises $IgG^{Ep2}$ with specificity for epitope 2 linked N-terminally to $Fab^{Ep1}$ with specificity for epitope 1. $Fab^{Ep1}$ is linked to $IgG^{Ep2}$ through heavy chain linker LH. A variety of linkers may be used to connect $Fab^{Ep1}$ to $IgG^{Ep2}$. The HC in r:Fab-IgG V1 comprises $VH_1$-CH1-LH-$VH_2$-CH1-Hinge-CH2-CH3. One LC comprises $VL_1$-CL, and the other LC comprises $VH_2$—CL. Correct pairing between heavy and light chains may be controlled using engineered variants in VH, CH1, VL, and/or CL domains, as described in the examples herein. In this format $Fv^{Ep2}$ with specificity for epitope 2 comprises $VH_2$ and $VL_2$ domains, and $Fv^{Ep1}$ with specificity for epitope 1 comprises $VH_1$ and $VL_1$ domains.

In the examples described herein, r:Fab-IgG V1 antibodies were constructed and tested that comprise the variable regions of the 1A7 and 3C8 antibodies. In some embodiments, $Fv^{Ep1}$ comprises the 3C8 variable region and $Fv^{Ep2}$ comprises the 1A7 variable region, referred to as r:Fab-IgG 3C8-1A7. In some embodiments, $Fv^{Ep1}$ comprises the 1A7 variable region and $Fv^{Ep2}$ comprises the 3C8 variable region, referred to as r:Fab-IgG 1A7-3C8. Sequences of the heavy and light chains of exemplary anti-OX40 r:Fab-IgG's are listed in SEQ IDs 244-249.

Figure 9:
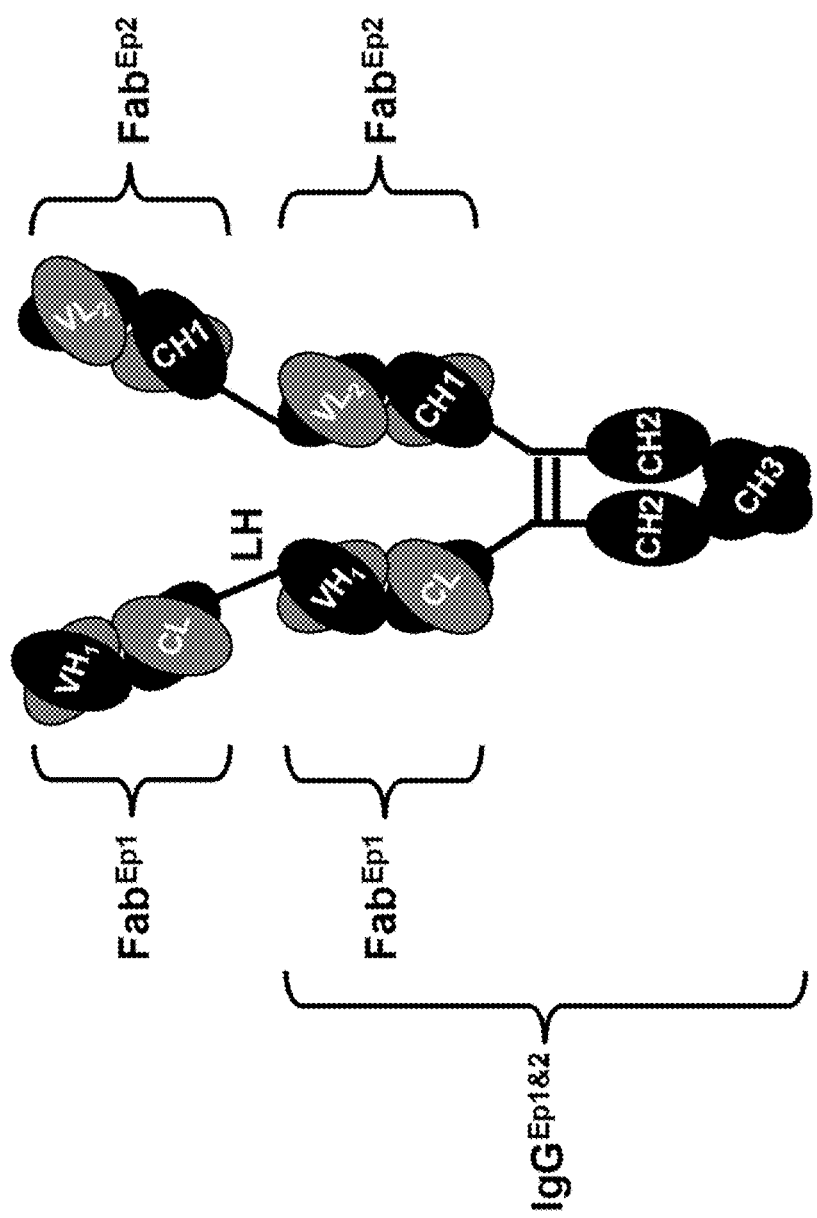
FIG. 9 depicts a second version of a biepitopic r:Fab-IgG format, in accordance with some embodiments.

FIG. 9 illustrates the components of an alternate version of the r:Fab-IgG format comprising a heterodimeric HC and two LC's. This r:Fab-IgG version (referred to herein as r:Fab-IgG V2) comprises $Fab^{Ep2}$ linked to one arm of $IgG^{Ep1\&2}$ through heavy chain linker LH, and $Fab^{Ep1}$ is linked to the other arm of $IgG^{Ep1\&2}$ through heavy chain linker LH. A variety of linkers may be used to connect Fab$^{Ep1}$ to IgG$^{Ep1\&2}$ and Fab$^{Ep2}$ to IgG$^{Ep1\&2}$. One HC of this format comprises VH$_2$-CH1-LH-VH$_2$-CH1-Hinge-CH2-CH3, and the other HC of this format comprises VH$_1$-CH1-LH-VH$_1$-CH1-Hinge-CH2-CH3. One LC of this format comprises VL$_2$-CL, and the other LC comprises VH$_1$-CL. Fv$^{Ep2}$ with specificity for epitope 2 comprises VH$_2$ and VL$_2$ domains. Fv$^{Ep1}$ with specificity for epitope 1 comprises VH$_1$ and VL$_1$ domains. Engineered variants may be used to promote heterodimer formation of the heavy chains.

A variety of linkers may be used to connect Fab$^{Ep1}$ to IgG$^{Ep2}$. Linkers may comprise sequences that substantially comprise serine, glycine, or serine and glycine. Such Gly-Ser linkers may comprise greater than 50% glycine and/or serine, greater than 70% glycine and/or serine, greater than 90% glycine and/or serine, or 100% glycine and/or serine. Serine and glycine are commonly used as linkers due to their flexibility and favorable solution properties. Linkers may otherwise or also comprise sequences that substantially comprise native antibody sequence. In these linkers, native sequences that compose antibody sequences are used as linkers. Particularly useful native antibody sequences for the r:Fab-IgG are heavy chain sequences that reside in the hinge region of a native antibody between heavy chain constant regions CH1 and CH2. The utility of native antibody sequence linkers is that they can be used to reduce some non-native sequence within a tetravalent antibody format. The length of a given linker can vary, from 1 residue to 20 or more residues. Greater length typically provides greater flexibility between linked immunoglobulin domains. Exemplary recombinant linkers for use in the r:Fab-IgGs of the present disclosure are described in SEQ ID NO:268 and 269.

SEQ ID NO:268. LH Linker for r:Fab-IgG: DKTHT

SEQ ID NO:269. LH Linker for r:Fab-IgG: DKTHTGGGGSGG

While r:Fab-IgG formats are described herein wherein a Fab is linked to an IgG through a single heavy chain linker (LH), it is contemplated that r:Fab-IgGs may also comprise linkers between light chains. Indeed linked light chain constructs were explored for the r:Fab-IgG format, but resulted in larger a higher population of aggregated species upon expression and purification (data not shown) and so were not characterized further.

Exemplary sequences of heavy and light chains of the anti-OX40 IgG and tetravalent formats described herein are provided below. Linkers are underlined where appropriate.

r:Fv-IgG Format
SEQ ID NO:240. r:Fv-IgG 1A7-3C8 Heavy Chain.
SEQ ID NO:241. r:Fv-IgG 1A7-3C8 Light Chain.
SEQ ID NO:242. r:Fv-IgG 3C8-1A7 Heavy Chain.
SEQ ID NO:243. r:Fv-IgG 3C8-1A7 Light Chain
SEQ ID NO:250. r: Fv-IgG 3C8-1A7 GS Short Linker Heavy Chain.
SEQ ID NO:251. r: Fv-IgG 3C8-1A7 GS Short Linker Light Chain.
SEQ ID NO:252. r: Fv-IgG 3C8-1A7 GS Long Linker Heavy Chain.
SEQ ID NO:253. r: Fv-IgG 3C8-1A7 GS Long Linker Light Chain.
SEQ ID NO:254. r: Fv-IgG 3C8-1A7 ES Short Elbow Linker Heavy Chain.
SEQ ID NO:255. r: Fv-IgG 3C8-1A7 ES Short Elbow Linker Light Chain.
SEQ ID NO:256. r: Fv-IgG 3C8-1A7 EL Long Elbow Linker Heavy Chain.
SEQ ID NO:257. r: Fv-IgG 3C8-1A7 EL Long Elbow Linker Light Chain.
SEQ ID NO:258. r: Fv-IgG 3C8-1A7(High) Heavy Chain.
SEQ ID NO:259. r: Fv-IgG 3C8-1A7(High) Light Chain.
SEQ ID NO:260. r: Fv-IgG 3C8(High)-1A7 Heavy Chain.
SEQ ID NO:261. r: Fv-IgG 3C8(High)-1A7 Light Chain
SEQ ID NO:262. r: Fv-IgG 3C8(High)-1A7(High) Heavy Chain
SEQ ID NO:263. r: Fv-IgG 3C8(High)-1A7(High) Light Chain
SEQ ID NO:264. r: Fv-IgG 3C8(High)-1A7(Low) Heavy Chain
SEQ ID NO:265. r: Fv-IgG 3C8(High)-1A7(Low) Light Chain
SEQ ID NO:266. r: Fv-IgG 3C8-1A7(Low) Heavy Chain
SEQ ID NO:267. r: Fv-IgG 3C8-1A7(Low) Light Chain r:Fab-IgG Format
SEQ ID NO:244. r:Fab-IgG 1A7-3C8 Heavy Chain.
SEQ ID NO:245. r:Fab-IgG 1A7-3C8 Light Chain 1.
SEQ ID NO:246. r:Fab-IgG 1A7-3C8 Light Chain 2.
SEQ ID NO:247. r: Fab-IgG 3C8-1A7 Heavy chain.
SEQ ID NO:248. r: Fab-IgG 3C8-1A7 Light chain 1.
SEQ ID NO:249. r: Fab-IgG 3C8-1A7 Light chain 2.

c:Fab-IgG Format
SEQ ID NO:232. 3C8_IgG1 (Full Length Heavy Chain).
SEQ ID NO:237. 3C8_Ckappa(K149C) (Light Chain).
SEQ ID NO:239. 1A7_CH1-SPPC (Fab Heavy Chain).
SEQ ID NO:231. 1A7_Ckappa (Light Chain).
SEQ ID NO:230. 1A7_IgG1 (Full Length Heavy Chain).
SEQ ID NO:236. 1A7_Ckappa(K149C) (Light Chain).
SEQ ID NO:238. 3C8_CH1-SPPC (Fab Heavy Chain).
SEQ ID NO:233. 3C8_Ckappa (Light Chain).

Sequences

```
SEQ ID NO: 230. 1A7_IgG1 (Full Length Heavy Chain).
EVQLVQSGAEVKKPGASVKVSCKASGYTFTDSYMSWVRQAPGQGLEWIG

DMYPDNGDSSYNQKFRERVTITRDTSTSTAYLELSSLRSEDTAVYYCVLAPRWYFSV

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPGK
```

SEQ ID NO: 231. 1A7_Ckappa (Light Chain).
DIQMTQSPSSLSASVGDRVTITCRASQDISNYLNWYQQKPGKAPKLLIYYTS

RLRSGVPSRFSGSGSGTDFTLTISSLQPEDFATYYCQQGHTLPPTFGQGTKVEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

SEQ ID NO: 232. 3C8_IgG1 (Full Length Heavy Chain).
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID NO: 233. 3C8_Ckappa (Light Chain).
DIQMTQSPSSLSASVGDRVTITCHASQDISSYIVWYQQKPGKSFKGLIYHGT

NLESGVPSRFSGSGSGTDFTLTISSLQPEDFATYYCVHYAQFPYTFGQGTKVEIKRTV

AAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

SEQ ID NO: 234. 1A7_CH1 (Fab Heavy Chain).
EVQLVQSGAEVKKPGASVKVSCKASGYTFTDSYMSWVRQAPGQGLEWIG

DMYPDNGDSSYNQKFRERVTITRDTSTSTAYLELSSLRSEDTAVYYCVLAPRWYFSV

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSC

SEQ ID NO: 235. 3C8_CH1 (Fab Heavy Chain).
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSC

SEQ ID NO: 236. 1A7_Ckappa(K149C) (Light Chain).
DIQMTQSPSSLSASVGDRVTITCRASQDISNYLNWYQQKPGKAPKLLIYYTS

RLRSGVPSRFSGSGSGTDFTLTISSLQPEDFATYYCQQGHTLPPTFGQGTKVEIKRTVA

APSVFIFPPSDEQLKSGTASVVCLLNNFYPREAKVQWCVDNALQSGNSQESVTEQDS

KDSTYSLSSTLTLSKADYEKHKVYACEVTHQGLSSPVTKSFNRGEC

SEQ ID NO: 237. 3C8_Ckappa(K149C) (Light Chain).
DIQMTQSPSSLSASVGDRVTITCHASQDISSYIVWYQQKPGKSFKGLIYHGT

NLESGVPSRFSGSGSGTDFTLTISSLQPEDFATYYCVHYAQFPYTFGQGTKVEIKRTV

AAPSVFIFPPSDEQLKSGTASVVCLLNNFYPREAKVQWCVDNALQSGNSQESVTEQD

SKDSTYSLSSTLTLSKADYEKHKVYACEVTHQGLSSPVTKSFNRGEC

SEQ ID NO: 238. 3C8_CH1-SPPC (Fab Heavy Chain).
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHT

SPPC

SEQ ID NO: 239. 1A7_CH1-SPPC (Fab Heavy Chain).
EVQLVQSGAEVKKPGASVKVSCKASGYTFTDSYMSWVRQAPGQGLEWIG

DMYPDNGDSSYNQKFRERVTITRDTSTSTAYLELSSLRSEDTAVYYCVLAPRWYFSV

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSCD

KTHTSPPC

SEQ ID NO: 240. r:Fv-IgG 1A7-3C8 Heavy Chain.
EVQLVQSGAEVKKPGASVKVSCKASGYTFTDSYMSWVRQAPGQGLEWIG

DMYPDNGDSSYNQKFRERVTITRDTSTSTAYLELSSLRSEDTAVYYCVLAPRWYFSV

WGQGTLVTVSSGGGGSGGGGSEVQLVQSGAEVKKPGASVKVSCKASGYAFTNYLIE

WVRQAPGQGLEWIGVINPGSGDTYYSEKFKGRVTLTADTSTSTAYLELSSLRSEDTA

VYYCARDRLDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNH

YTQKSLSLSPGK

SEQ ID NO: 241. r:Fv-IgG 1A7-3C8 Light Chain.
DIQMTQSPSSLSASVGDRVTITCRASQDISNYLNWYQQKPGKAPKLLIYYTS

RLRSGVPSRFSGSGSGTDFTLTISSLQPEDFATYYCQQGHTLPPTFGQGTKVEIKGGG

GSGGGGSDIQMTQSPSSLSASVGDRVTITCHASQDISSYIVWYQQKPGKSFKGLIYHG

TNLESGVPSRFSGSGSGTDFTLTISSLQPEDFATYYCVHYAQFPYTFGQGTKVEIKRT

VAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

SEQ ID NO: 242. r:Fv-IgG 3C8-1A7 Heavy Chain.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSSGGGGSGGGGSEVQLVQSGAEVKKPGASVKVSCKASGYTFTDSYMSWVR

QAPGQGLEWIGDMYPDNGDSSYNQKFRERVTITRDTSTSTAYLELSSLRSEDTAVYY

CVLAPRWYFSVWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTK

VDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNH

YTQKSLSLSPGK

SEQ ID NO: 243. r:Fv-IgG 3C8-1A7 Light Chain.
DIQMTQSPSSLSASVGDRVTITCHASQDISSYIVWYQQKPGKSFKGLIYHGT

NLESGVPSRFSGSGSGTDFTLTISSLQPEDFATYYCVHYAQFPYTFGQGTKVEIKGGG

GSGGGGSDIQMTQSPSSLSASVGDRVTITCRASQDISNYLNWYQQKPGKAPKLLIYY

TSRLRSGVPSRFSGSGSGTDFTLTISSLQPEDFATYYCQQGHTLPPTFGQGTKVEIKRT

VAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

SEQ ID NO: 244. r:Fab-IgG 1A7-3C8 Heavy Chain.
EVQLVQSGAEVKKPGASVKVSCKASGYTFTDSYMSWVRKAPGQGLEWIG

DMYPDNGDSSYNQKFRERVTITRDTSTSTAYLELSSLRSEDTAVYYCVLAPRWYFSV

WGQGTLVTVSSASTKGPSVFPLAPSSKSTSGGTAALGCLVKDYFPEPVTVSWNSGAL

TSGVHTFPAVLQSSGLYSLESVVTVPSSSLGTQTYICNVNHKPSNTKVDKKVEPKSC<u>D</u>

<u>KTHTGGGGSGG</u>EVQLVQSGAEVKKPGASVKVSCKASGYAFTNYLIEWVREAPGQG

LEWIGVINPGSGDTYYSEKFKGRVTLTADTSTSTAYLELSSLRSEDTAVYYCARDRL

DYWGQGTLVTVSSASTKGPSVFPLAPSSKSTSGGTAALGCLVKDYFPEPVTVSWNSG

ALTSGVHTFPAVLQSSGLYSLKSVVTVPSSSLGTQTYICNVNHKPSNTKVDKKVEPK

SCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLS

PG

SEQ ID NO: 245. r:Fab-IgG 1A7-3C8 Light Chain 1.
DIQMTQSPSSLSASVGDRVTITCRASQDISNYLNWYQEKPGKAPKLLIYYTS

RLRSGVPSRFSGSGSGTDFTLTISSLQPEDFATYYCQQGHTLPPTFGQGTKVEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

SEQ ID NO: 246. r:Fab-IgG 1A7-3C8 Light Chain 2.
DIQMTQSPSSLSASVGDRVTITCHASQDISSYIVWYQKKPGKSFKGLIYHGT

NLESGVPSRFSGSGSGTDFTLTISSLQPEDFATYYCVHYAQFPYTFGQGTKVEIKRTV

AAPSVFIFPPSDEQLKSGTASVECLLNNFYPREAKVQWKVDNALQSGNSQESVTEQD

SKDSTYSLSSTLTLSKADYEKHKVYACEVTHQGLSSPVTKSFNRGEC

SEQ ID NO: 247. r: Fab-IgG 3C8-1A7 Heavy chain.
EVQLVQSGAEVKKPGASVKVSCKASGYAFTNYLIEWVRKAPGQGLEWIGV

INPGSGDTYYSEKFKGRVTLTADTSTSTAYLELSSLRSEDTAVYYCARDRLDYWGQG

TLVTVSSASTKGPSVFPLAPSSKSTSGGTAALGCLVKDYFPEPVTVSWNSGALTSGV

HTFPAVLQSSGLYSLESVVTVPSSSLGTQTYICNVNHKPSNTKVDKKVEPKSC<u>DKTH</u>

<u>TGGGGSGG</u>EVQLVQSGAEVKKPGASVKVSCKASGYTFTDSYMSWVREAPGQGLEW

IGDMYPDNGDSSYNQKFRERVTITRDTSTSTAYLELSSLRSEDTAVYYCVLAPRWYF

SVWGQGTLVTVSSASTKGPSVFPLAPSSKSTSGGTAALGCLVKDYFPEPVTVSWNSG

ALTSGVHTFPAVLQSSGLYSLKSVVTVPSSSLGTQTYICNVNHKPSNTKVDKKVEPK

SCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLS

PG

SEQ ID NO: 248. r: Fab-IgG 3C8-1A7 Light chain 1.
DIQMTQSPSSLSASVGDRVTITCHASQDISSYIVWYQEKPGKSFKGLIYHGTN

LESGVPSRFSGSGSGTDFTLTISSLQPEDFATYYCVHYAQFPYTFGQGTKVEIKRTVA

APSVFIFPPSDEQLKSGTASVKCLLNNFYPREAKVQWKVDNALQSGNSQESVTEQDS

KDSTYSLSSTLTLSKADYEKHKVYACEVTHQGLSSPVTKSFNRGEC

SEQ ID NO: 249. r: Fab-IgG 3C8-1A7 Light chain 2.
DIQMTQSPSSLSASVGDRVTITCRASQDISNYLNWYQKKPGKAPKLLIYYTS

RLRSGVPSRFSGSGSGTDFTLTISSLQPEDFATYYCQQGHTLPPTFGQGTKVEIKRTVA

APSVFIFPPSDEQLKSGTASVECLLNNFYPREAKVQWKVDNALQSGNSQESVTEQDS

KDSTYSLSSTLTLSKADYEKHKVYACEVTHQGLSSPVTKSFNRGEC

SEQ ID NO: 250. r: Fv-IgG 3C8-1A7 GS Short Linker Heavy Chain, as described
in Example 16.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSS<u>GGGGS</u>EVQLVQSGAEVKKPGASVKVSCKASGYTFTDSYMSWVRQAPG

QGLEWIGDMYPDNGDSSYNQKFRERVTITRDTSTSTAYLELSSLRSEDTAVYYCVLA

PRWYFSVWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQ

KSLSLSPGK

SEQ ID NO: 251. r: Fv-IgG 3C8-
1A7 GS Short Linker Light Chain, as described in
Example 16.
DIQMTQSPSSLSASVGDRVTITCHASQDISSYIVWYQQKPGKSFKGLIYHGT NLESGVPSRFSGSGSGTDFTLTISSLQPEDFATYYCVHYAQFPYTFGQGTKVEIK<u>GGS</u>

<u>GG</u>DIQMTQSPSSLSASVGDRVTITCRASQDISNYLNWYQQKPGKAPKLLIYYTSRLRS

GVPSRFSGSGSGTDFTLTISSLQPEDFATYYCQQGHTLPPTFGQGTKVEIKRTVAAPSV

FIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC

SEQ ID NO: 252. r: Fv-IgG 3C8-1A7 GS Long Linker Heavy Chain, as described
in Example 16.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSS<u>GGGGSGGGGSGGGG</u>EVQLVQSGAEVKKPGASVKVSCKASGYTFTDSYM

SWVRQAPGQGLEWIGDMYPDNGDSSYNQKFRERVTITRDTSTSTAYLELSSLRSEDT

AVYYCVLAPRWYFSVWGQGTLVTVSSASTKGPSVFPLAPSSKSTSGGTAALGCLVK

DYFPEPVTVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHEA

LHNHYTQKSLSLSPGK

-continued

SEQ ID NO: 253. r: Fv-IgG 3C8-1A7 GS Long Linker Light Chain, as described in Example 16.
DIQMTQSPSSLSASVGDRVTITCHASQDISSYIVWYQQKPGKSFKGLIYHGT NLESGVPSRFSGSGSGTDFTLTISSLQPEDFATYYCVHYAQFPYTFGQGTKVEIK<u>GGS</u>

<u>GGGGSGGGGS</u>DIQMTQSPSSLSASVGDRVTITCRASQDISNYLNWYQQKPGKAPKLL

IYYTSRLRSGVPSRFSGSGSGTDFTLTISSLQPEDFATYYCQQGHTLPPTFGQGTKVEI

KRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC

SEQ ID NO: 254. r: Fv-IgG 3C8-1A7 ES Short Elbow Linker Heavy Chain, as described in Example 16.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSS<u>ASTKGP</u>EVQLVQSGAEVKKPGASVKVSCKASGYTFTDSYMSWVRQAPGQ

GLEWIGDMYPDNGDSSYNQKFRERVTITRDTSTSTAYLELSSLRSEDTAVYYCVLAP

RWYFSVWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKS

LSLSPGK

SEQ ID NO: 255. r: Fv-IgG 3C8-1A7 ES Short Elbow Linker Light Chain, as described in Example 16.
DIQMTQSPSSLSASVGDRVTITCHASQDISSYIVWYQQKPGKSFKGLIYHGT NLESGVPSRFSGSGSGTDFTLTISSLQPEDFATYYCVHYAQFPYTFGQGTKVEIK<u>RTV</u>

<u>AAP</u>DIQMTQSPSSLSASVGDRVTITCRASQDISNYLNWYQQKPGKAPKLLIYYTSRLR

SGVPSRFSGSGSGTDFTLTISSLQPEDFATYYCQQGHTLPPTFGQGTKVEIKRTVAAPS

VFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

SEQ ID NO: 256. r: Fv-IgG 3C8-1A7 EL Long Elbow Linker Heavy Chain, as described in Example 16.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDRLDYWGQG

TLVTVSS<u>ASTKGPSVFPLAP</u>EVQLVQSGAEVKKPGASVKVSCKASGYTFTDSYMSW

VRQAPGQGLEWIGDMYPDNGDSSYNQKFRERVTITRDTSTSTAYLELSSLRSEDTAV

YYCVLAPRWYFSVWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSVMHEALH

NHYTQKSLSLSPGK

SEQ ID NO: 257. r: Fv-IgG 3C8-1A7 EL Long Elbow Linker Light Chain, as described in Example 16.
DIQMTQSPSSLSASVGDRVTITCHASQDISSYIVWYQQKPGKSFKGLIYHGT NLESGVPSRFSGSGSGTDFTLTISSLQPEDFATYYCVHYAQFPYTFGQGTKVEIK<u>RTV</u>

<u>AAPSVFIFPPP</u>DIQMTQSPSSLSASVGDRVTITCRASQDISNYLNWYQQKPGKAPKLLIY

YTSRLRSGVPSRFSGSGSGTDFTLTISSLQPEDFATYYCQQGHTLPPTFGQGTKVEIKR

TVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

SEQ IDs 258 and 259 describe heavy and light chain sequences for r:Fv-IgG 3C8-1A7(High), which comprises 1A7 VH mutation M34I and VL mutation R53Y, described in Example 17.

SEQ ID NO: 258. r: Fv-IgG 3C8-1A7(High) Heavy Chain.
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDR

LDYWGQGTLVTVSS<u>GGGGSGGGGS</u>EVQLVQSGAEVKKPGASVKVSCKASG

YTFTDSYISWVRQAPGQGLEWIGDMYPDNGDSSYNQKFRERVTITRDTST

STAYLELSSLRSEDTAVYYCVLAPRWYFSVWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

SEQ ID NO:259. r: Fv-IgG 3C8-1A7(High) Light Chain.
DIQMTQSPSSLSASVGDRVTITCHASQDISSYIVWYQQKPGKSFKGLIYH

GTNLESGVPSRFSGSGSGTDFTLTISSLQPEDFATYYCVHYAQFPYTFGQ

GTKVEIK<u>GGGGSGGGGS</u>DIQMTQSPSSLSASVGDRVTITCRASQDISNYL

NWYQQKPGKAPKLLIYYTSYLRSGVPSRFSGSGSGTDFTLTISSLQPEDF

ATYYCQQGHTLPPTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

SEQ IDs 260 and 261 describe heavy and light chain sequences for r:Fv-IgG 3C8(High), which comprises 3C8 VH mutations M31I and K64L, as described in Example 17.

SEQ ID NO: 260. r: Fv-IgG 3C8(High)-1A7 Heavy Chain.
EVQLVQSGAEVKKPGASVKVSCKASGYAFTIYLIEWVRQAPGQGLEWIGV

INPGSGDTYYSEKFLGRVTLTADTSTSTAYLELSSLRSEDTAVYYCARDR

LDYWGQGTLVTVSS<u>GGGGSGGGGS</u>EVQLVQSGAEVKKPGASVKVSCKASG

YTFTDSYMSWVRQAPGQGLEWIGDMYPDNGDSSYNQKFRERVTITRDTST

STAYLELSSLRSEDTAVYYCVLAPRWYFSVWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

SEQ ID NO: 261. r: Fv-IgG 3C8(High)-1A7 Light Chain
DIQMTQSPSSLSASVGDRVTITCHASQDISSYIVWYQQKPGKSFKGLIYH

GTNLESGVPSRFSGSGSGTDFTLTISSLQPEDFATYYCVHYAQFPYTFGQ

GTKVEIK<u>GGGGSGGGGS</u>DIQMTQSPSSLSASVGDRVTITCRASQDISNYL

NWYQQKPGKAPKLLIYYTSRLRSGVPSRFSGSGSGTDFTLTISSLQPEDF

ATYYCQQGHTLPPTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

SEQ IDs 262 and 263 describe heavy and light chain sequences for r:Fv-IgG 3C8(High)-1A7(High), which comprises 3C8 VH mutations M31I and K64L, 1A7 VH mutation M34I, and 1A7 VL mutation R53Y, described in Example 17.

SEQ ID NO: 262. r: Fv-IgG 3C8(High)-1A7(High) Heavy Chain
EVQLVQSGAEVKKPGASVKVSCKASGYAFTIYLIEWVRQAPGQGLEWIGV

INPGSGDTYYSEKFLGRVTLTADTSTSTAYLELSSLRSEDTAVYYCARDR

LDYWGQGTLVTVSS<u>GGGGSGGGGS</u>EVQLVQSGAEVKKPGASVKVSCKASG

YTFTDSYISWVRQAPGQGLEWIGDMYPDNGDSSYNQKFRERVTITRDTST

STAYLELSSLRSEDTAVYYCVLAPRWYFSVWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

SEQ ID NO: 263. r: Fv-IgG 3C8(High)-1A7(High)
Light Chain
DIQMTQSPSSLSASVGDRVTITCHASQDISSYIVWYQQKPGKSFKGLIYH

GTNLESGVPSRFSGSGSGTDFTLTISSLQPEDFATYYCVHYAQFPYTFGQ

GTKVEIKGGGGSGGGGSDIQMTQSPSSLSASVGDRVTITCRASQDISNYL

NWYQQKPGKAPKLLIYYTSYLRSGVPSRFSGSGSGTDFTLTISSLQPEDF

ATYYCQQGHTLPPTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

SEQ IDs 264 and 265 describe heavy and light chain sequences for r:Fv-IgG 3C8(High)-1A7(Low), which comprises 3C8 VH mutations M31I and K64L and 1A7 VH mutation P96A, described in Example 17.

SEQ ID NO: 264. r: Fv-IgG 3C8(High)-1A7(Low) Heavy
Chain
EVQLVQSGAEVKKPGASVKVSCKASGYAFTIYLIEWVRQAPGQGLEWIGV

INPGSGDTYYSEKFLGRVTLTADTSTSTAYLELSSLRSEDTAVYYCARDR

LDYWGQGTLVTVSSGGGGSGGGGSEVQLVQSGAEVKKPGASVKVSCKASG

YTFTDSYMSWVRQAPGQGLEWIGDMYPDNGDSSYNQKFRERVTITRDTST

STAYLELSSLRSEDTAVYYCVLAARWYFSVWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

SEQ ID NO: 265. r: Fv-IgG 3C8(High)-1A7(Low) Light
Chain
DIQMTQSPSSLSASVGDRVTITCHASQDISSYIVWYQQKPGKSFKGLIYH

GTNLESGVPSRFSGSGSGTDFTLTISSLQPEDFATYYCVHYAQFPYTFGQ

GTKVEIKGGGGSGGGGSDIQMTQSPSSLSASVGDRVTITCRASQDISNYL

NWYQQKPGKAPKLLIYYTSRLRSGVPSRFSGSGSGTDFTLTISSLQPEDF

ATYYCQQGHTLPPTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

SEQ IDs 266 and 267 describe heavy and light chain sequences for r:Fv-IgG 3C8-1A7(Low), which comprises 1A7 VH mutation P96A, described in Example 17. SEQ ID NO:266. r: Fv-IgG 3C8-1A7(Low)
Heavy Chain
EVQLVQSGAEVKKPGASVKVSCKASGYAFTNYLIEWVRQAPGQGLEWIGV

INPGSGDTYYSEKFKGRVTLTADTSTSTAYLELSSLRSEDTAVYYCARDR

LDYWGQGTLVTVSSGGGGSGGGGSEVQLVQSGAEVKKPGASVKVSCKASG

YTFTDSYMSWVRQAPGQGLEWIGDMYPDNGDSSYNQKFRERVTITRDTST

STAYLELSSLRSEDTAVYYCVLAARWYFSVWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

SEQ ID NO: 267. r: Fv-IgG 3C8-1A7(Low) Light Chain
DIQMTQSPSSLSASVGDRVTITCHASQDISSYIVWYQQKPGKSFKGLIYH

GTNLESGVPSRFSGSGSGTDFTLTISSLQPEDFATYYCVHYAQFPYTFGQ

GTKVEIKGGGGSGGGGSDIQMTQSPSSLSASVGDRVTITCRASQDISNYL

NWYQQKPGKAPKLLIYYTSRLRSGVPSRFSGSGSGTDFTLTISSLQPEDF

ATYYCQQGHTLPPTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

Exemplary heavy chain constant regions (CH1-Hinge-CH2-CH3) and light chain constant regions (CL) that may find use in the present disclosure are provided in SEQ ID NO: 279-288. As is well known in the art, polymorphic, allotypic, and haplotypic variants of human constant chains exist, and these variants may find lice in the present disclosure.

SEQ ID NO: 279. Human IgG1 Heavy Constant Region
(CH1-Hinge-CH2-CH3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

SEQ ID NO: 295. Human IgG2 Heavy Constant Region
(CH1-Hinge-CH2-CH3)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

SEQ ID NO: 296. Human IgG3 Heavy Constant Region
(CH1-Hinge-CH2-CH3)
ASTKGPSVFPLAPCSRSTSGGTAALGCLVKDYFPEPVTVSWNSGALTSG

VHTFPAVLQSSGLYSLSSVVTVPSSSLGTQTYTCNVNHKPSNTKVDKRV

```
ELKTPLGDTTHTCPRCPEPKSCDTPPPCPRCPEPKSCDTPPPCPRCPEP

KSCDTPPPCPRCPAPELLGGPSVFLFPPKPKDTLMISRTPEVTCVVVDV

SHEDPEVQFKWYVDGVEVHNAKTKPREEQYNSTFRVVSVLTVLHQDWLN

GKEYKCKVSNKALPAPIEKTISKTKGQPREPQVYTLPPSREEMTKNQVS

LTCLVKGFYPSDIAVEWESSGQPENNYNTTPPMLDSDGSFFLYSKLTVD

KSRWQQGNIFSCSVMHEALHNRFTQKSLSLSPGK

SEQ ID NO: 297. Human IgG4 Heavy Constant Region
(CH1-Hinge-CH2-CH3)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

SEQ ID NO: 298. Human Ckappa Light Constant Region
(CL-kappa).
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC SEQ ID NO: 299. Human Clambda 1 Light Constant
Region (CL-lambda 1).
GQPKANPTVTLFPPSSEELQANKATLVCLISDFYPGAVTVAWKADGSPVK
AGVETTKPSKQSNNKYAASSYLSLTPEQWKSHRSYSCQVTHEGSTVEKTV
APTECS SEQ ID NO: 300. Human Clambda 2 Light Constant
Region (CL-lambda2).
GQPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKTV
APTECS SEQ ID NO: 301. Human Clambda 3 Light Constant
Region (CL-lambda3).
GQPKAAPSVTLFPPSSEELQANKATLVCLISDFYPGAVTVAWKADSSPVK
AGVETTTPSKQSNNKYAASSYLSLTPEQWKSHKSYSCQVTHEGSTVEKTV
APTECS SEQ ID NO: 302. Human Clambda 6 Light Constant
Region (CL-lambda6).
GQPKAAPSVTLFPPSSEELQANKATLVCLISDFYPGAVKVAWKADGSPVN
TGVETTTPSKQSNNKYAASSYLSLTPEQWKSHRSYSCQVTHEGSTVEKTV
APAECS SEQ ID NO: 303. Human Clambda 7 Light Constant
Region (CL-lambda7).
GQPKAAPSVTLFPPSSEELQANKATLVCLVSDFYPGAVTVAWKADGSPVK
VGVETTKPSKQSNNKYAASSYLSLTPEQWKSHRSYSCRVTHEGSTVEKTV
APAECS.
```

Example 3. Engineering and Characterization of Coupled IgG-IgG Antibodies

Materials and Methods

Monoepitopic and biepitopic coupled IgG-IgG (c:IgG-IgG) anti-OX40 antibodies were generated using the 1A7 and 3C8 variable regions. c:IgG-IgG antibodies were constructed by engineering an asymmetric thiomab, that is a bispecific antibody in which only one of the half-antibodies has a free cysteine. In the present experiments the substitution K149C on the human Ckappa constant region was used, but the present disclosure contemplates the use of an engineered cysteine at any antibody residue. Bispecific antibodies comprising a single free cysteine at K149C were generated as described above using knobs-into-hole variants (reference) and in vitro assembly of half-antibodies (Spiess et al., 2013, Nat Biotechnol 31(8):753-8). Antibodies were constructed in the pRK vector, and all antibody heavy chains contained the N297G mutation to remove glycosylation and attenuate binding to Fc receptors. 1A7 and 3C8 half-antibodies contained either Knob/His or Hole/Flag heavy chain, and native or K149C light chain depending on the desired construct. pRK vector DNA encoding heavy and light chains for each antibody were cotransfected into HEK293 cells for expression, resulting protein was purified from the supernatant, and bispecific antibodies were assembled and purified as described above.

c:IgG-IgG antibodies were generated by chemically coupling asymmetric thiomab bispecific antibodies using a bis-maleimido polyethylene glycol linker (Bis-maleimido (PEG). Asymmetric thiomab bispecific antibodies were generated using knob-into-hole technology mentioned above with a K149C mutation on the light chain of knob or hole. The IgG-IgG antibodies were made through the K149C site on knob or hole by linkers contained either 2 or 3 PEG units for the present experiments, although it is contemplated that a variety of PEG lengths could be utilized.

Results c:IgG-IgG antibodies were tested for their ability to agonize OX40 receptor. CD4+ memory T cells (CD4+ CD45R0+) were sorted from buffy coat, and irradiated L cells expressing either CD80 (B7-1) and CD32a (FcγRIIa) or CD32a (FcγRIIa) only were used as surrogate antigen presenting cells (APCs). CD4+ memory T cells were incubated with L cells, stimulated with soluble anti-CD3 antibody (mouse anti-human CD3 clone SP34) and increasing concentrations of anti-OX40 antibodies or anti-Her2 antibodies as control. Cells were cultured for 7 days, harvested, and assayed for T cell proliferation by CellTiter-Glo® (Promega) and cytokine release by ELISA.

Figure 10:
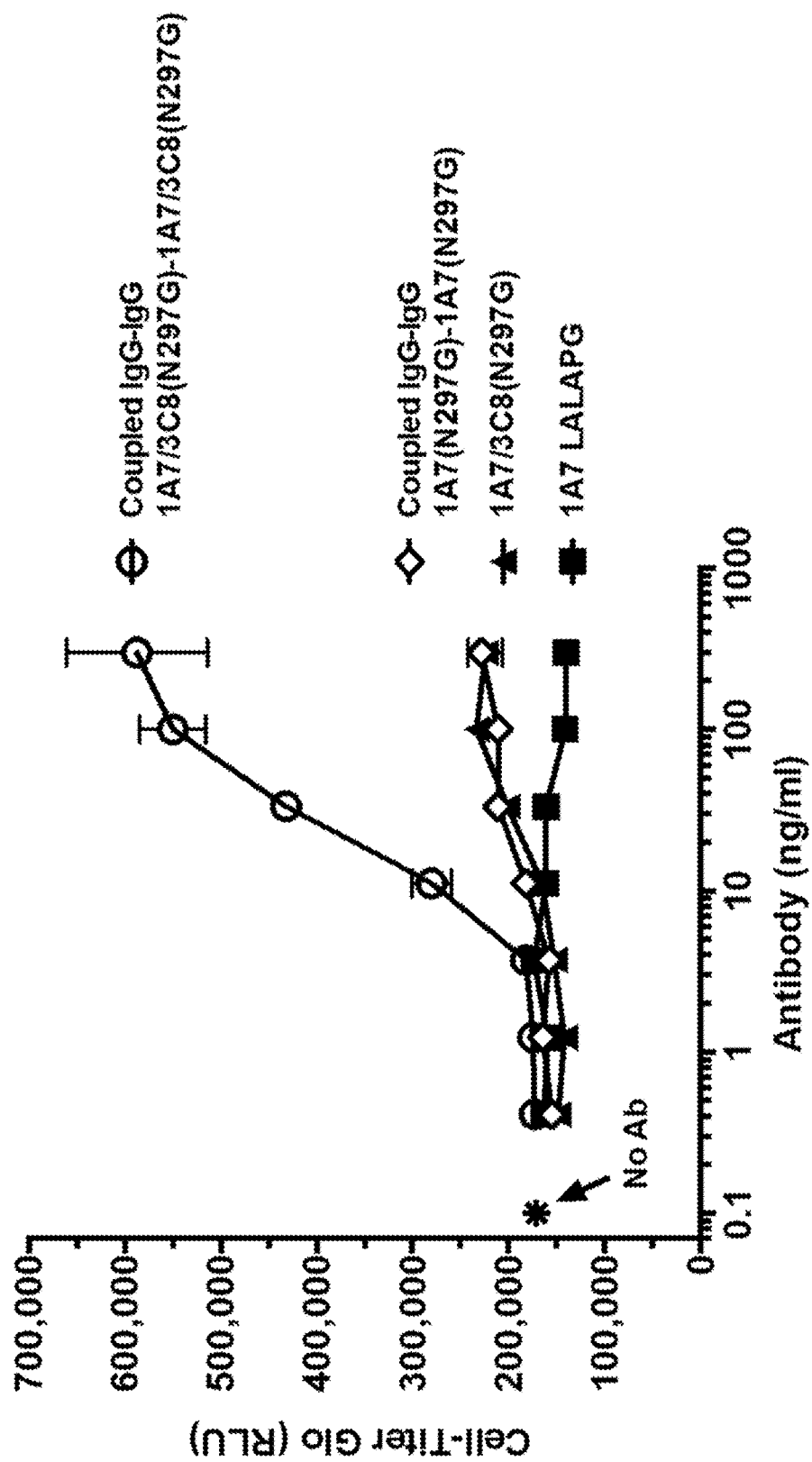
FIG. 10 shows co-stimulation of CD4+ memory T cell proliferation by anti-OX40 or control antibodies in the presence of anti-CD3 antibody and CD80+FcγRIIa+ L cells. T cell proliferation was monitored by CellTiter-Glo® (Promega). All groups included anti-CD3. Coupled IgGs include monoepitopic 1A7_hIgG1(N297G)-BM(PEG)2-1A7_hIgG1(N297G) and biepitopic 1A7/3C8_hIgG1(N297G)-BM(PEG)3-1A7/3C8_hIgG1(N297G).

T cell proliferation data are shown in FIG. 10. The results demonstrate that while tetravalent monoepitopic 1A7 (N297G)-1A7(N297G) and bivalent biepitopic 1A7/3C8 (N297G) provide a modest levels of agonist activity in the absence of FcR-mediated crosslinking, tetravalent biepitopic 1A7/3C8(N297G)-1A7/3C8(N297G) promotes a strong level of agonist activity.

Figure 11:
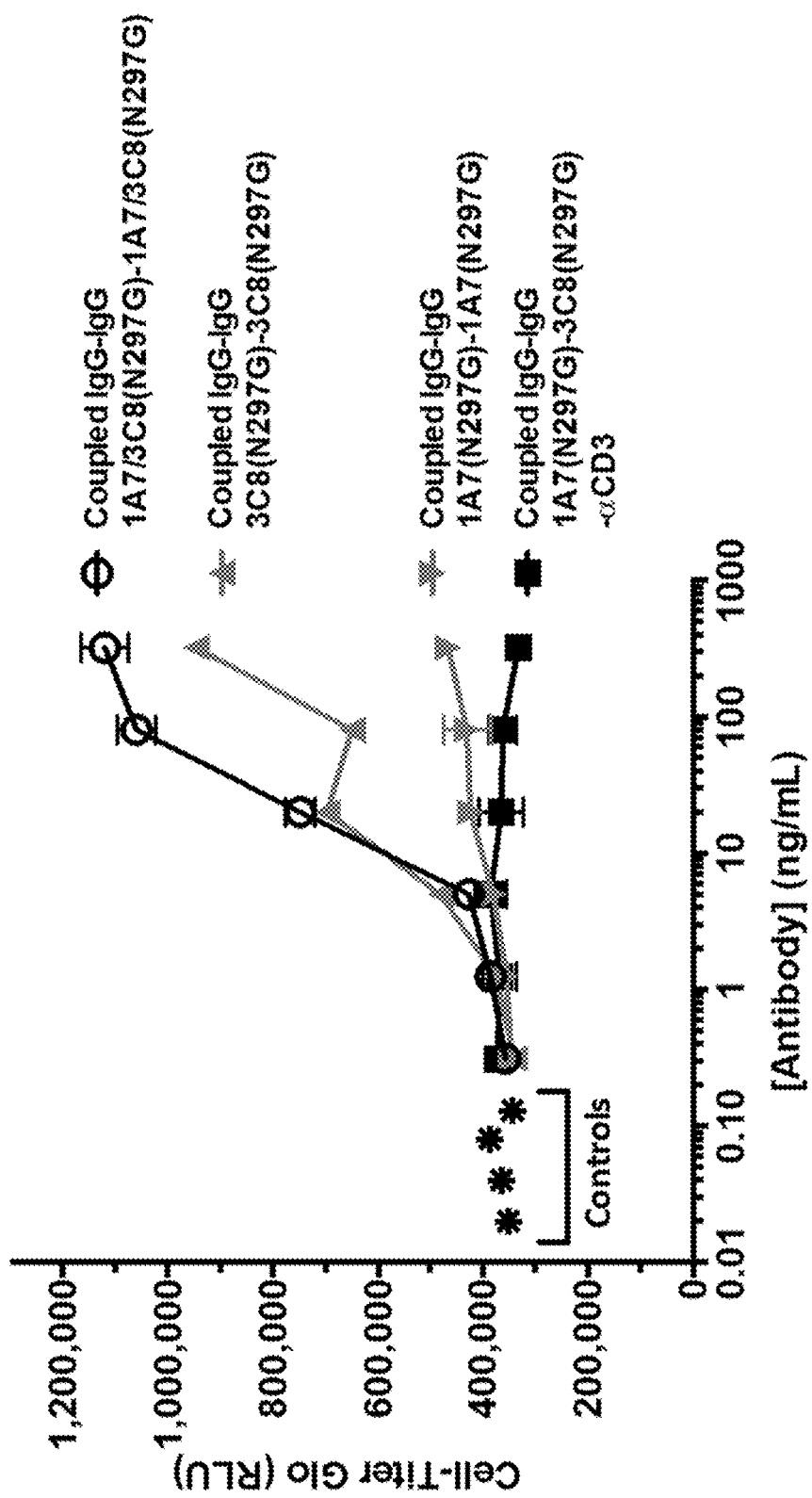
FIG. 11 shows co-stimulation of CD4+ memory T cell proliferation by anti-OX40 or control antibodies in the presence of anti-CD3 antibody and FcγRIIa+ L cells. T cell proliferation was monitored by CellTiter-Glo® (Promega). Coupled IgGs include monoepitopic 1A7_hIgG1(N297G)-BM(PEG)3-1A7_hIgG1(N297G), monoepitopic 3C8_hIgG1(N297G)-BM(PEG)3-3C8_hIgG1(N297G), and biepitopic 1A7/3C8_hIgG1(N297G)-BM(PEG)3-1A7/3C8_hIgG1(N297G). L cells in this assay are FcγRII+ but lack CD80. The four controls are L cells, L cells+anti-CD3, L cells+ T cells, and L cells+ T cells+anti-CD3. All antibodies tested included anti-CD3 unless noted ("-αCD3").

The assay was repeated wherein tetravalent monoepitopic 3C8(N297G)-3C8(N297G) was included in the test set. These data are shown in FIG. 11. The results again demonstrated the potent agonism of the 1A7/3C8 tetravalent format in the absence of crosslinking (N297G), and illustrated the synergistic combination of targeting 1A7 and 3C8 epitopes in the context of tetravalent engagement. Importantly, the data also demonstrate that the 1A7/3C8 c:IgG-IgG format is inactive in the absence of CD3 stimulation, indicating that despite its potent activity TCR engagement is still required.

Example 4. Engineering and Characterization of Coupled FAb-IgG Antibodies

Materials and Methods

Figure 12:
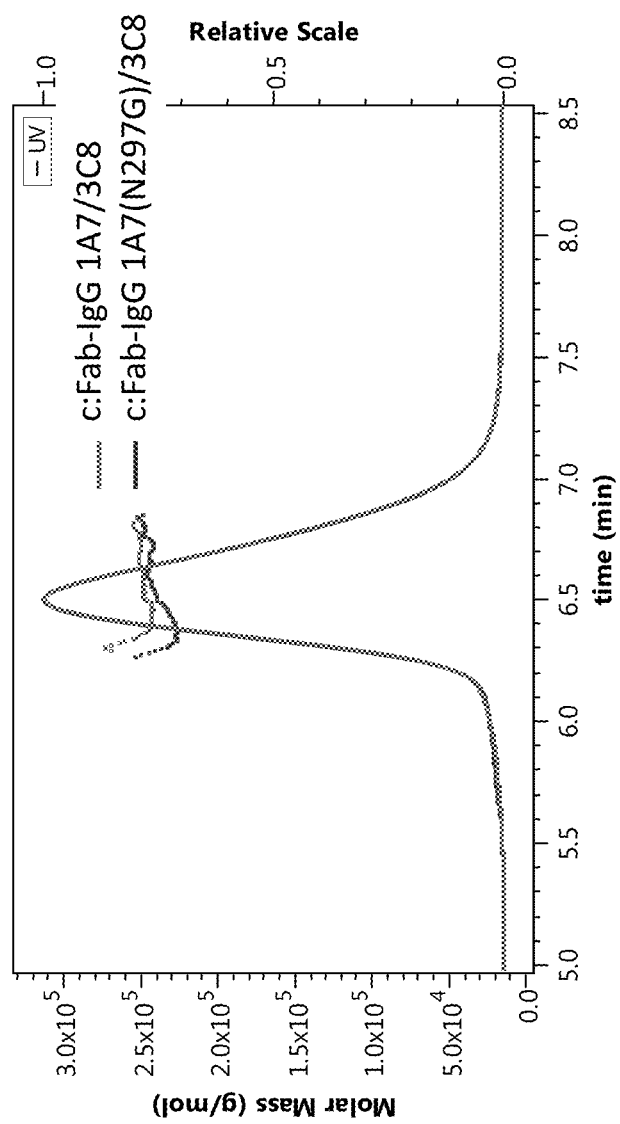
FIG. 12 shows SEC-MALS data on coupled Fab-IgGs 1A7/3C8 and 1A7(N297G)/3C8.
Figure 13:
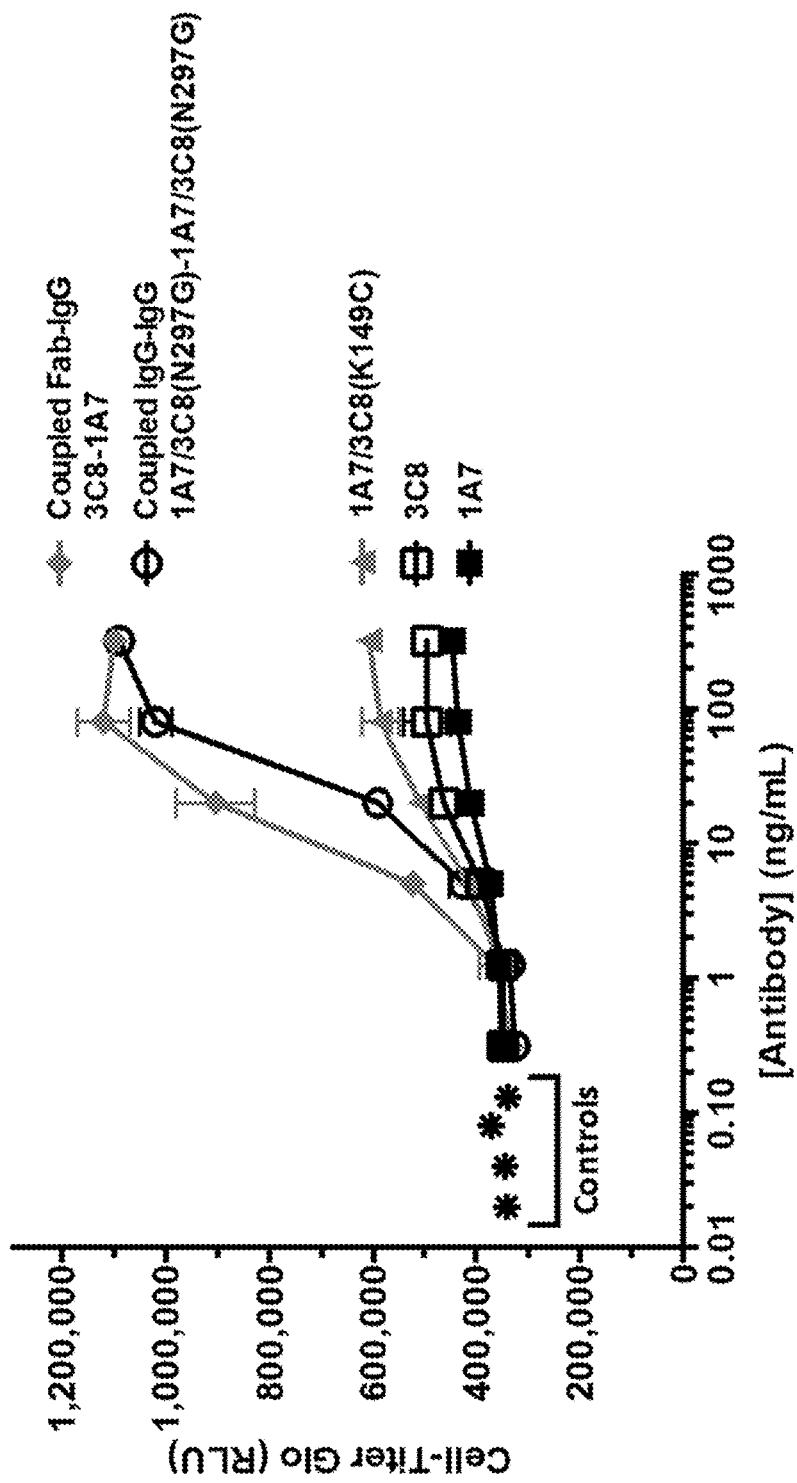
FIG. 13 shows co-stimulation of CD4+ memory T cell proliferation by anti-OX40 or control antibodies in the presence of anti-CD3 antibody and FcγRIIa+ L cells. T cell proliferation was monitored by CellTiter-Glo® (Promega). L cells in this assay are FcγRII+ but lack CD80. The four controls are L cells, L cells+anti-CD3, L cells+ T cells, and L cells+ T cells+anti-CD3. All antibodies tested included anti-CD3. Coupled Fab-IgG format is two 3C8 Fabs coupled with 1A7_hIgG1(K149C) via BM(PEG)3 linker.
Figure 14:
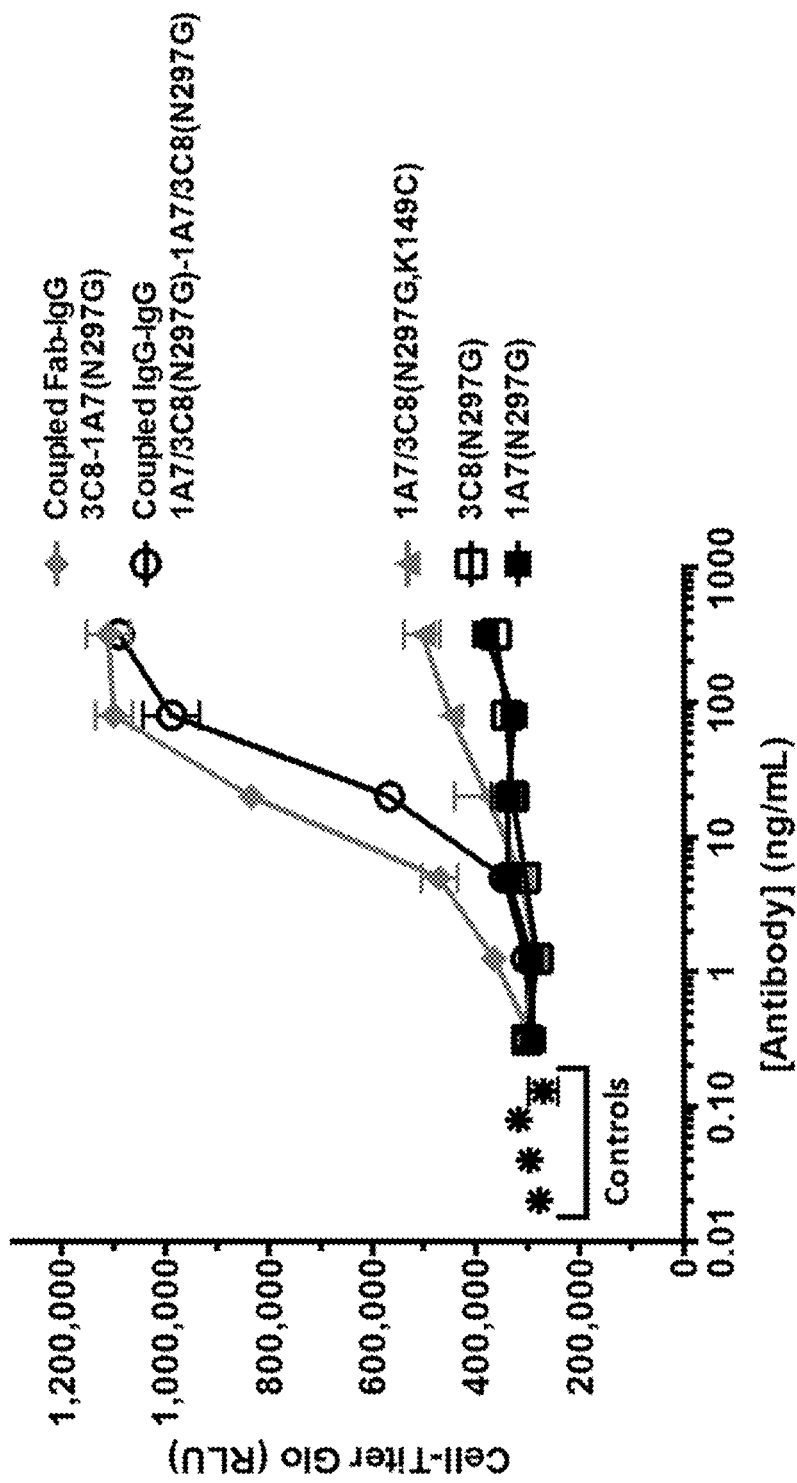
FIG. 14 shows co-stimulation of CD4+ memory T cell proliferation by anti-OX40 or control antibodies in the presence of anti-CD3 antibody and FcγRIIa+ L cells. T cell proliferation was monitored by CellTiter-Glo® (Promega). L cells in this assay are FcγRII+ but lack CD80. The four controls are L cells, L cells+anti-CD3, L cells+ T cells, and L cells+ T cells+anti-CD3. All antibodies tested included anti-CD3. Coupled Fab-IgG format is two 3C8 Fabs coupled with 1A7_hIgG1(K149C/N297G) via BM(PEG)3 linker.

Monoepitopic and biepitopic coupled Fab-IgG (c:Fab-IgG) anti-OX40 antibodies were generated based on the 1A7 and 3C8 variable regions. c:Fab-IgG antibodies were constructed by coupling a 1A7 full length human IgG1 comprising a free cysteine at K149C to a 3C8 Fab engineered with a C-terminal free cysteine. In the present experiments the substitution K149C on the human Ckappa constant region was used, but the present disclosure contemplates the use of an engineered cysteine at any antibody residue.

c:IgG-IgG antibodies were generated by chemically coupling Fab and IgG antibodies using a bis-maleimido polyethylene glycol linker (Bis-maleimido(PEG). Linkers contained either 2 or 3 PEG units for the present experiments. It is contemplated that a variety of PEG lengths could be utilized. 3C8 Fab was reacted with bismal BMPEG3, and then excess BMPEG3 was removed. Conjugated 3C8 Fab was then reacted with 1A7 IgG1 K149C, and coupled Fab-IgG was purified using an S200 SEC column followed by a Mono-Q column using conventional chromatography methods. Quality of the final purified c:Fab-IgG antibodies was assessed using analytical Size Exclusion Chromatography coupled with Multiple Angle Light Scattering (SEC-MALS) as well as mass spectrometry. SEC-MALS was run using an Xbridge BEH column in PBS at 08. ml/min Results The results are shown in FIG. 12. Fits of the data resulted in final radii and molecular weights as follows: c:Fab-IgG 1A7/3C8 had a Rh(Q)z (nm) of 7.3 nm+/−4.6% and a MW of 248.6+/−15% KDa; c:Fab-IgG 1A7(N297G)/3C8 had an Rh(Q)z of 7.3 nm+/−4.3% and a MW of 238.2 KDa+/−16.7%. Mass spectrometry confirmed (data not shown) confirmed that the purified c:Fab-IgG's had the predicted MW.

c:IgG-IgG antibodies were tested for their ability to agonize OX40 receptor using the primary T cell assay as described above, utilizing L cells expressing CD32a as surrogate antigen presenting cells (APCs). T cell proliferation data for the human IgG1 and human IgG1(N297G) versions are shown in FIG. 13 and FIG. 14 respectively. The results demonstrate that the 1A7/3C8 c:Fab-IgG format promotes a strong level of agonist activity, in contrast to the weak activity mediated by bivalent 1A7 IgG, bivalent 3C8 IgG, biepitopic 1A7/3C8 IgG. Together with the data on the c:IgG-IgG formats (included in the same assay), the results demonstrate the benefit of targeting two epitopes (in this example 1A7 and 3C8 OX40 epitopes) in the context of tetravalency.

Example 5. Engineering and Characterization of Recombinant Fv-IgG Antibodies

Materials and Methods

Monoepitopic and biepitopic recombinant Fv-IgG (r:Fv-IgG) anti-OX40 antibodies were generated based on the 1A7 and 3C8 variable regions. r:Fv-IgG antibodies were constructed by genetically engineering an additional VL region N-terminal to a native VL region, and an additional VH region N-terminal to a native VH region. The r:Fv-IgG constructed resulted in either tetravalent monoepitopic (1A7-1A7 and 3C8-3C8), or tetravalent biepitopic (1A7-3C8 and 3C8-1A7) formats. Heavy and light chain amino acid sequences of r:Fv-IgG 1A7-3C8 used in these examples are provided in SEQ ID NOs:240-241 respectively, and heavy and light chain amino acid sequences of r:Fv-IgG 3C8-1A7 used in these examples are provided in SEQ ID NOs:242-243 respectively. Antibodies were constructed in the pRK vector using conventional molecular biology methods. All antibodies comprised a native IgG1 constant region. pRK vector DNA encoding heavy and light chains for each r:Fv-IgG were cotransfected into HEK293 cells for expression, and resulting protein was purified from the supernatant using MabSelect Sure resin.

r:Fv-IgG antibodies were tested for their ability to agonize OX40 receptor using OX40 expressing Jurkat cells with a luciferase reporter (clone 2A4 Jurkat-OX40-luc). Cells were seeded in Corning 96 well plate (cat #3603) at $2 \times 10^5$ cells/well in 50 uL AIM-V media (Thermo Fischer Scientific, Cat. #12055-091) in 96 well tissue culture plate (Corning Inc., Cat #3603). Anti-OX40 antibodies were serially diluted in AIM-V media at 2× concentration and 50 uL of the diluted antibodies were added to the each well and incubated in 37° C. for 16-18 hours at 5% $CO_2$. 100 uL Bright Glo (Promega cat #E2610) was added and mixed at room temperature for 10 minutes. Luminescence was detected on an Infinite M1000 Pro plate reader (Tecan). In contrast to the primary T cell assay described above, this Jurkat reporter assay does not include co-incubation with FcR+ L cells. Agonist activity in this assay thus reflects only cross-linking mediated by the antibody in the absence of any artificial cross-linking.

Results

Figure 15:
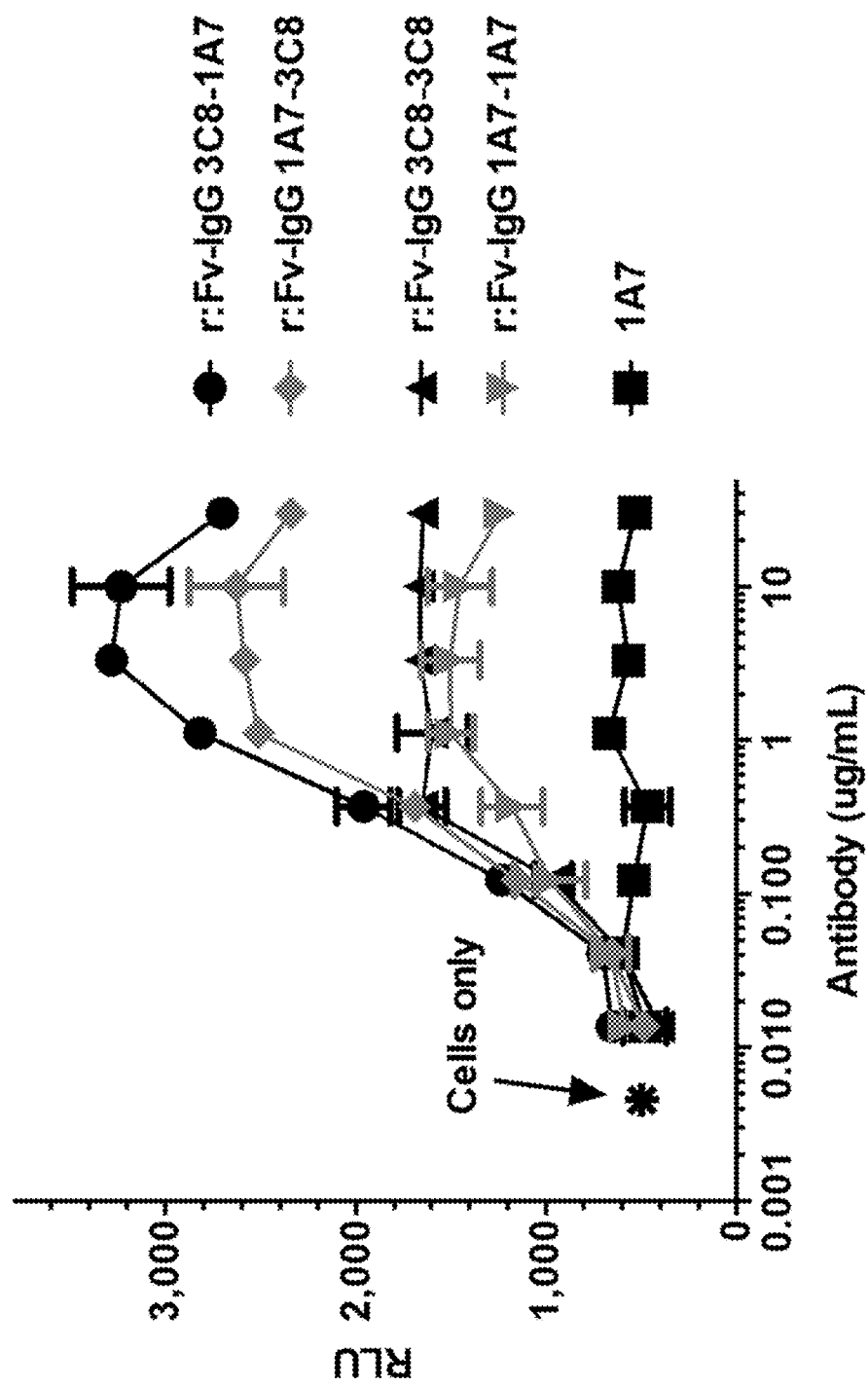
FIG. 15 shows agonist activity of anti-OX40 native (1A7) and recombinant Fv-IgG monoepitopic (1A7-1A7 and 3C8-

The data are shown in FIG. 15. In the absence of any crosslinking, the 1A7 IgG1 antibody mediated no OX40 receptor agonism. The tetravalent monoepitopic constructs (r:Fv-IgG 1A7-1A7 and r:Fv-IgG 3C8-3C8) mediated a moderate level of crosslink-independent activity. The strongest level of agonist activity was mediated by the tetravalent biepitopic constructs (r:Fv-IgG 3C8-1A7 and r:Fv-IgG 1A7-3C8).

r:Fv-IgG antibodies were tested for their ability to agonize OX40 receptor using the primary T cell assay as described above, utilizing L cells expressing CD32a. T cell proliferation data for the human IgG1 versions are shown in FIG. 16. Consistent with the Jurkat luciferase reporter assay, the biepitopic versions (1A7-3C8 and 3C8-1A7) promote receptor activation that is substantially greater than the activity of the monoepitopic versions (1A7-1A7 and 3C8-3C8). Together with the data on the c:IgG-IgG formats and c:Fab-IgG formats, the r:FAb-IgG results further support the benefit of targeting two epitopes (in this example 1A7 and 3C8 OX40 epitopes) in the context of tetravalency.

Example 6. Engineering and Characterization of Recombinant Fab-IgG Antibodies

Materials and Methods

Monoepitopic and biepitopic recombinant Fab-IgG (r:Fab-IgG's) anti-OX40 antibodies were generated comprising the 1A7 and 3C8 variable regions. r:Fab-IgG antibodies were constructed by genetically engineering an additional heavy chain Fab region (VH-CH1) N-terminal to the native heavy chain Fab (VH-CH1) region. Tetravalent monoepitopic versions of the r:Fab-IgG were engineered by constructing either the 1A7 or the 3C8 Fabs in tandem (i.e. 1A7-1A7 or 3C8-3C8) and co-expressing 1A7 or 3C8 light chains (VL-Ckappa) respectively. Tetravalent monoepitopic r:Fab-IgG's are a "two-chain system" in the same way as native IgG's, i.e. there is a single heavy chain and a single light chain. Tetravalent biepitopic versions of the r:Fab-IgG required additional engineering to control the heavy chain/light chain pairing. Biepitopic versions are made by co-expressing the tandem heavy chain (e.g. 1A7-3C8 or 3C8-1A7) with the light chains for both 1A7 and 3C8, resulting in a "three-chain system" (SEQ ID NOs: 244-246 for the 1A7-3C8 orientation or 247-249 for the 3C8-1A7 orientation). The variable regions do not on their own ensure proper pairing, and therefore orthogonal variants were incorporated into the VH/VL and CH1/CL regions as described in International Pub. No. WO2016172485. VH/VL regions utilized variant pairs VH-Q39K/VL-Q38E or VH Q39E/VL Q38K (Kabat numbering), and CH1/CL regions utilized variant pairs -CH1-S183E/CL-V133K or CH1-S183K/CL-V133E (EU numbering). Other contemplated variants for dictating proper heavy chain/light chain pairing include CH1 A141I, F170S, S181M, S183A, V185A, and CL F116A, L135V, S174A, S176F, and T178V (EU numbering). Antibodies were constructed in the pRK vector using conventional molecular biology methods. pRK vector DNA encoding heavy and light chains (one light chain [1A7 or 3C8] for monoepitopic and two light chains [1A7 and 3C8] for biepitopic) for each r:Fab-IgG were cotransfected into HEK293 cells for expression. Resulting protein was purified from the supernatant using MabSelect Sure resin.

Quality of the final purified r:Fab-IgG antibodies was assessed using analytical Size Exclusion Chromatography coupled with Multiple Angle Light Scattering (SEC-MALS) as well as mass spectrometry. SEC-MALS was run as described above using an Xbridge BEH column in PBS.

Results

The results are shown in FIG. 17 and FIG. 18 for the biepitopic r:Fab-IgG versions 3C8-1A7 and 1A7-3C8, respectively. Fits of the data resulted in final radii and molecular weights as follows: r:Fab-IgG 3C8-1A7 had a Rh(Q)z (nm) of 7.6 nm and a MW of approximately 236 KDa, and the r:Fab-IgG 1A7-3C8 had a Rh(Q)z of 7.2 nm and a MW of approximately 233.3 KDa.

r:Fab-IgG antibodies were tested for their ability to agonize OX40 receptor using OX40 expressing Jurkat cells with a luciferase reporter (2A4 Jurkat-OX40-luc) as described above. The data are shown in FIG. 19. The tetravalent monoepitopic constructs (r:Fab-IgG 1A7-1A7 and r:Fab-IgG 3C8-3C8) mediated no crosslink-independent activity. In contrast, strong agonist activity was mediated by the tetravalent biepitopic constructs (r:Fab-IgG 3C8-1A7 and r:Fab-IgG 1A7-3C8).

r:Fab-IgG antibodies were tested for their ability to agonize OX40 receptor using the primary T cell assay as described above, utilizing L cells expressing CD32a. T cell proliferation data for the human IgG1 versions are shown in FIG. 20. Tetravalent monoepitopic versions showed no (1A7-1A7) or modest activity (3C8-3C8). In contrast, and consistent with the Jurkat luciferase reporter assay, the biepitopic versions (1A7-3C8 and 3C8-1A7) promoted strong receptor activation. Together with the data on the c:IgG-IgG, c:Fab-IgG, and r:Fv-IgG formats, the r:FAb-IgG results further support the benefit of targeting two epitopes (in this example 1A7 and 3C8 OX40 epitopes) in the context of tetravalency.

Example 7. Large Scale Production of Tetravalent Formats

Tetravalent formats were expressed and purified at large scale for deeper in vitro and in vivo characterization. DNA of all new variants described below were constructed in the pRK mammalian expression vector through gene synthesis or mutagenesis as described above. Heavy and light chain DNAs were cotransfected into 293 or CHO cells for expression as described above. DNAs encoding Fabs were expressed in E. coli.

Purification of r:Fab-IgG and r:Fv-IgG Anti-OX40 Antibodies

Harvested CHO media was loaded onto a 5 mL MabSelect SuRe column (GE Healthcare, #17-5438-01). After the sample was loaded, the column was washed with 10 column volumes (CV) of Tris buffer (25 mM Tris pH 7.0, 150 mM NaCl, 5 mM EDTA, 2 mM sodium azide (NaN$_3$)), 5 CVs of Triton X-114 buffer (25 mM Tris pH 7.0, 150 mM NaCl, 5 mM EDTA, 0.1% Triton X-114, 2 mM NaN3), 10 CVs of Tris buffer, 2 CVs of KP wash buffer (0.4 M potassium phosphate pH 7.0, 5 mM EDTA, 0.02% Polysorbate Tween 20), and finally 10 CVs of Tris buffer. Protein was eluted with 5 CVs of elution buffer (50 mM sodium citrate pH 3.0, 150 mM NaCl) and immediately neutralized with 1M Tris pH 8.0 buffer. The neutralized elution was concentrated and purified over a HiLoad 16/600 Superdex 200 size exclusion chromatography (SEC) column (GE Healthcare, #28-983-36) with Arginine buffer (200 mM Arginine, 137 mM Succinic acid, 1 mM NaN$_3$) as the mobile phase. Eluted fractions were collected in 1 mL increments and analyzed by SDS-PAGE. The final eluant pool was concentrated and formulated into 20 mM Histidine Acetate (HisOAc) pH 5.5, 240 mM Sucrose, 0.02% Polysorbate Tween 20.

Production of c:Fab-IgG

Hinge-cysteine-Fabs (Fab-SPPC) were expressed in E. coli and were purified as previously described (Scheer, J. M. et al. Reorienting the Fab domains of trastuzumab results in potent HER2 activators. PLoS One 2012, 7, e51817). THIOMAB antibodies were recombinantely expressed in CHO cells and purified as previously described (Sadowsky, J. D. et al. Development of efficient chemistry to generate site-specific disulfide-linked protein- and peptide-payload conjugates: Application to THIOMAB™ antibody-drug conjugates. Bioconjug. Chem. 2017).

Hinge-cysteine-Fabs were functionalized with bis-maleimide crosslinker. Fresh bis-maleimide crosslinker (BMPEG) (ThermoFisher Scientific, 22337) was reconstituted to final concentration of 50 mM in N,N-Dimethylacetamide (Sigma Aldrich, D5511). The purified Fab-SPPC was then reacted with 10 mole equivalents of BMPEG at pH 5.0 for 2 hours at room temperature and reaction progress was monitored by mass spectrometry. After incubation for 2 hours, the reaction was complete and excess crosslinker was removed by simple buffer exchange with 10,000 MWCO Amicon Ultra-15 centrifugal filter units (UFC901096, Millipore) into conjugation buffer (25 mM sodium acetate (NaOAc) pH 5.0, 2 mM NaN$_3$). Post buffer exchange, the final functionalized Fab (Fab-BMPEG) was analyzed with mass spectrometry.

c:Fab-IgG was conjugated and purified. Purified THIOMAB antibody (5 mg/mL) was reacted with five molar excess of Fab-BMPEG (5 mg/mL). The reaction mixture was conditioned with conjugation buffer to a final pH of 5.0 and incubated at room temperature for 21 hours. Reaction progress was monitored with mass spectrometry. After incubation for 21 hours, the reaction was complete and the reaction mixture was purified with hydrophobic interaction chromatography (HIC). Briefly, the sample was conditioned with 1.5M ammonium sulfate and loaded onto a ProPac™ HIC-10 column (5 μm, 7.8 mm×75 mm) (Thermo Scientific, 063665). After sample load, the column was washed with 5 CVs of HIC-Buffer A (50 mM potassium phosphate pH 7.0, 1 M ammonium sulfate) and eluted with a linear gradient from 0% to 80% HIC-Buffer B (50 mM potassium phosphate pH 7.0, 20% isopropanol) over 60 CVs. Eluted fractions were collected and analyzed by LC/MS prior to formulation. The final conjugate was formulated into 20 mM HisOAc pH 5.5, 150 mM NaCl buffer and quality of final conjugate was assessed with LC/MS, SDS-PAGE, and SEC.

Production of c:IgG-IgG

ThioMab_KiH (knob-into-hole) antibody was expressed and purified. Half antibodies were expressed, purified, and annealed as previously described (Atwell, S., Ridgway, J. B., Wells, J. a & Carter, P. Stable heterodimers from remodeling the domain interface of a homodimer using a phage display library. J. Mol. Biol. 1997, 270, 26-35) to form the knob-into-hole THIOMAB antibody (ThioMab_KiH). Due to the annealing process, the engineered cysteine on the ThioMab_KiH antibody was blocked and thus unreactive towards maleimide crosslinker. To remove the adduct, the ThioMab_KiH antibody was reduced and reoxidized as previously described (Sadowsky, J. D. et al. Development of efficient chemistry to generate site-specific disulfide-linked protein- and peptide-payload conjugates: Application to THIO-MAB™ antibody-drug conjugates. Bioconjug. Chem. 2017). The final deprotected ThioMab_KiH antibody was formulated into conjugation buffer and stored at 4° C.

ThioMab_KiH antibody was coupled. Deprotected ThioMab_KiH antibody was reacted with 10 mole equivalents of freshly prepared BMPEG (see above) at pH 5.0 for 2 hours and reaction progress was monitored by mass spectrometry. After the reaction was completed, excess crosslinker was removed by ion exchange chromatography (IEX). Briefly, the reaction mixture was diluted 10 fold with IEX-Buffer A (25 mM NaOAc pH 5.0, 2 mM $NaN_3$) and loaded onto a pre-equilibrated Hi-Trap SPHP (GE Healthcare, 17115201) column. After sample load, the column was washed with 5 CVs of IEX-Buffer A and eluted with a step gradient from 0%-100% over 1 CV with IEX-Buffer B (25 mM NaOAc pH 5.0, 1000 mM NaCl, 2 mM $NaN_3$). Fractions were collected and analyzed by mass spectrometry. The final sample (ThioMab_KiH_BMPEG) was concentrated to 5 mg/mL and formulated into conjugation buffer.

The purified ThioMab_KiH_BMPEG was then added to 1.5 molar excess of ThioMab_KiH in the same buffer to form the coupled IgG. The reaction mixture was incubated at room temperature for 48 hours and reaction progress was monitored with LC/MS analysis. After 48 hours the reaction was complete and the mixture was purified with HIC as described earlier. The final purified CIgG was formulated into 20 mM HisOAc pH 5.5, 150 mM NaCl.

Example 8. Intrinsic Agonist Activity of Tetravalent Biepitopic Antibody Formats r:Fv-IgG antibodies were tested for their ability to activate T cells in the absence of crosslinking. r:Fv-IgG biepitopic versions 3C8-1A7 and 1A7-3C8, and monoepitopic versions 1A7-1A7 and 3C8-3C8 were engineered and produced with the LALAPG effector attentuation variants as described above. r:Fv-IgG's were tested in the primary human T cell assay using FcγRIIa+ L cells (L cells did not express B7-1) as described above.

T cell proliferation data are shown in FIG. 21. The biepitopic r:Fv-IgG's 3C8-1A7 and 1A7-3C8 demonstrated the highest level of activity and showed no dependence on Fc-mediated crosslinking—the curves looked virtually the same regardless of whether the r:Fv-IgG's were IgG1 or LALAPG. The monoepitopic r:Fv-IgG versions 1A7-1A7 and 3C8-3C8 showed enhanced activity relative to IgG1 1A7, but weaker activity relative to the biepitopic r:Fv-IgG formats. Moreover, in the absence of Fc-mediated crosslinking (LALAPG versions on the right panel), the monoepitopic r:Fv-IgG's showed no activity. Similar results were obtained from human IgG1 and human IgG1 LALAPG versions of r:Fab-IgG anti-OX40 antibodies (data not shown).

Example 9. Activity Comparison of Monoepitopic and Biepitopic Tetravalent Formats All four tetravalent formats were tested in the Jurkat reporter assay as described above. As described, agonist activity in this assay reflects the intrinsic activity of the antibody in the absence of any extrinsic cross-linking. Data in FIG. 22 and FIG. 23 demonstrate the clear superiority of tetravalent biepitopic over monoepitopic formats. Moreover, the bivalent biepitopic 1A7/3C8 antibody tested in this assay illustrates that a bivalent IgG targeting two epitopes alone is insufficient for agonist activity. It is the targeting of two epitopes in the context of tetravalency that provides optimal activity.

Tetravalent biepitopic formats were tested head-to-head in the Jurkat reporter assay. Data in FIG. 24 demonstrate that the recombinant biepitopic formats r:Fv-IgG and r:Fab-IgG provide greater activity relative to the bioconjugated biepitopic c:Fab-IgG and c:IgG-IgG formats. In this assay the r:Fv-IgG 3C8-1A7 antibody showed slight superiority to the other r:Fv-IgG and r:Fab-IgG formats.

Example 10. Measurement of Antibody: OX40 Complex Formation

The ability of tetravalent monepitopic and biepitopic antibody formats to form high-order (immune) complexes upon binding to target OX40 was tested using Size Exclusion Chromatography linked in-line with Multiple Angle Light Scattering (SEC-MALS). Purified antibodies and human OX40 (G&P Biosciences FCL2479) were mixed in varying molar ratios in PBS. The mixtures were run over a Waters xBrdige BEH200A SEC 3.5 um (7.8×300 mm) column and analyzed by an Agilent 1200 HPLC connected to Wyatt Technology detectors DAWN HELEOS-II multi-angle laser light scattering photometer and Optilab T-rEX differential refractive index detector.

FIG. 25 shows SEC chromatograms for r:Fv-IgGs. A much greater early shift in elution time, which is directly proportional to size, was observed for complexes formed between the biepitopic r:Fv-IgG 1A7-3C8 relative to the monoepitopic r:Fv-IgG 1A7-1A7. Similar results were obtained for r:Fab-IgG and c:Fab-IgG formats (data not shown), suggesting that tetravalent biepitopic formats are able to form larger immune complexes with target protein than tetravalent monoepitopic formats.

FIG. 26 shows the calculated size of the antibody/OX40 complex from the MALS data from these experiments. The data further support the larger immune complexes formed by target binding to tetravalent biepitopic formats relative to both tetravalent monoepitopic and bivalent biepitopic formats. These data are consistent with the superior agonist activity observed from targeting two epitopes in the context of valency greater than 2.

Example 11. Pharmacokinetics (PK) of Tetravalent Anti-OX40 Antibodies in Mice

PK of tetravalent antibody formats was tested in C57BL-6 or C.B-17 SCID (severe combined immunodeficiency) mice. Mouse PK studies described in this section were approved by the Institutional Animal Care and Use Committee (IACUC). All antibodies tested comprised native human IgG1 heavy constant and Ckappa light constant chains. PK of IgG1 1A7, r:Fv-IgG 1A7-1A7, r:Fv-IgG 1A7-3C8, r:Fab-IgG 1A7-1A7, r:Fab-IgG 1A7-3C8, c:Fab-IgG 1A7-1A7, c:Fab-IgG 3C8-1A7 and cIgG-cIgG 3C8-3C8 antibodies were evaluated in immune-deficient C.B-17 SCID mice. In addition, PK of 1A7 IgG1, r:Fv-IgG 1A7-3C8, r:Fab-IgG 1A7-3C8, cIgG-IgG 1A7-3C8 and c:Fab-IgG 1A7-3C8 antibodies were evaluated in immune-competent C57BL-6 mice. Anti-gD IgG1 antibody was included as isotype control. The mouse PK studies were performed with single intravenous (i.v) dose of 10 mg/kg of the anti-OX40 antibodies and serum samples (n=3/time point/group) were collected at various time points for PK analysis out to Day 21 post-dose.

A sandwich ELISA with a colorimetric detection system was used to quantitate anti-OX40 huIgG1 antibodies (IgG1, r:Fv-IgG, r:Fab-IgG, c:Fab-IgG, or c:IgG-IgG) and isotype control anti-gD huIgG1 antibody in C57BL-6 or C.B-17 SCID mouse serum. Microtiter plates were coated with sheep anti-human IgG to capture anti-OX40. Diluted samples, standards, and controls were added to the plate and incubated. Subsequently, goat anti-human IgG-HRP was added for detection and incubated. A peroxidase substrate (tetramethyl benzidine) was added to develop color, and the reaction was stopped by adding 1 M phosphoric acid. The plates were read at 450 nm for detection absorbance and 620 nm for reference absorbance. Sample concentration was determined by entering data into a four-parameter logistic curve-fitting program. The reporting range for the assay was 0.156-20 ng/mL anti-OX40. The minimum sample dilution was 1/100, resulting in a minimum quantifiable concentration of 15.6 ng/mL for C57BL-6 mouse serum or C.B-17 SCID mouse serum.

As shown in FIG. 27 and FIG. 28, anti-OX40 antibody formats including IgG1, r:Fv-IgG, r:Fab-IgG, c:Fab-IgG1 and cIgG1 showed similar PK properties, which is comparable to control anti-gD IgG1 antibody in C.B-17 SCID mice. All antibody formats showed a bi-exponential decline after i.v. dosing with a short distribution phase and a long terminal elimination phase. PK for IgG1, r:Fv-IgG, r: Fab-IgG and c:Fab-IgG were in general comparable to anti-gD control until day 10 in C57BL-6 mice (FIG. 29). Higher variability in PK for r:Fv-IgG, r:Fab-IgG and c:Fab-IgG1 at day 14 and 21 can be possibly because of anti-drug antibody development. c:IgG-IgG exposure is slightly lower compared to IgG1 until day 3, but rapid decline in exposure was observed from day 7 possibly because of anti-drug antibody development.

Example 12. Pharmacodynamic (PD) Studies in Human OX40-Knockin (hOX40ki) Mice

The in vivo PD of the anti-OX40 antibody formats was tested for their ability to stimulate T cell activation in response to immunization with keyhole limpet hemocyanin (KLH) antigen. On Day 0, human OX40-knockin mice (Genentech, Inc.) were subcutaneously (tail base) injected with PBS or 50 µg Imject mcKLH Subunits (ThermoFisher Scientific; Cat. No. 77649) emulsified in CFA H37 Ra (BD Difco; Cat. No. 231131) at 1:1 ratio for a total volume of 100 µL per mouse. On Day +1, animals were grouped and intravenously administered 10 mg/kg of anti-human OX40 antibodies (all human IgG1 heavy chain constant region) or anti-gD human IgG1 as a control. To quantify the anti-KLH IgG antibody responses, mice from different groups were bled on Day +14 and serum anti-KLH IgG levels were measured by ELISA kit according to the manufacturer's instruction (Life Diagnostics, Inc; Cat. No. KLHG-1).

To access memory responses, mice were intraperitoneally rechallenged on Day +16 with 50 µg soluble KLH and draining lymph nodes were profiled 4 days post-rechallenge (Day +20). In some experiments, CD4+ T cells were purified from draining lymph nodes on Day +20 and stimulated in vitro with 10 µg/mL soluble KLH in the presence of purified CD11c+ splenic DCs from WT mice. After 2 days, supernatants were collected and IFN-γ production was assayed using Luminex Statistical significance was analyzed by Student's t test. Unless otherwise indicated, data represent the mean±SEM, with $p<0.05$ considered statistically significant.

FIG. 30, FIG. 31, and FIG. 32 show results from the KLH immunization PD experiment comparing r:Fv-IgG 1A7-3C8 to IgG1 versions of 1A7 and 3C8. The tetravalent biepitopic antibody format superior CD4 T cell expansion and anti-KLH IgG response (FIG. 30), and CD8 T cell expansion and total cell expansion in the draining lymph node (dLN) (FIG. 31). The tetravalent biepitopic format also stimulated greater interferon gamma (IFN-γ) after ex vivo restimulation of purified CD4+ T cells with KLH (FIG. 32).

A repeat study directly compared r:Fv-IgG, c:Fab-IgG, and r:Fab-IgG tetravalent biepitopic formats, along with IgG1 versions of 1A7 and 3C8 antibodies. FIG. 33 shows the data from this experiment. r:Fv-IgG and c:Fab-IgG demonstrated clear superiority in expansion of CD4 and CD8 T cells, with r:Fab-IgG showing more modest levels of T cell activation. Altogether these results highlight that the superior in vitro agonist activity of the tetravalent biepitopic antibodies translates into greater T cell activation in vivo.

Example 13. Anti-Tumor Activity of Tetravalent Antibodies

Tetravalent antibodies were tested for anti-tumor activity in a syngeneic E.G7-OVA (EL4 expressing chicken ovalbumin (OVA)) lymphoma tumor model in female human OX40 (TNFRSF4) knockin C57BL/6N mice (huOX40.tnfrsf4.ki.B6N) generated at Genentech. Mice were inoculated subcutaneously into the right unilateral flank with 3 million E.G7-OVA tumor cells in 100 microliters of HBSS+matrigel. Mice were allowed to grow tumors until they achieved a mean tumor volume of ~250 mm$^3$ (5 days after inoculation). At this point (Day 0), mice were recruited into 3 groups, n=10 for all groups. Anti-gD binds to glycoprotein D of Herpes Simplex Virus and serves as a negative control. Antibodies were diluted in sterile PBS and dose volume was 100 ul. All groups were given a single 10 mg/kg dose intravenously on day 1. All antibodies tested comprised human IgG1 heavy chain constant region. Blood was collected 24 hrs post dose from 5 mice/group/timepoint. Blood was collected 6 days post dose from the other 5 mice/group. Blood was collected by orbital bleed (collection volume did not exceed 100 ul), under isofluorane-induced anesthesia (inhalation to effect). Serum was harvested from the blood for PK analysis. Measurements and weights were collected 2×/week. Animals exhibiting weight loss of >15% were weighed daily and euthanized if they lost >20% body weight. Animals showing adverse clinical issues were observed more frequently, up to daily depending on severity, and euthanized if moribund. However, no mice in this study showed adverse clinical signs. Mice were euthanized if tumor volumes exceeded 2,000 mm$^3$. The remaining tumors were measured and weighed 2×/week.

FIG. 34 shows tumor volume data from the experiment. Tetravalent biepitopic r:Fv-IgG 3C8-1A7 provided superior anti-tumor activity relative to the more modest activity of native IgG1 1A7. These results are consistent with the superior in vitro and in vivo PD activity of this antibody format, and demonstrate the utility of the r:Fv-IgG and other tetravalent biepitopic formats as therapeutic agents.

Example 14. Structure Determination and Epitope Mapping

Expression and Purification of Anti-OX40 Ligand Fabs and OX40 Ligand ECD

Two Fab fragments of anti-OX40 ligand were express and purified in the same way as following. The Fabs were expressed in *E. coli*. The proteins were purified in two steps. First, the cell lysate supernatant was loaded onto a G sepharose column and eluted with 0.6% acetic acid. Second, Fab-containing fractions were pooled and purified using a SP sepharose column (GE Healthcare). The loading buffer contained 2-(N-morpholino)ethanesulfonic acid (MES) at pH 5.5 and the protein was eluted on a NaCl gradient.

Human OX40 ligand extracellular domain (ECD, residues L29-D170) was co-expressed in SF9 insect cells with endoglycosidase H. OX40 ligand containing medium was separated from cell debris by centrifugation. Protein was purified by first using a 10 mL Ni-NTA Superflow (Qiagen) column. OX40 ligand was eluted with buffer containing 20 mM tris(hydroxymethyl)aminomethane (Tris) at pH 8.0, 300 mM NaCl and 300 mM imidazole. Fractions containing the OX40 ligand were pooled and purified by size exclusion chromatography (SEC) on a S-75 column (Pharmacia) equilibrated in 20 mM 4-(2-hydroxyethyl)-1-piperazineethanesulfonic acid) (Hepes) pH 7.2 and 200 mM NaCl. The N-terminal his-tag was cleaved by overnight incubation with Thrombin (Sigma) at 4° C. The cleaved OX40 ligand protein was collected in the flow through fraction of a 1.0 mL Ni-NTA Sepharose (Qiagen) column and was further purified by SEC on a S-75 column (Pharmacia) equilibrated in the same S-75 buffer mentioned above.

Generation and Crystallization of Anti-OX40 Ligand Fabs and Antigen Complex

Equimolar amounts of OX40 ECD (PUR #124725), 1A7 anti-OX40 ligand Fab (PUR #115810) and 3C8 anti-OX40 ligand Fab (PUR #109639) were mixed together and incubated overnight at 4° C. The ternary complex was then purified by SEC on a S200 16/60 column (GE Healthcare) equilibrated in 25 mM Tris pH 7.5 and 0.15 M NaCl. The purified complex was analyzed by SDS PAGE and liquid chromatography mass spectrometry (LC-MS), which revealed all three components in the high molecular weight (HMW) peak fractions of the final SEC step. The HMW peak fractions were concentrated to 10 mg/mL using a Vivaspin concentrator with 10,000 molecular weight cutoff.

Crystallization trials were performed using sitting-drop vapor diffusion method with commercially available sparse-matrix screens in 96-well format. Initial crystal hits were observed mostly in high salt conditions. An additive screen (Hampton Research) was performed to improve crystal diffraction quality. The final crystallization condition contained 0.1 M Tris pH 8.5, 1.5 M D-L malic acid pH 7.0 and 0.15 mM dimethylethylammonium propane sulfonate (also known as NDSB-195). Crystals were preserved for data collection by brief soaking in a cryo-protectant buffer (25% glycerol added to the reservoir solution), followed by sudden immersion into liquid nitrogen.

X-Ray Diffraction Data Collection and Structure Determination

A diffraction data set of the ternary complex crystal was collected using monochromatic X-rays at Advanced Light Source (ALS) beam line 5.0.2 using a Pilatus-6M detector. Rotation method was applied to a single crystal for the complete data set. Data reduction was performed using program XDS (Kabsch W., Acta Crystallogr D Biol Crystallogr, 2010, 66: 125-132) and the final statistics at 2.6 Å are shown in Table 1. The structure was solved by molecular replacement (MR) method using program Phaser (McCoy A. J., Grosse-Kunstleve R. W., Adams P. D., MWinn. D., Storoni L. C., Read R. J., Journal of applied crystallography 2007, 40, 658-674). The two Fab fragments elbow angles were determined by rotation searches against a series of Fab structure models (generated based PDB entry 1FVD) with varying elbow angles ranging from +90° to −10° at 5° interval. Models of elbow angles at +70° and 0° gave the highest signal to noise ratio (3×). A full MR search was then performed using the two best 1FVD-based models (+70°, 0° elbow angles) and a previously determined OX40 ECD-3C8 anti-OX40 fab complex structure (CRY #21829) that had the constant domain (CH1 and CL) of the Fab removed (Compaan D. M., Hymowitz S. G., The Crystal Structure of the costimulatory OX40-OX40L complex, Structure, 2006, 14(8):1321-30). This MR search resulted in solution of the ternary complex. Inspection of the electron density suggested the Fab model with 0° elbow angle give the best solution and corresponded to the Fab of 1A7. Further adjustment of the elbow angle to the 3C8 fab was required to fit the CH1 and CL domains. The correct 1A7 Fab sequences we built into the initial 1FVD-based MR solution using graphics modeling program COOT (Emsley, P., Lohkamp, B., Scott, W. G. & Cowtan, K. Features and development of Coot. *Acta Crystallogr D Biol Crystallogr* 66, 486-501 (2010)). The structure was further refined using program Phenix (Adams, P. D. et al. PHENIX: a comprehensive Python-based system for macromolecular structure solution. *Acta Crystallogr D Biol Crystallogr* 66, 213-221 (2010)) and BUSTER (Dsafa Bricogne G., Blanc E., Brandi M., Flensburg C., Keller P., Paciorek W., Roversi P, Sharff A., Smart O. S., Vonrhein C., Womack T. O. (2016); BUSTER version 2.11.5. Cambridge, United Kingdom: Global Phasing Ltd) in combination with manual model building in COOT (Emsley, P., Lohkamp, B., Scott, W. G. & Cowtan, K. Features and development of Coot. *Acta Crystallogr D Biol Crystallogr* 66, 486-501 (2010)) in an iterative manner. The computational refinement protocols included minimization of maximum likelihood target functions, anisotropic individual B-factor refinement and TLS refinement methods. The final refinement statistics are shown in Table 1.

TABLE 1

Data collection and refinement statistics

| | Anti-OX40 1A7, 3C8-OX40 ECD Ternary complex | Anti-OX40 3C8-OX40 ECD Binary complex |
|---|---|---|
| Data collection | ALS 5.0.2 | ALS 5.0.2 |
| Space group | I222 | P4122 |
| Cell dimensions | | |
| a, b, c (Å) | 109.8, 125.2, 197.5 | 117.0, 117.0, 118.9 |
| α, β, γ (°) | 90.0, 90.0, 90.0 | 90.0, 90.0, 90.0 |
| Resolution (Å) | 105.8-2.61 (2.70-2.61)* | 42.0-2.1 (2.17-2.1)* |
| $R_{sym}$ or $R_{merge}$ | 0.097 (1.13) | 0.068 (0.69) |
| I/σI | 11.08 (1.55) | 20.6 (3.65) |
| Completeness (%) | 100 (100) | 99.9 (99.4) |
| Redundancy | 6.4 (6.2) | 12.7 (12.4) |
| Refinement | | |
| Resolution (Å) | 105.8-2.61 | 42.0-2.1 |
| No. reflections | 41721 | 48695 |
| $R_{work}/R_{free}$ | 20.4/25.7 | 21.8/24.2 |
| No. atoms | 7690 | 4341 |
| Protein | 7470 | 4053 |
| Ligand/ion | 14 | 0 |

TABLE 1-continued

Data collection and refinement statistics

|  | Anti-OX40 1A7, 3C8-OX40 ECD Ternary complex | Anti-OX40 3C8-OX40 ECD Binary complex |
|---|---|---|
| Water | 206 | 268 |
| B-factors |  |  |
| Protein | 62.3 | 55.9 |
| Ligand/ion | 62.5 | 55.5 |
| Water | 93.1 |  |
|  | 52.9 | 62.0 |
| R.m.s deviations |  |  |
| Bond lengths (Å) | 0.019 | 0.013 |
| Bond angles (°) | 1.84 | 1.82 |

*Highest resolution shell is shown in parenthesis.

FIG. 35 shows the structure of the ternary complex of the two Fabs 1A7 and 3C8 bound to OX40. 1A7 and 3C8 bind on diametrically opposed regions of the OX40 receptor. The calculated distance between the C-termini of the 1A7 and 3C8 Fabs in the structure is ~120 Å. In contrast, the antibody hinge constrains the C-termini of two IgG Fab arms to a maximal distance of ~35 Å. This analysis suggests that the OX40 binding epitopes and as a consequence orientation of the two Fabs in the structure does not permit intra-IgG OX40 binding. This further suggests a model in which a single OX40 receptor is engaged by two separate r:Fv-IgG molecules, each of has three other Fv's that are binding other OX40 receptors. The result would in theory be immune complexation. This model is consistent with the SEC-MALS data described in Example 10, and the intrinsic agonist activity of the tetravalent biepitopic antibodies.

The OX40 epitopes bound by the 1A7 and 3C8 antibodies were determined by visual inspection of the ternary complex structure. FIG. 36 shows the sequence of human OX40 highlighting the binding epitopes of 1A7 (grey boxes) and 3C8 (black outlined boxes). Position numbering is according to that listed in UniProt (The UniProt Consortium, UniProt: the universal protein knowledgebase, Nucleic Acids Res. 45: D158-D169 (2017)). The 1A7 antibody binds to OX40 residues 114-119, 124, 126-127, 129-130, 132, 140, and 142. The 3C8 antibody binds to OX40 residues 68-71, 83-90, 95, and 98. The current disclosure provides data and structural/sequence analysis that suggests that antibodies that bind to these or overlapping epitopes may be good pairs for producing tetravalent biepitopic formats for agonizing the OX40 receptor.

Example 15. Expansion of Anti-OX40 Antibody Set and OX40 Epitope Space

An antibody discovery campaign was executed to increase the set of antibodies for tetravalent biepitopic targeting of OX40, and to expand coverage to other OX40 epitopes.

Materials and Methods

ClonaCell-HY MediumA (Cat #03801), Medium B (Cat #03802), Medium C (Cat #03803), and Medium E (Cat #03805) are from StemCell Technologies. Cytofusion Medium C (Cat #LCM-C) used for electrofusion is from Cyto Pulse Sciences. SP2ab fusion partner that expresses surface IgG is from Enzo Life Science ((ENZ-70008-0001), Goat anti-rat IgG Fc-HRP conjugated antibody is from Bethyl (A110-236P). TMB one component HRP microwell substrate (Cat #TMBW-1000-01) and TMB stop reagent (Cat #BSTP-1000-01) are from BioFx Laboratories.

Sprague Dawley rats were primed once with 50 ug human and cyno OX40 antigens following with 25 ug injection using CFA/IFA adjuvant for each rat, 6 total boosts had been performed at a week intervals. Three days after the final pre-fusion boost, lymphocytes from immunized rats were harvested.

Isolated rat lymphocytes were fused with SP2ab myeloma cells by using the Cyto Pulse CEEF-50 apparatus (Cyto Pulse Sciences). Briefly, after B cell enrichment and IgM+ rat B cells depletion, the isolated IgM-rat B cells and SP2ab cells were mixed at a 1:1 ratio and then resuspended at 10 million cells/ml in Cytofusion Medium C, electrofusion was performed according to manufacturer's guidance. Fused cells were cultured in ClonaCell-HY Medium C with HAT selection at 37° C. in a 7% $CO_2$ incubator. After 6 days culture, the fused cells were stained with Goat anti-rat IgG-Alexa Fluor® 647 (Jackson 112-606-071) for 30 mins, then washed twice with FACS buffer, after that, single rat IgG+ hybridoma cell was sorted by FACSAria into 96-well cell culture plates (#353075, Becton Dickinson) with 200 µL/well ClonaCell-HY Medium E. After 7 days culture, hybridoma supernatants were screened by ELISA and all ELISA positive hybridoma clones against both human and cyno OX40 were picked to new 96-well cell culture plates.

ELISA assay was performed as follows. 96-well microtiter ELISA plates (Greiner, Germany) were coated with 100 µL/well of either human/cyno OX40 at 1 □g/ml in 0.05 M carbonate buffer (pH 9.6) at 4° C. overnight. After washing three times with wash buffer (0.05% Tween 20 in PBS, Sigma), plates were blocked with 200 µL ELISA assay diluents with BSA. 100 µL of cultured supernatants or diluted purified mAbs were added and incubated for 1 h at room temperature. The plates were washed three times and incubated with HRP conjugated Goat anti-rat IgG Fc for 1 hour. After washing three times, bound enzyme was detected by addition of 100 µL/well the TMB substrate (BioFX Laboratories, MD, USA) for 5 min. The reactions were stopped by adding 100 µL/well of stop reagent (BioFX, Laboratories, MD, USA) and detection of color at $A_{630\ nm}$.

Jurkat cells overexpressing huOX40 were washed twice with phosphate-buffered saline (PBS) containing 1% fetal bovine serum (FBS) and then resuspended in FACS buffer (PBS containing 1% FBS) to final concentration of $5 \times 10^6$ cells/ml. 100 µl cells were added to each well of U-bottom 96 well tissue culture plate (#353077, Becton Dickinson), purified mAbs were added, after 30 mins incubation on ice, cells were washed twice with FACS buffer, and subsequently treated with Goat anti-rat IgG-Alexa Fluor® 647 (Jackson Lab, 112-606-071) at 1:400 dilution for 30 min. After twice washing with FACS buffer, stained cells were analyzed using FACS Calibur (BD Biosciences), flow cytometry data were analyzed using the FlowJo software (Tree Star, Inc.)

The hybridoma supernatants were purified by Protein A affinity chromatography, then sterile filtered (0.2 µm pore size, Nalge Nunc International, NY, USA) and stored at 4° C. in PBS. The purified mAbs were confirmed by ELISA before further testing in functional assays.

Epitope bins were determined by 96×96 array-based SPR imaging system (Carterra USA) as follows. Purified rat anti-OX40 antibodies were diluted at 10 ug/ml in 10 mM sodium acetate buffer pH 4.5 (Wasatch Microfluidics, CBNaOAc-pH4.5-0.1 L). Using amine coupling, antibodies were directly immobilized onto a SPR sensorprism CMD 200M chip (XanTec Bioanalytics, Germany) using a Continuous Flow Microspotter (Carterra, USA) to create an array of 96 antibodies.

For antibody binning, printed chip was loaded on IBIS MX96 SPRi (Carterra USA) and human OX40 protein, diluted to 50 nM in HBS-P buffer, was injected over the chip for 4 minutes at 25° C. followed by a second injection of purified antibody, diluted at 10 ug/ml in HBS-P buffer (GE, BR-1006-71) for 4 minutes. The epitope binning data was processed using Wasatch binning software tool.

For antibody kinetics, antibodies were immobilized as described above, serial diluted human or cyno OX40 protein, from 300 nM, 100 nM, 33.3 nM, 11.1 nM to 3.7 nM in HBS-P buffer, were injected over the chip and allowed to associate for 3 minutes and disassociate for 10 minutes at 25° C. The kinetic data was processed using Scrubber software (BioLogic Software)

Results 318 hybridoma-produced rat anti-OX40 antibodies were characterized for epitope bin, affinity for OX40 in solution, binding to cell surface OX40, and functional activity alone and when crosslinked with anti-Fc antibody. While numerous antibodies promoted agonism of OX40 when extrinsically crosslinked, none of the 318 antibodies mediated intrinsic agonism on their own (data not shown). Based on the binning, affinity and binding, and activity data, antibodies were cloned from hybridomas into chimeric rat VH and VL domains with human IgG1 heavy and human Ckappa light chains. Antibodies were expressed in HEK293 cells and purified as described above.

Table 2 summarizes the epitope bin and equilibrium dissociation constants (KDs) for 34 of the chimeric IgG1 anti-OX40 antibodies, measured using the array-based SPR imaging system (Carterra USA, Wasatch Microfluidics) as described above. Table 2 also shows affinities for the 1A7 and 3C8 IgG1 antibodies measured using a Biacore™ T200 instrument (GE Healthcare) by capturing antibody and testing binding to analyte OX40.

TABLE 2

Properties of expanded anti-OX40 antibody set as IgGs and r:Fv-IgGs

| | IgG Format | | r:Fv-IgG Format | | |
|---|---|---|---|---|---|
| Antibody | Bin | KD (nM) | Pair | KD (nM) | Maximal Activity (RLU) |
| 1A7 | 1A7 | 0.15 | | | |
| 3C8 | 3C8 | 1.2 | 3C8-1A7 | 0.23 | 1850 |
| 2A9 | 8 | 1.96 | 2A9-1A7 | 0.23 | 1421 |
| 2B4 | 9 | 129.3 | 2B4-1A7 | 0.91 | 420 |
| 2B5 | 11 | 16.5 | 2B5-1A7 | 0.31 | 1600 |
| 2D8 | 11 | 0.912 | 2D8-1A7 | 0.35 | 1555 |
| 2G7 | 10 | 1.79 | 2G7-1A7 | 0.27 | 1473 |
| 3F5 | 11 | 14.67 | 3F5-1A7 | 0.35 | 1392 |
| 3G5 | 10 | 22.58 | 3G5-1A7 | 0.59 | 1735 |
| 3G8 | 11 | 18.15 | | 0.66 | |
| 2C7 | 6 | 50 | | | |
| 2A2 | 2 | 5.506 | | | |
| 2F10 | 10 | 5.828 | | | |
| 2E12 | 4 | 0.01 | | | |
| 2D5 | 10 | ND | | | |
| 2B12 | 2 | 7.266 | | | |
| 3C2 | 2 | 2.399 | | | |
| 3B1 | 2 | 5.95 | | | |
| 2C10 | 5 | 0.763 | | | |
| 2B7 | ND | ND | | | |
| 2F6 | 2 | 30.31 | | | |
| 2E4 | 2 | 0.091 | | | |
| 3E10 | 2 | 2.146 | | | |
| 2H5 | 5 | 0.493 | | | |
| 2A3 | 5 | 5.52 | | | |
| 3A12 | ND | ND | | | |
| 2C9 | 10 | 5.15 | | | |
| 2D10 | ND | ND | | | |
| 3H12 | ND | ND | | | |
| 2D3 | 4 | 0.241 | | | |
| 3H4 | ND | ND | | | |
| 3D12 | ND | 5.855 | | | |
| 3D1 | 2 | ND | | | |
| 2E1 | 2 | 6.625 | | | |
| 2H1 | 4 | 53 | | | |
| 2A6 | 7 | 288.5 | | | |

27 lead antibodies were selected from non-1A7 epitope bins (i.e. antibodies that did not block binding of 1A7 to OX40) and constructed as r:Fv-IgGs paired with the 1A7 variable region. r:Fv-IgG DNAs were constructed and proteins were expressed and purified as described above. Binding affinity of the first 8 r:Fv-IgGs was measured by surface plasmon resonance (SPR) technology using a Biacore™ T200 instrument (GE Healthcare) as described above. Table 2 shows OX40 binding affinities (KDs) of the r:Fv-IgGs. IgG and r:Fv-IgG versions of the first 8 of these antibodies were tested for the ability to agonize OX40 receptor in the OX40+ Jurkat cell luciferase assay (FIG. 37). As expected, none of the new antibodies mediate agonist activity as IgGs in the absence of extrinsic crosslinking (left graph). In contrast, all but one of the antibody variable regions promotes OX40 agonism when paired with the 1A7 variable region in the r:Fv-IgG format (right graph). The exception is the 2B4 antibody, which did not mediate activity in the context of an r:Fv-IgG when paired with 1A7. The maximal activity of the r:Fv-IgGs are provided in Table 2.

Example 16. Engineered Linker Variants of r:Fv-IgG

A critical element of the antibody formats of the present disclosure is the use of linkers to connect immunoglobulin domains. A series of r:Fv-IgGs with variant linkers were designed. A first set of linkers comprised sequences that substantially comprise serine, glycine, or serine and glycine. Serine and glycine are commonly used as linkers due to their flexibility and favorable solution properties. A second set of linkers comprised sequences that substantially comprise native antibody sequence. In these linkers, native sequences that compose antibody sequences are used as linkers. Two particularly useful native antibody sequences are heavy chain sequences that reside at the elbow between VH1 and CH1 domains, and light chain sequences that reside at the elbow between the VL and CL domains. The utility of native antibody sequence linkers is that they can be used to reduce some non-native sequence within a tetravalent antibody format. The length of a given linker can vary, from 1 residue to 20 or more residues. Greater length typically provides greater flexibility between linked immunoglobulin domains. Table 3 describes the linkers that were engineered into the r:Fv-IgG 3C8-1A7 tetravalent biepitopic format.

TABLE 3

Description of linkers

| Name | Heavy Chain Linker (LH) | LH SEQ ID | Light Chain Linker (LL) | LL SEQ ID |
|---|---|---|---|---|
| Glycine/Serine Linkers | | | | |
| GS (Short) | GGGGSG | 270 | GGSGG | 271 |
| GS (Medium) | GGGGSGGGGS | 272 | GGGGSGGGGS | 272 |
| GS (Long) | GGGGSGGGGSGGGG | 273 | GGSGGGGSGGGGS | 274 |
| Native Antibody Sequence Linkers | | | | |
| Elbow (Short) | ASTKGP | 275 | RTVAAP | 276 |
| Elbow (Long) | ASTKGPSVFPLAP | 277 | RTVAAPSVFIFPP | 278 |

DNAs encoding variant linkers of r:Fv-IgG 3C8/1A7 were constructed as described above, and proteins were expressed in HEK293 cells and purified as described above. r:Fv-IgGs were tested for OX40 agonist activity in both the primary human T cell and Jurkat reporter assay as described above. Data in FIG. 38 demonstrate that while glycine-serine linkers provided marginally enhanced agonism of OX40 relative to native antibody elbow linkers in the Jurkat reporter assay, the data highlight that all engineered linkers provide effective links between Fv and IgG portions of the r:Fv-IgG to enable agonism of the OX40 receptor.

Example 17. Affinity Engineering of Tetravalent Formats

Variants of both the 1A7 and 3C8 variable regions were engineered in order to explore the dependence of agonist activity of tetravalent biepitopic formats on the affinity of individual OX40 binding components. The affinity engineering approach leveraged NNK-walk library generation coupled with phage display and Next Generation Sequencing (NGS) (described more fully in Koenig et al., J Biol Chem 2015, 290(36):21773-21786).

Variable domain NNK-Walk libraries of 1A7 and 3C8 were designed and constructed. 1A7 and 3C8 Fabs were subcloned into a phagemid construct. Diversified 1A7 VH residues were 28-35, 49-65, 93-102 and VL residues were 28-34, 50-56, 91-96. Diversified 3C8 VH residues were 28-35, 50-65, 95-97 and VL residues 28-34, 50-56, 89-96. Diversified residues in the phagemid construct were randomized by NNK walk, each with an NNK codon at one position targeted for randomization. NNK encodes for all 20 amino acids (n=G, A, T, and C; K=G and T, in equal proportions). The template for each mutagenesis reaction was generated by introducing stop codons (TAA) at all of the positions targeted for randomization in each reaction. VH and VL libraries were generated separately by electroporating the pool of DNA products from mutagenesis reactions into *Escherichia coli* XL1 cells, yielding ~10$^9$ transformants.

Phage encoding 1A7 and 3C8 libraries were panned against recombinant OX40 protein. OX40-binding clones were selected using 96 well ELISA plate. Phage display libraries were incubated with 5 ug/ml plate bound OX40 as 1$^{st}$ round, followed by a few rounds of solution bound OX40 selection at 50, 10, 2, 0.5, 0.1 nM, and 0.1 nM biotinlayted+ 100 nM non-biotinylated on Streptavidin coated plate. Bound phage from each run was washed and eluted in 100 mM HCl for 20 min, then neutralized with $^1/_{10}$ volume of 1 M Tris pH 11.0 and used to infect *E. coli* for amplification and next round selection. Phage titer was monitored at each run. Panning was stopped at the run at which enrichment was not observed. DNA was extracted from the bacteria pellet from the previous run.

Enriched NNK walk libraries post-panning were deep sequenced. Phagemid DNA was isolated from *E. coli* XL1 cells from both the unselected and the selected 1A7 and 3C8 NNK library and used for PCR amplification of VL and VH regions using Phusion polymerase (New England BioLabs). PCR products were purified to generate libraries using the TruSeq Nano DNA library preparation kit (Illumina). Multiplexed adapter-ligated libraries with unique barcodes were sequenced on an Illumina MiSeq sequencing system for 300-bp paired-end sequencing. The sequences for enrichment analysis were from the panning at 0.1 nM and 0.5 nM biotinlated human OX40 for 1A7 and 3C8 respectively.

For analysis of NGS results, sequencing reads were splitted into R1/R2 reads if the amplicon size was greater than 300 bps. In that case, a merging step was conducted using the FLASH program[Magoč, T. & Salzberg, S. L. Bioinformatics 2011] to reconstruct the full amplicon. For each reconstructed full amplicon, nucleotide sequences (9 bps long each) flanking the mutational region were used to locate and extract the mutated section sequence. The extracted sequence was checked against a known template length to screen for unwanted indel sequences. Remaining sequences were translated to amino acids and could be further filtered depending on the researchers' needs. (i.e. keeping only extracted sequence with only 1 mutation, or discarding extracted sequence with mutation on known unmutated position). After screening and keeping those amino acids sequences that satisfied the criteria (i.e. the ones listed above), these sequences were counted based on their unique amino acids sequence. Then, only amino acids sequence above certain cutoffs (i.e. standard >2 counts or Vivian's>20 counts) could be used to further discard unwanted amino acids sequence. These "cleaned" amino acids sequence would then be used to calculate the Log 2 ratio of the amino acids' frequencies in the mutated section. In particular, the frequency of each of the 20 residues in each position was determined from the "cleaned" amino acids sequences for the pre-panned and the post-panned libraries. The pre-panned library was sometime the first round panned libraries given the major under-sampling issue with the very initial library. Thereafter, log 2 was taken to the frequency ratio of the post-over pre-panned library. Log 2 ratio of at least 4-5 (i.e. >=16×-32× enrichments) was considered real enrichment.

Based on the NNK walk phage panning NGS results, substitutions were select to both increase and reduce the affinity of the 1A7 and 3C8 variable regions. DNAs encoding heavy (human IgG1 constant region) and light chain (Ckappa constant region) variants were constructed as described above, and antibodies were expressed in HEK293 cells and purified as described above. Binding of variants to OX40 was tested using Biacore as described above. Table 4 and Table 5 present the variant name, substitution(s), and OX40 affinities (KDs) of all variants generated and tested. Positions of all substitutions are numbered according to the Kabat convention.

TABLE 4

1A7 Affinity Variants

| Variant | Also Called | Substitution(s) | KD (M) |
|---|---|---|---|
| 1A7 | 1A7 | WT | 1.40E−10 |
| 1A7.HC.T28E | | T28E | 1.36E−10 |
| 1A7.LC.N31Q | | N31Q | 1.00E−10 |
| 1A7VH.001 | | S32H; N54Q; V102Y | 3.46E−10 |
| 1A7VH.003 | | T30F; N54L; L94H | 5.84E−10 |
| 1A7VH.004 | | M34L; N60Q; S101A | 2.26E−10 |
| 1A7VH.005 | | T30I; E65S | 2.39E−10 |
| 1A7VH.006 | | S32A; V93S | 2.32E−10 |
| 1A7VH.007 | | T30G; D56E | 2.76E−10 |
| 1A7VH.008 | | D31R; D53Y; L94F | 4.92E−10 |
| 1A7VH.009 | | K62V; V102R | 1.33E−10 |
| 1A7VH.010 | | F29L; S58L; S101V | 2.21E−10 |
| 1A7VH.01 | | T28S | 1.89E−10 |
| 1A7VH.02 | | T30E | 2.17E−10 |
| 1A7VH.03 | | T30Q | 1.65E−09 |
| 1A7VH.04 | | D31E | 2.42E−10 |
| 1A7VH.05 | | S32Q | 1.07E−09 |
| 1A7VH.06 | | S32T | 3.68E−10 |
| 1A7VH.07 | | Y33L | 5.08E−09 |
| 1A7VH.08 | | Y33P | 1.98E−10 |
| 1A7VH.09 | | M34I | 5.83E−11 |
| 1A7VH.10 | | M34S | 5.84E−11 |
| 1A7VH.12 | | N54Q | 2.52E−10 |
| 1A7VH.13 | | G55P | 3.38E−10 |
| 1A7VH.14 | | G55Q | 2.05E−10 |
| 1A7VH.15 | | D56E | 1.27E−10 |
| 1A7VH.16 | | D56N | 4.95E−10 |
| 1A7VH.17 | | S57A | 1.37E−10 |
| 1A7VH.18 | | S57N | 3.93E−10 |
| 1A7VH.19 | | S58Q | 2.21E−10 |
| 1A7VH.20 | | N60T | 1.46E−10 |
| 1A7VH.21 | | F63S | 1.84E−10 |
| 1A7VH.22 | | R64N | 1.96E−10 |
| 1A7VH.23 | | E65Q | 1.02E−10 |
| 1A7VH.24 | | V93I | 1.84E−10 |
| 1A7VH.25 | | L94F | 1.57E−10 |
| 1A7VH.26 | | L94I | 1.62E−10 |
| 1A7VH.27 | | L94Y | 4.49E−10 |
| 1A7VH.28 | | A95T | 3.38E−10 |
| 1A7VH.29 | | R97S | 2.83E−08 |
| 1A7VH.30 | | W98F | 8.78E−11 |
| 1A7VH.31 | | W98L | 2.91E−09 |
| 1A7VH.32 | | W98N | 4.04E−08 |
| 1A7VH.33 | | W98Y | 5.19E−10 |
| 1A7VH.34 | | Y199N | 3.63E−10 |
| 1A7VH.35 | | F100A | 2.87E−09 |
| 1A7VH.36 | | S101N | 1.52E−10 |
| 1A7VH.37 | | V102A | 1.68E−10 |
| 1A7VH.38 | | V102Q | 1.95E−10 |
| | 1A7 (Low) | P96A | 4.89E−09 |
| 1A7VH09/VL19 | 1A7 (High) | M34I/R53Y | 9.00E−11 |
| 1A7-VL001 | | S30L; L54I; L94E | 6.12E−11 |
| 1A7-VL002 | | N31M; S56A; P96V | 3.03E−10 |
| 1A7-VL003 | | Y32F; L54A; L94S | 1.60E−10 |
| 1A7-VL004 | | S30G; S52I; H92Q | 1.74E−10 |
| 1A7-VL005 | | L33I; S56V | 1.48E−10 |
| 1A7-VL006 | | S56M; P96A | 3.76E−10 |
| 1A7-VL007 | | N31S; L54S; L94S | 1.22E−10 |
| 1A7-VL008 | | D28S; L54N; T93G | 3.73E−10 |
| 1A7-VL009 | | S30G; R53A; T93G | 1.38E−10 |
| 1A7-VL010 | | N31L; L54S; T93S | 1.06E−10 |
| 1A7-VL01 | | D28E | 1.07E−10 |
| 1A7-VL02 | | D28Q | 1.81E−10 |
| 1A7-VL03 | | I29N | 3.31E−10 |
| 1A7-VL04 | | I29Q | 6.52E−10 |
| 1A7-VL05 | | S30D | 1.39E−10 |
| 1A7-VL06 | | S30G | 1.46E−10 |
| 1A7-VL07 | | S30N | 9.58E−11 |
| 1A7-VL08 | | N31E | 1.19E−10 |
| 1A7-VL09 | | Y32A | 3.33E−08 |
| 1A7-VL10 | | L33A | 1.66E−10 |
| 1A7-VL11 | | L33I | 1.30E−10 |
| 1A7-VL12 | | N34S | 1.90E−09 |
| 1A7-VL13 | | Y50A | 3.20E−10 |
| 1A7-VL14 | | Y50Q | 2.53E−09 |
| 1A7-VL15 | | T51G | 1.40E−10 |
| 1A7-VL16 | | S52D | 1.20E−10 |
| 1A7-VL17 | | R53F | 7.75E−11 |
| 1A7-VL18 | | R53N | 9.34E−11 |
| 1A7-VL19 | | R53Y | 4.80E−11 |
| 1A7-VL20 | | L54I | 1.57E−10 |
| 1A7-VL21 | | G91E | 1.86E−09 |
| 1A7-VL23 | | H92N | 2.47E−10 |
| 1A7-VL24 | | L94I | 1.60E−10 |
| 1A7-VL25 | | L94N | 1.38E−10 |
| 1A7-VL26 | | L94Q | 1.39E−10 |
| 1A7-VL27 | | P95A | 1.30E−10 |
| 1A7-VL28 | | P96S | 4.06E−10 |

TABLE 5

3C8 Affinity Variants

| Variant | Also Called | Substitution(s) | KD (M) |
|---|---|---|---|
| 3C8_hIgG1 | 3C8 | WT | 1.23E−09 |
| 3C8VH-01 | | A28K | 1.39E−09 |
| 3C8VH-02 | | F29E | 8.98E−10 |
| 3C8VH-03 | | T30H | 7.99E−10 |
| 3C8VH-04 | | T30K | 2.13E−09 |
| 3C8VH-05 | | Y32L | 9.81E−08 |
| 3C8VH-06 | | Y32V | 4.18E−08 |
| 3C8VH-07 | | L33S | 0.0000018 |
| 3C8VH-08 | | E35I | 3.59667E−08 |
| 3C8VH-09 | | V50F | 7.735E−09 |
| 3C8VH-10 | | V50S | 2.01E−09 |
| 3C8VH-11 | | I51P | 0.000000137 |
| 3C8VH-12 | | N52L | 2.15E−08 |
| 3C8VH-13 | | G53H | 2.13E−09 |
| 3C8VH-14 | | G53Q | 1.76E−09 |
| 3C8VH-15 | | S54F | 2.7565E−09 |
| 3C8VH-16 | | S54I | 1.09E−09 |
| 3C8VH-17 | | S54P | 1.59E−09 |
| 3C8VH-18 | | G55E | 9.285E−10 |
| 3C8VH-19 | | D56E | 7.99E−10 |
| 3C8VH-20 | | D56Q | 1.56E−09 |
| 3C8VH-21 | | T57F | 1.755E−09 |
| 3C8VH-22 | | T57H | 1.32E−09 |
| 3C8VH-23 | | T57I | 1.57E−09 |
| 3C8VH-24 | | T57N | 1.35E−09 |
| 3C8VH-25 | | Y58E | 1.43E−09 |
| 3C8VH-26 | | Y58P | 0.000000495 |
| 3C8VH-27 | | Y59P | 1.19E−09 |
| 3C8VH-28 | | E61K | 2.02E−09 |
| 3C8VH-29 | | F63H | 1.41E−09 |
| 3C8VH-30 | | K64Q | 6.96E−10 |
| 3C8VH-31 | | D95I | 1.22E−08 |
| 3C8VH-32 | | D95T | 1.5E−09 |
| 3C8VH-33 | | R96F | 3.92E−09 |
| 3C8VH-34 | | R96G | 1.39E−08 |
| 3C8VH-35 | | R96Y | 1.42E−09 |
| 3C8VH-36 | | L97E | 0.000000122 |
| 3C8VH-37 | | L97S | 4.28E−08 |
| 3C8VH-triple01 | | A28K/E61A | 1.31E−09 |
| 3C8VH-triple02 | | I34V/G55E | 1.03E−09 |
| 3C8VH-triple03 | | T30V/F63A | 9.51E−10 |
| 3C8VH-triple04 | | T30K/F63S | 1.03E−09 |
| 3C8VH-triple05 | 3C8 (High) | N31I/K64L | 3.735E−10 |
| 3C8VH-triple06 | | A28Q/F63Y | 1.17E−09 |
| 3C8VH-triple07 | | F29Y/G65S | 1.25E−09 |
| 3C8VH-triple08 | | T30L/Y59F | 1.12E−09 |
| 3C8VH-triple09 | | T30E/I51G | 9.73E−10 |
| 3C8VH-triple10 | | N31I/F63V | 4.8125E−10 |
| 3C8VL-01 | | H24P | 4.78E−09 |
| 3C8VL-02 | | H24R | 1.03E−09 |
| 3C8VL-03 | | H24S | 1.38E−09 |
| 3C8VL-04 | | H24V | 8.72E−10 |
| 3C8VL-05 | | A25L | 1.03E−09 |

TABLE 5-continued

3C8 Affinity Variants

| Variant | Also Called | Substitution(s) | KD (M) |
|---|---|---|---|
| 3C8VL-06 | | A25P | 1.63E-09 |
| 3C8VL-07 | | A25V | 1.71E-09 |
| 3C8VL-08 | | S26G | 9.51E-10 |
| 3C8VL-09 | | S26P | 4.46E-09 |
| 3C8VL-10 | | Q27E | 5.80E-10 |
| 3C8VL-11 | | Q27P | 1.63E-09 |
| 3C8VL-12 | | Q27S | 9.76E-10 |
| 3C8VL-13 | | D28P | 1.65E-09 |
| 3C8VL-14 | | I29Q | 2.47E-08 |
| 3C8VL-15 | | I29Y | 8.35E-09 |
| 3C8VL-16 | | S30E | 7.54E-10 |
| 3C8VL-17 | | S30Q | 1.09E-09 |
| 3C8VL-18 | | S31E | 9.63E-10 |
| 3C8VL-19 | | S31Q | 9.12E-10 |
| 3C8VL-20 | | Y32L | 2.13E-08 |
| 3C8VL-21 | | Y32P | 2.51E-09 |
| 3C8VL-22 | | I33E | 2.78E-09 |
| 3C8VL-23 | | I33L | 1.02E-09 |
| 3C8VL-24 | | I33Y | 1.83E-08 |
| 3C8VL-27 | | H50N | 6.76E-10 |
| 3C8VL-28 | | G51P | 5.01E-08 |
| 3C8VL-29 | | N53P | 3.50E-09 |
| 3C8VL-30 | | L54D | 4.06E-08 |
| 3C8VL-31 | | L54F | 3.80E-08 |
| 3C8VL-32 | | E55F | 2.59E-08 |
| 3C8VL-33 | | E55T | 1.49E-08 |
| 3C8VL-34 | | S56D | 7.70E-10 |
| 3C8VL-35 | | S56E | 5.91E-10 |
| 3C8VL-36 | | S56I | 7.10E-10 |
| 3C8VL-37 | | S56V | 3.86E-10 |
| 3C8VL-38 | | S56Y | 7.88E-10 |
| 3C8VL-39 | | V89G | 1.43E-09 |
| 3C8VL-40 | | V89K | 6.87E-06 |
| 3C8VL-41 | | H90F | 2.68E-10 |
| 3C8VL-42 | | H90Q | 1.44E-09 |
| 3C8VL-43 | | Y91E | 2.70E-08 |
| 3C8VL-44 | | Y91V | 8.31E-09 |
| 3C8VL-45 | | A92P | 3.08E-08 |
| 3C8VL-46 | | A92S | 7.14E-10 |
| 3C8VL-47 | | Q93P | 7.41E-09 |
| 3C8VL-48 | | F94G | 1.18E-08 |
| 3C8VL-49 | | F94Q | 9.77E-09 |
| 3C8VL-50 | | F94R | 6.74E-10 |
| 3C8VL-51 | | P95I | 9.89E-09 |
| 3C8VL-52 | 3C8 (Low) | P95Y | 5.45E-08 |
| 3C8VL-53 | | Y96E | 3.66E-10 |
| 3C8VL-54 | | Y96L | 8.43E-10 |
| 3C8VL-triple01 | | D28S; T52S; F94L | 9.38E-10 |
| 3C8VL-triple02 | | S30Y; N53K; A92S | 4.77E-10 |
| 3C8VL-triple03 | | S30N; S56L; Y96L | 6.02E-10 |
| 3C8VL-triple04 | | I33V; G51S; Y96F | 4.98333E-10 |
| 3C8VL-triple05 | | V34S; S56V; V89G | 9.315E-10 |
| 3C8VL-triple06 | | S56E; Q93N | 8.07E-10 |
| 3C8VL-triple07 | | V34T; S56L; H90Q | 1.22E-09 |
| 3C8VL-triple08 | | S30G; T52S; Y96L | 1.0345E-09 |
| 3C8VL-triple09 | | S31N; T52S; Q93S | 1.01E-09 |
| 3C8VL-triple10 | | I33L; S56E | 4.79E-10 |
| 3C8VL-YA | | | 2.10567E-08 |

Variants were selected for incorporation into r:Fv-IgG 3C8-1A7. Selected variants are designated as High or Low in Table 4 and Table 5 above. Variants of 1A7 and 3C8 with increased affinity (lower KD) are referred to as 1A7(High) and 3C8(High) respectively. Variants of 1A7 and 3C8 with reduced affinity (higher KD) are referred to as 1A7(Low) and 3C8(Low) respectively.

DNAs encoding high and low affinity variants of r:Fv-IgG 3C8-1A7 were constructed as described above. All constructs comprised a human IgG1 heavy constant region and human Ckappa light constant region. Variants were expressed in HEK293 cells and purified as described above. Binding of variants to OX40 was tested using Biacore as described above. FIG. 39 shows a plot of the affinities of high and low affinity variant versions of IgG1 and r:Fv-IgG formats. Affinity differences of up to 2 logs in IgG1 format translated to more modest affinity differences in r:Fv-IgG format.

Affinity variant r:Fv-IgGs were tested for OX40 agonist activity in the primary human CD4+ memory T cell assay and OX40+ Jurkat cell luciferase reporter assay. The data are shown in FIG. 40. Increased and/or reduced affinity in 1A7 and 3C8 Fv's resulted in modest differences in OX40 agonism activity, and overall a range of affinities for the independent binding units are permissive for enabling intrinsic agonism activity of tetravalent biepitopic formats.

Example 18. Agonism of Death Receptor 5 Using Tetravalent Biepitopic Antibodies

The multivalent biepitopic approach was explored to engineer agonism activity into antibodies targeting the TNFRSF member Death Receptor 5 (DR5), also known as TNF-related apoptosis-inducing ligand receptor 2 (TRAILR2) and TNFRSF10B. DR5 is a target of therapeutic interest due to its role in mediating mediating apoptosis of cancer cells (Ashkenazi 2015, J Clin Invest 125(2): 487-489). It has been established that antibodies against DR5 rely on FcγR-mediated crosslinking in vivo for activity (Wilson et al., 2011, Cancer Cell 19:101-13; Kim & Ashkenazi, 2013, J Exp Med 210:1647-51).

A set of 16 mouse anti-DR5 monoclonal Abs were generated from classical hybridoma-based technology. DNAs encoding heavy and light chains were cloned from hybridomas and subcloned into the pRK vector as described above with mouse IgG2a heavy constant and mouse Ckappa constant chains. The humanized anti-DR5 human IgG1 antibody drozitumab (Kang et al., 2011, Clin Cancer Res 17(10): 3181-3192), which has been previously characterized pre-clinically and clinically, was also produced as a comparator. Antibodies were expressed using CHO cells with a double-knock out for pro-apoptotic factors Bax and Bak (Bax$^-$/Bak$^-$) (Macaraeg N F et al., 2013, Biotechnol Prog 29:1050-8) and purified over a Protein A column. When needed, most active antibodies were further purified to remove aggregate species via chromatography with either a size exclusion column, an SP cation exchange column, or a hydrophobic interaction column.

Anti-DR5 antibodies were classified into different epitope groups utilizing the array-based surface plasmon resonance imaging (SPRi) technique (Carterra USA, Wasatch Microfluidics). The epitope binning assay, analogous to a "classical" sandwich assay, utilized microfluidics technology to immobilize the anti-DR5 antibodies on a label-free biosensor, saturate all surface bound antibodies with purified recombinant flag-tagged DR5 extracellular domain (ECD) followed by the addition of each antibody to compete for binding to DR5. Antibodies were immobilized onto a gold surface biosensor using EDC/NHS chemistry in pre-defined locations. The immobilized antibodies were saturated with the extracellular domain of DR5 antigen followed by competition of the antibody/DR5 complex with a second antibody in the set. Blocking the binding of a solution antibody against an immobilized antibody/antigen complex indicated that antibodies belong to the same epitope group. Removal of antigen and solution antibody, re-saturation of the immobilized antibody with the DR5 antigen, and addition of a different antibody was repeated until all antibodies were tested. Once all antibodies were tested and placed into epitope groups, a network plot was generated to identify different epitopes that are recognized by the 16 mouse antibodies. The 16 mouse antibodies were distributed between three distinct epitope groups that were identified for the DR5 antigen represented as a network plot. Upon closer examination of the SPR sensorgrams, 3 mouse antibodies demonstrated low binding affinities with SPR responses at baseline. Removal of these antibodies defined the remaining 13 antibodies into their respective epitope groups. Epitope groups of the murine antibodies and drozitumab are provided in Table 6.

TABLE 6

Summary of epitope bin and affinities of DR5-specific mouse monoclonal antibodies.

| Epitope Group | Antibody | KD (nM) | Stdev (+/−) |
|---|---|---|---|
| 1 | 12A1 | 20.43 | 3.57 |
| 1 | 13E11 | 52.23 | 2.35 |
| 1 | 13E3 | 12.23 | 1.33 |
| 2 | 11H12 | 0.72 | 0.18 |
| 2 | 3F11 | 1.03 | 0.17 |
| 2 | 3H3 | 0.97 | 0.24 |
| 2 | 5C7 | 6.43 | 0.75 |
| 2 | 7G4 | 52.37 | 4.48 |
| 3 | 1B10 | 8.71 | 0.17 |
| 3 | 14G8 | 4.46 | 1.99 |
| 3 | 3C9 | ND | |
| 3 | 3D5 | 2.63 | 0.16 |
| 3 | 3H1 | ND | |
| 3 | 4D9 | 0.33 | 0.12 |
| 3 | 4H10 | 0.41 | 0.1 |
| 3 | 6A5 | 57.83 | 1.51 |
| Drozitumab | Drozitumab | 3.35 | 0.7 |

Binding affinities of antibodies to soluble DR5 antigen was measured using surface plasmon resonance (SPR). Binding experiments were carried out using SPR measurements on a Biacore T200 instrument (GE Healthcare) at 25° C. Test proteins were immobilized at 1 ug/mL on an Protein-A coated sensor chip. Fivefold serial dilutions of the analyte, DR5-flag (100 to 0.16 nM) were injected in running buffer (HBS-P+ Buffer 1×; 0.01 M HEPES, 0.15 M NaCl, 0.05% (v/v) Surfactant-20 pH 7.4) at a flow rate of 30 µL/min and sensorgrams for association and disassociation phases were recorded. Analytes were injected for 180 s and allowed to dissociate for 600 s. Nonlinear regression analysis of the data fitted to a 1:1 Langmuir binding model provided association ($k_{on}$), dissociation ($k_{off}$) rate constants, and equilibrium dissociation constants (KD). For antibodies with fast association and dissociation rate constants, steady-state affinity analysis was also obtained. Affinities of mouse antibodies and drozitumab are shown in Table 6. KDs ranged from 0.1 to 100 nM for antibodies of epitope groups 2 and 3, while antibodies from group 1 displayed KD>10 nM.

Bivalent biepitopic and tetravalent monoepitopic and biepitopic versions of select anti-DR5 antibodies were engineered. DNAs encoding the VH and VL domains of select murine antibodies 13E3, 3H3, 4D9, and 11H12 were inserted into the pRK vector comprising human IgG1 heavy constant and human Ckappa light constant regions, as described above to create mouse Fv—human IgG1/Ckappa chimeric IgGs. Biepitopic versions of select combinations of 13E3, 3H3, 4D9, 11H12, and drozitumab antibodies were engineered by inserting VH regions into the appropriate heavy chain constructs with "knob" or "hole" variants (Ridgway J B B et al., 1996, Protein Eng 9:617-21). DNA encoding VH regions was subcloned into a variant human IgG1 comprising knob mutation T366W (EU numbering), with a C-terminal 6His tag, or subcloned into a variant human IgG1 comprising hole mutations T366S/L368A/Y407V (EU numbering), with a C-terminal Flag tag. Tetravalent biepitopic versions of select combinations of 13E3, 3H3, 4D9, 11H12, and drozitumab antibodies were engineered using the r:Fab-IgG version 2 (V2) format as described in Example 2 and illustrated FIG. 9. This format uses the knob/hole variants described above to promote heterodimer formation. DNA encoding VH regions was subcloned into a variant human IgG1 comprising knob mutation T366W (EU numbering) or subcloned into a variant human IgG1 comprising hole mutations T366S/L368A/Y407V (EU numbering). IgGs, Biepitopic IgGs, and r:Fab-IgGs were expressed the Bax⁻/Bak⁻ CHO strain and purified as described above. Biepitopic IgGs and r:Fab-IgGs were produced using a method based on in vitro assembly of separate half-antibodies (Spiess et al., 2013, Nat Biotechnol 31(8):753-8). Knob/Hole variant half-antibodies were expressed as half-antibodies, assembled in vitro, and purified as described above.

IgG, Biepitopic IgG, and r:Fab-IgG anti-DR5 antibodies were tested for their ability to promote caspase 8 activity. HT-29 and Colo205 cell lines were obtained from the American Type Cell Culture Collection. Cells were maintained in RPMI medium supplemented with L-glutamine (L-glut) and 10% fetal bovine serum (FBS) (Invitrogen Inc., Carlsbad, Calif., USA) under 5% $CO_2$ at 37° C. Antibodies were either tested at 50 nM, or dilutions of antibodies were prepared in growth media. 100 µL of each antibody sample was added to each well in a 96-white walled plate (Thermo Scientific). Adherent cells were trypsinized and detached from tissue culture flasks. 50 µL of a 1.0×10⁶ cells/mL cell suspension was added to 100 µL of Ab in the 96-white walled plate. Cells were incubated for 4 hr for caspase-8 and 24 hr for cell viability at 37° C., 5% $CO_2$. Caspase activity and cell viability were assessed using Caspase-Glo 8 and CellTiter-Glo (Cell Viability) luminescence assays from Promega. Experiments were done in triplicate and luminescence was read using Envision (PerkinElmer). Fold caspase 8 activity and % cell viability were calculated by normalizing to cells alone.

FIG. 41 shows caspase 8 activity at 50 nM antibody concentration for IgG1, biepitopic IgG1, and biepitopic r:Fab-IgG versions of the anti-DR5 antibodies against human colorectal adenocarcinoma HT-29 cells. Neither the bivalent monoepitopic IgG1 nor bivalent biepitopic IgG1 antibodies mediated caspase 8 activity on their own, consistent with the requirement of extrinsic crosslinking for activity. Drozitumab IgG1 may have exhibited some modest level of activity in this experiment. In contrast, teravalent biepitopic r:Fab-IgG formats that paired drozitumab with 4D9 (Droz-4D9) and 11H12 with 4D9 (11H12-4D9) mediated intrinsic agonist activity against DR5 to promote caspase 8 signaling. Interestingly, the tetravalent monoepitopic r:Fab-IgG drozitumab-drozitumab format, wherein all 4 Fvs in the r:Fv-IgG are the drozitumab Fv, also mediated intrinsic agonist activity. Both tetravalent biepitopic r:Fab-IgG 13E3-3H3 and tetravalent monoepitopic r:Fab-IgG 4D9-4D9 mediated marginal to no DR5 agonist activity.

The drozitumab-4D9 combinations were selected for further characterization. IgG, biepitopic IgG, and r:Fab-IgG antibodies were tested for caspase 8 activity and antiproliferative activity against both HT-29 cells and a human colorectal adenocarcinoma Colo205 cell line. FIGS. 42-43 show dose-response curves measuring caspase 8 activity (FIG. 42) and antiproliferative activity (FIG. 43) against HT-29 cells. FIGS. 44-45 show dose-response curves measuring caspase 8 activity (FIG. 44) and antiproliferative activity (FIG. 45) against Colo205 cells. Neither the IgG1 version of 4D9, the tetravalent monoepitopic r:Fab-IgG version of 4D9, nor the bivalent biepitopic combination of drozitumab with 4D9 mediated caspase 8 activity nor had any effect on cell viability of either cell line. IgG1 drozitumab mediated modest caspase 8 activity against both cell lines and anti-proliferative activity against Colo205 cells at higher concentrations. Tetravalent monoepitopic r:Fab-IgG drozitumab-drozitumab promoted superior caspase 8 activity to the IgG1 version for both cells lines, and mediated potent anti-proliferative activity against Colo205 cells. The tetravalent biepitopic combination of drozitumab and 4D9, r:Fab-IgG drozitumab-4D9, mediated the strongest level of agonist activity in terms of both potency and maximal activity relative to the other antibodies. r:Fab-IgG drozitumab-4D9 promoted profound caspase 8 activity in both cell lines and anti-proliferative activity against Colo205 cells. The lack of impact of these agents on HT-29 cell viability despite the strong caspase 8 activity suggests that this cell line is insensitive or weakly sensitive to signaling through the extrinsic death receptor-mediated pathway. This contrasts with the Colo205 cell line, where DR5 agonism and caspase 8 activation by r:Fab-IgG drozitumab-4D9, r:Fab-IgG drozitumab-drozitumab, and to a lesser extent IgG1 drozitumab leads to inhibition of cell proliferation. Nonetheless, altogether the data support the optimal targeting of multiple epitopes in multivalent antibody formats to agonize target receptors for therapeutic purposes.

What is claimed is:

1. A tetravalent antigen binding complex having agonist activity for OX40, the complex comprising four antigen binding domains that bind OX40, wherein each of the four antigen binding domains comprises an antibody heavy chain variable (VH) domain and an antibody light chain variable (VL) domain, wherein the complex comprises one or more antigen binding domains that bind a first epitope of OX40 and one or more antigen binding domains that bind a second epitope of OX40, wherein the first and second epitopes of OX40 are different; and wherein:
   (1) the antigen binding domain that binds the first epitope of OX40 comprises: (a) a VH domain comprising an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and (b) a VL domain comprising an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7; and
   (2) the antigen binding domain that binds the second epitope of OX40 comprises: (a) a VH domain comprising an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; and (b) a VL domain comprising: an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42.

2. The complex of claim 1, wherein the antigen binding domains that bind the first epitope do not cross-compete for binding OX40 with the antigen binding domains that bind the second epitope.

3. A tetravalent antigen binding complex having agonist activity for OX40, the complex comprising four antigen binding domains that bind OX40, wherein each of the four antigen binding domains comprises an antibody heavy chain variable (VH) domain and an antibody light chain variable (VL) domain, wherein the complex comprises one or more antigen binding domains that bind a first epitope of OX40 and one or more antigen binding domains that bind a second epitope of OX40, wherein the antigen binding domains that bind the first epitope do not cross-compete for binding OX40 with the antigen binding domains that bind the second epitope; and wherein:
   (1) the antigen binding domain that binds the first epitope of OX40 comprises: (a) a VH domain comprising an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and (b) a VL domain comprising an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7; and
   (2) the antigen binding domain that binds the second epitope of OX40 comprises: (a) a VH domain comprising an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; and (b) a VL domain comprising: an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42.

4. The complex of claim 1, wherein the complex comprises two antigen binding domains that bind to the first epitope and two antigen binding domains that bind to the second epitope.

5. The complex of claim 1, wherein the first epitope comprises one or more amino acid residues selected from the group consisting of: 114-119, 124, 126, 127, 129, 130, 132, 140, and 142 of SEQ ID NO:281.

6. The complex of claim 1, wherein the second epitope comprises one or more amino acid residues selected from the group consisting of: 68-71, 83-90, 95, and 98 of SEQ ID NO:281.

7. The complex of claim 1, wherein the VH domain of the antigen binding domain that binds the first epitope of OX40 comprises the amino acid sequence of SEQ ID NO:56, and wherein the VL domain of the antigen binding domain that binds the first epitope of OX40 comprises the amino acid sequence of SEQ ID NO:57.

8. The complex of claim 1, wherein the VH domain of the antigen binding domain that binds the second epitope of OX40 comprises the amino acid sequence of SEQ ID NO:128, and wherein the VL domain of the antigen binding domain that binds the second epitope of OX40 comprises the amino acid sequence of SEQ ID NO:129.

9. The complex of claim 1, wherein the VH domain of the antigen binding domain that binds the first epitope of OX40 comprises the amino acid sequence of SEQ ID NO:56, and wherein the VL domain of the antigen binding domain that binds the first epitope of OX40 comprises the amino acid sequence of SEQ ID NO:57; and wherein the VH domain of the antigen binding domain that binds the second epitope of OX40 comprises the amino acid sequence of SEQ ID NO:128, and wherein the VL domain of the antigen binding domain that binds the second epitope of OX40 comprises the amino acid sequence of SEQ ID NO:129.

10. The complex of claim 1, wherein the complex comprises two antibody heavy chain polypeptides and two antibody light chain polypeptides;

wherein each of the antibody heavy chain polypeptides comprises:

$$VH_1\text{-}L_1\text{-}VH_2\text{-}L_2\text{-}CH_1\text{-hinge-}CH_2\text{-}CH_3 \qquad [I];$$

wherein each of the antibody light chain polypeptides comprises:

$$VL_1\text{-}L_3\text{-}VL_2\text{-}L_4\text{-}CL \qquad [II];$$

wherein each of the antibody heavy chain polypeptides associates with one antibody light chain polypeptide such that $VH_1$ and $VL_1$ form an antigen binding domain and $VH_2$ and $VL_2$ form an antigen binding domain;

wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, $CH_3$ is an antibody third heavy chain constant domain, and $L_1$, $L_2$, $L_3$, and $L_4$ are amino acid linkers.

11. The complex of claim 10, wherein $VH_1$ and $VL_1$ form an antigen binding domain that binds the first epitope of OX40, and wherein $VH_2$ and $VL_2$ form an antigen binding domain that binds the second epitope of OX40.

12. The complex of claim 10, wherein $VH_1$ and $VL_1$ form an antigen binding domain that binds the second epitope of OX40, and wherein $VH_2$ and $VL_2$ form an antigen binding domain that binds the first epitope of OX40.

13. The complex of claim 10, wherein $L_2$ and $L_4$ are 0 amino acids in length.

14. The complex of claim 10, wherein $L_1$ is between 0 and 20 amino acids in length.

15. The complex of claim 14, wherein at least 90% of the amino acids of $L_1$ are glycine and/or serine amino acids.

16. The complex of claim 15, wherein $L_1$ comprises an amino acid sequence selected from the group consisting of GGGGSG (SEQ ID NO:270), GGGGSGGGGS (SEQ ID NO:272), and GGGGSGGGGSGGGG (SEQ ID NO:273).

17. The complex of claim 10, wherein $L_3$ comprises an amino acid sequence selected from the group consisting of GGSGG (SEQ ID NO:271), GGGGSGGGGS (SEQ ID NO:272), and GGSGGGGSGGGGS (SEQ ID NO:274).

18. The complex of claim 10, wherein $L_1$ comprises the amino acid sequence GGGGSG (SEQ ID NO:270), and wherein $L_3$ comprises the amino acid sequence GGSGG (SEQ ID NO:271).

19. The complex of claim 10, wherein $L_1$ and $L_3$ both comprise the amino acid sequence GGGGSGGGGS (SEQ ID NO:272).

20. The complex of claim 10, wherein $L_1$ comprises the amino acid sequence GGGGSGGGGSGGGG (SEQ ID NO:273), and wherein $L_3$ comprises the amino acid sequence GGSGGGGSGGGGS (SEQ ID NO:274).

21. The complex of claim 10, wherein $L_1$ comprises an amino acid sequence found within a human antibody constant domain sequence.

22. The complex of claim 21, wherein $L_1$ comprises the amino acid sequence ASTKGP (SEQ ID NO:275) or ASTKGPSVFPLAP (SEQ ID NO:277).

23. The complex of claim 10, wherein $L_3$ comprises the amino acid sequence RTVAAP (SEQ ID NO:276) or RTVAAPSVFIFPP (SEQ ID NO:278).

24. The complex of claim 10, wherein $L_1$ comprises the amino acid sequence ASTKGP (SEQ ID NO:275), and wherein $L_3$ comprises the amino acid sequence RTVAAP (SEQ ID NO:276).

25. The complex of claim 10, wherein $L_1$ comprises the amino acid sequence ASTKGPSVFPLAP (SEQ ID NO:277), and wherein $L_3$ comprises the amino acid sequence RTVAAPSVFIFPP (SEQ ID NO:278).

26. The complex of claim 10, wherein $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

27. The complex of claim 10, wherein $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

28. The complex of claim 10, wherein $VH_1$ comprises the amino acid sequence of SEQ ID NO:128, wherein $VL_1$ comprises the amino acid sequence of SEQ ID NO:129, wherein VH$_2$ comprises the amino acid sequence of SEQ ID NO:56, and wherein VL$_2$ comprises the amino acid sequence of SEQ ID NO:57.

29. The complex of claim 10, wherein VH$_2$ comprises the amino acid sequence of SEQ ID NO:128, wherein VL$_2$ comprises the amino acid sequence of SEQ ID NO:129, wherein VH$_1$ comprises the amino acid sequence of SEQ ID NO:56, and wherein VL$_1$ comprises the amino acid sequence of SEQ ID NO:57.

30. The complex of claim 10, wherein:
    (a) both of the antibody heavy chain polypeptides comprise the amino acid sequence of SEQ ID NO:240, and both of the antibody light chain polypeptides comprise the amino acid sequence of SEQ ID NO:241;
    (b) both of the antibody heavy chain polypeptides comprise the amino acid sequence of SEQ ID NO:242, and both of the antibody light chain polypeptides comprise the amino acid sequence of SEQ ID NO:243;
    (c) both of the antibody heavy chain polypeptides comprise the amino acid sequence of SEQ ID NO:250, and both of the antibody light chain polypeptides comprise the amino acid sequence of SEQ ID NO:251;
    (d) both of the antibody heavy chain polypeptides comprise the amino acid sequence of SEQ ID NO:252, and both of the antibody light chain polypeptides comprise the amino acid sequence of SEQ ID NO:253;
    (e) both of the antibody heavy chain polypeptides comprise the amino acid sequence of SEQ ID NO:254, and both of the antibody light chain polypeptides comprise the amino acid sequence of SEQ ID NO:255;
    (f) both of the antibody heavy chain polypeptides comprise the amino acid sequence of SEQ ID NO:256, and both of the antibody light chain polypeptides comprise the amino acid sequence of SEQ ID NO:257;
    (g) both of the antibody heavy chain polypeptides comprise the amino acid sequence of SEQ ID NO:258, and both of the antibody light chain polypeptides comprise the amino acid sequence of SEQ ID NO:259;
    (h) both of the antibody heavy chain polypeptides comprise the amino acid sequence of SEQ ID NO:260, and both of the antibody light chain polypeptides comprise the amino acid sequence of SEQ ID NO:261;
    (i) both of the antibody heavy chain polypeptides comprise the amino acid sequence of SEQ ID NO:262, and both of the antibody light chain polypeptides comprise the amino acid sequence of SEQ ID NO:263;
    (j) both of the antibody heavy chain polypeptides comprise the amino acid sequence of SEQ ID NO:264, and both of the antibody light chain polypeptides comprise the amino acid sequence of SEQ ID NO:265; or
    (k) both of the antibody heavy chain polypeptides comprise the amino acid sequence of SEQ ID NO:266, and both of the antibody light chain polypeptides comprise the amino acid sequence of SEQ ID NO:267.

31. The complex of claim 30, wherein:
    (a) both of the antibody heavy chain polypeptides comprise the amino acid sequence of SEQ ID NO:240, and both of the antibody light chain polypeptides comprise the amino acid sequence of SEQ ID NO:241; or
    (b) both of the antibody heavy chain polypeptides comprise the amino acid sequence of SEQ ID NO:242, and both of the antibody light chain polypeptides comprise the amino acid sequence of SEQ ID NO:243.

32. The complex of claim 31, wherein both of the antibody heavy chain polypeptides comprise the amino acid sequence of SEQ ID NO:242, and both of the antibody light chain polypeptides comprise the amino acid sequence of SEQ ID NO:243.

33. The complex of claim 1, wherein the complex comprises two antibody heavy chain polypeptides and four antibody light chain polypeptides;
    wherein each of the antibody heavy chain polypeptides comprises:
    $$\text{VH}_1\text{-L}_1\text{-(CH}_1)_x\text{-L}_2\text{-VH}_2\text{-L}_3\text{-(CH}_1)_y\text{-hinge-CH}_2\text{-CH}_3 \qquad [\text{III}];$$
    wherein two of the four antibody light chain polypeptides comprise:
    $$\text{VL}_1\text{-(CL)}_x \qquad [\text{IV}]; \text{ and}$$
    wherein two of the four antibody light chain polypeptides comprise:
    $$\text{VL}_2\text{-(CL)}_y \qquad [\text{V}];$$
    wherein each of the antibody heavy chain polypeptides associates with one light chain polypeptide comprising formula [IV] such that VH$_1$ and VL$_1$ form an antigen binding domain and one light chain polypeptide comprising formula [V] such that VH$_2$ and VL$_2$ form an antigen binding domain; and
    wherein VH$_1$ is a first antibody heavy chain variable domain, VH$_2$ is a second antibody heavy chain variable domain, VL$_1$ is a first antibody light chain variable domain, VL$_2$ is a second antibody light chain variable domain, (CL)$_x$ and (CL)$_y$ are antibody light chain constant domains, (CH1)$_x$ and (CH1)$_y$ are antibody first heavy chain constant domains, hinge is an antibody hinge region, CH$_2$ is an antibody second heavy chain constant domain, CH$_3$ is an antibody third heavy chain constant domain, and L$_1$, L$_2$, and L$_3$ are amino acid linkers.

34. The complex of claim 33, wherein the complex comprises one or more amino acid substitutions in VH$_1$, VL$_1$, (CH$_1$)$_x$, or (CL)$_x$ that promote VH$_1$ and VL$_1$ forming an antigen binding domain; and/or one or more amino acid substitutions in VH$_2$, VL$_2$, (CH$_1$)$_y$, or (CL)$_y$ that promote VH$_2$ and VL$_2$ forming an antigen binding domain.

35. The complex of claim 34, wherein the complex comprises one or more of the following sets of amino acid substitutions:
    (a) a Q39K substitution in VH$_1$ and a Q38E substitution in VL$_1$, and a Q39E substitution in VH$_2$ and a Q38K substitution in VL$_2$, numbering according to Kabat;
    (b) a Q39K substitution in VH$_2$ and a Q38E substitution in VL$_2$, and a Q39E substitution in VH$_1$ and a Q38K substitution in VL$_1$, numbering according to Kabat;
    (c) an S183E substitution in (CH$_1$)$_x$ and a V133K substitution in (CL)$_x$, and an S183K substitution in (CH$_1$)$_y$ and a V133E substitution in (CL)$_y$, numbering according to EU index; or
    (d) an S183E substitution in (CH$_1$)$_y$ and a V133K substitution in (CL)$_y$, and an S183K substitution in (CH$_1$)$_x$ and a V133E substitution in (CL)$_x$, numbering according to EU index.

36. The complex of claim 35, wherein the complex comprises:
    (a) a Q39K substitution in VH$_1$ and a Q38E substitution in VL$_1$, and a Q39E substitution in VH$_2$ and a Q38K substitution in VL$_2$, with numbering according to Kabat; and an S183E substitution in (CH$_1$)$_x$ and a V133K substitution in (CL)$_x$, and an S183K substitution in (CH$_1$)$_y$ and a V133E substitution in (CL)$_y$, numbering according to EU index; or (b) Q39K substitution in $VH_2$ and a Q38E substitution in $VL_2$, and a Q39E substitution in $VH_1$ and a Q38K substitution in $VL_1$, numbering according to Kabat; and or an S183E substitution in $(CH_1)_y$ and a V133K substitution in $(CL)_y$, and an S183K substitution in $(CH_1)_x$ and a V133E substitution in $(CL)_x$, numbering according to EU index.

37. The complex of claim 33, wherein $VH_1$ and $VL_1$ form an antigen binding domain that binds the first epitope of OX40, and wherein $VH_2$ and $VL_2$ form an antigen binding domain that binds the second epitope of OX40.

38. The complex of claim 33, wherein $VH_1$ and $VL_1$ form an antigen binding domain that binds the second epitope of OX40, and wherein $VH_2$ and $VL_2$ form an antigen binding domain that binds the first epitope of OX40.

39. The complex of claim 33, wherein $L_2$ comprises an amino acid sequence found within a human antibody constant domain sequence.

40. The complex of claim 39, wherein $L_2$ comprises the amino acid sequence DKTHT (SEQ ID NO:268) or DKTHTGGGGSGG (SEQ ID NO:269).

41. The complex of claim 33, wherein $L_1$ and $L_3$ are 0 amino acids in length.

42. The complex of claim 33, wherein $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

43. The complex of claim 33, wherein $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

44. The complex of claim 33, wherein $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57.

45. The complex of claim 33, wherein $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57.

46. The complex of claim 33, wherein:
(a) both of the antibody heavy chain polypeptides comprise the amino acid sequence of SEQ ID NO:244, both of the antibody light chain polypeptides comprising formula [IV] comprise the amino acid sequence of SEQ ID NO:245, and both of the antibody light chain polypeptides comprising formula [V] comprise the amino acid sequence of SEQ ID NO:246; or
(b) both of the antibody heavy chain polypeptides comprise the amino acid sequence of SEQ ID NO:247, both of the antibody light chain polypeptides comprising formula [IV] comprise the amino acid sequence of SEQ ID NO:248, and both of the antibody light chain polypeptides comprising formula [V] comprise the amino acid sequence of SEQ ID NO:249.

47. The complex of claim 1, wherein the complex comprises:
a first antibody heavy chain polypeptide that comprises:

$$VH_1\text{-}L_1\text{-}CH_1\text{-}L_2\text{-}VH_1\text{-}L_3\text{-}CH_1\text{-}hinge\text{-}CH_2\text{-}(CH_3)_x \qquad [VI];$$

two first antibody light chain polypeptides that each comprise:

$$VL_1\text{-}CL \qquad [VII];$$

a second antibody heavy chain polypeptide that comprises:

$$VH_2\text{-}L_7\text{-}CH_1\text{-}L_8\text{-}VH_2\text{-}L_9\text{-}CH_1\text{-}hinge\text{-}CH_2\text{-}(CH_3)_y \qquad [VIII];\ \text{and}$$

two second antibody light chain polypeptides that each comprise:

$$VL_2\text{-}CL \qquad [IX];$$

wherein the first antibody heavy chain polypeptide associates with two first antibody light chain polypeptides comprising formula [VII] such that each $VH_1$ forms an antigen binding domain with a $VL_1$; wherein the second antibody heavy chain polypeptide associates with two second antibody light chain polypeptides comprising formula [IX] such that each $VH_2$ forms an antigen binding domain with a $VL_2$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, $(CH_3)_x$ and $(CH_3)_y$ are antibody third heavy chain constant domains, and $L_1$, $L_2$, $L_3$, $L_7$, $L_8$, and $L_9$ are amino acid linkers.

48. The complex of claim 47, wherein $(CH_3)_x$ comprises a protuberance or cavity, wherein $(CH_3)_y$ comprises a protuberance or cavity, and wherein the protuberance or cavity of $(CH_3)_x$ is positionable in the protuberance or cavity of $(CH_3)_y$.

49. The complex of claim 48, wherein:
(a) $(CH_3)_x$ comprises a T366Y substitution, and $(CH_3)_y$ comprises a Y407T substitution, numbering according to EU index;
(b) $(CH_3)_x$ comprises a T366W substitution, and $(CH_3)_y$ comprises a Y407A substitution, numbering according to EU index;

(c) $(CH_3)_x$ comprises a F405A substitution, and $(CH_3)_y$ comprises a T394W substitution, numbering according to EU index;
(d) $(CH_3)_x$ comprises a Y407T substitution, and $(CH_3)_y$ comprises a T366Y substitution, numbering according to EU index;
(e) $(CH_3)_x$ comprises T366Y and F405A substitutions, and $(CH_3)_y$ comprises T394W and Y407T substitutions, numbering according to EU index;
(f) $(CH_3)_x$ comprises T366W and F405W substitutions, and $(CH_3)_y$ comprises T394S and Y407A substitutions, numbering according to EU index;
(g) $(CH_3)_x$ comprises F405W and Y407A substitutions, and $(CH_3)_y$ comprises T366W and T394S substitutions, numbering according to EU index; or
(h) $(CH_3)_x$ comprises a F405W substitution, and $(CH_3)_y$ comprises a T394S substitution, numbering according to EU index.

50. The complex of claim 47, wherein $VH_1$ and $VL_1$ form an antigen binding domain that binds the first epitope of OX40, and wherein $VH_2$ and $VL_2$ form an antigen binding domain that binds the second epitope of OX40.

51. The complex of claim 47, wherein $VH_1$ and $VL_1$ form an antigen binding domain that binds the second epitope of OX40, and wherein $VH_2$ and $VL_2$ form an antigen binding domain that binds the first epitope of OX40.

52. The complex of claim 47, wherein $L_2$ and $L_8$ both comprise an amino acid sequence found within a human antibody constant domain sequence.

53. The complex of claim 52, wherein $L_2$ and $L_8$ both comprise the same amino acid sequence selected from the group consisting of DKTHT (SEQ ID NO:268) and DKTHTGGGGSGG (SEQ ID NO:269).

54. The complex of claim 47, wherein $L_1$, $L_3$, $L_7$, and $L_9$ are 0 amino acids in length.

55. The complex of claim 47, wherein $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

56. The complex of claim 47, wherein $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

57. The complex of claim 47, wherein $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57.

58. The complex of claim 47, wherein $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57.

59. The complex of claim 1, wherein the complex comprises: an antibody comprising two antibody heavy chains associated with two antibody light chains, and two antibody Fab fragments;
wherein each of the antibody heavy chains of the antibody comprises:

$VH_1$-$CH_1$-hinge-$CH_2$-$CH_3$ [X];

wherein each of the antibody light chains of the antibody comprises:

$VL_1$-CL [VII];

wherein each of the antibody Fab fragments comprises:
a heavy chain fragment comprising:

$VH_2$-$CH_1$ [XI]; and a light chain comprising:

$VL_2$-CL [IX];

wherein each of the antibody heavy chains is associated with one of the antibody light chains such that $VH_1$ and $VL_1$ form an antigen binding domain; wherein each of the antibody Fab fragments comprises one heavy chain fragment comprising formula [XI] associated with one light chain fragment comprising formula [IX] such that $VH_2$ and $VL_2$ form an antigen binding domain; wherein each of the antibody Fab fragments is coupled with one of the antibody heavy chains or one of the antibody light chains of the antibody via linker $L_1$; and
wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, and $CH_3$ is an antibody third heavy chain constant domain.

60. The complex of claim 59, wherein each of the $L_1$ linkers is a bis-maleimido polyethylene glycol (PEG) linker.

61. The complex of claim 60, wherein the PEG linker comprises between one and eleven PEG subunits.

62. The complex of claim 61, wherein the PEG linker comprises one, two, or three PEG subunits.

63. The complex of claim 59, wherein each of the $L_1$ linkers couples a first engineered free cysteine of one of the antibody heavy chains or one of the antibody light chains with a second engineered free cysteine of one of the antibody Fab fragments.

64. The complex of claim 63, wherein the first engineered free cysteine is a cysteine amino acid in the antibody heavy chain independently selected from the group consisting of T114C, A118C, A140C, L174C, L179C, T187C, T209C, V262C, G371C, Y373C, E382C, S400C, S424C, N434C and Q438C, according to EU numbering.

65. The complex of claim 63, wherein the first engineered free cysteine is a cysteine amino acid in the antibody light chain independently selected from the group consisting of I106C, R108C, R142C, K149C, and V205C, according to Kabat numbering.

66. The complex of claim 63, wherein the second engineered free cysteine is a C-terminal cysteine residue.

67. The complex of claim 59, wherein $VH_1$ and $VL_1$ form an antigen binding domain that binds the first epitope of OX40, and wherein $VH_2$ and $VL_2$ form an antigen binding domain that binds the second epitope of OX40.

68. The complex of claim 59, wherein $VH_1$ and $VL_1$ form an antigen binding domain that binds the second epitope of OX40, and wherein $VH_2$ and $VL_2$ form an antigen binding domain that binds the first epitope of OX40.

69. The complex of claim 59, wherein $VH_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

70. The complex of claim 59, wherein $VH_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein $VL_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein $VH_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein $VL_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

71. The complex of claim 59, wherein $VH_1$ comprises the amino acid sequence of SEQ ID NO:128, wherein $VL_1$ comprises the amino acid sequence of SEQ ID NO:129, wherein $VH_2$ comprises the amino acid sequence of SEQ ID NO:56, and wherein $VL_2$ comprises the amino acid sequence of SEQ ID NO:57.

72. The complex of claim 59, wherein $VH_2$ comprises the amino acid sequence of SEQ ID NO:128, wherein $VL_2$ comprises the amino acid sequence of SEQ ID NO:129, wherein $VH_1$ comprises the amino acid sequence of SEQ ID NO:56, and wherein $VL_1$ comprises the amino acid sequence of SEQ ID NO:57.

73. The complex of claim 59, wherein: each of the antibody heavy chains of the antibody comprises the amino acid sequence of SEQ ID NO:232, each of the antibody light chains of the antibody comprises the amino acid sequence of SEQ ID NO:237, each of the antibody Fab fragments comprises a heavy chain fragment comprising the amino acid sequence of SEQ ID NO:239, and each of the antibody Fab fragments comprises a light chain fragment comprising the amino acid sequence of SEQ ID NO:231.

74. The complex of claim 59, wherein each of the antibody heavy chains of the antibody comprises the amino acid sequence of SEQ ID NO:230, each of the antibody light chains of the antibody comprises the amino acid sequence of SEQ ID NO:236, each of the antibody Fab fragments comprises a heavy chain fragment comprising the amino acid sequence of SEQ ID NO:238, and each of the antibody Fab fragments comprises a light chain fragment comprising the amino acid sequence of SEQ ID NO:233.

75. The complex of claim 1, wherein the complex comprises two antibodies, wherein each of the antibodies comprises:

a first antibody heavy chain comprising:

$$VH_1\text{-}CH_1\text{-hinge-}CH_2\text{-}(CH_3)_x \qquad [X];$$

a first antibody light chain comprising:

$$VL_1\text{-}CL \qquad [VII];$$

a second antibody heavy chain comprising:

$$VH_2\text{-}CH_1\text{-hinge-}CH_2\text{-}(CH_3)_y \qquad [XII]; \text{ and}$$

a second antibody light chain comprising:

$$VL_2\text{-}CL \qquad [IX];$$

wherein the first antibody heavy chain associates with the first antibody light chain such that $VH_1$ and $VL_1$ form an antigen binding domain; wherein the second antibody heavy chain associates with the second antibody light chain such that $VH_2$ and $VL_2$ form an antigen binding domain; wherein the two antibodies are coupled via linker $L_1$; and wherein $VH_1$ is a first antibody heavy chain variable domain, $VH_2$ is a second antibody heavy chain variable domain, $VL_1$ is a first antibody light chain variable domain, $VL_2$ is a second antibody light chain variable domain, CL is an antibody light chain constant domain, $CH_1$ is an antibody first heavy chain constant domain, hinge is an antibody hinge region, $CH_2$ is an antibody second heavy chain constant domain, and $(CH_3)_x$ and $(CH_3)_y$ are antibody third heavy chain constant domains.

76. The complex of claim 75, wherein $(CH_3)_x$ comprises a protuberance or cavity, wherein $(CH_3)_y$ comprises a protuberance or cavity, and wherein the protuberance or cavity of $(CH_3)_x$ is positionable in the protuberance or cavity of $(CH_3)_y$.

77. The complex of claim 76, wherein:

(a) $(CH_3)_x$ comprises a T366Y substitution, and $(CH_3)_y$ comprises a Y407T substitution, numbering according to EU index;

(b) $(CH_3)_x$ comprises a T366W substitution, and $(CH_3)_y$ comprises a Y407A substitution, numbering according to EU index;

(c) $(CH_3)_x$ comprises a F405A substitution, and $(CH_3)_y$ comprises a T394W substitution, numbering according to EU index;

(d) $(CH_3)_x$ comprises a Y407T substitution, and $(CH_3)_y$ comprises a T366Y substitution, numbering according to EU index;

(e) $(CH_3)_x$ comprises T366Y and F405A substitutions, and $(CH_3)_y$ comprises T394W and Y407T substitutions, numbering according to EU index;

(f) (CH$_3$)$_x$ comprises T366W and F405W substitutions, and (CH$_3$)$_y$ comprises T394S and Y407A substitutions, numbering according to EU index;
(g) (CH$_3$)$_x$ comprises F405W and Y407A substitutions, and t(CH$_3$)$_y$ comprises T366W and T394S substitutions, numbering according to EU index; or
(h) (CH$_3$)$_x$ comprises a F405W substitution, and (CH$_3$)$_y$ comprises a T394S substitution, numbering according to EU index.

78. The complex of claim 1, wherein the complex comprises:
a first antibody comprising two antibody heavy chains and two antibody light chains, wherein each of the two antibody heavy chains of the first antibody comprises:

VH$_1$-CH$_1$-hinge-CH$_2$-CH$_3$  [X];

and wherein each of the two antibody light chains of the first antibody comprises:

VL$_1$-CL  [VII]; and a second antibody comprising two antibody heavy chains and two antibody light chains, wherein each of the two antibody heavy chains of the second antibody comprises:

VH$_2$-CH$_1$-hinge-CH$_2$-CH$_3$  [XII];

and wherein each of the two antibody light chains of the second antibody comprises:

VL$_2$-CL  [IX];

wherein each of the antibody heavy chains of the first antibody associates with one of the antibody light chains of the first antibody such that VH$_1$ and VL$_1$ form an antigen binding domain; wherein each of the antibody heavy chains of the second antibody associates with one of the antibody light chains of the second antibody such that VH$_2$ and VL$_2$ form an antigen binding domain; wherein the first and the second antibodies are coupled via linker L$_1$; and
wherein VH$_1$ is a first antibody heavy chain variable domain, VH$_2$ is a second antibody heavy chain variable domain, VL$_1$ is a first antibody light chain variable domain, VL$_2$ is a second antibody light chain variable domain, CL is an antibody light chain constant domain, CH$_1$ is an antibody first heavy chain constant domain, hinge is an antibody hinge region, CH$_2$ is an antibody second heavy chain constant domain, and CH$_3$ is an antibody third heavy chain constant domain.

79. The complex of claim 75, wherein the L$_1$ linker is a bis-maleimido polyethylene glycol (PEG) linker.

80. The complex of claim 79, wherein the PEG linker comprises between one and eleven PEG subunits.

81. The complex of claim 80, wherein the PEG linker comprises one, two, or three PEG subunits.

82. The complex of claim 75, wherein the L$_1$ linker couples a first engineered free cysteine of a first of the two antibodies with a second engineered free cysteine of a second of the two antibodies.

83. The complex of claim 82, wherein at least one of the first or the second engineered free cysteine is a cysteine residue in the heavy chain independently selected from the group consisting of T114C, A118C, A140C, L174C, L179C, T187C, T209C, V262C, G371C, Y373C, E382C, S400C, S424C, N434C and Q438C, according to EU numbering.

84. The complex of claim 82, wherein at least one of the first or the second engineered free cysteine is a cysteine residue in the light chain independently selected from the group consisting of I106C, R108C, R142C, K149C, and V205C, according to Kabat numbering.

85. The complex of claim 75, wherein VH$_1$ and VL$_1$ form an antigen binding domain that binds the first epitope of OX40, and wherein VH$_2$ and VL$_2$ form an antigen binding domain that binds the second epitope of OX40.

86. The complex of claim 75, wherein VH$_1$ and VL$_1$ form an antigen binding domain that binds the second epitope of OX40, and wherein VH$_2$ and VL$_2$ form an antigen binding domain that binds the first epitope of OX40.

87. The complex of claim 75, wherein VH$_1$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein VL$_1$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein VH$_2$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein VL$_2$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

88. The complex of claim 75, wherein VH$_2$ comprises an HVR-H1 comprising the amino acid sequence of SEQ ID NO:29, an HVR-H2 comprising the amino acid sequence of SEQ ID NO:30, and an HVR-H3 comprising the amino acid sequence of SEQ ID NO:33; wherein VL$_2$ comprises an HVR-L1 comprising the amino acid sequence of SEQ ID NO:37, an HVR-L2 comprising the amino acid sequence of SEQ ID NO:39, and an HVR-L3 comprising the amino acid sequence of SEQ ID NO:42; wherein VH$_1$ comprises an HVR-H1 comprising the amino acid sequence of SEQ ID NO:2, an HVR-H2 comprising the amino acid sequence of SEQ ID NO:3, and an HVR-H3 comprising the amino acid sequence of SEQ ID NO:4; and wherein VL$_1$ comprises an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7.

89. The complex of claim 75, wherein VH$_1$ comprises the amino acid sequence of SEQ ID NO:128, wherein VL$_1$ comprises the amino acid sequence of SEQ ID NO:129, wherein VH$_2$ comprises the amino acid sequence of SEQ ID NO:56, and wherein VL$_2$ comprises the amino acid sequence of SEQ ID NO:57.

90. The complex of claim 75, wherein VH$_2$ comprises the amino acid sequence of SEQ ID NO:128, wherein VL$_2$ comprises the amino acid sequence of SEQ ID NO:129, wherein VH$_1$ comprises the amino acid sequence of SEQ ID NO:56, and wherein VL$_1$ comprises the amino acid sequence of SEQ ID NO:57.

91. The complex of claim 1, wherein the complex comprises an antibody Fc region that comprises a modification for attenuating effector function.

92. The complex of claim 91, wherein the complex comprises an antibody Fc region that comprises an amino acid substitution at one or more amino acid positions (EU numbering) selected from the group consisting of:
(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2, (e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

93. The complex of claim 91, wherein the complex comprises an antibody Fc region that comprises one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) one or more substitutions in the region spanning amino acid residues 118 to 260 in the Fc region of human IgG2 or in the region spanning amino acids 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

94. The complex of claim 91, wherein the complex comprises an antibody Fc region that comprises a modification for attenuating effector function that results in an aglycosylated Fc region.

95. The complex of claim 91, wherein the complex comprises an antibody Fc region that comprises a modification for attenuating effector function that does not eliminate glycosylation of the Fc region.

96. A pharmaceutical formulation comprising the complex of claim 1 and a pharmaceutically acceptable carrier.

* * * * *